United States Patent
Lee et al.

(10) Patent No.: US 10,676,510 B2
(45) Date of Patent: Jun. 9, 2020

(54) SUBSTITUTED UREA DEPSIPEPTIDE ANALOGS AS ACTIVATORS OF THE CLPP ENDOPEPTIDASE

(71) Applicant: ST. JUDE CHILDREN'S RESEARCH HOSPITAL, Memphis, TN (US)

(72) Inventors: Richard E. Lee, Cordova, TN (US); Ying Zhao, Memphis, TN (US); Elizabeth Griffith, Germantown, TN (US); Zhong Zheng, Irvine, CA (US); Aman P. Singh, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 15/863,673

(22) Filed: Jan. 5, 2018

(65) Prior Publication Data

US 2018/0127469 A1    May 10, 2018

Related U.S. Application Data

(63) Continuation of application No. 14/914,449, filed as application No. PCT/US2014/053610 on Aug. 30, 2014, now Pat. No. 9,879,050.

(60) Provisional application No. 61/872,565, filed on Aug. 30, 2013, provisional application No. 62/004,119, filed on May 28, 2014.

(51) Int. Cl.
| | |
|---|---|
| C07K 11/02 | (2006.01) |
| A61K 38/15 | (2006.01) |
| A61K 45/06 | (2006.01) |
| C12N 9/50 | (2006.01) |
| C07K 7/06 | (2006.01) |
| A61K 38/00 | (2006.01) |

(52) U.S. Cl.
CPC .............. *C07K 11/02* (2013.01); *A61K 38/15* (2013.01); *A61K 45/06* (2013.01); *C07K 7/06* (2013.01); *C12N 9/50* (2013.01); *A61K 38/00* (2013.01); *C12Y 304/21* (2013.01); *Y02A 50/471* (2018.01); *Y02A 50/475* (2018.01); *Y02A 50/481* (2018.01)

(58) Field of Classification Search
CPC .......... A61K 31/00; A61K 38/00; A61K 38/15
See application file for complete search history.

(56) References Cited

U.S. PATENT DOCUMENTS

| | | | |
|---|---|---|---|
| 4,492,650 A | 1/1985 | Michel et al. | |
| 5,792,444 A | 8/1998 | Fischman et al. | |
| 9,193,767 B2 | 11/2015 | Sello | |
| 2005/0107288 A1 | 5/2005 | Hinzen et al. | |
| 2011/0196027 A1 | 8/2011 | Sieber et al. | |
| 2014/0094403 A1 | 4/2014 | Sello | |
| 2015/0166608 A1 | 6/2015 | Mitomi et al. | |
| 2016/0200770 A1 | 7/2016 | Lee et al. | |

FOREIGN PATENT DOCUMENTS

| | | |
|---|---|---|
| EP | 14841099.6 | 8/2014 |
| EP | 16759625.3 | 3/2016 |
| WO | WO-2003/024996 A2 | 3/2003 |
| WO | WO-2012/135615 A2 | 10/2012 |
| WO | WO-2012/135846 A1 | 10/2012 |
| WO | PCT/US2014/053610 | 8/2014 |
| WO | WO-2015/031871 A1 | 3/2015 |
| WO | PCT/US2016/021043 | 3/2016 |
| WO | WO-2016/141351 A1 | 9/2016 |
| WO | PCT/US2017/049902 | 9/2017 |
| WO | WO-2018/045313 A1 | 3/2018 |

OTHER PUBLICATIONS

Non Final Rejection was dated Jan. 10, 2019 by the USPTO for U.S. Appl. No. 16/160,724, filed Oct. 15, 2018 and published as US-2019/0048040-A1 on Feb. 14, 2019 (Inventor—Richard E. Lee) (9 pages).

Almarasson, Ö. et al., Crystal Engineering of the Composition of Pharmaceutical Phases. Do Pharmaceutical Co-crystals Represent a New Path to Improved Medicines? The Royal Society of Chemistry. 2004; 1889-96.

Brotz-Oesterhel, H. et al., Dysregulation of bacterial proteolytic machinery by a new class of A antibiotics. Nature Med. 2005; 11(10):1082-7.

Carney, D.W. et al., Restriction of the Conformational Dynamics of the Cyclic Acyldepsipeptide Antibiotics Improves Their Antibacterial Activity. J Am Chem Soc. 2014; 136(5):1922-9.

Di, L. et al., Development and Application of High Throughput Plasma Stability Assay for Drug Discovery. Int J Pharm. 2005; 297(1-2):110-9.

Gottesman, S. and Maurizi, M.R., Regulation by proteolysis: energy-dependent proteases and their targets. Microbiol Rev. 1992; 56:592-621.

Gottesman, S. et al., The ClpXP and ClpAP proteases degrade proteins with carboxy-terminal peptide tails added by the SsrA-tagging system. Genes Dev. 1998; 12:1338-47.

Hinzen, B., et al. Medicinal Chemistry Optimization of Acyldepsipeptides of the Enopeptin Class Antibiotics. ChemMedChem. 2006; 1(7):689-93.

Levin, B.R. and Rozen, D.E., Non-inherited antibiotic resistance. Nat Rev Microbiol. 2006; 4:556-62.

Lewis, K., Persister cells. Annu Rev Microbiol. 2010; 64:357-72.

Maurizi, M.R. et al., Endopeptidase Clp: ATP-dependent Clp Protease from *Escherichia coli*. Methods Enzymol. 1994; 244:314-31.

(Continued)

*Primary Examiner* — James H Alstrum-Acevedo
*Assistant Examiner* — Kaipeen E Yang
(74) *Attorney, Agent, or Firm* — Ballard Spahr LLP

(57) ABSTRACT

In one aspect, the invention relates to substituted urea depsipeptide analogs, derivatives thereof, and related compounds, which are useful as activators the ClpP endopeptidease; synthesis methods for making the compounds; pharmaceutical compositions comprising the compounds; and methods of treating infectious disease using the compounds and compositions. This abstract is intended as a scanning tool for purposes of searching in the particular art and is not intended to be limiting of the present invention.

9 Claims, No Drawings

(56) References Cited

OTHER PUBLICATIONS

Mayo Clinic, Infectious Disease; Last visited 2018; https://www.mayoclinic.org/diseases-conditions/infectious-diseases/symptoms-causes/syc-20351173 (7 pages).
North, E. J. et al., Design, synthesis and anti-tuberculosis activity of 1-adamantyl-3-heteroaryl ureas with improved in vitro pharmacokinetic properties. Bioorg Med Chem. 2013; 21(9):2587-99.
Sass, P. et al., Antibiotic acyldepsipeptides activate ClpP peptidase to degrade the cell division protein FtsZ. Proc Natl Acad Sci. 2011; 108:17474-9.
Waters, N.J. et al., Validation of a Rapid Equilibrium Dialysis Approach for the Measurement of Plasma Protein Binding. J Pharm Sci. 2008; 97(10):4586-95.
Supplementary European Search Report dated Mar. 8, 2017 by the European Patent Office for Patent Application No. 14841099.6, which was filed on Aug. 30, 2014 and published as EP3038640 on Jul. 6, 2016 (Inventor—Lee et al.; Applicant—St. Jude Children's Research Hospital; (6 pages).
Communication Pursuant to Article 94(3) EPC dated Oct. 27, 2017 by the European Patent Office for Patent Application No. 14841099.6, which was filed on Aug. 30, 2014 and published as EP3038640 on Jul. 6, 2016 (Inventor—Lee et al.; Applicant—St. Jude Children's Research Hospital; (4 pages).
International Search Report and Written Opinion were dated Nov. 12, 2014 by the International Searching Authority for Application No. PCT/US2014/053610 dated Aug. 30, 2014 and published as WO 2015/031871 on Mar. 5, 2015(Applicant—St. Jude Children's Research Hospital) (10 pages).
International Preliminary Report on Patentability dated Mar. 1, 2016 for Application No. PCT/US2014/053610 which was filed on Aug. 30, 2014 and published as WO 2015/031871 on Mar. 5, 2015(Inventor—Richard E. Lee; Applicant—St. Jude Children's Research Hospital; (8 pages).
Preliminary Amendment filed on Feb. 25, 2016 with the U.S. Patent and Trademark Office for U.S. Appl. No. 14/914,449, filed Feb. 25, 2016 and granted as 9,879,050 on Jan. 30, 2018 (Inventor—Lee et al.; Applicant—St. Jude Children's Research Hospital; (8 pages).
Restriction Requirement dated Sep. 25, 2016 by the U.S. Patent and Trademark Office for U.S. Appl. No. 14/914,449, filed Feb. 25, 2016 and granted as 9,879,050 on Jan. 30, 2018 (Inventor—Lee et al.; Applicant—St. Jude Children's Research Hospital; (11 pages).
Response to Restriction Requirement filed on Nov. 14, 2016 with the U.S. Patent and Trademark Office for U.S. Appl. No. 14/914,449, filed Feb. 25, 2016 and granted as 9,879,050 on Jan. 30, 2018 (Inventor—Lee et al.; Applicant—St. Jude Children's Research Hospital; (11 pages).
Non-Final Office Action dated Feb. 15, 2017 by the U.S. Patent and Trademark Office for U.S. Appl. No. 14/914,449, filed Feb. 25, 2016 and granted as 9,879,050 on Jan. 30, 2018 (Inventor—Lee et al.; Applicant—St. Jude Children's Research Hospital; (8 pages).
Response to Non-Final Office Action filed on Jun. 20, 2017 with the U.S. Patent and Trademark Office for U.S. Appl. No. 14/914,449, filed Feb. 25, 2016 and granted as 9,879,050 on Jan. 30, 2018 (Inventor—Lee et al.; Applicant—St. Jude Children's Research Hospital; (34 pages).
Notice of Allowance dated Sep. 5, 2017 by the U.S. Patent and Trademark Office for U.S. Appl. No. 14/914,449, filed Feb. 25, 2016 and granted as 9,879,050 on Jan. 30, 2018 (Inventor—Lee et al.; Applicant—St. Jude Children's Research Hospital; (9 pages).
Amendment After Notice of Allowance (Rule 312) filed on Sep. 29, 2017 with the U.S. Patent and Trademark Office for U.S. Appl. No. 14/914,449, filed Feb. 25, 2016 and granted as 9,879,050 on Jan. 30, 2018 (Inventor—Lee et al.; Applicant—St. Jude Children's Research Hospital; (5 pages).
Response to Amendment under Rule 312 dated Oct. 18, 2017 by the U.S. Patent and Trademark Office for U.S. Appl. No. 14/914,449, filed Feb. 25, 2016 and granted as 9,879,050 on Jan. 30, 2018 (Inventor—Lee et al.; Applicant—St. Jude Children's Research Hospital; (2 pages).
Issue Notification dated Jan. 10, 2018 by the U.S. Patent and Trademark Office for U.S. Appl. No. 14/914,449, filed Feb. 25, 2016 and granted as 9,879,050 on Jan. 30, 2018 (Inventor—Lee et al.; Applicant—St. Jude Children's Research Hospital; (1 page).
International Search Report and Written Opinion dated May 20, 2016 by the International Searching Authority for Patent Application No. PCT/US2016/021043, filed Mar. 4, 2016 and published as WO 2016/141351 on Sep. 9, 2016 (Inventor—Lee et al.; Applicant—St. Jude Children's Research Hospital; (8 pages).
International Preliminary Report on Patentability dated Sep. 5, 2017 by the International Searching Authority for Patent Application No. PCT/US2016/021043, which was filed on Mar. 4, 2016 and published as WO 2016/141351 on Sep. 9, 2016 (Inventor—Lee et al.; Applicant—St. Jude Children's Research Hospital; (6 pages).
Preliminary Amendment filed on Aug. 30, 2017 with the U.S. Patent and Trademark Office for U.S. Appl. No. 15/554,707, filed Aug. 30, 2017 (Inventor—Lee et al.; Applicant—St. Jude Children's Research Hospital; (16 pages).
Non-Final Office Action dated Feb. 7, 2018 by the U.S. Patent and Trademark Office for U.S. Appl. No. 15/554,707, filed Aug. 30, 2017 (Inventor—Lee et al.; Applicant—St. Jude Children's Research Hospital; (10 pages).
International Search Report and Written Opinion dated Dec. 5, 2017 by the International Searching Authority for Patent Application No. PCT/US2017/049902, which was filed on Sep. 1, 2017 and published as WO 2018/045313 on Mar. 8, 2018 (Inventor—Lee et al.; Applicant—St. Jude Children's Research Hospital; (7 pages).
U.S. Appl. No. 61/872,565, filed Aug. 30, 2013, Richard E. Lee (St. Jude Children's Research Hospital).
U.S. Appl. No. 62/004,119, filed May 28, 2014, Richard E. Lee (St. Jude Children's Research Hospital).
U.S. Appl. No. 14/914,449, filed May 28, 2014, U.S. Pat. No. 9,879,050, Jan. 30, 2018, Richard E. Lee (St. Jude Children's Research Hospital).
U.S. Appl. No. 62/128,497, filed Mar. 4, 2015, Richard E. Lee (St. Jude Children's Research Hospital).
U.S. Appl. No. 15/554,707, filed Aug. 30, 2017, Richard E. Lee (St. Jude Children's Research Hospital).
U.S. Appl. No. 62/383,190, filed Sep. 2, 2016, Richard E. Lee (St. Jude Children's Research Hospital).
Non-Final Office Action dated Apr. 16, 2019 by the U.S. Patent and Trademark Office for U.S. Appl. No. 16/329,168, filed Sep. 1, 2017 (Inventor—Richard E. Lee) (12 pages).

SUBSTITUTED UREA DEPSIPEPTIDE ANALOGS AS ACTIVATORS OF THE CLPP ENDOPEPTIDASE

CROSS-REFERENCE TO RELATED APPLICATIONS

This Application is a continuation of U.S. application Ser. No. 14/914,449, filed Feb. 25, 2016, which is a U.S. national stage of International Application No. PCT/US2014/053610, filed on Aug. 30, 2014, which claims the benefit of U.S. Provisional Application No. 61/872,565, filed on Aug. 30, 2013, and U.S. Provisional Application No. 62/004,119, filed on May 28, 2014, all of which are incorporated herein by reference in their entirety.

STATEMENT REGARDING FEDERALLY SPONSORED RESEARCH

This invention was made with government support under grants AI098327 and AI110578 awarded by the National Institutes of Health. The government has certain rights in the invention.

BACKGROUND

There are two major unsolved problems in the field of antimicrobials: how to develop effective approaches to combat drug-resistant pathogens; and how to treat chronic infections tolerant to antimicrobials. Although drug resistance is a formidable challenge, there at least exists an arsenal of antibiotics, both currently in use and in various stages of the drug development pipeline, which can be used against a variety of pathogenic bacteria. Nevertheless, there remains a significant need for new types of antibiotics for use against emerging drug resistance in bacterial populations.

Unfortunately, the situation with regard to treatment of chronic infections tolerant to antibiotics is very different. Antibiotics are typically effective because of cooperation with the immune system. For example, an antibiotic can eliminate most of the pathogen population or simply stop growth, and then immune system completes the eradication of the infectious bacterial population. This does not work when an exopolymer matrix restricts access of the immune system to the pathogen within a biofilm. The result is a chronic infection, requiring treatment with multiple antibiotics over the course of months to years, accompanied by significant morbidity and mortality. These include endocarditis, osteomyelitis, cystic fibrosis, deep-seated infections, infections of indwelling devices, and dental diseases.

Moreover, all communities of cells produce persisters, dormant variants of the wild type that are tolerant to most antibiotics (Lewis, K. Ann. Rev. Microbiol. (2010) 64:357-372). A lingering chronic infection maintains a large effective population size, favoring development of resistance (Levin, B. R. & Rozen, D. E. Nat. Rev. Microbiol. (2006) 4:556-562) Finding countermeasures against persisters is a considerable unmet need in addressing infectious diseases, and success in finding countermeasures will be significant not only for treatment of chronic infections, but for stemming the spread of resistance as well.

Despite advances in antimicrobial research, there remains a significant need for antibiotic compounds that are potent and effective for the treatment of diseases associated with infection by gram positive and gram negative bacteria. There is also particular need for antimicrobials combatting resistant bacterial strains and for use in treatment of chronic infections, including those associated with biofilm populations comprising dormant persister cells tolerant to currently available antimicrobials. These needs and other needs are satisfied by the present invention.

SUMMARY

In accordance with the purpose(s) of the invention, as embodied and broadly described herein, the invention, in one aspect, relates to compounds useful as activators of the ClpP protease, methods of making same, pharmaceutical compositions comprising same, and methods of treating infectious disease using the disclosed compounds and products of the disclosed methods of making the compounds.

Disclosed are compounds having a structure represented by a formula:

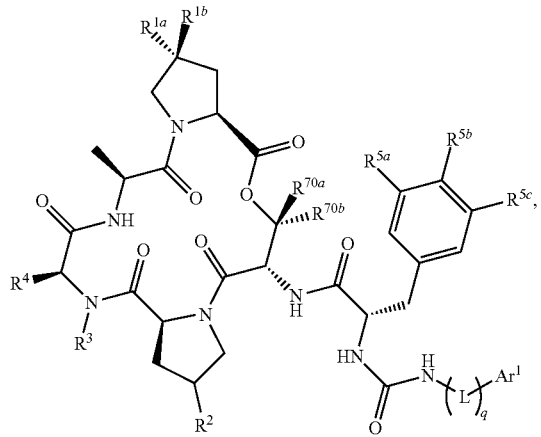

wherein q is an integer selected from 0 and 1; wherein L is moiety selected from —$CH_2$—, —$(CH_2)_2$—, —CH=CH—, and -(cyclopropyl)-; wherein each of $R^{1a}$ and $R^{1b}$ is independently selected from hydrogen, halogen, hydroxyl, cyano, and C1-C3 alkyl; or wherein $R^{1a}$ and $R^{1b}$ are optionally covalently bonded, and together with the intermediate carbon comprise an optionally substituted 3- to 7-membered spirocycloalkyl; wherein $R^2$ is selected from hydrogen, halogen, —$NH_2$, —OH, —$NO_2$, C1-C3 alkyl, —C1-C3 alkylamino, C1-C3 dialkylamino, and C1-C3 aminoalkyl; wherein $R^3$ is C1-C6 alkyl; wherein $R^4$ is C1-C6 alkyl; or wherein $R^3$ and $R^4$ are covalently bonded, together with the intermediate atoms, comprise a 3- to 10-membered heterocycle having 1, 2, or 3 heteroatoms selected from O, N, and S; and wherein the heterocycle is substituted with 0, 1, 2, or 3 groups independently selected from halogen, —$NH_2$, —OH, —$NO_2$, C1-C3 alkyl, C1-C3 alkoxy, C1-C3 aminoalkyl, C1-C3 alkylamino, C1-C3 dialkylamino, C1-C3 hydroxyalkyl, —(C=O)$OR^{30}$, —(C=O)$NR^{32a}R^{32b}$, —(C1-C3 alkyl)-(C=O)$OR^{30}$, and —(C1-C3 alkyl)-(C=O)$NR^{32a}R^{32b}$; wherein $R^{30}$, when present, is selected from hydrogen and C1-C3 alkyl; wherein each of $R^{32a}$ and $R^{32b}$, when present, is independently selected from hydrogen and C1-C3 alkyl; wherein $Ar^1$ is selected from aryl and heteroaryl; and wherein $Ar^1$ is substituted with 0, 1, 2, or 3 groups independently selected from halogen, —$NH_2$, —OH, —$NO_2$, difluoromethoxy, trifluoromethoxy, C1-C6 alkyl, C1-C6 monohaloalkyl, C1-C6 alkoxy, C1-C6 alkylamino, C1-C6 dialkylamino, —$S(O)_nR^{40}$, —$S(O)_n$ $NR^{41a}R^{41b}$, —(C=O)$NR^{42a}R^{42b}$, —$NR^{43}$(C=O) $NR^{44a}R^{44b}$, —$NR^{43}$(C=O)$R^{45}$, —(C=O)$OR^{46}$, $Ar^2$, —(C1-C3 alkyl)-S(O)$_n$R$^{40}$, —(C1-C3 alkyl)-S(O)$_n$NR$^{41a}$R$^{41b}$, —(C1-C3 alkyl)-(C=O)NR$^{42a}$R$^{42b}$, —(C1-C3 alkyl)-NR$^{43}$(C=O)NR$^{44a}$R$^{44b}$, —NR$^{43}$(C=O)R$^{45}$, —(C1-C3 alkyl)-(C=O)OR$^{46}$, and —(C1-C3 alkyl)-Ar$^2$; wherein each n is an integer independently selected from 0, 1, and 2; wherein each occurrence of R$^{40}$, when present, is independently selected from hydrogen, C1-C6 alkyl, phenyl, benzyl, naphthyl, and monocyclic heteroaryl; wherein each occurrence of R$^{41a}$ and R$^{41b}$, when present, is independently selected from hydrogen, C1-C6 alkyl, phenyl, benzyl, naphthyl, and monocyclic heteroaryl; wherein each occurrence of R$^{42}$, when present, is independently selected from hydrogen and C1-C6 alkyl; wherein each occurrence of R$^{43}$, when present, is independently selected from hydrogen and C1-C6 alkyl; wherein each occurrence of R$^{44a}$ and R$^{44b}$, when present, is independently selected from hydrogen and C1-C6 alkyl; wherein each occurrence of R$^{45}$, when present, is independently selected from hydrogen and C1-C6 alkyl; wherein each occurrence of R$^{46}$, when present, is independently selected from hydrogen and C1-C6 alkyl; wherein each Ar$^2$, when present, is independently selected from phenyl, naphthyl, and heteroaryl, and wherein each Ar$^2$ is independently substituted with 0, 1, 2, or 3 groups independently selected from halogen, —NH$_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino; or a pharmaceutically acceptable salt thereof.

Also disclosed are pharmaceutical compositions comprising a therapeutically effective amount of one or more disclosed compounds, or pharmaceutically acceptable salt, solvate, or polymorph thereof, and a pharmaceutically acceptable carrier.

Also disclosed are methods for the treatment of an infectious disease comprising the step of administering to the mammal a therapeutically effective amount of at least one disclosed compound or pharmaceutically acceptable salt, solvate, or polymorph thereof.

Also disclosed are methods enhancing C1pP in at least one cell, comprising the step of contacting the cell with an effective amount of at least one disclosed compound or pharmaceutically acceptable salt, solvate, or polymorph thereof.

Also disclosed are uses of a disclosed compound, a disclosed product of making, or a pharmaceutically acceptable salt, solvate, or polymorph thereof.

Also disclosed are uses of a disclosed compound, a disclosed product of making, or a pharmaceutically acceptable salt, solvate, or polymorph thereof, in the manufacture of a medicament for the treatment of an infectious disease.

Also disclosed are uses of a disclosed compound, a disclosed product of making, or a pharmaceutically acceptable salt, solvate, or polymorph thereof, in the manufacture of a medicament for the enhancing C1pP activity in a bacterial cell, wherein enhancing C1pP activity has a bacteriostatic or bactericidal effect.

Also disclosed are methods for the manufacture of a medicament to treat an infectious disease comprising combining at least one disclosed compound or at least one disclosed product of making with a pharmaceutically acceptable carrier or diluent.

Also disclosed are kits comprising at least one disclosed compound, or a pharmaceutically acceptable salt, solvate, or polymorph thereof, and one or more of: (a) at least one agent known to increase C1pP activity; (b) at least one agent known to have antimicrobial activity; (c) at least one agent known to treat an infectious disease; (d) instructions for treating an infectious disease; (e) instructions for administering the compound in connection with treating a microbial infection; or (f) instructions for administering the compound with at least one agent known to treat an infectious disease.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

In this specification and in the claims which follow, reference will be made to a number of terms which shall be defined herein.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and in the claims, the term "comprising" can include the aspects "consisting of" and "consisting essentially of." Thus, for example, an aspect such as "a composition comprising A, B, and C" also includes aspects such as "a composition consisting of A, B, and C" and "a composition consisting essentially of A, B, and C."

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

In some aspects of the disclosed methods, the subject has been diagnosed with a need for treatment of an infectious disease prior to the administering step. In some aspects of the disclosed methods, the subject has been diagnosed with a need for enhancing bacterial ClpP activity prior to the administering step. In some aspects of the disclosed methods, the subject has been diagnosed with having a gram positive or gram negative infection prior to the administering step. In some aspects of the disclosed methods, the subject has been identified with an infectious disease that is treatable by enhancing the activity of bacterial ClpP prior to the administering step. In some aspects of the disclosed methods, the subject has been identified with a gram positive bacterial infection prior to the administering step. In various aspects of the disclosed methods, the subject has been identified with a gram negative bacterial infection prior to the administering step. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with an infectious disease treatable by enhancing ClpP activity" means having been subjected to a physical examination by a person of skill, for example, a physician, and found to have a condition that can be diagnosed or treated by a compound or composition that can enhance ClpP activity. As a further example, "diagnosed with a need for treatment of an infectious disease" refers to having been subjected to a physical examination by a person of skill, for example, a physician, and found to have a condition characterized by infection with a pathogenic microbe, such as a gram positive or gram negative bacteria.

As used herein, the phrase "identified to be in need of treatment for an infectious disease," or the like, refers to selection of a subject based upon need for treatment of the infectious disease. For example, a subject can be identified as having a need for treatment of an infectious disease (e.g., an infectious disease related to infection with a pathogenic gram negative or gram positive bacteria) based upon an earlier diagnosis by a person of skill and thereafter subjected to treatment for the infectious disease. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target protein (e.g. the ClpP endopeptidase), or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% activation or enhancement of a biological process, or component of a process. For example, $EC_{50}$ can refer to the concentration of a compound that provokes a response halfway between the baseline and maximum response in an appropriate assay of the target activity. For example, an $EC_{50}$ for the C1pP endopeptidase can be determined in an in vitro assay system. Such in vitro assay systems include assay such as the Casein-BODIPY digestion assay as described herein.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," . . . "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group.

The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched)alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

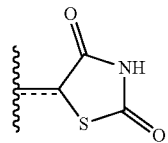

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al. The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

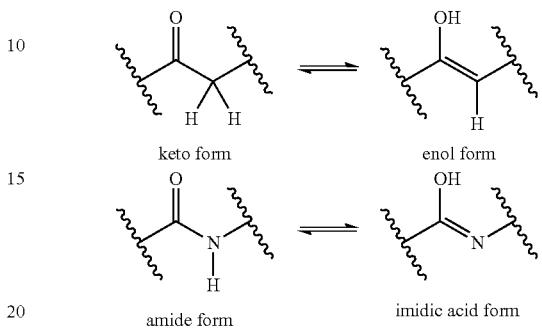

keto form      enol form amide form      imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

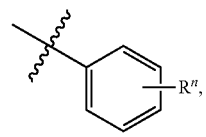

which is understood to be equivalent to a formula:

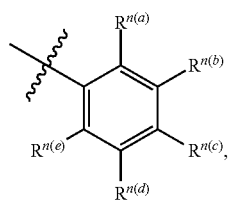

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful as activators of the C1pP protease. In one aspect, the compounds of the invention are useful in the treatment of infectious disease, including infectious disease associated with bacterial infections, and other diseases in which activation of the C1pP protease can have therapeutic benefit, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

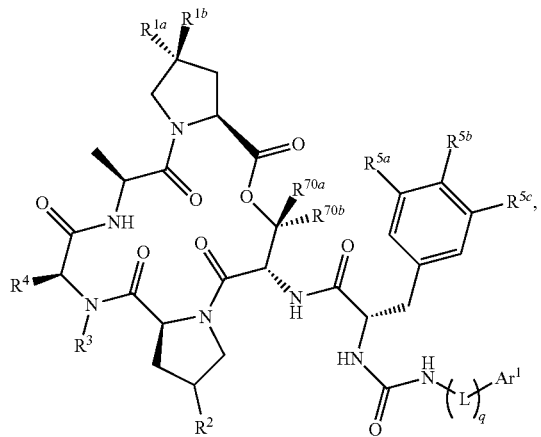

wherein q is an integer selected from 0 and 1; wherein L is moiety selected from —$CH_2$—, —$(CH_2)_2$—, —CH=CH—, and -(cyclopropyl)-; wherein each of $R^{1a}$ and $R^{1b}$ is independently selected from hydrogen, halogen, hydroxyl, cyano, and C1-C3 alkyl; or wherein $R^{1a}$ and $R^{1b}$ are optionally covalently bonded, and together with the intermediate carbon comprise an optionally substituted 3- to 7-membered spirocycloalkyl; wherein $R^2$ is selected from hydrogen, halogen, —$NH_2$, —OH, —$NO_2$, C1-C3 alkyl, —C1-C3 alkylamino, C1-C3 dialkylamino, and C1-C3 aminoalkyl; wherein $R^3$ is C1-C6 alkyl; wherein $R^4$ is C1-C6 alkyl; or wherein $R^3$ and $R^4$ are covalently bonded, together with the intermediate atoms, comprise a 3- to 10-membered heterocycle having 1, 2, or 3 heteroatoms selected from O, N, and S; and wherein the heterocycle is substituted with 0, 1, 2, or 3 groups independently selected from halogen, —$NH_2$, —OH, —$NO_2$, C1-C3 alkyl, C1-C3 alkoxy, C1-C3 aminoalkyl, C1-C3 alkylamino, C1-C3 dialkylamino, C1-C3 hydroxyalkyl, —(C=O)$OR^{30}$, —(C=O)$NR^{32a}R^{32b}$, —(C1-C3 alkyl)-(C=O)$OR^{30}$, and —(C1-C3 alkyl)-(C=O)$NR^{32a}R^{32b}$; wherein $R^{30}$, when present, is selected from hydrogen and C1-C3 alkyl; wherein each of $R^{32a}$ and $R^{32b}$, when present, is independently selected from hydrogen and C1-C3 alkyl; wherein $Ar^1$ is selected from aryl and heteroaryl; and wherein $Ar^1$ is substituted with 0, 1, 2, or 3 groups independently selected from halogen, —$NH_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, Ar$^2$, —(C1-C3 alkyl)-S(O)$_n$R$^{40}$, —(C1-C3 alkyl)-S(O)$_n$NR$^{41a}$R$^{41b}$, —(C1-C3 alkyl)-(C=O)NR$^{42a}$R$^{42b}$, —(C1-C3 alkyl)-NR$^{43}$(C=O)NR$^{44a}$R$^{44b}$, —NR$^{43}$(C=O)R$^{45}$, —(C1-C3 alkyl)-(C=O)OR$^{46}$, and —(C1-C3 alkyl)-Ar$^2$; wherein each n is an integer independently selected from 0, 1, and 2; wherein each occurrence of R$^{40}$, when present, is independently selected from hydrogen, C1-C6 alkyl, phenyl, benzyl, naphthyl, and monocyclic heteroaryl; wherein each occurrence of R$^{41a}$ and R$^{41b}$, when present, is independently selected from hydrogen, C1-C6 alkyl, phenyl, benzyl, naphthyl, and monocyclic heteroaryl; wherein each occurrence of R$^{42}$, when present, is independently selected from hydrogen and C1-C6 alkyl; wherein each occurrence of R$^{43}$, when present, is independently selected from hydrogen and C1-C6 alkyl; wherein each occurrence of R$^{44a}$ and R$^{44b}$, when present, is independently selected from hydrogen and C1-C6 alkyl; wherein each occurrence of R$^{45}$, when present, is independently selected from hydrogen and C1-C6 alkyl; wherein each occurrence of R$^{46}$, when present, is independently selected from hydrogen and C1-C6 alkyl; wherein each Ar$^2$, when present, is independently selected from phenyl, naphthyl, and heteroaryl, and wherein each Ar$^2$ is independently substituted with 0, 1, 2, or 3 groups independently selected from halogen, —NH$_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino; or a pharmaceutically acceptable salt thereof.

In one aspect, the invention relates to a compound having a structure represented by a formula:

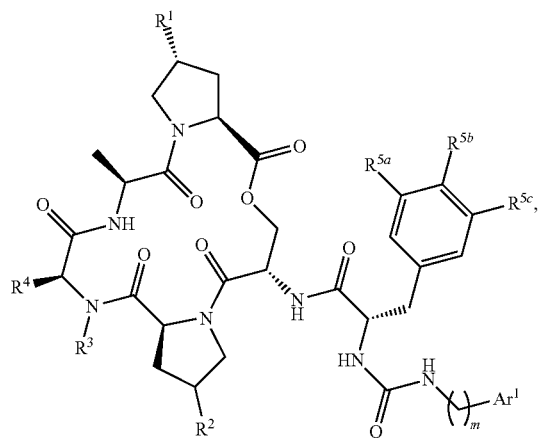

wherein m is an integer selected from 0, 1, and 2; wherein R$^1$ is selected from hydrogen, halogen, and C1-C3 alkyl; wherein R$^2$ is selected from hydrogen, halogen, —NH$_2$, —OH, —C1-C3 alkylamino, C1-C3 dialkylamino, C1-C3 aminoalkyl, C1-C3 hydroxyalkyl, —(C=O)OR$^{10}$, —(C=O)NR$^{12a}$R$^{12b}$, —(C1-C2 alkyl)-(C=O)OR$^{10}$, —(C1-C2 alkyl)-(C=O)NR$^{12a}$R$^{12b}$, and —C(NR$^{12a}$R$^{12b}$)R$^{11}$—(C1-C3 alkyl)-R$^{13}$; wherein R$^{10}$, when present, is selected from hydrogen and C1-C3 alkyl; wherein R$^{11}$, when present, is selected from hydrogen and C1-C3 alkyl; wherein each of R$^{12a}$ and R$^{12b}$, when present, is independently selected from hydrogen and C1-C3 alkyl; wherein R$^{13}$, when present, is selected from —NH$_2$, —OH, —(C=O)OR$^{10}$, —(C=O)NR$^{14a}$R$^{14b}$, —(C=O)—(C1-C3 alkyl)-OR$^{10}$, —(C=O)—(C1-C3 alkyl)-NR$^{14a}$R$^{14b}$, and -Cy$^1$; wherein each of R$^{14a}$ and R$^{14b}$, when present, is independently selected from hydrogen and C1-C3 alkyl; and wherein Cy$^1$, when present, is selected from C2-C7 heterocycloalkyl substituted with 0, 1, 2, or 3 groups selected from halogen, —NH$_2$, —OH, and methyl; wherein R$^3$ is selected from hydrogen, C1-C3 alkyl, C1-C3 hydroxyalkyl, —(C1-C3 alkyl)-(C=O)OR$^{20}$, —(C1-C3 alkyl)-(C=O)NR$^{21a}$R$^{21b}$, and -Cy$^2$; wherein j is an integer selected from 0, 1, and 2; wherein R$^{20}$, when present, is selected from hydrogen and C1-C3 alkyl; wherein each of R$^{21a}$ and R$^{21b}$, when present, is independently selected from hydrogen and C1-C3 alkyl; wherein Cy$^2$, when present, is selected from C2-C7 heterocycloalkyl substituted with 0, 1, 2, or 3 groups selected from halogen, —NH$_2$, —OH, and methyl; wherein R$^4$ is selected from hydrogen, C1-C6 alkyl, —C1-C6 alkylamino, C1-C6 dialkylamino, C1-C6 hydroxyalkyl, —(C=O)OR$^{30}$, —(C=O)NR$^{32a}$R$^{32b}$, —(C1-C4 alkyl)-(C=O)OR$^{30}$, —(C1-C4 alkyl)-(C=O)NR$^{32a}$R$^{32b}$, —C(NR$^{32a}$R$^{32b}$)R$^{31}$—(C1-C3 alkyl)-R$^{33}$, —(C1-C3 alkyl)-R$^{33}$, and Cy$^3$; wherein R$^{30}$, when present, is selected from hydrogen and C1-C3 alkyl; wherein R$^{31}$, when present, is selected from hydrogen and C1-C3 alkyl; wherein each of R$^{32a}$ and R$^{32b}$, when present, is independently selected from hydrogen and C1-C3 alkyl; wherein R$^{33}$, when present, is selected from —NH$_2$, —OH, —(C=O)OR$^{30}$, —(C=O)NR$^{34a}$R$^{34b}$, —(C=O)—(C1-C3 alkyl)-OR$^{30}$, —(C=O)—(C1-C3 alkyl)-NR$^{34a}$R$^{34b}$, and Cy$^3$; wherein each of R$^{34a}$ and R$^{34b}$, when present, is independently selected from hydrogen and C1-C3 alkyl; wherein Cy$^3$, when present, is selected from C2-C7 heterocycloalkyl substituted with 0, 1, 2, or 3 groups selected from halogen, —NH$_2$, —OH, and methyl; or wherein R$^3$ and R$^4$ are optionally covalently bonded, and together with the intermediate carbon, oxygen, and/or nitrogen, comprise a 3- to 10-membered heterocycle substituted with 0, 1, 2, or 3 groups independently selected from halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —(C1-C3 alkyl)-R$^{33}$, and —C(NR$^{32a}$R$^{32b}$)R$^{31}$—(C1-C3 alkyl)-R$^{33}$; wherein each of R$^{5a}$, R$^{5b}$, and R$^{5c}$ is independently selected from hydrogen, halogen, difluoromethoxy, and trifluoromethoxy; and wherein Ar$^1$ is selected from aryl and heteroaryl; and wherein Ar$^1$ is substituted with 0, 1, 2, or 3 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$; wherein each n is an integer independently selected from 0, 1, and 2; wherein each occurrence of R$^{40}$, when present, is independently selected from hydrogen and C1-C6 alkyl; wherein each occurrence of R$^{41a}$ and R$^{41b}$, when present, is independently selected from hydrogen and C1-C6 alkyl; wherein each occurrence of R$^{42}$, when present, is independently selected from hydrogen and C1-C6 alkyl; wherein each occurrence of R$^{43}$, when present, is independently selected from hydrogen and C1-C6 alkyl; wherein each occurrence of R$^{44a}$ and R$^{44b}$, when present, is independently selected from hydrogen and C1-C6 alkyl; wherein each occurrence of R$^{45}$, when present, is independently selected from hydrogen and C1-C6 alkyl; wherein each occurrence of R$^{46}$, when present, is independently selected from hydrogen and C1-C6 alkyl; wherein each Ar$^2$, when present, is independently selected from phenyl, naphthyl, and heteroaryl, and wherein each Ar² is independently substituted with 0, 1, 2, or 3 groups independently selected from halogen, —NH₂, —OH, —CN, C1-C6 alkyl, C1-C6 monohaloalkyl, C1-C6 polyhaloalkyl, C1-C6 alkoxy, C1-C6 alkylamino, and C1-C6 dialkylamino; or a pharmaceutically acceptable salt, solvate, or polymorph thereof.

In one aspect, the invention relates to a compound having a structure represented by a formula:

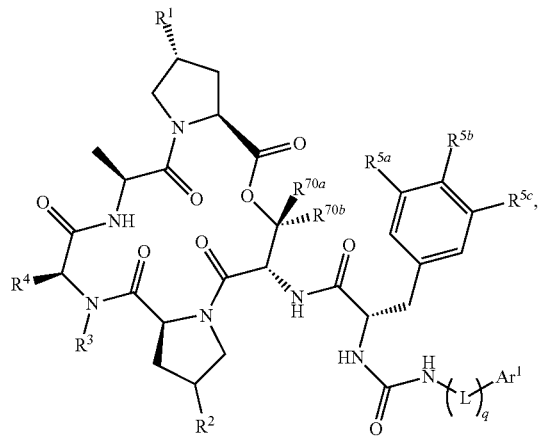

wherein q is an integer selected from 0 and 1; wherein L is moiety selected from —CH₂—, —(CH₂)₂—, —CH=CH—, and -(cyclopropyl)-; wherein R¹ is selected from hydrogen, halogen, and C1-C3 alkyl; wherein R² is selected from hydrogen, halogen, —NH₂, —OH, —NO₂, C1-C3 alkyl, —C1-C3 alkylamino, C1-C3 dialkylamino, and C1-C3 aminoalkyl; wherein R³ is selected from hydrogen, C1-C3 alkyl, C1-C3 hydroxyalkyl, —(C1-C3 alkyl)-(C=O)OR²⁰, —(C1-C3 alkyl)-(C=O)NR²¹ᵃR²¹ᵇ, and -Cy²; wherein R²⁰, when present, is selected from hydrogen and C1-C3 alkyl; wherein each of R²¹ᵃ and R²¹ᵇ, when present, is independently selected from hydrogen and C1-C3 alkyl; wherein Cy², when present, is selected from C2-C7 heterocycloalkyl substituted with 0, 1, 2, or 3 groups selected from halogen, —NH₂, —OH, and methyl; wherein R⁴ is selected from hydrogen, C1-C6 alkyl, —C1-C6 alkylamino, C1-C6 dialkylamino, C1-C6 hydroxyalkyl, —(C=O)OR³⁰, —(C=O)NR³²ᵃR³²ᵇ, —(C1-C4 alkyl)-(C=O)OR³⁰, —(C1-C4 alkyl)-(C=O)NR³²ᵃR³²ᵇ, —C(NR³²ᵃR³²ᵇ)R³¹—(C1-C3 alkyl)-R³³, —(C1-C3 alkyl)-R³³, and Cy³; wherein R³⁰, when present, is selected from hydrogen and C1-C3 alkyl; wherein R³¹, when present, is selected from hydrogen and C1-C3 alkyl; wherein each of R³²ᵃ and R³²ᵇ, when present, is independently selected from hydrogen and C1-C3 alkyl; wherein R³³, when present, is selected from —NH₂, —OH, —(C=O)OR³⁰, —(C=O)NR³⁴ᵃR³⁴ᵇ, —(C=O)—(C1-C3 alkyl)-OR³⁰, —(C=O)—(C1-C3 alkyl)-NR³⁴ᵃR³⁴ᵇ, and Cy³; wherein each of R³⁴ᵃ and R³⁴ᵇ, when present, is independently selected from hydrogen and C1-C3 alkyl; wherein Cy³, when present, is selected from C2-C7 heterocycloalkyl substituted with 0, 1, 2, or 3 groups selected from halogen, —NH₂, —OH, and methyl; or wherein R³ and R⁴ are optionally covalently bonded, and together with the intermediate carbon, oxygen, and/or nitrogen, comprise a 3- to 10-membered heterocycle substituted with 0, 1, 2, or 3 groups independently selected from halogen, —NH₂, —OH, —C1-C3 alkylamino, C1-C3 dialkylamino, C1-C6 hydroxyalkyl, —(C=O)OR³⁰, —(C=O)NR³²ᵃR³²ᵇ, —(C1-C3 alkyl)-(C=O)OR³⁰, —(C1-C3 alkyl)-(C=O)NR³²ᵃR³²ᵇ, —(C1-C3 alkyl)-R³³, and —C(NR³²ᵃR³²ᵇ)R³¹—(C1-C3 alkyl)-R³³; wherein each of R⁵ᵃ, R⁵ᵇ, and R⁵ᶜ is independently selected from hydrogen, halogen, difluoromethoxy, and trifluoromethoxy; and wherein each of R⁷⁰ᵃ and R⁷⁰ᵇ is independently selected from hydrogen, methyl, and ethyl; wherein Ar¹ is selected from aryl and heteroaryl; and wherein Ar¹ is substituted with 0, 1, 2, or 3 groups independently selected from halogen, —NH₂, —OH, —NO₂, difluoromethoxy, trifluoromethoxy, C1-C6 alkyl, C1-C6 monohaloalkyl, C1-C6 alkoxy, C1-C6 alkylamino, C1-C6 dialkylamino, —S(O)ₙR⁴⁰, —S(O)ₙNR⁴¹ᵃR⁴¹ᵇ, —(C=O)NR⁴²ᵃR⁴²ᵇ, —NR⁴³(C=O)NR⁴⁴ᵃR⁴⁴ᵇ, —NR⁴³(C=O)R⁴⁵, —(C=O)OR⁴⁶, and Ar²; wherein each n is an integer independently selected from 0, 1, and 2; wherein each occurrence of R⁴⁰, when present, is independently selected from hydrogen, C1-C6 alkyl, phenyl, benzyl, naphthyl, and monocyclic heteroaryl; wherein each occurrence of R⁴¹ᵃ and R⁴¹ᵇ, when present, is independently selected from hydrogen, C1-C6 alkyl, phenyl, benzyl, naphthyl, and monocyclic heteroaryl; wherein each occurrence of R⁴², when present, is independently selected from hydrogen and C1-C6 alkyl; wherein each occurrence of R⁴³, when present, is independently selected from hydrogen and C1-C6 alkyl; wherein each occurrence of R⁴⁴ᵃ and R⁴⁴ᵇ, when present, is independently selected from hydrogen and C1-C6 alkyl; wherein each occurrence of R⁴⁵, when present, is independently selected from hydrogen and C1-C6 alkyl; wherein each occurrence of R⁴⁶, when present, is independently selected from hydrogen and C1-C6 alkyl; wherein each Ar², when present, is independently selected from phenyl, naphthyl, and heteroaryl, and wherein each Ar² is independently substituted with 0, 1, 2, or 3 groups independently selected from halogen, —NH₂, —OH, —CN, C1-C6 alkyl, C1-C6 monohaloalkyl, C1-C6 polyhaloalkyl, C1-C6 alkoxy, C1-C6 alkylamino, and C1-C6 dialkylamino; or a pharmaceutically acceptable salt thereof.

In a further aspect, each j is an integer independently selected from 0 and 1. In a still further aspect, each j is an integer independently selected from 1 and 2. In a yet further aspect, each j is an integer independently selected from 0 and 2. In an even further aspect, each j is an integer with a value of 0. In a still further aspect, each j is an integer with a value of 1. In a yet further aspect, each j is an integer with a value of 2.

In a further aspect, each m is an integer independently selected from 0 and 1. In a still further aspect, each m is an integer independently selected from 1 and 2. In a yet further aspect, each m is an integer independently selected from 0 and 2. In an even further aspect, each m is an integer with a value of 0. In a still further aspect, each m is an integer with a value of 1. In a yet further aspect, each m is an integer with a value of 2.

In a further aspect, each n is an integer independently selected from 0 and 1. In a still further aspect, each n is an integer independently selected from 1 and 2. In a yet further aspect, each n is an integer independently selected from 0 and 2. In an even further aspect, each n is an integer with a value of 0. In a still further aspect, each n is an integer with a value of 1. In a yet further aspect, each n is an integer with a value of 2.

In a further aspect, each q is an integer independently selected from 0 and 1. In a still further aspect, each q is an integer with a value of 0. In a still further aspect, each q is an integer with a value of 1.

In a further aspect, the compound has a structure represented by a formula listed below:

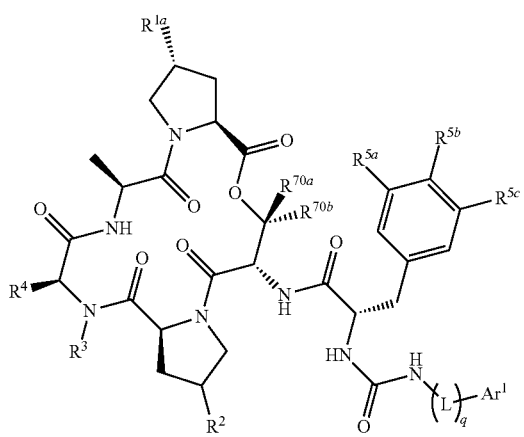

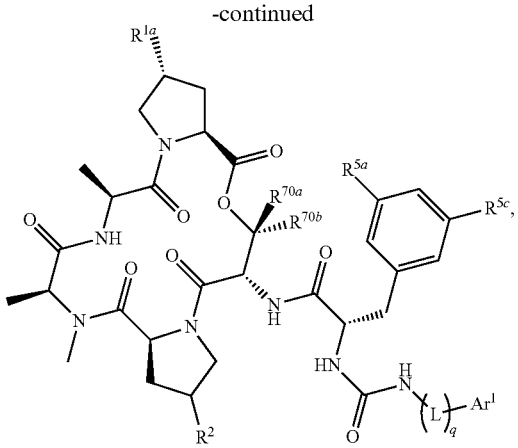

and wherein all variables are as defined herein.

In a further aspect, the compound has a structure represented by a formula listed below:

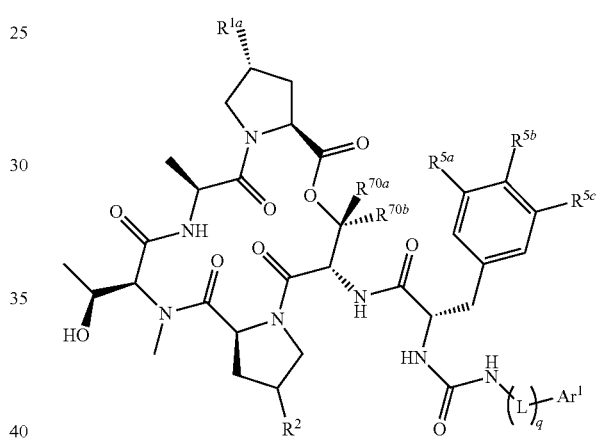

or

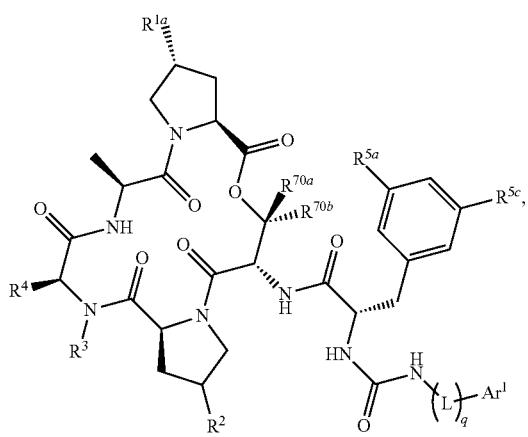

and wherein all variables are as defined herein.

In a further aspect, the compound has a structure represented by a formula listed below:

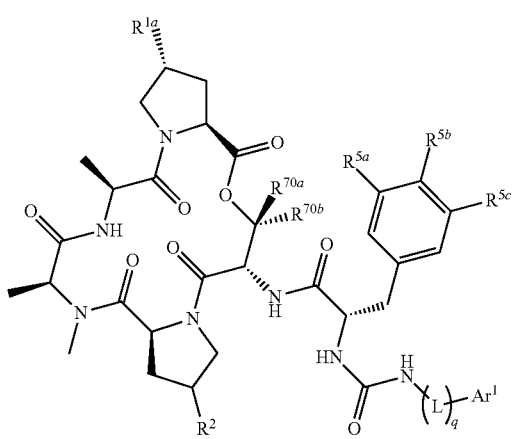

or

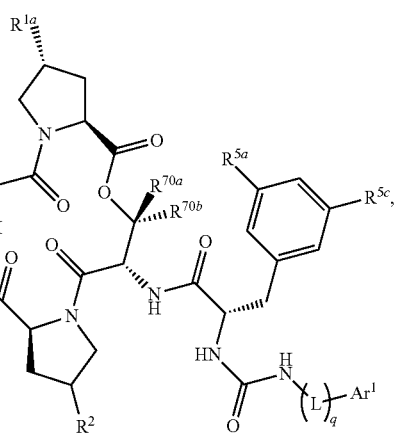

and wherein all variables are as defined herein.

In a further aspect, the compound has a structure represented by a formula listed below:

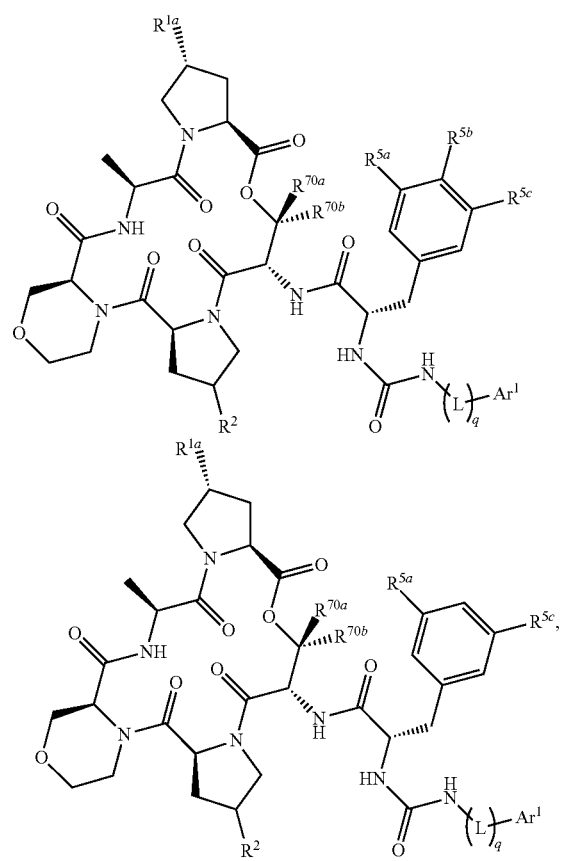

and wherein all variables are as defined herein.

In a further aspect, the compound has a structure represented by a formula listed below:

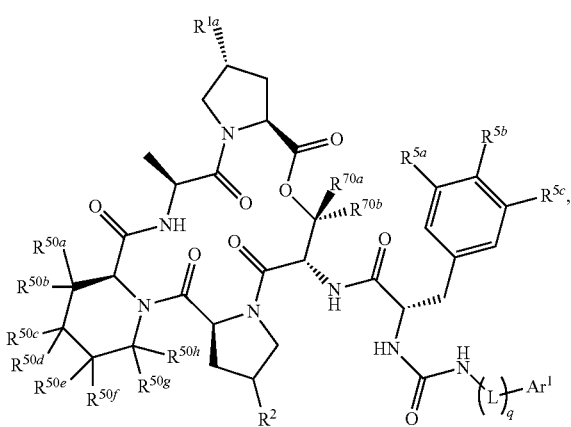

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —C(NR$^{32a}$R$^{32b}$)R$^{31}$—(C1-C3 alkyl)-R$^{33}$, and —(C1-C3 alkyl)-R$^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen; and wherein all variables are as defined herein.

In a further aspect, the compound has a structure represented by a formula listed below:

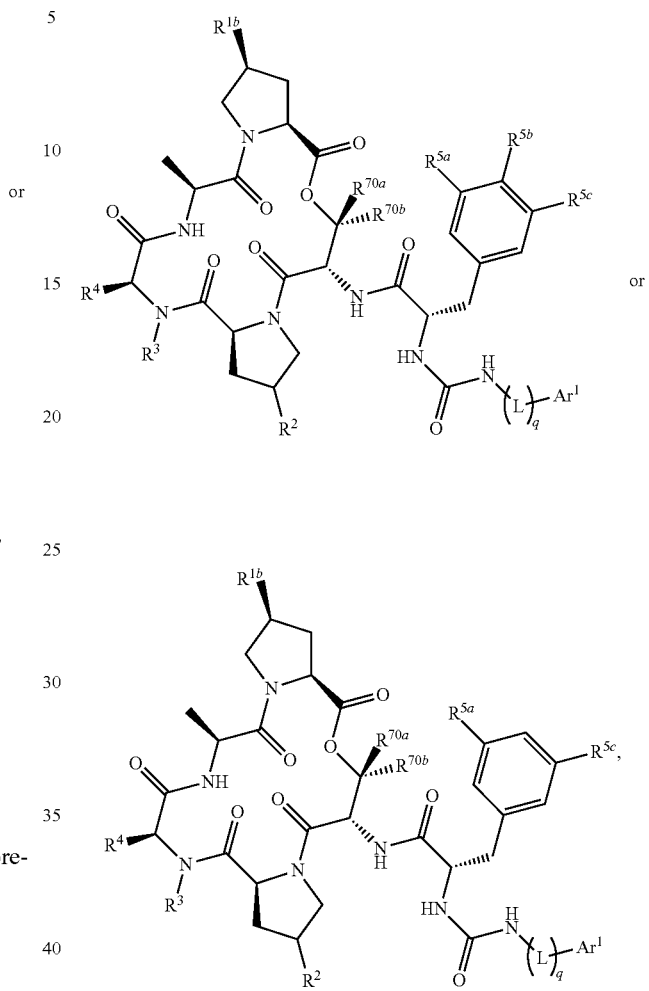

and wherein all variables are as defined herein.

In a further aspect, the compound has a structure represented by a formula listed below:

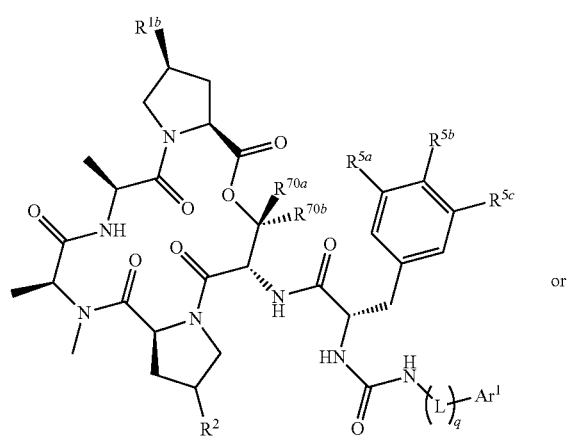

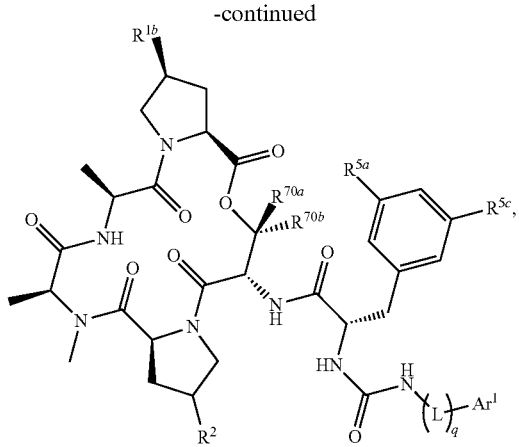

and wherein all variables are as defined herein.

In a further aspect, the compound has a structure represented by a formula listed below:

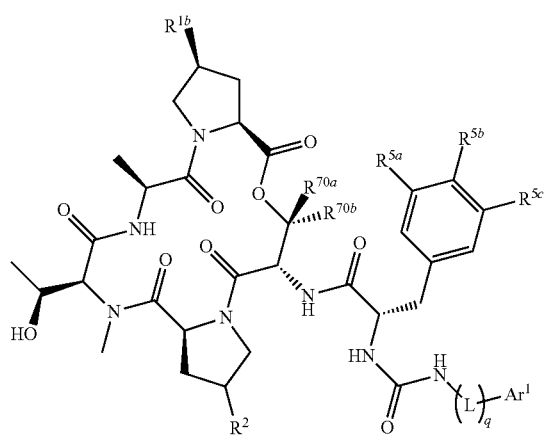

or

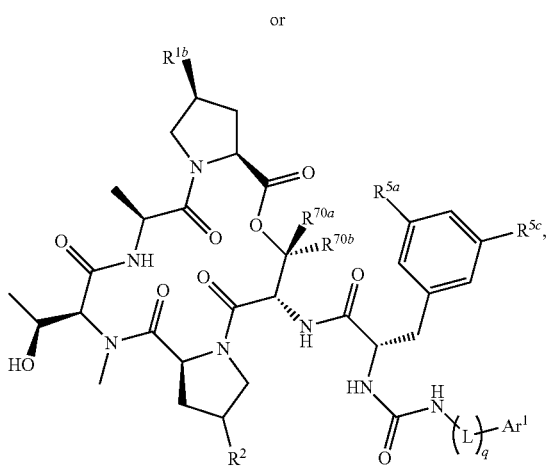

and wherein all variables are as defined herein.

In a further aspect, the compound has a structure represented by a formula listed below:

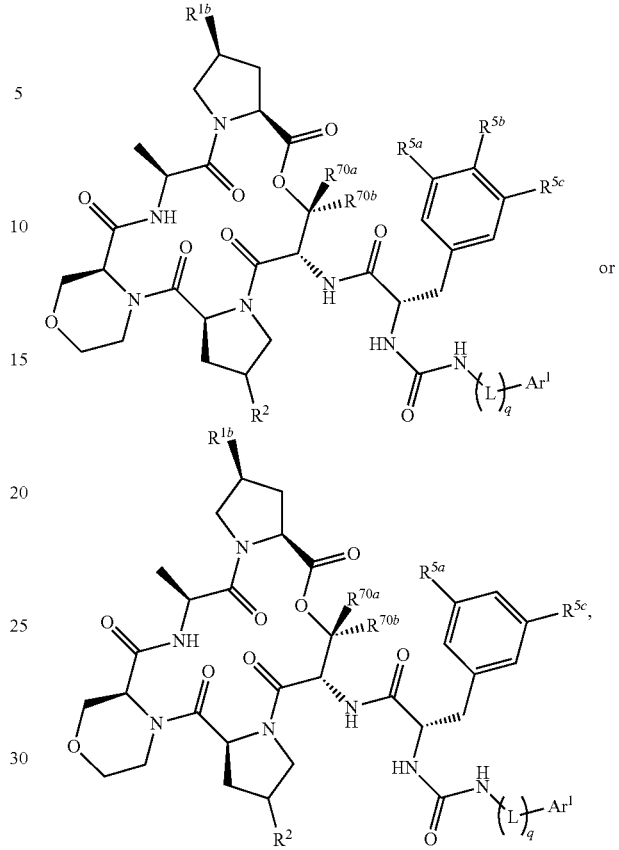

or and wherein all variables are as defined herein.

In a further aspect, the compound has a structure represented by a formula listed below:

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —C(NR$^{32a}$R$^{32b}$)R$^{31}$—(C1-C3 alkyl)-R$^{33}$, and —(C1-C3 alkyl)-R$^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen; and wherein all variables are as defined herein.

In a further aspect, the compound has a structure represented by a formula listed below:

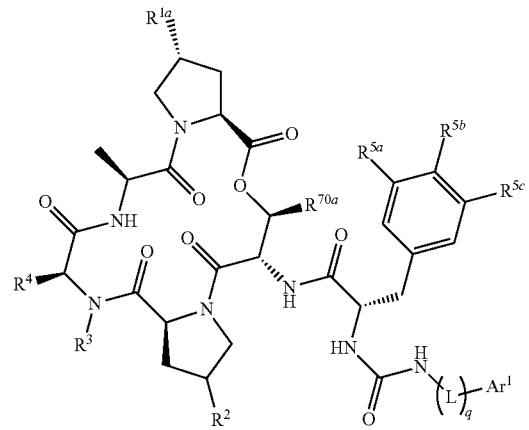

or

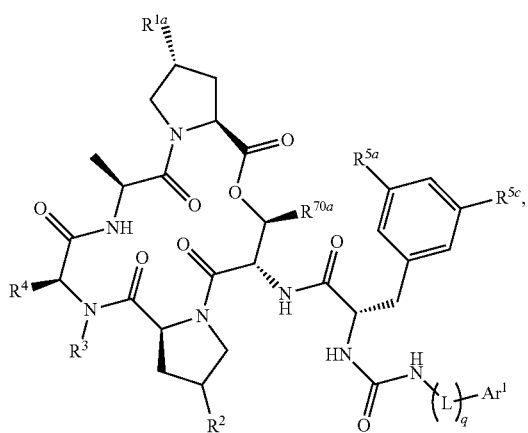

and wherein all variables are as defined herein.

In a further aspect, the compound has a structure represented by a formula listed below:

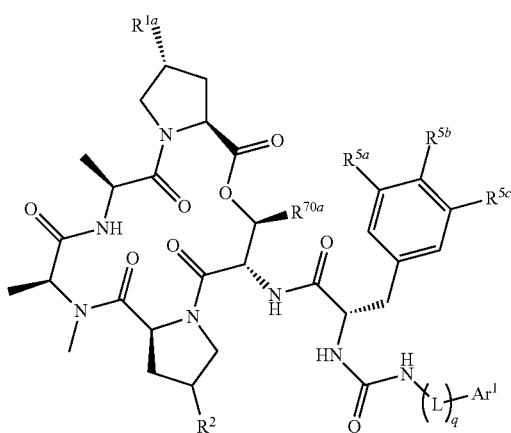

or

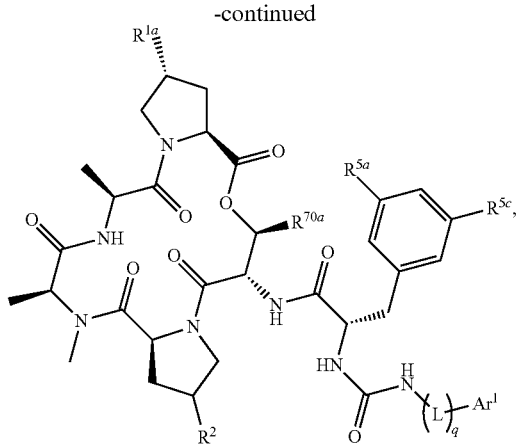

and wherein all variables are as defined herein.

In a further aspect, the compound has a structure represented by a formula listed below:

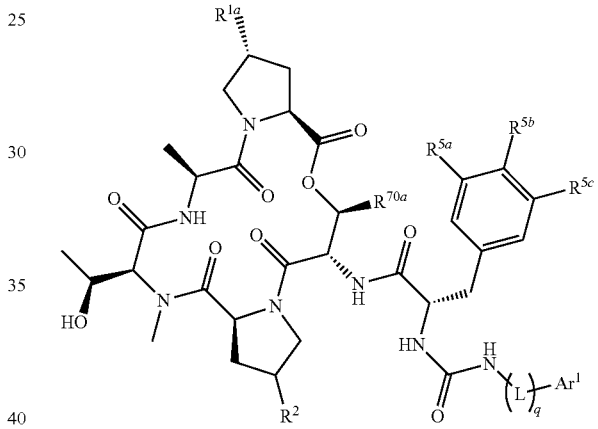

or

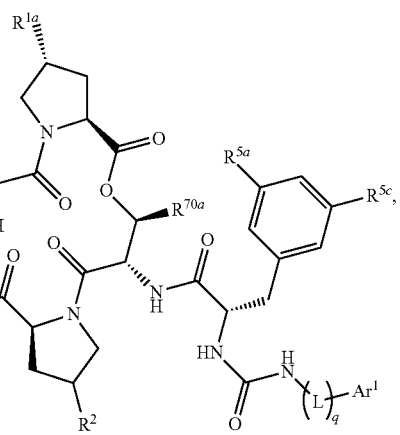

and wherein all variables are as defined herein.

In a further aspect, the compound has a structure represented by a formula listed below:

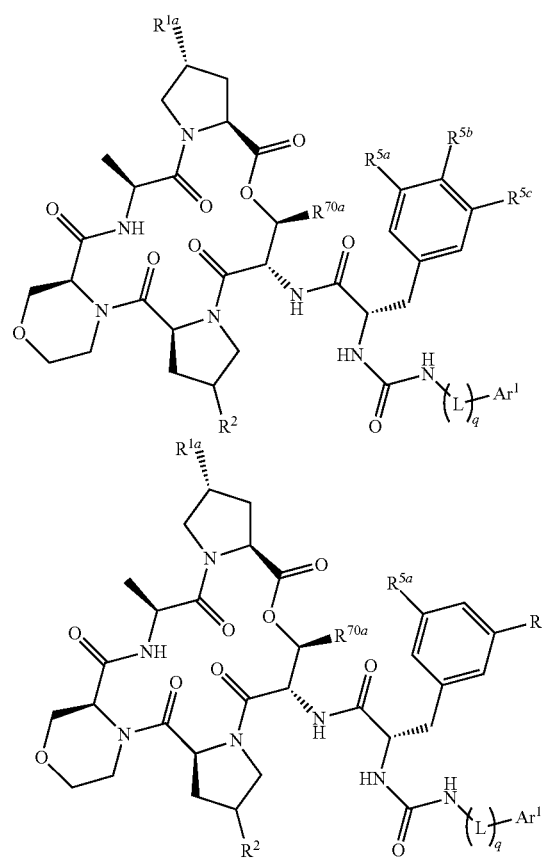

and wherein all variables are as defined herein.

In a further aspect, the compound has a structure represented by a formula listed below:

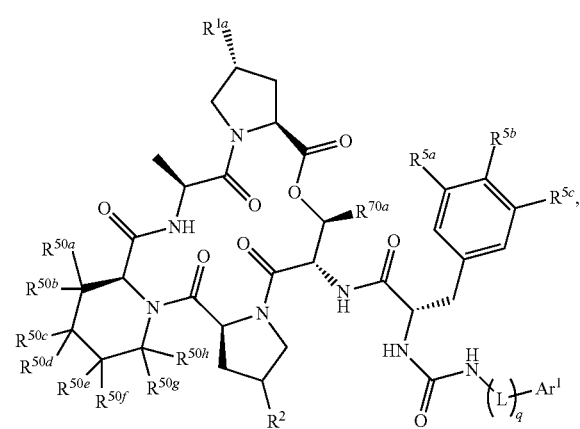

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —$NH_2$, —OH, —C1-C3 alkylamino, C1-C3 dialkylamino, C1-C6 hydroxyalkyl, —(C=O)$OR^{30}$, —(C=O)$NR^{32a}R^{32b}$, —(C1-C3 alkyl)-(C=O)$OR^{30}$, —(C1-C3 alkyl)-(C=O)$NR^{32a}R^{32b}$, —$C(NR^{32a}R^{32b})R^{31}$—(C1-C3 alkyl)-$R^{33}$, and —(C1-C3 alkyl)-$R^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen; and wherein all variables are as defined herein.

In a further aspect, the compound has a structure represented by a formula listed below:

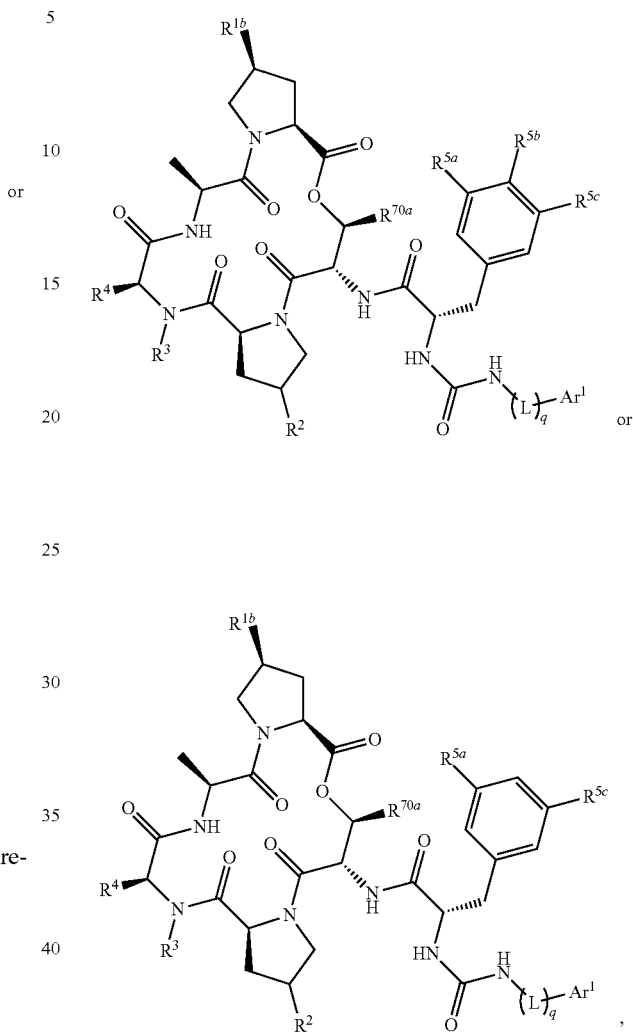

and wherein all variables are as defined herein.

In a further aspect, the compound has a structure represented by a formula listed below:

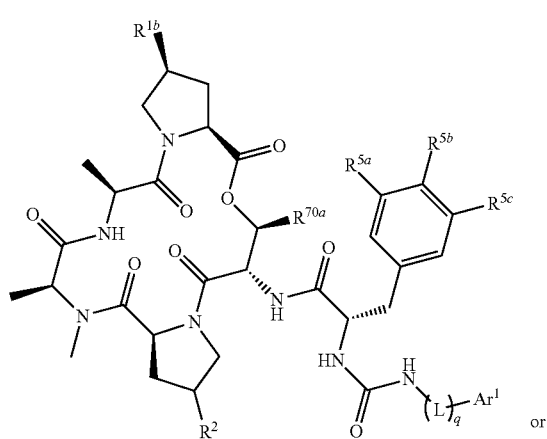

or

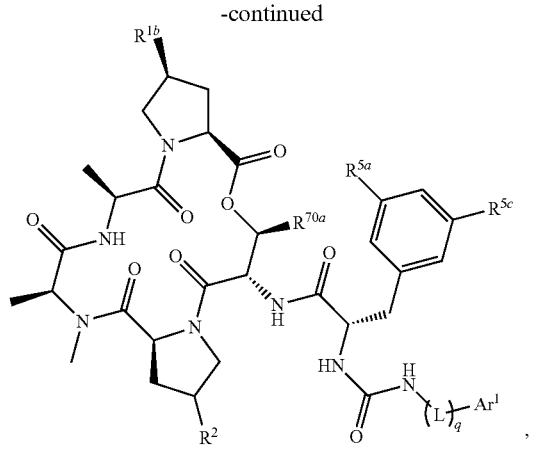

and wherein all variables are as defined herein.

In a further aspect, the compound has a structure represented by a formula listed below:

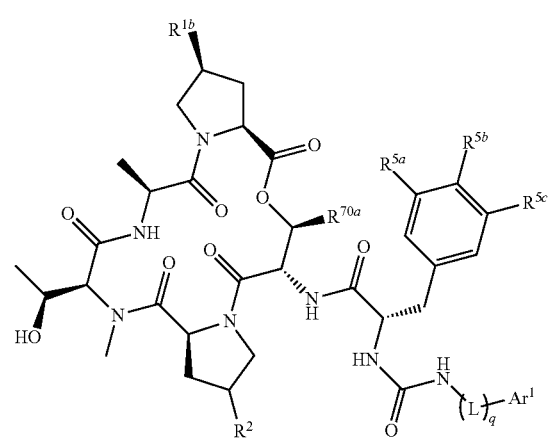

or and wherein all variables are as defined herein.

In a further aspect, the compound has a structure represented by a formula listed below:

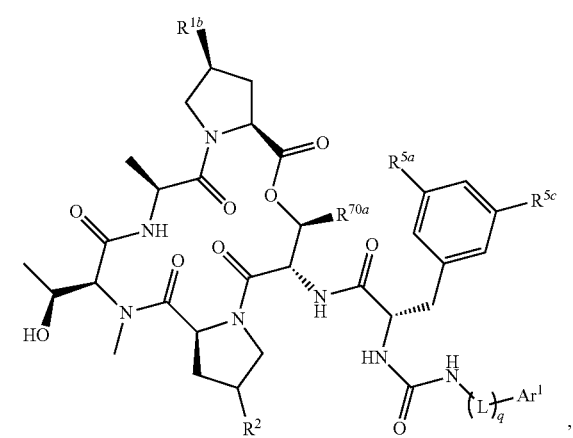

and wherein all variables are as defined herein.

In a further aspect, the compound has a structure represented by a formula listed below:

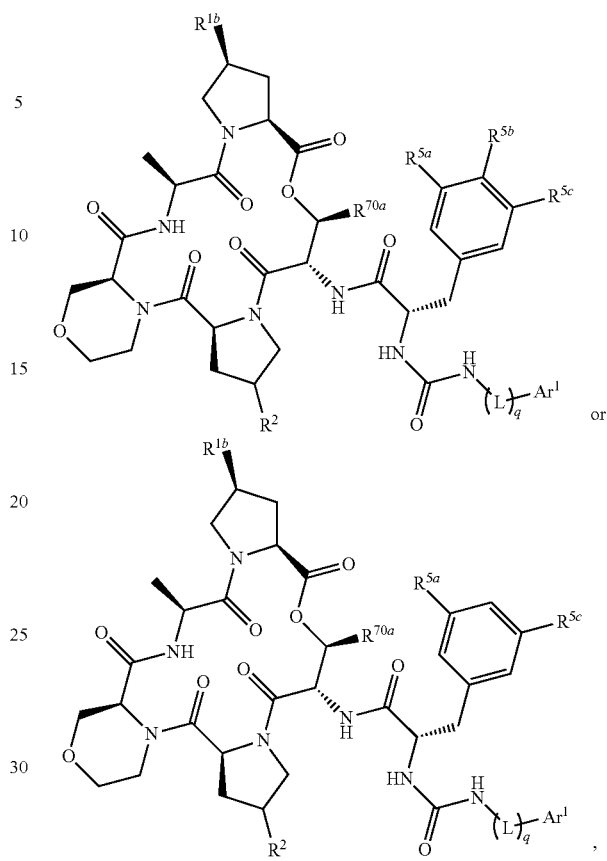

or and wherein all variables are as defined herein.

In a further aspect, the compound has a structure represented by a formula listed below:

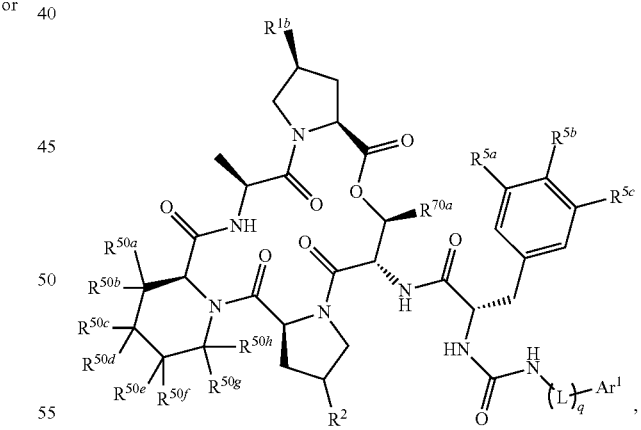

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —C(NR$^{32a}$R$^{32b}$)R$^{31}$— (C1-C3 alkyl)-R$^{33}$, and —(C1-C3 alkyl)-R$^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen; and wherein all variables are as defined herein.

In a further aspect, the compound has a structure represented by a formula listed below:

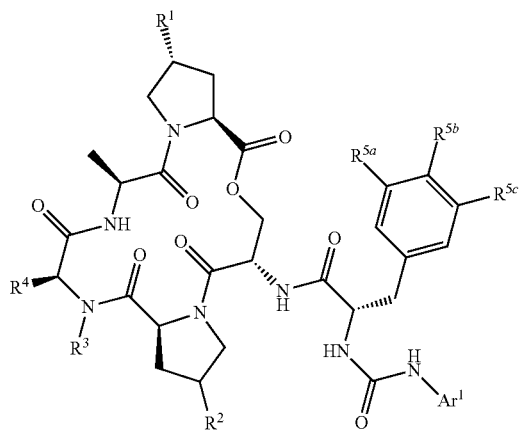

or

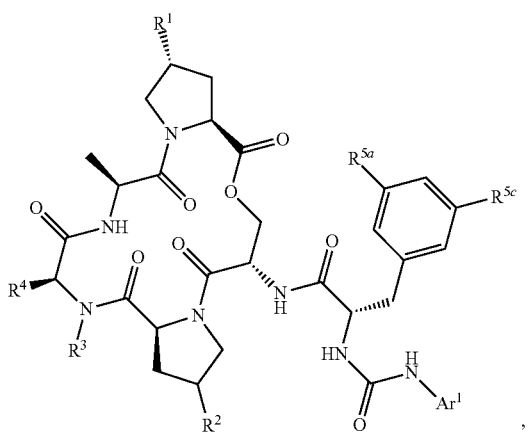

and wherein all variables are as defined herein.

In a further aspect, the compound has a structure represented by a formula listed below:

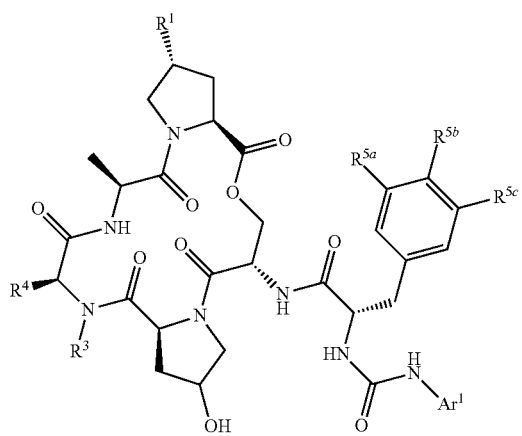

or

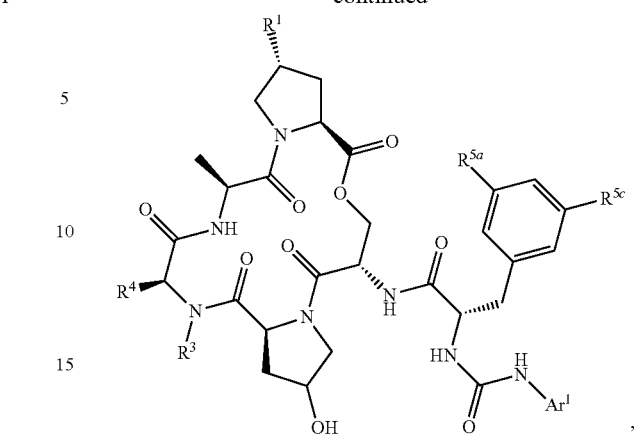

and wherein all variables are as defined herein.

In a further aspect, the compound has a structure represented by a formula listed below:

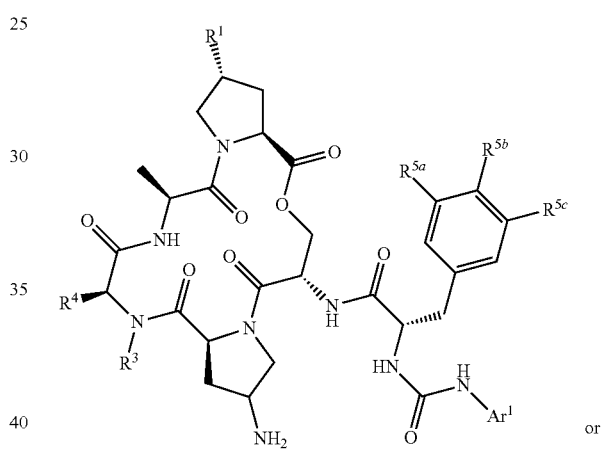

or

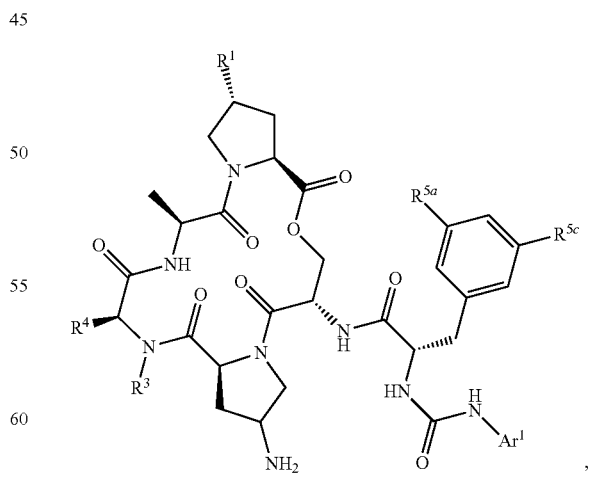

and wherein all variables are as defined herein.

In a further aspect, the compound has a structure represented by a formula listed below:

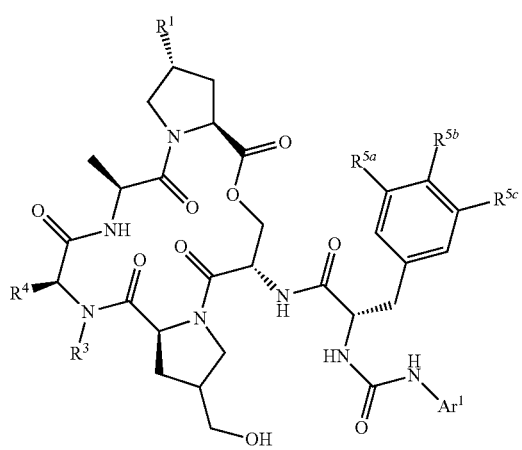

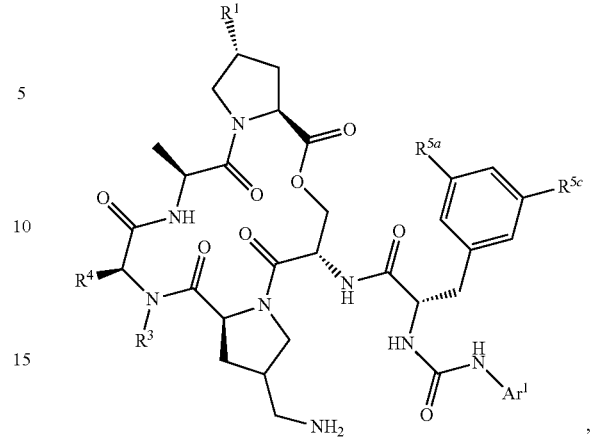

and wherein all variables are as defined herein.

In a further aspect, the compound has a structure represented by a formula listed below:

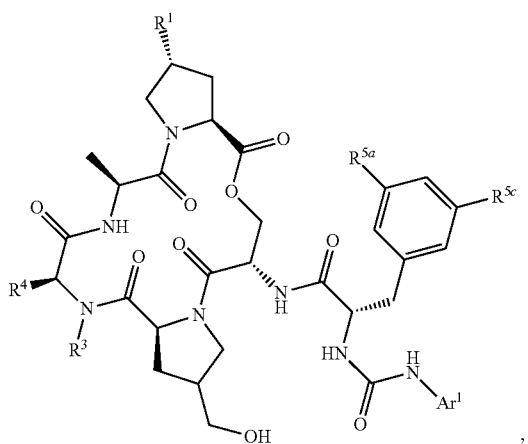

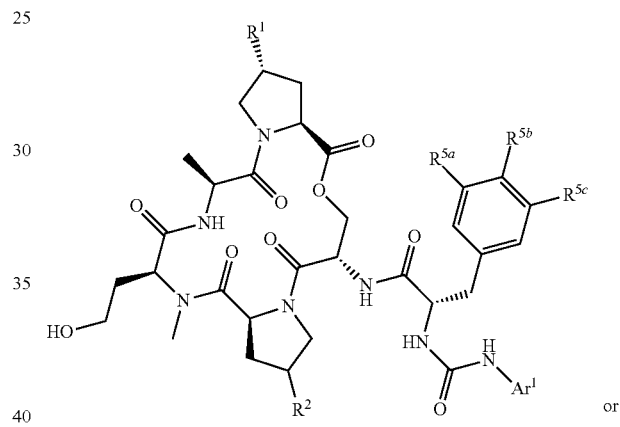

and wherein all variables are as defined herein.

In a further aspect, the compound has a structure represented by a formula listed below:

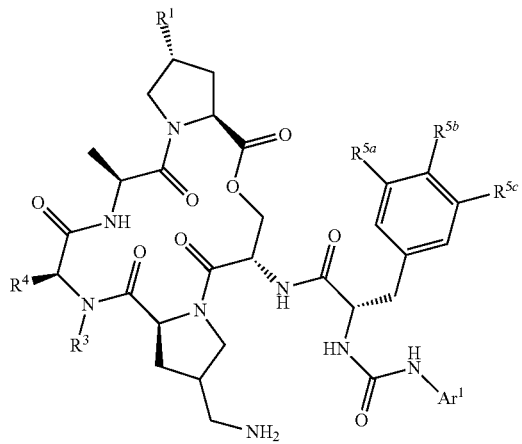

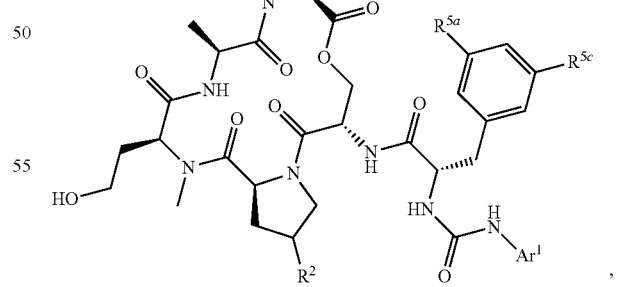

and wherein all variables are as defined herein.

In a further aspect, the compound has a structure represented by a formula listed below:

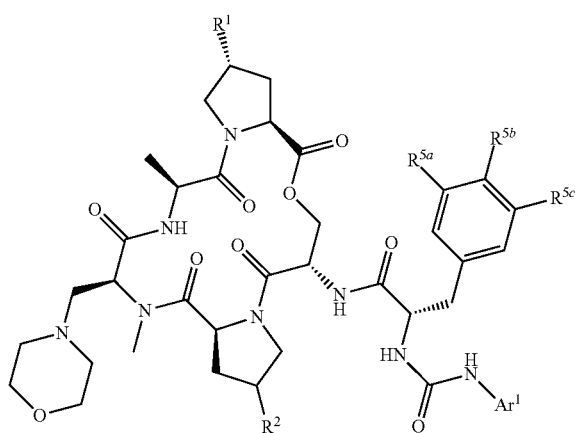

or

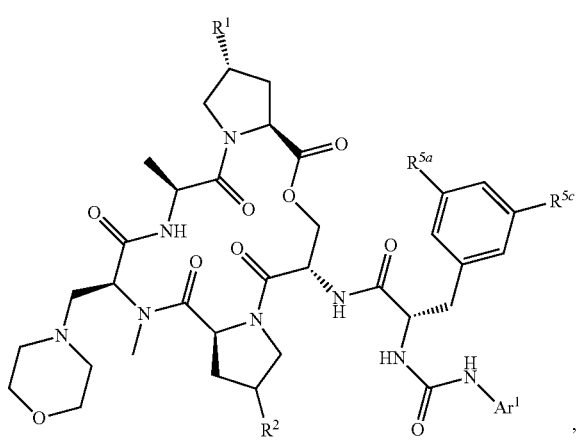

and wherein all variables are as defined herein.

In a further aspect, the compound has a structure represented by a formula listed below:

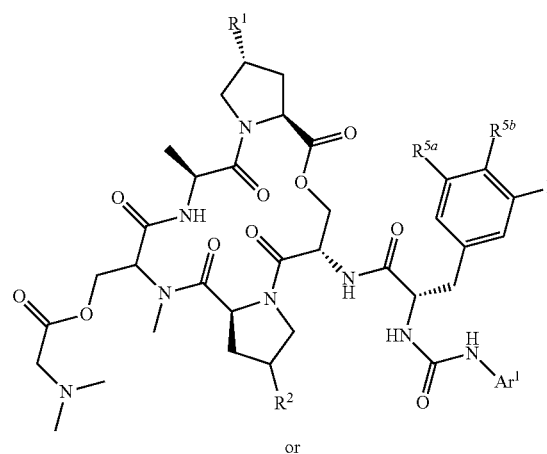

or

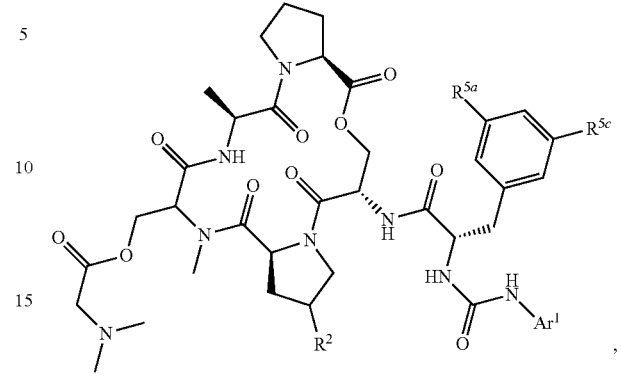

and wherein all variables are as defined herein.

In a further aspect, the compound has a structure represented by a formula listed below:

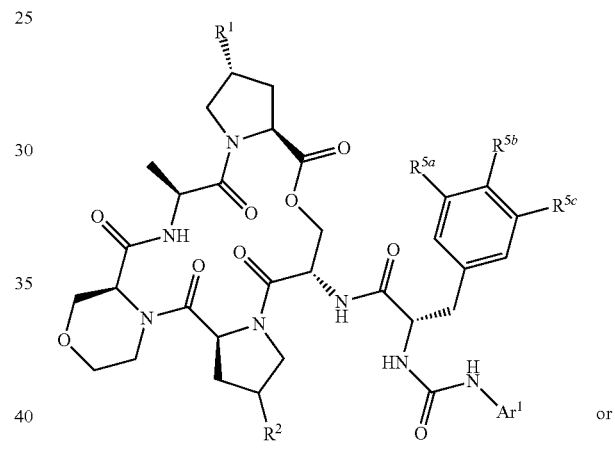

or

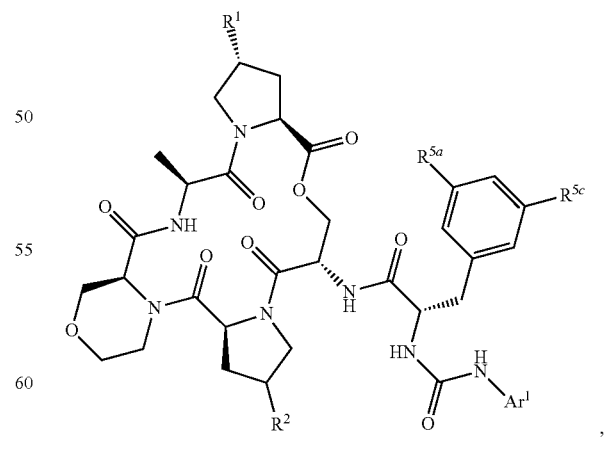

and wherein all variables are as defined herein.

In a further aspect, the compound has a structure represented by a formula listed below:

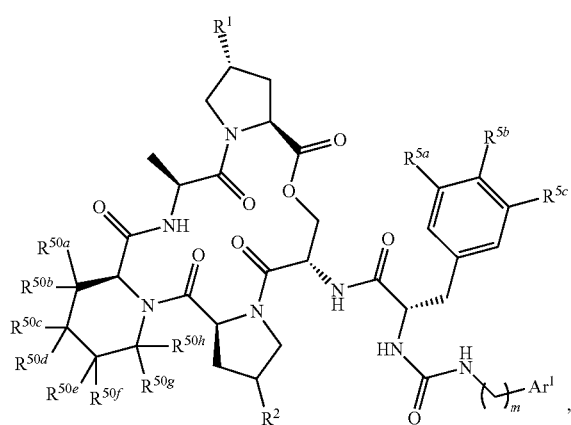

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —C(NR$^{32a}$R$^{32b}$)R$^{31}$—(C1-C3 alkyl)-R$^{33}$, and —(C1-C3 alkyl)-R$^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen; and wherein all variables are as defined herein.

In a further aspect, the compound has a structure represented by a formula listed below:

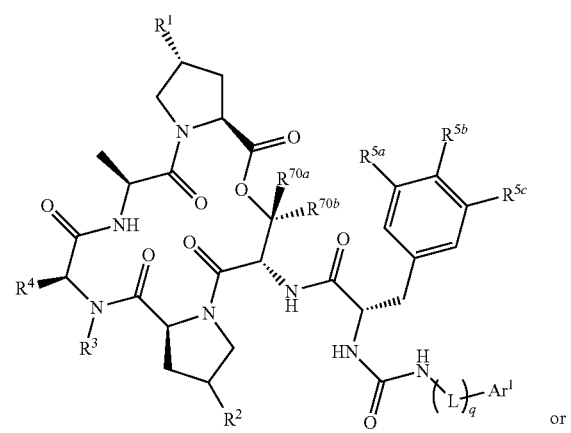

and wherein all variables are as defined herein.

In a further aspect, the compound has a structure represented by a formula listed below:

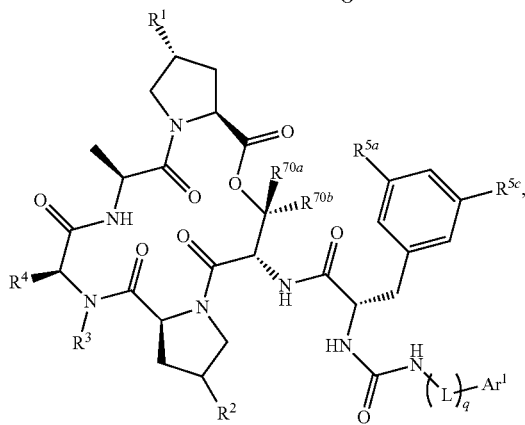

In a further aspect, the compound has a structure represented by a formula listed below:

[structure]

or

[structure]

and wherein all variables are as defined herein.

In a further aspect, the compound has a structure represented by a formula listed below:

[structure]

or

-continued

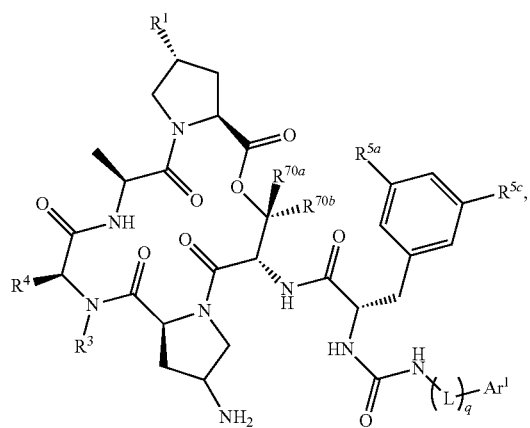

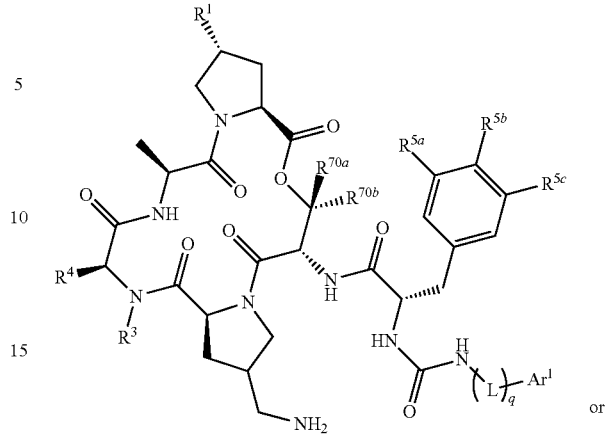

and wherein all variables are as defined herein.

In a further aspect, the compound has a structure represented by a formula listed below:

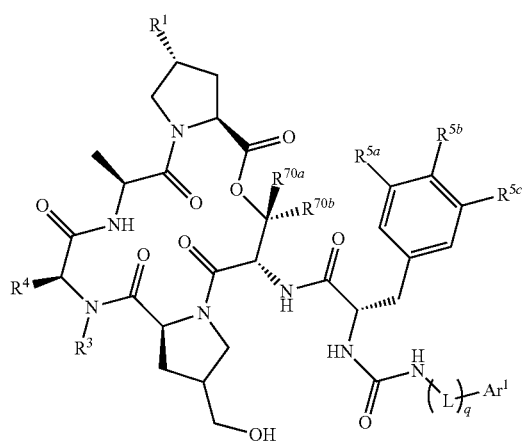

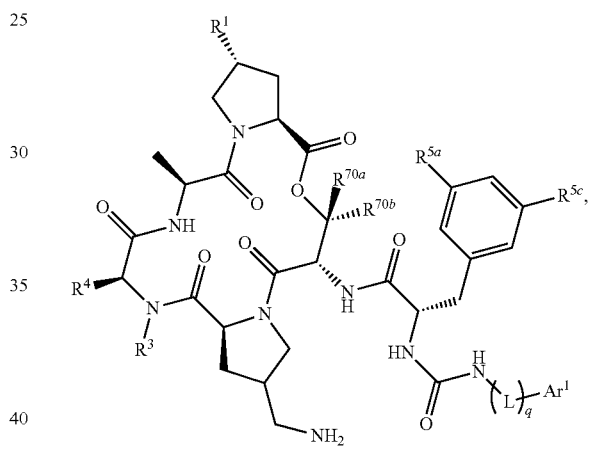

and wherein all variables are as defined herein.

In a further aspect, the compound has a structure represented by a formula listed below:

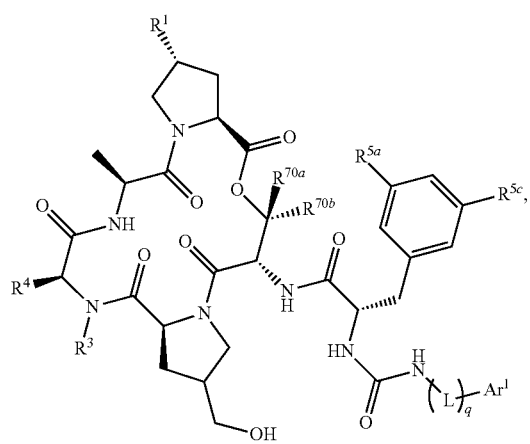

and wherein all variables are as defined herein.

In a further aspect, the compound has a structure represented by a formula listed below:

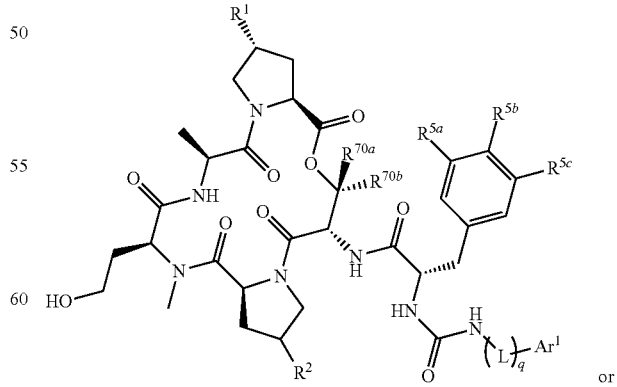

-continued

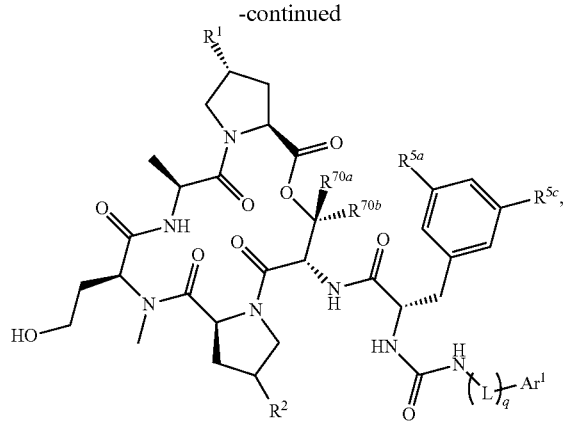

and wherein all variables are as defined herein.

In a further aspect, the compound has a structure represented by a formula listed below:

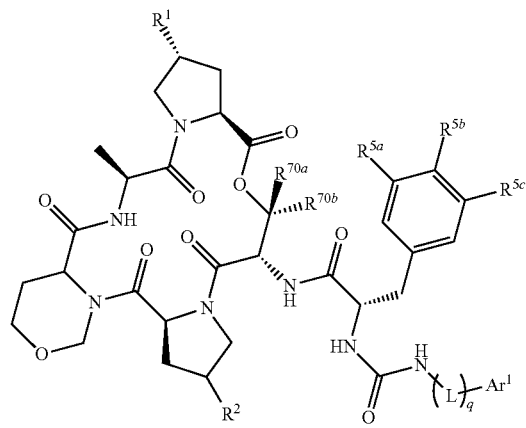

or and wherein all variables are as defined herein.

In a further aspect, the compound has a structure represented by a formula listed below:

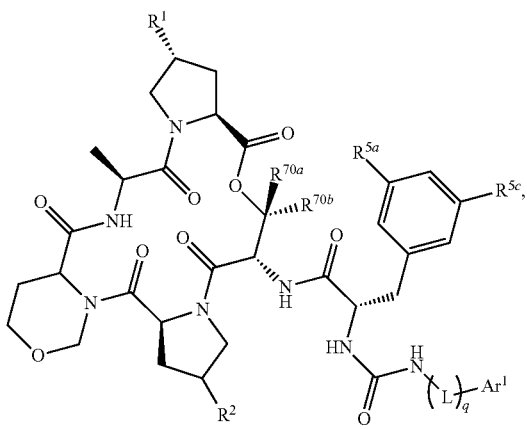

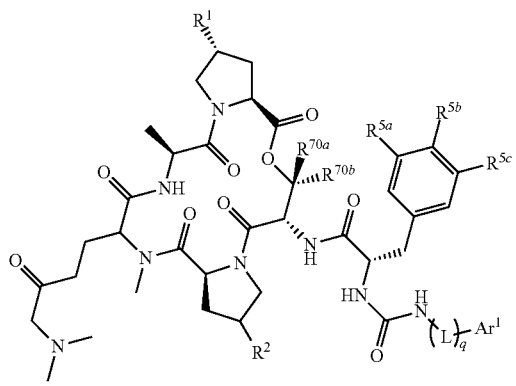

or and wherein all variables are as defined herein.

In a further aspect, the compound has a structure represented by a formula listed below:

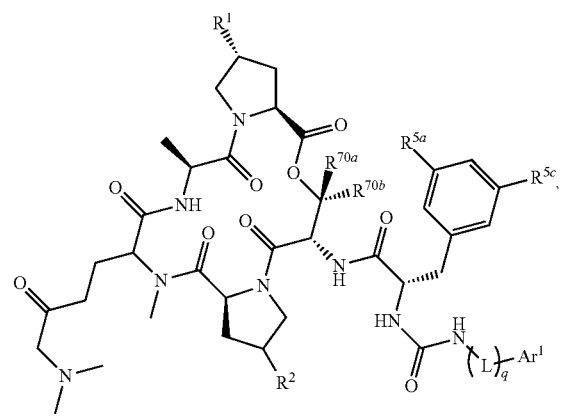

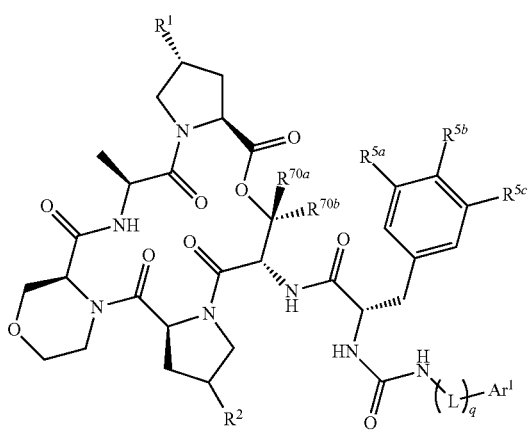

or

-continued

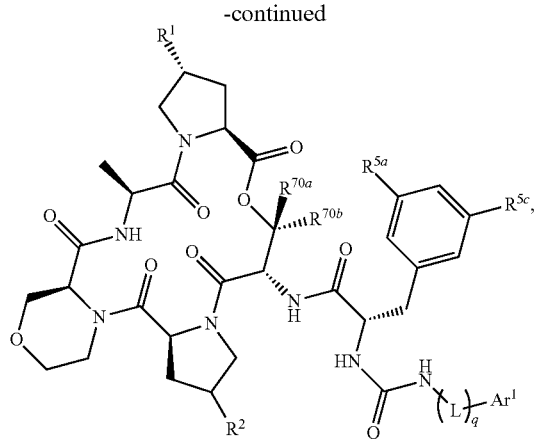

and wherein all variables are as defined herein.

In a further aspect, the compound has a structure represented by a formula listed below:

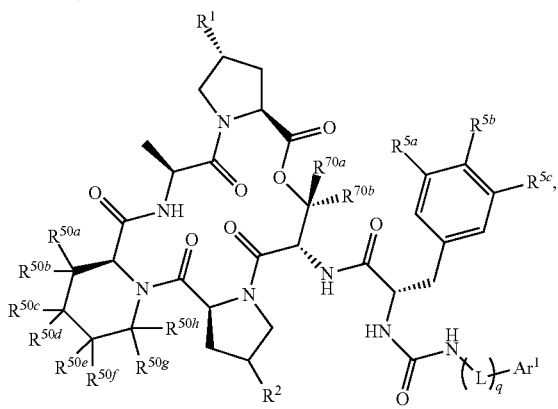

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —C(NR$^{32a}$R$^{32b}$)R$^{31}$— (C1-C3 alkyl)-R$^{33}$, and —(C1-C3 alkyl)-R$^{33}$, provided that no more than three of R$^{50a}$, R$^{50b}$, R$^{50c}$, R$^{50d}$, R$^{50e}$, R$^{50f}$, R$^{50g}$, and R$^{50h}$ are not hydrogen; and wherein all variables are as defined herein.

In a further aspect, the compound has a structure represented by a formula listed below:

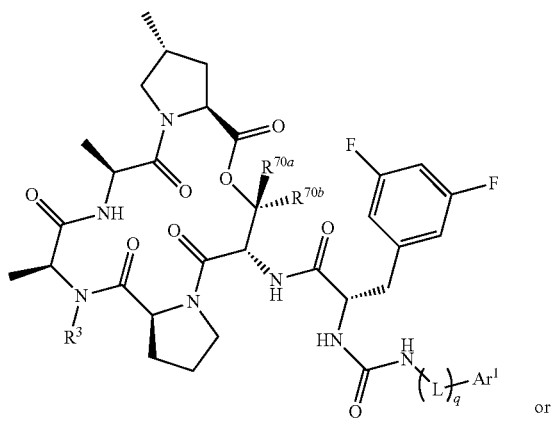

or

-continued

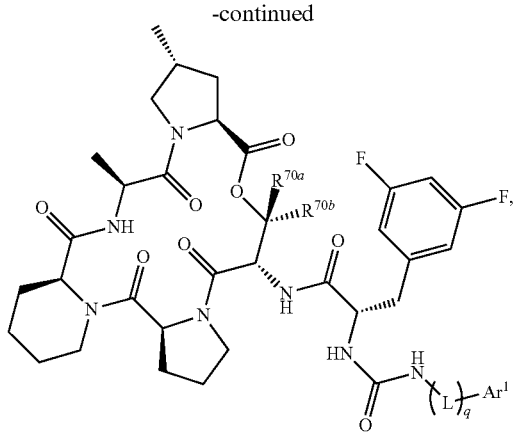

and wherein all variables are as defined herein.

In a further aspect, the compound has a structure represented by a formula listed below:

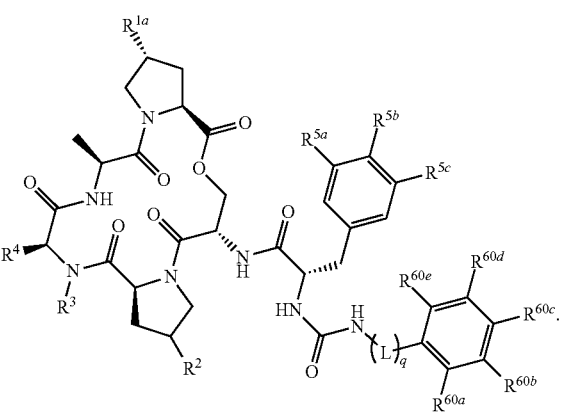

wherein each of R$^{60a}$, R$^{60b}$, R$^{60c}$, R$^{60d}$, and R$^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O) NR$^{44a}$R$^{44b}$, —NR$^{43}$(C=O)R$^{45}$, —(C=O)OR$^{46}$, and Ar$^2$, provided that no more than three of R$^{60a}$, R$^{60b}$, R$^{60c}$, R$^{60d}$, and R$^{60e}$ are not hydrogen; and wherein all variables are as defined herein.

In a further aspect, the compound has a structure represented by a formula listed below:

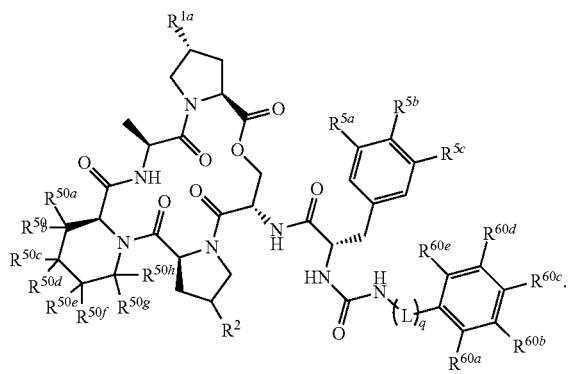

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —C(NR$^{32a}$R$^{32b}$)R$^{31}$—(C1-C3 alkyl)-R$^{33}$, and —(C1-C3 alkyl)-R$^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen; and wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

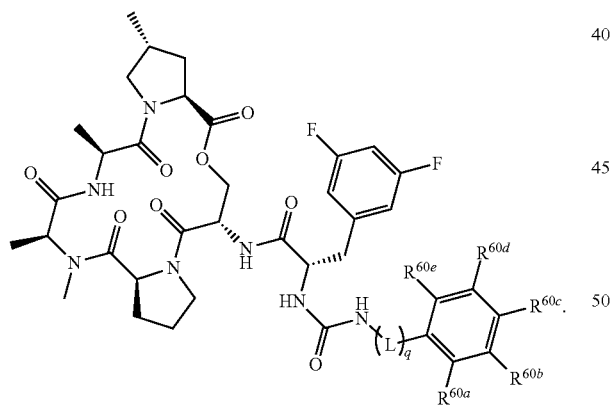

wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$, are not hydrogen; and wherein all variables are as defined herein.

In a further aspect, the compound has a structure represented by a formula listed below:

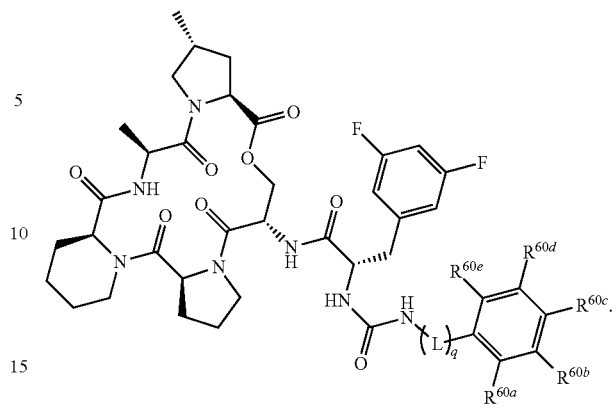

wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

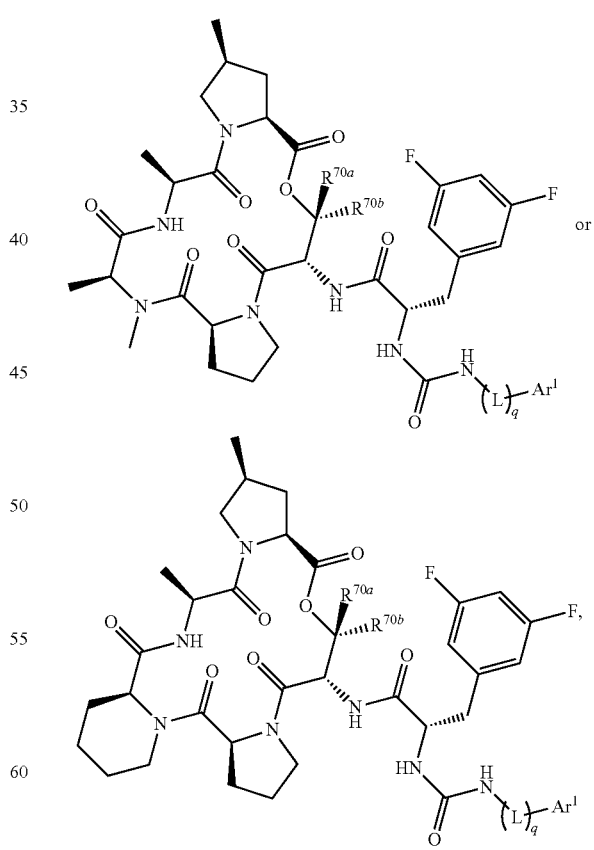

and wherein all variables are as defined herein.

In a further aspect, the compound has a structure represented by a formula listed below:

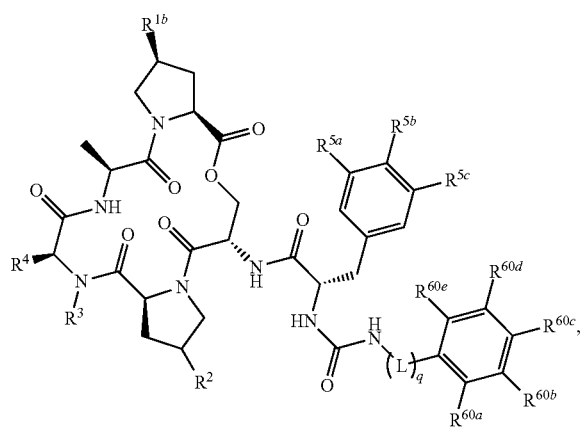

wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

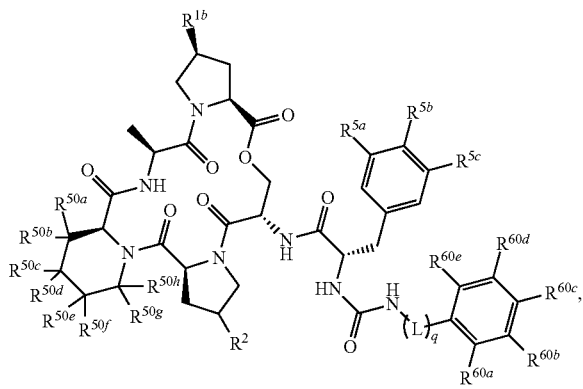

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —C(NR$^{32a}$R$^{32b}$)R$^{31}$—(C1-C3 alkyl)-R$^{33}$, and —(C1-C3 alkyl)-R$^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen; and wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)OR$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

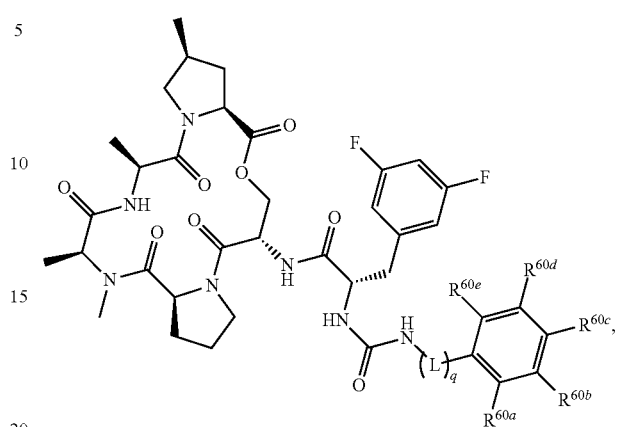

wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

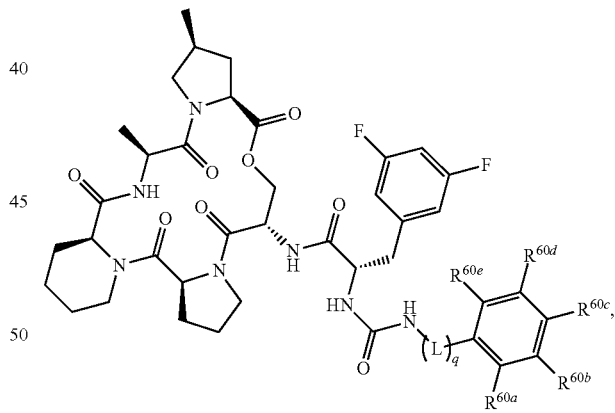

wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

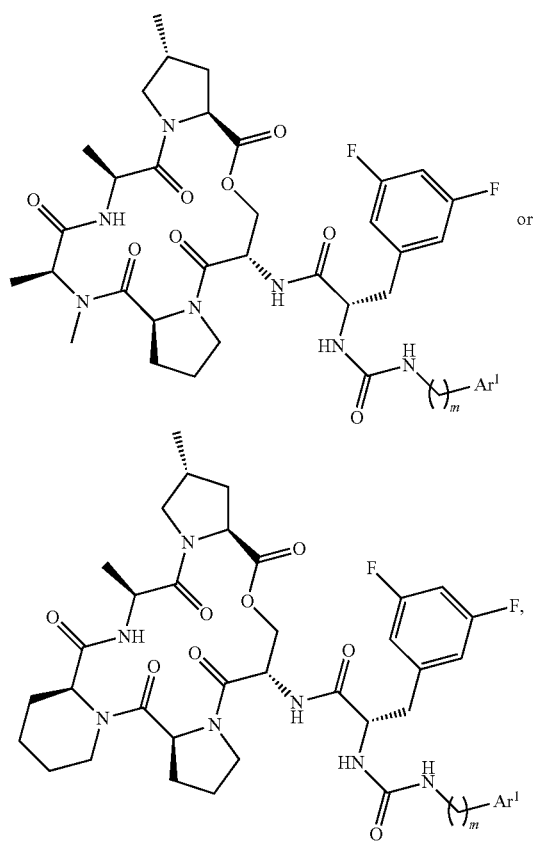

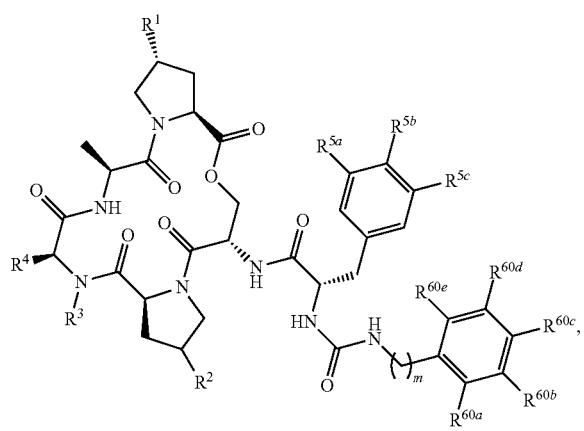

and wherein all variables are as defined herein.

In a further aspect, the compound has a structure represented by a formula listed below:

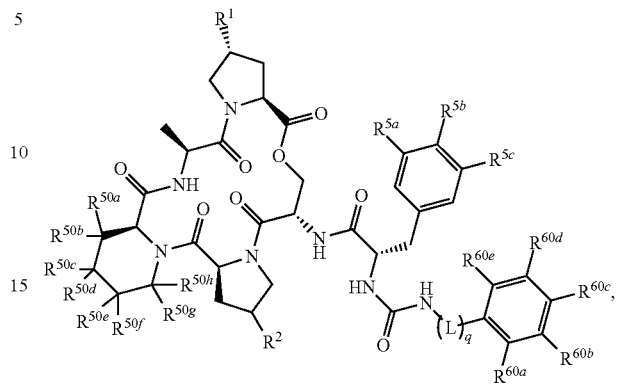

wherein each of $R^{60a}$, $R^{60b}$, $R^{60c}$, $R^{60d}$, and $R^{60e}$, when present, is independently selected from hydrogen, halogen, —$NH_2$, —OH, —$NO_2$, difluoromethoxy, trifluoromethoxy, C1-C6 alkyl, C1-C6 monohaloalkyl, C1-C6 alkoxy, C1-C6 alkylamino, C1-C6 dialkylamino, —$S(O)_nR^{40}$, —$S(O)_nNR^{41a}R^{41b}$, —(C=O)$NR^{42a}R^{42b}$, —$NR^{43}$(C=O)$NR^{44a}R^{44b}$, —$NR^{43}$(C=O)$R^{45}$, —(C=O)$OR^{46}$, and $Ar^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —$NH_2$, —OH, —C1-C3 alkylamino, C1-C3 dialkylamino, C1-C6 hydroxyalkyl, —(C=O)$OR^{30}$, —(C=O)$NR^{32a}R^{32b}$, —(C1-C3 alkyl)-(C=O)$OR^{30}$, —(C1-C3 alkyl)-(C=O)$NR^{32a}R^{32b}$, —C($NR^{32a}R^{32b}$)$R^{31}$—(C1-C3 alkyl)-$R^{33}$, and —(C1-C3 alkyl)-$R^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen; and wherein each of $R^{60a}$, $R^{60b}$, $R^{60c}$, $R^{60d}$, and $R^{60e}$, when present, is independently selected from hydrogen, halogen, —$NH_2$, —OH, —$NO_2$, difluoromethoxy, trifluoromethoxy, C1-C6 alkyl, C1-C6 monohaloalkyl, C1-C6 alkoxy, C1-C6 alkylamino, C1-C6 dialkylamino, —$S(O)_nR^{40}$, —$S(O)_nNR^{41a}R^{41b}$, —(C=O)$NR^{42a}R^{42b}$, —$NR^{43}$(C=O)$NR^{44a}R^{44b}$, —$NR^{43}$(C=O)$R^{45}$, —(C=O)$OR^{46}$, and $Ar^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

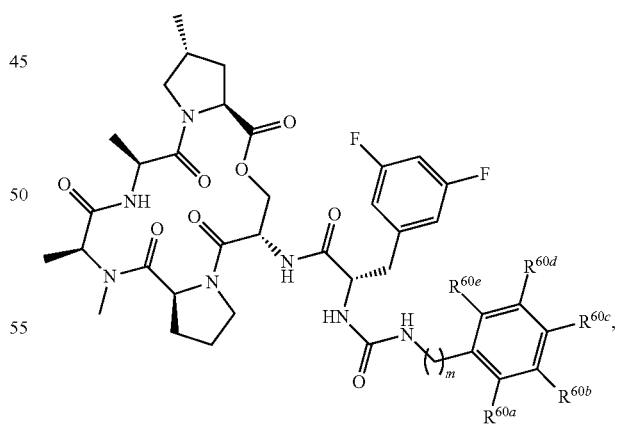

wherein each of $R^{60a}$, $R^{60b}$, $R^{60c}$, $R^{60d}$, and $R^{60e}$, when present, is independently selected from hydrogen, halogen, —$NH_2$, —OH, —$NO_2$, difluoromethoxy, trifluoromethoxy, C1-C6 alkyl, C1-C6 monohaloalkyl, C1-C6 alkoxy, C1-C6 alkylamino, C1-C6 dialkylamino, —$S(O)_nR^{40}$, —$S(O)_nNR^{41a}R^{41b}$, —(C=O)$NR^{42a}R^{42b}$, —$NR^{43}$(C=O)$NR^{44a}R^{44b}$, —$NR^{43}$(C=O)$R^{45}$, —(C=O)$OR^{46}$, and $Ar^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

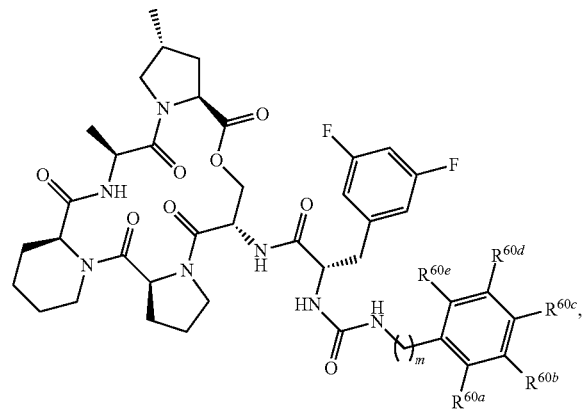

wherein each of $R^{60a}$, $R^{60b}$, $R^{60c}$, $R^{60d}$, and $R^{60e}$, when present, is independently selected from hydrogen, halogen, —$NH_2$, —OH, —$NO_2$, difluoromethoxy, trifluoromethoxy, C1-C6 alkyl, C1-C6 monohaloalkyl, C1-C6 alkoxy, C1-C6 alkylamino, C1-C6 dialkylamino, —$S(O)_nR^{40}$, —$S(O)_nNR^{41a}R^{41b}$, —$(C=O)NR^{42a}R^{42b}$, —$NR^{43}(C=O)NR^{44a}R^{44b}$, —$NR^{43}(C=O)R^{45}$, —$(C=O)OR^{46}$, and $Ar^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

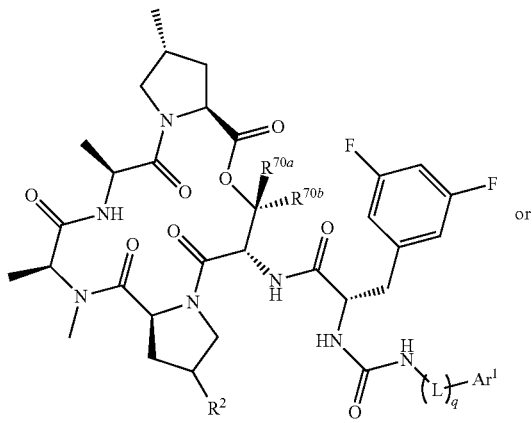 or

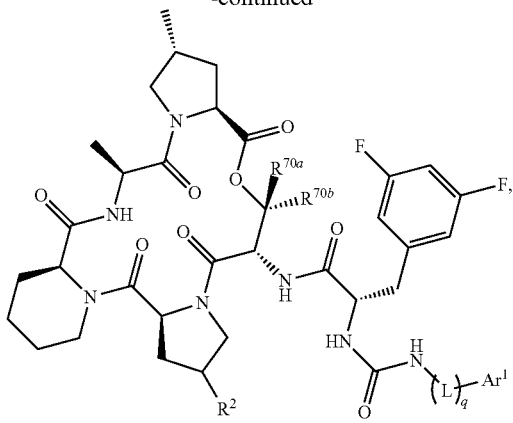

and wherein all variables are as defined herein.

In a further aspect, the compound has a structure represented by a formula listed below:

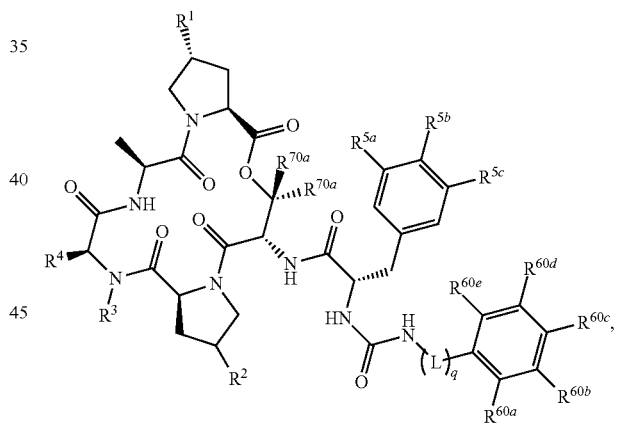

wherein each of $R^{60a}$, $R^{60b}$, $R^{60c}$, $R^{60d}$, and $R^{60e}$, when present, is independently selected from hydrogen, halogen, —$NH_2$, —OH, —$NO_2$, difluoromethoxy, trifluoromethoxy, C1-C6 alkyl, C1-C6 monohaloalkyl, C1-C6 alkoxy, C1-C6 alkylamino, C1-C6 dialkylamino, —$S(O)_nR^{40}$, —$S(O)_nNR^{41a}R^{41b}$, —$(C=O)NR^{42a}R^{42b}$, —$NR^{43}(C=O)NR^{44a}R^{44b}$, —$NR^{43}(C=O)R^{45}$, —$(C=O)OR^{46}$, and $Ar^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

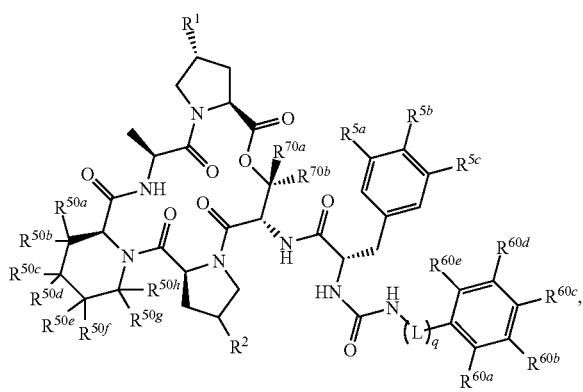

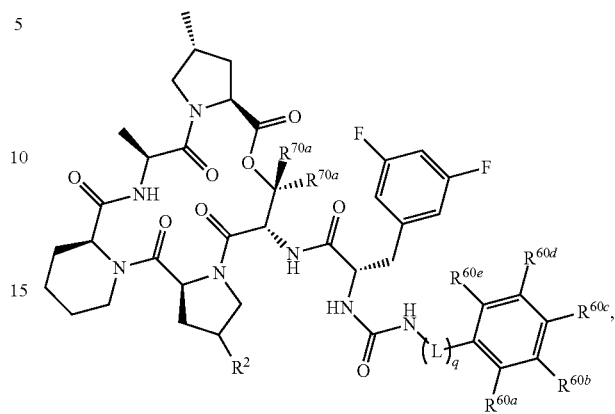

wherein each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —C(NR$^{32a}$R$^{32b}$)R$^{31}$—(C1-C3 alkyl)-R$^{33}$, and —(C1-C3 alkyl)-R$^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen; and wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

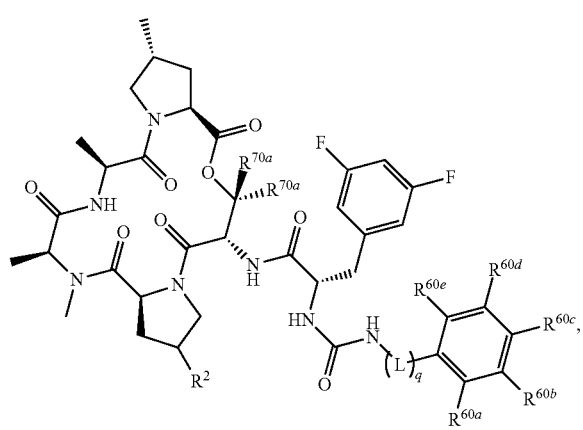

wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O) NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen; and wherein all variables are as defined herein.

wherein each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O) NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen; and wherein all variables are as defined herein.

In a further aspect, the compound has a structure represented by a formula listed below:

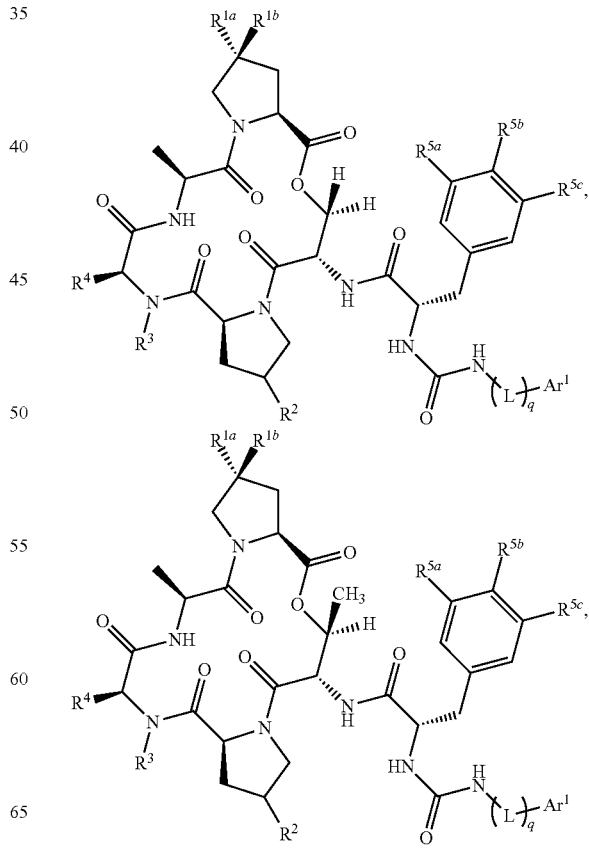

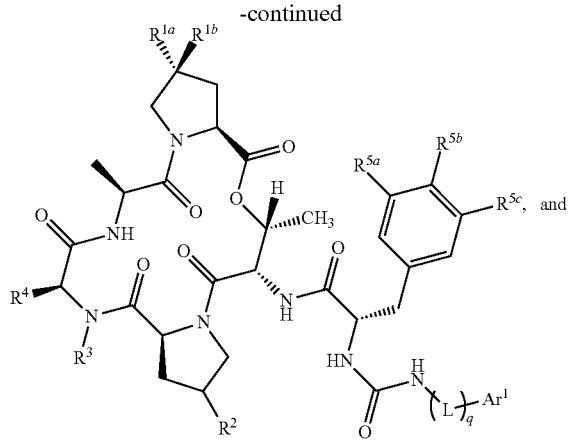
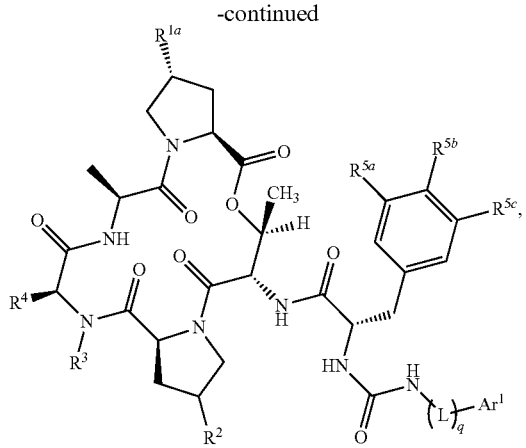
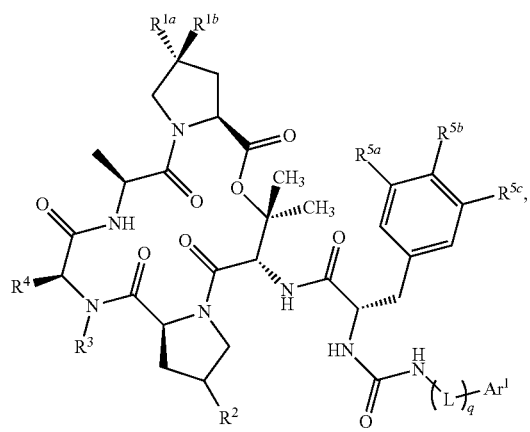
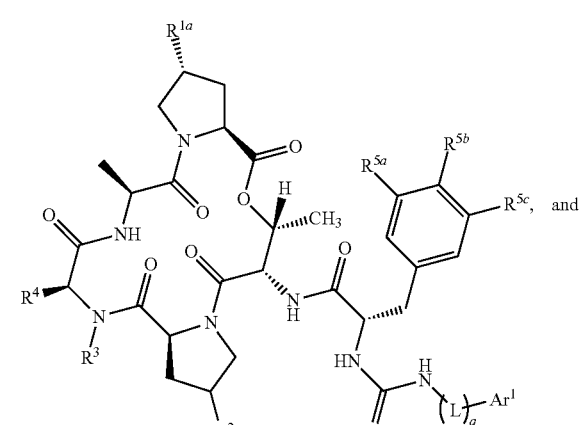
and wherein all variables are as defined herein.
In a further aspect, the compound has a structure represented by a formula listed below:
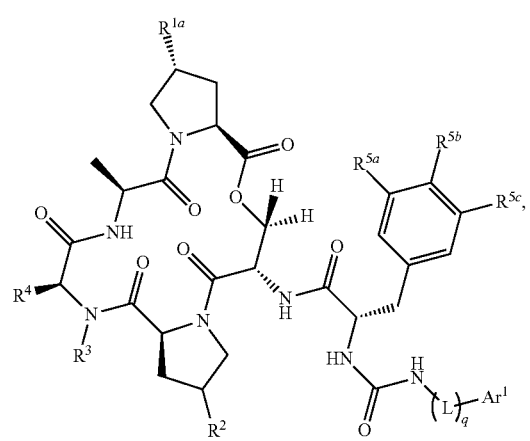
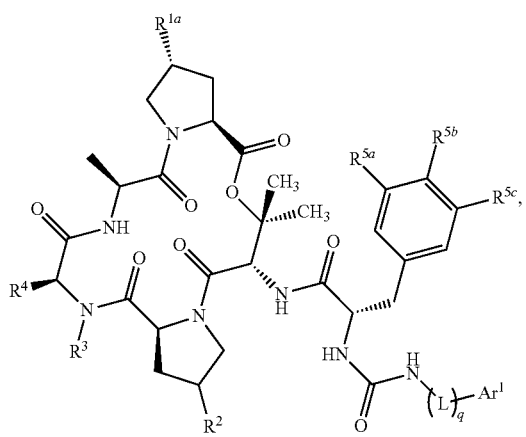
and wherein all variables are as defined herein.
In a further aspect, the compound has a structure represented by a formula listed below:

In a further aspect, the compound has a structure represented by a formula listed below:
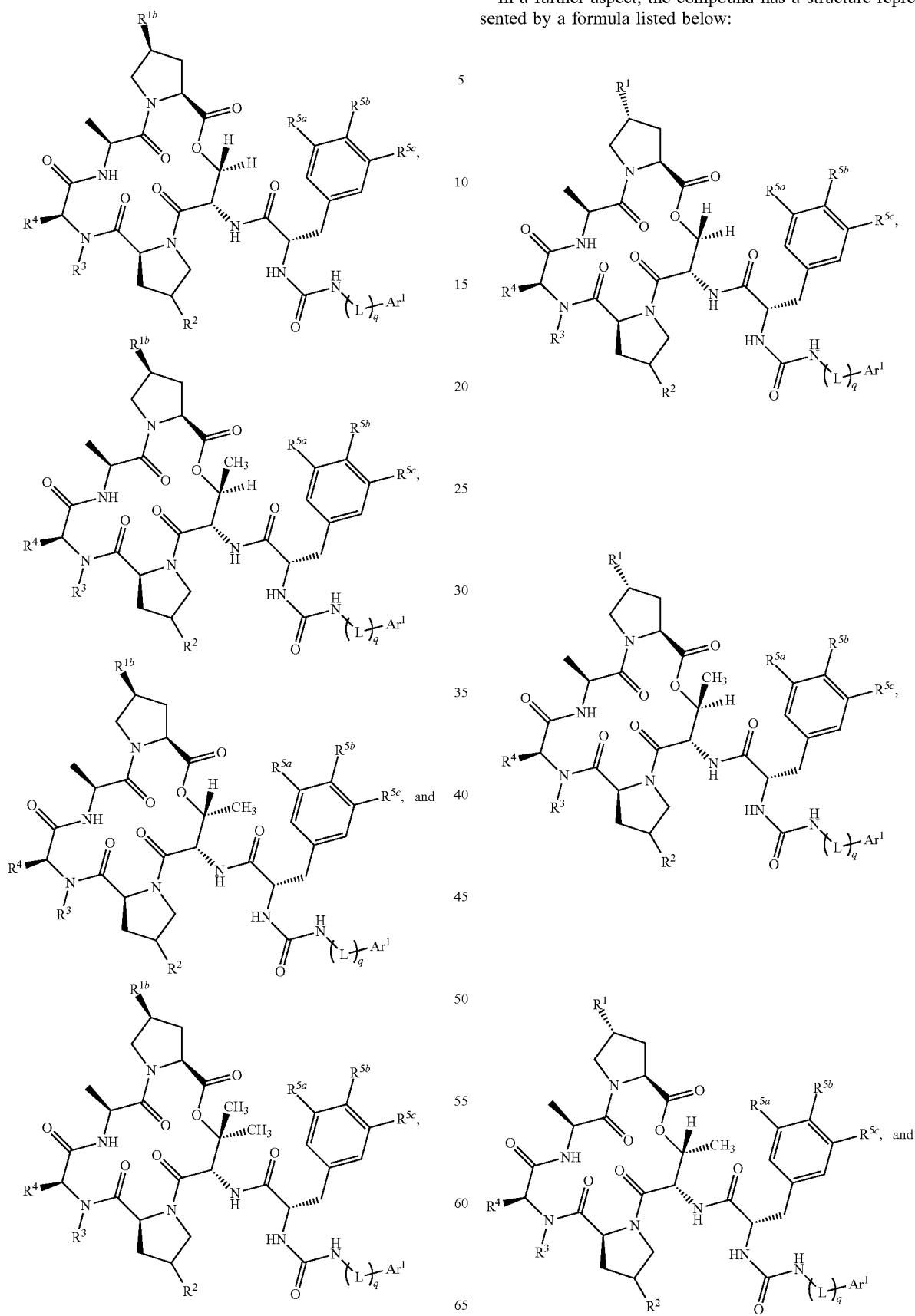
and wherein all variables are as defined herein.

-continued

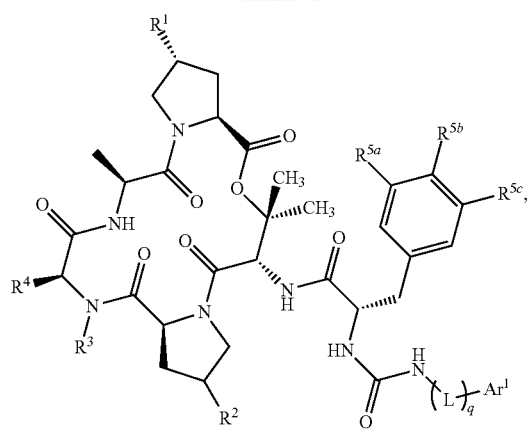

and wherein all variables are as defined herein.

In a further aspect, the compound has a structure represented by a formula listed below:

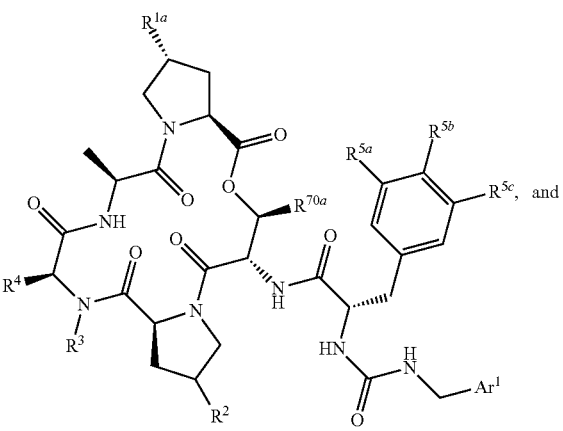

and wherein all variables are as defined herein.

In a further aspect, the compound has a structure represented by a formula listed below:

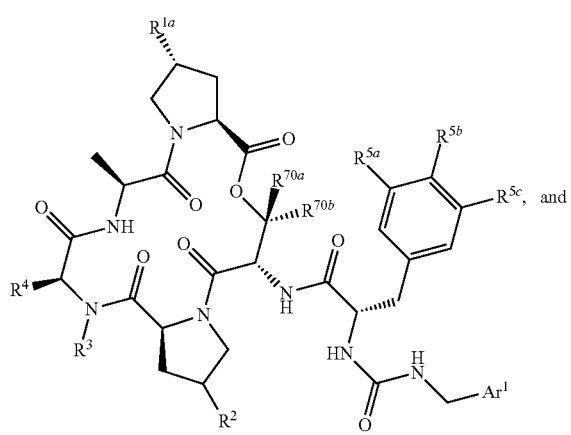

and wherein all variables are as defined herein.

In a further aspect, the compound has a structure represented by a formula listed below:

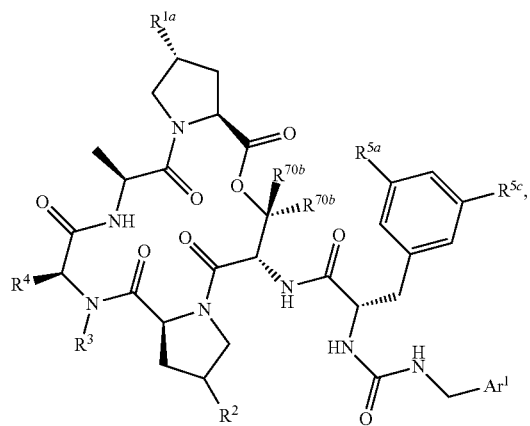

and wherein all variables are as defined herein.

In a further aspect, the compound has a structure represented by a formula listed below:

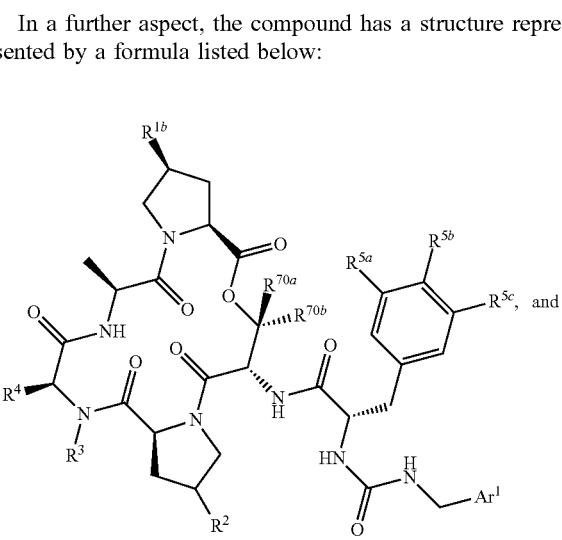

-continued

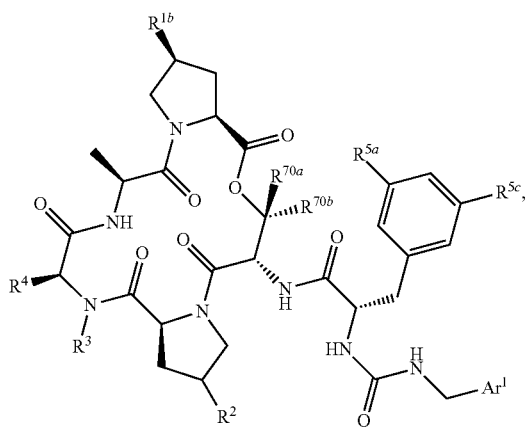

and wherein all variables are as defined herein.

In a further aspect, the compound has a structure represented by a formula listed below:

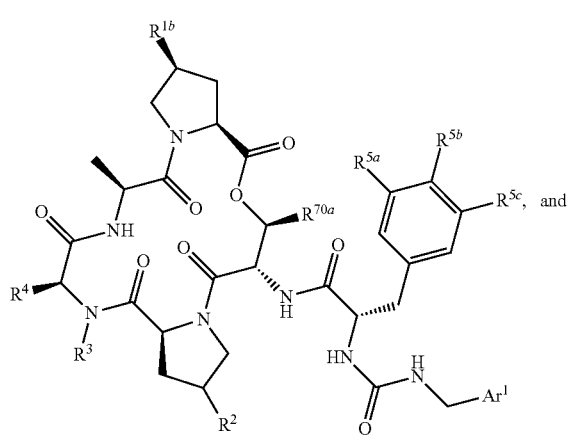

and wherein all variables are as defined herein.

In a further aspect, the compound has a structure represented by a formula listed below:

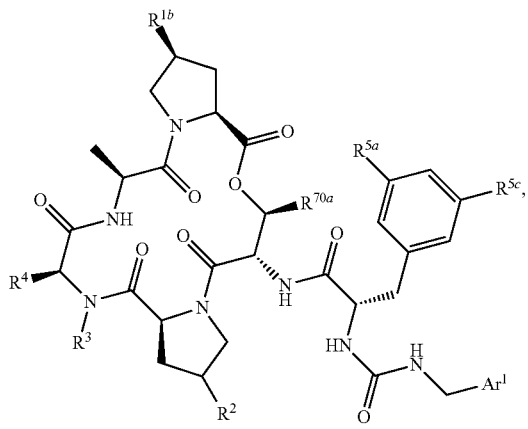

and wherein all variables are as defined herein.

In a further aspect, the compound has a structure represented by a formula listed below:

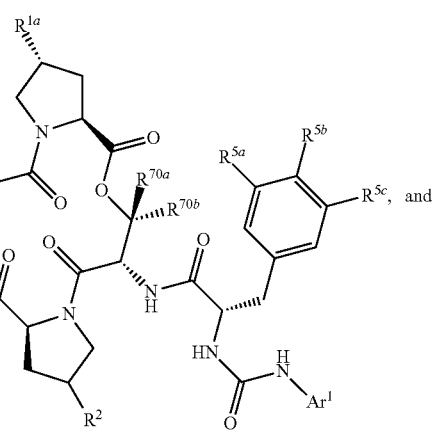

and wherein all variables are as defined herein.

In a further aspect, the compound has a structure represented by a formula listed below:

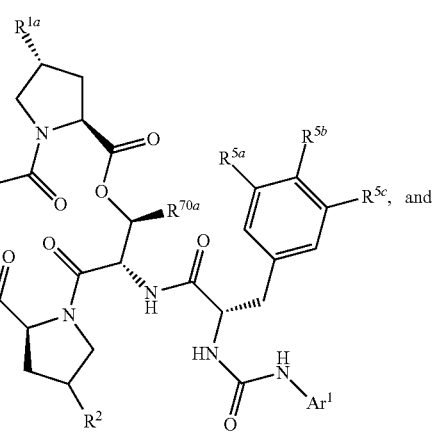

-continued

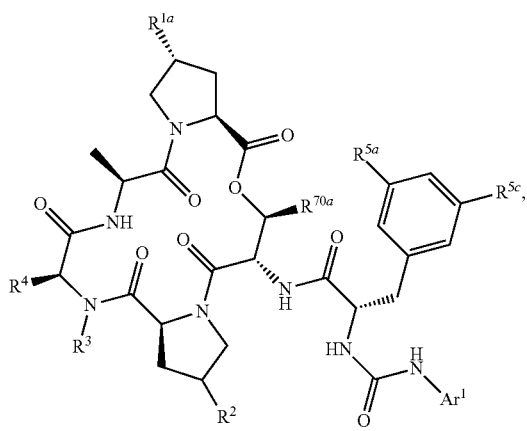

and wherein all variables are as defined herein.

In a further aspect, the compound has a structure represented by a formula listed below:

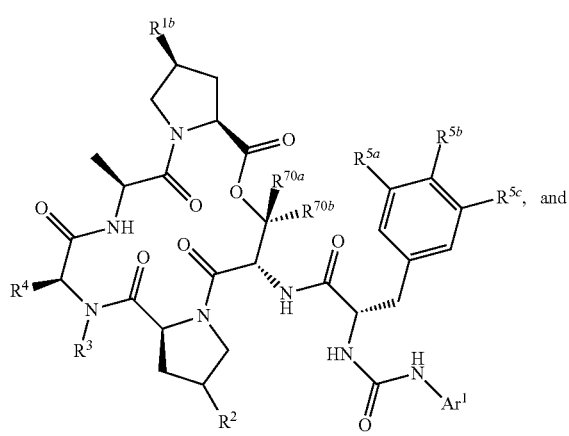

and wherein all variables are as defined herein.

In a further aspect, the compound has a structure represented by a formula listed below:

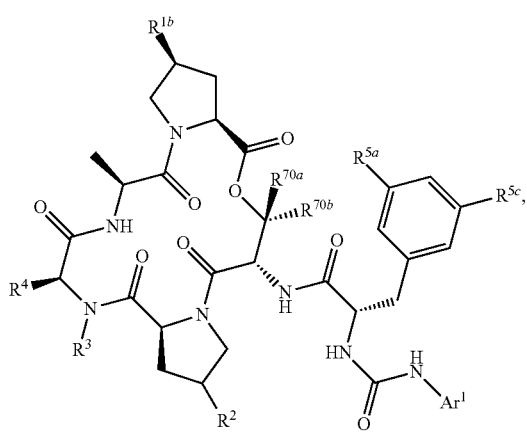

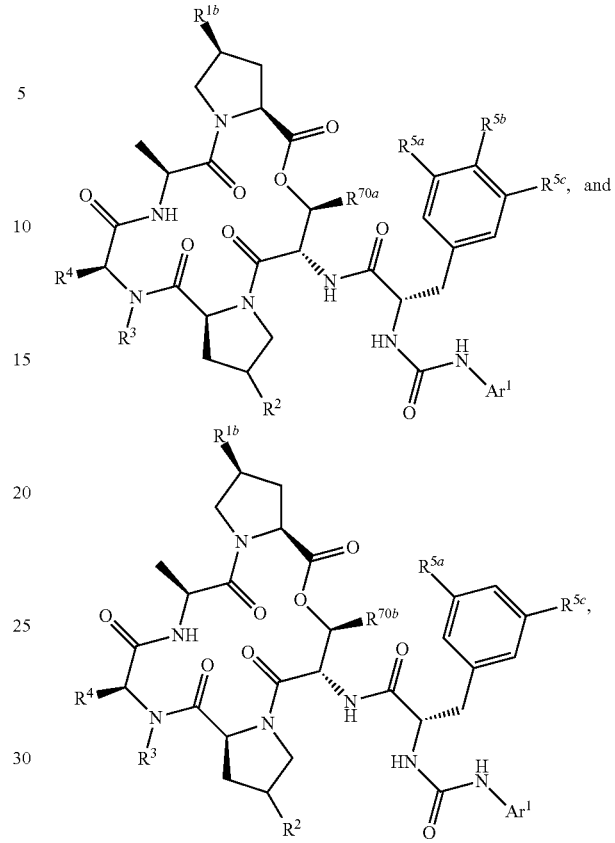

and wherein all variables are as defined herein.

Suitable substituents are described below.

a. L Moiety

In one aspect, L is a moiety selected from —CH$_2$—, —(CH$_2$)$_2$—, —CH=CH—, and -(cyclopropyl)-. In a further aspect, L is a moiety selected from —CH$_2$—, —(CH$_2$)$_2$—, and —CH=CH—. In a still further aspect, L is a moiety selected from —CH$_2$— and —(CH$_2$)$_2$—. In yet a further aspect, L is —CH$_2$—. In an even further aspect, L is —(CH$_2$)$_2$—. In a still further aspect, L is —CH=CH—. In a still further aspect, L is -(cyclopropyl)-.

b. R$^1$ Groups

In one aspect, R$^1$ is selected from hydrogen, halogen, and C1-C3 alkyl. In a further aspect, R$^1$ is C1-C3 alkyl. In a still further aspect, R$^1$ is hydrogen.

In a further aspect, R$^1$ is C1-C3 alkyl. In a still further aspect, R$^1$ is selected methyl and ethyl. In a yet further aspect, R$^1$ is ethyl. In an even further aspect, R$^1$ is methyl.

In a further aspect, R$^1$ is selected from hydrogen and C1-C3 alkyl. In a still further aspect, R$^1$ is selected from hydrogen, ethyl, and methyl. In a yet further aspect, R$^1$ is selected from hydrogen and methyl.

In a further aspect, R$^1$ is selected from hydrogen and halogen. In a still further aspect, R$^1$ is selected from hydrogen, —F, —Cl, and —Br. In a yet further aspect, R$^1$ is selected from hydrogen, —Cl, —Br, and —I. In an even further aspect In a still further aspect, R$^1$ is selected from hydrogen, —Br, and —I.

In a further aspect, R$^1$ is halogen. In a still further aspect, R$^1$ is selected from —F, —Cl, and —Br. In a yet further aspect, R$^1$ is selected from —Cl, —Br, and —I. In an even further aspect, R$^1$ is selected from —Br and —I. In a still further aspect, $R^1$ is —F. In a yet further aspect, $R^1$ is —Cl. In an even further aspect, $R^1$ is —Br. In a still further aspect, $R^1$ is —I.

c. $R^{1A}$ and $R^{1B}$ Groups

In one aspect, each of $R^{1a}$ and $R^{1b}$ is independently selected from hydrogen, halogen, hydroxyl, cyano, and C1-C3 alkyl; or $R^{1a}$ and $R^{1b}$ are optionally covalently bonded, and together with the intermediate carbon comprise an optionally substituted 3- to 7-membered spirocycloalkyl.

In a further aspect, each of $R^{1a}$ and $R^{1b}$ is independently selected from hydrogen, halogen, hydroxyl, cyano, and C1-C3 alkyl. In a still further aspect, each of $R^{1a}$ and $R^{1b}$ is hydrogen.

In a further aspect, $R^{1a}$ is hydrogen and $R^{1b}$ is C1-C3 alkyl. In a still further aspect, $R^{1a}$ is hydrogen and $R^{1b}$ is selected methyl and ethyl. In a yet further aspect, $R^{1a}$ is hydrogen and $R^{1b}$ is ethyl. In an even further aspect, $R^{1a}$ is hydrogen and $R^{1b}$ is methyl.

In a further aspect, $R^{1b}$ is hydrogen and $R^{1a}$ is C1-C3 alkyl. In a still further aspect, $R^{1b}$ is hydrogen and $R^{1a}$ is selected methyl and ethyl. In a yet further aspect, $R^{1b}$ is hydrogen and $R^{1a}$ is ethyl. In an even further aspect, $R^{1b}$ is hydrogen and $R^{1a}$ is methyl.

In a further aspect, each of $R^{1a}$ and $R^{1b}$ is selected from hydrogen and C1-C3 alkyl. In a still further aspect, each of $R^{1a}$ and $R^{1b}$ is selected from hydrogen, ethyl, and methyl. In a yet further aspect, each of $R^{1a}$ and $R^{1b}$ is selected from hydrogen and methyl.

In a further aspect, each of $R^{1a}$ and $R^{1b}$ is selected from hydrogen and halogen. In a still further aspect, each of $R^{1a}$ and $R^{1b}$ is selected from hydrogen, —F, —Cl, and —Br. In a yet further aspect, each of $R^{1a}$ and $R^{1b}$ is selected from hydrogen, —Cl, —Br, and —I. In an even further aspect, each of $R^{1a}$ and $R^{1b}$ is selected from hydrogen, —Br, and —I.

In a further aspect, $R^{1a}$ is hydrogen and $R^{1b}$ is halogen. In a still further aspect, $R^{1a}$ is hydrogen and $R^{1b}$ is selected from —F, —Cl, and —Br. In a yet further aspect, $R^{1a}$ is hydrogen and $R^{1b}$ is selected from —Cl, —Br, and —I. In an even further aspect, $R^{1a}$ is hydrogen and $R^{1b}$ is selected from —Br and —I. In a still further aspect, $R^{1a}$ is hydrogen and $R^{1b}$ is —F. In a yet further aspect, $R^{1a}$ is hydrogen and $R^{1b}$ is —Cl. In an even further aspect, $R^{1a}$ is hydrogen and $R^{1b}$ is —Br. In a still further aspect, $R^{1a}$ is hydrogen and $R^{1b}$ is —I.

In a further aspect, $R^{1b}$ is hydrogen and $R^{1a}$ is halogen. In a still further aspect, $R^{1b}$ is hydrogen and $R^{1a}$ is from —F, —Cl, and —Br. In a yet further aspect, $R^{1b}$ is hydrogen and $R^{1a}$ is selected from —Cl, —Br, and —I. In an even further aspect, $R^{1b}$ is hydrogen and $R^{1a}$ is selected from —Br and —I. In a still further aspect, $R^{1b}$ is hydrogen and $R^{1a}$ is —F. In a yet further aspect, $R^{1b}$ is hydrogen and $R^{1a}$ is —Cl. In an even further aspect, $R^{1b}$ is hydrogen and $R^{1a}$ is —Br. In a still further aspect, $R^{1b}$ is hydrogen and $R^{1a}$ is —I.

In a further aspect, $R^{1a}$ and $R^{1b}$ are optionally covalently bonded, and together with the intermediate carbon comprise an optionally substituted 3- to 7-membered spirocycloalkyl. In a still further aspect, $R^{1a}$ and $R^{1b}$ are optionally covalently bonded, and together with the intermediate carbon comprise an optionally substituted 4- to 7-membered spirocycloalkyl. In yet a further aspect, $R^{1a}$ and $R^{1b}$ are optionally covalently bonded, and together with the intermediate carbon comprise an optionally substituted 5- to 7-membered spirocycloalkyl. In an even further aspect, $R^{1a}$ and $R^{1b}$ are optionally covalently bonded, and together with the intermediate carbon comprise an optionally substituted 6- to 7-membered spirocycloalkyl. In a still further aspect, $R^{1a}$ and $R^{1b}$ are option- ally covalently bonded, and together with the intermediate carbon comprise an optionally substituted 3-membered spirocycloalkyl. In yet a further aspect, $R^{1a}$ and $R^{1b}$ are optionally covalently bonded, and together with the intermediate carbon comprise an optionally substituted 4-membered spirocycloalkyl. In an even further aspect, $R^{1a}$ and $R^{1b}$ are optionally covalently bonded, and together with the intermediate carbon comprise an optionally substituted 5-membered spirocycloalkyl. In a still further aspect, $R^{1a}$ and $R^{1b}$ are optionally covalently bonded, and together with the intermediate carbon comprise an optionally substituted 6-membered spirocycloalkyl. In yet a further aspect, $R^{1a}$ and $R^{1b}$ are optionally covalently bonded, and together with the intermediate carbon comprise an optionally substituted 7-membered spirocycloalkyl.

d. $R^2$ Groups

In one aspect, $R^2$ is selected from hydrogen, halogen, —NH$_2$, —OH, —C1-C3 alkylamino, C1-C3 dialkylamino, C1-C3 aminoalkyl, C1-C3 hydroxyalkyl, —(C=O)OR$^{10}$, —(C=O)NR$^{12a}$R$^{12b}$, —(C1-C2 alkyl)-(C=O)OR$^{10}$, —(C1-C2 alkyl)-(C=O)NR$^{12a}$R$^{12b}$, and —C(NR$^{12a}$R$^{12b}$)R$^{11}$—(C1-C3 alkyl)-R$^{13}$. In a further aspect, $R^2$ is hydrogen.

In one aspect, $R^2$ is selected from hydrogen, halogen, —NH$_2$, —OH, —NO$_2$, C1-C3 alkyl, C1-C3 alkylamino, C1-C3 dialkylamino, C1-C3 aminoalkyl.

In a further aspect, $R^2$ is selected from hydrogen, —F, —Cl, —Br, —NH$_2$, —OH, —NHCH$_3$, —NHCH$_2$CH$_3$, —N(CH$_3$)$_2$, —N(CH$_3$)CH$_2$CH$_3$, —CH$_2$CH$_2$NH$_2$, —CH$_2$NH$_2$, —CH$_2$OH, —(CH$_2$)$_2$OH, —(CHOH)CH$_3$, —(C=O)OCH$_2$CH$_3$, —(C=O)OCH$_3$, —(C=O)NHCH$_3$, —(C=O)N(CH$_3$)$_2$, —(C=O)NHCH$_2$CH$_3$, —(C=O)N(CH$_3$)CH$_2$CH$_3$, —(CH$_2$)$_2$—(C=O)OCH$_2$CH$_3$, —(CH$_2$)$_2$—(C=O)OCH$_3$, —(CH$_2$)—(C=O)OCH$_2$CH$_3$, —(CH$_2$)—(C=O)OCH$_3$, —(CH$_2$)$_2$—(C=O)NHCH$_3$, —(CH$_2$)$_2$—(C=O)N(CH$_3$)$_2$, —(CH$_2$)$_2$—(C=O)NHCH$_2$CH$_3$, —(CH$_2$)$_2$—(C=O)N(CH$_3$)CH$_2$CH$_3$, —(CH$_2$)—(C=O)NHCH$_3$, —(CH$_2$)—(C=O)N(CH$_3$)$_2$, —(CH$_2$)—(C=O)NHCH$_2$CH$_3$, —(CH$_2$)—(C=O)N(CH$_3$)CH$_2$CH$_3$, —C(NH$_2$)H—(CH$_2$)$_2$—NH$_2$, and —C(NH$_2$)H—(CH$_2$)—NH$_2$.

In a further aspect, $R^2$ is selected from hydrogen, —F, —NH$_2$, —OH, —NHCH$_3$, —N(CH$_3$)$_2$, —CH$_2$NH$_2$, —CH$_2$OH, —(C=O)OCH$_3$, —(C=O)NHCH$_3$, —(C=O)N(CH$_3$)$_2$, —(CH$_2$)$_2$—(C=O)OCH$_3$, —(CH$_2$)—(C=O)OCH$_3$, —(CH$_2$)—(C=O)NHCH$_3$, and —(CH$_2$)—(C=O)N(CH$_3$)$_2$. In a still further aspect, $R^2$ is selected from hydrogen, —F, —NH$_2$, —OH, —NHCH$_3$, —N(CH$_3$)$_2$, —CH$_2$NH$_2$, and —CH$_2$OH.

In a further aspect, $R^2$ is selected from hydrogen, halogen, —NH$_2$, and —OH. In a still further aspect, $R^2$ is selected from hydrogen, —F, —Cl, —Br, —NH$_2$, and —OH. In a yet further aspect, $R^2$ is selected from hydrogen, —F, —NH$_2$, and —OH.

In a further aspect, $R^2$ is —F. In a still further aspect, $R^2$ is —Cl. In a yet further aspect, $R^2$ is —NH$_2$. In an even further aspect, $R^2$ is —OH. In a still further aspect, $R^2$ is —CH$_2$NH$_2$. In a yet further aspect, $R^2$ is —CH$_2$OH.

In a further aspect, $R^2$ is selected from hydrogen, halogen, —NH$_2$, and —OH. In a still further aspect, $R^2$ is selected from hydrogen, —F, —Cl, —NH$_2$, and —OH. In yet a further aspect, $R^2$ is selected from hydrogen, —F, —NH$_2$, and —OH.

In a further aspect, $R^2$ is selected from hydrogen, —F, —Cl, —Br, —NH$_2$, —OH, —NO$_2$, methyl, ethyl, —NHCH$_3$, —NHCH$_2$CH$_3$, —N(CH$_3$)$_2$, —N(CH$_3$)CH$_2$CH$_3$, —CH$_2$CH$_2$NH$_2$, —CH$_2$NH$_2$. In a still further aspect, $R^2$ is selected from hydrogen, —F, —NH$_2$, —OH, —NO$_2$, methyl, —NHCH$_3$, —N(CH$_3$)$_2$, and —CH$_2$NH$_2$.

In a further aspect, $R^2$ is selected from hydrogen, halogen, —NH$_2$, —OH, and —NO$_2$. In a still further aspect, $R^2$ is selected from hydrogen, —F, —Cl, —Br, —NH$_2$, —OH, and —NO$_2$. In a yet further aspect, $R^2$ is selected from hydrogen, —F, —NH$_2$, —OH, and —NO$_2$.

In a further aspect, $R^2$ is —F. In a still further aspect, $R^2$ is —Cl. In a yet further aspect, $R^2$ is —NH$_2$. In an even further aspect, $R^2$ is —OH. In a still further aspect, $R^2$ is —CH$_2$NH$_2$. In yet a further aspect, $R^2$ is —CH$_2$NH$_2$. In an even further aspect, $R^2$ is —NO$_2$.

e. $R^3$ Groups

In one aspect, $R^3$ is selected from hydrogen, C1-C3 alkyl, C1-C3 hydroxyalkyl, —(C1-C3 alkyl)-(C=O)OR$^{20}$, —(C1-C3 alkyl)-(C=O)NR$^{21a}$R$^{21b}$, and -Cy$^2$. In a further aspect, $R^3$ is hydrogen.

In a further aspect, $R^3$ is selected from hydrogen and C1-C6 alkyl. In a yet further aspect, $R^3$ is selected from hydrogen and C1-C3 alkyl. In a still further aspect, $R^3$ is selected from hydrogen, methyl, and ethyl. In a yet further aspect t, $R^3$ is selected from hydrogen and methyl. In an even further aspect, $R^3$ is selected from hydrogen and ethyl.

In a further aspect, $R^3$ is selected from hydrogen and C1-C6 alkyl optionally substituted with 1, 2, or 3 independently groups selected from —NH$_2$, —OH, and —SH. In a still further aspect, $R^3$ is selected from hydrogen and C1-C3 alkyl optionally substituted with 1, 2, or 3 groups independently selected from —NH$_2$, —OH, and —SH.

In a further aspect, $R^3$ is selected from hydrogen and C1-C6 alkyl optionally substituted with 1 or 2 groups independently selected from —NH$_2$, —OH, and —SH. In a further aspect, $R^3$ is selected from hydrogen and C1-C3 alkyl optionally substituted with 1 or 2 groups selected from —NH$_2$, —OH, and —SH.

In a further aspect, $R^3$ is selected from hydrogen and C1-C6 alkyl optionally substituted with one group selected from —NH$_2$, —OH, and —SH. In a further aspect, $R^3$ is selected from hydrogen and C1-C3 alkyl optionally substituted with one group selected from —NH$_2$, —OH, and —SH.

In various further aspects, $R^3$ is selected from hydrogen and ethyl optionally substituted with 1, 2, or 3 independently groups selected from —NH$_2$, —OH, and —SH. In a still further aspect, $R^3$ is selected from hydrogen and ethyl optionally substituted with 1 or 2 groups independently selected from —NH$_2$, —OH, and —SH. In a yet further aspect, $R^3$ is selected from hydrogen, methyl, and ethyl optionally substituted with one group selected from —NH$_2$, —OH, and —SH. In an even further aspect, $R^3$ is selected from hydrogen and methyl optionally substituted with one group selected from —NH$_2$, —OH, and —SH.

In a further aspect, $R^3$ is C1-C6 alkyl optionally substituted with 1, 2, or 3 independently groups selected from —NH$_2$, —OH, and —SH. In a still further aspect, $R^3$ is C1-C3 alkyl optionally substituted with 1, 2, or 3 groups independently selected from —NH$_2$, —OH, and —SH.

In a further aspect, $R^3$ is C1-C6 alkyl optionally substituted with 1 or 2 groups independently selected from —NH$_2$, —OH, and —SH. In a further aspect, $R^3$ is C1-C3 alkyl optionally substituted with 1 or 2 groups selected from —NH$_2$, —OH, and —SH.

In a further aspect, $R^3$ is C1-C6 alkyl optionally substituted with one group selected from —NH$_2$, —OH, and —SH. In a further aspect, $R^3$ is C1-C3 alkyl optionally substituted with one group selected from —NH$_2$, —OH, and —SH.

In various further aspects, $R^3$ is ethyl optionally substituted with 1, 2, or 3 independently groups selected from —NH$_2$, —OH, and —SH. In a still further aspect, $R^3$ is ethyl optionally substituted with 1 or 2 groups independently selected from —NH$_2$, —OH, and —SH. In a yet further aspect, $R^3$ is selected from methyl and ethyl optionally substituted with one group selected from —NH$_2$, —OH, and —SH. In an even further aspect, $R^3$ is methyl optionally substituted with one group selected from —NH$_2$, —OH, and —SH.

In a further aspect, $R^3$ is C1-C3 alkyl. In a still further aspect, $R^3$ is selected from methyl and ethyl. In a yet further aspect, $R^3$ is methyl. In an even further aspect, $R^3$ is ethyl.

In a further aspect, $R^3$ is selected from hydrogen, methyl, ethyl, —CH$_2$OH, —(CH$_2$)$_2$OH, —(CHOH)CH$_3$, —(CH$_2$)$_2$—(C=O)OCH$_2$CH$_3$, —(CH$_2$)$_2$—(C=O)OCH$_3$, —(CH$_2$)—(C=O)OCH$_2$CH$_3$, —(CH$_2$)—(C=O)OCH$_3$, —(CH$_2$)$_2$—(C=O)NHCH$_3$, —(CH$_2$)$_2$—(C=O)N(CH$_3$)$_2$, —(CH$_2$)$_2$—(C=O)NHCH$_2$CH$_3$, —(CH$_2$)$_2$—(C=O)N(CH$_3$)CH$_2$CH$_3$, —(CH$_2$)—(C=O)NHCH$_3$, —(CH$_2$)—(C=O)N(CH$_3$)$_2$, —(CH$_2$)—(C=O)NHCH$_2$CH$_3$, —(CH$_2$)—(C=O)N(CH$_3$)CH$_2$CH$_3$, -piperidinyl, and -tetrahydrofuranyl.

In a further aspect, $R^3$ is selected from hydrogen, methyl, ethyl, —CH$_2$OH, —(CH$_2$)$_2$OH, -piperidinyl, and -tetrahydrofuranyl. In a still further aspect, $R^3$ is selected from hydrogen, methyl, ethyl, —(CH$_2$)$_2$OH, -piperidinyl, and -tetrahydrofuranyl. In a yet further aspect, $R^3$ is —(CH$_2$)$_2$OH. In an even further aspect, $R^3$ is -tetrahydrofuranyl. In a still further aspect, $R^3$ is -piperidinyl.

f. $R^4$ Groups

In one aspect, $R^4$ is selected hydrogen, C1-C6 alkyl, —C1-C6 alkylamino, C1-C6 dialkylamino, C1-C6 hydroxyalkyl, —(C=O)OR$^{30}$, —(C=O)NR$^{32a}$R$^{32b}$, —(C1-C4 alkyl)-(C=O)OR$^{30}$, —(C1-C4 alkyl)-(C=O)NR$^{32a}$R$^{32b}$, —C(NR$^{32a}$R$^{32b}$)R$^{31}$—(C1-C3 alkyl)-R$^{33}$, —(C1-C3 alkyl)-R$^{33}$, and Cy$^3$; or wherein $R^3$ and $R^4$ are covalently bonded, together with the intermediate atoms, comprise a 3- to 10-membered heterocycle having 1, 2, or 3 heteroatoms selected from O, N, and S; and wherein the heterocycle is substituted with 0, 1, 2, or 3 groups independently selected from halogen, —NH$_2$, —OH, —NO$_2$, C1-C3 alkyl, C1-C3 alkoxy, C1-C3 aminoalkyl, C1-C3 alkylamino, C1-C3 dialkylamino, C1-C3 hydroxyalkyl, —(C=O)OR$^{30}$, —(C=O)NR$^{32a}$R$^{32b}$, —(C1-C3 alkyl)-(C=O)OR$^{30}$, and —(C1-C3 alkyl)-(C=O)NR$^{32a}$R$^{32b}$.

In one aspect, $R^4$ is selected hydrogen, C1-C6 alkyl, —C1-C6 alkylamino, C1-C6 dialkylamino, C1-C6 hydroxyalkyl, —(C=O)OR$^{30}$, —(C=O)NR$^{32a}$R$^{32b}$, —(C1-C4 alkyl)-(C=O)OR$^{30}$, —(C1-C4 alkyl)-(C=O)NR$^{32a}$R$^{32b}$, —C(NR$^{32a}$R$^{32b}$)R$^{31}$—(C1-C3 alkyl)-R$^{33}$, —(C1-C3 alkyl)-R$^{33}$, and Cy$^3$; or wherein $R^3$ and $R^4$ are optionally covalently bonded, and together with the intermediate carbon, oxygen, and/or nitrogen, comprise a 3- to 10-membered heterocycle substituted with 0, 1, 2, or 3 groups independently selected from halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —(C1-C3 alkyl)-R$^{33}$, and —C(NR$^{32a}$R$^{32b}$)R$^{31}$—(C1-C3 alkyl)-R$^{33}$.

In a further aspect, $R^4$ is selected hydrogen, C1-C6 alkyl, —C1-C6 alkylamino, C1-C6 dialkylamino, C1-C6 hydroxyalkyl, —(C=O)OR$^{30}$, —(C=O)NR$^{32a}$R$^{32b}$, —(C1-C4 alkyl)-(C=O)OR$^{30}$, —(C1-C4 alkyl)-(C=O)NR$^{32a}$R$^{32b}$, —C(NR$^{32a}$R$^{32b}$)R$^{31}$—(C1-C3 alkyl)-R$^{33}$, —(C1-C3 alkyl)-R$^{33}$, and Cy$^3$.

In a further aspect, $R^4$ is selected from hydrogen and C1-C6 alkyl. In a still further aspect, $R^4$ is selected from hydrogen and C1-C4 alkyl. In yet a further aspect, $R^4$ is selected from hydrogen, methyl, ethyl, i-propyl, and n-propyl. In an even further aspect, $R^4$ is selected from hydrogen, methyl, and ethyl. In a still further aspect, $R^4$ is selected from hydrogen and methyl. In yet a further aspect, $R^4$ is methyl. In an even further aspect, $R^4$ is ethyl.

In a further aspect, $R^4$ is selected from hydrogen and C1-C6 alkyl optionally substituted with 1, 2, or 4 independently groups selected from —NH$_2$, —OH, and —SH. In a still further aspect, $R^4$ is selected from hydrogen and C1-C4 alkyl optionally substituted with 1, 2, or 4 groups independently selected from —NH$_2$, —OH, and —SH.

In a further aspect, $R^4$ is selected from hydrogen and C1-C6 alkyl optionally substituted with 1 or 2 groups independently selected from —NH$_2$, —OH, and —SH. In a further aspect, $R^4$ is selected from hydrogen and C1-C4 alkyl optionally substituted with 1 or 2 groups selected from —NH$_2$, —OH, and —SH.

In a further aspect, $R^4$ is selected from hydrogen and C1-C6 alkyl optionally substituted with one group selected from —NH$_2$, —OH, and —SH. In a further aspect, $R^4$ is selected from hydrogen and C1-C4 alkyl optionally substituted with one group selected from —NH$_2$, —OH, and —SH.

In various further aspects, $R^4$ is selected from hydrogen and ethyl optionally substituted with 1, 2, or 4 independently groups selected from —NH$_2$, —OH, and —SH. In a still further aspect, $R^4$ is selected from hydrogen and ethyl optionally substituted with 1 or 2 groups independently selected from —NH$_2$, —OH, and —SH. In a yet further aspect, $R^4$ is selected from hydrogen, methyl, and ethyl optionally substituted with one group selected from —NH$_2$, —OH, and —SH. In an even further aspect, $R^4$ is selected from hydrogen and methyl optionally substituted with one group selected from —NH$_2$, —OH, and —SH.

In a further aspect, $R^4$ is C1-C6 alkyl optionally substituted with 1, 2, or 4 independently groups selected from —NH$_2$, —OH, and —SH. In a still further aspect, $R^4$ is C1-C4 alkyl optionally substituted with 1, 2, or 4 groups independently selected from —NH$_2$, —OH, and —SH.

In a further aspect, $R^4$ is C1-C6 alkyl optionally substituted with 1 or 2 groups independently selected from —NH$_2$, —OH, and —SH. In a further aspect, $R^4$ is C1-C4 alkyl optionally substituted with 1 or 2 groups selected from —NH$_2$, —OH, and —SH.

In a further aspect, $R^4$ is C1-C6 alkyl optionally substituted with one group selected from —NH$_2$, —OH, and —SH. In a further aspect, $R^4$ is C1-C4 alkyl optionally substituted with one group selected from —NH$_2$, —OH, and —SH.

In various further aspects, $R^4$ is ethyl optionally substituted with 1, 2, or 4 independently groups selected from —NH$_2$, —OH, and —SH. In a still further aspect, $R^4$ is ethyl optionally substituted with 1 or 2 groups independently selected from —NH$_2$, —OH, and —SH. In a yet further aspect, $R^4$ is selected from methyl and ethyl optionally substituted with one group selected from —NH$_2$, —OH, and —SH. In an even further aspect, $R^4$ is methyl optionally substituted with one group selected from —NH$_2$, —OH, and —SH.

In a further aspect, $R^3$ and $R^4$ are covalently bonded, together with the intermediate atoms, comprise a 3- to 10-membered heterocycle having 1, 2, or 3 heteroatoms selected from O, N, and S; and wherein the heterocycle is substituted with 0, 1, 2, or 3 groups independently selected from halogen, —NH$_2$, —OH, —NO$_2$, C1-C3 alkyl, C1-C3 alkoxy, C1-C3 aminoalkyl, C1-C3 alkylamino, C1-C3 dialkylamino, C1-C3 hydroxyalkyl, —(C=O)OR$^{30}$, —(C=O)NR$^{32a}$R$^{32b}$, —(C1-C3 alkyl)-(C=O)OR$^{30}$, and —(C1-C3 alkyl)-(C=O)NR$^{32a}$R$^{32b}$.

In a further aspect, $R^3$ and $R^4$ are covalently bonded, together with the intermediate atoms, comprise a 3- to 10-membered heterocycle having 1, 2, or 3 heteroatoms selected from O, N, and S; and wherein the heterocycle is substituted with 0, 1, 2, or 3 groups independently selected from halogen, —NH$_2$, —OH, —NO$_2$, methyl, ethyl, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —N(CH$_2$CH$_3$)$_2$, —CH$_2$NH$_2$, —(CH$_2$)$_2$NH$_2$, —CH$_2$OH, —(CH$_2$)$_2$OH, —(C=O)OCH$_3$, —(C=O)OCH$_2$CH$_3$, —(C=O)NHCH$_3$, —(C=O)NHCH$_2$CH$_3$, —(C=O)N(CH$_3$)$_2$, —(C=O)(CH$_3$)CH$_2$CH$_3$, —(C=O)(CH$_2$CH$_3$)$_2$, —CH$_2$(C=O)OCH$_3$, —(CH$_2$)$_2$(C=O)OCH$_2$CH$_3$, —CH$_2$(C=O)NHCH$_3$, —CH$_2$(C=O)NHCH$_2$CH$_3$, —CH$_2$(C=O)N(CH$_3$)$_2$, —CH$_2$(C=O)(CH$_3$)CH$_2$CH$_3$, —(CH$_2$)$_2$(C=O)NHCH$_3$, —(CH$_2$)$_2$(C=O)NHCH$_2$CH$_3$, —(CH$_2$)$_2$(C=O)N(CH$_3$)$_2$, and —(CH$_2$)$_2$(C=O)(CH$_3$)CH$_2$CH$_3$.

In a further aspect, $R^3$ and $R^4$ are covalently bonded, together with the intermediate atoms, comprise a 8-membered heterocycle having 1, 2, or 3 heteroatoms selected from O, N, and S; and wherein the heterocycle is substituted with 0, 1, 2, or 3 groups independently selected from halogen, —NH$_2$, —OH, —NO$_2$, C1-C3 alkyl, C1-C3 alkoxy, C1-C3 aminoalkyl, C1-C3 alkylamino, C1-C3 dialkylamino, C1-C3 hydroxyalkyl, —(C=O)OR$^{30}$, —(C=O)NR$^{32a}$R$^{32b}$, —(C1-C3 alkyl)-(C=O)OR$^{30}$, and —(C1-C3 alkyl)-(C=O)NR$^{32a}$R$^{32b}$.

In a further aspect, $R^3$ and $R^4$ are covalently bonded, together with the intermediate atoms, comprise a 8-membered heterocycle having 1, 2, or 3 heteroatoms selected from O, N, and S; and wherein the heterocycle is substituted with 0, 1, 2, or 3 groups independently selected from halogen, —NH$_2$, —OH, —NO$_2$, methyl, ethyl, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —N(CH$_2$CH$_3$)$_2$, —CH$_2$NH$_2$, —(CH$_2$)$_2$NH$_2$, —CH$_2$OH, —(CH$_2$)$_2$OH, —(C=O)OCH$_3$, —(C=O)OCH$_2$CH$_3$, —(C=O)NHCH$_3$, —(C=O)NHCH$_2$CH$_3$, —(C=O)N(CH$_3$)$_2$, —(C=O)(CH$_3$)CH$_2$CH$_3$, —(C=O)(CH$_2$CH$_3$)$_2$, —CH$_2$(C=O)OCH$_3$, —(CH$_2$)$_2$(C=O)OCH$_2$CH$_3$, —CH$_2$(C=O)NHCH$_3$, —CH$_2$(C=O)NHCH$_2$CH$_3$, —CH$_2$(C=O)N(CH$_3$)$_2$, —CH$_2$(C=O)(CH$_3$)CH$_2$CH$_3$, —(CH$_2$)$_2$(C=O)NHCH$_3$, —(CH$_2$)$_2$(C=O)NHCH$_2$CH$_3$, —(CH$_2$)$_2$(C=O)N(CH$_3$)$_2$, and —(CH$_2$)$_2$(C=O)(CH$_3$)CH$_2$CH$_3$.

In a further aspect, $R^3$ and $R^4$ are covalently bonded, together with the intermediate atoms, comprise a 6-membered heterocycle having 1, 2, or 3 heteroatoms selected from O, N, and S; and wherein the heterocycle is substituted with 0, 1, 2, or 3 groups independently selected from halogen, —NH$_2$, —OH, —NO$_2$, C1-C3 alkyl, C1-C3 alkoxy, C1-C3 aminoalkyl, C1-C3 alkylamino, C1-C3 dialkylamino, C1-C3 hydroxyalkyl, —(C=O)OR$^{30}$, —(C=O)NR$^{32a}$R$^{32b}$, —(C1-C3 alkyl)-(C=O)OR$^{30}$, and —(C1-C3 alkyl)-(C=O)NR$^{32a}$R$^{32b}$.

In a further aspect, $R^3$ and $R^4$ are covalently bonded, together with the intermediate atoms, comprise a 6-membered heterocycle having 1, 2, or 3 heteroatoms selected from O, N, and S; and wherein the heterocycle is substituted with 0, 1, 2, or 3 groups independently selected from halogen, —NH$_2$, —OH, —NO$_2$, methyl, ethyl, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —N(CH$_2$CH$_3$)$_2$, —CH$_2$NH$_2$, —(CH$_2$)$_2$NH$_2$, —CH$_2$OH, —(CH$_2$)$_2$OH, —(C=O)OCH$_3$, —(C=O)OCH$_2$CH$_3$, —(C=O)NHCH$_3$, —(C=O)NHCH$_2$CH$_3$, —(C=O)N(CH$_3$)$_2$, —(C=O)(CH$_3$)CH$_2$CH$_3$, —(C=O)(CH$_2$CH$_3$)$_2$, —CH$_2$(C=O)OCH$_3$, —(CH$_2$)$_2$(C=O)OCH$_2$CH$_3$, —CH$_2$(C=O)NHCH$_3$, —CH$_2$(C=O)NHCH$_2$CH$_3$, —CH$_2$(C=O)N(CH$_3$)$_2$, —CH$_2$(C=O)(CH$_3$)CH$_2$CH$_3$, —(CH$_2$)$_2$(C=O)NHCH$_3$, —(CH$_2$)$_2$(C=O)NHCH$_2$CH$_3$, —(CH$_2$)$_2$(C=O)N(CH$_3$)$_2$, and —(CH$_2$)$_2$(C=O)(CH$_3$)CH$_2$CH$_3$.

In a further aspect, R$^3$ and R$^4$ are covalently bonded, together with the intermediate atoms, comprise a 5-membered heterocycle having 1, 2, or 3 heteroatoms selected from O, N, and S; and wherein the heterocycle is substituted with 0, 1, 2, or 3 groups independently selected from halogen, —NH$_2$, —OH, —NO$_2$, C1-C3 alkyl, C1-C3 alkoxy, C1-C3 aminoalkyl, C1-C3 alkylamino, C1-C3 dialkylamino, C1-C3 hydroxyalkyl, —(C=O)OR$^{30}$, —(C=O)NR$^{32a}$R$^{32b}$, —(C1-C3 alkyl)-(C=O)OR$^{30}$, and —(C1-C3 alkyl)-(C=O)NR$^{32a}$R$^{32b}$.

In a further aspect, R$^3$ and R$^4$ are covalently bonded, together with the intermediate atoms, comprise a 5-membered heterocycle having 1, 2, or 3 heteroatoms selected from O, N, and S; and wherein the heterocycle is substituted with 0, 1, 2, or 3 groups independently selected from halogen, —NH$_2$, —OH, —NO$_2$, methyl, ethyl, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —N(CH$_2$CH$_3$)$_2$, —CH$_2$NH$_2$, —(CH$_2$)$_2$NH$_2$, —CH$_2$OH, —(CH$_2$)$_2$OH, —(C=O)OCH$_3$, —(C=O)OCH$_2$CH$_3$, —(C=O)NHCH$_3$, —(C=O)NHCH$_2$CH$_3$, —(C=O)N(CH$_3$)$_2$, —(C=O)(CH$_3$)CH$_2$CH$_3$, —(C=O)(CH$_2$CH$_3$)$_2$, —CH$_2$(C=O)OCH$_3$, —(CH$_2$)$_2$(C=O)OCH$_2$CH$_3$, —CH$_2$(C=O)NHCH$_3$, —CH$_2$(C=O)NHCH$_2$CH$_3$, —CH$_2$(C=O)N(CH$_3$)$_2$, —CH$_2$(C=O)(CH$_3$)CH$_2$CH$_3$, —(CH$_2$)$_2$(C=O)NHCH$_3$, —(CH$_2$)$_2$(C=O)NHCH$_2$CH$_3$, —(CH$_2$)$_2$(C=O)N(CH$_3$)$_2$, and —(CH$_2$)$_2$(C=O)(CH$_3$)CH$_2$CH$_3$.

In a further aspect, R$^3$ and R$^4$ are optionally covalently bonded, and together with the intermediate carbon, oxygen, and/or nitrogen, comprise a 6-membered heterocycle substituted with 0, 1, 2, or 3 groups independently selected from halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —(C1-C3 alkyl)-R$^{33}$, and —C(NR$^{32a}$R$^{32b}$)R$^{31}$—(C1-C3 alkyl)-R$^{33}$. In a still further aspect, R$^3$ and R$^4$ are optionally covalently bonded, and together with the intermediate carbon, oxygen, and/or nitrogen, comprise an unsubstituted 6-membered heterocycle.

In various further aspects, wherein R$^3$ and R$^4$ are optionally covalently bonded, and together with the intermediate carbon, oxygen, and/or nitrogen, comprise a 3- to 10-membered heterocycle substituted with 0, 1, 2, or 3 groups independently selected from halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —(C1-C3 alkyl)-R$^{33}$, and —C(NR$^{32a}$R$^{32b}$)R$^{31}$—(C1-C3 alkyl)-R$^{33}$.

In various further aspects, wherein R$^3$ and R$^4$ are optionally covalently bonded, and together with the intermediate atoms comprise a morpholinyl ring substituted with 0, 1, 2, or 3 groups independently selected from halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —(C1-C3 alkyl)-R$^{33}$, and —C(NR$^{32a}$R$^{32b}$)R$^{31}$—(C1-C3 alkyl)-R$^{33}$.

In various further aspects, wherein R$^3$ and R$^4$ are optionally covalently bonded, and together with the intermediate atoms comprise a morpholinyl ring substituted with 0, 1, 2, or 3 groups independently selected from halogen, —NH$_2$, —OH, —NO$_2$, methyl, ethyl, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —N(CH$_2$CH$_3$)$_2$, —CH$_2$NH$_2$, —(CH$_2$)$_2$NH$_2$, —CH$_2$OH, —(CH$_2$)$_2$OH, —(C=O)OCH$_3$, —(C=O)OCH$_2$CH$_3$, —(C=O)NHCH$_3$, —(C=O)NHCH$_2$CH$_3$, —(C=O)N(CH$_3$)$_2$, —(C=O)(CH$_3$)CH$_2$CH$_3$, —(C=O)(CH$_2$CH$_3$)$_2$, —CH$_2$(C=O)OCH$_3$, —(CH$_2$)$_2$(C=O)OCH$_2$CH$_3$, —CH$_2$(C=O)NHCH$_3$, —CH$_2$(C=O)NHCH$_2$CH$_3$, —CH$_2$(C=O)N(CH$_3$)$_2$, —CH$_2$(C=O)(CH$_3$)CH$_2$CH$_3$, —(CH$_2$)$_2$(C=O)NHCH$_3$, —(CH$_2$)$_2$(C=O)NHCH$_2$CH$_3$, —(CH$_2$)$_2$(C=O)N(CH$_3$)$_2$, and —(CH$_2$)$_2$(C=O)(CH$_3$)CH$_2$CH$_3$.

In various further aspects, wherein R$^3$ and R$^4$ are optionally covalently bonded, and together with the intermediate atoms comprise a piperazinyl ring substituted with 0, 1, 2, or 3 groups independently selected from halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —(C1-C3 alkyl)-R$^{33}$, and —C(NR$^{32a}$R$^{32b}$)R$^{31}$—(C1-C3 alkyl)-R$^{33}$.

In various further aspects, wherein R$^3$ and R$^4$ are optionally covalently bonded, and together with the intermediate atoms comprise a piperazinyl ring substituted with 0, 1, 2, or 3 groups independently selected from halogen, —NH$_2$, —OH, —NO$_2$, methyl, ethyl, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —N(CH$_2$CH$_3$)$_2$, —CH$_2$NH$_2$, —(CH$_2$)$_2$NH$_2$, —CH$_2$OH, —(CH$_2$)$_2$OH, —(C=O)OCH$_3$, —(C=O)OCH$_2$CH$_3$, —(C=O)NHCH$_3$, —(C=O)NHCH$_2$CH$_3$, —(C=O)N(CH$_3$)$_2$, —(C=O)(CH$_3$)CH$_2$CH$_3$, —(C=O)(CH$_2$CH$_3$)$_2$, —CH$_2$(C=O)OCH$_3$, —(CH$_2$)$_2$(C=O)OCH$_2$CH$_3$, —CH$_2$(C=O)NHCH$_3$, —CH$_2$(C=O)NHCH$_2$CH$_3$, —CH$_2$(C=O)N(CH$_3$)$_2$, —CH$_2$(C=O)(CH$_3$)CH$_2$CH$_3$, —(CH$_2$)$_2$(C=O)NHCH$_3$, —(CH$_2$)$_2$(C=O)NHCH$_2$CH$_3$, —(CH$_2$)$_2$(C=O)N(CH$_3$)$_2$, and —(CH$_2$)$_2$(C=O)(CH$_3$)CH$_2$CH$_3$.

In a further aspect, R$^4$ is selected from hydrogen and C1-C6 alkyl. In a still further aspect, R$^4$ is selected from hydrogen and C1-C3 alkyl. In a yet further aspect, R$^4$ is selected from hydrogen, methyl, and ethyl. In an even further aspect, R$^4$ is selected from hydrogen and methyl. In a still further aspect, R$^4$ is selected from hydrogen and ethyl.

In a further aspect, R$^4$ is C1-C3 alkyl. In a still further aspect, R$^4$ is selected from methyl and ethyl. In a yet further aspect t, R$^4$ is methyl. In an even further aspect, R$^4$ is ethyl.

In a further aspect, R$^4$ is selected from hydrogen, methyl, ethyl, —CH$_2$OH, —(CH$_2$)$_2$OH, —(CHOH)CH$_3$, —(CH$_2$)$_2$—(C=O)OCH$_2$CH$_3$, —(CH$_2$)$_2$—(C=O)OCH$_3$, —(CH$_2$)—(C=O)OCH$_2$CH$_3$, —(CH$_2$)—(C=O)OCH$_3$, —(CH$_2$)$_2$—(C=O)NHCH$_3$, —(CH$_2$)$_2$—(C=O)N(CH$_3$)$_2$, —(CH$_2$)$_2$—(C=O)NHCH$_2$CH$_3$, —(CH$_2$)$_2$—(C=O)N(CH$_3$)CH$_2$CH$_3$, —(CH$_2$)—(C=O)NHCH$_3$, —(CH$_2$)—(C=O)N(CH$_3$)$_2$, —(CH$_2$)—(C=O)NHCH$_2$CH$_3$, —(CH$_2$)—(C=O)N(CH$_3$)CH$_2$CH$_3$, —(CH$_2$)$_2$-morpholinyl, —(CH$_2$)$_2$-piperidinyl, —(CH$_2$)$_2$-tetrahydrofuranyl, —(CH$_2$)$_2$-piperazinyl, —(CH$_2$)-morpholinyl, —(CH$_2$)-piperidinyl, —(CH$_2$)-tetrahydrofuranyl, and —(CH$_2$)-piperazinyl.

In a further aspect, R$^4$ is selected from hydrogen, methyl, ethyl, —CH$_2$OH, —(CH$_2$)$_2$OH, —(CH$_2$)-morpholinyl, —(CH$_2$)-piperidinyl, —(CH$_2$)-tetrahydrofuranyl, and —(CH$_2$)-piperazinyl. In a still further aspect, R$^4$ is selected from hydrogen, methyl, ethyl, —CH$_2$OH, —(CH$_2$)$_2$OH, and —(CH$_2$)-morpholinyl. In a yet further aspect, R$^4$ is —CH$_2$OH. In an even further aspect, R$^3$ is —(CH$_2$)$_2$OH. In an even further aspect, R$^4$ is —(CH$_2$)-morpholinyl.

g. R$^{5a}$, R$^{5b}$, and R$^{5c}$ Groups

In one aspect, each of R$^{5a}$, R$^{5b}$, and R$^{5c}$ is independently selected from hydrogen, halogen, difluoromethoxy, and trifluoromethoxy.

In a further aspect, R$^{5b}$ is hydrogen; and each of R$^{5a}$ and R$^{5c}$ is independently selected from hydrogen, halogen, difluoromethoxy, and trifluoromethoxy. In a still further aspect, R$^{5b}$ is hydrogen; and each of R$^{5a}$ and R$^{5c}$ is independently selected from hydrogen, —F, difluoromethoxy, and trifluoromethoxy.

In a further aspect, R$^{5b}$ is hydrogen; and each of R$^{5a}$ and R$^{5c}$ is independently selected from halogen, difluoromethoxy, and trifluoromethoxy. In a still further aspect, R$^{5b}$ is hydrogen; and each of R$^{5a}$ and R$^{5c}$ is independently selected from —F, difluoromethoxy, and trifluoromethoxy.

In a further aspect, R$^{5b}$ is —F; and each of R$^{5a}$ and R$^{5c}$ is independently selected from hydrogen, halogen, difluoromethoxy, and trifluoromethoxy. In a still further aspect, R$^{5b}$ is —F; and each of R$^{5a}$ and R$^{5c}$ is independently selected from hydrogen, —F, difluoromethoxy, and trifluoromethoxy.

In a further aspect, R$^{5b}$ is —F; and each of R$^{5a}$ and R$^{5c}$ is independently selected from halogen, difluoromethoxy, and trifluoromethoxy. In a still further aspect, R$^{5b}$ is —F; and each of R$^{5a}$ and R$^{5c}$ is independently selected from —F, difluoromethoxy, and trifluoromethoxy.

In a further aspect, each of R$^{5a}$, R$^{5b}$, and R$^{5c}$ is independently selected from hydrogen, —F, difluoromethoxy, and trifluoromethoxy. In a still further aspect, each of R$^{5a}$ and R$^{5c}$ is independently selected from —F, difluoromethoxy, and trifluoromethoxy; and wherein R$^{5b}$ is hydrogen. In yet a further aspect, each of R$^{5a}$ and R$^{5c}$ is —F; and wherein R$^{5b}$ is hydrogen.

In a further aspect, each of R$^{5a}$, R$^{5b}$, and R$^{5c}$ is —F. In a still further aspect, R$^{5b}$ is hydrogen; and each of R$^{5a}$ and R$^{5c}$—F. In a yet further aspect, R$^{5a}$ is —F; and each of R$^{5b}$ and R$^{5c}$ is hydrogen.

h. R$^{10}$ Groups

In one aspect, R$^{10}$, when present, is selected from hydrogen and C1-C3 alkyl. In a further aspect, R$^{10}$, when present, is hydrogen.

In a further aspect, R$^{10}$, when present, is selected from hydrogen, methyl, and ethyl. In a still further aspect, R$^{10}$, when present, is selected from hydrogen and methyl. In a yet further aspect, R$^{10}$, when present, is selected from hydrogen and ethyl.

In a further aspect, R$^{10}$, when present, is C1-C3 alkyl. In a still further aspect, R$^{10}$, when present, is selected from methyl and ethyl. In a yet further aspect, R$^{10}$, when present, is ethyl. In an even further aspect, R$^{10}$, when present, is methyl.

i. R$^{11}$ Groups

In one aspect, R$^{11}$, when present, is selected from hydrogen and C1-C3 alkyl. In a further aspect, R$^{11}$, when present, is hydrogen.

In a further aspect, R$^{11}$, when present, is selected from hydrogen, methyl, and ethyl. In a still further aspect, R$^{11}$, when present, is selected from hydrogen and methyl. In a yet further aspect, R$^{11}$, when present, is selected from hydrogen and ethyl.

In a further aspect, R$^{11}$, when present, is C1-C3 alkyl. In a still further aspect, R$^{11}$, when present, is selected from methyl and ethyl. In a yet further aspect, R$^{11}$, when present, is ethyl. In an even further aspect, R$^{11}$, when present, is methyl.

j. R$^{12a}$ and R$^{12b}$ Groups

In one aspect, each of R$^{12a}$ and R$^{12b}$, when present, is independently selected from hydrogen and C1-C3 alkyl. In a further aspect, each of R$^{12a}$ and R$^{12b}$, when present, is hydrogen.

In a further aspect, each of R$^{12a}$ and R$^{12b}$, when present, is independently selected from hydrogen, methyl, and ethyl. In a still further aspect, each of R$^{12a}$ and R$^{12b}$, when present, is independently selected from hydrogen and methyl. In a yet further aspect, each of R$^{12a}$ and R$^{12b}$, when present, is independently selected from hydrogen and ethyl.

In a further aspect, each of R$^{12a}$ and R$^{12b}$, when present, is independently is C1-C3 alkyl. In a still further aspect, each of R$^{12a}$ and R$^{12b}$, when present, is independently selected from methyl and ethyl. In a yet further aspect, each of R$^{12a}$ and R$^{12b}$, when present, is selected is ethyl. In an even further aspect, each of R$^{12a}$ and R$^{12b}$, when present, is methyl.

In a further aspect, R$^{12a}$, when present, is hydrogen and R$^{12b}$, when present, is selected from hydrogen, methyl, and ethyl. In a still further aspect, R$^{12a}$, when present, is hydrogen and R$^{12b}$, when present, is selected from hydrogen and methyl. In a yet further aspect, R$^{12a}$, when present, is hydrogen and R$^{12b}$, when present, is selected from hydrogen and ethyl.

In a further aspect, R$^{12a}$, when present, is hydrogen and R$^{12b}$, when present, is C1-C3 alkyl. In a still further aspect, R$^{12a}$, when present, is hydrogen and R$^{12b}$, when present, is selected from methyl and ethyl. In a yet further aspect, R$^{12a}$, when present, is hydrogen and R$^{12b}$, when present, is ethyl. In an even further aspect, R$^{12a}$, when present, is hydrogen and R$^{12b}$, when present, is methyl.

k. R$^{13}$ Groups

In one aspect, R$^{13}$, when present, is selected from —NH$_2$, —OH, —(C═O)OR$^{10}$, —(C═O)NR$^{14a}$R$^{14b}$, —(C═O)—(C1-C3 alkyl)-OR$^{10}$, —(C═O)—(C1-C3 alkyl)-NR$^{14a}$R$^{14b}$, and —Cy$^1$.

In a further aspect, R$^{13}$, when present, is selected from —NH$_2$, —OH, —(C═O)OCH$_3$, —(C═O)OCH$_2$CH$_3$, —(C═O)NH$_2$, —(C═O)NHCH$_3$, —(C═O)N(CH$_3$)$_2$, —(C═O)NHCH$_2$CH$_3$, —(C═O)N(CH$_3$)CH$_2$CH$_3$, —(C═O)—(CH$_2$)$_2$—OCH$_3$, —(C═O)—(CH$_2$)$_2$—OCH$_2$CH$_3$, —(C═O)—(CH$_2$)—OCH$_3$, —(C═O)—(CH$_2$)—OCH$_2$CH$_3$, —(C═O)—(CH$_2$)$_2$—NH$_2$, —(C═O)—(CH$_2$)$_2$—NHCH$_3$, —(C═O)—(CH$_2$)$_2$—N(CH$_3$)$_2$, —(C═O)—(CH$_2$)$_2$—NHCH$_2$CH$_3$, —(C═O)—(CH$_2$)$_2$—N(CH$_3$)CH$_2$CH$_3$, -morpholinyl, -piperidinyl, -tetrahydrofuranyl, and -piperazinyl.

l. R$^{14a}$ and R$^{4b}$ Groups

In one aspect, each of R$^{14a}$ and R$^{14b}$, when present, is independently selected from hydrogen and C1-C3 alkyl. In a further aspect, each of R$^{14a}$ and R$^{14b}$, when present, is hydrogen.

In a further aspect, each of R$^{14a}$ and R$^{14b}$, when present, is independently selected from hydrogen, methyl, and ethyl. In a still further aspect, each of R$^{14a}$ and R$^{14b}$, when present, is independently selected from hydrogen and methyl. In a yet further aspect, each of R$^{14a}$ and R$^{14b}$, when present, is independently selected from hydrogen and ethyl.

In a further aspect, each of R$^{14a}$ and R$^{14b}$, when present, is independently is C1-C3 alkyl. In a still further aspect, each of R$^{14a}$ and R$^{14b}$, when present, is independently selected from methyl and ethyl. In a yet further aspect, each of R$^{14a}$ and $R^{14b}$, when present, is selected is ethyl. In an even further aspect, each of $R^{14a}$ and $R^{14b}$, when present, is methyl.

In a further aspect, $R^{14a}$, when present, is hydrogen and $R^{14b}$, when present, is selected from hydrogen, methyl, and ethyl. In a still further aspect, $R^{14a}$, when present, is hydrogen and $R^{14b}$, when present, is selected from hydrogen and methyl. In a yet further aspect, $R^{14a}$, when present, is hydrogen and $R^{14b}$, when present, is selected from hydrogen and ethyl.

In a further aspect, $R^{14a}$, when present, is hydrogen and $R^{14b}$, when present, is C1-C3 alkyl. In a still further aspect, $R^{14a}$, when present, is hydrogen and $R^{14b}$, when present, is selected from methyl and ethyl. In a yet further aspect, $R^{12a}$, when present, is hydrogen and $R^{14b}$, when present, is ethyl. In an even further aspect, $R^{14a}$, when present, is hydrogen and $R^{14b}$, when present, is methyl.

m. $R^{20}$ Groups

In one aspect, $R^{20}$, when present, is selected from hydrogen and C1-C3 alkyl. In a further aspect, $R^{20}$, when present, is hydrogen.

In a further aspect, $R^{20}$, when present, is selected from hydrogen, methyl, and ethyl. In a still further aspect, $R^{20}$, when present, is selected from hydrogen and methyl. In a yet further aspect, $R^{20}$, when present, is selected from hydrogen and ethyl.

In a further aspect, $R^{20}$, when present, is C1-C3 alkyl. In a still further aspect, $R^{20}$, when present, is selected from methyl and ethyl. In a yet further aspect, $R^{20}$, when present, is ethyl. In an even further aspect, $R^{20}$, when present, is methyl.

n. $R^{21a}$ and $R^{21b}$ Groups

In one aspect, each of $R^{21a}$ and $R^{21b}$, when present, is independently selected from hydrogen and C1-C3 alkyl. In a further aspect, each of $R^{21a}$ and $R^{21b}$, when present, is hydrogen.

In a further aspect, each of $R^{21a}$ and $R^{21b}$, when present, is independently selected from hydrogen, methyl, and ethyl. In a still further aspect, each of $R^{21a}$ and $R^{21b}$, when present, is independently selected from hydrogen and methyl. In a yet further aspect, each of $R^{21a}$ and $R^{21b}$, when present, is independently selected from hydrogen and ethyl.

In a further aspect, each of $R^{21a}$ and $R^{21b}$, when present, is independently is C1-C3 alkyl. In a still further aspect, each of $R^{21a}$ and $R^{21b}$, when present, is independently selected from methyl and ethyl. In a yet further aspect, each of $R^{21a}$ and $R^{21b}$, when present, is selected is ethyl. In an even further aspect, each of $R^{21a}$ and $R^{21b}$, when present, is methyl.

In a further aspect, $R^{21a}$, when present, is hydrogen and $R^{21b}$, when present, is selected from hydrogen, methyl, and ethyl. In a still further aspect, $R^{21a}$, when present, is hydrogen and $R^{21b}$, when present, is selected from hydrogen and methyl. In a yet further aspect, $R^{21a}$, when present, is hydrogen and $R^{21b}$, when present, is selected from hydrogen and ethyl.

In a further aspect, $R^{21a}$, when present, is hydrogen and $R^{21b}$, when present, is C1-C3 alkyl. In a still further aspect, $R^{21a}$, when present, is hydrogen and $R^{21b}$, when present, is selected from methyl and ethyl. In a yet further aspect, $R^{21a}$, when present, is hydrogen and $R^{21b}$, when present, is ethyl. In an even further aspect, $R^{21a}$, when present, is hydrogen and $R^{21b}$, when present, is methyl.

o. $R^{30}$ Groups

In one aspect, $R^{30}$, when present, is selected from hydrogen and C1-C3 alkyl. In a further aspect, $R^{30}$, when present, is hydrogen.

In a further aspect, $R^{30}$, when present, is selected from hydrogen, methyl, and ethyl. In a still further aspect, $R^{30}$, when present, is selected from hydrogen and methyl. In a yet further aspect, $R^{30}$, when present, is selected from hydrogen and ethyl.

In a further aspect, $R^{30}$, when present, is C1-C3 alkyl. In a still further aspect, $R^{30}$, when present, is selected from methyl and ethyl. In a yet further aspect, $R^{30}$, when present, is ethyl. In an even further aspect, $R^{30}$, when present, is methyl.

p. $R^{31}$ Groups

In one aspect, $R^{31}$, when present, is selected from hydrogen and C1-C3 alkyl. In a further aspect, $R^{31}$, when present, is hydrogen.

In a further aspect, $R^{31}$, when present, is selected from hydrogen, methyl, and ethyl. In a still further aspect, $R^{31}$, when present, is selected from hydrogen and methyl. In a yet further aspect, $R^{31}$, when present, is selected from hydrogen and ethyl.

In a further aspect, $R^{31}$, when present, is C1-C3 alkyl. In a still further aspect, $R^{31}$, when present, is selected from methyl and ethyl. In a yet further aspect, $R^{31}$, when present, is ethyl. In an even further aspect, $R^{31}$, when present, is methyl.

q. $R^{32a}$ and $R^{32b}$ Groups

In one aspect, each of $R^{32a}$ and $R^{32b}$, when present, is independently selected from hydrogen and C1-C3 alkyl. In a further aspect, each of $R^{32a}$ and $R^{32b}$, when present, is hydrogen.

In a further aspect, each of $R^{32a}$ and $R^{32b}$, when present, is independently selected from hydrogen, methyl, and ethyl. In a still further aspect, each of $R^{32a}$ and $R^{32b}$, when present, is independently selected from hydrogen and methyl. In a yet further aspect, each of $R^{32a}$ and $R^{32b}$, when present, is independently selected from hydrogen and ethyl.

In a further aspect, each of $R^{32a}$ and $R^{32b}$, when present, is independently is C1-C3 alkyl. In a still further aspect, each of $R^{32a}$ and $R^{32b}$, when present, is independently selected from methyl and ethyl. In a yet further aspect, each of $R^{32a}$ and $R^{32b}$, when present, is selected is ethyl. In an even further aspect, each of $R^{32a}$ and $R^{32b}$, when present, is methyl.

In a further aspect, $R^{32a}$, when present, is hydrogen and $R^{32b}$, when present, is selected from hydrogen, methyl, and ethyl. In a still further aspect, $R^{32a}$, when present, is hydrogen and $R^{32b}$, when present, is selected from hydrogen and methyl. In a yet further aspect, $R^{32a}$, when present, is hydrogen and $R^{32b}$, when present, is selected from hydrogen and ethyl.

In a further aspect, $R^{32a}$, when present, is hydrogen and $R^{32b}$, when present, is C1-C3 alkyl. In a still further aspect, $R^{32a}$, when present, is hydrogen and $R^{32b}$, when present, is selected from methyl and ethyl. In a yet further aspect, $R^{32a}$, when present, is hydrogen and $R^{32b}$, when present, is ethyl. In an even further aspect, $R^{32a}$, when present, is hydrogen and $R^{32b}$, when present, is methyl.

r. $R^{33}$ Groups

In one aspect, $R^{33}$, when present, is selected from —NH$_2$, —OH, —(C=O)OR$^{30}$, —(C=O)NR$^{34a}$R$^{34b}$, —(C=O)—(C1-C3 alkyl)-OR$^{30}$, —(C=O)—(C1-C3 alkyl)-NR$^{34a}$R$^{34b}$, and Cy$^3$.

In a further aspect, $R^{33}$, when present, is selected from —NH$_2$, —OH, —(C=O)OCH$_3$, —(C=O)OCH$_2$CH$_3$, —(C=O)NH$_2$, —(C=O)NHCH$_3$, —(C=O)N(CH$_3$)$_2$, —(C=O)NHCH$_2$CH$_3$, —(C=O)N(CH$_3$)CH$_2$CH$_3$, —(C=O)—(CH$_2$)$_2$—OCH$_3$, —(C=O)—(CH$_2$)$_2$—OCH$_2$CH$_3$, —(C=O)—(CH$_2$)—OCH$_3$, —(C=O)—

—(CH$_2$)—OCH$_2$CH$_3$, —(C=O)—(CH$_2$)$_2$—NH$_2$, —(C=O)—(CH$_2$)$_2$—NHCH$_3$, —(C=O)—(CH$_2$)$_2$—N(CH$_3$)$_2$, —(C=O)—(CH$_2$)$_2$—NHCH$_2$CH$_3$, —(C=O)—(CH$_2$)$_2$—N(CH$_3$)CH$_2$CH$_3$, -morpholinyl, -piperidinyl, -tetrahydrofuranyl, and -piperazinyl.

s. $R^{40}$ Groups

In one aspect, each occurrence of $R^{40}$, when present, is independently selected from hydrogen and C1-C6 alkyl. In one aspect, each occurrence of $R^{40}$, when present, is independently selected from hydrogen, C1-C6 alkyl, phenyl, benzyl, naphthyl, and monocyclic heteroaryl. In a further aspect, each occurrence of $R^{40}$, when present, is hydrogen.

In a further aspect, each occurrence of $R^{40}$, when present, is independently selected from hydrogen and C1-C6 alkyl. In a still further aspect, each occurrence of $R^{40}$, when present, is independently selected from hydrogen and C1-C3 alkyl. In yet a further aspect, each occurrence of $R^{40}$, when present, is independently selected from hydrogen, methyl, and ethyl. In an even further aspect, each occurrence of $R^{40}$, when present, is independently selected from hydrogen and methyl. In a still further aspect, each occurrence of $R^{40}$, when present, is independently selected from hydrogen and ethyl.

In a further aspect, each occurrence of $R^{40}$, when present, is C1-C6 alkyl. In a still further aspect, each occurrence of $R^{40}$, when present, is C1-C3 alkyl. In yet a further aspect, each occurrence of $R^{40}$, when present, is independently selected from methyl and ethyl. In an even further aspect, each occurrence of $R^{40}$, when present, is methyl. In a still further aspect, each occurrence of $R^{40}$, when present, is ethyl.

In a further aspect, each occurrence of $R^{40}$, when present, is selected from hydrogen, phenyl, benzyl, and naphthyl. In a still further aspect, each occurrence of $R^{40}$, when present, is selected from hydrogen, phenyl, and benzyl. In a yet further aspect, each occurrence of $R^{40}$, when present, is selected from hydrogen, phenyl, and naphthyl. In an even further aspect, each occurrence of $R^{40}$, when present, is selected from hydrogen, benzyl, and naphthyl. In a yet further aspect, each occurrence of $R^{40}$, when present, is hydrogen or phenyl. In an even further aspect, each occurrence of $R^{40}$, when present, is hydrogen or benzyl. In a still further aspect, each occurrence of $R^{40}$, when present, is hydrogen or naphthyl.

In a further aspect, each occurrence of $R^{40}$, when present, is selected from phenyl, benzyl, and naphthyl. In a still further aspect, each occurrence of $R^{40}$, when present, is selected from phenyl and benzyl. In a yet further aspect, each occurrence of $R^{40}$, when present, is selected from phenyl and naphthyl. In an even further aspect, each occurrence of $R^{40}$, when present, is selected from benzyl and naphthyl. In a yet further aspect, each occurrence of $R^{40}$, when present, is phenyl. In an even further aspect, each occurrence of $R^{40}$, when present, is benzyl. In a still further aspect, each occurrence of $R^{40}$, when present, is naphthyl.

In a further aspect, each occurrence of $R^{40}$, when present, is selected from hydrogen, methyl, ethyl, propyl, isopropyl, butyl, isobutyl, sec-butyl, phenyl, benzyl, and naphthyl. In a still further aspect, each occurrence of $R^{40}$, when present, is selected from hydrogen, methyl, ethyl, propyl, isopropyl, butyl, isobutyl, sec-butyl, phenyl, and benzyl. In a yet further aspect, each occurrence of $R^{40}$, when present, is selected from hydrogen, methyl, ethyl, propyl, isopropyl, butyl, isobutyl, sec-butyl, and phenyl. In an even further aspect, each occurrence of $R^{40}$, when present, is selected from hydrogen, methyl, ethyl, propyl, isopropyl, butyl, isobutyl, sec-butyl, and benzyl. In an even further aspect, each occurrence of $R^{40}$, when present, is selected from hydrogen, methyl, ethyl, propyl, isopropyl, butyl, isobutyl, sec-butyl, and naphthyl.

In a further aspect, each occurrence of $R^{40}$, when present, is selected from methyl, ethyl, propyl, isopropyl, butyl, isobutyl, sec-butyl, phenyl, benzyl, and naphthyl. In a still further aspect, each occurrence of $R^{40}$, when present, is selected from methyl, ethyl, propyl, isopropyl, butyl, isobutyl, sec-butyl, phenyl, and benzyl. In a yet further aspect, each occurrence of $R^{40}$, when present, is selected from methyl, ethyl, propyl, isopropyl, butyl, isobutyl, sec-butyl, and phenyl. In an even further aspect, each occurrence of $R^{40}$, when present, is selected from methyl, ethyl, propyl, isopropyl, butyl, isobutyl, sec-butyl, and benzyl. In an even further aspect, each occurrence of $R^{40}$, when present, is selected from methyl, ethyl, propyl, isopropyl, butyl, isobutyl, sec-butyl, and naphthyl.

In a further aspect, each occurrence of $R^{40}$, when present, is selected from hydrogen and monocyclic heteroaryl. In a still further aspect, each occurrence of $R^{40}$, when present, is selected from hydrogen, pyrrole, furan, thiophene, imidazole, pyrazole, oxazole, isoxazole, thiazole, isothiazole, and pyridine. In yet a further aspect, each occurrence of $R^{40}$, when present, is selected from hydrogen, pyrrole, furan, thiophene, and pyridine. In an even further aspect, each occurrence of $R^{40}$, when present, is selected from hydrogen, pyrrole, furan, and thiophene. In a still further aspect, each occurrence of $R^{40}$, when present, is pyrrole. In yet a further aspect, each occurrence of $R^{40}$, when present, is furan. In an even further aspect, each occurrence of $R^{40}$, when present, is thiophene. In a still further aspect, each occurrence of $R^{40}$, when present, is pyridine.

t. $R^{41a}$ and $R^{41b}$ Groups

In one aspect, each occurrence of $R^{41a}$ and $R^{41b}$, when present, is independently selected from hydrogen and C1-C6 alkyl. In various aspects, each occurrence of $R^{41a}$ and $R^{41b}$, when present, is independently selected from hydrogen, C1-C6 alkyl, phenyl, benzyl, naphthyl, and monocyclic heteroaryl. In a further aspect, each occurrence of $R^{41a}$ and $R^{41b}$, when present, is hydrogen.

In a further aspect, each occurrence of $R^{41a}$ and $R^{41b}$, when present, is independently selected from hydrogen and C1-C6 alkyl. In a still further aspect, each occurrence of $R^{41a}$ and $R^{41b}$, when present, is independently selected from hydrogen and C1-C3 alkyl. In yet a further aspect, each occurrence of $R^{41a}$ and $R^{41b}$, when present, is independently selected from hydrogen, methyl, and ethyl. In an even further aspect, each occurrence of $R^{41a}$ and $R^{41b}$, when present, is independently selected from hydrogen and methyl. In a still further aspect, each occurrence of $R^{41a}$ and $R^{41b}$, when present, is independently selected from hydrogen and ethyl.

In a further aspect, each occurrence of $R^{41a}$ and $R^{41b}$, when present, is independently selected from C1-C6 alkyl. In a still further aspect, each occurrence of $R^{41a}$ and $R^{41b}$, when present, is independently selected from C1-C3 alkyl. In yet a further aspect, each occurrence of $R^{41a}$ and $R^{41b}$, when present, is independently selected from methyl and ethyl. In an even further aspect, each occurrence of $R^{41a}$ and $R^{41b}$, when present, is methyl. In a still further aspect, each occurrence of $R^{41a}$ and $R^{41b}$, when present, is ethyl.

In a further aspect, each occurrence of $R^{41a}$ and $R^{41b}$, when present, is selected from hydrogen, phenyl, benzyl, and naphthyl. In a still further aspect, each occurrence of $R^{41a}$ and $R^{41b}$, when present, is selected from hydrogen, phenyl, and benzyl. In a yet further aspect, each occurrence of $R^{41a}$ and $R^{41b}$, when present, is selected from hydrogen, phenyl, and naphthyl. In an even further aspect, each occurrence of $R^{41a}$ and $R^{41b}$, when present, is selected from hydrogen, benzyl, and naphthyl. In a yet further aspect, each occurrence of $R^{41a}$ and $R^{41b}$, when present, is hydrogen or phenyl. In an even further aspect, each occurrence of $R^{41a}$ and $R^{41b}$, when present, is hydrogen or benzyl. In a still further aspect, each occurrence of $R^{41a}$ and $R^{41b}$, when present, is hydrogen or naphthyl.

In a further aspect, each occurrence of $R^{41a}$ and $R^{41b}$, when present, is selected from phenyl, benzyl, and naphthyl. In a still further aspect, each occurrence of $R^{41a}$ and $R^{41b}$, when present, is selected from phenyl and benzyl. In a yet further aspect, each occurrence of $R^{41a}$ and $R^{41b}$, when present, is selected from phenyl and naphthyl. In an even further aspect, each occurrence of $R^{41a}$ and $R^{41b}$, when present, is selected from benzyl and naphthyl. In a yet further aspect, each occurrence of $R^{41a}$ and $R^{41b}$, when present, is phenyl. In an even further aspect, each occurrence of $R^{41a}$ and $R^{41b}$, when present, is benzyl. In a still further aspect, each occurrence of $R^{41a}$ and $R^{41b}$, when present, is naphthyl.

In a further aspect, each occurrence of $R^{41a}$ and $R^{41b}$, when present, is selected from hydrogen, methyl, ethyl, propyl, isopropyl, butyl, isobutyl, sec-butyl, phenyl, benzyl, and naphthyl. In a still further aspect, each occurrence of $R^{41a}$ and $R^{41b}$, when present, is selected from hydrogen, methyl, ethyl, propyl, isopropyl, butyl, isobutyl, sec-butyl, phenyl, and benzyl. In a yet further aspect, each occurrence of $R^{41a}$ and $R^{41b}$, when present, is selected from hydrogen, methyl, ethyl, propyl, isopropyl, butyl, isobutyl, sec-butyl, and phenyl. In an even further aspect, each occurrence of $R^{41a}$ and $R^{41b}$, when present, is selected from hydrogen, methyl, ethyl, propyl, isopropyl, butyl, isobutyl, sec-butyl, and benzyl. In an even further aspect, each occurrence of $R^{41a}$ and $R^{41b}$, when present, is selected from hydrogen, methyl, ethyl, propyl, isopropyl, butyl, isobutyl, sec-butyl, and naphthyl.

In a further aspect, each occurrence of $R^{41a}$ and $R^{41b}$, when present, is selected from methyl, ethyl, propyl, isopropyl, butyl, isobutyl, sec-butyl, phenyl, benzyl, and naphthyl. In a still further aspect, each occurrence of $R^{41a}$ and $R^{41b}$, when present, is selected from methyl, ethyl, propyl, isopropyl, butyl, isobutyl, sec-butyl, phenyl, and benzyl. In a yet further aspect, each occurrence of $R^{41a}$ and $R^{41b}$, when present, is selected from methyl, ethyl, propyl, isopropyl, butyl, isobutyl, sec-butyl, and phenyl. In an even further aspect, each occurrence of $R^{41a}$ and $R^{41b}$, when present, is selected from methyl, ethyl, propyl, isopropyl, butyl, isobutyl, sec-butyl, and benzyl. In an even further aspect, each occurrence of $R^{41a}$ and $R^{41b}$, when present, is selected from methyl, ethyl, propyl, isopropyl, butyl, isobutyl, sec-butyl, and naphthyl.

In a further aspect, each occurrence of $R^{41a}$ and $R^{41b}$, when present, is selected from hydrogen and monocyclic heteroaryl. In a still further aspect, each occurrence of $R^{41a}$ and $R^{41b}$, when present, is selected from hydrogen, pyrrole, furan, thiophene, imidazole, pyrazole, oxazole, isoxazole, thiazole, isothiazole, and pyridine. In yet a further aspect, each occurrence of $R^{41a}$ and $R^{41b}$, when present, is selected from hydrogen, pyrrole, furan, thiophene, and pyridine. In an even further aspect, each occurrence of $R^{41a}$ and $R^{41b}$, when present, is selected from hydrogen, pyrrole, furan, and thiophene. In a still further aspect, each occurrence of $R^{41a}$ and $R^{41b}$, when present, is pyrrole. In yet a further aspect, each occurrence of $R^{41a}$ and $R^{41b}$, when present, is furan. In an even further aspect, each occurrence of $R^{41a}$ and $R^{41b}$, when present, is thiophene. In a still further aspect, each occurrence of $R^{41a}$ and $R^{41b}$, when present, is pyridine.

u. $R^{42}$ Groups

In one aspect, each occurrence of $R^{42}$, when present, is independently selected from hydrogen and C1-C6 alkyl. In a further aspect, each occurrence of $R^{42}$, when present, is hydrogen.

In a further aspect, each occurrence of $R^{42}$, when present, is independently selected from hydrogen, methyl, ethyl, propyl, and isopropyl. In a further aspect, each occurrence of $R^{42}$, when present, is independently selected from hydrogen, methyl, and ethyl. In a still further aspect, each occurrence of $R^{42}$, when present, is independently selected from hydrogen and methyl. In an even further aspect, each occurrence of $R^{42}$, when present, is independently selected from hydrogen and ethyl.

In a further aspect, each occurrence of $R^{42}$, when present, is independently selected from methyl, ethyl, propyl, and isopropyl. In a further aspect, each occurrence of $R^{42}$, when present, is independently selected from methyl and ethyl. In a still further aspect, each occurrence of $R^{42}$, when present, is methyl. In an even further aspect, each occurrence of $R^{42}$, when present, is ethyl.

v. $R^{43}$ Groups

In one aspect, each occurrence of $R^{43}$, when present, is independently selected from hydrogen and C1-C6 alkyl. In a further aspect, each occurrence of $R^{43}$, when present, is hydrogen.

In a further aspect, each occurrence of $R^{43}$, when present, is independently selected from hydrogen, methyl, ethyl, propyl, and isopropyl. In a further aspect, each occurrence of $R^{43}$, when present, is independently selected from hydrogen, methyl, and ethyl. In a still further aspect, each occurrence of $R^{43}$, when present, is independently selected from hydrogen and methyl. In an even further aspect, each occurrence of $R^{43}$, when present, is independently selected from hydrogen and ethyl.

In a further aspect, each occurrence of $R^{43}$, when present, is independently selected from methyl, ethyl, propyl, and isopropyl. In a further aspect, each occurrence of $R^{43}$, when present, is independently selected from methyl and ethyl. In a still further aspect, each occurrence of $R^{43}$, when present, is methyl. In an even further aspect, each occurrence of $R^{43}$, when present, is ethyl.

w. $R^{44a}$ and $R^{44b}$ Groups

In one aspect, each occurrence of $R^{44a}$ and $R^{44b}$, when present, is independently selected from hydrogen and C1-C6 alkyl. In a further aspect, each occurrence of $R^{44a}$ and $R^{44b}$, when present, is hydrogen.

In a further aspect, each occurrence of $R^{44a}$ and $R^{44b}$, when present, is independently selected from hydrogen, methyl, ethyl, propyl, and isopropyl. In a further aspect, each occurrence of $R^{44a}$ and $R^{44b}$, when present, is independently selected from hydrogen, methyl, and ethyl. In a still further aspect, each occurrence of $R^{44a}$ and $R^{44b}$, when present, is independently selected from hydrogen and methyl. In an even further aspect, each occurrence of $R^{44a}$ and $R^{44b}$, when present, is independently selected from hydrogen and ethyl.

In a further aspect, each occurrence of $R^{44a}$ and $R^{44b}$, when present, is independently selected from methyl, ethyl, propyl, and isopropyl. In a further aspect, each occurrence of $R^{44a}$ and $R^{44b}$, when present, is independently selected from methyl and ethyl. In a still further aspect, each occurrence of $R^{44a}$ and $R^{44b}$, when present, is methyl. In an even further aspect, each occurrence of $R^{44a}$ and $R^{44b}$, when present, is ethyl.

x. $R^{45}$ Groups

In one aspect, each occurrence of $R^{45}$, when present, is independently selected from hydrogen and C1-C6 alkyl. In a further aspect, each occurrence of $R^{45}$, when present, is hydrogen.

In a further aspect, each occurrence of $R^{45}$, when present, is independently selected from hydrogen, methyl, ethyl, propyl, and isopropyl. In a further aspect, each occurrence of $R^{45}$, when present, is independently selected from hydrogen, methyl, and ethyl. In a still further aspect, each occurrence of $R^{45}$, when present, is independently selected from hydrogen and methyl. In an even further aspect, each occurrence of $R^{45}$, when present, is independently selected from hydrogen and ethyl.

In a further aspect, each occurrence of $R^{45}$, when present, is independently selected from methyl, ethyl, propyl, and isopropyl. In a further aspect, each occurrence of $R^{45}$, when present, is independently selected from methyl and ethyl. In a still further aspect, each occurrence of $R^{45}$, when present, is methyl. In an even further aspect, each occurrence of $R^{45}$, when present, is ethyl.

y. $R^{46}$ Groups

In one aspect, each occurrence of $R^{46}$, when present, is independently selected from hydrogen and C1-C6 alkyl. In a further aspect, each occurrence of $R^{46}$, when present, is hydrogen.

In a further aspect, each occurrence of $R^{46}$, when present, is independently selected from hydrogen, methyl, ethyl, propyl, and isopropyl. In a further aspect, each occurrence of $R^{46}$, when present, is independently selected from hydrogen, methyl, and ethyl. In a still further aspect, each occurrence of $R^{46}$, when present, is independently selected from hydrogen and methyl. In an even further aspect, each occurrence of $R^{46}$, when present, is independently selected from hydrogen and ethyl.

In a further aspect, each occurrence of $R^{46}$, when present, is independently selected from methyl, ethyl, propyl, and isopropyl. In a further aspect, each occurrence of $R^{46}$, when present, is independently selected from methyl and ethyl. In a still further aspect, each occurrence of $R^{46}$, when present, is methyl. In an even further aspect, each occurrence of $R^{46}$, when present, is ethyl.

z. $R^{50a}$, $R^{50b}$, $R^{50c}$, $R^{50d}$, $R^{50e}$, $R^{50f}$, $R^{50g}$, and $R^{50h}$ Groups In one aspect, each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, halogen, —NH$_2$, —OH, —C1-C3 alkylamino, C1-C3 dialkylamino, C1-C6 hydroxyalkyl, —(C=O)OR$^{30}$, —(C=O)NR$^{32a}$R$^{32b}$, —(C1-C3 alkyl)-(C=O)OR$^{30}$, —(C1-C3 alkyl)-(C=O)NR$^{32a}$R$^{32b}$, —C(NR$^{32a}$R$^{32b}$)R$^{31}$—(C1-C3 alkyl)-R$^{33}$, and —(C1-C3 alkyl)-R$^{33}$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen.

In a further aspect, each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, methyl, ethyl, —CH$_2$OH, —(CH$_2$)$_2$OH, —(CHOH)CH$_3$, —(CH$_2$)$_2$—(C=O)OCH$_2$CH$_3$, —(CH$_2$)$_2$—(C=O)OCH$_3$, —(CH$_2$)$_2$—(C=O)OCH$_2$CH$_3$, —(CH$_2$)—(C=O)OCH$_3$, —(CH$_2$)$_2$—(C=O)NHCH$_3$, —(CH$_2$)$_2$—(C=O)N(CH$_3$)$_2$, —(CH$_2$)$_2$—(C=O)NHCH$_2$CH$_3$, —(CH$_2$)—(C=O)NHCH$_3$, —(CH$_2$)—(C=O)N(CH$_3$)$_2$, —(CH$_2$)—(C=O)NHCH$_2$CH$_3$, —(CH$_2$)—(C=O)N(CH$_3$)CH$_2$CH$_3$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen.

In a further aspect, each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, —(CH$_2$)$_2$—NH$_2$, —(CH$_2$)$_2$—OH, —(CH$_2$)$_2$—(C=O)OCH$_3$, —(CH$_2$)$_2$—(C=O)OCH$_2$CH$_3$, —(CH$_2$)$_2$—(C=O)NH$_2$, —(CH$_2$)$_2$—(C=O)NHCH$_3$, —(CH$_2$)$_2$—(C=O)N(CH$_3$)$_2$, —(CH$_2$)$_2$—(C=O)NHCH$_2$CH$_3$, —(CH$_2$)$_2$—(C=O)N(CH$_3$)CH$_2$CH$_3$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen.

In a further aspect, each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, —(CH$_2$)$_2$—(C=O)—(CH$_2$)$_2$—OCH$_3$, —(CH$_2$)$_2$—(C=O)—(CH$_2$)$_2$—OCH$_2$CH$_3$, —(CH$_2$)$_2$—(C=O)—(CH$_2$)—OCH$_3$, —(CH$_2$)$_2$—(C=O)—(CH$_2$)—OCH$_2$CH$_3$, —(CH$_2$)$_2$—(C=O)—(CH$_2$)$_2$—NH$_2$, —(CH$_2$)$_2$—(C=O)—(CH$_2$)$_2$—NHCH$_3$, —(CH$_2$)$_2$—(C=O)—(CH$_2$)$_2$—N(CH$_3$)$_2$, —(CH$_2$)$_2$—(C=O)—(CH$_2$)$_2$—NHCH$_2$CH$_3$, —(CH$_2$)$_2$—(C=O)—(CH$_2$)$_2$—N(CH$_3$)CH$_2$CH$_3$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen.

In a further aspect, each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, —(CH$_2$)$_2$-morpholinyl, —(CH$_2$)$_2$-piperidinyl, —(CH$_2$)$_2$-tetrahydrofuranyl, and —(CH$_2$)$_2$-piperazinyl, provided that no more than three of $R^{50a}$, $R^{50b}$, $R^{50c}$, $R^{50d}$, $R^{50e}$, $R^{50f}$, $R^{50g}$, and $R^{50h}$ are not hydrogen.

In a further aspect, each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, —(CH$_2$)—NH$_2$, —(CH$_2$)—OH, —(CH$_2$)—(C=O)OCH$_3$, —(CH$_2$)—(C=O)OCH$_2$CH$_3$, —(CH$_2$)—(C=O)NH$_2$, —(CH$_2$)—(C=O)NHCH$_3$, —(CH$_2$)—(C=O)N(CH$_3$)$_2$, —(CH$_2$)—(C=O)NHCH$_2$CH$_3$, —(CH$_2$)—(C=O)N(CH$_3$)CH$_2$CH$_3$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen.

In a further aspect, each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, —(CH$_2$)—(C=O)—(CH$_2$)$_2$—OCH$_3$, —(CH$_2$)—(C=O)—(CH$_2$)$_2$—OCH$_2$CH$_3$, —(CH$_2$)—(C=O)—(CH$_2$)—OCH$_3$, —(CH$_2$)—(C=O)—(CH$_2$)—OCH$_2$CH$_3$, —(CH$_2$)—(C=O)—(CH$_2$)$_2$—NH$_2$, —(CH$_2$)—(C=O)—(CH$_2$)$_2$—NHCH$_3$, —(CH$_2$)—(C=O)—(CH$_2$)$_2$—N(CH$_3$)$_2$, —(CH$_2$)—(C=O)—(CH$_2$)$_2$—NHCH$_2$CH$_3$, —(CH$_2$)—(C=O)—(CH$_2$)$_2$—N(CH$_3$)CH$_2$CH$_3$, provided that no more than three of $R^{50a}$, $R^{50b}$, $R^{50c}$, $R^{50d}$, $R^{50e}$, $R^{50f}$, $R^{50g}$, and $R^{50h}$ are not hydrogen.

In a further aspect, each of $R^{50a}$, $R^{50b}$, $R^{50c}$, $R^{50d}$, $R^{50e}$, $R^{50f}$, $R^{50g}$, and $R^{50h}$, when present, is independently selected from hydrogen, —(CH$_2$)-morpholinyl, —(CH$_2$)-piperidinyl, —(CH$_2$)-tetrahydrofuranyl, and —(CH$_2$)-piperazinyl, provided that no more than three of $R^{50a}$, $R^{50b}$, $R^{50c}$, $R^{50d}$, $R^{50e}$, $R^{50f}$, $R^{50g}$, and $R^{50h}$ are not hydrogen.

aa. $R^{60a}$, $R^{60b}$, $R^{60c}$, $R^{60d}$, and $R^{60e}$ Groups

In one aspect, each of $R^{60a}$, $R^{60b}$, $R^{60c}$, $R^{60d}$, and $R^{60e}$, when present, is independently selected from hydrogen, halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$, provided that no more than three of $R^{60a}$, $R^{60b}$, $R^{60c}$, $R^{60d}$, and $R^{60e}$ are not hydrogen.

In a further aspect, each of $R^{60a}$, $R^{60b}$, $R^{60c}$, $R^{60d}$, and $R^{60e}$, when present, is independently selected from hydrogen, —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, —N(CH$_3$)CH$_2$CH$_3$, —SO$_2$H, —SO$_2$CH$_3$, —SO$_2$NH$_2$, —SO$_2$NHCH$_3$, —SO$_2$N(CH$_3$)$_2$, —(C=O)

NH$_2$, —(C=O)NHCH$_3$, —(C=O)N(CH$_3$)$_2$, —NH(C=O)NH$_2$, —NH(C=O)NHCH$_3$, —NH(C=O)N(CH$_3$)$_2$, —NH(C=O)H, —NH(C=O)CH$_3$, —NH(C=O)CH$_2$CH$_3$, —(C=O)OH, —(C=O)OCH$_3$, —(C=O)OCH$_2$CH$_3$, and Ar$^2$, provided that no more than three of R$^{60a}$, R$^{60b}$, R$^{60c}$, R$^{60d}$, and R$^{60e}$ are not hydrogen.

In a further aspect, each of R$^{60a}$, R$^{60b}$, R$^{60c}$, R$^{60d}$, and R$^{60e}$, when present, is independently selected from hydrogen, —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, —N(CH$_3$)CH$_2$CH$_3$, —SO$_2$H, —SO$_2$CH$_3$, —SO$_2$NH$_2$, —SO$_2$NHCH$_3$, —SO$_2$N(CH$_3$)$_2$, —(C=O)NH$_2$, —(C=O)NHCH$_3$, —(C=O)N(CH$_3$)$_2$, —NH(C=O)NH$_2$, —NH(C=O)NHCH$_3$, —NH(C=O)N(CH$_3$)$_2$, —NH(C=O)H, —NH(C=O)CH$_3$, —NH(C=O)CH$_2$CH$_3$, —(C=O)OH, —(C=O)OCH$_3$, and —(C=O)OCH$_2$CH$_3$, provided that no more than three of R$^{60a}$, R$^{60b}$, R$^{60c}$, R$^{60d}$, and R$^{60e}$ are not hydrogen.

In a further aspect, each of R$^{60a}$, R$^{60b}$, R$^{60c}$, R$^{60d}$, and R$^{60e}$, when present, is independently selected from hydrogen, —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, and —N(CH$_3$)CH$_2$CH$_3$, provided that no more than three of R$^{60a}$, R$^{60b}$, R$^{60c}$, R$^{60d}$, and R$^{60e}$ are not hydrogen.

bb. R$^{70a}$ and R$^{70b}$ Groups

In one aspect, each of R$^{70a}$ and R$^{70b}$ is independently selected from hydrogen, methyl, and ethyl. In a further aspect, each of R$^{70a}$ and R$^{70b}$ is hydrogen.

In a further aspect, each of R$^{70a}$ and R$^{70b}$ is independently selected from hydrogen and methyl. In a still further aspect, each of R$^{70a}$ and R$^{70b}$ is independently selected from hydrogen and ethyl. In yet a further aspect, each of R$^{70a}$ and R$^{70b}$ is methyl. In an even further aspect, each of R$^{70a}$ and R$^{70b}$ is ethyl.

In a further aspect, R$^{70a}$ is hydrogen and R$^{70b}$ is selected from methyl and ethyl. In a still further aspect, R$^{70a}$ is hydrogen and R$^{70b}$ is methyl. In yet a further aspect, R$^{70a}$ is hydrogen and R$^{70b}$ is ethyl.

In a further aspect, R$^{70b}$ is hydrogen and R$^{70a}$ is selected from methyl and ethyl. In a still further aspect, R$^{70b}$ is hydrogen and R$^{70a}$ is methyl. In yet a further aspect, R$^{70b}$ is hydrogen and R$^{70a}$ is ethyl.

cc. Ar$^1$ Groups

In one aspect, Ar$^1$ is selected from aryl and heteroaryl; and wherein Ar$^1$ is substituted with 0, 1, 2, or 3 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In a further aspect, Ar$^1$ is selected from aryl and heteroaryl; and wherein Ar$^1$ is substituted with 0, 1, 2, or 3 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, and —(C=O)OR$^{46}$. In a still further aspect, Ar$^1$ is selected from aryl and heteroaryl; and wherein Ar$^1$ is substituted with 0, 1, 2, or 3 groups independently selected from —F, —NH$_2$, —OH, —NO$_2$, difluoromethoxy, trifluoromethoxy, C1-C3 alkyl, C1-C3 monohaloalkyl, C1-C3 alkoxy, C1-C3 alkylamino, C1-C3 dialkylamino, —SO$_2$R$^{40}$, —SO$_2$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, and —(C=O)OR$^{46}$. In a yet further aspect, Ar$^1$ is selected from aryl and heteroaryl, and wherein Ar$^1$ is unsubstituted.

In a further aspect, Ar$^1$ is selected from phenyl, pyridinyl, pyrimidinyl, indolinyl, indolyl, oxazolyl, thiazolyl, isoxazolyl, and pyrazolyl; and wherein Ar$^1$ is substituted with 0, 1, 2, or 3 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, and —(C=O)OR$^{46}$. In a still further aspect, Ar$^1$ is selected from phenyl, pyridinyl, pyrimidinyl, indolinyl, indolyl, oxazolyl, thiazolyl, isoxazolyl, and pyrazolyl; and wherein Ar$^1$ is substituted with 0, 1, 2, or 3 groups independently selected from —F, —NH$_2$, —OH, —NO$_2$, difluoromethoxy, trifluoromethoxy, C1-C3 alkyl, C1-C6 monohaloalkyl, C1-C3 alkoxy, C1-C3 alkylamino, C1-C3 dialkylamino, —SO$_2$R$^{40}$, —SO$_2$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, and —(C=O)OR$^{46}$. In a yet further aspect, Ar$^1$ is selected from phenyl, pyridinyl, pyrimidinyl, indolinyl, indolyl, oxazolyl, thiazolyl, isoxazolyl, and pyrazolyl; and wherein Ar$^1$ is substituted with 0, 1, 2, or 3 groups independently selected from —F, —NH$_2$, —OH, —NO$_2$, difluoromethoxy, trifluoromethoxy, methyl, ethyl, —CH$_2$F, —CHF$_2$, —CF$_3$, —OCH$_3$, —OCH$_2$CH$_3$, —NHCH$_3$, —N(CH$_3$)$_2$, —SO$_2$H, —SO$_2$CH$_3$, —SO$_2$NHCH$_3$, —SO$_2$N(CH$_3$)$_2$, —(C=O)NHCH$_3$, —(C=O)N(CH$_3$)$_2$, —NH(C=O)NHCH$_3$, —NH(C=O)N(CH$_3$)$_2$, —NH(C=O)CH$_3$, —(C=O)OH, and —(C=O)OCH$_3$.

In a further aspect, Ar$^1$ is selected from aryl and heteroaryl; and wherein Ar$^1$ is substituted with 0, 1, or 2 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In a further aspect, Ar$^1$ is selected from aryl and heteroaryl; and wherein Ar$^1$ is substituted with 0 or 1 group selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In one aspect, Ar$^1$ is selected from aryl and heteroaryl; and wherein Ar$^1$ is substituted with 1, 2, or 3 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In one aspect, Ar$^1$ is selected from aryl and heteroaryl; and wherein Ar$^1$ is substituted with 2 or 3 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In one aspect, Ar$^1$ is selected from aryl and heteroaryl; and wherein Ar$^1$ is substituted with 1 or 2 groups independently selected from halogen, —NH$_2$, —OH, —NO$_2$, difluororomethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In one aspect, Ar$^1$ is selected from aryl and heteroaryl; and wherein Ar$^1$ is monosubstituted with a group selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In a further aspect, Ar$^1$ is selected from aryl and heteroaryl; and wherein Ar$^1$ is substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, —N(CH$_3$)CH$_2$CH$_3$, —SO$_2$H, —SO$_2$CH$_3$, —SO$_2$NH$_2$, —SO$_2$NHCH$_3$, —SO$_2$N(CH$_3$)$_2$, —(C=O)NH$_2$, —(C=O)NHCH$_3$, —(C=O)N(CH$_3$)$_2$, —NH(C=O)NH$_2$, —NH(C=O)NHCH$_3$, —NH(C=O)N(CH$_3$)$_2$, —NH(C=O)H, —NH(C=O)CH$_3$, —NH(C=O)CH$_2$CH$_3$, —(C=O)OH, —(C=O)OCH$_3$, —(C=O)OCH$_2$CH$_3$, and Ar$^2$. In a still further aspect, Ar$^1$ is selected from aryl and heteroaryl; and wherein Ar$^1$ is substituted with 0, 1, 2, or 3 groups independently selected from —F, —NH$_2$, —OH, —NO$_2$, difluoromethoxy, trifluoromethoxy, methyl, ethyl, —CH$_2$F, —CHF$_2$, —CF$_3$, —OCH$_3$, —OCH$_2$CH$_3$, —NHCH$_3$, —N(CH$_3$)$_2$, —SO$_2$H, —SO$_2$CH$_3$, —SO$_2$NHCH$_3$, —SO$_2$N(CH$_3$)$_2$, —(C=O)NHCH$_3$, —(C=O)N(CH$_3$)$_2$, —NH(C=O)NHCH$_3$, —NH(C=O)N(CH$_3$)$_2$, —NH(C=O)CH$_3$, —(C=O)OH, and —(C=O)OCH$_3$.

In a further aspect, Ar$^1$ is selected from aryl and heteroaryl; and wherein Ar$^1$ is substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, —N(CH$_3$)CH$_2$CH$_3$, —SO$_2$H, —SO$_2$CH$_3$, —SO$_2$NH$_2$, —SO$_2$NHCH$_3$, —SO$_2$N(CH$_3$)$_2$, —(C=O)NH$_2$, —(C=O)NHCH$_3$, —(C=O)N(CH$_3$)$_2$, —NH(C=O)NH$_2$, —NH(C=O)NHCH$_3$, —NH(C=O)N(CH$_3$)$_2$, —NH(C=O)H, —NH(C=O)CH$_3$, —NH(C=O)CH$_2$CH$_3$, —(C=O)OH, —(C=O)OCH$_3$, and —(C=O)OCH$_2$CH$_3$.

In a further aspect, Ar$^1$ is selected from aryl and heteroaryl; and wherein Ar$^1$ is substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, and —N(CH$_3$)CH$_2$CH$_3$.

In a further aspect, Ar$^1$ is phenyl substituted with 0, 1, 2, or 3 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In a further aspect, Ar$^1$ is phenyl substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, —N(CH$_3$)CH$_2$CH$_3$, —SO$_2$H, —SO$_2$CH$_3$, —SO$_2$NH$_2$, —SO$_2$NHCH$_3$, —SO$_2$N(CH$_3$)$_2$, —(C=O)NH$_2$, —(C=O)NHCH$_3$, —(C=O)N(CH$_3$)$_2$, —NH(C=O)NH$_2$, —NH(C=O)NHCH$_3$, —NH(C=O)N(CH$_3$)$_2$, —NH(C=O)H, —NH(C=O)CH$_3$, —NH(C=O)CH$_2$CH$_3$, —(C=O)OH, —(C=O)OCH$_3$, and —(C=O)OCH$_2$CH$_3$.

In a further aspect, Ar$^1$ is phenyl substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, and —N(CH$_3$)CH$_2$CH$_3$.

In a further aspect, Ar$^1$ is pyridinyl substituted with 0, 1, 2, or 3 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In a further aspect, Ar$^1$ is pyridinyl substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, —N(CH$_3$)CH$_2$CH$_3$, —SO$_2$H, —SO$_2$CH$_3$, —SO$_2$NH$_2$, —SO$_2$NHCH$_3$, —SO$_2$N(CH$_3$)$_2$, —(C=O)NH$_2$, —(C=O)NHCH$_3$, —(C=O)N(CH$_3$)$_2$, —NH(C=O)NH$_2$, —NH(C=O)NHCH$_3$, —NH(C=O)N(CH$_3$)$_2$, —NH(C=O)H, —NH(C=O)CH$_3$, —NH(C=O)CH$_2$CH$_3$, —(C=O)OH, —(C=O)OCH$_3$, —(C=O)OCH$_2$CH$_3$, and Ar$^2$.

In a further aspect, Ar$^1$ is pyridinyl substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, —N(CH$_3$)CH$_2$CH$_3$, —SO$_2$H, —SO$_2$CH$_3$, —SO$_2$NH$_2$, —SO$_2$NHCH$_3$, —SO$_2$N(CH$_3$)$_2$, —(C=O)NH$_2$, —(C=O)NHCH$_3$, —(C=O)N(CH$_3$)$_2$, —NH(C=O)NH$_2$, —NH(C=O)NHCH$_3$, —NH(C=O)N(CH$_3$)$_2$, —NH(C=O)H, —NH(C=O)CH$_3$, —NH(C=O)CH$_2$CH$_3$, —(C=O)OH, —(C=O)OCH$_3$, and —(C=O)OCH$_2$CH$_3$.

In a further aspect, Ar$^1$ is pyridinyl substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, and —N(CH$_3$)CH$_2$CH$_3$.

In a further aspect, Ar$^1$ is pyrimidinyl substituted with 0, 1, 2, or 3 groups independently selected from halogen, —NH$_2$, —OH, —NO$_2$, difluoromethoxy, trifluoromethoxy, C1-C6 alkyl, C1-C6 monohaloalkyl, C1-C6 alkoxy, C1-C6 alkylamino, C1-C6 dialkylamino, —S(O)$_n$R$^{40}$, —S(O)$_n$NR$^{41a}$R$^{41b}$, —(C=O)NR$^{42a}$R$^{42b}$, —NR$^{43}$(C=O)NR$^{44a}$R$^{44b}$, —NR$^{43}$(C=O)R$^{45}$, —(C=O)OR$^{46}$, and Ar$^2$.

In a further aspect, Ar$^1$ is pyrimidinyl substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, —N(CH$_3$)CH$_2$CH$_3$, —SO$_2$H, —SO$_2$CH$_3$, —SO$_2$NH$_2$, —SO$_2$NHCH$_3$, —SO$_2$N(CH$_3$)$_2$, —(C=O)NH$_2$, —(C=O)NHCH$_3$, —(C=O)N(CH$_3$)$_2$, —NH(C=O)NH$_2$, —NH(C=O)NHCH$_3$, —NH(C=O)N(CH$_3$)$_2$, —NH(C=O)H, —NH(C=O)CH$_3$, —NH(C=O)CH$_2$CH$_3$, —(C=O)OH, —(C=O)OCH$_3$, —(C=O)OCH$_2$CH$_3$, and Ar$^2$.

In a further aspect, Ar$^1$ is pyrimidinyl substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, —N(CH$_3$)CH$_2$CH$_3$, —SO$_2$H, —SO$_2$CH$_3$, —SO$_2$NH$_2$, —SO$_2$NHCH$_3$, —SO$_2$N(CH$_3$)$_2$, —(C=O)NH$_2$, —(C=O)NHCH$_3$, —(C=O)N(CH$_3$)$_2$, —NH(C=O)NH$_2$, —NH(C=O)NHCH$_3$, —NH(C=O)N(CH$_3$)$_2$, —NH(C=O)H, —NH(C=O)CH$_3$, —NH(C=O)CH$_2$CH$_3$, —(C=O)OH, —(C=O)OCH$_3$, and —(C=O)OCH$_2$CH$_3$.

In a further aspect, Ar$^1$ is pyrimidinyl substituted with 0, 1, 2, or 3 groups independently selected from —F, —Cl, —Br, —NH$_2$, —OH, —NO$_2$, difluoromethoxy, trifluoromethoxy, methyl, ethyl, —CH$_2$F, —CH$_2$Cl, —OCH$_2$CH$_3$, —OCH$_3$, —N(CH$_3$)$_2$, —NHCH$_3$, —NHCH$_2$CH$_3$, and —N(CH$_3$)CH$_2$CH$_3$.

dd. Ar$^2$ Groups

In one aspect, each Ar$^2$, when present, is independently selected from phenyl, naphthyl, and heteroaryl, and wherein each Ar$^2$ is independently substituted with 0, 1, 2, or 3 groups independently selected from halogen, —NH$_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino. In a further aspect, each Ar$^2$, when present, is independently selected from phenyl, naphthyl, and heteroaryl, and wherein each Ar$^2$ is independently substituted with 0, 1, 2, or 3 groups independently selected from —F, —Cl, —Br, —OH, —CN, methyl, ethyl, —CH$_2$F, —CHF$_2$, —CF$_3$, —CH$_2$Cl, —CHCl$_2$, —CCl$_3$, —OCH$_3$, —CH$_2$CH$_3$, —NHCH$_3$, —NHCH$_2$CH$_3$, —N(CH$_3$)$_2$, and —N(CH$_3$)CH$_2$CH$_3$.

In a further aspect, each Ar$^2$, when present, is phenyl substituted with 0, 1, 2, or 3 groups independently selected from halogen, —NH$_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino. In a still further aspect, each Ar$^2$, when present, is phenyl substituted with 0, 1, 2, or 3 groups independently selected from —F, —Cl, —Br, —OH, —CN, methyl, ethyl, —CH$_2$F, —CHF$_2$, —CF$_3$, —CH$_2$Cl, —CHCl$_2$, —CCl$_3$, —OCH$_3$, —CH$_2$CH$_3$, —NHCH$_3$, —NHCH$_2$CH$_3$, —N(CH$_3$)$_2$, and —N(CH$_3$)CH$_2$CH$_3$.

In a further aspect, each Ar$^2$, when present, is naphthyl substituted with 0, 1, 2, or 3 groups independently selected from halogen, —NH$_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino. In a still further aspect, each Ar$^2$, when present, is naphthyl substituted with 0, 1, 2, or 3 groups independently selected from —F, —Cl, —Br, —OH, —CN, methyl, ethyl, —CH$_2$F, —CHF$_2$, —CF$_3$, —CH$_2$Cl, —CHCl$_2$, —CCl$_3$, —OCH$_3$, —CH$_2$CH$_3$, —NHCH$_3$, —NHCH$_2$CH$_3$, —N(CH$_3$)$_2$, and —N(CH$_3$)CH$_2$CH$_3$.

In a further aspect, each Ar$^2$, when present, is heteroaryl substituted with 0, 1, 2, or 3 groups independently selected from halogen, —NH$_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino. In a still further aspect, each Ar$^2$, when present, is heteroaryl substituted with 0, 1, 2, or 3 groups independently selected from —F, —Cl, —Br, —OH, —CN, methyl, ethyl, —CH$_2$F, —CHF$_2$, —CF$_3$, —CH$_2$Cl, —CHCl$_2$, —CCl$_3$, —OCH$_3$, —CH$_2$CH$_3$, —NHCH$_3$, —NHCH$_2$CH$_3$, —N(CH$_3$)$_2$, and —N(CH$_3$)CH$_2$CH$_3$.

In a further aspect, each Ar$^2$, when present, is pyridinyl substituted with 0, 1, 2, or 3 groups independently selected from halogen, —NH$_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino. In a still further aspect, each Ar$^2$, when present, is pyridinyl substituted with 0, 1, 2, or 3 groups independently selected from —F, —Cl, —Br, —OH, —CN, methyl, ethyl, —CH$_2$F, —CHF$_2$, —CF$_3$, —CH$_2$Cl, —CHCl$_2$, —CCl$_3$, —OCH$_3$, —CH$_2$CH$_3$, —NHCH$_3$, —NHCH$_2$CH$_3$, —N(CH$_3$)$_2$, and —N(CH$_3$)CH$_2$CH$_3$.

In a further aspect, each Ar$^2$, when present, is pyrimidinyl substituted with 0, 1, 2, or 3 groups independently selected from halogen, —NH$_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino. In a still further aspect, each Ar$^2$, when present, is pyrimidinyl substituted with 0, 1, 2, or 3 groups independently selected from —F, —Cl, —Br, —OH, —CN, methyl, ethyl, —CH$_2$F, —CHF$_2$, —CF$_3$, —CH$_2$Cl, —CHCl$_2$, —CCl$_3$, —OCH$_3$, —CH$_2$CH$_3$, —NHCH$_3$, —NHCH$_2$CH$_3$, —N(CH$_3$)$_2$, and —N(CH$_3$)CH$_2$CH$_3$.

ee. Cy$^1$ Groups

In one aspect, Cy$^1$, when present, is selected from a C2-C7 heterocycloalkyl substituted with 0, 1, 2, or 3 groups selected from halogen, —NH$_2$, —OH, and methyl. In a further aspect, Cy$^1$, when present, is a C2-C7 heterocycloalkyl monosubstituted with a group selected from halogen, —NH$_2$, —OH, and methyl. In a still further aspect, Cy$^1$, when present, is a C2-C7 heterocycloalkyl monosubstituted with a group selected from —F, —Cl, —Br, —NH$_2$, —OH, and methyl. In a yet further aspect, Cy$^1$, when present, is a C2-C7 heterocycloalkyl and unsubstituted.

In a further aspect, Cy$^1$, when present, is morpholinyl substituted with 0, 1, 2, or 3 groups selected from halogen, —NH$_2$, —OH, and methyl. In a still further aspect, Cy$^1$, when present, is morpholinyl monosubstituted with a group selected from halogen, —NH$_2$, —OH, and methyl. In a yet further aspect, Cy$^1$, when present, is morpholinyl monosubstituted with a group selected from —F, —Cl, —Br, —NH$_2$, —OH, and methyl. In an even further aspect, Cy$^1$, when present, is unsubstituted morpholinyl.

In a further aspect, Cy$^1$, when present, is piperidinyl substituted with 0, 1, 2, or 3 groups selected from halogen, —NH$_2$, —OH, and methyl. In a still further aspect, Cy$^1$, when present, is piperidinyl monosubstituted with a group selected from halogen, —NH$_2$, —OH, and methyl. In a yet further aspect, Cy$^1$, when present, is piperidinyl monosubstituted with a group selected from —F, —Cl, —Br, —NH$_2$, —OH, and methyl. In an even further aspect, Cy$^1$, when present, is unsubstituted piperidinyl.

In a further aspect, Cy$^1$, when present, is tetrahydrofuranyl substituted with 0, 1, 2, or 3 groups selected from halogen, —NH$_2$, —OH, and methyl. In a still further aspect, Cy$^1$, when present, is tetrahydrofuranyl monosubstituted with a group selected from halogen, —NH$_2$, —OH, and methyl. In a yet further aspect, Cy$^1$, when present, is tetrahydrofuranyl monosubstituted with a group selected from —F, —Cl, —Br, —NH$_2$, —OH, and methyl. In an even further aspect, Cy$^1$, when present, is unsubstituted tetrahydropyranyl.

In a further aspect, $Cy^1$, when present, is pyrrolidinyl substituted with 0, 1, 2, or 3 groups selected from halogen, —$NH_2$, —OH, and methyl. In a still further aspect, $Cy^1$, when present, is pyrrolidinyl monosubstituted with a group selected from halogen, —$NH_2$, —OH, and methyl. In a yet further aspect, $Cy^1$, when present, is pyrrolidinyl monosubstituted with a group selected from —F, —Cl, —Br, —$NH_2$, —OH, and methyl. In an even further aspect, $Cy^1$, when present, is unsubstituted pyrrolidinyl.

In a further aspect, $Cy^1$, when present, is tetrahydrofuranyl substituted with 0, 1, 2, or 3 groups selected from halogen, —$NH_2$, —OH, and methyl. In a still further aspect, $Cy^1$, when present, is tetrahydrofuranyl monosubstituted with a group selected from halogen, —$NH_2$, —OH, and methyl. In a yet further aspect, $Cy^1$, when present, is tetrahydrofuranyl monosubstituted with a group selected from —F, —Cl, —Br, —$NH_2$, —OH, and methyl. In an even further aspect, $Cy^1$, when present, is unsubstituted tetrahydrofuranyl.

In a further aspect, $Cy^1$, when present, is piperazinyl substituted with 0, 1, 2, or 3 groups selected from halogen, —$NH_2$, —OH, and methyl. In a still further aspect, $Cy^1$, when present, is piperazinyl monosubstituted with a group selected from halogen, —$NH_2$, —OH, and methyl. In a yet further aspect, $Cy^1$, when present, is piperazinyl monosubstituted with a group selected from —F, —Cl, —Br, —$NH_2$, —OH, and methyl. In an even further aspect, $Cy^1$, when present, is unsubstituted piperazinyl.

ff. $Cy^2$ Groups

In one aspect, $Cy^2$, when present, is a C2-C7 heterocycloalkyl substituted with 0, 1, 2, or 3 groups selected from halogen, —$NH_2$, —OH, and methyl. In a further aspect, $Cy^2$, when present, is a C2-C7 heterocycloalkyl monosubstituted with a group selected from halogen, —$NH_2$, —OH, and methyl. In a still further aspect, $Cy^2$, when present, is a C2-C7 heterocycloalkyl monosubstituted with a group selected from —F, —Cl, —Br, —$NH_2$, —OH, and methyl. In a yet further aspect, $Cy^2$, when present, is a C2-C7 heterocycloalkyl and unsubstituted.

In a further aspect, $Cy^2$, when present, is morpholinyl substituted with 0, 1, 2, or 3 groups selected from halogen, —$NH_2$, —OH, and methyl. In a still further aspect, $Cy^2$, when present, is morpholinyl monosubstituted with a group selected from halogen, —$NH_2$, —OH, and methyl. In a yet further aspect, $Cy^2$, when present, is morpholinyl monosubstituted with a group selected from —F, —Cl, —Br, —$NH_2$, —OH, and methyl. In an even further aspect, $Cy^2$, when present, is unsubstituted morpholinyl.

In a further aspect, $Cy^2$, when present, is piperidinyl substituted with 0, 1, 2, or 3 groups selected from halogen, —$NH_2$, —OH, and methyl. In a still further aspect, $Cy^2$, when present, is piperidinyl monosubstituted with a group selected from halogen, —$NH_2$, —OH, and methyl. In a yet further aspect, $Cy^2$, when present, is piperidinyl monosubstituted with a group selected from —F, —Cl, —Br, —$NH_2$, —OH, and methyl. In an even further aspect, $Cy^2$, when present, is unsubstituted piperidinyl.

In a further aspect, $Cy^2$, when present, is tetrahydrofuranyl substituted with 0, 1, 2, or 3 groups selected from halogen, —$NH_2$, —OH, and methyl. In a still further aspect, $Cy^2$, when present, is tetrahydrofuranyl monosubstituted with a group selected from halogen, —$NH_2$, —OH, and methyl. In a yet further aspect, $Cy^2$, when present, is tetrahydrofuranyl monosubstituted with a group selected from —F, —Cl, —Br, —$NH_2$, —OH, and methyl. In an even further aspect, $Cy^2$, when present, is unsubstituted tetrahydropyranyl.

In a further aspect, $Cy^2$, when present, is pyrrolidinyl substituted with 0, 1, 2, or 3 groups selected from halogen, —$NH_2$, —OH, and methyl. In a still further aspect, $Cy^2$, when present, is pyrrolidinyl monosubstituted with a group selected from halogen, —$NH_2$, —OH, and methyl. In a yet further aspect, $Cy^2$, when present, is pyrrolidinyl monosubstituted with a group selected from —F, —Cl, —Br, —$NH_2$, —OH, and methyl. In an even further aspect, $Cy^2$, when present, is unsubstituted pyrrolidinyl.

In a further aspect, $Cy^2$, when present, is tetrahydrofuranyl substituted with 0, 1, 2, or 3 groups selected from halogen, —$NH_2$, —OH, and methyl. In a still further aspect, $Cy^2$, when present, is tetrahydrofuranyl monosubstituted with a group selected from halogen, —$NH_2$, —OH, and methyl. In a yet further aspect, $Cy^2$, when present, is tetrahydrofuranyl monosubstituted with a group selected from —F, —Cl, —Br, —$NH_2$, —OH, and methyl. In an even further aspect, $Cy^2$, when present, is unsubstituted tetrahydrofuranyl.

gg. $Cy^3$ Groups

In one aspect, $Cy^3$, when present, is a C2-C7 heterocycloalkyl substituted with 0, 1, 2, or 3 groups selected from halogen, —$NH_2$, —OH, and methyl. In a further aspect, $Cy^3$, when present, is a C2-C7 heterocycloalkyl monosubstituted with a group selected from halogen, —$NH_2$, —OH, and methyl. In a still further aspect, $Cy^3$, when present, is a C2-C7 heterocycloalkyl monosubstituted with a group selected from —F, —Cl, —Br, —$NH_2$, —OH, and methyl. In a yet further aspect, $Cy^3$, when present, is a C2-C7 heterocycloalkyl and unsubstituted.

In a further aspect, 3 when present, is morpholinyl substituted with 0, 1, 2, or 3 groups selected from halogen, —$NH_2$, —OH, and methyl. In a still further aspect, $Cy^3$, when present, is morpholinyl monosubstituted with a group selected from halogen, —$NH_2$, —OH, and methyl. In a yet further aspect, $Cy^3$, when present, is morpholinyl monosubstituted with a group selected from —F, —Cl, —Br, —$NH_2$, —OH, and methyl. In an even further aspect, $Cy^3$, when present, is unsubstituted morpholinyl.

In a further aspect, $Cy^3$, when present, is piperidinyl substituted with 0, 1, 2, or 3 groups selected from halogen, —$NH_2$, —OH, and methyl. In a still further aspect, $Cy^3$, when present, is piperidinyl monosubstituted with a group selected from halogen, —$NH_2$, —OH, and methyl. In a yet further aspect, $Cy^3$, when present, is piperidinyl monosubstituted with a group selected from —F, —Cl, —Br, —$NH_2$, —OH, and methyl. In an even further aspect, $Cy^3$, when present, is unsubstituted piperidinyl.

In a further aspect, $Cy^3$, when present, is tetrahydrofuranyl substituted with 0, 1, 2, or 3 groups selected from halogen, —$NH_2$, —OH, and methyl. In a still further aspect, $Cy^3$, when present, is tetrahydrofuranyl monosubstituted with a group selected from halogen, —$NH_2$, —OH, and methyl. In a yet further aspect, $Cy^3$, when present, is tetrahydrofuranyl monosubstituted with a group selected from —F, —Cl, —Br, —$NH_2$, —OH, and methyl. In an even further aspect, $Cy^3$, when present, is unsubstituted tetrahydropyranyl.

In a further aspect, $Cy^3$, when present, is pyrrolidinyl substituted with 0, 1, 2, or 3 groups selected from halogen, —$NH_2$, —OH, and methyl. In a still further aspect, $Cy^3$, when present, is pyrrolidinyl monosubstituted with a group selected from halogen, —$NH_2$, —OH, and methyl. In a yet further aspect, $Cy^3$, when present, is pyrrolidinyl monosubstituted with a group selected from —F, —Cl, —Br, —$NH_2$, —OH, and methyl. In an even further aspect, $Cy^3$, when present, is unsubstituted pyrrolidinyl.

In a further aspect, Cy$^3$, when present, is tetrahydrofuranyl substituted with 0, 1, 2, or 3 groups selected from halogen, —NH$_2$, —OH, and methyl. In a still further aspect, Cy$^3$, when present, is tetrahydrofuranyl monosubstituted with a group selected from halogen, —NH$_2$, —OH, and methyl. In a yet further aspect, Cy$^3$, when present, is tetrahydrofuranyl monosubstituted with a group selected from —F, —Cl, —Br, —NH$_2$, —OH, and methyl. In an even further aspect, Cy$^3$, when present, is unsubstituted tetrahydrofuranyl.

In a further aspect, Cy$^3$, when present, is piperazinyl substituted with 0, 1, 2, or 3 groups selected from halogen, —NH$_2$, —OH, and methyl. In a still further aspect, Cy$^3$, when present, is piperazinyl monosubstituted with a group selected from halogen, —NH$_2$, —OH, and methyl. In a yet further aspect, Cy$^3$, when present, is piperazinyl monosubstituted with a group selected from —F, —Cl, —Br, —NH$_2$, —OH, and methyl. In an even further aspect, Cy$^3$, when present, is unsubstituted piperazinyl.

2. Example Compounds

In one aspect, a compound can be present as one or more of the following structures:

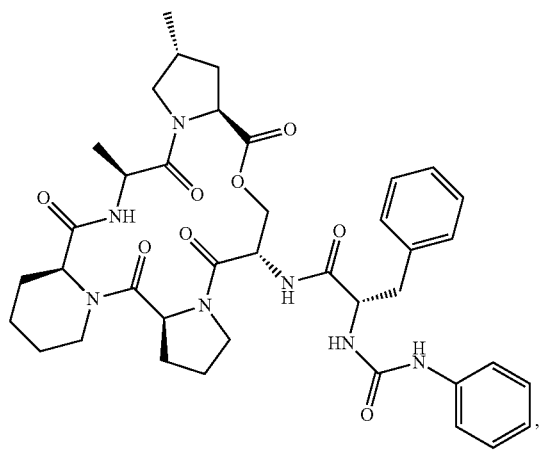

,

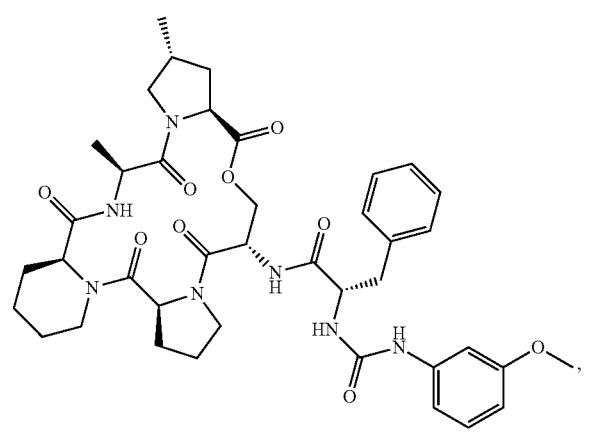

,

-continued

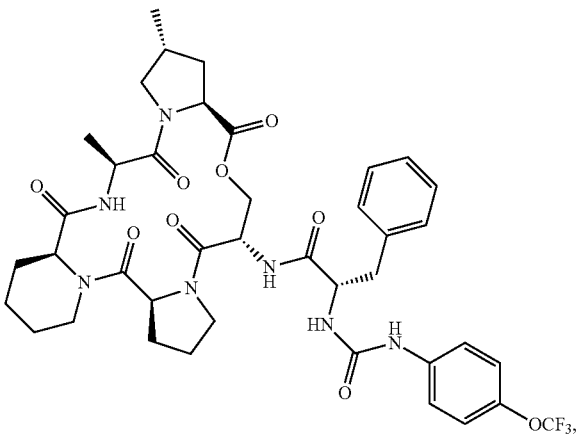

,

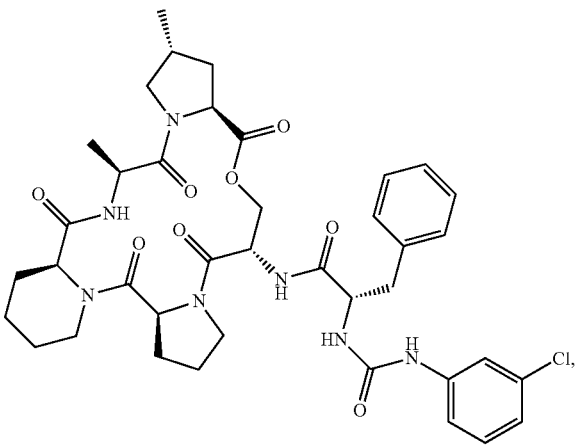

,

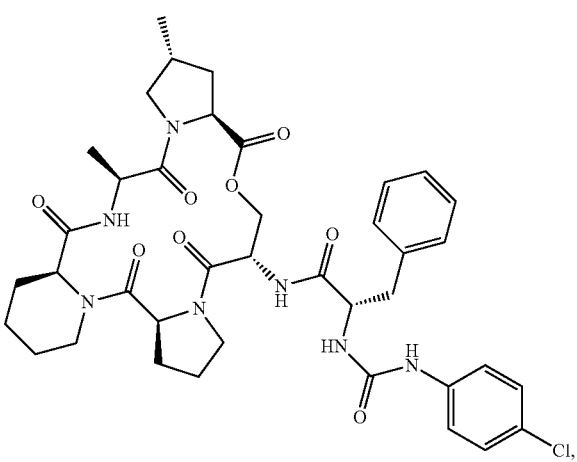

,

103
-continued
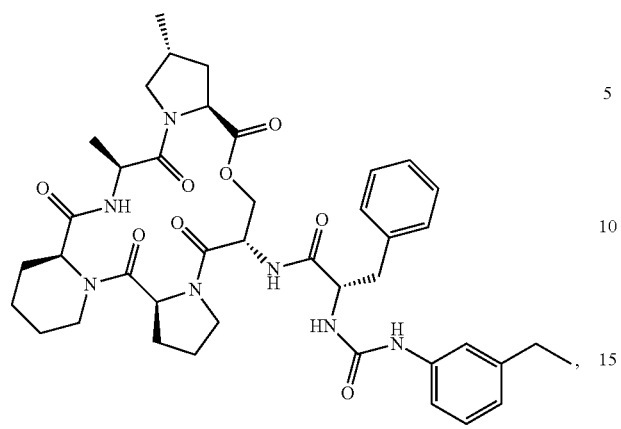
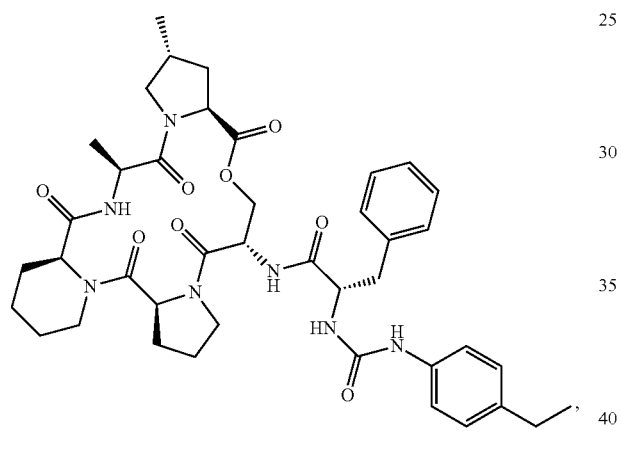
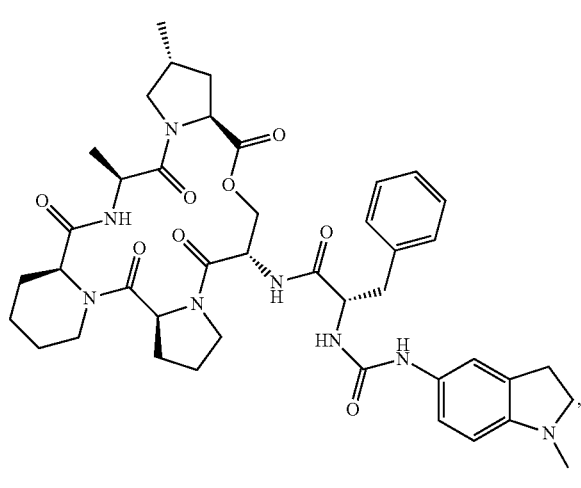
104
-continued
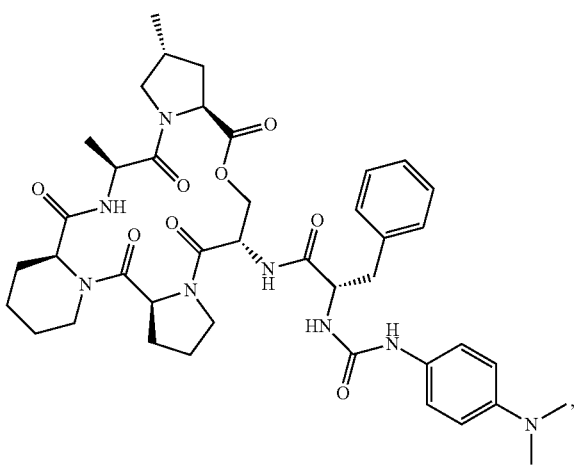
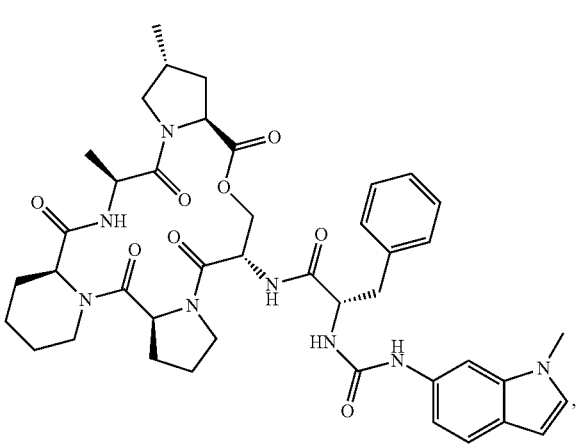
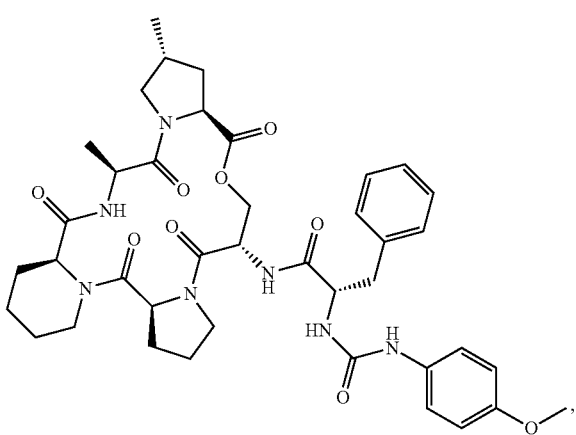

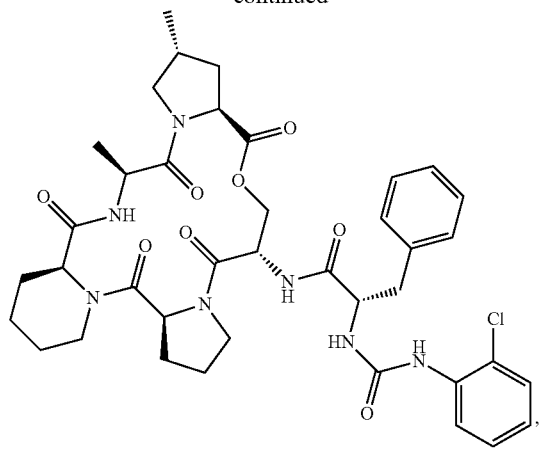
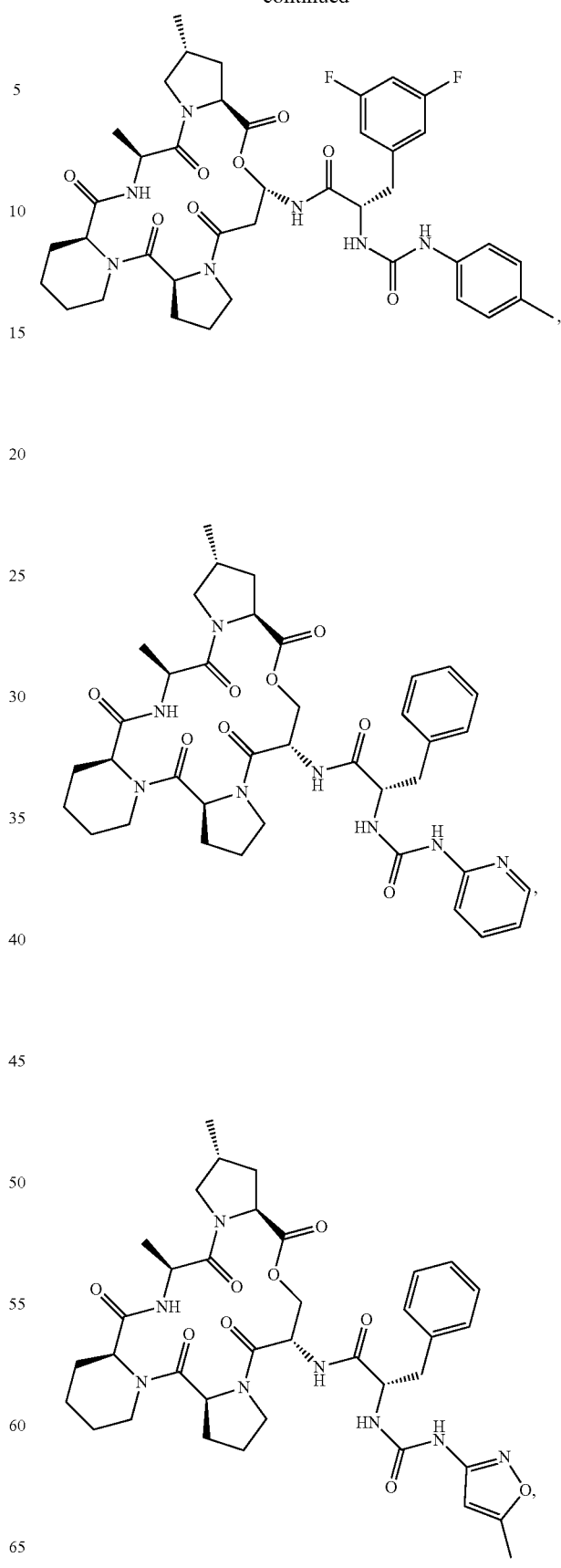

107
-continued
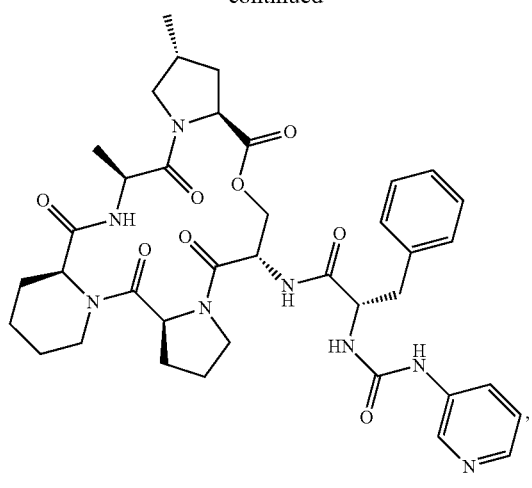
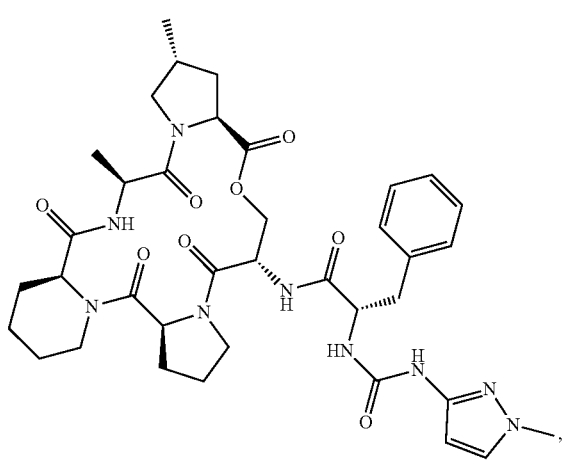
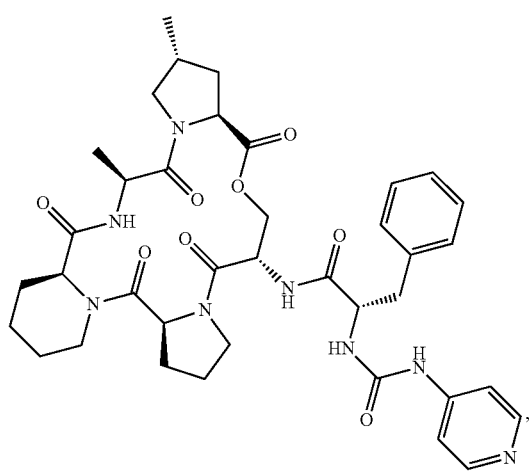
108
-continued
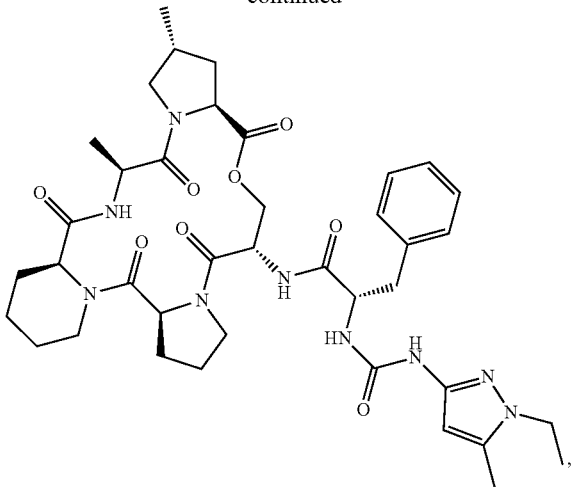
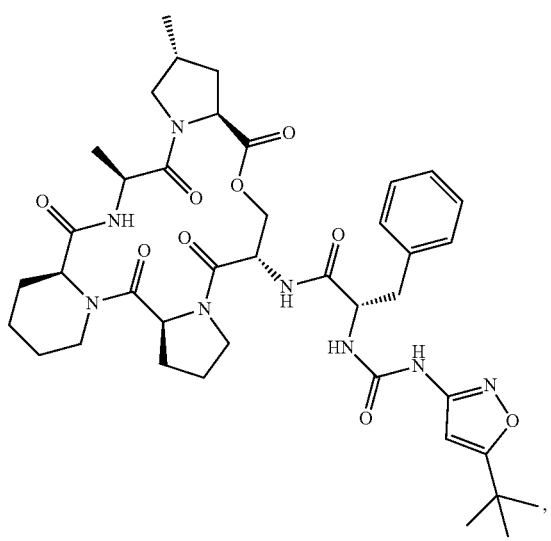

109
-continued
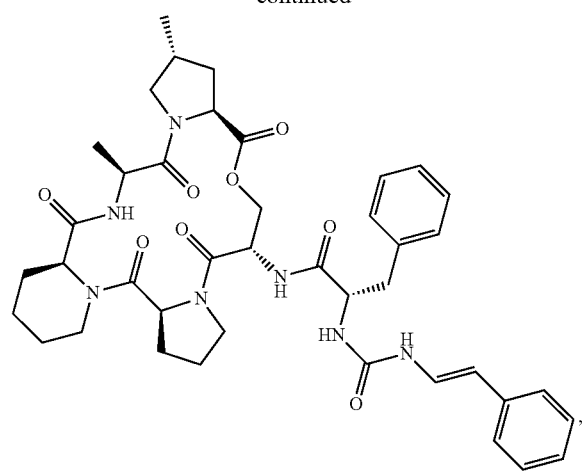
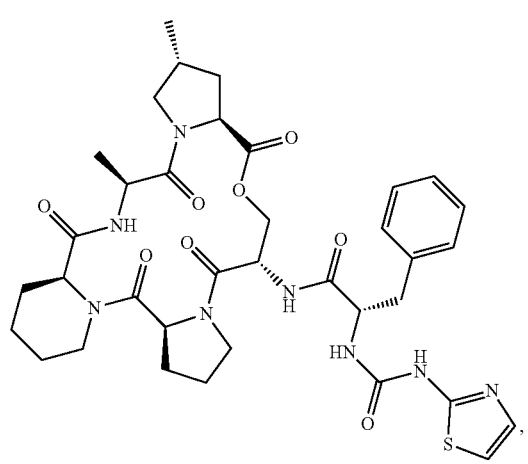
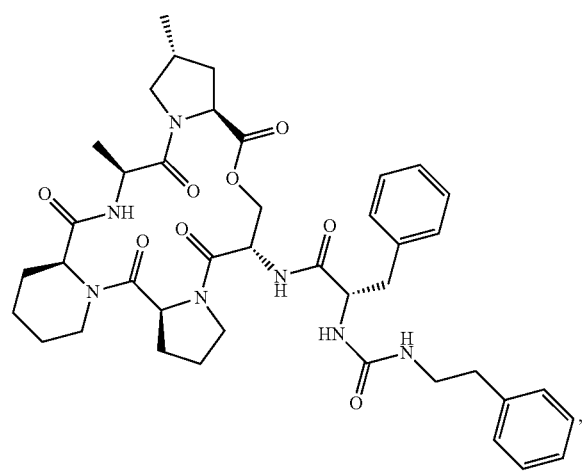
110
-continued
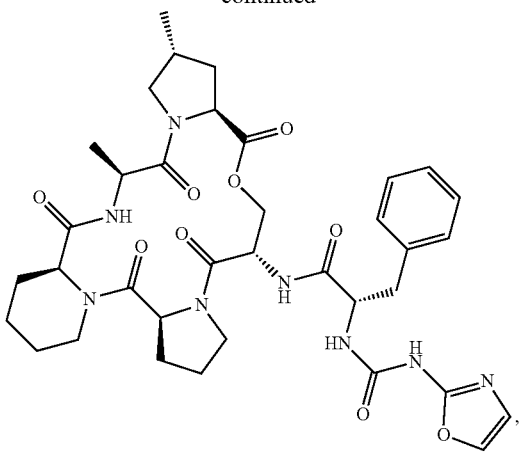
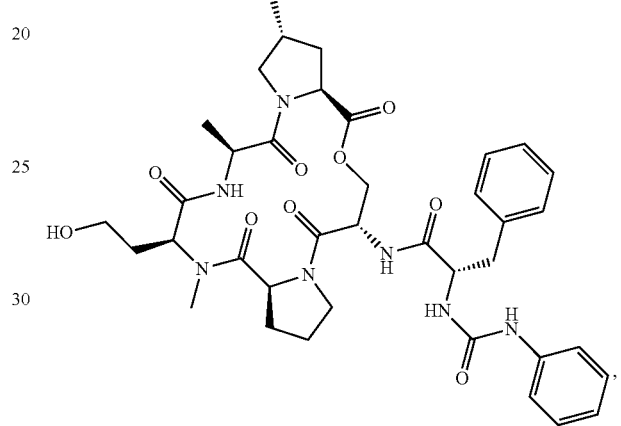
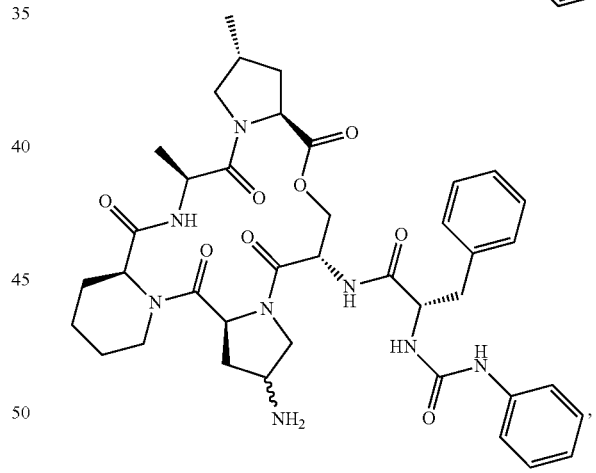
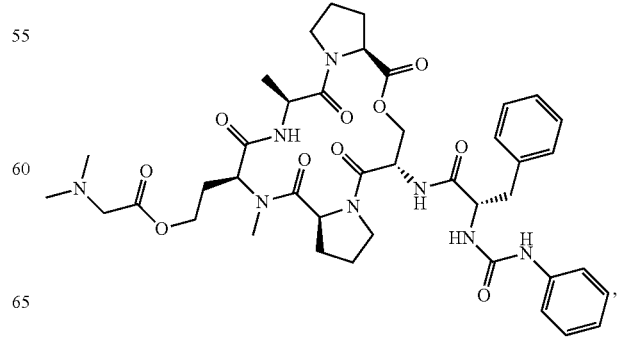

111
-continued
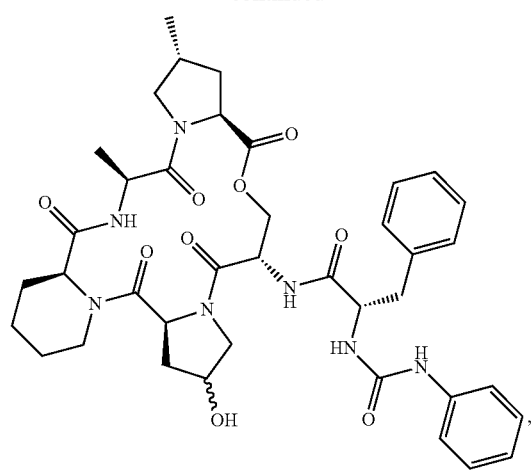
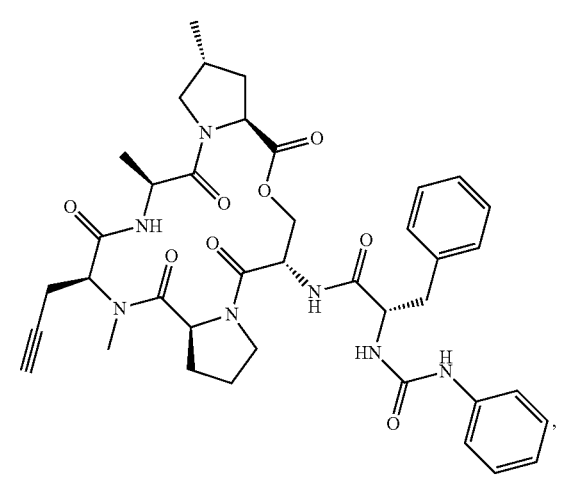
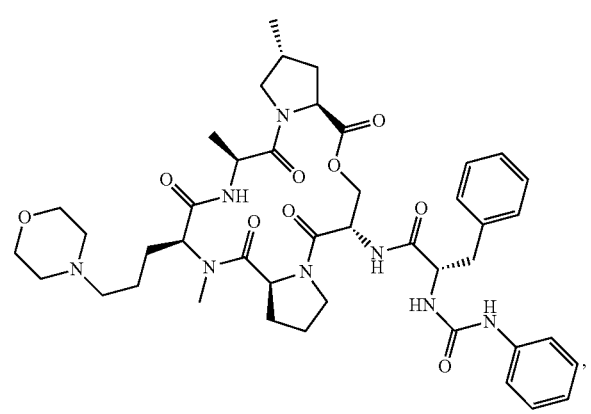
112
-continued
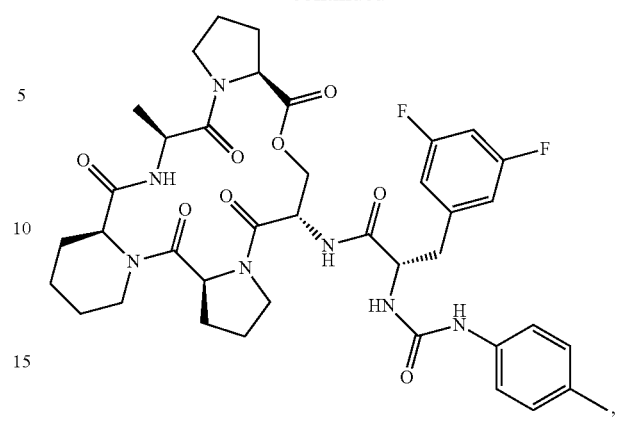
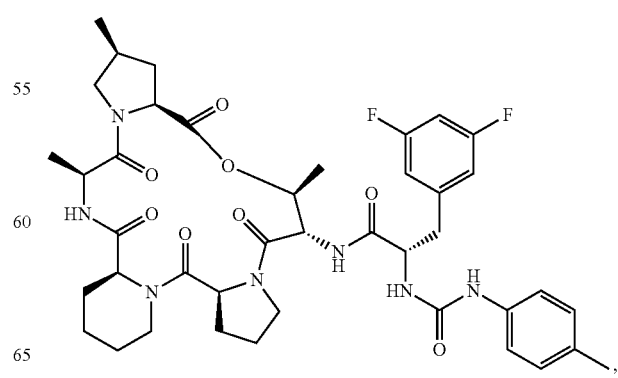

113 -continued
114 -continued
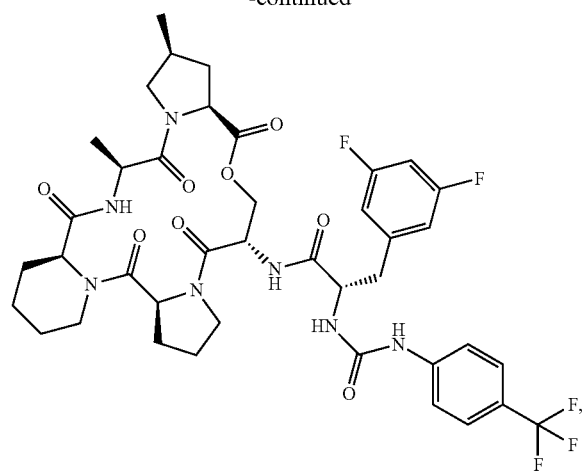
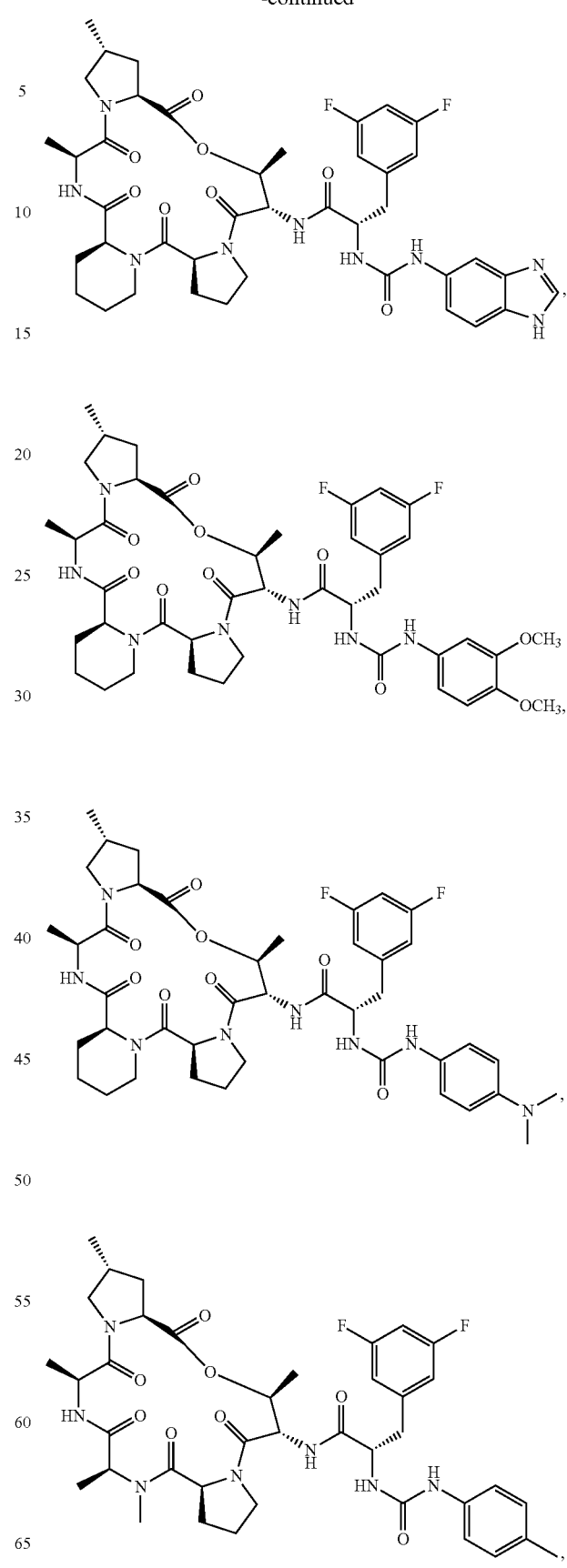

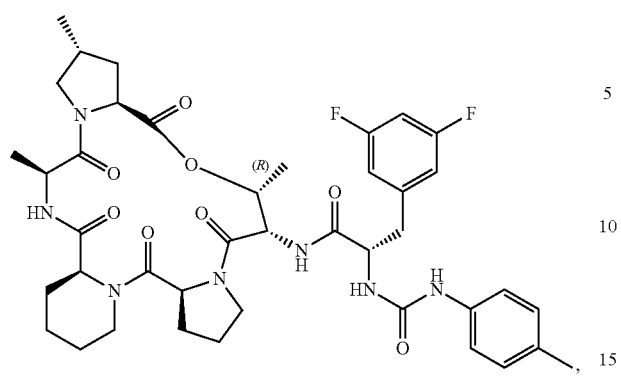
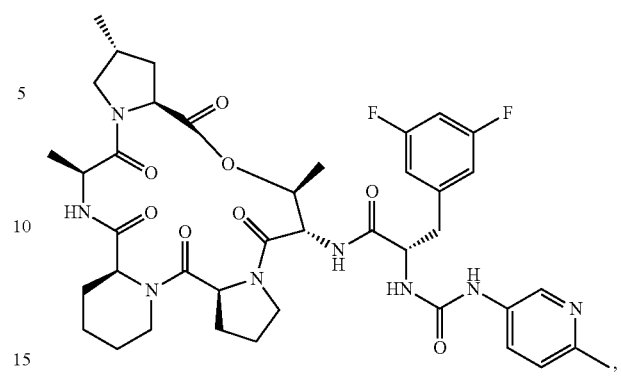
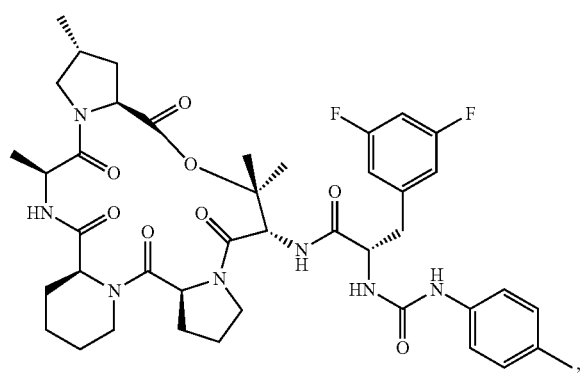
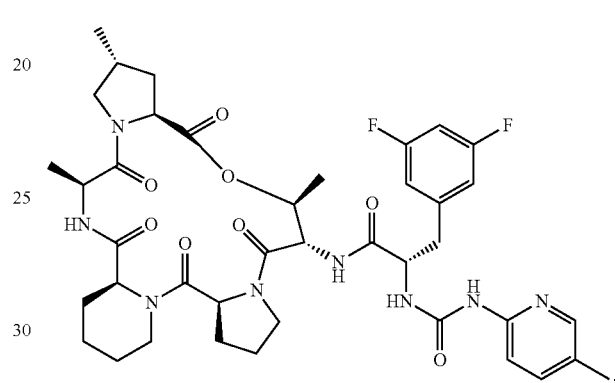
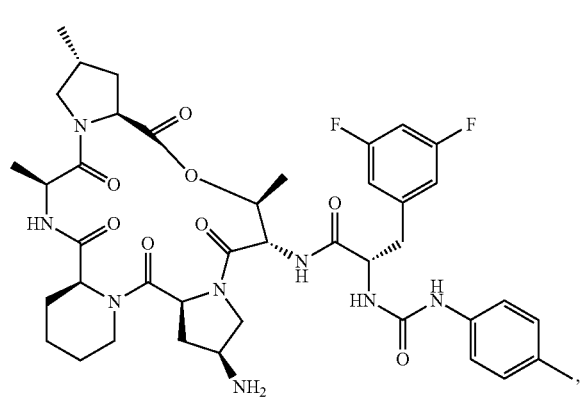
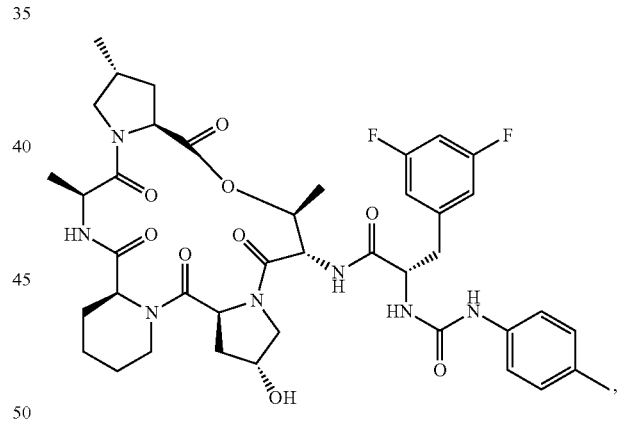
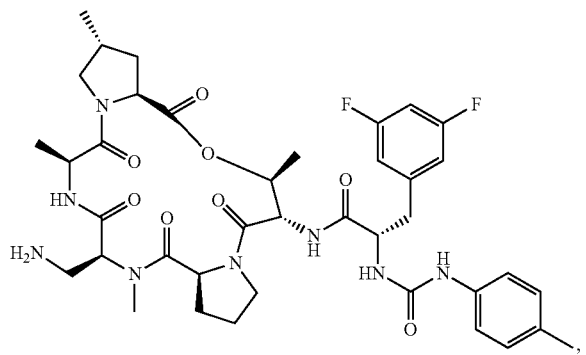
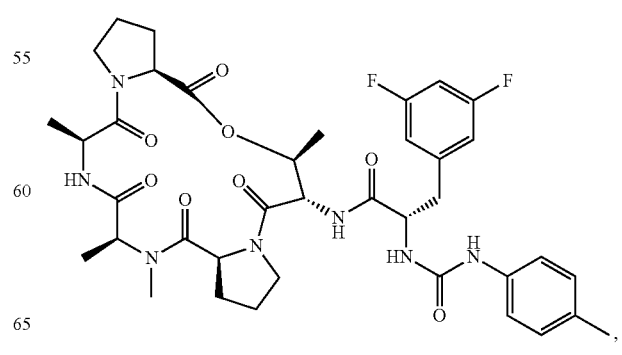

117
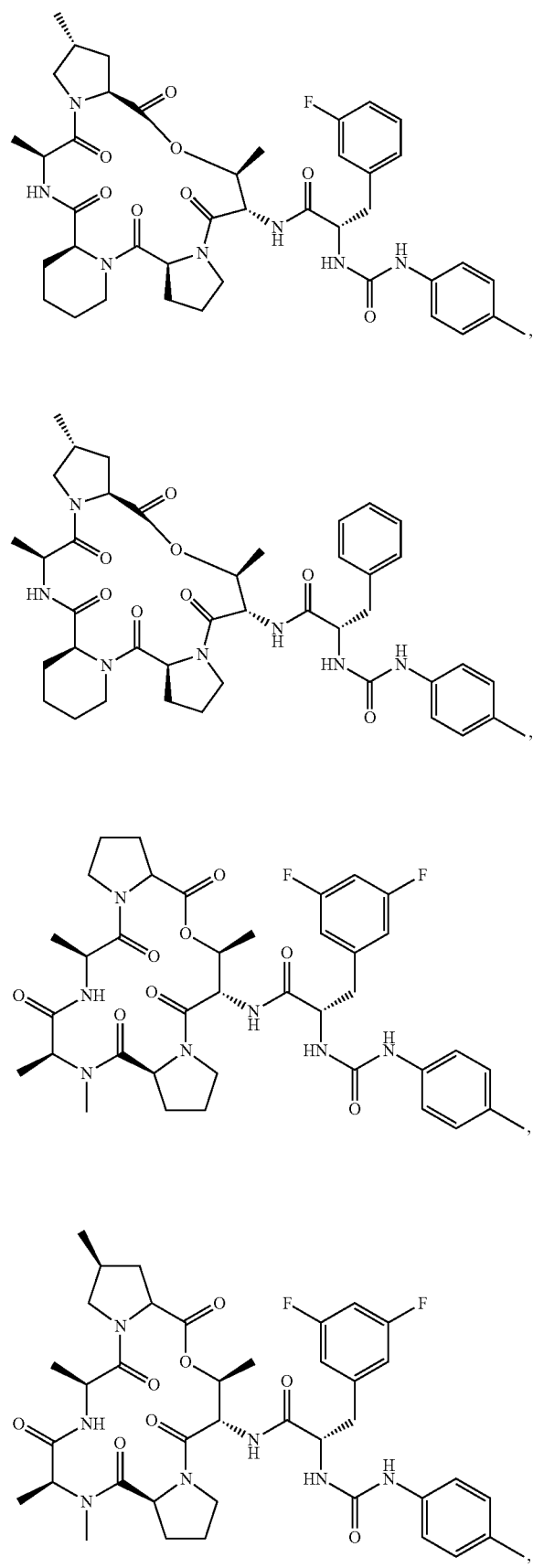
118
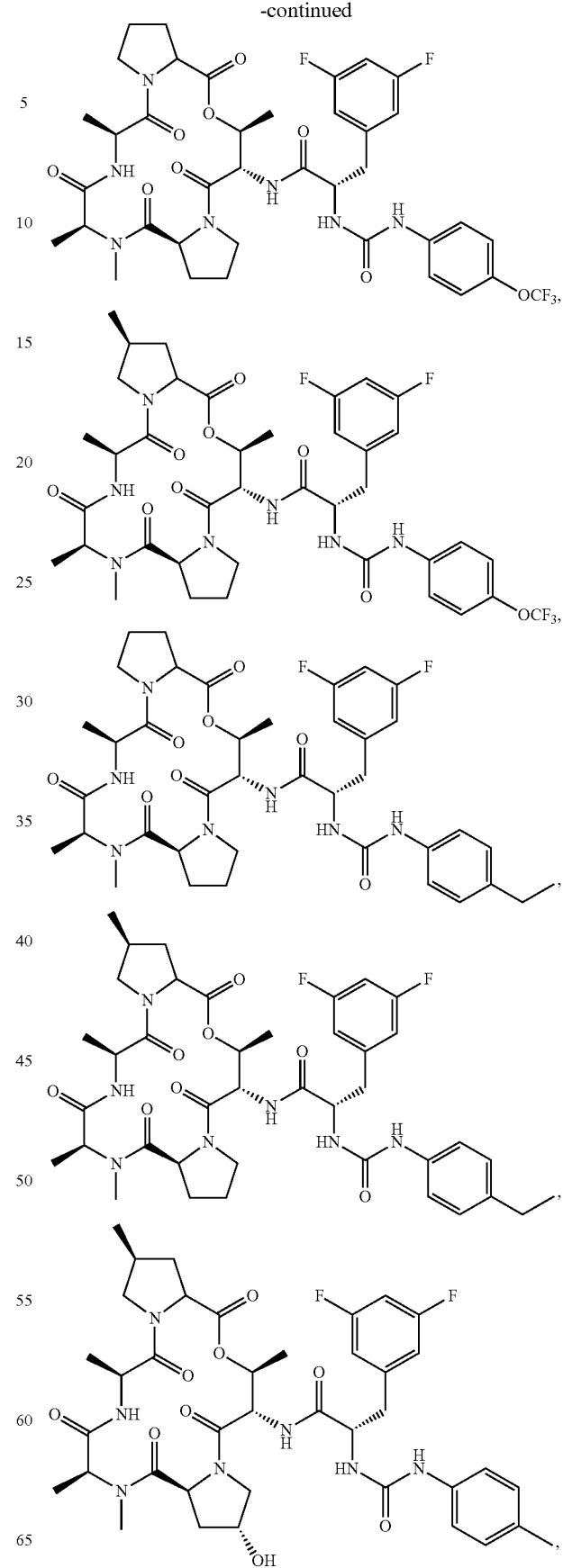

119
-continued
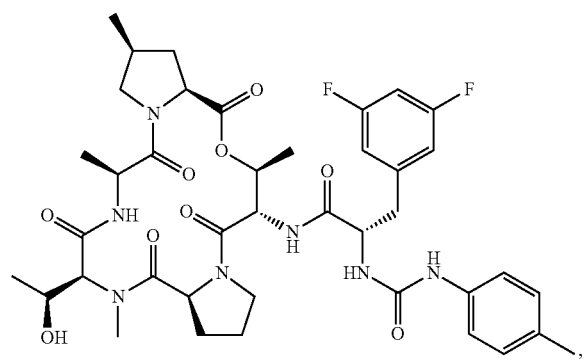
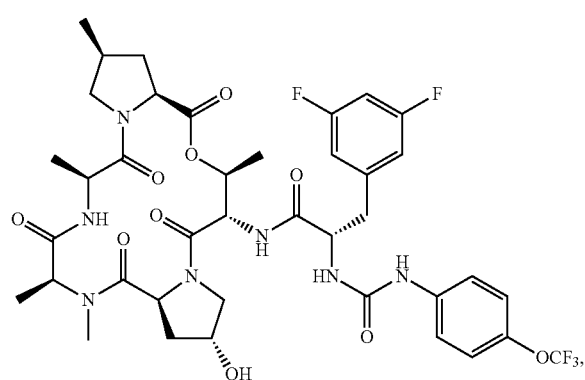
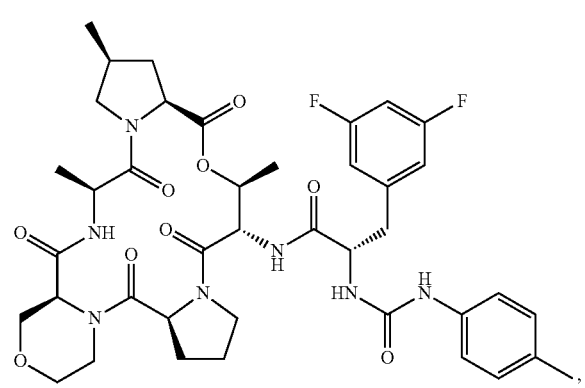
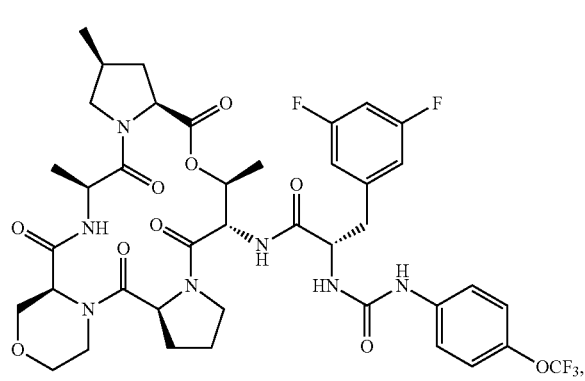
120
-continued
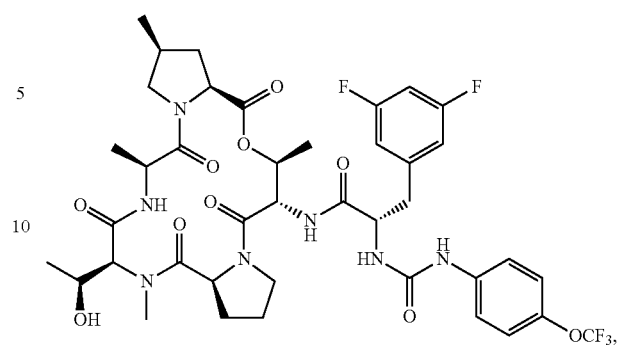
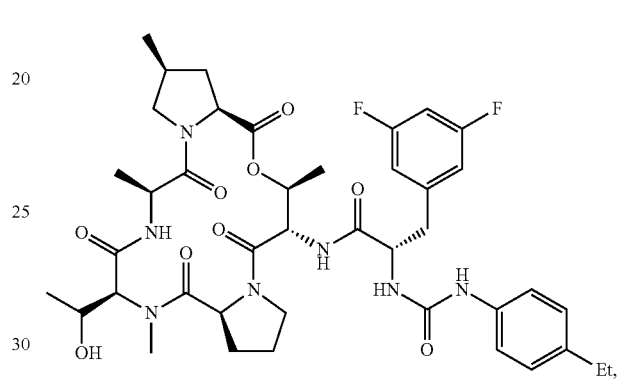
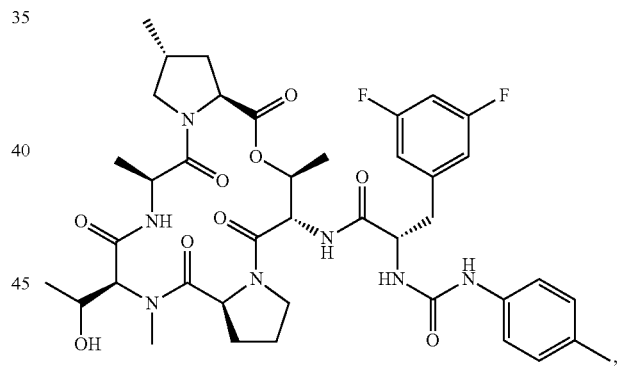
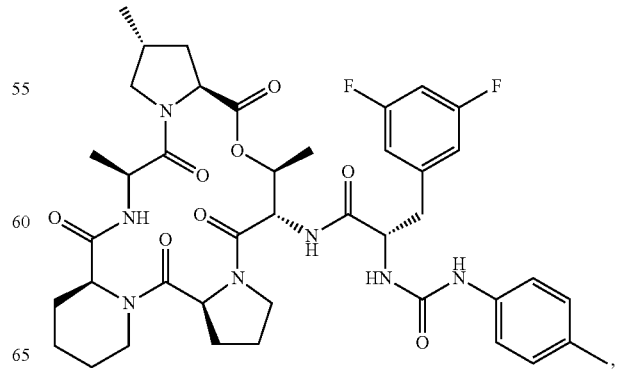

121
-continued
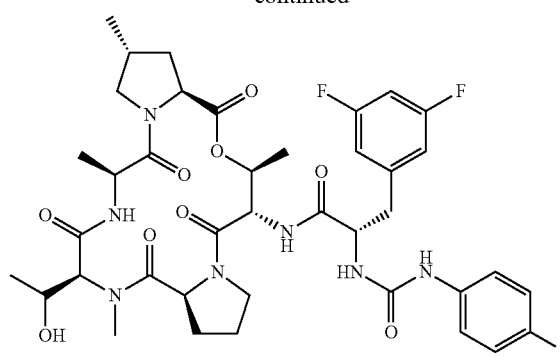
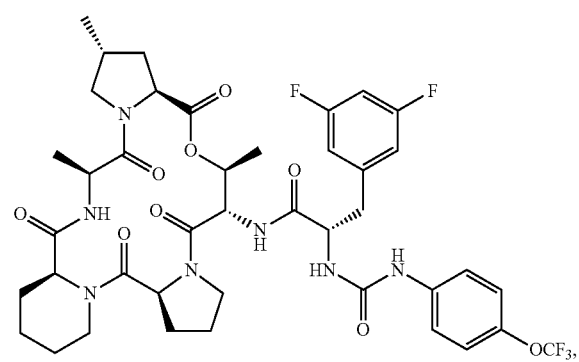
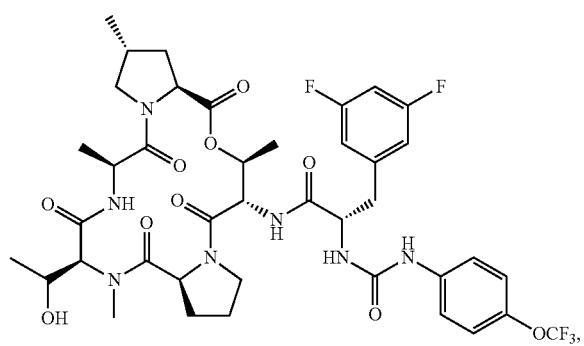
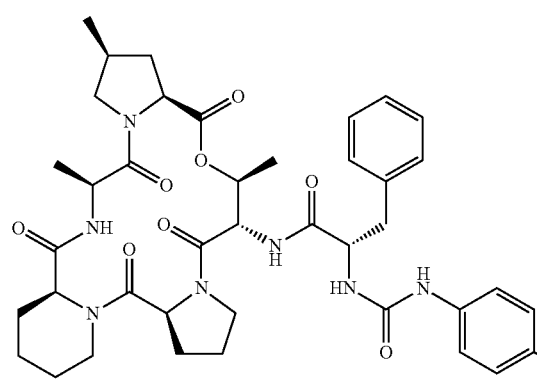
122
-continued
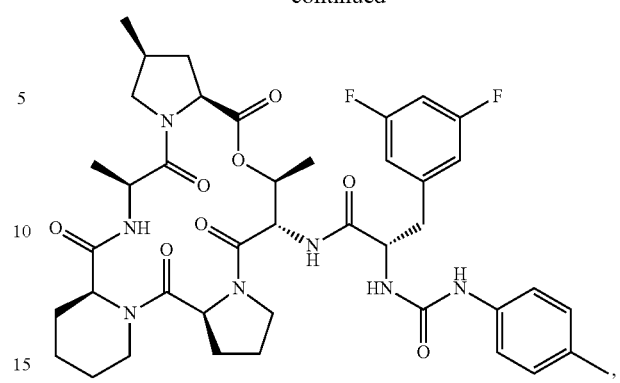
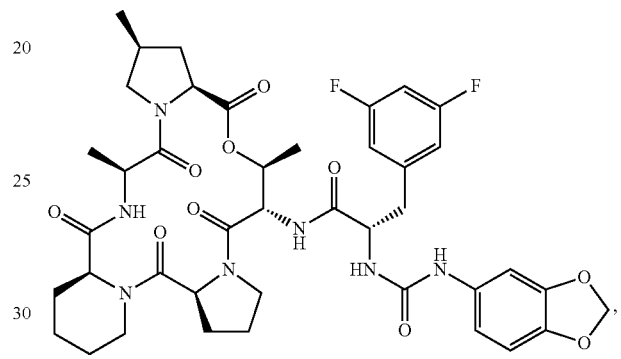
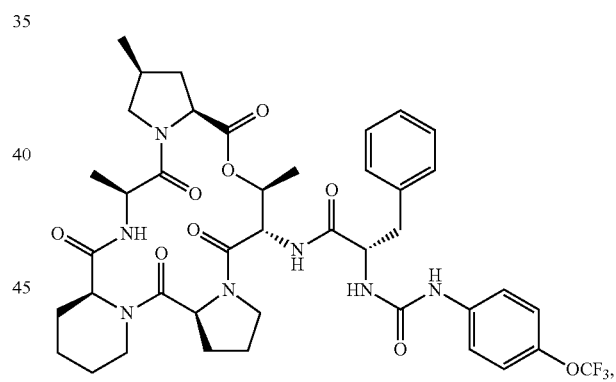
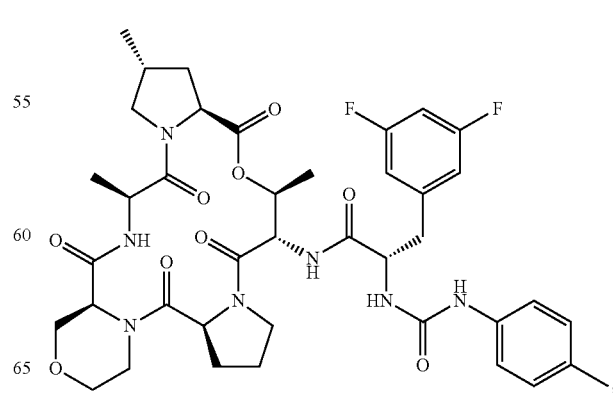

123
-continued
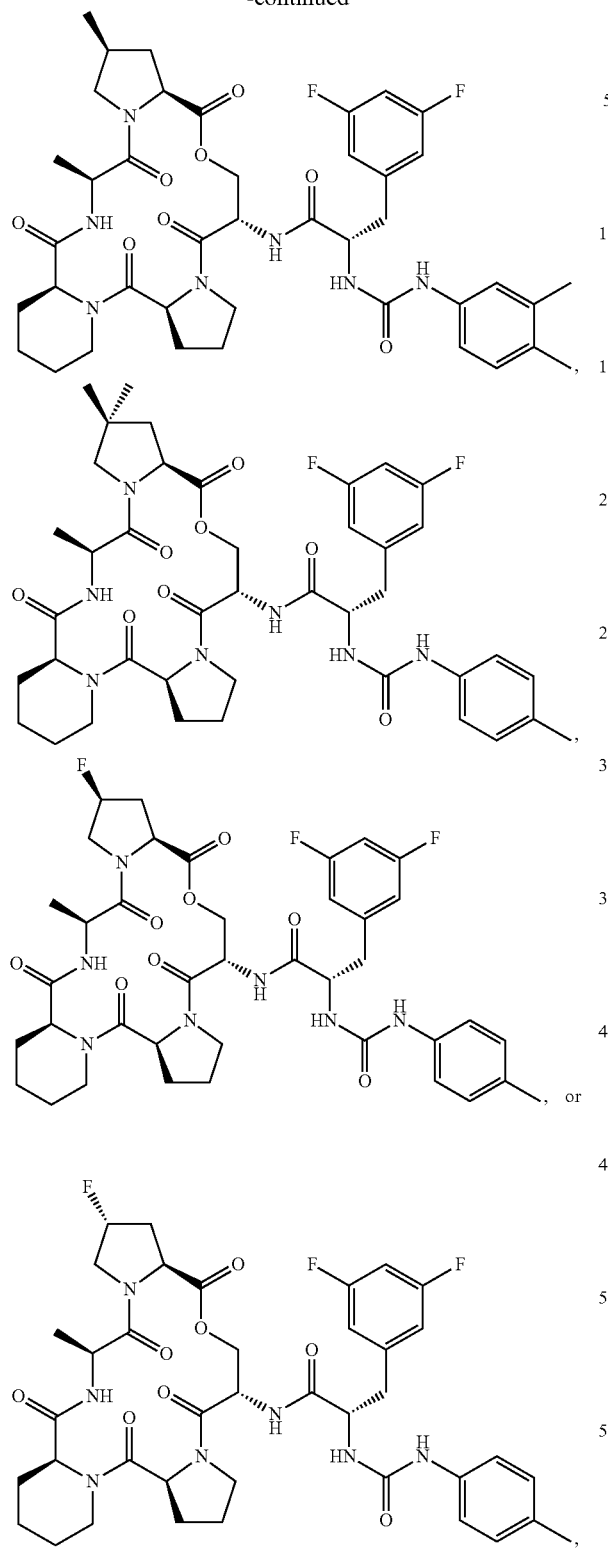
or a subgroup thereof.
In one aspect, a compound can be present as one or more of the following structures:
124
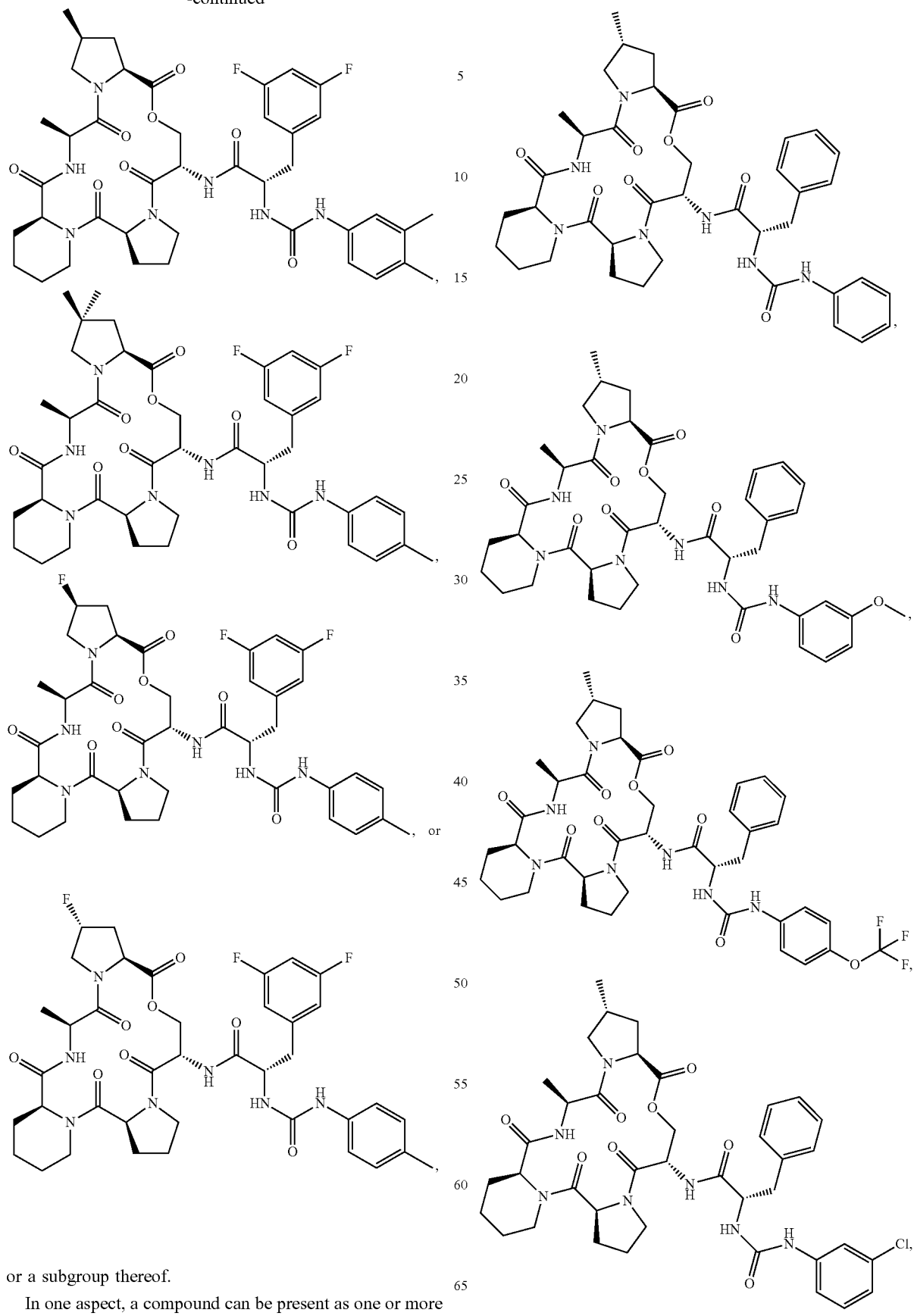

125
-continued
126
-continued
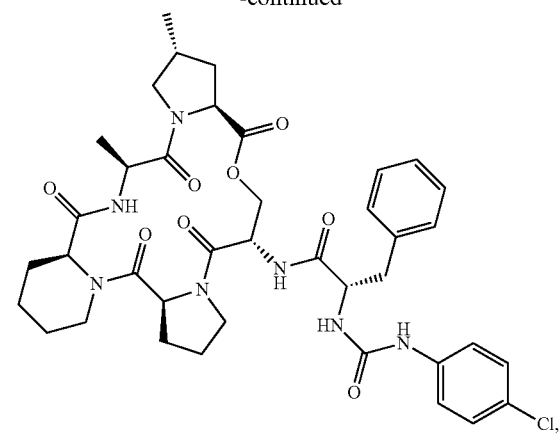
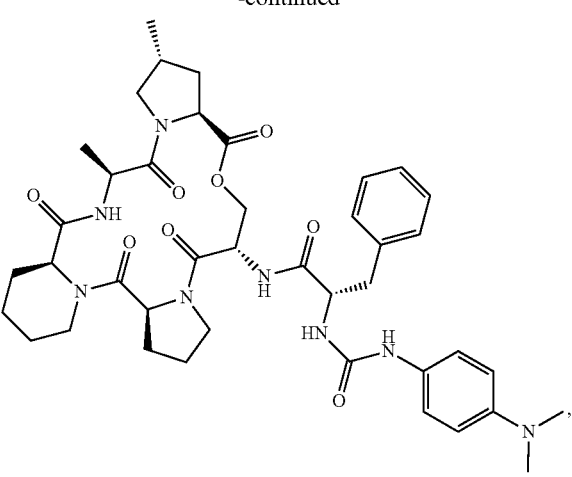
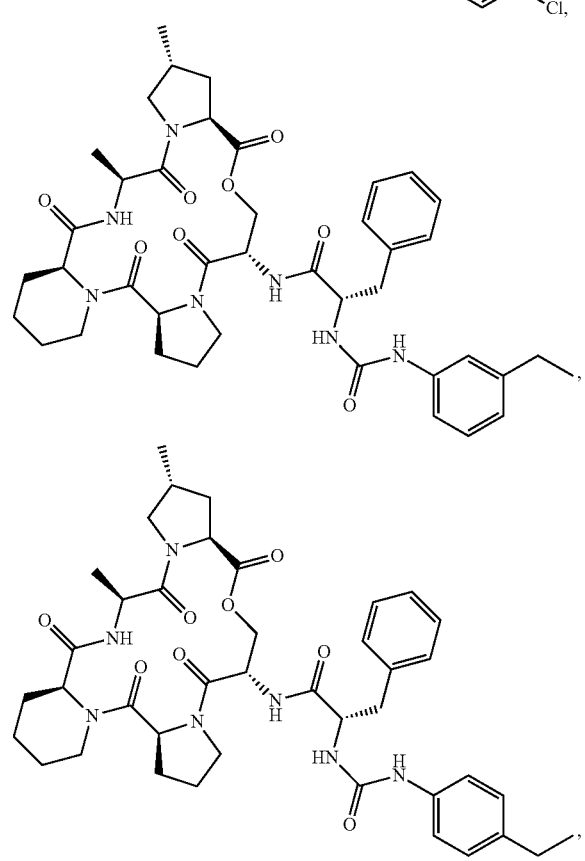
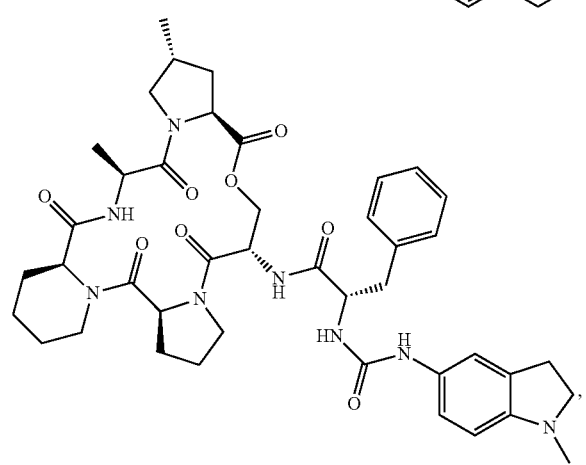

127
-continued
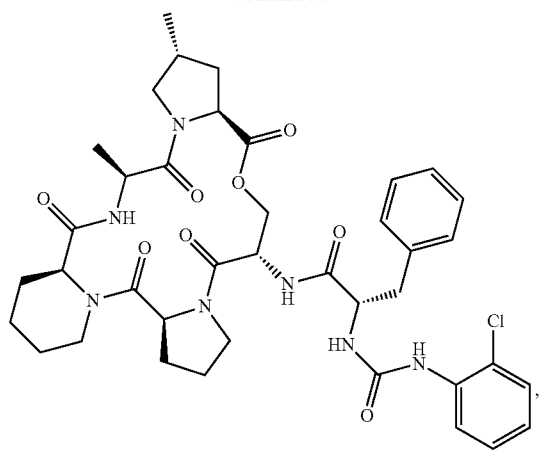
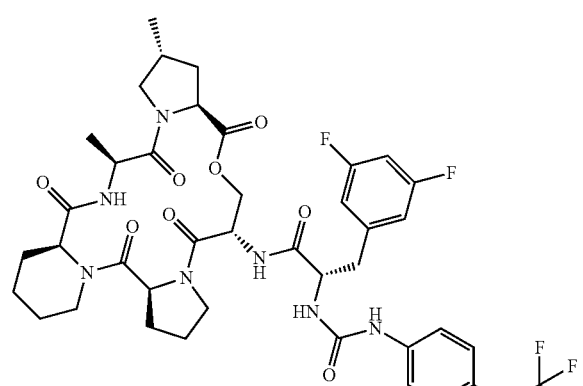
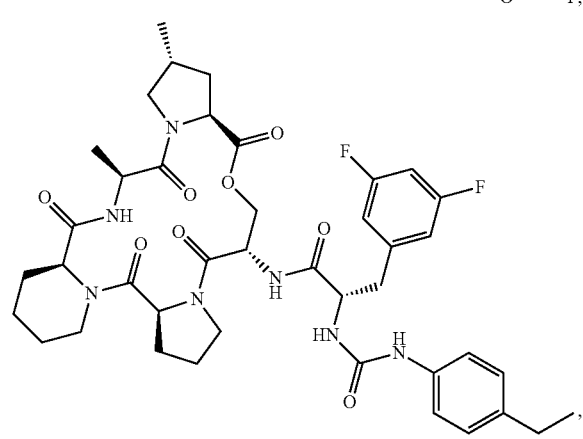
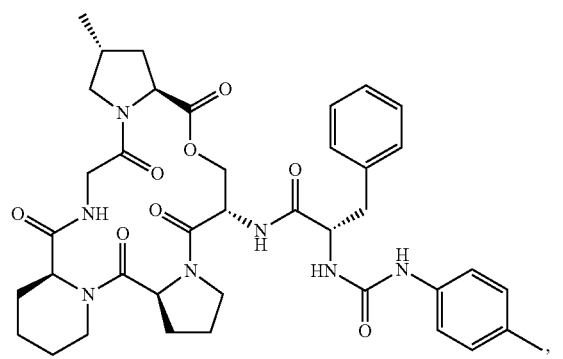, or
128
-continued
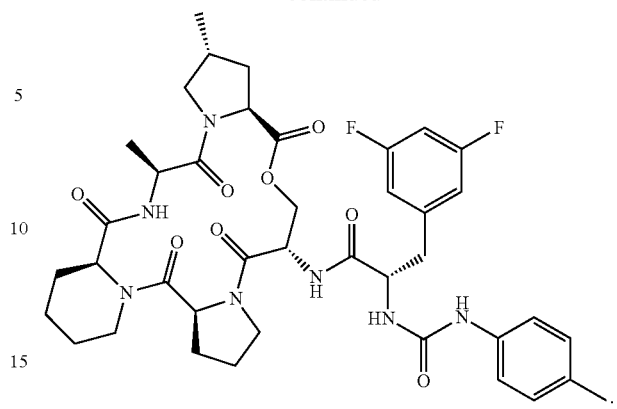
or a subgroup thereof.
In one aspect, a compound can be present as one or more of the following structures:
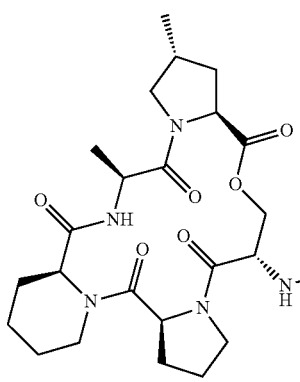
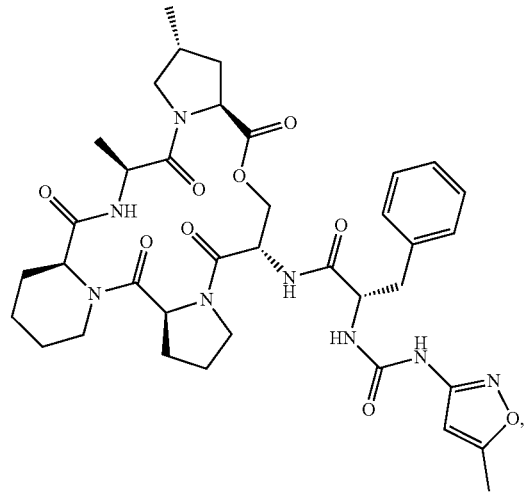

129
-continued
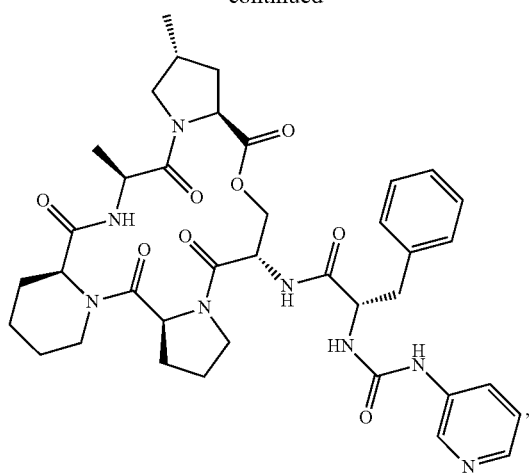
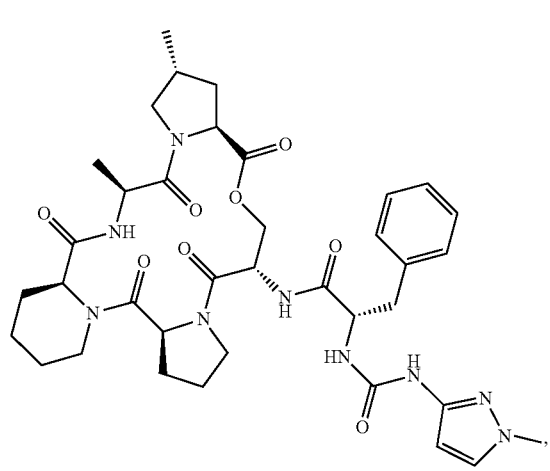
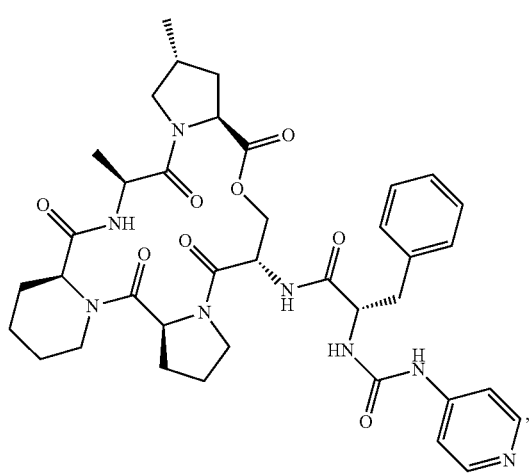
130
-continued
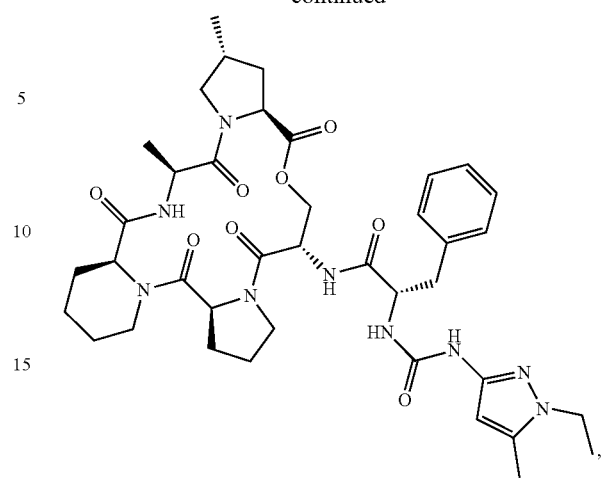
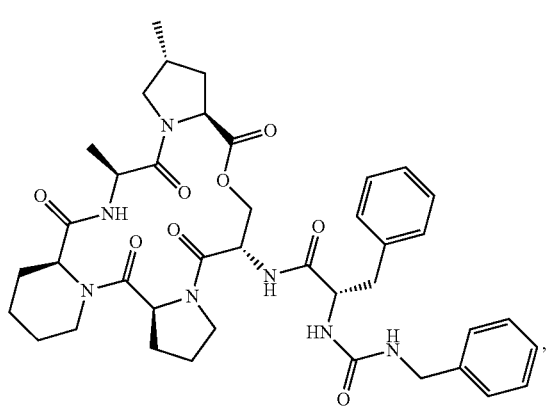
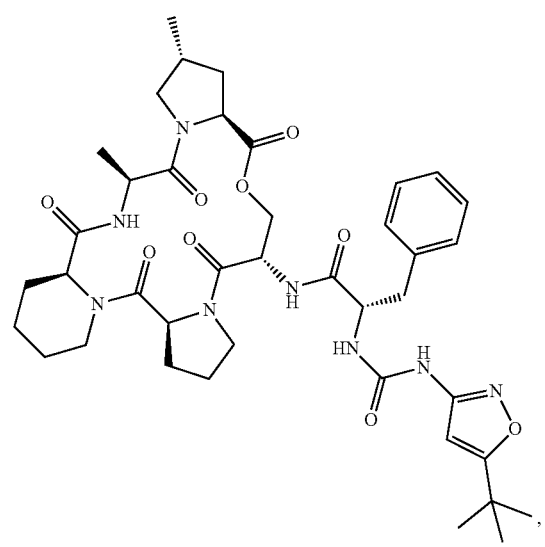

131
-continued
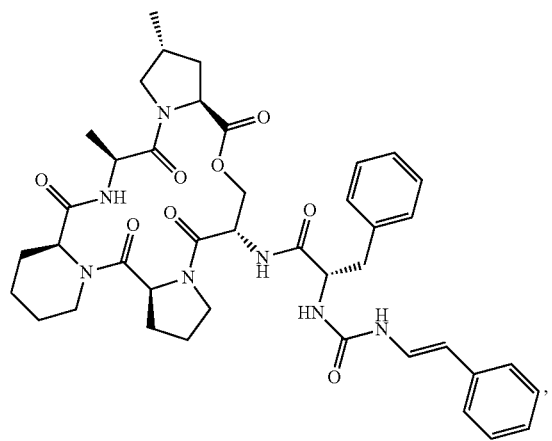
132
-continued
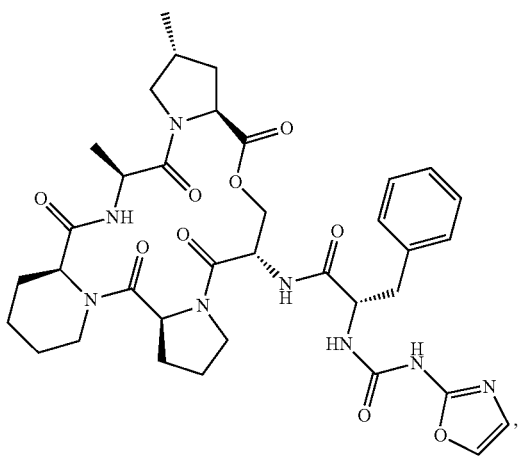
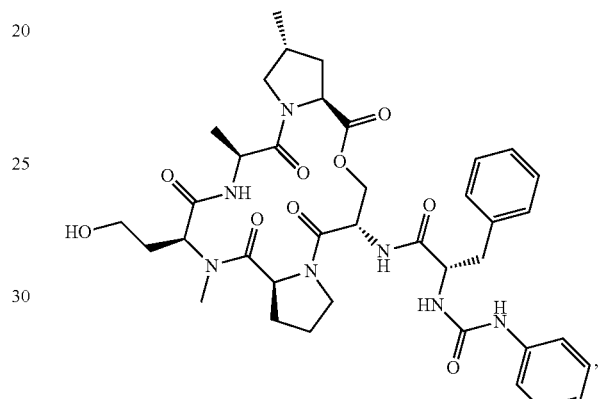
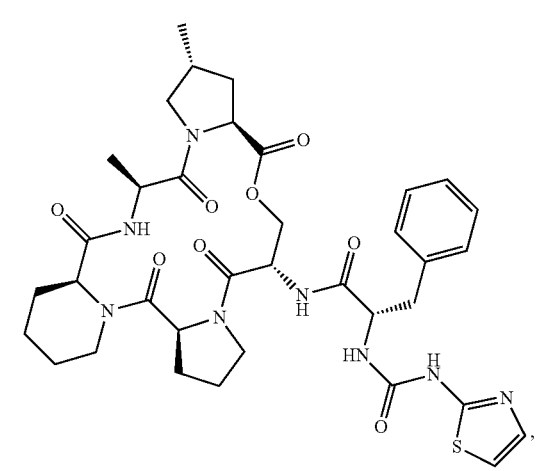
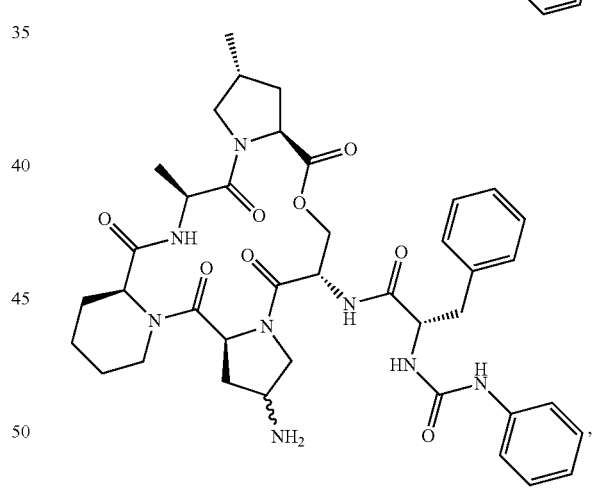
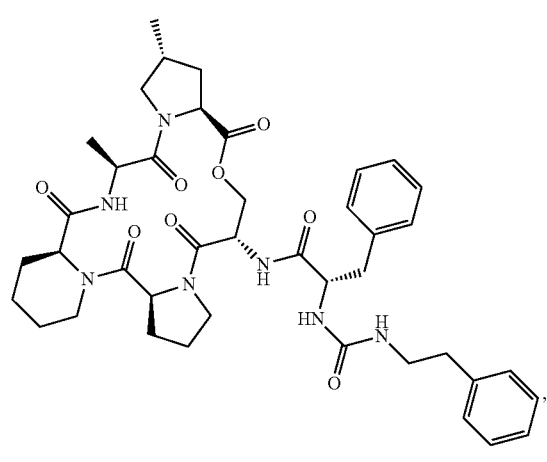
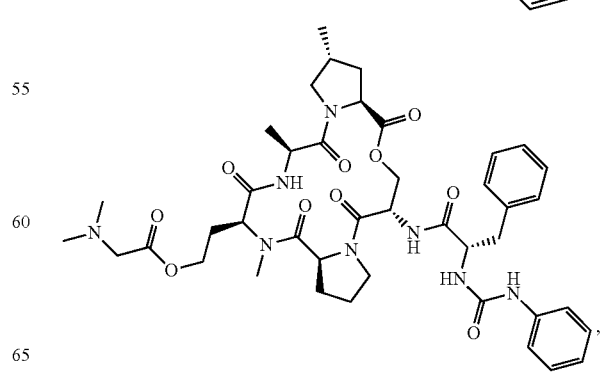

133
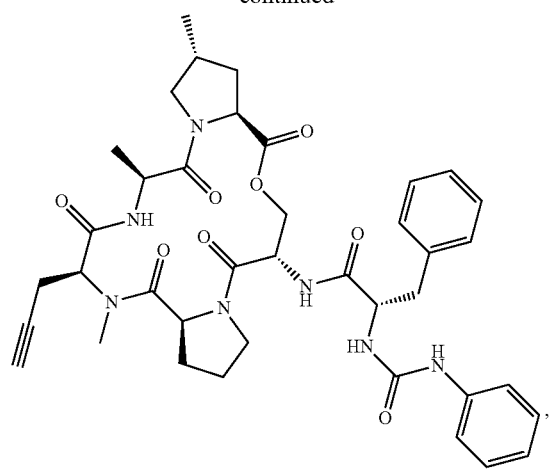
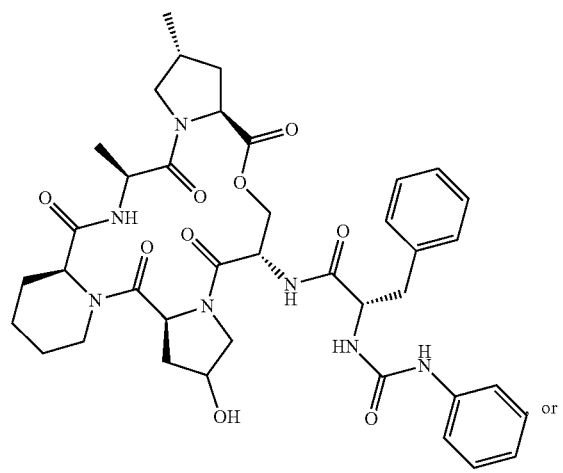
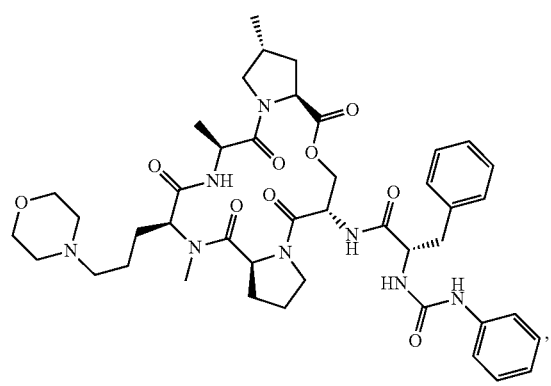
or a subgroup thereof.
In one aspect, a compound can be present as one or more of the following structures:
134
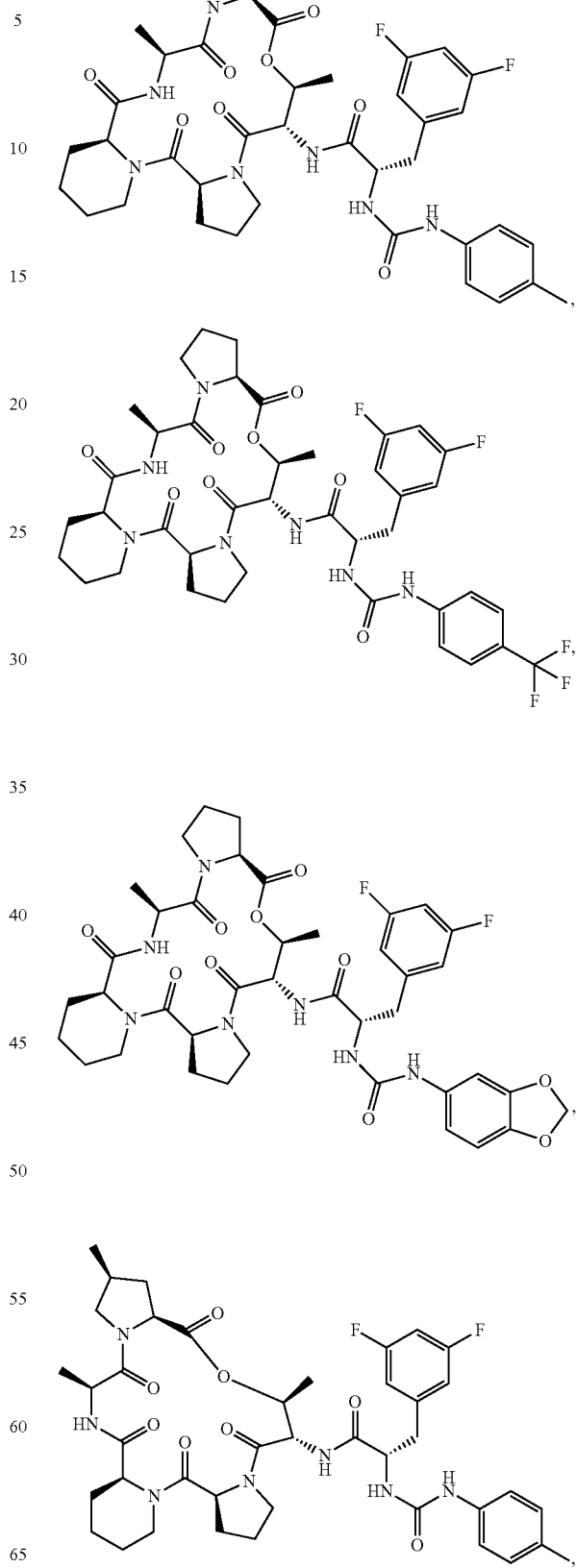

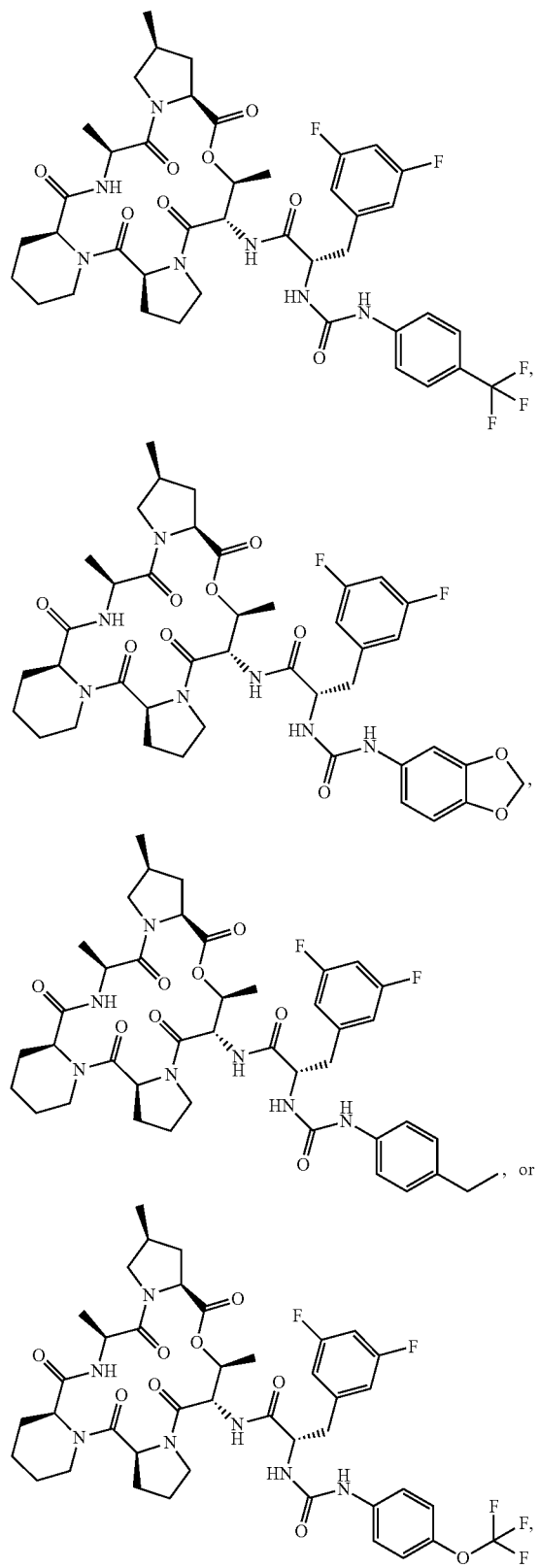
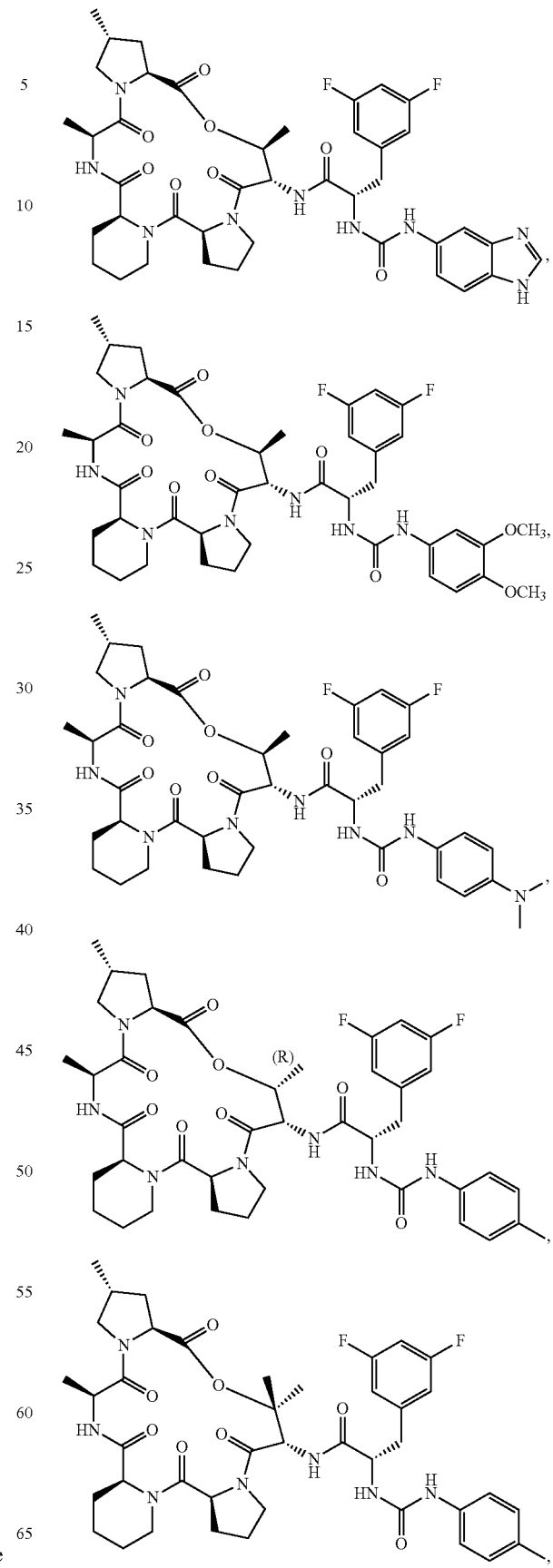
or a subgroup thereof.
In one aspect, a compound can be present as one or more of the following structures:

-continued
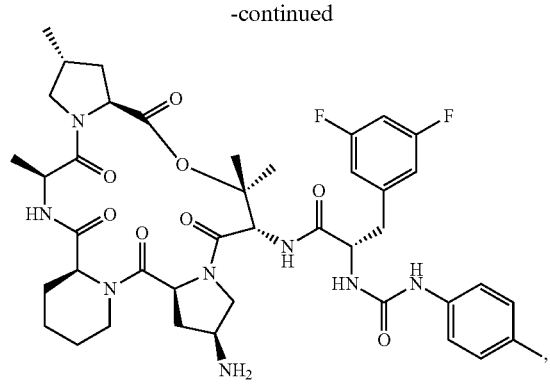
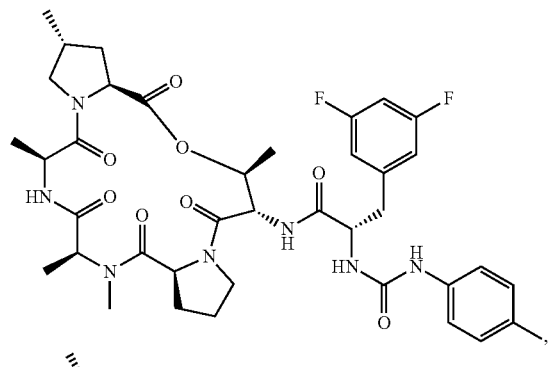
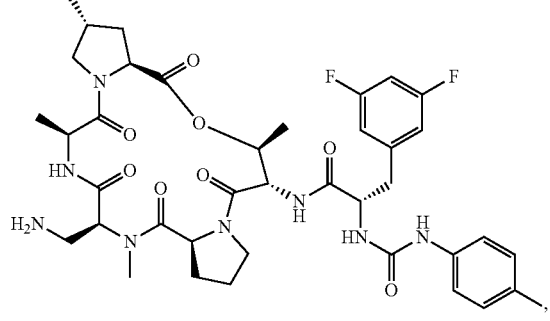
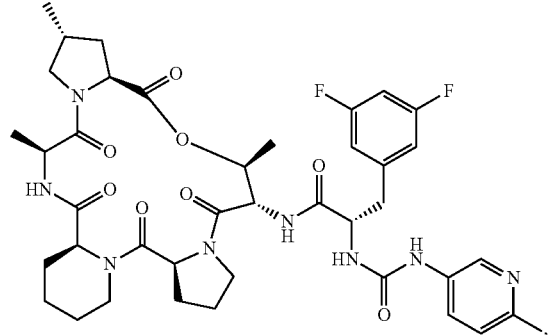
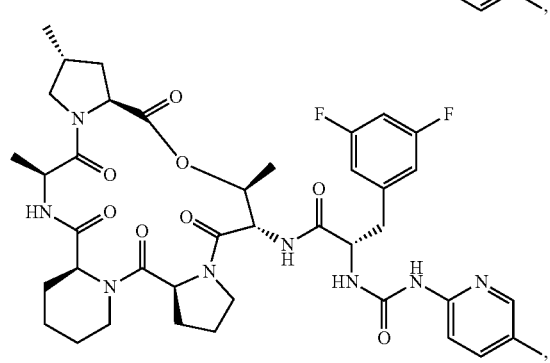
-continued
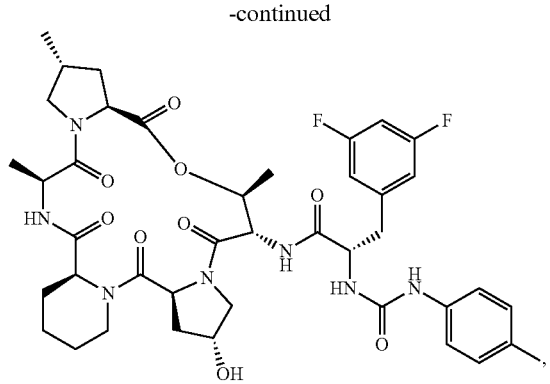
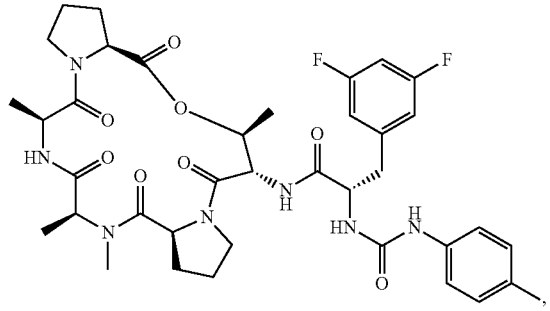
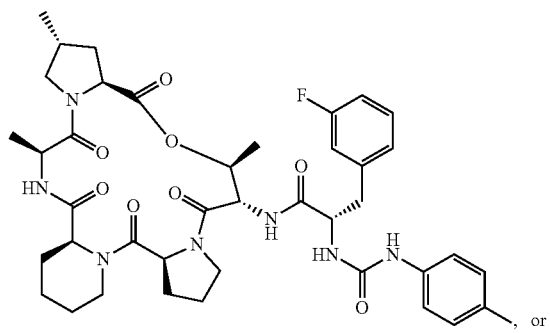
, or
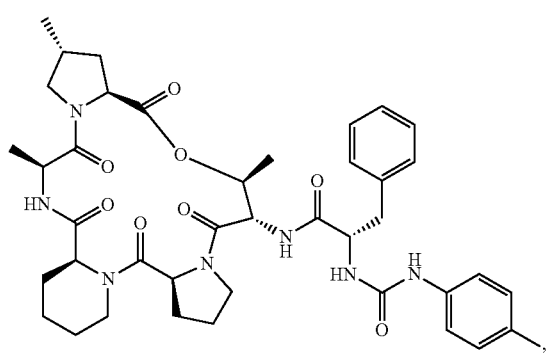
,
or a subgroup thereof.
In one aspect, a compound can be present as one or more of the following structures:

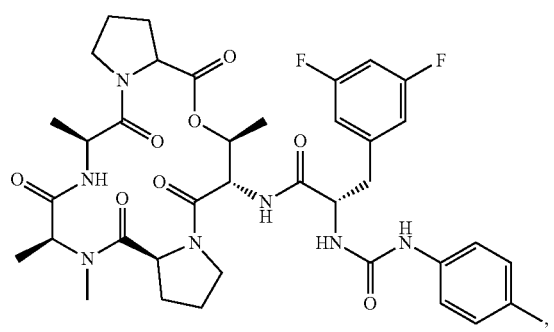
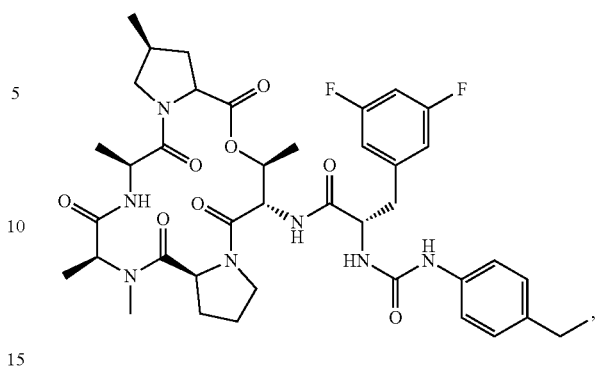
-continued
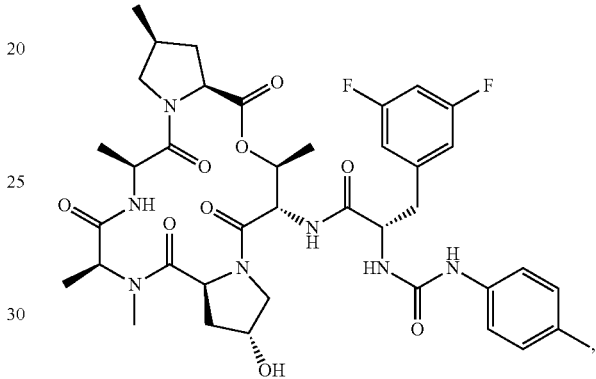
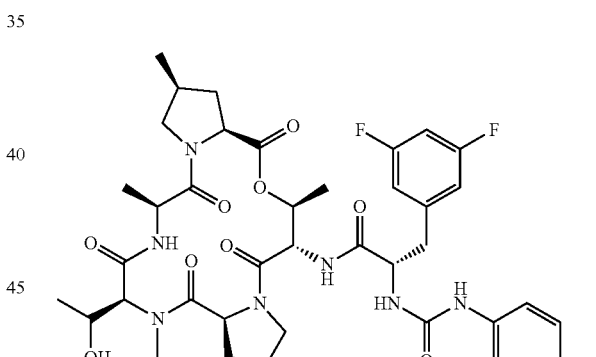
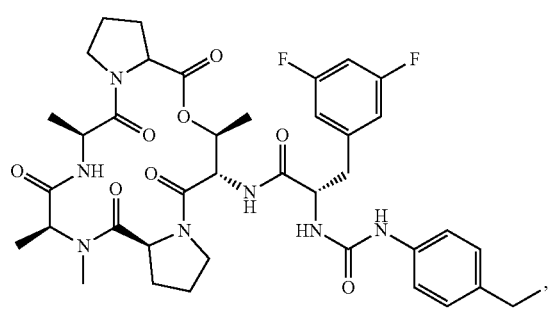
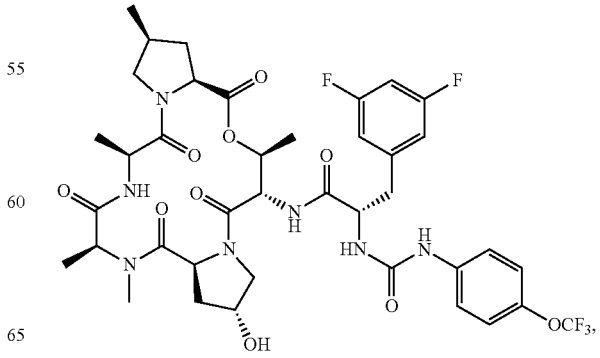

141
-continued
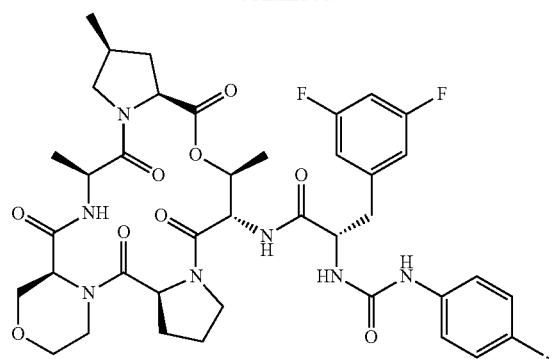
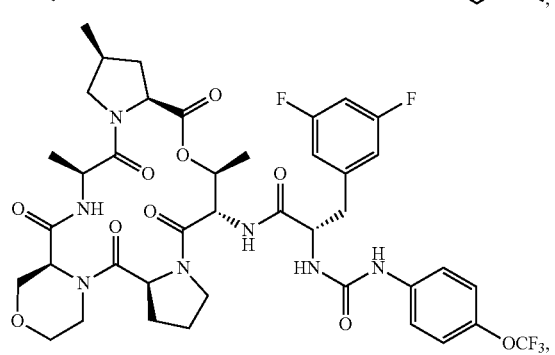
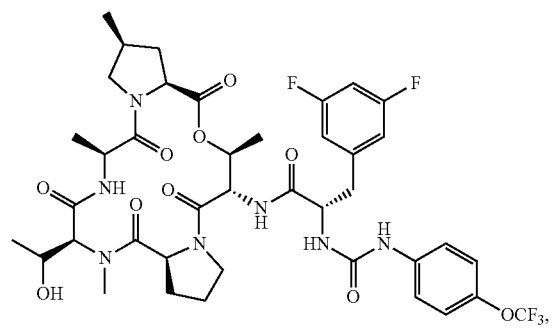
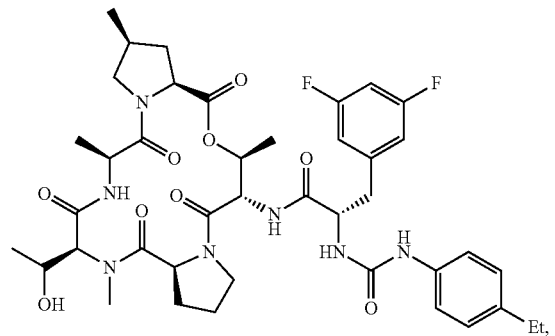
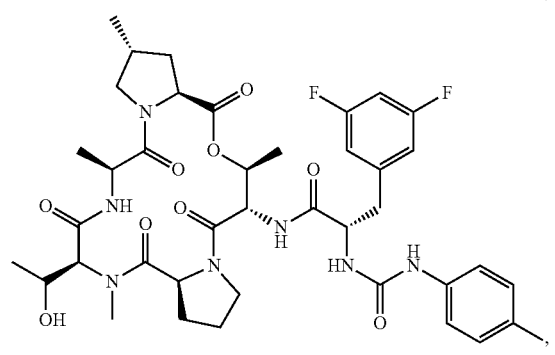
142
-continued
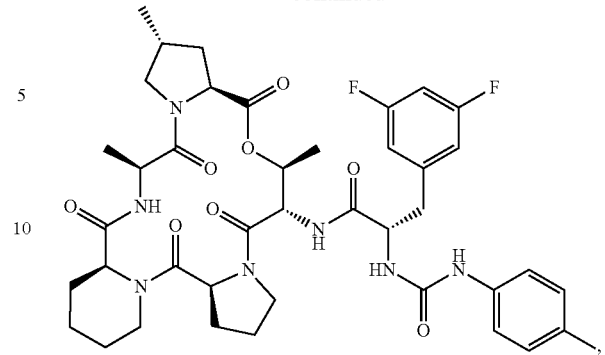
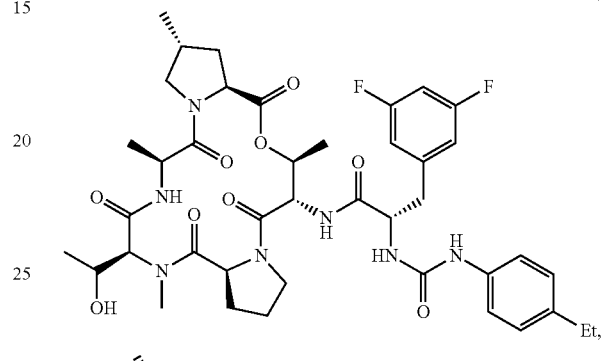
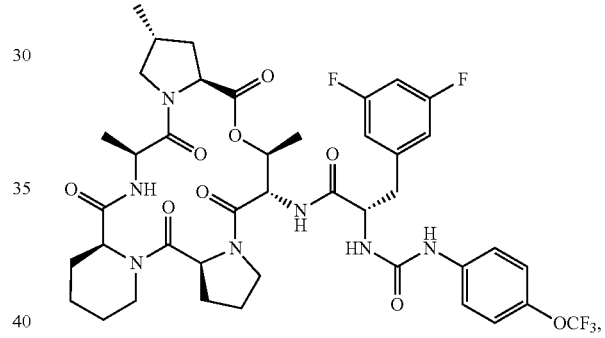
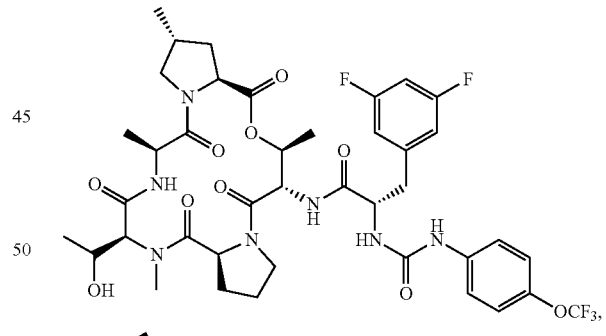
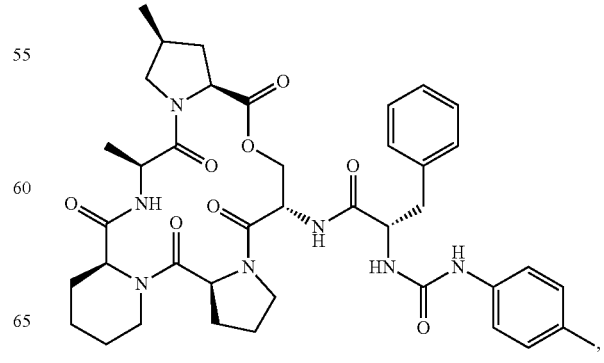

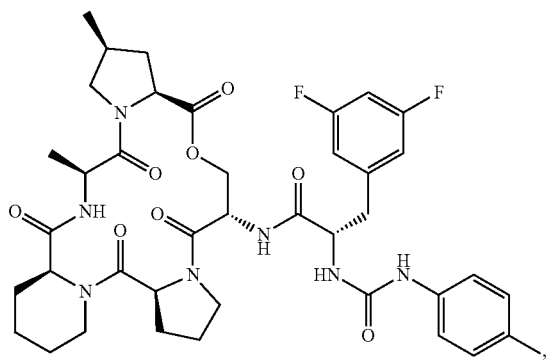

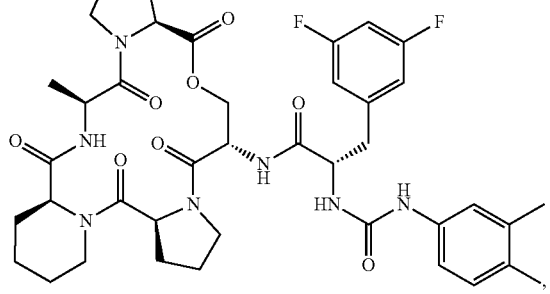

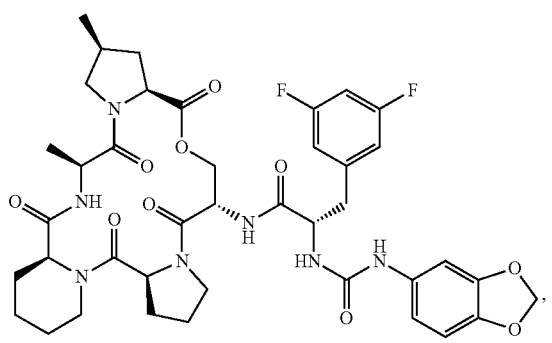

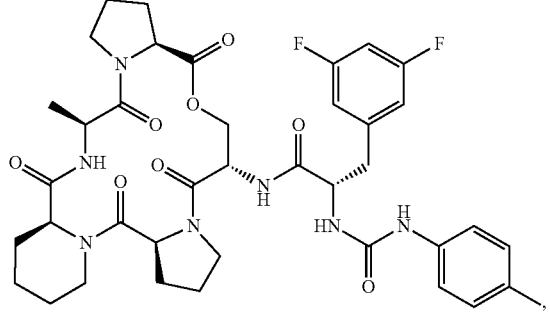

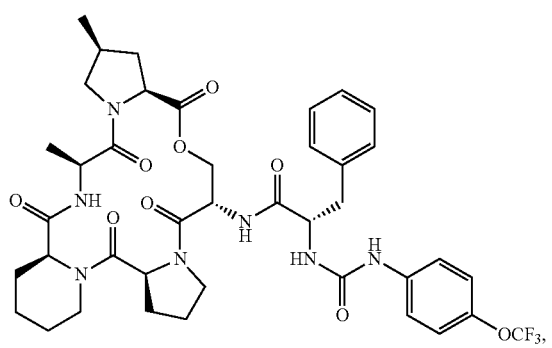

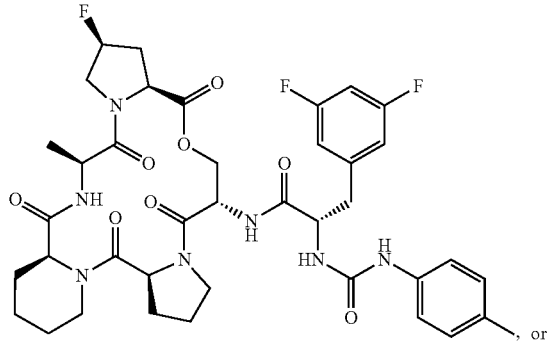

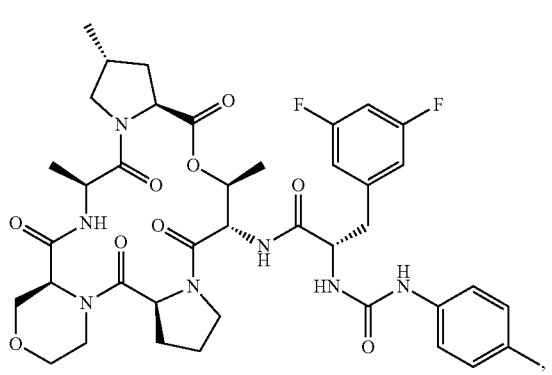

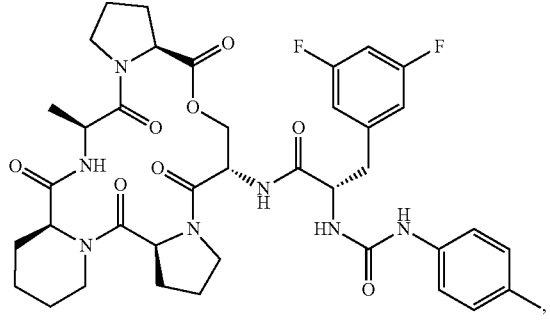

or a subgroup thereof.

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

3. ClpP Enhancer Activity

ClpP protease is normally fairly selective—it clears misfolded proteins that are fed into the enzyme by accessory ClpA, ClpC and ClpX subunits that use ATP to specifically recognize, unfold and translocate the substrate into the ClpP proteolytic chamber for degradation (Gottesman, S. & Maurizi, M. R. Microbiol Rev (1992) 56:592-621; Gottesman, S., et al. Genes & development (1998) 12:1338-1347). Acyldepsipeptide (ADEP) is an antimicrobial lipopeptide that binds to the ClpX activation domain of ClpP, widening the entry pore on the proximal and distal ends of the protein (Sass, P., et al. Proc. Natl. Acad. Sci. (2011) 108:17474-17479). The result is that ClpP becomes an unregulated protease that does not require ATP, which forces even dormant cells to self-digest. Without wishing to be bound by a particular theory, the disclosed compounds of the present invention are believed to bind to the activation domain of ClpP and exert their antibacterial activity by opening the entry to the proteolytic chamber of ClpP, thereby resulting in self-digestion of target bacteria.

C. METHODS OF MAKING THE COMPOUNDS

In one aspect, the invention relates to compounds useful as activators of the ClpP protease, methods of making same, pharmaceutical compositions comprising same, and methods of treating infectious disease. In one aspect, the invention relates to the disclosed synthetic manipulations. In a further aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising at least one compound of any of disclosed compounds or at least one product of the disclosed methods, and combining the compound with a pharmaceutically acceptable carrier or diluent.

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Route I

In one aspect, synthetic intermediates useful for the synthesis of substituted urea depsipeptide analogs of the present invention can be prepared generically by the synthetic scheme as shown below.

SCHEME 1A.

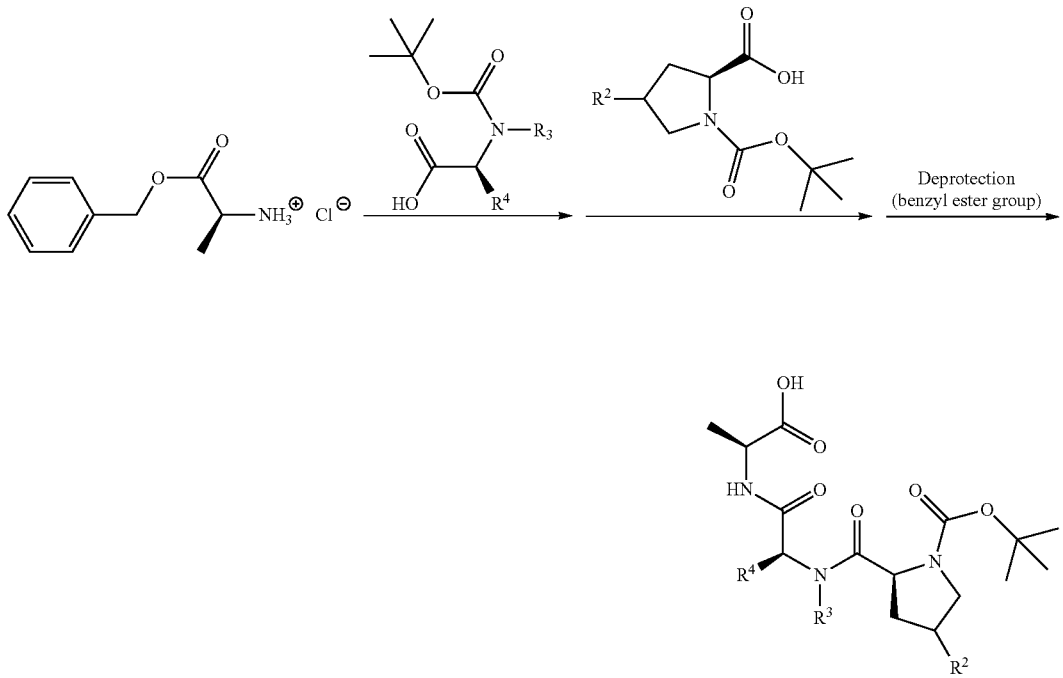

Deprotection (benzyl ester group)

ucts of the synthetic methods described herein. In a further aspect, the disclosed compounds comprise a compound produced by a synthetic method described herein. In a still Compounds are represented in generic form, with substituents as noted in compound descriptions elsewhere herein. A more specific example is set forth below.

SCHEME 1B.

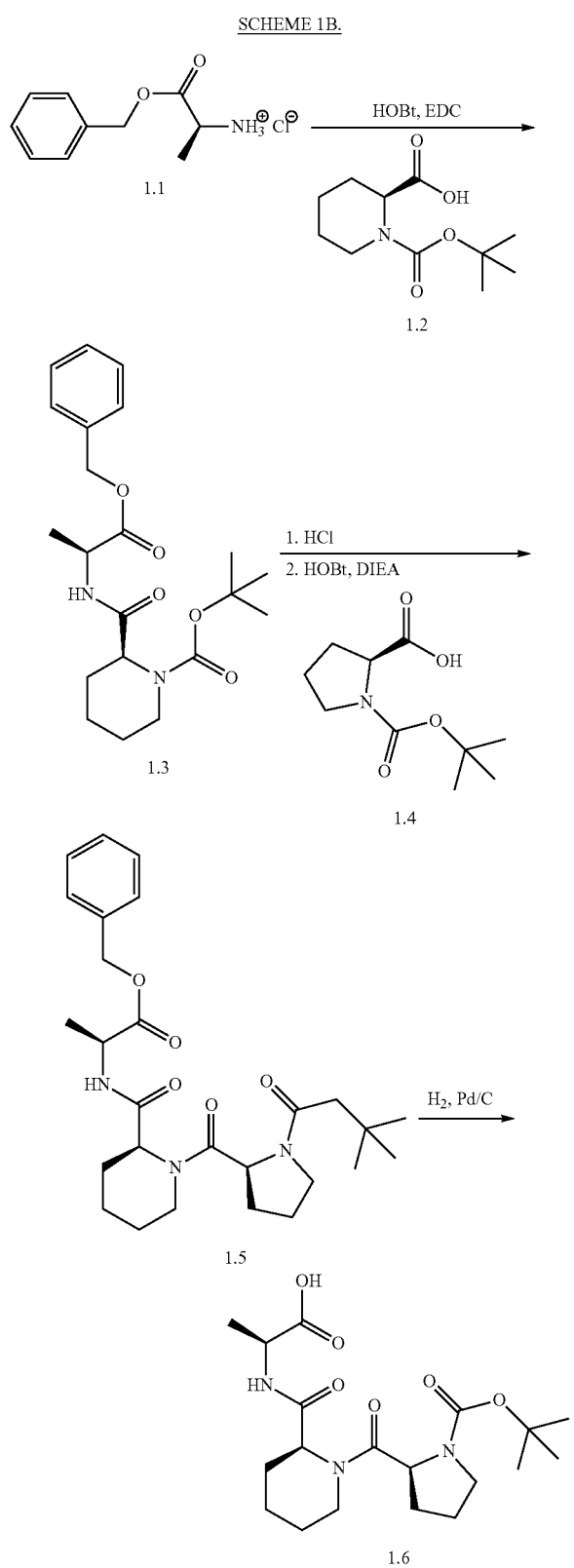

In one aspect, compounds of the present invention, e.g., compounds of Formula 1.6, can be prepared beginning with reaction of compounds of Formulas 1.1 and 1.2 to yield compounds of Formula 1.3. The coupling of 1.1 and 1.2 can be carried out using an appropriate dehydrating (or coupling) agent, e.g., EDC (N-(3-dimethylaminopropyl)-N'-ethylcarbodiimide), with an appropriate additive agent, e.g., HOBt (N-hydroxybenzotriazole), in a suitable solvent, e.g., DMF, and the reaction carried out at a suitable temperature, e.g., about 15° C. to about 30° C., for an appropriate period of time to complete the reaction, e.g., about 10 hr to about 30 hr. The next step of the synthesis sequence involves a multi-step reaction that can be carried out in a single reaction vessel. In the first step, the product from the preceding reaction, 1.3, is treated with an acid, e.g., HCl, in a suitable solvent, e.g., DMF, and carried out at a suitable temperature, e.g., about 15° C. to about 30° C., for a suitable period of time to complete the reaction, e.g., about 30 min to about 120 min. The next is the coupling of the Boc-protected 1.4 with 1.3, which was deprotected in the prior step with HCl. The coupling reaction involves a suitable catalyst, e.g. HOBt, with a suitable base, e.g., DIEA, and carried out at a suitable temperature, e.g., about 15° C. to about 30° C., for an appropriate period of time to complete the reaction, e.g., about 10 h to about 30 h. The last step, preparation of 1.5 from 1.4 involves hydrogenation and is carried out using a suitable transition metal catalyst such as, palladium absorbed on activated carbon, in the presence of hydrogen gas.

In amide bond formation reaction (or alternatively peptide bond formation reaction) above, the reaction involves a dehydrating (or coupling) agent, and as specifically illustrated above in the preparation of 1.3, an agent such as EDC. Other suitable dehydrating agents generally include carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbo-diimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino) phosphonium hexafluorophosphate, or O-(benzotriazol-1-yl)-N,N,N',N'-tetra-methyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyluronium hexafluorophosphate (HATU), or 1-hydroxybenztriazole (HOBt), or benzotriazol-1-yloxytris(dimethylamino)-phosphonium hexafluoro-phosphate (BOP), or mixtures of these, with bases.

Reactions of the type discussed above involving a dehydrating agent often require the use of a base, which in the preparation of 1.3 was indicated as DIEA (diisopropylethylamine). Other suitable bases include, for example, alkali metal carbonates, such as, for example, sodium or potassium carbonate, or sodium or potassium hydrogen carbonate, organic bases such as, for example, trialkylamines, for example triethylamine, N-methylmorpholine, N-methylpiperidine, or 4-dimethylaminopyridine.

2. Route II

In one aspect, synthetic intermediates useful for the synthesis of substituted urea depsipeptide analogs of the present invention can be prepared generically by the synthetic scheme as shown below.

SCHEME 2A.

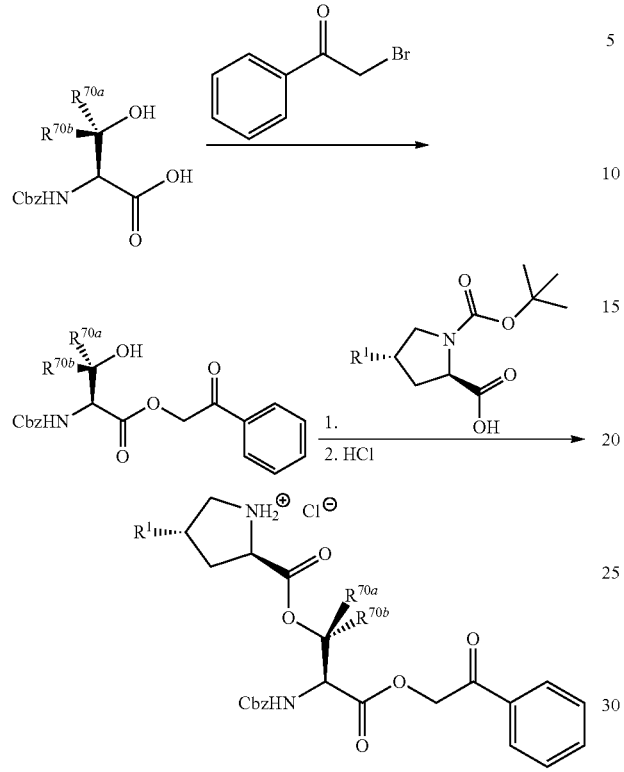

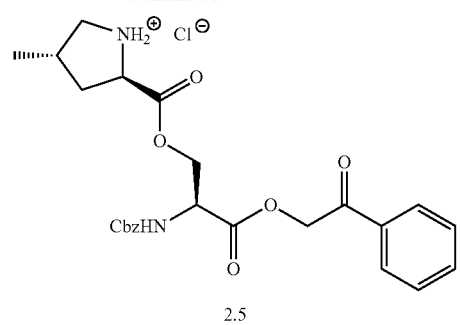

2.5

The intermediate 2.5 is prepared by starting with the preparation of 2.3 from the reaction of 2.1 and 2.2 in the presence of a suitable base, e.g., triethylamine, in a suitable solvent and the reaction is carried out under standard conditions known to one skilled in the art. Next, 2.3 is used to form a ester linkage with 2.4 in the presence of a suitable base, e.g., 4-dimethylaminopyridine (DMAP), and a suitable carbodiimide, e.g., EDC, and the reaction is carried out in a suitable solvent and at a suitable temperature for a time sufficient to complete the reaction, providing 2.5, after deprotection with 4N hydrochloric acid in dixoane.

3. Route III

In one aspect, synthetic intermediates useful for the synthesis of substituted urea depsipeptide analogs of the present invention can be prepared generically by the synthetic scheme as shown below.

Compounds are represented in generic form, with substituents as noted in compound descriptions elsewhere herein. A more specific example is set forth below.

SCHEME 3A.

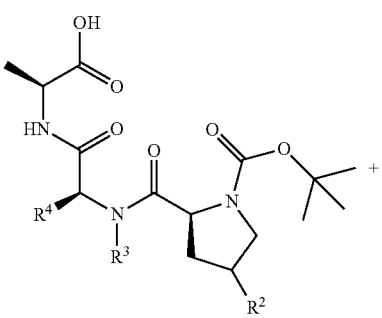

SCHEME 2B.

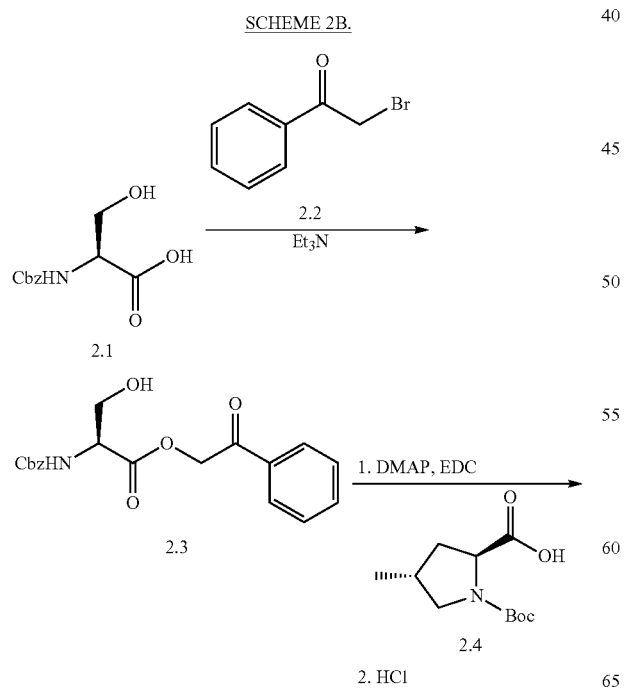

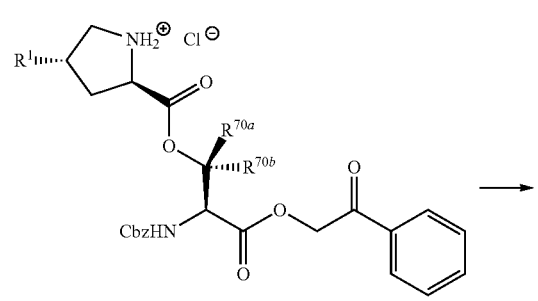

151
-continued

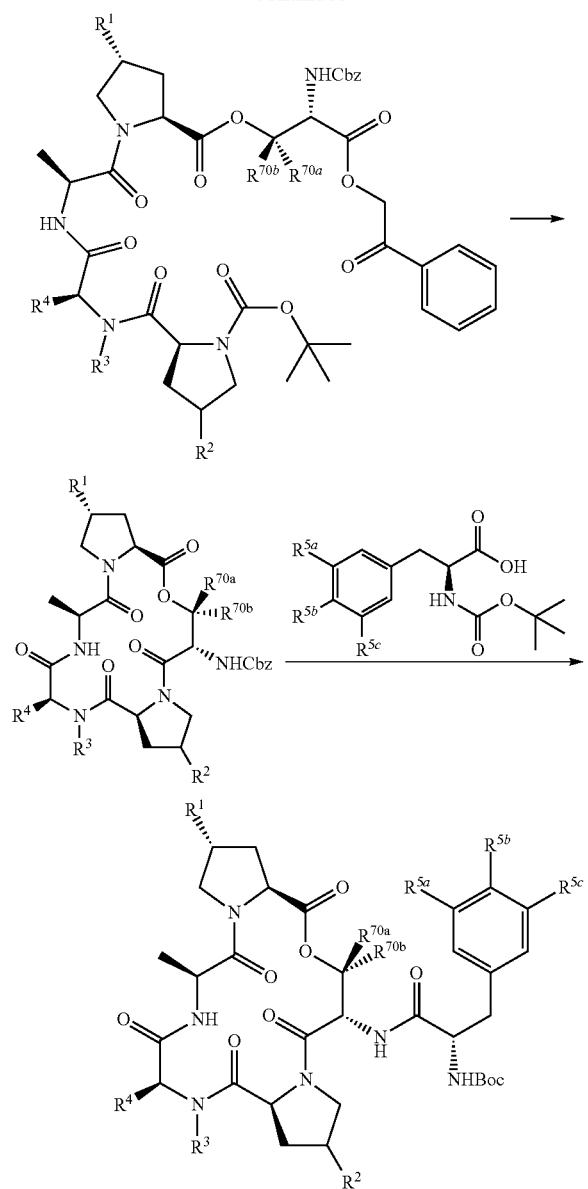

Compounds are represented in generic form, with substituents as noted in compound descriptions elsewhere herein. A more specific example is set forth below.

SCHEME 3B.

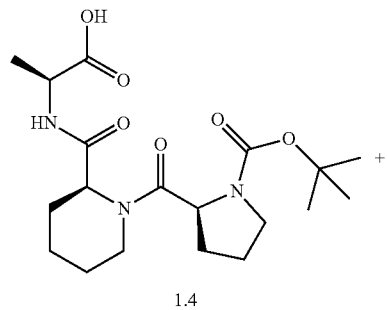

1.4

152
-continued

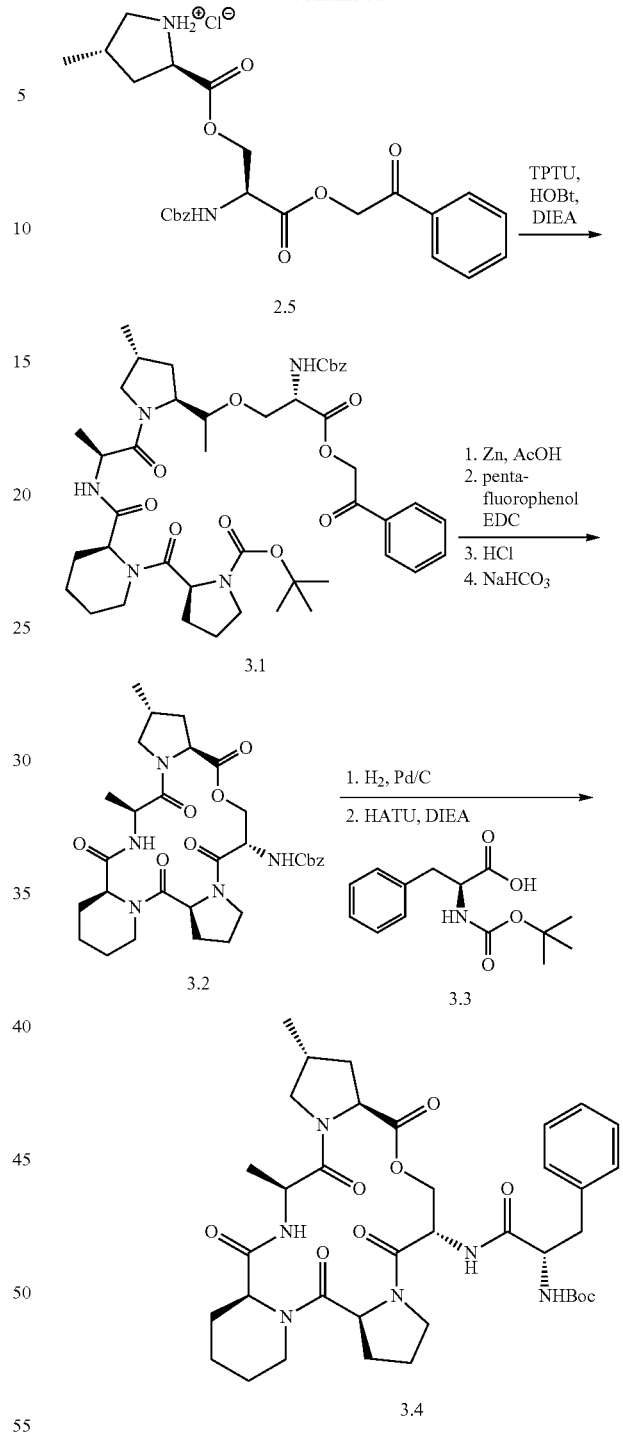

In one aspect, compounds of the present invention, e.g., compounds of similar in structure to Formula 3.4 can be prepared beginning with coupling reaction of intermediate compounds similar in structure to compounds of Formulas 1.6 and 2.5 to yield compounds similar in structure to compounds of Formula 3.1. Compounds of Formulas 1.6 and 2.5 can be obtained from by the methods described herein above for Routes I and II. The coupling reaction of compounds of Formulas 1.6 and 2.5 can carried out by peptide coupling chemistries such as those shown above, or other similar methods known to one skilled in the art. For example, the coupling is carried out in the presence a suitable coupling agents, e.g., HOBt (N-Hydroxybenzotriazole) and TPTU (O-(2-Oxo-1(2H)pyridyl)-N,N,N',N'-tetramethyluronium tetrafluoroborate), and a suitable base, e.g., DIEA (N,N-diisopropylethylamine), and the reaction carried out a suitable temperature, e.g., about 0° C. to about 30° C., for a suitable period of time, e.g., about 12 h to about 24 h, to insure completion of the reaction, thus providing compounds such as 3.1.

The product of the foregoing reaction, a compound such as 3.1, is then subjected to reaction conditions to in order to carry out macrolactonization. The reaction can be accomplished in successive reactions carried out in a one-pot multistage reaction. For example, in the first step, reductive ester hydrolysis is carried out using suitable reagents, e.g., zinc in the presence of about 90% (v/v) acetic acid, and carrying the reaction out at a suitable temperature, e.g., about 15° C. to about 30° C., for a suitable period of time to complete the reaction, e.g., about 1 h to about 3 h. The second step involves formation of an active ester, e.g., using a suitable carbodiimide such as EDC (N-(3-dimethylaminopropyl)-N'-ethylcarbodiimide), and a reagent to introduce an ester activating group, e.g., pentafluorophenol, in a suitable inert solvent, e.g. dichloromethane, and the reaction is carried out at a suitable temperature, e.g., about −20° C. to about 25° C., for a suitable period of time to complete the reaction, e.g., about 16 h to about 30 h. In the next step, the Boc protecting group is removed by treatment with acid, e.g., 1-4N HCl, in a suitable inert solvent, e.g., dioxane, for a period of time to complete selective deprotection, e.g., about 30 min to about 120 min, followed by solvent removal. Finally, cyclization is accomplished by in a two-phase mixture, e.g., water/dichloromethane or water/chloroform, by neutralization with aqueous buffer, e.g., sodium hydrogen carbonate solution, under dilution conditions, to yield the desired macrolactone, i.e., a compound such as 3.2.

In the cyclization reaction above, the second step involves a dehydrating (or coupling) agent, and as specifically illustrated above, an agent such as EDC. Other suitable dehydrating agents generally include carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbo-diimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyluronium hexafluorophosphate (HATU), or 1-hydroxybenztriazole (HOBt), or benzotriazol-1-yloxytris(dimethylamino)-phosphonium hexafluoro-phosphate (BOP), or mixtures of these, with bases.

In the last step of the cyclization reaction, a base is required, which in the specific foregoing example was indicated as sodium hydrogen carbonate. Other suitable bases include, for example, alkali metal carbonates, such as, for example, sodium or potassium carbonate, or sodium or potassium hydrogen carbonate, or organic bases such as trialkylamines, for example triethylamine, N-methylmorpholine, N-methylpiperidine, 4-dimethylaminopyridine or diisopropylethylamine.

Compounds such as 3.5 can be prepared by coupling a suitable amino acid derivative, such as compound 3.3, with the macrolactone, a compound such as 3.2, prepared as described above. Again, a multi-step reaction can be carried out in a single pot reaction. For example, initially hydrogenation is carried out, e.g., using a suitable transition metal catalyst such as, palladium absorbed on activated carbon, in the presence of hydrogen gas. The second step involves coupling of a suitable amino acid, such as compound such as 3.3, with the hydrogenated macrolactone 3.2, in the presence of a suitable dehydrating (or coupling) agent, e.g., HATU (1-[Bis-(dimethylamino)methyliumyl]-1H-1,2,3-triazolo[4,5-b]pyridine-3-oxide hexafluorophosphate), and a suitable base, e.g., DIEA, in a suitable solvent, e.g., dimethylformamide, and the reaction carried out at a suitable temperature, e.g., about 15° C. to about 30° C., for a suitable period of time to complete the reaction, e.g., about 30 min to about 120 min.

In the foregoing reaction, the initial hydrogenation of compound 3.2 can be accomplished utilizing other transition metals, including, for example, palladium, platinum or rhodium. The amount of transition metal catalyst in the reaction can be from about 0.01 to about 1 equivalent based on the amount of compound 3.2. In various aspects, the amount of transition metal catalyst can be from about 0.05 to about 0.2 equivalents of the macrolactone compound such as compound 3.2. Suitable dehydrating (or coupling) agents in this context, i.e., the preparation of compounds similar to 3.4 from macrolactones similar to 3.2, are those described previously above, or mixtures of such dehydrating agents with bases. Suitable bases, in this context, are also as described above. In various aspects, as shown in the specific foregoing example, the dehydrating agent is HATU and the base is DIEA. Suitable solvents in this context are inert organic solvents which do not change under the reaction conditions. These include halogenohydrocarbons such as dichloromethane or trichloromethane, hydrocarbon such as benzene, nitromethane, dioxane, dimethylformamide, acetonitrile or hexamethylphosphoramide. It is also possible to employ mixtures of the solvents. In various aspects, the solvent in this context is dimethylformamide.

As can be appreciated by one skilled in the art, the above reaction provides an example of a generalized approach wherein compounds similar in structure to the specific reactants illustrated above, i.e., compounds similar in structure to Formulas (1.6), (2.5), (3.1), (3.2), and (3.3), and appropriate reagents, can be substituted in the reaction to provide an intermediate similar to Formula (3.4).

4. Route IV

In one aspect, substituted urea depsipeptide analogs of the present invention can be prepared generically by the synthetic scheme as shown below.

SCHEME 4A.1
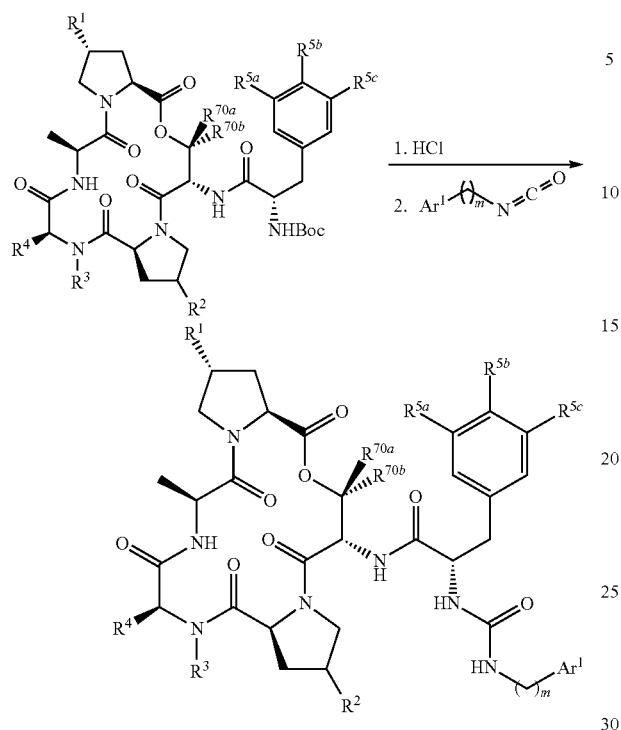
Compounds are represented in generic form, with substituents as noted in compound descriptions elsewhere herein. A more specific example is set forth below.
SCHEME 4B.
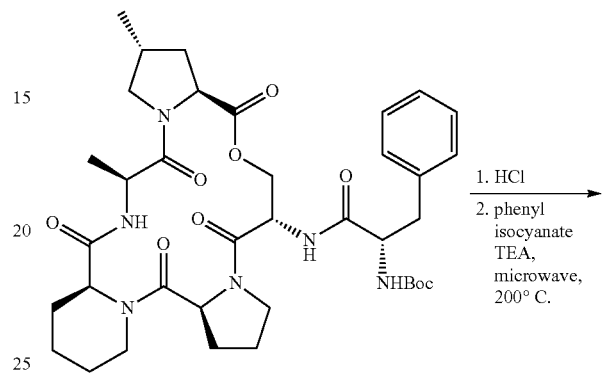
3.4
SCHEME 4A.2
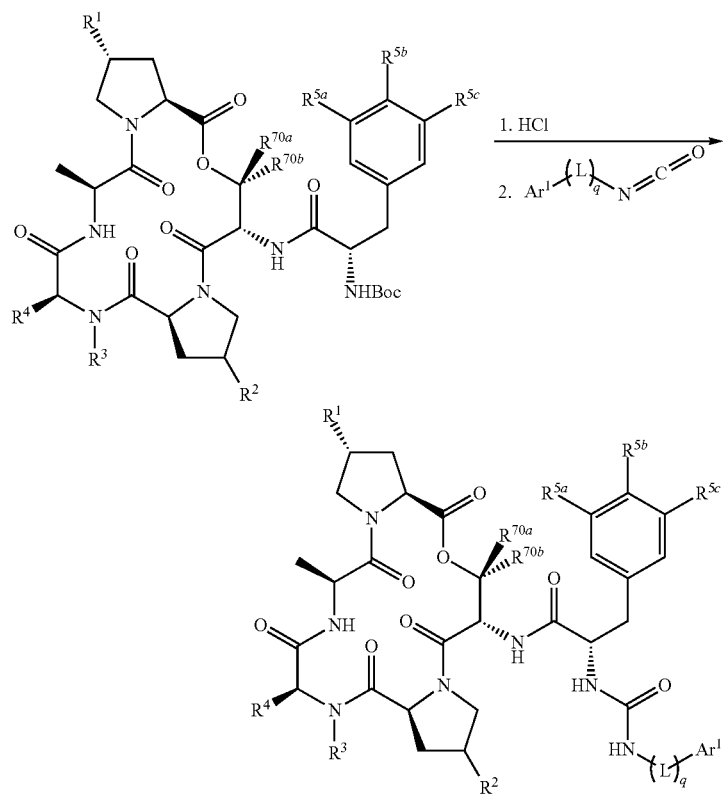

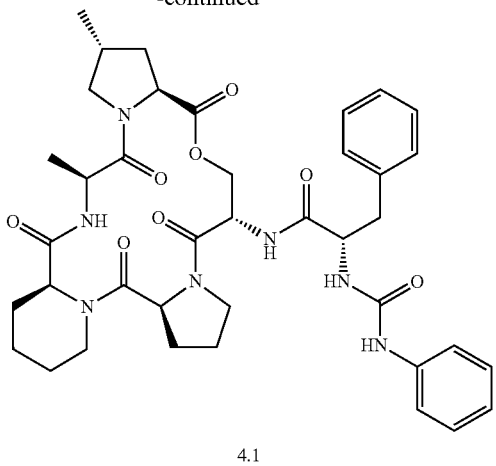

4.1

In one aspect, compounds of the present invention, e.g., compounds such as 4.1, or similar in structure to 4.1, can be prepared by reaction of a macrolactone, e.g., a compound such as 3.4, or compounds similar in structure to 3.4, with a suitable isocyanates, e.g., as shown above, phenyl isocyanates. The preparation of suitable macrolactones, such as 3.4, or compounds similar in structure to 3.4, are prepared as described herein above. Suitable isocyanates, such as aryl isocyanates or alkaryl isocyanates, can be obtained from commercial sources or can be readily prepared by skilled in the art according to methods described in the literature. Phenyl isocyanate is available commercially. The preparation of 4.1 is carried out in a two-step reaction, the first step involving acid catalyzed deprotection, e.g., treatment of 3.4 with 4 N HCl in dioxane to effect removal of the Boc protecting group. The deprotected 3.4 is then reacted with the desired isocyanates, e.g., phenyl isocyanates as shown above, under microwave irradiation in the presence of triethylamine, to provide the target compound, 4.1. Briefly, about 1.2 equivalents of the isocyanate, 1 equivalent of 3.4, and about 3 to about 5 equivalents of triethylamine are mixed together in a suitable solvent, e.g., THF/DMF (v/v 1:1), in a microwave safe tube, and then heated by microwave irradiation to a suitable temperature, e.g., about 200° C., for a period of time sufficient to complete the reaction, e.g., about 10 to about 20 min. The reaction is then cooled, solvents removed under reduced pressure, and the crude residue purified by a suitable chromatographic method, e.g., reverse-phase flash column chromatography, with a suitable gradient, e.g., water to acetonitrile gradient.

5. Route V

In one aspect, synthetic intermediates useful for the synthesis of substituted urea depsipeptide analogs of the present invention can be prepared generically by the synthetic scheme as shown below.

SCHEME 5A.

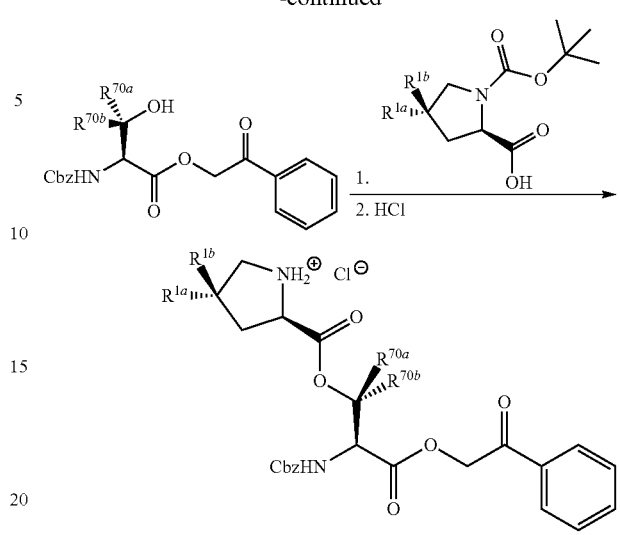

Compounds are represented in generic form, with substituents as noted in compound descriptions elsewhere herein. A more specific example is set forth below.

SCHEME 5B.

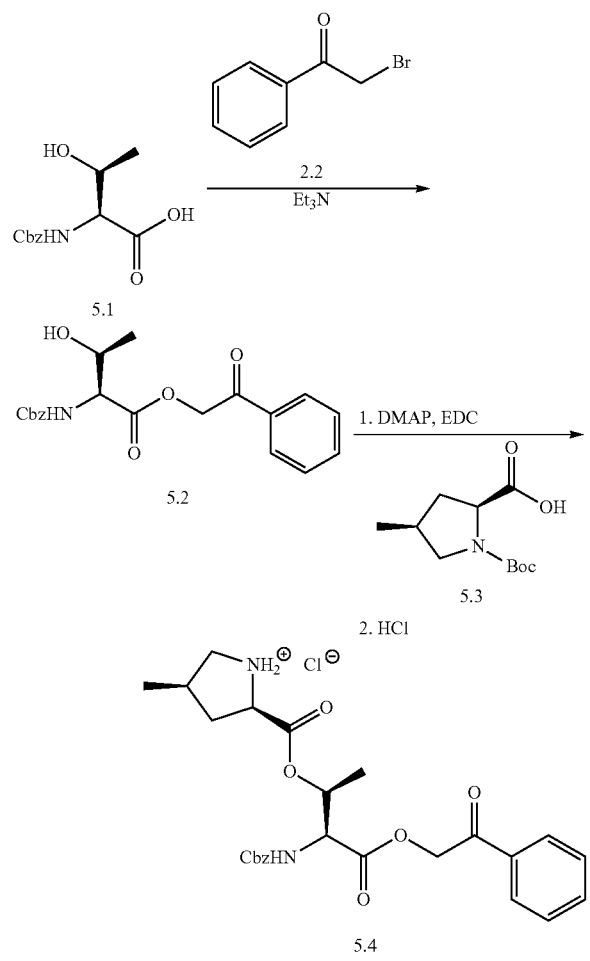

The intermediate 5.4 is prepared by starting with the preparation of 5.2 from the reaction of 5.1 and 2.2 in the presence of a suitable base, e.g., triethylamine, in a suitable solvent and the reaction is carried out under standard conditions known to one skilled in the art. Next, 5.2 is used to form a ester linkage with 5.3 in the presence of a suitable base, e.g., 4-dimethylaminopyridine (DMAP), and a suitable carbodiimide, e.g., EDC, and the reaction is carried out in a suitable solvent and at a suitable temperature for a time sufficient to complete the reaction, providing 5.4, after deprotection with 4N hydrochloric acid in dixoane.

6. Route VI

In one aspect, synthetic intermediates useful for the synthesis of substituted urea depsipeptide analogs of the present invention can be prepared generically by the synthetic scheme as shown below.

SCHEME 6A.

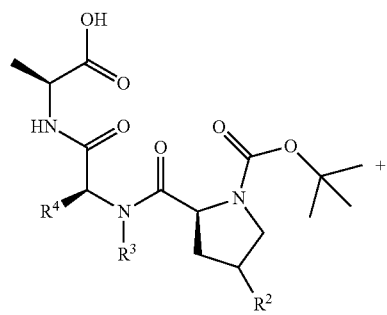

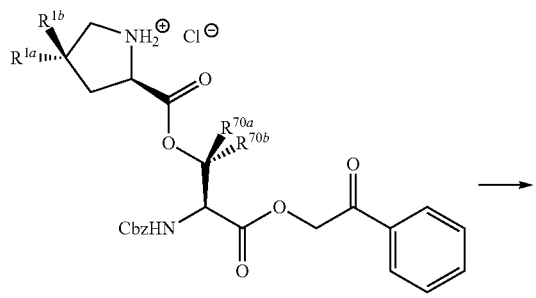

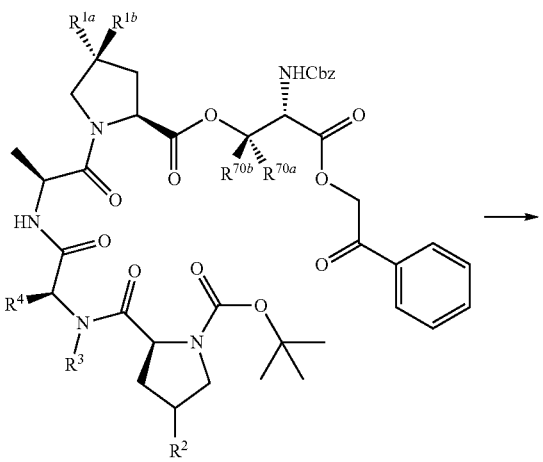

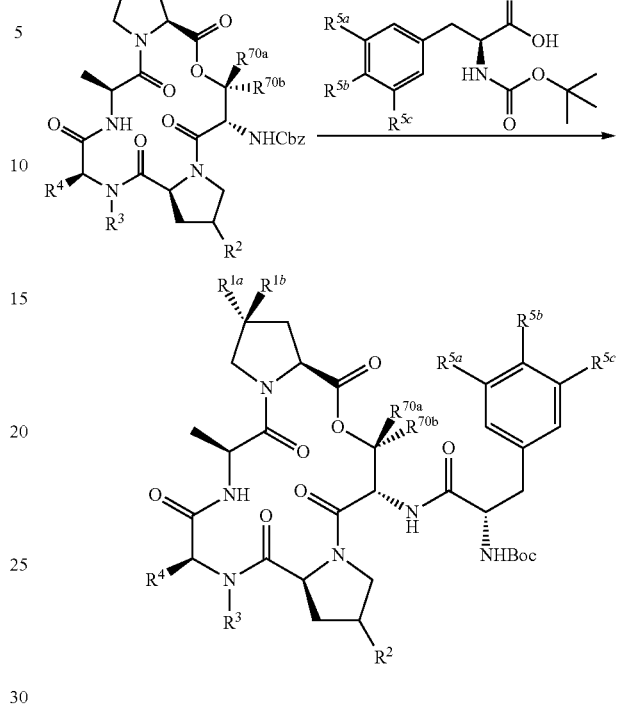

Compounds are represented in generic form, with substituents as noted in compound descriptions elsewhere herein. A more specific example is set forth below.

SCHEME 6B.

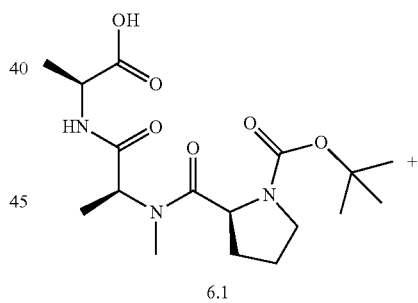

6.1

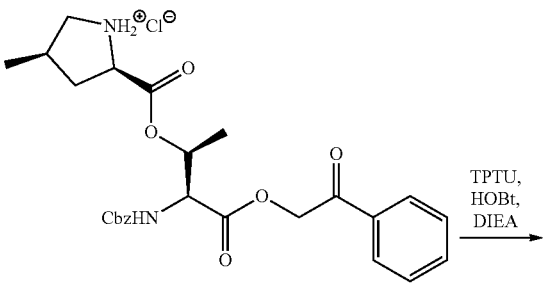

5.4

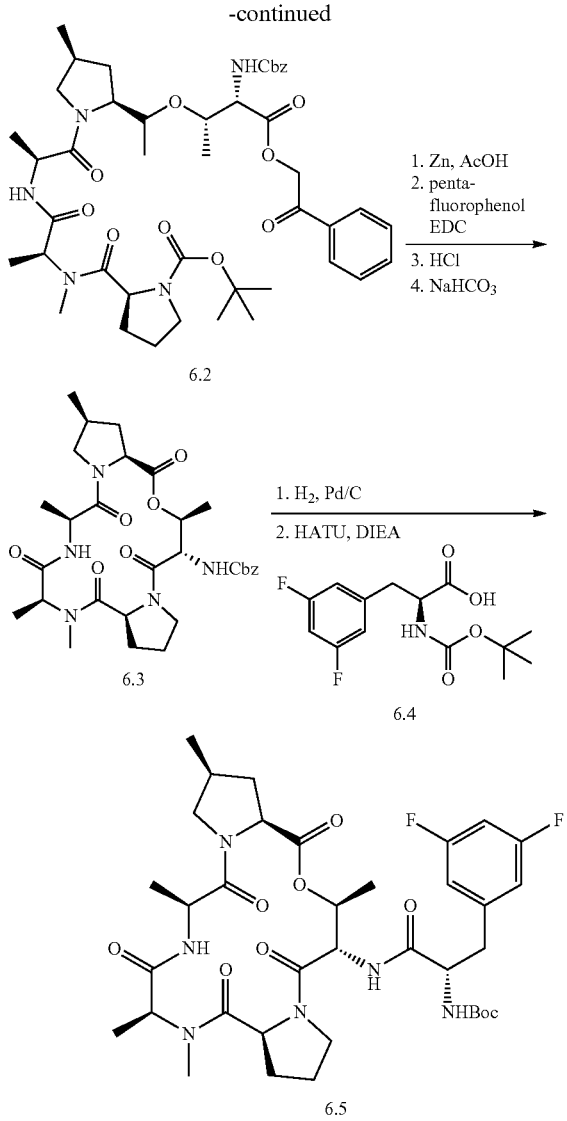

In one aspect, compounds of the present invention, e.g., compounds similar in structure to Formula 6.5 can be prepared beginning with coupling reaction of intermediate compounds similar in structure to compounds of Formulas 6.1 and 5.4 to yield compounds similar in structure to compounds of Formula 6.2. Compounds of Formulas 6.1 and 5.4 can be obtained from by the methods described herein in above for Routes I and V. The coupling reaction of compounds of Formulas 6.1 and 5.4 can be carried out by peptide coupling chemistries such as those shown above, or other similar methods known to one skilled in the art. For example, the coupling may be carried out in the presence of a suitable coupling agent, e.g., HOBt (N-Hydroxybenzotriazole) and TPTU (O-(2-Oxo-1(2H)pyridyl)-N,N,N',N'-tetramethyluronium tetrafluoroborate), and a suitable base, e.g., DIEA (N,N-diisopropylethylamine), and the reaction carried out a suitable temperature, e.g., about 0° C. to about 30° C., for a suitable period of time, e.g., about 12 h to about 24 h, to insure completion of the reaction, thus providing compounds such as 6.2.

The product of the foregoing reaction, a compound such as 6.2, is then subjected to reaction conditions in order to carry out macrolactonization. The reaction can be accomplished in successive reactions carried out in a one-pot multistage reaction. For example, in the first step, reductive ester hydrolysis is carried out using suitable reagents, e.g., zinc in the presence of about 90% (v/v) acetic acid, and carrying the reaction out at a suitable temperature, e.g., about 15° C. to about 30° C., for a suitable period of time to complete the reaction, e.g., about 1 h to about 3 h. The second step involves formation of an active ester using a suitable carbodiimide, e.g., EDC (N-(3-dimethylaminopropyl)-N'-ethylcarbodiimide), and a reagent to introduce an ester activating group, e.g., pentafluorophenol, in a suitable inert solvent, e.g., dichloromethane, and the reaction is carried out at a suitable temperature, e.g., about −20° C. to about 25° C., for a suitable period of time to complete the reaction, e.g., about 16 h to about 30 h. In the next step, the Boc protecting group is removed by treatment with an acid, e.g., 1-4N HCl, in a suitable inert solvent, e.g., dioxane, for a period of time to complete selective deprotection, e.g., about 30 min to about 120 min, followed by solvent removal. Finally, cyclization is accomplished by a two-phase mixture, e.g., water/dichloromethane or water/chloroform, by neutralization with an aqueous buffer, e.g., sodium hydrogen carbonate solution, under dilution conditions, to yield the desired macrolactone 6.3.

In the cyclization reaction above, the second step involves a dehydrating (or coupling) agent, and as specifically illustrated above, an agent such as EDC. Other suitable dehydrating agents generally include carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbo-diimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyluronium hexafluorophosphate (HATU), or 1-hydroxybenztriazole (HOBt), or benzotriazol-1-yloxytris(dimethylamino)-phosphonium hexafluoro-phosphate (BOP), or mixtures of these, with bases.

In the last step of the cyclization reaction, a base is required, which in the specific foregoing example was indicated as sodium hydrogen carbonate. Other suitable bases include, for example, alkali metal carbonates, such as, for example, sodium or potassium carbonate, or sodium or potassium hydrogen carbonate, or organic bases such as trialkylamines, for example triethylamine, N-methylmorpholine, N-methylpiperidine, 4-dimethylaminopyridine or diisopropylethylamine.

Compounds such as 6.5 can be prepared by coupling a suitable amino acid derivative, such as compound 6.4, with the macrolactone, a compound such as 6.3, prepared as described above. Again, a multi-step reaction can be carried out in a single pot reaction. For example, initially hydrogenation is carried out, e.g., using a suitable transition metal catalyst such as, palladium absorbed on activated carbon, in the presence of hydrogen gas. The second step involves coupling of a suitable amino acid, such as compound such as 6.4, with the hydrogenated macrolactone 6.3, in the presence of a suitable dehydrating (or coupling) agent, e.g., HATU (1-[Bis-(dimethylamino)methyliumyl]-1H-1,2,3-triazolo[4,5-b]pyridine-3-oxide hexafluorophosphate), and a suitable base, e.g., DIEA, in a suitable solvent, e.g., dimethylformamide, and the reaction carried out at a suitable temperature, e.g., about 15° C. to about 30° C., for a suitable period of time to complete the reaction, e.g., about 30 min to about 120 min.

In the foregoing reaction, the initial hydrogenation of compound 6.3 can be accomplished utilizing other transition metals, including, for example, palladium, platinum or rhodium. The amount of transition metal catalyst in the reaction can be from about 0.01 to about 1 equivalent based on the amount of compound 6.3. In various aspects, the amount of transition metal catalyst can be from about 0.05 to about 0.2 equivalents of the macrolactone compound such as compound 6.3. Suitable dehydrating (or coupling) agents in this context, i.e., the preparation of compounds similar to 6.5 from macrolactones similar to 6.3, are those described previously above, or mixtures of such dehydrating agents with bases. Suitable bases, in this context, are also as described above. In various aspects, as shown in the specific foregoing example, the dehydrating agent is HATU and the base is DIEA. Suitable solvents in this context are inert organic solvents which do not change under the reaction conditions. These include halogenohydrocarbons such as dichloromethane or trichloromethane, hydrocarbon such as benzene, nitromethane, dioxane, dimethylformamide, acetonitrile or hexamethylphosphoramide. It is also possible to employ mixtures of the solvents. In various aspects, the solvent in this context is dimethylformamide.

As can be appreciated by one skilled in the art, the above reaction provides an example of a generalized approach wherein compounds similar in structure to the specific reactants illustrated above, i.e., compounds similar in structure to Formulas (5.4), (6.1), (6.2), (6.3), and (6.4), and appropriate reagents, can be substituted in the reaction to provide an intermediate similar to Formula (6.5).

7. Route VII

In one aspect, substituted urea depsipeptide analogs of the present invention can be prepared generically by the synthetic scheme as shown below.

SCHEME 7A.

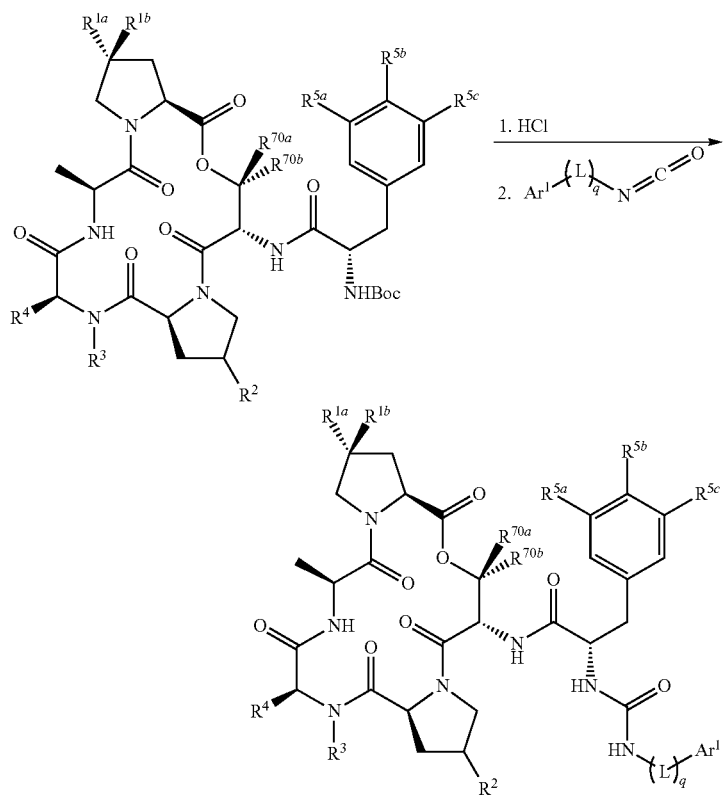

Compounds are represented in generic form, with substituents as noted in compound descriptions elsewhere herein. A more specific example is set forth below.

SCHEME 7B.

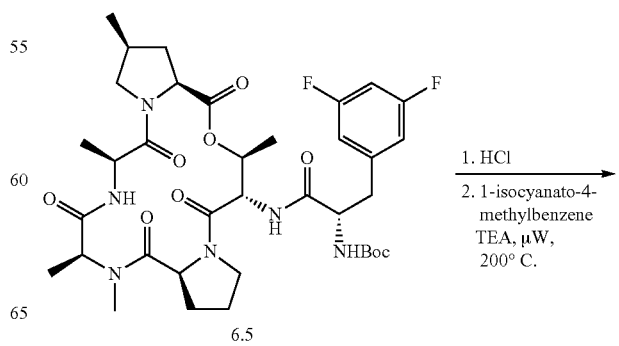

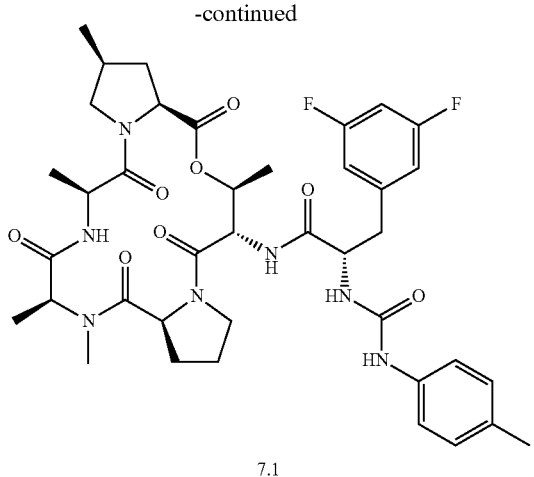

7.1

In one aspect, compounds of the present invention, e.g., compounds such as 7.1, or similar in structure to 7.1, can be prepared by reaction of a macrolactone, e.g., a compound such as 6.5, or compounds similar in structure to 6.5, with a suitable isocyanate, e.g., as shown above, 1-isocyanato-4-methylbenzene. The preparation of suitable macrolactones, such as 6.5, or compounds similar in structure to 6.5, are prepared as described herein above. Suitable isocyanates, such as aryl isocyanates or alkaryl isocyanates, can be obtained from commercial sources or can be readily prepared by skilled in the art according to methods described in the literature. The preparation of 7.1 is carried out in a two-step reaction, the first step involving acid catalyzed deprotection, e.g., treatment of 6.5 with 4 N HCl in dioxane to effect removal of the Boc protecting group. The deprotected 6.5 is then reacted with the desired isocyanate, e.g., 1-isocyanato-4-methylbenzene as shown above, under microwave irradiation in the presence of triethylamine, to provide the target compound, 7.1. Briefly, about 1.2 equivalents of the isocyanate, 1 equivalent of 6.5, and from about 3 to about 5 equivalents of triethylamine are mixed together in a suitable solvent, e.g., THF/DMF (v/v 1:1), in a microwave safe tube, and then heated by microwave irradiation to a suitable temperature, e.g., about 200° C., for a period of time sufficient to complete the reaction, e.g., about 10 to about 20 min. The reaction is then cooled, solvents removed under reduced pressure, and the crude residue purified by a suitable chromatographic method, e.g., reverse-phase flash column chromatography, with a suitable gradient, e.g., water to acetonitrile gradient.

8. Chiral Resolution

The disclosed methods of making can provide compounds that can contain one or more asymmetric centers and, thus, potentially give rise to enantiomers and diastereomers. Unless stated to the contrary, the compounds prepared by the disclosed methods include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

In one aspect, the disclosed methods of making can provide racemic or scalemic mixtures that can be resolved to pure or substantially pure enantiomers using chiral phase chromatography or other suitable methods known to one skilled in the art. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases. As known to one skilled in the art, a variety specific columns and/or mobile phases can affect the desired resolution of enantiomers, and the specific choice can be determined by one skilled in the art. As known to one skilled in the art, chiral chromatography can be carried out in a variety of formats (e.g. SFC, HPLC, and SMB), and other formats can be used to obtain similar results. Moreover, other suitable methods known to one skilled in the art for the separation and isolation of individual enantiomers from a racemic or scalemic mixture can be used to isolate specific enantiomers as needed.

D. PHARMACEUTICAL COMPOSITIONS

In one aspect, the invention relates to pharmaceutical compositions comprising the disclosed compounds and products of disclosed methods. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In one aspect, the invention relates to pharmaceutical compositions comprising a pharmaceutically acceptable carrier and an effective amount of at least one disclosed compound; or a pharmaceutically acceptable salt, solvate, or polymorph thereof.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition comprises a disclosed compound. In a yet further aspect, the pharmaceutical composition comprises a product of a disclosed method of making.

In a further aspect, the pharmaceutical composition comprises a disclosed compound that exhibits an $EC_{50}$ for activation of Sa-C1pP in a casein-BODIPY digestion assay of less than or equal to about 10 μM. In a still further aspect, the pharmaceutical composition comprises a disclosed compound that has an $EC_{50}$ for activation of Sa-C1pP in a casein-BODIPY digestion assay of less than or equal to about 5.0 μM. In a yet further aspect, the pharmaceutical composition comprises a disclosed compound that has an $EC_{50}$ for activation of Sa-C1pP in a casein-BODIPY digestion assay of less than or equal to about 2.5 μM. In an even further aspect, the pharmaceutical composition comprises a disclosed compound that has an $EC_{50}$ for activation of Sa-C1pP in a casein-BODIPY digestion assay of less than or equal to about 1.0 μM.

In one aspect, the pharmaceutical composition is used to treat a mammal. In a yet further aspect, the mammal is a human. In a further aspect, the mammal has been diagnosed with a need for treatment of an infectious disease prior to the administering step. In a further aspect, the mammal has been identified to be in need of treatment an infectious disease. In a further aspect, the pharmaceutical composition is used to treat an infectious disease.

In various aspects, the pharmaceutical composition of the present invention comprises a pharmaceutically acceptable carrier; an effective amount of at least one disclosed compound; or a pharmaceutically acceptable salt, solvate, or polymorph thereof; and an antibacterial agent. In a further aspect, the antibacterial agent comprises a compound selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, dalbavancin, dalfopristin, daptomycin, demeclocycline, dicloxacillin, dirithromycin, doxycycline, erythromycin, enrofloxacin, enoxacin, enviomycin, ertepenem, ethambutol, flucloxacillin, fosfomycin, furazolidone, gatifloxacin, gentamicin, imipenem, isoniazid, kanamycin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, tedolizid, thioacetazone, thioridazine, ticarcillin, tinidazole, tobramycin, torezolid, tosufloxacin, trimethoprim, troleandomycin, trovafloxacin, and vancomycin, or combinations thereof.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids," includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require modulation of C1pP activity, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating C1pP activity (e.g., treatment of one or more microbial infections) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. METHODS OF USING THE COMPOUNDS AND COMPOSITIONS

Also provided is a method of use of a disclosed compound, composition, or medicament. In one aspect, the method of use is directed to the treatment of an infectious disease. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In one aspect, the compounds can be coadministered with an antibacterial agent. In a further aspect, the compounds can be coadministered with an antibacterial agent selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, dalbavancin, dalfopristin, daptomycin, demeclocycline, dicloxacillin, dirithromycin, doxycycline, erythromycin, enrofloxacin, enoxacin, enviomycin, ertepenem, ethambutol, flucloxacillin, fosfomycin, furazolidone, gatifloxacin, gentamicin, imipenem, isoniazid, kanamycin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, tedolizid, thioacetazone, thioridazine, ticarcillin, tinidazole, tobramycin, torezolid, tosufloxacin, trimethoprim, troleandomycin, trovafloxacin, and vancomycin, or combinations thereof.

In a further aspect, the compounds can be administered in combination with one or more antibacterial agents, and salts thereof and combinations thereof. In a still further aspect, the compounds can be administered in combination with an antibacterial agent selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, dalbavancin, dalfopristin, daptomycin, demeclocycline, dicloxacillin, dirithromycin, doxycycline, erythromycin, enrofloxacin, enoxacin, enviomycin, ertepenem, ethambutol, flucloxacillin, fosfomycin, furazolidone, gatifloxacin, gentamicin, imipenem, isoniazid, kanamycin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, tedolizid, thioacetazone, thioridazine, ticarcillin, tinidazole, tobramycin, torezolid, tosufloxacin, trimethoprim, troleandomycin, trovafloxacin, and vancomycin, or combinations thereof.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of infectious diseases, including infectious diseases in mammal associated with infection by a gram positive or gram negative bacteria. For example, a treatment can include enhancing the activity of a bacterial ClpP endopeptidase. Thus, provided is a method of treating or preventing a disorder in a subject comprising the step of administering to the subject at least one disclosed compound; at least one disclosed pharmaceutical composition; and/or at least one disclosed product in a dosage and amount effective to treat the infectious disease in the subject.

Also provided is a method for the treatment of one or more disorders associated with infection by a pathogenic bacteria wherein enhancing ClpP activity can sterilize or decrease the presence of the pathogenic bacteria in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of a disorder in a mammal comprising the step of administering to the mammal at least one disclosed compound, composition, or medicament.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with antibacterial or antimicrobial agents, and combinations thereof, and the like, or the subject compound can be administered in conjunction with the use of physical methods such as with debridement of a wound or infected tissue.

In the treatment of an infectious disease condition, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to a method for enhancing ClpP activity in at least one cell, e.g. a bacterial cell, comprising the step of contacting the at least one cell with at least one disclosed compound or at least one product of a disclosed method in an amount effective to enhance ClpP activity in the at least one cell. In a further aspect, the cell is bacterial cell, e.g. a gram positive or gram negative bacterial cell. In a further aspect, the cell has been isolated from a subject prior to the contacting step. In a further aspect, contacting is via administration to a subject.

a. Treating an Infectious Disease in a Mammal

In one aspect, the invention relates to a method for the treatment of an infectious disease in a mammal comprising the step of administering to the mammal a therapeutically effective amount of at least one disclosed compound; or a pharmaceutically acceptable salt, solvate, or polymorph thereof.

In a further aspect, the compound administered is a product of a disclosed method of making. In a still further aspect, an effective amount is a therapeutically effective amount. In a yet further aspect, an effective amount is a prophylactically effective amount.

In a further aspect, the mammal is a human. In a yet further aspect, the human has been diagnosed with cystic fibrosis. In a still further aspect, the human has been diagnosed with an infectious disease. In a yet further aspect, the mammal has been diagnosed with a need for treatment an infectious disease prior to the administering step. In an even further aspect, the method further comprises the step of identifying a mammal in need of treatment of the infectious disease.

In a further aspect, the human has been diagnosed with a biofilm mediated disease. In a still further aspect, the biofilm mediated disease is bacterial endocarditis and osteomyelitis. In a yet further aspect, the method further comprises the step of identifying a mammal in need of treatment of the biofilm mediated disease.

In various aspects, the compound administered exhibits a minimal inhibitory concentration (MIC) of less than about 15 μM. In a further aspect, the compound administered exhibits a minimal inhibitory concentration (MIC) of less than about 10 μM. In a still further aspect, the compound administered exhibits a minimal inhibitory concentration (MIC) of less than about 5.0 μM. In a yet further aspect, a minimal inhibitory concentration (MIC) of less than about 2.5 μM. In an even further aspect, the compound administered exhibits a minimal inhibitory concentration (MIC) of less than about 1.0 μM. In a still further aspect, the compound administered exhibits a minimal inhibitory concentration (MIC) of less than about 0.75 μM. In a yet further aspect, the compound administered exhibits a minimal inhibitory concentration (MIC) of less than about 0.50 μM.

It is understood, that in various aspects, the MIC is determined by a microbroth dilution method. In a further aspect, the MIC is determined by a microbroth dilution method using *Staphylococcus aureus*, ATCC 29213. In a still further aspect, the MIC is determined by a microbroth dilution method using *Staphylococcus aureus*, NRS70. In a yet further aspect, the MIC is determined by a microbroth dilution method using *Streptococcus pyogenes*, ATCC 700294. In an even further aspect, the MIC is determined by a microbroth dilution method using *Streptococcus pneumoniae*, DAW27. In a still further aspect, the MIC is determined by a microbroth dilution method using *Bacillus subtilis*, ATCC 23857. In a yet further aspect, the MIC is determined by a microbroth dilution method using *Enterococcus faecalis*, ATCC 33186. In an even further aspect, the MIC is determined using *Staphylococcus aureus*, USA 300. In a still further aspect, the MIC is determined using *Streptococcus pneumoniae*, R6. In a further aspect, the MIC is determined using *Staphylococcus aureus*, USA 300 and compared to the MIC determined using *Staphylococcus aureus*, USA 300 wherein C1pP is inactivated, thus allowing confirmation that killing is via a C1pP-dependent pathway.

In various aspects, the compound administered exhibits an $EC_{50}$ for activation of Sa-C1pP in a casein-BODIPY digestion assay of less than or equal to about 10 µM. In a further aspect, the compound administered exhibits an $EC_{50}$ for activation of Sa-C1pP in a casein-BODIPY digestion assay of less than or equal to about 5.0 µM. In a still further aspect, the compound administered exhibits an $EC_{50}$ for activation of Sa-C1pP in a casein-BODIPY digestion assay of less than or equal to about 2.5 µM. In a yet further aspect, the compound administered exhibits an $EC_{50}$ for activation of Sa-C1pP in a casein-BODIPY digestion assay of less than or equal to about 1.0 µM. It is understood that the casein-BODIPY assay is carried out as described herein below.

In various aspects, the infectious disease is associated with a gram positive bacterial infection. In a further aspect, the gram positive bacteria is selected from *Streptococcus* spp., *Staphylococcus* spp., *Enterococcus* spp., *Clostridium* spp., and *Corynebacterium* spp. In a still further aspect, the gram positive bacteria is vancomycin resistant *Enterococcus* spp. (VRE). In a yet further aspect, the gram positive bacteria is selected from *Bacillus anthracis, Bacillus cereus, Bacillus subtilis, Clostridium difficile, Clostridium tetani, Clostridium botulinum, Clostridium perfringens, Corynebacterium diphtheria, Enterococcus faecalis, Enterococcus faecium, Listeria monocytogenes, Listeria ivanovii, Micrococcus luteus, Staphylococcus aureus, Staphylococcus epidermidis, Staphylococcus saprophyticus, Staphylococcus hyicus, Staphylococcus intermedius, Streptococcus pneumoniae,* and *Streptococcus pyogenes*. In an even further aspect, the gram positive bacteria is selected from *Clostridium difficile, Corynebacterium diphtheria, Enterococcus faecalis, Enterococcus faecium, Staphylococcus aureus, Staphylococcus epidermidis,* and *Streptococcus pneumoniae, Streptococcus pyogenes*. In a still further aspect, the gram positive bacteria is selected from methicillin resistant *Staphylococcus aureus* (MRSA), methicillin resistant *Staphylococcus epidermidis* (MRSE), and penicillin resistant *Streptococcus pneumoniae* (PRSP).

In various aspects, the infectious disease is associated with a gram negative bacterial infection. In a further aspect, the gram negative bacteria is selected from *Aeromonas* spp., *Bordatella* spp., *Citrobacter* spp., *Enterobacter* spp., *Escherichia* spp., *Haemophilus* spp., *Klebsiella* spp., *Moraxella* spp., *Neisseria* spp., *Proteus* spp., *Pseudomonas* spp., *Salmonella* spp., *Shigella* spp., *Stenotrophomonas* spp., *Vibrio* spp., and *Yersinia* spp. In a still further aspect, the gram negative bacteria is selected from *Aeromonas hydrophila, Bordetella pertussis, Bordetella parapertussis, Bordetella bronchiseptica, Citrobacter freundii, Enterobacter aerogenes, Enterobacter cloacae, Enterobacter sakazakii, Escherichia coli, Haemophilus influenzae, Haemophilus aegypticus, Haemophilus ducreyi, Klebsiella edwardsii, Klebsiella pneumoniae, Moraxella catarrhalis, Neisseria meningitidis, Neisseria gonorrhoeae, Proteus mirabilis, Salmonella enterica, Shigella boydii, Shigella dysenteriae, Shigella flexneri, Shigella sonnei, Stenotrophomonas maltophilia, Vibrio cholerae, Vibrio parahaemolyticus, Vibrio vulnificus, Vibrio fluvialis, Yersinia pestis, Yersina enterocolitica,* and *Yersina pseudotuberculosis*. In a yet further aspect, the gram negative bacteria is selected from *Aeromonas hydrophila, Citrobacter freundii, Escherichia coli, Klebsiella edwardsii, Moraxella catarrhalis, Proteus mirabilis, Salmonella enterica, Shigella flexneri, Stenotrophomonas maltophilia, Vibrio cholerae,* and *Yersinia enterocolitica*.

In a further aspect, the infectious disease is selected from urinary tract infection, skin infection, intestinal infection, lung infection, ocular infection, otitis, sinusitis, pharyngitis, osteo-articular infection, genital infection, dental infection, oral infection, septicemia, nocosomial infection, bacterial meningitis, gastroenteritis, gastritis, diarrhea, ulcer, endocarditis, sexually transmitted disease, tetanus, diphtheria, leprosy, cholera, listeriosis, tuberculosis, salmonellosis, dysentery, and soft tissue.

In a further aspect, the infectious disease is selected from endocardititis, osteomyelitis, skin and soft tissue infection ("SSTI"), and infection associated with an indwelling device. In a still further aspect, the infectious disease is endocardititis. In a yet further aspect, the infectious disease is osteomyelitis. In an even further aspect, the infectious disease is an SSTI. In a still further aspect, the SSTI is a complicated SSTI (cSSTI). In a yet further aspect, the infectious disease is associated with an indwelling device.

In a further aspect, the infectious disease is a chronic bacterial infection.

In various aspects, the method further comprises administering to the mammal a therapeutically effective amount of at least one antibacterial agent. In a further aspect, the antibacterial agent comprises a compound selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, dalbavancin, dalfopristin, daptomycin, demeclocycline, dicloxacillin, dirithromycin, doxycycline, erythromycin, enrofloxacin, enoxacin, enviomycin, ertepenem, ethambutol, flucloxacillin, fosfomycin, furazolidone, gatifloxacin, gentamicin, imipenem, isoniazid, kanamycin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, tedolizid, thioacetazone, thioridazine, ticarcillin, tinidazole, tobramycin, torezolid, tosufloxacin, trimethoprim, troleandomycin, trovafloxacin, and vancomycin, or combinations thereof.

In a further aspect, the method comprises co-administering to the mammal a therapeutically effective amount of the antibacterial agent. In a still further aspect, the co-administration is administration in a substantially simultaneous manner. In a yet further aspect, the administration in a substantially simultaneous manner comprises a single dose form containing a fixed ratio of the compound and the antibacterial agent. In an even further aspect, the single dose form is a capsule or a tablet. In a still further aspect, the single dose form is an ampule for a single intravenous administration. In a yet further aspect, the co-administration is administration in a substantially sequential manner.

b. Enhancing the Activity of ClpP Protease Activity in Cells

In one aspect, the invention relates to a method for enhancing the activity of ClpP protease in at least one cell, comprising the step of contacting the at least one cell with an effective amount of at least one disclosed compound; or a pharmaceutically acceptable salt, solvate, or polymorph thereof.

In a further aspect, the compound administered is a product of a disclosed method of making a compound. In a still further aspect, an effective amount is a therapeutically effective amount. In a yet further aspect, an effective amount is a prophylactically effective amount.

In one aspect, the cell is bacterial. In a further aspect, the cell is a gram positive bacterial cell. In a still further aspect, the cell is a gram negative bacterial cell. In an even further aspect, the cell is a fungus. In a still further aspect, the cell has been isolated from a mammal prior to the contacting step. In a yet further aspect, contacting the cell is via administration of the compound to a mammal. In an even further aspect, the cell is a bacterial cell, and is infecting a mammal.

In a further aspect, the mammal has been diagnosed with a need for treatment of an infectious disease prior to the administering step. In a still further aspect, the method further comprises the step of identifying a mammal in need of enhancing the activity of ClpP protease prior to the administering step. In a yet further aspect, the enhancing ClpP activity treats an infectious disease in a mammal.

In a further aspect, the mammal has been diagnosed with a need for treatment of a biofilm mediated disease prior to the administering step. In a yet further aspect, the the enhancing ClpP activity treats a biofilm mediated disease in a mammal. In a still further aspect, the biofilm mediated disease is bacterial endocarditis and osteomyelitis.

In various aspects, the compound contacting the cell exhibits a minimal inhibitory concentration (MIC) of less than about 15 µM. In a further aspect, the compound contacting the cell exhibits a minimal inhibitory concentration (MIC) of less than about 10 µM. In a still further aspect, the compound contacting the cell exhibits a minimal inhibitory concentration (MIC) of less than about 5.0 µM. In a yet further aspect, a minimal inhibitory concentration (MIC) of less than about 2.5 µM. In an even further aspect, the compound contacting the cell exhibits a minimal inhibitory concentration (MIC) of less than about 1.0 µM. In a still further aspect, the compound contacting the cell exhibits a minimal inhibitory concentration (MIC) of less than about 0.75 µM. In a yet further aspect, the compound contacting the cell exhibits a minimal inhibitory concentration (MIC) of less than about 0.50 µM.

It is understood, that in various aspects, the MIC is determined by a microbroth dilution method. In a further aspect, the MIC is determined by a microbroth dilution method using *Staphylococcus aureus*, ATCC 29213. In a still further aspect, the MIC is determined by a microbroth dilution method using *Staphylococcus aureus*, NRS70. In a yet further aspect, the MIC is determined by a microbroth dilution method using *Streptococcus pyogenes*, ATCC 700294. In an even further aspect, the MIC is determined by a microbroth dilution method using *Streptococcus pneumoniae*, DAW27. In a still further aspect, the MIC is determined by a microbroth dilution method using *Bacillus subtilis*, ATCC 23857. In a yet further aspect, the MIC is determined by a microbroth dilution method using *Enterococcus faecalis*, ATCC 33186. In an even further aspect, the MIC is determined using *Staphylococcus aureus*, USA 300.

In a still further aspect, the MIC is determined using *Streptococcus pneumoniae*, R6. In a further aspect, the MIC is determined using *Staphylococcus aureus*, USA 300 and compared to the MIC determined using *Staphylococcus aureus*, USA 300 wherein ClpP is inactivated, thus allowing confirmation that killing is via a ClpP-dependent pathway.

In various aspects, the compound contacting the cell exhibits an $EC_{50}$ for activation of Sa-ClpP in a casein-BODIPY digestion assay of less than or equal to about 10 µM. In a further aspect, the compound contacting the cell exhibits an $EC_{50}$ for activation of Sa-ClpP in a casein-BODIPY digestion assay of less than or equal to about 5.0 µM. In a still further aspect, the compound contacting the cell exhibits an $EC_{50}$ for activation of Sa-ClpP in a casein-BODIPY digestion assay of less than or equal to about 2.5 µM. In a yet further aspect, the compound contacting the cell exhibits an $EC_{50}$ for activation of Sa-ClpP in a casein-BODIPY digestion assay of less than or equal to about 1.0 µM. It is understood that the casein-BODIPY assay is carried out as described herein below.

In a further aspect, contacting the cell treats an infectious disease. In a still further aspect, the infectious disease is selected from urinary tract infection, skin infection, intestinal infection, lung infection, ocular infection, otitis, sinusitis, pharyngitis, osteo-articular infection, genital infection, dental infection, oral infection, septicemia, nocosomial infection, bacterial meningitis, gastroenteritis, gastritis, diarrhea, ulcer, endocarditis, sexually transmitted disease, tetanus, diphtheria, leprosy, cholera, listeriosis, tuberculosis, salmonellosis, dysentery, and soft tissue.

In a further aspect, contacting the cell treats an infectious disease selected from endocardititis, osteomyelitis, skin and soft tissue infection ("SSTI"), and infection associated with an indwelling device. In a still further aspect, the infectious disease is endocarditis. In a yet further aspect, the infectious disease is osteomyelitis. In an even further aspect, the infectious disease is an SSTI. In a still further aspect, the SSTI is a complicated SSTI (cSSTI). In a yet further aspect, the infectious disease is associated with an indwelling device.

In a further aspect, contacting the cell treats a chronic bacterial infection.

In various aspects, the method further comprises contacting the cell with the compound and at least one antibacterial agent. In a further aspect, the antibacterial agent comprises a compound selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, dalbavancin, dalfopristin, daptomycin, demeclocycline, dicloxacillin, dirithromycin, doxycycline, erythromycin, enrofloxacin, enoxacin, enviomycin, ertepenem, ethambutol, flucloxacillin, fosfomycin, furazolidone, gatifloxacin, gentamicin, imipenem, isoniazid, kanamycin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, tedolizid, thioacetazone, thioridazine, ticarcillin, tinidazole, tobramycin, torezolid, tosufloxacin, trimethoprim, troleandomycin, trovafloxacin, and vancomycin, or combinations thereof.

2. Manufacture of a Medicament

In one aspect, the invention relates to a medicament comprising one or more disclosed compounds; or a pharmaceutically acceptable salt, solvate, or polymorph thereof. In a further aspect, the one or more compounds is a product of a disclosed method of making.

In various aspect, the invention relates methods for the manufacture of a medicament for enhancing the activity of ClpP protease (e.g., treatment of one or more infectious diseases) in mammals (e.g., humans) comprising combining one or more disclosed compounds, products, or compositions or a pharmaceutically acceptable salt, solvate, hydrate, or polymorph thereof, with a pharmaceutically acceptable carrier. It is understood that the disclosed methods can be performed with the disclosed compounds, products, and pharmaceutical compositions. It is also understood that the disclosed methods can be employed in connection with the disclosed methods of using.

3. Use of Compounds

Also provided are the uses of the disclosed compounds and products. In one aspect, the invention relates to use of at least one disclosed compound; or a pharmaceutically acceptable salt, solvate, or polymorph thereof. In a further aspect, the compound used is a product of a disclosed method of making.

In various aspects, the compound used exhibits a minimal inhibitory concentration (MIC) of less than about 15 µM. In a further aspect, the compound used exhibits a minimal inhibitory concentration (MIC) of less than about 10 µM. In a still further aspect, the compound used exhibits a minimal inhibitory concentration (MIC) of less than about 5.0 µM. In a yet further aspect, a minimal inhibitory concentration (MIC) of less than about 2.5 µM. In an even further aspect, the compound used exhibits a minimal inhibitory concentration (MIC) of less than about 1.0 µM. In a still further aspect, the compound used exhibits a minimal inhibitory concentration (MIC) of less than about 0.75 µM. In a yet further aspect, the compound used exhibits a minimal inhibitory concentration (MIC) of less than about 0.50 µM.

It is understood, that in various aspects, the MIC is determined by a microbroth dilution method. In a further aspect, the MIC is determined by a microbroth dilution method using *Staphylococcus aureus*, ATCC 29213. In a still further aspect, the MIC is determined by a microbroth dilution method using *Staphylococcus aureus*, NRS70. In a yet further aspect, the MIC is determined by a microbroth dilution method using *Streptococcus pyogenes*, ATCC 700294. In an even further aspect, the MIC is determined by a microbroth dilution method using *Streptococcus pneumoniae*, DAW27. In a still further aspect, the MIC is determined by a microbroth dilution method using *Bacillus subtilis*, ATCC 23857. In a yet further aspect, the MIC is determined by a microbroth dilution method using *Enterococcus faecalis*, ATCC 33186. In an even further aspect, the MIC is determined using *Staphylococcus aureus*, USA 300. In a still further aspect, the MIC is determined using *Streptococcus pneumoniae*, R6. In a further aspect, the MIC is determined using *Staphylococcus aureus*, USA 300 and compared to the MIC determined using *Staphylococcus aureus*, USA 300 wherein ClpP is inactivated, thus allowing confirmation that killing is via a ClpP-dependent pathway.

In various aspects, the compound used exhibits an $EC_{50}$ for activation of Sa-ClpP in a casein-BODIPY digestion assay of less than or equal to about 10 µM. In a further aspect, the compound used exhibits an $EC_{50}$ for activation of Sa-ClpP in a casein-BODIPY digestion assay of less than or equal to about 5.0 µM. In a still further aspect, the compound used exhibits an $EC_{50}$ for activation of Sa-ClpP in a casein-BODIPY digestion assay of less than or equal to about 2.5 µM. In a yet further aspect, the compound used exhibits an $EC_{50}$ for activation of Sa-ClpP in a casein-BODIPY digestion assay of less than or equal to about 1.0 µM. It is understood that the casein-BODIPY assay is carried out as described herein below.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

4. Kits

In one aspect, the invention relates to kits comprising at least one disclosed compound; or a pharmaceutically acceptable salt, solvate, or polymorph thereof, and one or more of:

(a) at least one agent known to increase ClpP activity;
(b) at least one agent known to have antimicrobial activity;
(c) at least one agent known to treat an infectious disease;
(d) instructions for treating an infectious disease;
(e) instructions for administering the compound in connection with treating a microbial infection; or
(f) instructions for administering the compound with at least one agent known to treat an infectious disease.

In various further aspects, the invention relates to kits comprising the disclosed compound and the agent known to treat an infectious disease.

In various further aspects, the invention relates to kits comprising the product of a disclosed method of making and the agent known to treat an infectious disease.

In various further aspects, the invention relates to kits comprising the disclosed compound and the agent known to have antimicrobial activity.

In various further aspects, the invention relates to kits comprising the product of a disclosed method of making and the agent known have antimicrobial activity.

In a further aspect, the kit comprises a disclosed compound or a product of a disclosed method of making.

In a further aspect, the compound and the agent known to treat an infectious disease are co-formulated. In a still further aspect, the compound and the agent known to treat an infectious disease are co-packaged.

In a further aspect, the compound and the agent known to have anti-microbial activity are co-formulated. In a still further aspect, the compound and the agent known to have anti-microbial activity are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

In various aspects, the kit further comprises a plurality of dosage forms, the plurality comprising one or more doses; wherein each dose comprises an effective amount of the compound and the agent known to have antimicrobial activity. In a further aspect, an effective amount is a therapeutically effective amount. In a still further aspect, an effective amount is a prophylactically effective amount.

In a further aspect, each dose of the compound and the agent known to have antimicrobial activity are co-formulated. In a still further aspect, each dose of the compound and the agent known to have antimicrobial activity are co-packaged. In a yet further aspect, the dosage forms are formulated for oral administration and/or intravenous administration. In an even further aspect, the dosage forms are formulated for oral administration. In a still further aspect, the dosage forms are formulated for intravenous administration. In a yet further aspect, the dosage form for the compound is formulated for oral administration and the dosage form for the agent known to have antimicrobial activity is formulated for intravenous administration. In an even further aspect, the dosage form for the compound is formulated for intravenous administration and the dosage form for the agent known to have antimicrobial activity is formulated for oral administration.

In various aspects, the agent known to have antimicrobial activity is selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, dalbavancin, dalfopristin, daptomycin, demeclocycline, dicloxacillin, dirithromycin, doxycycline, erythromycin, enrofloxacin, enoxacin, enviomycin, ertepenem, ethambutol, flucloxacillin, fosfomycin, furazolidone, gatifloxacin, gentamicin, imipenem, isoniazid, kanamycin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, tedolizid, thioacetazone, thioridazine, ticarcillin, tinidazole, tobramycin, torezolid, tosufloxacin, trimethoprim, troleandomycin, trovafloxacin, and vancomycin, or combinations thereof.

In a further aspect, the instructions for treating an infectious disease provide for treatment of a gram positive bacterial infection. In a still further aspect, the instructions for treating an infectious disease provide for treatment of a gram negative bacterial infection. In yet further aspect, the instructions for treating an infectious disease provide for treatment of an infectious disease selected from urinary infection, skin infection, intestinal infection, lung infection, ocular infection, otitis, sinusitis, pharyngitis, osteo-articular infection, genital infection, dental infection, oral infection, septicemia, nocosomial infection, bacterial meningitis, gastroenteritis, gastritis, diarrhea, ulcer, endocarditis, sexually transmitted disease, tetanus, diphtheria, leprosy, cholera, listeriosis, tuberculosis, salmonellosis, and dysentery.

In a further aspect, the instructions for treating an infectious disease provide for treatment of an infectious disease selected endocardititis, osteomyelitis, skin and soft tissue infection (SSTI), and infection associated with an indwelling device. In a still further aspect, the instructions for treating an infectious disease provide for treatment of endocardititis. In a yet further aspect, the instructions for treating an infectious disease provide for treatment of osteomyelitis. In an even further aspect, the instructions for treating an infectious disease provide for treatment of an SSTI. In a still further aspect, the instructions for treating an infectious disease provide for treatment of a complicated SSTI (cSSTI). In a yet further aspect, the instructions for treating an infectious disease provide for treatment of an infection associated with an indwelling device.

In various aspects, the instructions for treating an infectious disease provide for treatment of a chronic infection. In a further aspect, the instructions for treating an infectious disease provide for treatment of a chronic bacterial infection. In a still further aspect, the instructions for treating an infectious disease provide for treatment of a chronic gram positive bacterial infection. In a yet further aspect, the instructions for treating an infectious disease provide for treatment of gram negative bacterial infection.

In various aspects, the instructions for administering the compound with the agent known to treat an infectious disease provide for co-administering of the compound and the agent. In a further aspect, the co-administration is administration in a substantially simultaneous manner. In a still further aspect, the administration in a substantially simultaneous manner comprises a single dose form containing a fixed ratio of the compound and the antibacterial agent. In a yet further aspect, the single dose form is a capsule or a tablet. In an even further aspect, the single dose form is an ampule for a single intravenous administration. In a still further aspect, the co-administration is administration in a substantially sequential manner.

5. Subjects

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, rodent, including, but not limited to, rat and mouse, and poultry, including, but not limited to, chicken, turkey, and goose. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder treatable by enhancing the activity of a bacterial C1pP protease prior to the administering step. In some aspects of the disclosed method, the subject has been diagnosed with an infectious disease prior to the administering step. In some aspects of the disclosed methods, the subject has been identified with a need for treatment prior to the administering step. In one aspect, a subject can be treated prophylactically with a compound or composition disclosed herein, as discussed herein elsewhere.

F. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

1. GENERAL METHODS

Starting materials were purchased from commercial sources and were used without further purification. The reactions were monitored by HPLC. All $^1$H spectra were recorded on a Bruker ULTRASHIELD™ 400 plus. The chemical shift values were expressed in ppm (parts per million) relative to tetramethylsilane as internal standard; s=singlet, d=double, t=triplet, q=quartet, m=multiplet, br.s=broad singlet. Coupling constants (J) are reported in hertz (Hz).

2. SYNTHESIS OF (S)-3-(3,5-DIFLUOROPHENYL)-1-OXO-1-(((2S,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)AMINO)PROPAN-2-AMINIUM CHLORIDE

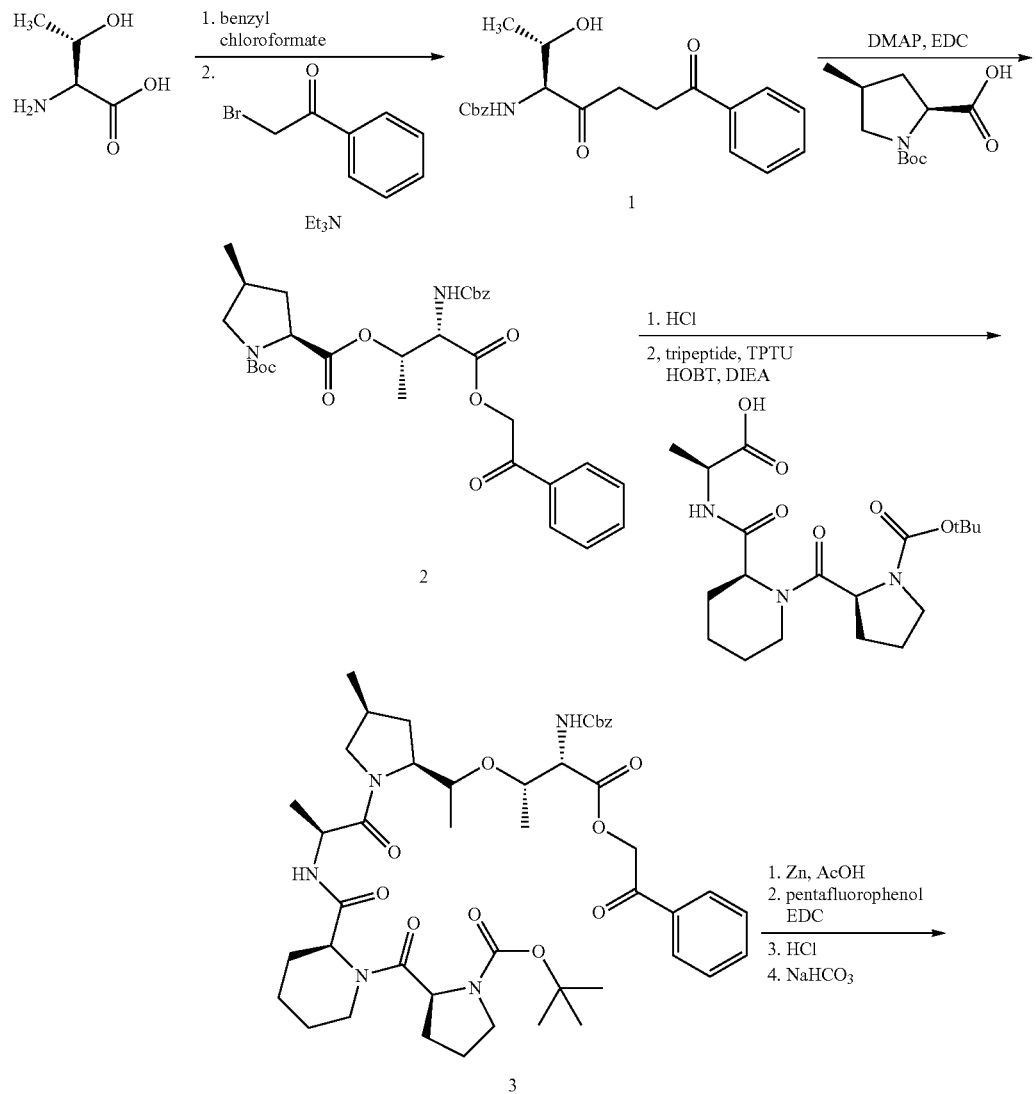

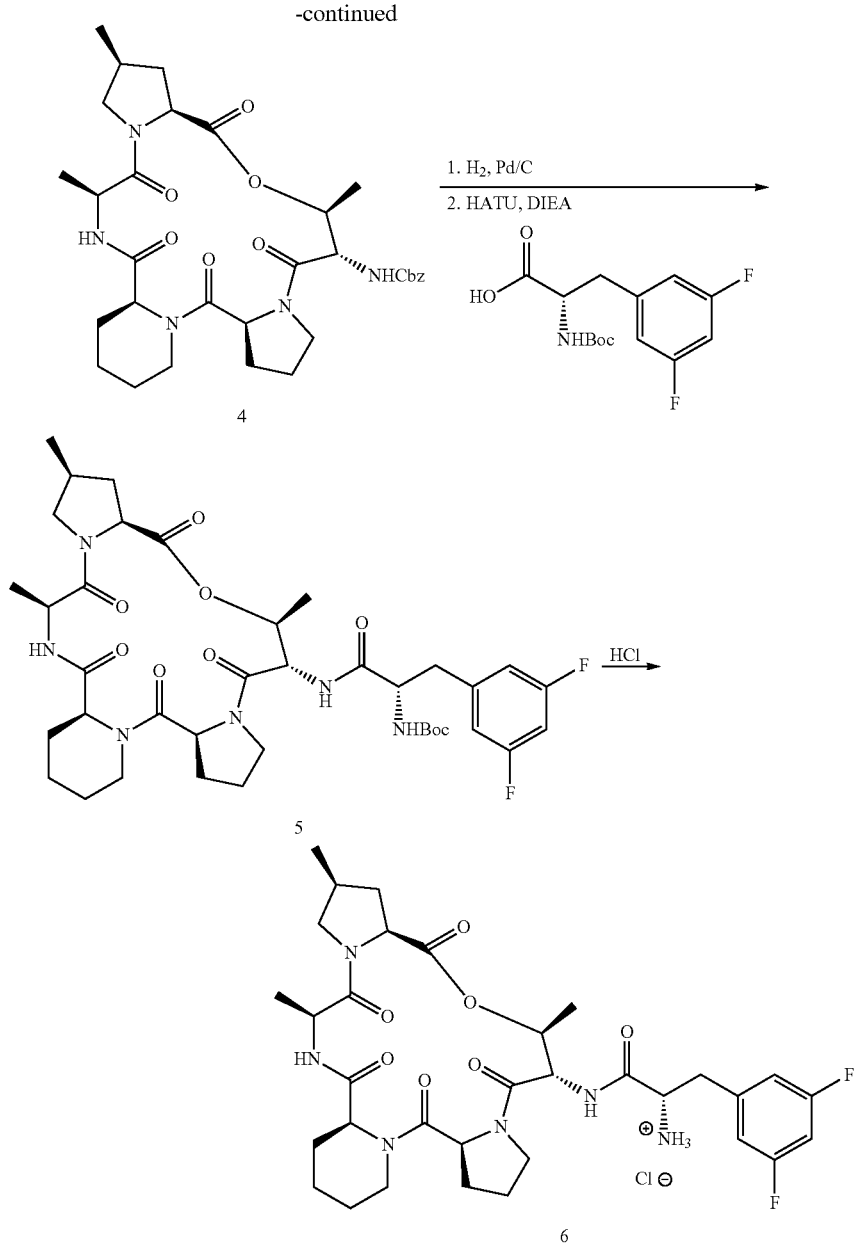

a. PREPARATION OF 2-OXO-2-PHENYLETHYL ((BENZYLOXY)CARBONYL)-L-ALLOTHREONINATE

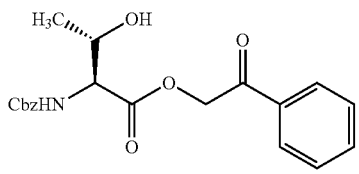 [SMILES: C[C@H](O)[C@H](NC(=O)OCc1ccccc1)C(=O)OCC(=O)c1ccccc1]

H-allo-Thr-OH (1 g, 8.39 mmol) was dissolved in saturated aqueous NaHCO$_3$ (50 mL) and THF (20 mL) and the whole was cooled to 0° C. To this solution, a solution of benzyl chloroformate (1.58 g, 9.23 mmol) in THF (20 mL) was added at 0° C. and the whole was stirred for 1.5 h at 0° C. After quenching with 3N aqueous HCl, the separated organic layer was washed with 3N aqueous HCl and brine and dried over Na$_2$SO$_4$. The organic solvent was evaporated, and the residue was used in next step reaction without purification. To the above residue in EtOAc (25 mL) were added 2-bromo-1-phenylethanone (1.833 g, 9.21 mmol) and Et$_3$N (1.303 mL, 10.05 mmol) in an ice-bath then the clear mixture was stirred overnight. After overnight reaction, white salt was precipitate from the mixture. 50 mL of EtOAc was added to the reaction, and then washed with sat. NaHCO$_3$, 1N HCl, sat. NaCl and distilled water. The organic layer was dried with anhydrous Na$_2$SO$_4$, filtered and removed under reduced pressure. The residue was chromatographed with hexane:ethyl acetate 3:2 to give target compound as a colorless liquid (2.2 g, 71%); $^1$H NMR (400 MHz, Chloroform-d) δ 1.42 (d, J=6.5 Hz, 3H), 3.60 (d, J=8.7 Hz, 1H), 4.44-4.52 (m, 1H), 5.14 (s, 2H), 5.51 (s, 2H), 5.72 (d, J=8.4 Hz, 1H), 7.31-7.37 (m, 5H), 7.50-7.53 (m, 2H), 7.63-7.68 (m, 1H), 7.92 (d, J=7.3 Hz, 2H); ESI-MS: [m/z+H$^+$]=372.33.

b. PREPARATION OF 2-((2S,3S)-3-(((BENZYLOXY)CARBONYL)AMINO)-4-OXO-4-(2-OXO-2-PHENYLETHOXY)BUTAN-2-YL) 1-(TERT-BUTYL) (2S,4S)-4-METHYLPYRROLIDINE-1,2-DICARBOXYLATE

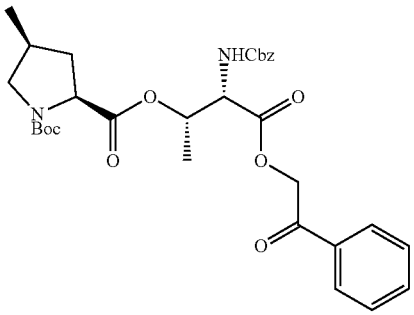 [SMILES: C[C@H]1C[C@@H](C(=O)O[C@@H](C)[C@H](NC(=O)OCc2ccccc2)C(=O)OCC(=O)c2ccccc2)N(C(=O)OC(C)(C)C)C1]

EDC.HCl (0.29 g, 1.84 mmol) was added to a stirring solution of 1 (0.8 g, 2.154 mmol), (2S,4R)-1-Boc-4-methylpyrrolidine-2-carboxylic acid (0.593 g, 2.58 mmol) and DMAP (53 mg, 0.431 mmol) in $CH_2Cl_2$ (20 mL) at 0° C. The mixture was slowly warmed to room temperature and stirred overnight, diluted with EtOAc, and washed successively with 1N HCl, sat. $NaHCO_3$, and brine. The organic layer was dried over anhydrous $Na_2SO_4$ and the solvent was removed under reduced pressure after filtration. The resulting oil was purified by silica gel column chromatography (EtOAc:hexane 3:7) to give 2 as colorless oil (1.04 g, 83%); $^1$H NMR (400 MHz, Chloroform-d) δ 1.00-1.08 (m, 3H), 1.41 (d, J=3.6 Hz, 9H), 1.48 (dd, J=14.7, 6.7 Hz, 3H), 1.54-1.67 (m, 1H), 2.08-2.25 (m, 1H), 2.28-2.37 (m, 1H), 2.89-2.99 (m, 1H), 3.61 (dd, J=10.2, 7.5 Hz, 0.52H), 3.69-3.77 (m, 0.58H), 4.14 (t, J=8.3 Hz, 0.51H), 4.19-4.25 (m, 0.53H), 4.77 (dd, J=9.3, 2.9 Hz, 0.48H), 4.87 (dd, J=8.5, 2.7 Hz, 0.42H), 5.05-5.19 (m, 2H), 5.30 (dd, J=16.2, 11.4 Hz, 1H), 5.40-5.44 (m, 1H), 5.53-5.60 (m, 1H), 6.13 (d, J=9.2 Hz, 0.45H), 7.28-7.39 (m, 5H), 7.50 (t, J=7.1 Hz, 2H), 7.61-7.64 (m, 1H), 7.84-7.95 (m, 2H); ESI-MS: [m/z+Na$^+$]=605.39.

c. PREPARATION OF TERT-BUTYL (S)-2-((S)-2-(((S)-1-((2S,4S)-2-((((2S,3S)-3-(((BENZYLOXY)CARBONYL)AMINO)-4-OXO-4-(2-OXO-2-PHENYLETHOXY)BUTAN-2-YL)OXY)CARBONYL)-4-METHYLPYRROLIDIN-1-YL)-1-OXOPROPAN-2-YL)CARBAMOYL)PIPERIDINE-1-CARBONYL)PYRROLIDINE-1-CARBOXYLATE

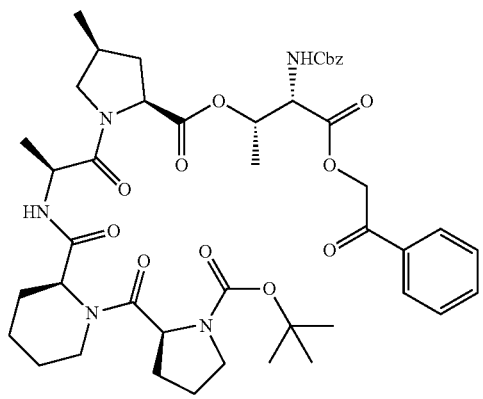 [SMILES: C[C@H]1C[C@@H](C(=O)O[C@@H](C)[C@H](NC(=O)OCc2ccccc2)C(=O)OCC(=O)c2ccccc2)N(C(=O)[C@H](C)NC(=O)[C@@H]2CCCCN2C(=O)[C@@H]2CCCN2C(=O)OC(C)(C)C)C1]

To the solution of 2 (0.92 g, 1.773 mmol) and tripeptide (0.705 g, 1.773 mmol) in dichloromethane (30 mL) at 0° C. under nitrogen were added TPTU (0.632 g, 2.127 mmol), HOBT (0.38 g, 2.482 mmol) and DIEA (0.83 mL, 4.96 mmol). The reaction mixture was stirred overnight with slow warming to room temperature and then concentrated. The residue was taken up with EtOAc, extracted by shaking with 10% $NaHCO_3$ solution and brine. The organic layer was dried over anhydrous $Na_2SO_4$ and the solvent was removed under reduced pressure after filtration. The product was purified by silica gel column chromatography (EtOAc:methanol 9:1) to give 3 as a white foam solid (1.2 g, 79%); $^1$H NMR (400 MHz, Chloroform-d) δ 1.097-1.10 (m, 3H), 1.37-1.54 (m, 15H), 1.57-1.73 (m, 6H), 1.79-1.87 (m, 1H), 1.93-1.97 (m, 1H), 2.06-2.21 (m, 1H), 2.22-2.40 (m, 2H), 2.42-2.48 (m, 0.53H), 3.05-3.14 (m, 1.5H), 3.33-3.49 (m, 1H), 3.50-3.66 (m, 1H), 3.68-3.85 (m, 1H), 4.03-4.16 (m, 0.37H), 4.29-4.39 (m, 1H), 4.47-4.74 (m, 2.57H), 4.78-4.87 (m, 1H), 5.07-5.16 (m, 2.53H), 5.28 (d, J=16.3 Hz, 1H), 5.39-5.45 (m, 1H), 5.50-5.61 (m, 1H), 5.71 (d, J=8.9 Hz, 0.31H), 5.80 (t, J=9.3 Hz, 0.58H), 6.62-6.73 (m, 0.59H), 7.28-7.41 (m, 5H), 7.51 (t, J=7.7 Hz, 2H), 7.63 (t, J=7.4 Hz, 1H), 7.89 (d, J=7.9 Hz, 2H), 8.46 (d, J=5.9 Hz, 0.23H); ESI-MS: [m/z+H$^+$]=862.61.

d. PREPARATION OF BENZYL ((2S,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)CARBAMATE

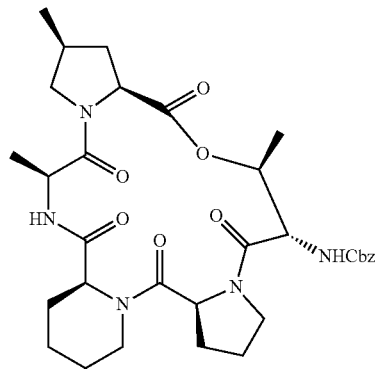 [SMILES: C[C@H]1C[C@H]2C(=O)O[C@@H](C)[C@H](NC(=O)OCc3ccccc3)C(=O)N3CCC[C@H]3C(=O)N3CCCC[C@H]3C(=O)N[C@@H](C)C(=O)N2C1]

To the solution of 3 (1.18 g, 1.369 mmol) in 90% aqueous acetic acid (10 mL) was added (0.671 g, 10.27 mmol) zinc powder. The reaction mixture was stirred at room temperature for 2 h. The reaction solution was filtered off through kieselguhr and washed with methanol. The organic solvent was concentrated in vacuo, the residue was taken up with EtOAc and washed with 1N hydrochloric acid. The organic layer was dried over anhydrous $Na_2SO_4$ and the solvent was removed under reduced pressure after filtration. The residue is taken up with ether, extracted by shaking with saturated aqueous $NaHCO_3$ and the aqueous phase is washed with diethyl ether again. The aqueous phase is subsequently adjusted to pH 2.7 with 5N hydrochloric acid and extracted twice with ethyl acetate. The combined organic extracts are dried over $Na_2SO_4$, filtered and the solvent was removed in vacuo to give a white foam solid. The above foam solid and pentafluorophenol (0.881 g, 4.79 mmol) were dissolved in CH₂Cl₂ and cooled to −20° C. under nitrogen, then to the mixture was added EDC.HCl (0.298 g, 1.55 mmol). The reaction mixture was stirred overnight with slowly warmed slowly to rt. The reaction solution was concentrated to dryness. To the residue, 4N hydrochloride solution in dioxane (10 mL) was added. The mixture was stirred at room temperature for 1 h and the solvent was subsequently removed in vacuo. The residue was dissolved in DCM (300 mL) and slowly added dropwise to a vigorously stirred two-phase mixture of 1N aqueous NaHCO₃ solution (300 mL) and DCM (500 mL). The reaction mixture was stirred overnight. The phase was separated, the aqueous phase was extracted with DCM and the combined organic phase was dried over Na₂SO₄ and the solvent was removed under reduced pressure after filtration. The residue was purified by reverse chromatography (water:ACN 2:3) as a white foam solid (0.55 g, 74% over two steps); ¹H NMR (400 MHz, Chloroform-d) δ 1.06 (d, J=6.7 Hz, 3H), 1.27 (d, J=6.5 Hz, 3H), 1.40 (d, J=6.6 Hz, 3H), 1.48-1.55 (m, 2H), 1.58-1.61 (m, 2H), 1.73-1.77 (m, 1H), 1.91-1.99 (m, 2H), 2.05-2.27 (m, 2H), 2.29-2.40 (m, 1H), 2.48-2.57 (m, 1H), 2.62-2.76 (m, 2H), 2.91 (dd, J=11.4, 9.5 Hz, 1H), 3.45-3.55 (m, 1H), 3.75-3.86 (m, 1H), 4.28-4.35 (m, 2H), 4.45-4.49 (m, 2H), 4.68 (s, 1H), 4.95-5.14 (m, 4H), 5.32 (dd, J=8.8, 2.8 Hz, 1H), 5.56 (d, J=9.6 Hz, 1H), 7.27-7.42 (m, 5H), 8.40 (d, J=9.7 Hz, 1H); ESI-MS: [m/z+H⁺]=626.19.

e. PREPARATION OF TERT-BUTYL ((S)-3-(3,5-DIFLUOROPHENYL)-1-OXO-1-(((2S,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)AMINO)PROPAN-2-YL)CARBAMATE

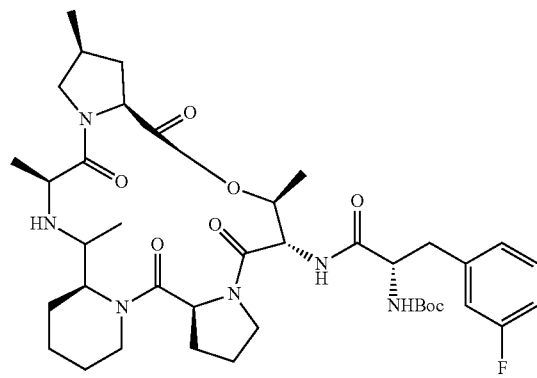

To the solution of 10% Pd/C (50 mg) in methanol (20 mL) under nitrogen was added compound 4 (0.5 g, 0.799 mmol). The mixture was then hydrogenated with a balloon filled with hydrogen for 1 h at rt. The reaction solution was filtered off through kieselguhr, which was washed with methanol and the solvent was removed in vacuo. The residue was dissolved in DMF (10 mL). To the solution were added Boc-L-(3,5-diF) Phe-OH (0.313 g, 1.039 mmol), HATU (0.395 g, 1.039 mmol) and DIEA (0.544 mL, 3.12 mmol) at 0° C. The reaction mixture was stirred overnight, taken up with EtOAc, and then washes with 1N hydrochloride acid solution, sat. NaHCO₃ solution and brine. The organic layer was dried over anhydrous Na₂SO₄ and the solvent was removed under reduced pressure after filtration. The product was purified by reverse phase chromatography (water:ACN 2:3) as a white solid (0.54 g, 87% over two steps); ¹H NMR (400 MHz, Chloroform-d) δ 1.07 (d, J=6.6 Hz, 3H), 1.25 (d, J=6.6 Hz, 3H), 1.41-1.47 (m, 15H), 1.51 (dd, J=8.4, 5.0 Hz, 2H), 1.74-1.77 (m, 1H), 1.88-2.00 (m, 2H), 2.07-2.27 (m, 2H), 2.29-2.39 (m, 1H), 2.58-2.75 (m, 3H), 2.82-2.97 (m, 2H), 3.08 (dd, J=13.8, 7.4 Hz, 1H), 3.44-3.54 (m, 1H), 3.72-3.82 (m, 1H), 4.18-4.34 (m, 2H), 4.48 (dd, J=9.6, 4.5 Hz, 1H), 4.58-4.72 (m, 3H), 4.91-5.01 (m, 1H), 5.07-5.16 (m, 1H), 5.19-5.29 (m, 1H), 5.99 (d, J=9.4 Hz, 1H), 6.65 (t, J=9.0 Hz, 1H), 6.71-6.82 (m, 3H), 8.68 (d, J=9.7 Hz, 1H); ESI-MS: [m/z+H⁺]=775.33.

f. PREPARATION OF (S)-3-(3,5-DIFLUOROPHENYL)-1-OXO-1-(((2S,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)AMINO)PROPAN-2-AMINIUM CHLORIDE

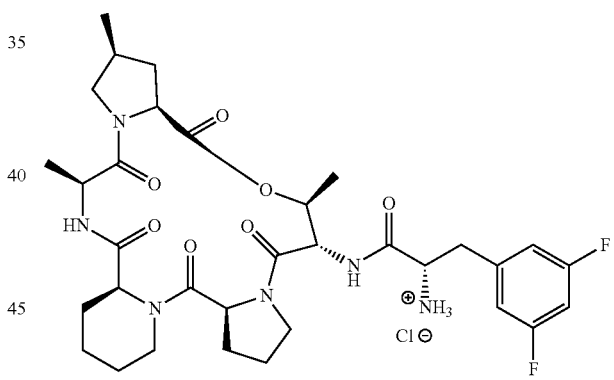

The solution of 5 (0.53 g, 0.684 mmol) in 4M HCl solution in dioxane (5 mL) was stirred at room temperature and then the solvent was removed under reduced pressure to give 6 as a white foam solid; ¹H NMR (400 MHz, DMSO-d₆) δ 1.00 (d, J=6.7 Hz, 3H), 1.22 (d, J=6.4 Hz, 3H), 1.26 (d, J=6.5 Hz, 3H), 1.41-1.52 (m, 2H), 1.55-1.68 (m, 2H), 1.86-1.95 (m, 2H), 2.15-2.26 (m, 1H), 2.43-2.46 (m, 2H), 2.60-2.74 (m, 2H), 2.81 (dd, J=11.5, 9.2 Hz, 1H), 2.88-3.00 (m, 1H), 3.18-3.22 (m, 1H), 3.96 (dd, J=11.7, 8.2 Hz, 1H), 4.25-4.34 (m, 1H), 4.39-4.49 (m, 2H), 4.55-4.67 (m, 2H), 4.88-4.98 (m, 1H), 5.04-5.11 (m, 1H), 5.24-5.30 (m, 1H), 7.08-7.22 (m, 3H), 7.97-8.05 (m, 3H), 9.55 (d, J=9.8 Hz, 1H); ESI-MS: [m/z+H⁺]=675.24.

3. GENERAL SYNTHESIS OF UREA ANALOGS 1-14
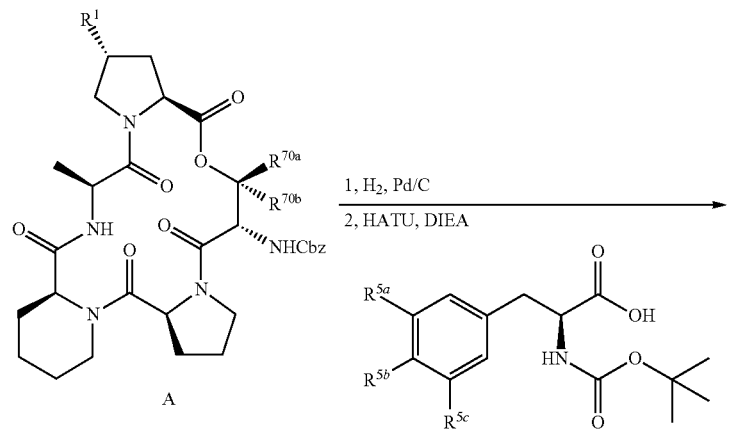
A
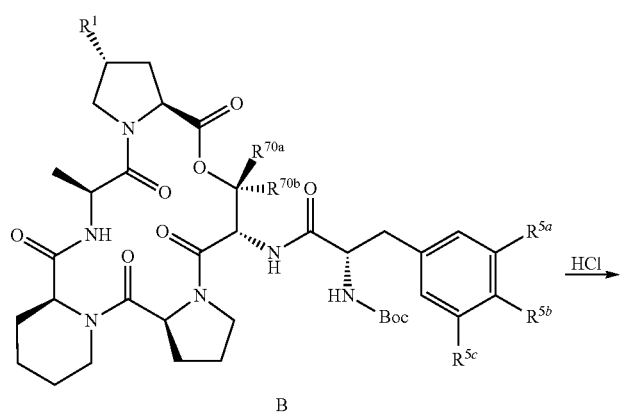
B
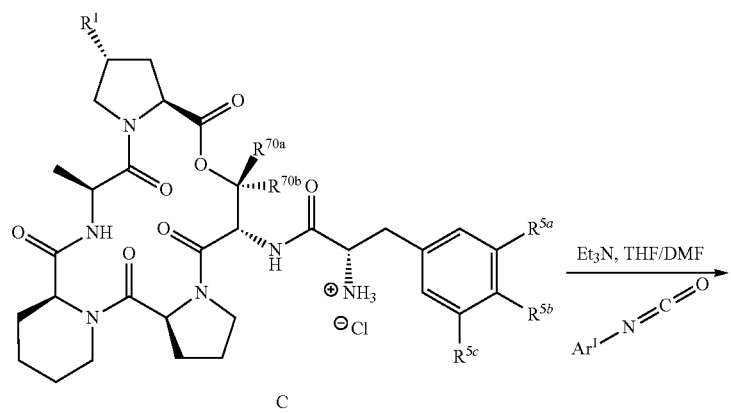
C

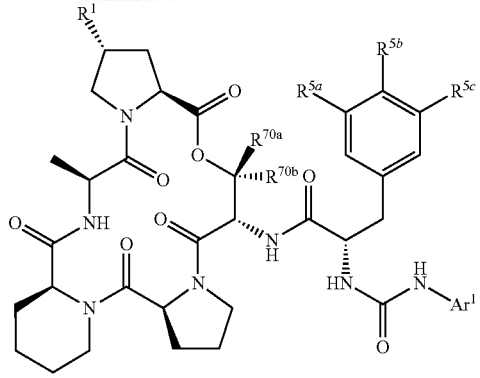

Compounds 1-14

The target compound was synthesized from intermediate A, which was deprotected by hydrogenation in the presence of palladium on carbon following by coupling with Boc-L-phenylalaine to give compound B (for general methods for coupling of Boc-L-phenylalanine see (a) Hinzen, B., et al. ChemMedChem (2006) 1(7):689-693; and (b) U.S. Pat. No. 4,492,650). Compound B was treated with 4N hydrocholoride acid in dioaxane to afford free amine C, which was coupled with appropriate isocyanate under microwave irradiation in the presence of triethylamine to give substituted urea depsipeptide analogs 1-14 (for coupling of an isocyanate under microwave irradiation see North, E. J., et al. Bioorganic & Medicinal Chemistry (2013) 21(9):2587-2599).

Briefly, Ar—NCO (about 1.2 eq.), compound C (about 1 eq), and triethylamine (about 3.6 or alternatively about 4.8 eq.) were mixed in THF/DMF (v/v=1:1, 2 mL) in a microwave safe tube and stirred at 200° C. for 10 min. The solvents were removed under reduced pressure and the crude residue was purified by reverse-phase flash column chromatography using water to acetonitrile gradient. The fractions containing desired compound were pooled and dried to the desired afford target compounds. Table 1 below provides information for the particular substituted Boc-L-phenylalanine derivative and aryl isocyanate used in the general scheme shown above. The substituent groups are as follows:

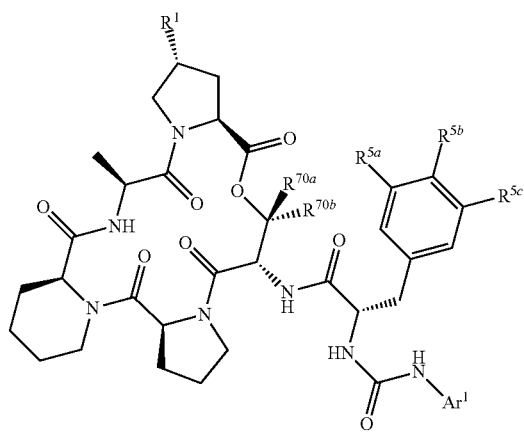

TABLE 1

| No. | $R^1$ | $R^{5a}$ | $R^{5b}$ | $R^{5c}$ | $R^{70a}$ | $R^{70b}$ | $Ar^1$ |
|---|---|---|---|---|---|---|---|
| 1 | $CH_3$ | H | H | H | H | H | phenyl |
| 2 | $CH_3$ | H | H | H | H | H | 4-(OCF_3)-phenyl |
| 3 | $CH_3$ | H | H | H | H | H | 4-Cl-phenyl |
| 4 | $CH_3$ | H | H | H | H | H | 4-ethyl-phenyl |
| 5 | $CH_3$ | H | H | H | H | H | 4-N(CH_3)_2-phenyl |
| 6 | $CH_3$ | H | H | H | H | H | 4-OCH_3-phenyl |
| 7 | $CH_3$ | H | H | H | H | H | 2-Cl-phenyl |

TABLE 1-continued

| No. | R¹ | R⁵ᵃ | R⁵ᵇ | R⁵ᶜ | R⁷⁰ᵃ | R⁷⁰ᵇ | Ar¹ |
|---|---|---|---|---|---|---|---|
| 8 | CH₃ | H | H | H | H | H | 3-methoxyphenyl |
| 9 | CH₃ | H | H | H | H | H | 3-chlorophenyl |
| 10 | CH₃ | H | H | H | H | H | 3-ethylphenyl |
| 11 | CH₃ | H | H | H | H | H | 1-methylindolin-5-yl |
| 12 | CH₃ | H | H | H | H | H | 1-methylindol-6-yl |
| 13 | CH₃ | F | H | F | H | H | 4-(trifluoromethoxy)phenyl |
| 14 | CH₃ | F | H | F | H | H | 4-ethylphenyl | a. PREPARATION OF (S)—N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-3-PHENYL-2-(3-PHENYLUREIDO)PROPANAMIDE (COMPOUND 1)

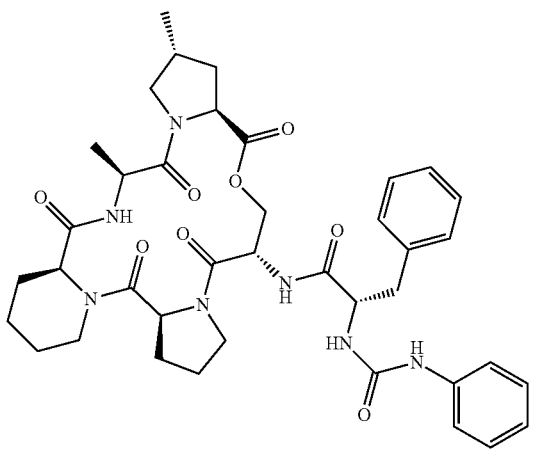 [SMILES: C[C@@H]1C[C@H]2C(=O)OC[C@H](NC(=O)[C@H](Cc3ccccc3)NC(=O)Nc3ccccc3)C(=O)N3CCC[C@H]3C(=O)N3CCCC[C@H]3C(=O)N[C@@H](C)C(=O)N2C1]

Compound 1 was synthesized from compound C (61 mg, 0.097 mmol), isocyanatobenzene (14 mg, 0.117 mmol) and triethylamine (48 µL, 0.352 mmol) following the general synthesis method as described herein above. Compound 1 was provided as a white solid (29.3 mg, 40%); 1H NMR (400 MHz, Chloroform-d) δ 0.93 (d, J=6.6 Hz, 3H), 1.39 (d, J=6.6 Hz, 3H), 1.43-1.58 (m, 2H), 1.75-1.85 (m, 2H), 1.93-2.03 (m, 2H), 2.03-2.12 (m, 1H), 2.13-2.26 (m, 1H), 2.31-2.46 (m, 2H), 2.59-2.65 (m, 1H), 2.69-2.75 (m, 1H), 2.91-2.96 (m, 1H), 3.00-3.05 (m, 1H), 3.06-3.15 (m, 1H), 3.45-3.53 (m, 1H), 3.53-3.63 (m, 2H), 3.73-3.79 (m, 1H), 4.43-4.59 (m, 3H), 4.67-4.72 (m, 2H), 4.79 (d, J=11.6 Hz, 1H), 4.98-5.08 (m, 1H), 5.12-5.15 (m, 1H), 5.83 (d, J=7.9 Hz, 1H), 6.80 (d, J=9.6 Hz, 1H), 6.97 (t, J=7.4 Hz, 1H), 7.13-7.26 (m, 4H), 7.27-7.32 (m, 3H), 7.45 (d, J=8.4 Hz, 2H), 7.88 (s, 1H), 8.68 (d, J=9.6 Hz, 1H); ESI-MS: [m/z+H⁺]=744.63.

b. PREPARATION OF (S)—N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-3-PHENYL-2-(3-(4-(TRIFLUOROMETHOXY)PHENYL)UREIDO)PROPANAMIDE (COMPOUND 2)

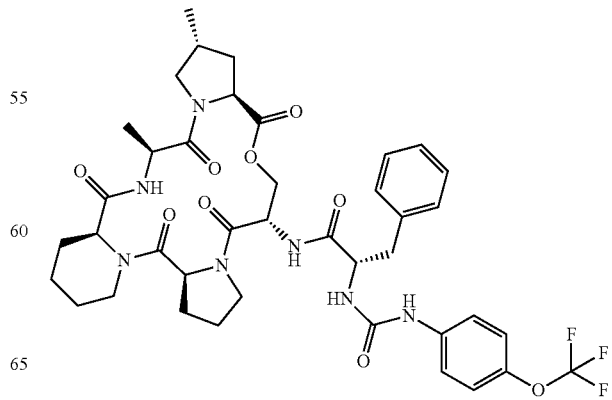

Compound 2 was synthesized from compound C (49.3 mg, 0.079 mmol), isocyanatobenzene (19.3 mg, 0.095 mmol) and triethylamine (38.9 μL, 0.284 mmol) following the general synthesis method as described herein above. Compound 2 was provided as a white solid (26.7 mg, 41%); 1H NMR (400 MHz, Chloroform-d) δ 0.94 (d, J=6.5 Hz, 3H), 1.38 (d, J=6.5 Hz, 3H), 1.42-1.55 (m, 2H), 1.77-1.85 (m, 2H), 1.96-2.02 (m, 2H), 2.05-2.10 (m, 1H), 2.13-2.26 (m, 1H), 2.33-2.44 (m, 2H), 2.62 (t, J=12.3 Hz, 1H), 2.72 (d, J=11.1 Hz, 1H), 2.90-2.95 (m, 1H), 2.98-3.11 (m, 2H), 3.44-3.64 (m, 3H), 3.73-3.79 (m, 1H), 4.40-4.48 (m, 1H), 4.51-4.57 (m, 2H), 4.67-4.72 (m, 2H), 4.80 (d, J=11.6 Hz, 1H), 4.98-5.08 (m, 1H), 5.10-5.14 (m, 1H), 5.84 (d, J=7.9 Hz, 1H), 6.71 (d, J=9.5 Hz, 1H), 7.09-7.18 (m, 4H), 7.21 (t, J=7.9 Hz, 1H), 7.28-7.32 (m, 2H), 7.48 (d, J=9.0 Hz, 2H), 8.02 (s, 1H), 8.65 (d, J=9.6 Hz, 1H); ESI-MS: [m/z+H⁺]=828.79.

c. PREPARATION OF (S)-2-(3-(4-CHLOROPHE-NYL)UREIDO)-N-((2R,6S,8AS,14AS,20S,23AS)-2,6-DIMETHYL-5,8,14,19,23-PENTAOXOOCTA-DECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-3-PHENYLPROPANAMIDE (COMPOUND 3)

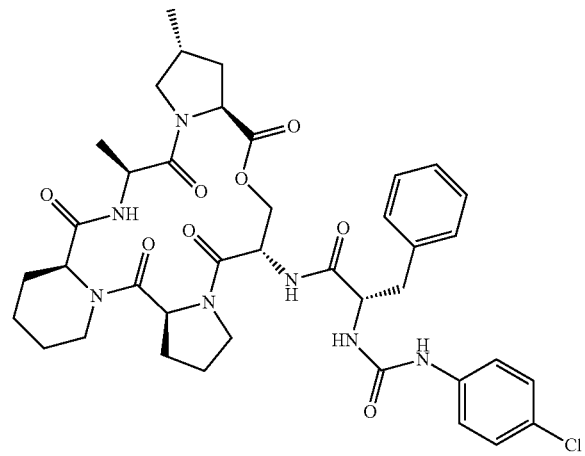 [SMILES: C[C@@H]1C[C@H]2C(=O)OC[C@H](NC(=O)[C@H](Cc3ccccc3)NC(=O)Nc3ccc(Cl)cc3)C(=O)N3CCC[C@H]3C(=O)N3CCCC[C@H]3C(=O)N[C@@H](C)C(=O)N2C1]

Compound 3 was synthesized from compound C (37 mg, 0.059 mmol), 1-chloro-4-isocyanatobenzene (10.91 mg, 0.071 mmol) and triethylamine (29.2 μL, 0.213 mmol) following the general synthesis method as described herein above. Compound 3 was provided as a white solid (22.9 mg, 49.7%); 1H NMR (400 MHz, Chloroform-d) δ 0.95 (d, J=6.6 Hz, 3H), 1.38 (d, J=6.6 Hz, 3H), 1.43-1.57 (m, 2H), 1.77-1.85 (m, 2H), 1.92-2.04 (m, 2H), 2.05-2.10 (m, 1H), 2.13-2.26 (m, 1H), 2.30-2.47 (m, 2H), 2.56-2.68 (m, 1H), 2.71-2.74 (m, 1H), 2.89-2.95 (m, 1H), 2.99-3.12 (m, 2H), 3.43-3.63 (m, 3H), 3.73-3.79 (m, 1H), 4.39-4.48 (m, 1H), 4.51-4.57 (m, 2H), 4.66-4.72 (m, 2H), 4.78-4.81 (m, 1H), 4.98-5.08 (m, 1H), 5.10-5.16 (m, 1H), 5.84 (d, J=7.9 Hz, 1H), 6.68 (d, J=9.5 Hz, 1H), 7.14-7.16 (m, 2H), 7.19-7.24 (m, 3H), 7.28-7.32 (m, 2H), 7.39-7.43 (m, 2H), 7.99 (s, 1H), 8.65 (d, J=9.7 Hz, 1H); ESI-MS: [m/z+H⁺]=778.61.

d. PREPARATION OF (S)—N-((2R,6S,8AS,14AS,20S,23AS)-2,6-DIMETHYL-5,8,14,19,23-PEN-TAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(4-ETHYLPHENYL)UREIDO)-3-PHENYLPROPANAMIDE (COMPOUND 4)

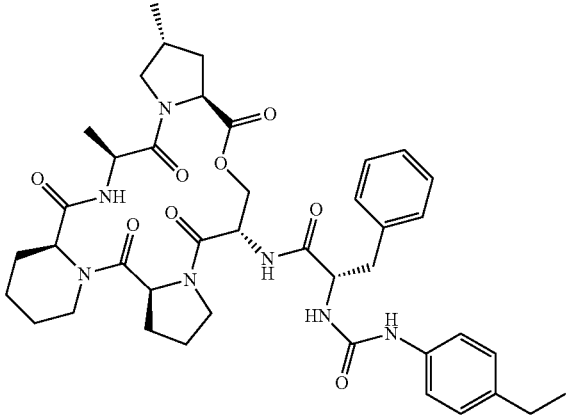 [SMILES: CCc1ccc(NC(=O)N[C@@H](Cc2ccccc2)C(=O)N[C@H]2COC(=O)[C@@H]3C[C@@H](C)CN3C(=O)[C@H](C)NC(=O)[C@@H]3CCCCN3C(=O)[C@@H]3CCCN3C2=O)cc1]

Compound 4 was synthesized from compound C (78 mg, 0.118 mmol), 1-ethyl-4-isocyanatobenzene (20.83 mg, 0.141 mmol) and triethylamine (77.4 μL, 0.566 mmol) following the general synthesis method as described herein above. Compound 4 was provided as a white solid (14.9 mg, 16%); 1H NMR (400 MHz, Chloroform-d) δ 0.93 (d, J=6.5 Hz, 3H), 1.18-1.25 (t, J=7.8 Hz, 3H), 1.39 (d, J=6.6 Hz, 3H), 1.44-1.53 (m, 2H), 1.76-1.85 (m, 2H), 1.91-2.03 (m, 2H), 2.03-2.12 (m, 1H), 2.12-2.23 (m, 1H), 2.29-2.45 (m, 2H), 2.51-2.68 (m, 4H), 2.72 (d, J=11.7 Hz, 1H), 2.89-2.95 (m, 1H), 3.00-3.05 (m, 1H), 3.08-3.13 (m, 1H), 3.45-3.64 (m, 3H), 3.71-3.77 (m, 1H), 4.39-4.44 (m, 1H), 4.49-4.59 (m, 2H), 4.67-4.71 (m, 2H), 4.79 (d, J=11.6 Hz, 1H), 4.98-5.08 (m, 1H), 5.10-5.17 (m, 1H), 5.81 (d, J=7.9 Hz, 1H), 6.56 (d, J=9.5 Hz, 1H), 7.09 (d, J=8.2 Hz, 2H), 7.18-7.31 (m, 5H), 7.36 (d, J=8.2 Hz, 2H), 7.74 (s, 1H), 8.69 (d, J=9.6 Hz, 1H); ESI-MS: [m/z+H⁺]=772.84.

e. PREPARATION OF (S)—N-((2R,6S,8AS,14AS,20S,23AS)-2,6-DIMETHYL-5,8,14,19,23-PEN-TAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(4-(DIMETHYLAMINO)PHENYL)UREIDO)-3-PHENYLPROPANAMIDE (COMPOUND 5)

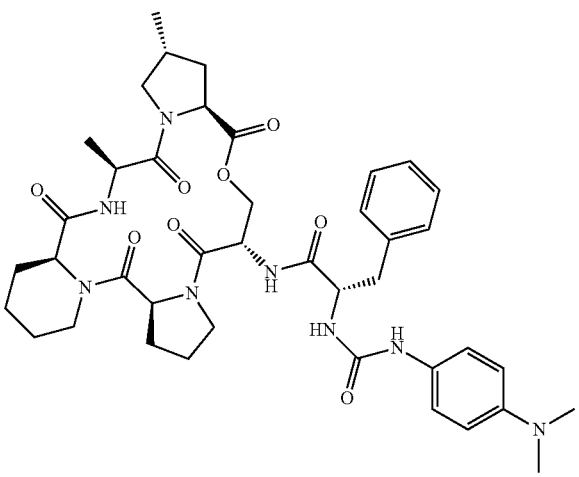 [SMILES: C[C@@H]1C[C@H]2C(=O)OC[C@H](NC(=O)[C@H](Cc3ccccc3)NC(=O)Nc3ccc(N(C)C)cc3)C(=O)N3CCC[C@H]3C(=O)N3CCCC[C@H]3C(=O)N[C@@H](C)C(=O)N2C1]

Compound 5 was synthesized from compound C (95 mg, 0.144 mmol), 4-isocyanato-N,N-dimethylaniline (27.9 mg, 0.172 mmol) and triethylamine (93.9 µL, 0.69 mmol) following the general synthesis method as described herein above. Compound 5 was provided as a white solid (13.2 mg, 11.5%); 1H NMR (400 MHz, Chloroform-d) δ 0.96 (d, J=6.6 Hz, 3H), 1.40 (d, J=6.6 Hz, 3H), 1.43-1.55 (m, 2H), 1.75-1.87 (m, 2H), 1.92-2.02 (m, 2H), 2.05-2.10 (m, 1H), 2.12-2.23 (m, 1H), 2.31-2.45 (m, 2H), 2.61-2.74 (m, 2H), 2.88 (s, 6H), 2.91-2.98 (m, 3H), 2.98-3.06 (m, 1H), 3.09-3.15 (m, 1H), 3.47-3.65 (m, 3H), 3.69-3.77 (m, 1H), 4.37-4.44 (m, 1H), 4.50-4.57 (m, 2H), 4.66-4.74 (m, 2H), 4.79 (d, J=10.4 Hz, 1H), 4.99-5.06 (m, 1H), 5.11-5.14 (m, 1H), 5.74 (d, J=8.0 Hz, 1H), 6.55 (d, J=9.6 Hz, 1H), 6.71 (d, J=9.0 Hz, 2H), 7.14-7.22 (m, 3H), 7.27-7.33 (m, 4H), 7.46 (s, 1H), 8.70 (d, J=9.7 Hz, 1H); ESI-MS: [m/z+H$^+$]=787.76.

f. PREPARATION OF (S)—N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(4-METHOXYPHENYL)UREIDO)-3-PHENYLPROPANAMIDE (COMPOUND 6)

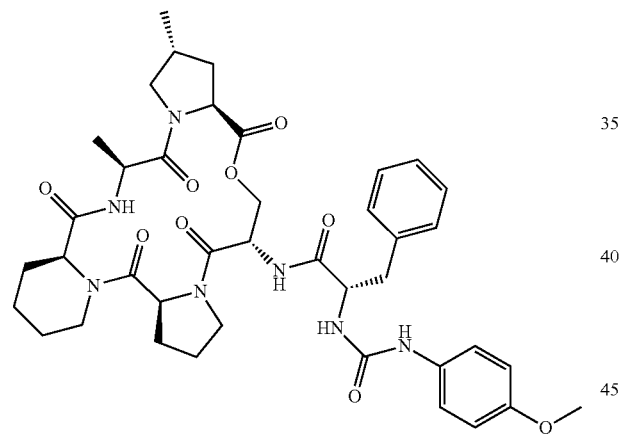

Compound 6 was synthesized from compound C (90 mg, 0.136 mmol), 1-isocyanato-4-methoxybenzene (24.4 mg, 0.163 mmol) and triethylamine (89 µL, 0.653 mmol) following the general synthesis method as described herein above. Compound 6 was provided as a white solid (22 mg, 20.9%); 1H NMR (400 MHz, Chloroform-d) δ 0.95 (d, J=6.6 Hz, 3H), 1.40 (d, J=6.6 Hz, 3H), 1.43-1.56 (m, 2H), 1.76-1.83 (m, 2H), 1.94-2.01 (m, 2H), 2.01-2.10 (m, 1H), 2.14-2.22 (m, 2H), 2.34-2.45 (m, 2H), 2.60-2.74 (m, 2H), 2.88-2.96 (m, 1H), 2.99-3.15 (m, 2H), 3.47-3.62 (m, 3H), 3.73-3.76 (m, 1H), 3.78 (s, 3H), 4.36-4.45 (m, 1H), 4.51-4.57 (m, 2H), 4.66-4.71 (s, 2H), 4.79 (d, J=11.7 Hz, 1H), 4.99-5.06 (m, 1H), 5.11-5.14 (m, 1H), 5.78 (d, J=7.9 Hz, 1H), 6.51 (d, J=9.5 Hz, 1H), 6.82 (d, J=8.9 Hz, 2H), 7.14-7.23 (m, 3H), 7.28-7.32 (m, 2H), 7.35 (d, J=8.9 Hz, 2H), 7.65 (br.s, 1H), 8.68 (br.d, J=9.6 Hz, 1H); ESI-MS: [m/z+H$^+$]=774.79.

g. PREPARATION OF (S)-2-(3-(2-CHLOROPHENYL)UREIDO)-N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-3-PHENYLPROPANAMIDE (COMPOUND 7)

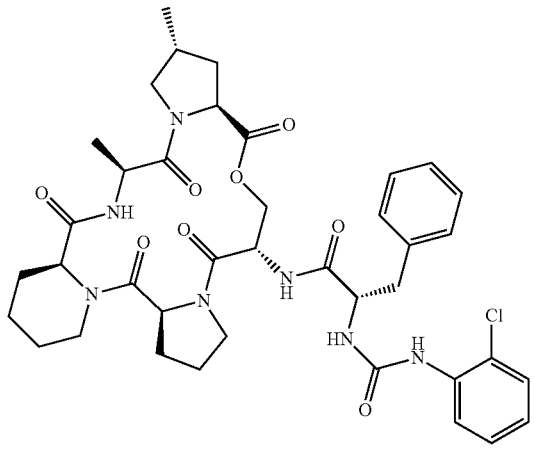

Compound 7 was synthesized from compound C (47 mg, 0.071 mmol), 1-chloro-2-isocyanatobenzene (13.1 mg, 0.085 mmol) and triethylamine (46.7 µL, 0.341 mmol) following the general synthesis method as described herein above. Compound 7 was provided as an off-white solid (8 mg, 14.5%); 1H NMR (400 MHz, Chloroform-d) δ 0.98 (d, J=6.6 Hz, 3H), 1.42 (d, J=6.6 Hz, 3H), 1.58-1.65 (m, 1H), 1.75-1.89 (m, 2H), 1.93-2.04 (m, 2H), 2.05-2.12 (m, 1H), 2.13-2.24 (m, 1H), 2.33-2.47 (m, 2H), 2.63-2.74 (m, 2H), 2.91-2.97 (m, 1H), 3.07-3.12 (m, 1H), 3.24-3.29 (m, 1H), 3.48-3.56 (m, 2H), 3.60-3.65 (m, 1H), 3.70-3.77 (m, 1H), 4.31-4.36 (m, 1H), 4.50-4.61 (m, 2H), 4.69-4.73 (m, 2H), 4.80 (d, J=11.8 Hz, 1H), 4.96-5.07 (m, 1H), 5.11-5.14 (m, 1H), 6.34 (br.d, J=9.6 Hz, 1H), 6.39 (d, J=7.5 Hz, 1H), 6.92 (t, J=7.7 Hz, 1H), 7.15 (d, J=7.5 Hz, 2H), 7.20-7.23 (m, 2H), 7.29-7.32 (m, 4H), 7.94 (br.s, 1H), 8.29 (br.d, J=8.3 Hz, 1H), 8.67 (br.d, J=9.5 Hz, 1H); ESI-MS: [m/z+H$^+$]=778.69.

h. PREPARATION OF (S)—N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(3-METHOXYPHENYL)UREIDO)-3-PHENYLPROPANAMIDE (COMPOUND 8)

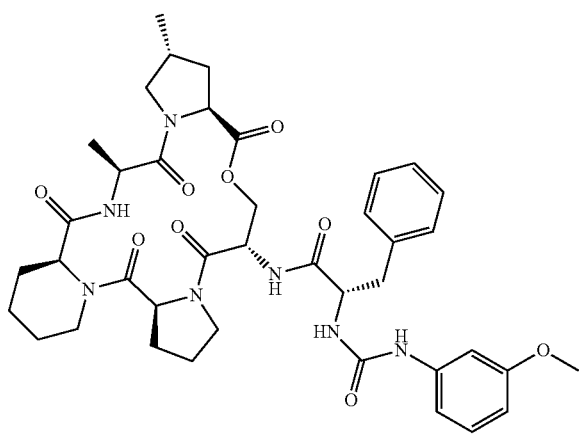 [SMILES: COc1cccc(NC(=O)N[C@@H](Cc2ccccc2)C(=O)N[C@H]2COC(=O)[C@@H]3C[C@@H](C)CN3C(=O)[C@H](C)NC(=O)[C@@H]3CCCCN3C(=O)[C@@H]3CCCN3C2=O)c1]

Compound 8 was synthesized from compound C (86 mg, 0.130 mmol), 1-isocyanato-3-methoxybenzene (23.21 mg, 0.156 mmol) and triethylamine (85 µL, 0.624 mmol) following the general synthesis method as described herein above. Compound 8 was provided as an off-white solid (26 mg, 25.8%); 1H NMR (400 MHz, Chloroform-d) δ 0.93 (d, J=6.6 Hz, 3H), 1.38 (d, J=6.6 Hz, 3H), 1.44-1.52 (m, 2H), 1.77-1.86 (m, 2H), 1.93-2.03 (m, 2H), 2.04-2.09 (m, 1H), 2.14-2.22 (m, 1H), 2.31-2.44 (m, 2H), 2.59-2.66 (m, 1H), 2.69-2.75 (m, 1H), 2.91-2.96 (m, 1H), 3.00-3.05 (m, 1H), 3.18-3.13 (m, 1H), 3.46-3.54 (m, 1H), 3.55-3.61 (m, 2H), 3.71-3.80 (m, 2H), 3.80 (s, 3H), 4.43-4.49 (m, 1H), 4.50-4.57 (m, 2H), 4.67-4.73 (m, 2H), 4.78-4.81 (m, 1H), 4.99-4.07 (m, 1H), 5.12-5.15 (m, 1H), 5.84 (d, J=8.0 Hz, 1H), 6.51-6.56 (m, 1H), 6.79 (d, J=9.5 Hz, 1H), 6.89-6.95 (m, 1H), 7.11-7.23 (m, 4H), 7.25-7.26 (m, 1H), 7.26-7.32 (m, 3H), 7.92 (s, 1H), 8.68 (d, J=9.6 Hz, 1H); ESI-MS: [m/z+H$^+$]=774.86.

i. PREPARATION OF (S)-2-(3-(3-CHLOROPHENYL)UREIDO)-N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-3-PHENYLPROPANAMIDE (COMPOUND 9)

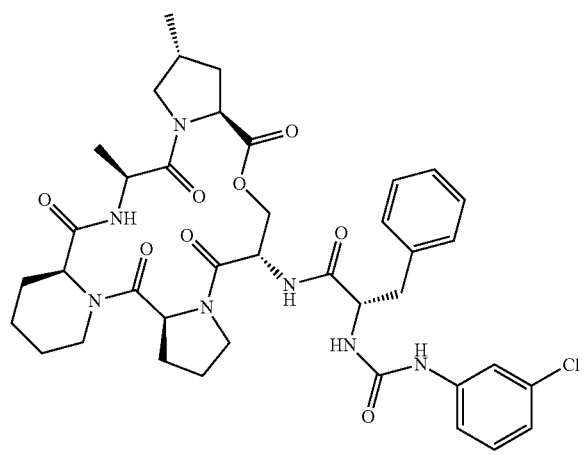 [SMILES: C[C@@H]1C[C@H]2C(=O)OC[C@H](NC(=O)[C@H](Cc3ccccc3)NC(=O)Nc3cccc(Cl)c3)C(=O)N3CCC[C@H]3C(=O)N3CCCC[C@H]3C(=O)N[C@@H](C)C(=O)N2C1]

Compound 9 was synthesized from compound C (80 mg, 0.121 mmol), 1-chloro-3-isocyanatobenzene (22.3 mg, 0.145 mmol) and triethylamine (79 µL, 0.581 mmol) following the general synthesis method as described herein above. Compound 9 was provided as an off-white solid (23.4 mg, 24.9%); 1H NMR (400 MHz, Chloroform-d) δ 0.95 (d, J=6.6 Hz, 3H), 1.38 (d, J=6.6 Hz, 3H), 1.45-1.53 (m, 2H), 1.78-1.86 (m, 2H), 1.96-2.02 (m, 2H), 2.05-2.10 (m, 1H), 2.13-2.25 (m, 1H), 2.30-2.46 (m, 2H), 2.59-2.66 (m, 1H), 2.71-2.74 (m, 1H), 2.88-2.97 (m, 1H), 2.98-3.14 (m, 2H), 3.44-3.63 (m, 3H), 3.71-3.81 (m, 1H), 4.42-4.50 (m, 1H), 4.50-4.59 (m, 2H), 4.66-4.72 (m, 2H), 4.79 (br.d, J=12.7 Hz, 1H), 4.98-5.09 (m, 1H), 5.12-5.15 (m, 1H), 5.87 (d, J=7.9 Hz, 1H), 6.82 (d, J=9.5 Hz, 1H), 6.93-6.95 (m, 1H), 7.12-7.24 (m, 5H), 7.30 (t, J=7.5 Hz, 3H), 7.57 (t, J=2.0 Hz, 1H), 8.04 (s, 1H), 8.66 (d, J=9.7 Hz, 1H); ESI-MS: [m/z+H$^+$]=778.76.

j. PREPARATION OF (S)—N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(3-ETHYLPHENYL)UREIDO)-3-PHENYLPROPANAMIDE (COMPOUND 10)

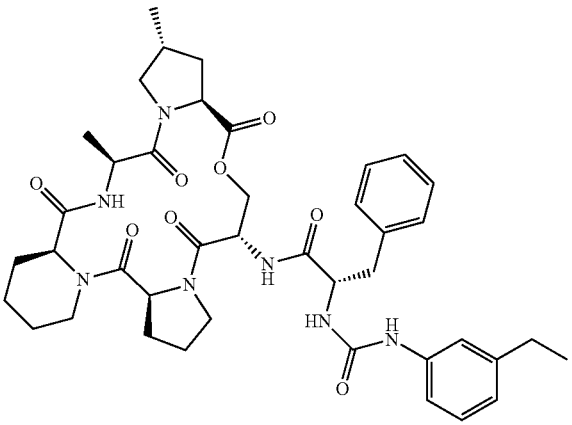

Compound 10 was synthesized from compound C (50 mg, 0.08 mmol), 1-ethyl-3-isocyanatobenzene (14.13 mg, 0.096 mmol) and triethylamine (52.5 µL, 0.384 mmol) following the general synthesis method as described herein above. Compound 10 was provided as a white solid (14 mg, 22.7%); 1H NMR (400 MHz, Chloroform-d) δ 0.92 (d, J=6.5 Hz, 3H), 1.19-1.24 (m, 6H), 1.39 (d, J=6.6 Hz, 3H), 1.44-1.54 (m, 2H), 1.76-1.86 (m, 2H), 1.93-2.03 (m, 2H), 2.04-2.09 (m, 1H), 2.12-2.24 (m, 1H), 2.32-2.41 (m, 2H), 2.61 (p, J=7.4 Hz, 4H), 2.71-2.74 (m, 1H), 2.87-2.98 (m, 1H), 3.00-3.04 (m, 1H), 3.10-3.15 (m, 1H), 3.44-3.63 (m, 3H), 3.72-3.78 (m, 1H), 4.42-4.59 (m, 3H), 4.67-4.74 (m, 2H), 4.78 (d, J=10.7 Hz, 1H), 4.98-5.08 (m, 1H), 5.12-5.15 (m, 1H), 5.83 (d, J=7.9 Hz, 1H), 6.77-6.85 (m, 2H), 6.93 (d, J=7.5 Hz, 1H), 6.97 (s, 1H), 7.14-7.32 (m, 9H), 7.86 (s, 1H), 8.70 (d, J=9.6 Hz, 1H); ESI-MS: [m/z+H$^+$]=772.84.

k. PREPARATION OF (S)—N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(1-METHYLINDOLIN-5-YL)UREIDO)-3-PHENYLPROPANAMIDE (COMPOUND 11)

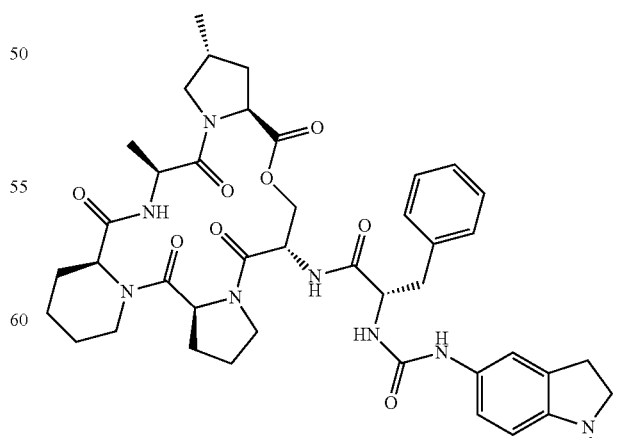

Compound 11 was synthesized from compound C (80 mg, 0.128 mmol), 5-isocyanato-1-methylindoline (26.8 mg, 0.154 mmol) and triethylamine (84 µL, 0.615 mmol) following the general synthesis method as described herein above. Compound 11 was provided as a greyish solid (45 mg, 44.1%); 1H NMR (400 MHz, Chloroform-d) δ 0.97 (d, J=6.5 Hz, 3H), 1.40 (d, J=6.6 Hz, 3H), 1.44-1.53 (m, 2H), 1.74-1.86 (m, 2H), 1.93-2.03 (m, 2H), 2.05-2.10 (m, 1H), 2.12-2.24 (m, 1H), 2.30-2.47 (m, 2H), 2.59-2.70 (m, 2H), 2.71-2.74 (m, 4H), 2.88-2.94 (m, 3H), 2.99-3.04 (m, 1H), 3.10-3.16 (m, 1H), 3.20-3.27 (m, 2H), 3.49-3.65 (m, 3H), 3.70-3.78 (m, 2H), 4.35-4.42 (m, 1H), 4.49-4.59 (m, 2H), 4.66-4.74 (m, 2H), 4.79 (dd, J=11.7, 1.3 Hz, 1H), 4.97-5.07 (m, 1H), 5.11-5.14 (m, 1H), 5.73 (d, J=8.0 Hz, 1H), 6.39-6.46 (m, 2H), 7.01 (d, J=10.2 Hz, 1H), 7.12-7.24 (m, 4H), 7.29 (t, J=7.3 Hz, 3H), 7.42 (br.s, 1H), 8.70 (d, J=9.6 Hz, 1H); ESI-MS: [m/z+H$^+$]=799.91.

l. PREPARATION OF (S)—N-((2R,6S,8AS,14AS, 20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(1-METHYL-1H-INDOL-6-YL)UREIDO)-3-PHENYLPROPANAMIDE (COMPOUND 12)

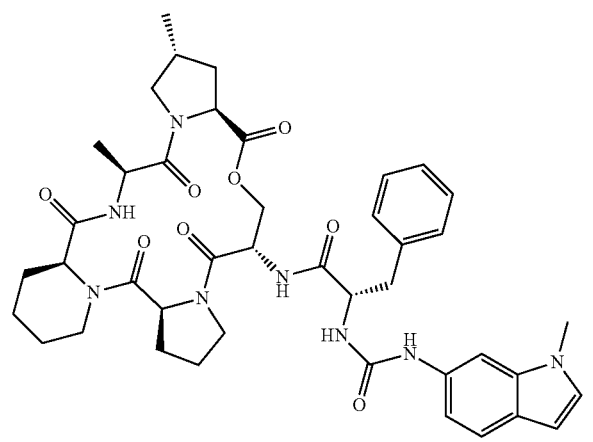 [SMILES: C[C@@H]1C[C@H]2C(=O)OC[C@H](NC(=O)[C@H](Cc3ccccc3)NC(=O)Nc3ccc4ccn(C)c4c3)C(=O)N3CCC[C@H]3C(=O)N3CCCC[C@H]3C(=O)N[C@@H](C)C(=O)N2C1]

Compound 12 was synthesized from compound C (80 mg, 0.128 mmol), 6-isocyanato-1-methyl-1H-indole (26.5 mg, 0.154 mmol) and triethylamine (84 µL, 0.615 mmol) following the general synthesis method as described herein above. Compound 12 was provided as a white solid (45 mg, 44.1%); 1H NMR (400 MHz, Chloroform-d) δ 0.90 (d, J=6.5 Hz, 3H), 1.42 (d, J=6.5 Hz, 3H), 1.46-1.56 (m, 2H), 1.75-1.91 (m, 2H), 1.94-2.03 (m, 2H), 2.03-2.08 (m, 1H), 2.12-2.24 (m, 1H), 2.32-2.41 (m, 2H), 2.60-2.77 (m, 2H), 2.92-2.98 (m, 1H), 3.03-3.08 (m, 1H), 3.14-3.19 (dd, J=11.8, 8.7 Hz, 1H), 3.47-3.65 (m, 3H), 3.71-3.78 (m, 4H), 4.40-4.48 (m, 1H), 4.51-4.58 (m, 2H), 4.67-4.72 (m, 2H), 4.79 (d, J=10.8 Hz, 1H), 4.99-5.10 (m, 1H), 5.12-5.14 (m, 1H), 5.86 (d, J=7.9 Hz, 1H), 6.39 (d, J=3.1 Hz, 1H), 6.47 (d, J=9.5 Hz, 0.74H), 6.50 (d, J=3.1 Hz, 0.66H), 6.82 (dd, J=8.4, 1.6 Hz, 1H), 6.96 (d, J=3.1 Hz, 1H), 7.10-7.25 (m, 4H), 7.39-7.32 (m, 2H), 7.41-7.42 (m, 0.5H), 7.45 (d, J=8.4 Hz, 0.5H), 7.69 (d, J=8.4 Hz, 1H), 7.91 (d, J=8.8 Hz, 2H), 8.70 (d, J=9.6 Hz, 1H); ESI-MS: [m/z+H$^+$]=797.89.

m. PREPARATION OF (S)-3-(3,5-DIFLUOROPHENYL)-N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(4-(TRIFLUOROMETHOXY)PHENYL)UREIDO)PROPANAMIDE (COMPOUND 13)

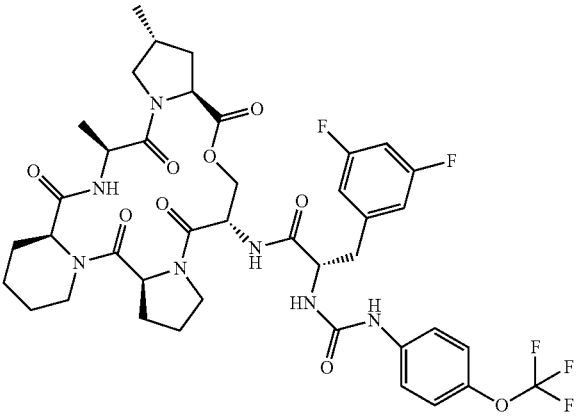 [SMILES: C[C@@H]1C[C@H]2C(=O)OC[C@H](NC(=O)[C@H](Cc3cc(F)cc(F)c3)NC(=O)Nc3ccc(OC(F)(F)F)cc3)C(=O)N3CCC[C@H]3C(=O)N3CCCC[C@H]3C(=O)N[C@@H](C)C(=O)N2C1]

Compound 13 was synthesized from compound C (70 mg, 0.100 mmol), 1-isocyanato-4-(trifluoromethoxy)benzene (24.5 mg, 0.12 mmol) and triethylamine (66 µL, 0.482 mmol) following the general synthesis method as described herein above. Compound 13 was provided as a greyish solid (19.8 mg, 22.8%); 1H NMR (400 MHz, Chloroform-d) δ 0.95 (d, J=6.5 Hz, 3H), 1.34 (d, J=6.6 Hz, 3H), 1.43-1.51 (m, 2H), 1.76-1.86 (m, 2H), 1.96-2.02 (m, 2H), 2.06-2.11 (m, 1H), 2.14-2.21 (m, 1H), 2.35-2.46 (m, 2H), 2.55-2.62 (m, 1H), 2.70-2.72 (m, 1H), 2.90-3.00 (m, 2H), 3.05-3.10 (m, 1H), 3.47-3.65 (m, 3H), 3.75-3.83 (m, 1H), 4.49-4.58 (m, 3H), 4.68-4.72 (m, 2H), 4.81 (d, J=11.5 Hz, 1H), 4.98-5.06 (m, 1H), 5.12-5.15 (m, 1H), 5.82 (d, J=7.7 Hz, 1H), 6.63-6.70 (m, 1H), 6.72-6.74 (m, 2H), 7.05-7.15 (m, 3H), 7.18 (d, J=8.8 Hz, 0.5H), 7.41 (d, J=8.8 Hz, 0.5H), 7.47 (d, J=8.9 Hz, 2H), 8.05 (s, 1H), 8.55 (d, J=9.7 Hz, 1H); ESI-MS: [m/z+H$^+$]=864.86.

n. PREPARATION OF (S)-3-(3,5-DIFLUOROPHENYL)-N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(4-ETHYLPHENYL)UREIDO)PROPANAMIDE (COMPOUND 14)

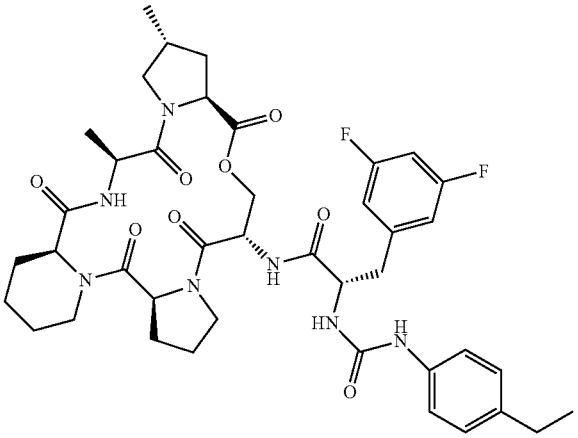 [SMILES: CCc1ccc(NC(=O)N[C@@H](Cc2cc(F)cc(F)c2)C(=O)N[C@H]2COC(=O)[C@@H]3C[C@@H](C)CN3C(=O)[C@H](C)NC(=O)[C@@H]3CCCCN3C(=O)[C@@H]3CCCN3C2=O)cc1]

Compound 14 was synthesized from compound C (70 mg, 0.100 mmol), 1-ethyl-4-isocyanatobenzene (17.7 mg, 0.12 mmol) and triethylamine (66 μL, 0.482 mmol) following the general synthesis method as described herein above. Compound 14 was provided as a light yellow solid (35.7 mg, 44%); 1H NMR (400 MHz, Chloroform-d) δ 0.94 (d, J=6.6 Hz, 3H), 1.18 (t, J=7.6 Hz, 3H), 1.35 (d, J=6.6 Hz, 3H), 1.43-1.51 (m, 2H), 1.74-1.88 (m, 2H), 1.93-2.04 (m, 2H), 2.05-2.10 (m, 1H), 2.13-2.20 (m, 1H), 2.30-2.47 (m, 2H), 2.54-2.64 (m, 4H), 2.70-2.72 (m, 1H), 2.89-3.01 (m, 2H), 3.08-3.13 (m, 1H), 3.49-3.62 (m, 3H), 3.74-3.83 (m, 1H), 4.45-4.57 (m, 3H), 4.68-4.72 (m, 2H), 4.81 (d, J=11.6 Hz, 1H), 4.98-5.05 (m, 1H), 5.11-5.14 (m, 1H), 5.78 (d, J=7.8 Hz, 1H), 6.60-6.70 (m, 1H), 6.74 (d, J=6.1 Hz, 2H), 6.93 (d, J=9.7 Hz, 0.85H), 7.10 (d, J=8.3 Hz, 2H), 7.16 (d, J=8.3 Hz, 0.6H), 7.35 (d, J=8.4 Hz, 2H), 7.76 (s, 1H), 8.57 (d, J=9.6 Hz, 1H); ESI-MS: [m/z+H$^+$]=808.84.

4. GENERAL SYNTHESIS OF UREA ANALOGS 15-37

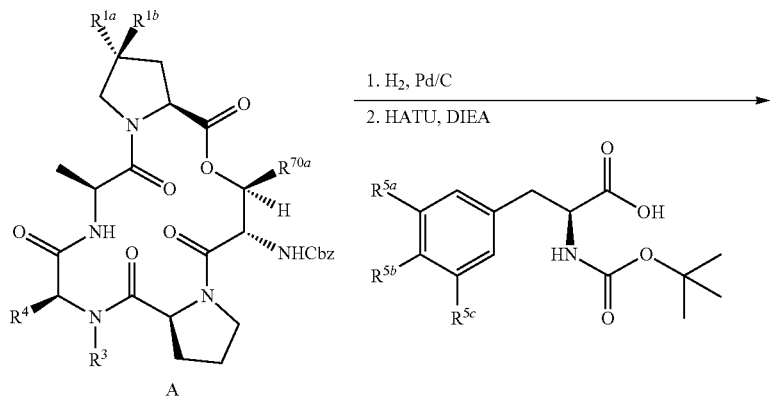

A

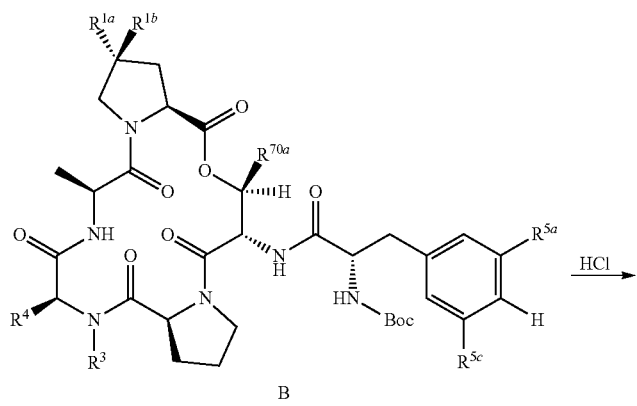

B

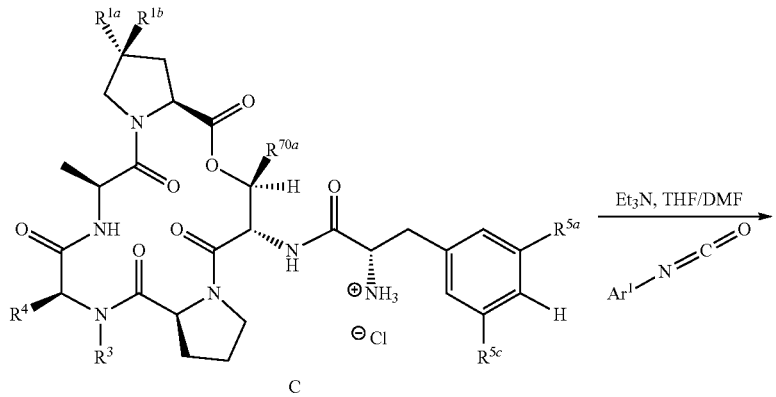

C

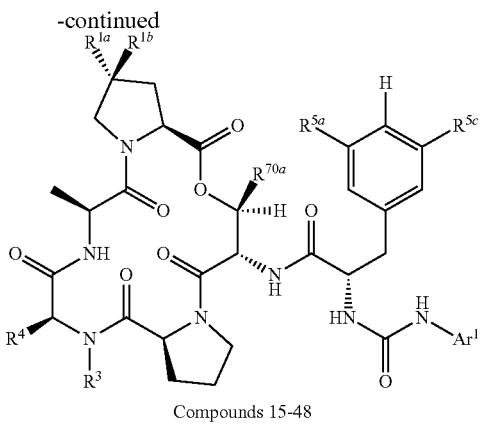

Compounds 15-48

The target compound was synthesized from intermediate A, which was deprotected by hydrogenation in the presence of palladium on carbon following by coupling with Boc-L-phenylalaine to give compound B (for general methods for coupling of Boc-L-phenylalanine see (a) Hinzen, B., et al. ChemMedChem (2006) 1(7):689-693; and (b) U.S. Pat. No. 4,492,650). Compound B was treated with 4N hydrocholoride acid in dioaxane to afford free amine C, which was coupled with appropriate isocyanate under microwave irradiation in the presence of triethylamine to give substituted urea depsipeptide analogs 15-48 (for coupling of an isocyanate under microwave irradiation see North, E. J., et al. Bioorganic & Medicinal Chemistry (2013) 21(9):2587-2599).

Briefly, Ar—NCO (about 1.2 eq.), compound C (about 1 eq), and triethylamine (about 3.6 or alternatively about 4.8 eq.) were mixed in THF/DMF (v/v=1:1, 2 mL) in a microwave safe tube and stirred at 200° C. for 10 min. The solvents were removed under reduced pressure and the crude residue was purified by reverse-phase flash column chromatography using water to acetonitrile gradient. The fractions containing desired compound were pooled and dried to the desired afford target compounds. Table 2 below provides information for the particular substituted Boc-L-phenylalanine derivative and aryl isocyanate used in the general scheme shown above. The substituent groups are as follows:

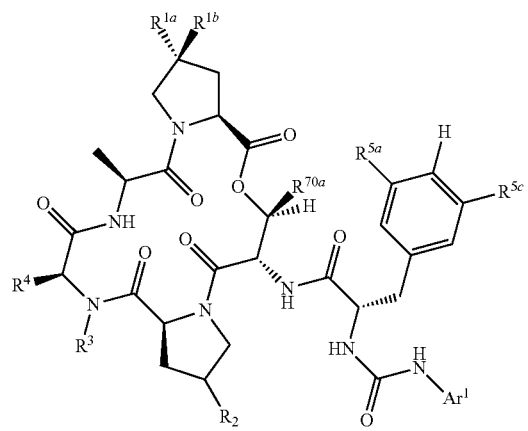

TABLE 2

| No. | $R^{1a}$ | $R^{1b}$ | $R^2$ | $R^3$ | $R^4$ | $R^{5a}$ | $R^{5c}$ | $R^{70a}$ | $Ar^1$ |
|---|---|---|---|---|---|---|---|---|---|
| 15 | H | H | | H | —CH$_2$CH$_2$CH$_2$CH$_2$— | F | F | CH$_3$ | 4-methylphenyl |
| 16 | H | H | | H | —CH$_2$CH$_2$CH$_2$CH$_2$— | F | F | CH$_3$ | 4-CF$_3$-phenyl |
| 17 | H | H | | H | —CH$_2$CH$_2$CH$_2$CH$_2$— | F | F | CH$_3$ | benzo[1,3]dioxol-5-yl |

TABLE 2-continued
| No. | R^{1a} | R^{1b} | R^2 | R^3 | R^4 | R^{5a} | R^{5c} | R^{70a} | A^{r1} |
|---|---|---|---|---|---|---|---|---|---|
| 18 | H | CH$_3$ | H | | —CH$_2$CH$_2$CH$_2$CH$_2$— | F | F | CH$_3$ | 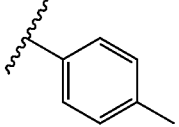 |
| 19 | H | CH$_3$ | H | | —CH$_2$CH$_2$CH$_2$CH$_2$— | F | F | CH$_3$ | 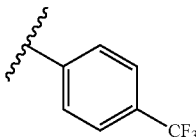 |
| 20 | H | CH$_3$ | H | | —CH$_2$CH$_2$CH$_2$CH$_2$— | F | F | CH$_3$ | 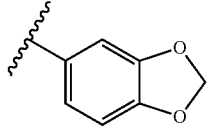 [SMILES: *c1ccc2c(c1)OCO2] |
| 21 | H | CH$_3$ | H | | —CH$_2$CH$_2$CH$_2$CH$_2$— | F | F | CH$_3$ | 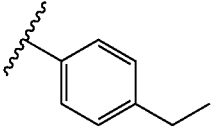 [SMILES: *c1ccc(CC)cc1] |
| 22 | H | CH$_3$ | H | | —CH$_2$CH$_2$CH$_2$CH$_2$— | F | F | CH$_3$ | 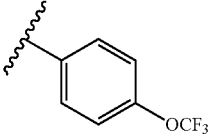 |
| 23 | CH$_3$ | H | H | | —CH$_2$CH$_2$CH$_2$CH$_2$— | H | H | H | 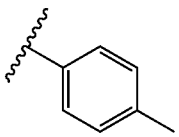 [SMILES: *c1ccc(C)cc1] |
| 24 | CH$_3$ | H | H | | —CH$_2$CH$_2$CH$_2$CH$_2$— | F | F | H | 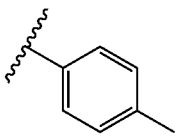 [SMILES: *c1ccc(C)cc1] |
| 25 | H | H | H | CH$_3$ | CH$_3$ | F | F | CH$_3$ | 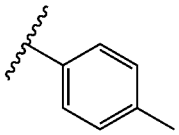 [SMILES: *c1ccc(C)cc1] |
| 26 | H | CH$_3$ | H | CH$_3$ | CH$_3$ | F | F | CH$_3$ | 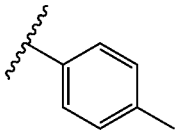 [SMILES: *c1ccc(C)cc1] |
| 27 | H | H | H | CH$_3$ | CH$_3$ | F | F | CH$_3$ | 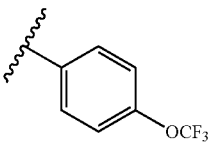 |

TABLE 2-continued
| No. | R$^{1a}$ | R$^{1b}$ | R$^2$ | R$^3$ | R$^4$ | R$^{5a}$ | R$^{5c}$ | R$^{70a}$ | A$^{r1}$ |
|---|---|---|---|---|---|---|---|---|---|
| 28 | H | CH$_3$ | H | CH$_3$ | CH$_3$ | F | F | CH$_3$ | 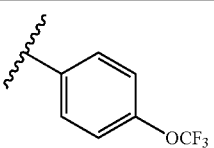 [SMILES: *c1ccc(OC(F)(F)F)cc1] |
| 29 | H | H | H | CH$_3$ | CH$_3$ | F | F | CH$_3$ | 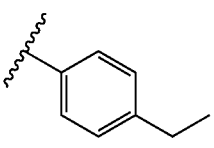 [SMILES: *c1ccc(CC)cc1] |
| 30 | H | CH$_3$ | H | CH$_3$ | CH$_3$ | F | F | CH$_3$ | 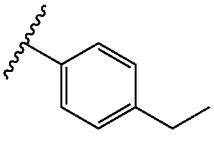 [SMILES: *c1ccc(CC)cc1] |
| 31 | H | CH$_3$ | OH | CH$_3$ | CH$_3$ | F | F | CH$_3$ | 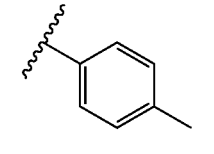 [SMILES: *c1ccc(C)cc1] |
| 32 | H | CH$_3$ | OH | CH$_3$ | CH$_3$ | F | F | CH$_3$ | 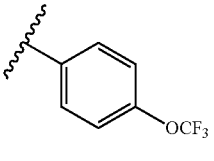 |
| 33 | H | CH$_3$ | H | —CH$_2$OCH$_2$CH$_2$— | | F | F | CH$_3$ | 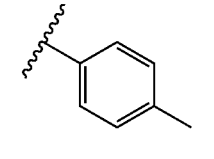 [SMILES: *c1ccc(C)cc1] |
| 34 | H | CH$_3$ | H | —CH$_2$OCH$_2$CH$_2$— | | F | F | CH$_3$ | 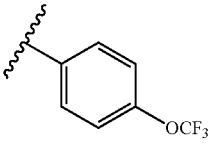 [SMILES: *c1ccc(OC(F)(F)F)cc1] |
| 35 | H | CH$_3$ | H | CH$_3$ | CH(CH$_3$)OH | F | F | CH$_3$ | 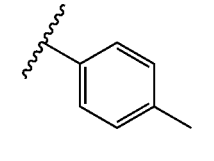 [SMILES: *c1ccc(C)cc1] |
| 36 | H | CH$_3$ | H | CH$_3$ | CH(CH$_3$)OH | F | F | CH$_3$ | 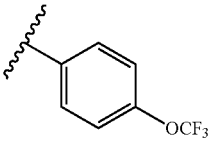 [SMILES: *c1ccc(OC(F)(F)F)cc1] |
| 37 | H | CH$_3$ | H | CH$_3$ | CH(CH$_3$)OH | F | F | CH$_3$ | 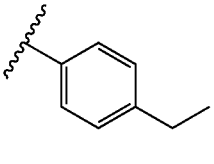 [SMILES: *c1ccc(CC)cc1] |

TABLE 2-continued

| No. | R$^{1a}$ | R$^{1b}$ | R$^2$ | R$^3$ | R$^4$ | R$^{5a}$ | R$^{5c}$ | R$^{70a}$ | A$^{r1}$ |
|---|---|---|---|---|---|---|---|---|---|
| 38 | CH$_3$ | H | H | CH$_3$ | CH(CH$_3$)OH | F | F | CH$_3$ | 4-methylphenyl |
| 39 | CH$_3$ | H | H | —CH$_2$CH$_2$CH$_2$CH$_2$— | | F | F | CH$_3$ | 4-methylphenyl |
| 40 | CH$_3$ | H | H | —CH$_2$CH$_2$CH$_2$CH$_2$— | | F | F | CH$_3$ | 4-OCF$_3$-phenyl |
| 41 | CH$_3$ | H | H | CH$_3$ | CH(CH$_3$)OH | F | F | CH3 | 4-OCF$_3$-phenyl |
| 42 | CH$_3$ | H | H | CH$_3$ | CH(CH$_3$)OH | F | F | CH3 | 4-ethylphenyl |
| 43 | H | CH$_3$ | H | —CH$_2$CH$_2$CH$_2$CH$_2$— | | H | H | H | 4-methylphenyl |
| 44 | H | CH$_3$ | H | —CH$_2$CH$_2$CH$_2$CH$_2$— | | H | H | H | 4-OCF$_3$-phenyl |
| 45 | H | CH$_3$ | H | —CH$_2$CH$_2$CH$_2$CH$_2$— | | F | F | H | 4-methylphenyl |
| 46 | H | CH$_3$ | H | —CH$_2$CH$_2$CH$_2$CH$_2$— | | F | F | H | benzo[1,3]dioxol-5-yl |
| 47 | CH$_3$ | H | H | —CH$_2$OCH$_2$CH$_2$— | | F | F | CH$_3$ | 4-methylphenyl |

TABLE 2-continued

| No. | $R^{1a}$ | $R^{1b}$ | $R^2$ | $R^3$ | $R^4$ | $R^{5a}$ | $R^{5c}$ | $R^{70a}$ | $A^{r1}$ |
|---|---|---|---|---|---|---|---|---|---|
| 48 | H | CH$_3$ | H | | —CH$_2$CH$_2$CH$_2$CH$_2$— | F | F | H | 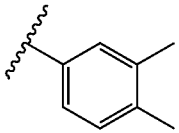 [SMILES: *c1ccc(C)c(C)c1] |
| 49 | CH$_3$ | CH$_3$ | H | | —CH$_2$CH$_2$CH$_2$CH$_2$— | F | F | H | 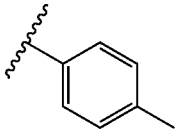 [SMILES: *c1ccc(C)cc1] |
| 50 | F | H | H | | —CH$_2$CH$_2$CH$_2$CH$_2$— | F | F | H | 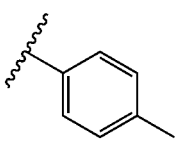 [SMILES: *c1ccc(C)cc1] |
| 51 | H | F | H | | —CH$_2$CH$_2$CH$_2$CH$_2$— | F | F | H | 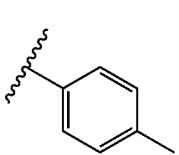 [SMILES: *c1ccc(C)cc1] | a. PREPARATION OF (S)-3-(3,5-DIFLUOROPHE-NYL)-N-((6S,8AS,14AS,20S,21S,23AS)-6,21-DIM-ETHYL-5,8,14,19,23-PENTAOXOOCTADECA-HYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(P-TOLYL)UREIDO)PROPANAMIDE (COMPOUND 15)

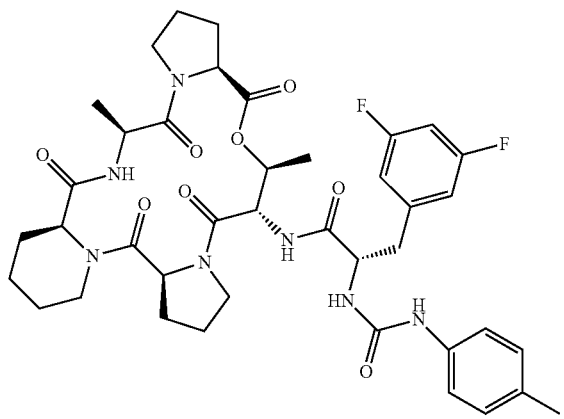 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3CCC[C@H]3C(=O)O[C@H]2C)cc1]

Compound 15 was synthesized from compound C (100 mg, 0.143 mmol), p-tolylisocyanate (21.7 µL, 0.172 mmol) and triethylamine (94 µL, 0.688 mmol) as a white solid (61.6 mg, 54%) following the general synthesis pathway described herein above; $^1$H NMR (400 MHz, Chloroform-d) δ 1.19 (d, J=6.6 Hz, 3H), 1.34 (d, J=6.6 Hz, 3H), 1.47 (q, J=11.1, 10.0 Hz, 3H), 1.64 (t, J=12.2 Hz, 1H), 1.83-1.91 (m, 2H), 1.95-2.03 (m, 3H), 2.11-2.19 (m, 3H), 2.29 (s, 3H), 2.34-2.44 (m, 1H), 2.596-2.63 (m, 1H), 2.71-2.73 (m, 1H), 2.92-3.00 (m, 2H), 3.29-3.39 (m, 1H), 3.49-3.67 (m, 2H), 3.79-3.85 (m, 1H), 4.46-4.54 (m, 2H), 4.68-4.72 (m, 3H), 4.97-5.05 (m, 1H), 5.12-5.17 (m, 1H), 5.22-5.24 (m, 1H), 5.83 (d, J=7.6 Hz, 1H), 6.66 (t, J=9.0 Hz, 1H), 6.75 (d, J=7.7 Hz, 2H), 6.85 (d, J=9.8 Hz, 1H), 7.08 (d, J=8.3 Hz, 2H), 7.34 (d, J=8.4 Hz, 2H), 7.80 (s, 1H), 8.57 (d, J=9.7 Hz, 1H); ESI-MS: [m/z+H$^+$]=794.53.

b. PREPARATION OF (S)-3-(3,5-DIFLUOROPHE-NYL)-N-((6S,8AS,14AS,20S,21S,23AS)-6,21-DIM-ETHYL-5,8,14,19,23-PENTAOXOOCTADECA-HYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(4-(TRIFLUOROMETHYL)PHENYL)UREIDO)PROPANAMIDE (COMPOUND 16)

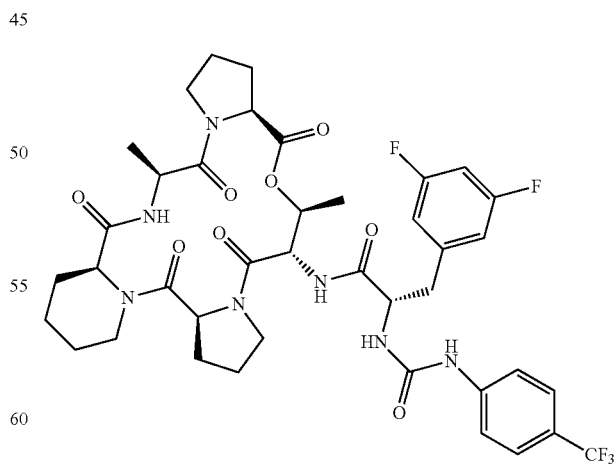

Compound 16 was synthesized from compound C (90 mg, 0.129 mmol), 4-(trifluoromethyl)phenyl isocyanate (23.2 µL, 0.155 mmol) and triethylamine (85 µL, 0.620 mmol) as a white-off solid (52.6 mg, 48%) following the general synthesis pathway described herein above; ¹H NMR (400 MHz, Chloroform-d) δ 1.20 (d, J=6.6 Hz, 3H), 1.34 (d, J=6.6 Hz, 3H), 1.44-1.54 (m, 2H), 1.65-1.68 (m, 1H), 1.85-1.92 (m, 2H), 1.97-2.05 (m, 3H), 2.09-2.23 (m, 4H), 2.33-2.44 (m, 1H), 2.53-2.66 (m, 1H), 2.71-2.73 (m, 1H), 2.96-2.98 (m, 2H), 3.25-3.37 (m, 1H), 3.51-3.64 (m, 2H), 3.78-3.89 (m, 1H), 4.47-4.56 (m, 2H), 4.69-4.72 (m, 3H), 4.98-5.08 (m, 1H), 5.14-5.19 (m, 1H), 5.21-5.28 (m, 1H), 5.95 (d, J=7.6 Hz, 1H), 6.62-6.75 (m, 3H), 7.00 (d, J=9.7 Hz, 1H), 7.51-7.58 (m, 4H), 8.29 (s, 1H), 8.53 (d, J=9.7 Hz, 1H). ESI-MS: [m/z+H⁺]=848.53.

c. PREPARATION OF (S)-2-(3-(BENZO[D][1,3]DIOXOL-5-YL)UREIDO)-3-(3,5-DIFLUOROPHENYL)-N-((6S,8AS,14AS,20S,21S,23AS)-6,21-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 17)

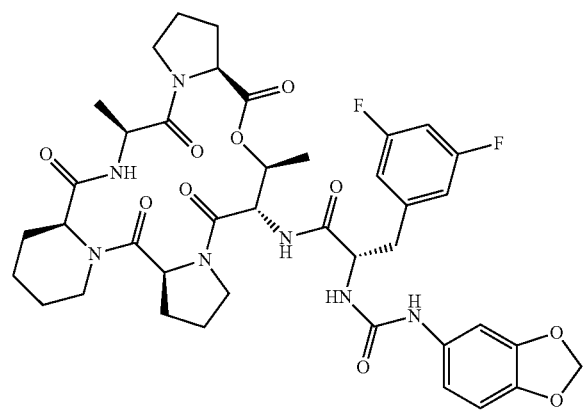 [SMILES: C[C@@H]1NC(=O)[C@@H]2CCCCN2C(=O)[C@@H]2CCCN2C(=O)[C@@H](NC(=O)[C@H](Cc2cc(F)cc(F)c2)NC(=O)Nc2ccc3c(c2)OCO3)[C@H](C)OC(=O)[C@@H]2CCCN2C1=O]

Compound 17 was synthesized from compound C (90 mg, 0.129 mmol), 5-isocyanatobenzo[d][1,3]dioxole (25.3 mg, 0.155 mmol) and triethylamine (85 μL, 0.620 mmol) as a white-off solid (45 mg, 42%) following the general synthesis pathway described herein above; ¹H NMR (400 MHz, Chloroform-d) δ 1.19 (d, J=6.6 Hz, 3H), 1.35 (d, J=6.6 Hz, 3H), 1.46-1.51 (m, 2H), 1.64-1.76 (m, 1H), 1.84-1.94 (m, 2H), 1.94-2.05 (m, 3H), 2.09-2.22 (m, 4H), 2.31-2.42 (m, 1H), 2.54-2.65 (m, 1H), 2.71-2.77 (m, 1H), 2.90-3.02 (m, 2H), 3.28-3.39 (m, 1H), 3.46-3.66 (m, 2H), 3.75-3.86 (m, 1H), 4.43-4.48 (m, 2H), 4.67-4.72 (m, 3H), 4.95-5.06 (m, 1H), 5.12-5.17 (m, 1H), 5.19-5.26 (m, 1H), 5.80 (d, J=7.6 Hz, 1H), 5.91 (s, 2H), 6.65-6.76 (m, 6H), 7.18 (d, J=1.9 Hz, 1H), 7.77 (s, 1H), 8.56 (d, J=9.6 Hz, 1H). ESI-MS: [m/z+H⁺]=824.53.

d. PREPARATION OF (S)-3-(3,5-DIFLUOROPHENYL)-2-(3-(P-TOLYL)UREIDO)-N-((2R,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 18)

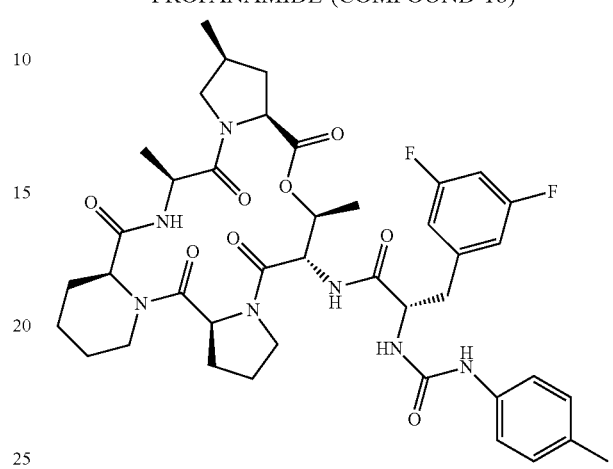

Compound 18 was synthesized from compound C (90 mg, 0.127 mmol), p-tolylisocyanate (19 μL, 0.152 mmol) and triethylamine (83 μL, 0.607 mmol) as a white-off solid (39.8 mg, 39%) following the general synthesis pathway described herein above; ¹H NMR (400 MHz, Chloroform-d) δ 0.87 (d, J=6.7 Hz, 3H), 1.22 (d, J=6.6 Hz, 3H), 1.36 (d, J=6.5 Hz, 3H), 1.43-1.50 (m, 3H), 1.92-2.02 (m, 2H), 2.09-2.20 (m, 2H), 2.29 (s, 3H), 2.33-2.40 (m, 1H), 2.55-2.75 (m, 4H), 2.90-3.04 (m, 2H), 3.48-3.54 (m, 1H), 3.78-3.84 (m, 1H), 4.03-4.11 (m, 1H), 4.38-4.49 (m, 2H), 4.68-4.71 (m, 3H), 4.96-5.03 (m, 1H), 5.09-5.14 (m, 1H), 5.23-5.25 (m, 1H), 5.88 (d, J=7.8 Hz, 1H), 6.62-6.71 (m, 2H), 6.74-6.79 (m, 2H), 7.08 (d, J=8.2 Hz, 2H), 7.33 (d, J=8.4 Hz, 2H), 7.53 (s, 1H), 8.61 (d, J=9.6 Hz, 1H); ESI-MS: [m/z+H⁺]=808.61.

e. PREPARATION OF (S)-3-(3,5-DIFLUOROPHENYL)-2-(3-(4-(TRIFLUOROMETHYL)PHENYL)UREIDO)-N-((2R,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 19)

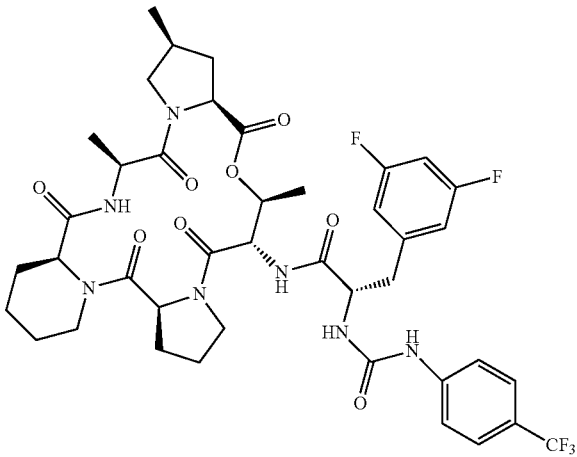 [SMILES: C[C@H]1C[C@H]2C(=O)O[C@@H](C)[C@H](NC(=O)[C@H](Cc3cc(F)cc(F)c3)NC(=O)Nc3ccc(C(F)(F)F)cc3)C(=O)N3CCC[C@H]3C(=O)N3CCCC[C@H]3C(=O)N[C@@H](C)C(=O)N2C1]

Compound 19 was synthesized from compound C (90 mg, 0.127 mmol), 4-(trifluoromethyl)phenyl isocyanate (23 μL, 0.152 mmol) and triethylamine (83 μL, 0.607 mmol) as a white-off solid (35.9 mg, 33%) following the general synthesis pathway described herein above; $^1$H NMR (400 MHz, Chloroform-d) δ 0.89 (d, J=6.7 Hz, 3H), 1.21 (d, J=6.6 Hz, 3H), 1.36 (d, J=6.6 Hz, 3H), 1.44-1.54 (m, 3H), 1.93-2.04 (m, 2H), 2.08-2.23 (m, 3H), 2.35-2.42 (m, 1H), 2.6557-2.76 (m, 4H), 2.90-3.04 (m, 2H), 3.47-3.58 (m, 1H), 3.79-3.85 (m, 1H), 4.03-4.08 (m, 1H), 4.40-4.50 (m, 2H), 4.65-4.76 (m, 3H), 4.98-5.05 (m, 1H), 5.11-5.16 (m, 1H), 5.21-5.29 (m, 1H), 6.00 (d, J=7.5 Hz, 1H), 6.61-6.84 (m, 4H), 7.49-7.62 (m, 4H), 8.05 (s, 1H), 8.56 (d, J=9.6 Hz, 1H); ESI-MS: [m/z+H$^+$]=862.61.

f. PREPARATION OF (S)-2-(3-(BENZO[D][1,3]DIOXOL-5-YL)UREIDO)-3-(3,5-DIFLUOROPHENYL)-N-((2R,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 20)

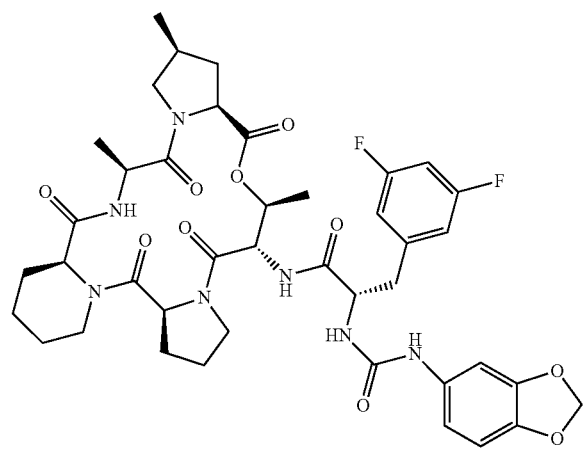 [SMILES: C[C@H]1C[C@H]2C(=O)O[C@@H](C)[C@H](NC(=O)[C@H](Cc3cc(F)cc(F)c3)NC(=O)Nc3ccc4c(c3)OCO4)C(=O)N3CCC[C@H]3C(=O)N3CCCC[C@H]3C(=O)N[C@@H](C)C(=O)N2C1]

Compound 20 was synthesized from compound C (90 mg, 0.127 mmol), 5-isocyanatobenzo[d][1,3]dioxole (24.8 mg, 0.152 mmol) and triethylamine (83 μL, 0.607 mmol) as a white-off solid (30.9 mg, 29%) following the general synthesis pathway described herein above; $^1$H NMR (400 MHz, Chloroform-d) δ 0.91 (d, J=6.7 Hz, 3H), 1.22 (d, J=6.6 Hz, 3H), 1.35 (d, J=6.6 Hz, 3H), 1.43-1.52 (m, 3H), 1.92-2.02 (m, 2H), 2.10-2.21 (m, 2H), 2.31-2.42 (m, 1H), 2.55-2.78 (m, 4H), 2.90-3.03 (m, 2H), 3.46-3.56 (m, 1H), 3.78-3.84 (m, 1H), 4.05-4.10 (m, 1H), 4.38-4.50 (m, 2H), 4.69-4.72 (m, 3H), 4.93-5.04 (m, 1H), 5.10-5.15 (m, 1H), 5.21-5.28 (m, 1H), 5.84 (d, J=7.7 Hz, 1H), 5.91 (s, 2H), 6.63-6.80 (m, 6H), 7.16-7.23 (m, 1H), 7.53 (s, 1H), 8.59 (d, J=9.6 Hz, 1H); ESI-MS: [m/z+H$^+$]=838.53.

g. PREPARATION OF (S)-3-(3,5-DIFLUOROPHENYL)-2-(3-(4-ETHYLPHENYL)UREIDO)-N-((2R,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 21)

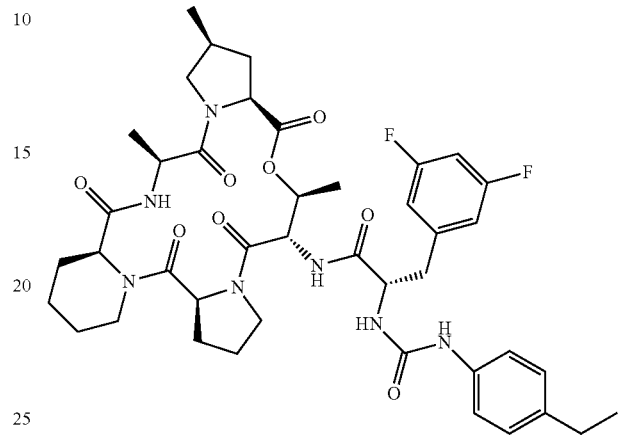

Compound 21 was synthesized from compound C (85 mg, 0.12 mmol), 1-ethyl-4-isocyanatobenzene (21.1 mg, 0.143 mmol) and triethylamine (78 μL, 0.574 mmol) as a white-off solid (36 mg, 37%) following the general synthesis pathway described herein above; $^1$H NMR (400 MHz, Chloroform-d) δ 0.86 (d, J=6.8 Hz, 3H), 1.18-1.23 (m, 6H), 1.35 (d, J=6.5 Hz, 3H), 1.42-1.52 (m, 3H), 1.62-1.67 (m, 1H), 1.72-1.82 (m, 2H), 1.91-2.03 (m, 2H), 2.08-2.18 (m, 2H), 2.30-2.42 (m, 1H), 2.56-2.65 (m, 4H), 2.67-2.76 (m, 2H), 2.90-3.03 (m, 2H), 3.47-3.57 (m, 1H), 3.78-3.84 (m, 1H), 4.07 (dd, J=11.6, 8.2 Hz, 1H), 4.41-4.50 (m, 2H), 4.69-4.72 (m, 3H), 4.95-5.03 (m, 1H), 5.08-5.16 (m, 1H), 5.24 (dd, J=8.6, 2.6 Hz, 1H), 5.87 (d, J=7.8 Hz, 1H), 6.63-6.79 (m, 4H), 7.10 (d, J=8.4 Hz, 2H), 7.35 (d, J=8.5 Hz, 2H), 7.53 (s, 1H), 8.61 (d, J=9.6 Hz, 1H); ESI-MS: [m/z+H$^+$]=822.61.

h. PREPARATION OF (S)-3-(3,5-DIFLUOROPHENYL)-2-(3-(4-(TRIFLUOROMETHOXY)PHENYL)UREIDO)-N-((2R,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 22)

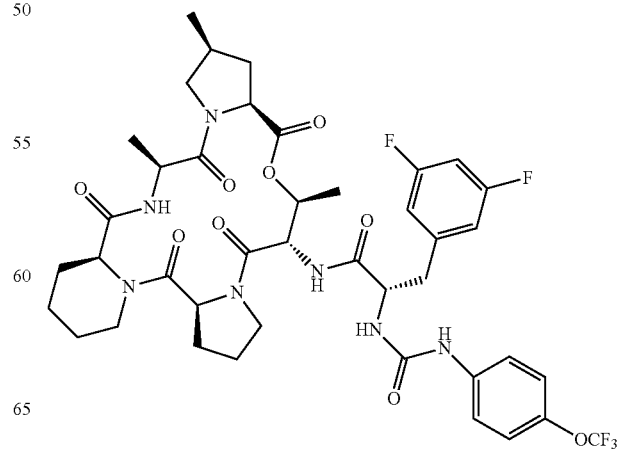

Compound 22 was synthesized from compound C (85 mg, 0.12 mmol), 1-isocyanato-4-(trifluoromethoxy)benzene (29.1 mg, 0.143 mmol) and triethylamine (78 µL, 0.574 mmol) as a white-off solid (40.8 mg, 39%) following the general synthesis pathway described herein above; $^1$H NMR (400 MHz, Chloroform-d) δ 0.88 (d, J=6.7 Hz, 3H), 1.22 (d, J=6.6 Hz, 3H), 1.35 (d, J=6.6 Hz, 3H), 1.42-1.54 (m, 3H), 1.65-1.68 (m, 1H), 1.71-1.82 (m, 2H), 1.92-2.03 (m, 2H), 2.09-2.23 (m, 2H), 2.30-2.43 (m, 1H), 2.54-2.76 (m, 4H), 2.89-3.04 (m, 2H), 3.46-3.58 (m, 1H), 3.77-3.86 (m, 1H), 4.05 (dd, J=11.5, 8.2 Hz, 1H), 4.41-4.51 (m, 2H), 4.65-4.77 (m, 3H), 4.94-5.05 (m, 1H), 5.09-5.17 (m, 1H), 5.25 (dd, J=8.6, 2.7 Hz, 1H), 5.93 (d, J=7.6 Hz, 1H), 6.63-6.70 (m, 1H), 6.74-6.77 (m, 2H), 6.87 (d, J=9.8 Hz, 1H), 7.13 (d, J=8.9 Hz, 2H), 7.48 (d, J=9.1 Hz, 2H), 7.84 (s, 1H), 8.58 (d, J=9.6 Hz, 1H); ESI-MS: [m/z+H$^+$]=878.69.

i. PREPARATION OF (S)—N-((2R,6S,8AS,14AS, 20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-3-PHENYL-2-(3-(P-TOLYL)UREIDO)PROPANAMIDE (COMPOUND 23)

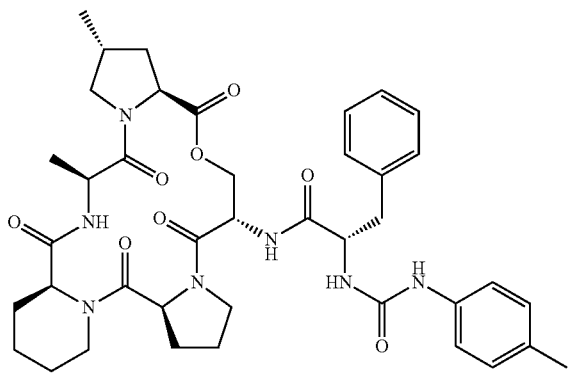 [SMILES: Cc1ccc(NC(=O)N[C@@H](Cc2ccccc2)C(=O)N[C@H]2COC(=O)[C@@H]3C[C@@H](C)CN3C(=O)[C@H](C)NC(=O)[C@@H]3CCCCN3C(=O)[C@@H]3CCCN3C2=O)cc1]

Compound 23 was synthesized from macrocycle C (100 mg, 0.151 mmol), 1-isocyanato-4-methylbenzene (24.1 mg, 0.181 mmol) and triethylamine (99 µL, 0.726 mmol) as a white-off solid (34 mg, 30%) following the general synthesis pathway described herein above; $^1$H NMR (400 MHz, Chloroform-d) δ 0.94 (d, J=6.5 Hz, 3H), 1.25 (s, 3H), 1.38 (d, J=6.5 Hz, 3H), 1.42-1.55 (m, 2H), 1.76-1.85 (m, 2H), 1.93-2.03 (m, 2H), 2.04-2.09 (m, 1H), 2.13-2.24 (m, 1H), 2.34-2.44 (m, 2H), 2.62 (t, J=12.4 Hz, 1H), 2.71-2.74 (m, 1H), 2.87-2.98 (m, 1H), 3.00-3.04 (m, 1H), 3.06-3.15 (m, 1H), 3.48 (t, J=10.8 Hz, 1H), 3.54-3.61 (m, 2H), 3.72-3.78 (m, 1H), 4.41-4.59 (m, 3H), 4.69-4.71 (m, 2H), 4.79 (d, J=11.6 Hz, 1H), 4.99-5.04 (m, 1H), 5.12-5.14 (m, 1H), 5.80 (d, J=7.9 Hz, 1H), 6.71 (d, J=9.2 Hz, 1H), 7.05-7.34 (m, 9H), 7.76 (s, 1H), 8.69 (d, J=9.6 Hz, 1H); ESI-MS: [m/z+H$^+$]=758.60.

j. PREPARATION OF (S)-3-(3,5-DIFLUOROPHENYL)-N-((2R,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(P-TOLYL)UREIDO)PROPANAMIDE (COMPOUND 24)

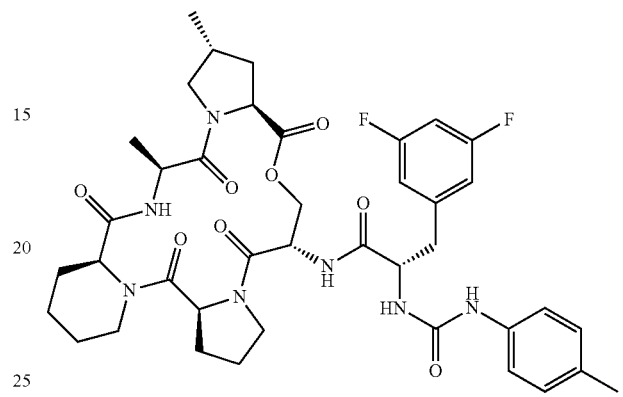

Compound 24 was synthesized from macrocycle C (100 mg, 0.143 mmol), 1-isocyanato-4-methylbenzene (22.9 mg, 0.172 mmol) and triethylamine (94 µL, 0.688 mmol) as a white-off solid (34.8 mg, 31%) following the general synthesis pathway described herein above; $^1$H NMR (400 MHz, Chloroform-d) δ 0.95 (d, J=6.7 Hz, 3H), 1.33 (d, J=6.6 Hz, 3H), 1.41-1.51 (m, 2H), 1.60-1.71 (m, 1H), 1.79-1.85 (m, 2H), 1.93-2.04 (m, 2H), 2.05-2.10 (m, 1H), 2.11-2.23 (m, 1H), 2.28 (s, 3H), 2.35-2.44 (m, 2H), 2.55-2.63 (m, 1H), 2.710-2.72 (m, 1H), 2.90-3.00 (m, 2H), 3.09-3.14 (m, 1H), 3.46-3.67 (m, 3H), 3.74-3.83 (m, 1H), 4.49-4.62 (m, 3H), 4.68-4.72 (m, 2H), 4.81 (d, J=11.5 Hz, 1H), 4.97-5.05 (m, 1H), 5.13-5.15 (m, 1H), 5.76 (d, J=7.8 Hz, 1H), 6.61-6.70 (m, 1H), 6.72-6.77 (m, 2H), 7.08 (d, J=8.2 Hz, 2H), 7.23 (d, J=9.6 Hz, 0.8H), 7.33 (d, J=8.4 Hz, 2H), 7.80 (s, 1H), 8.58 (d, J=9.7 Hz, 1H). ESI-MS: [m/z+H$^+$]=794.37.

k. PREPARATION OF (2S)-3-(3,5-DIFLUOROPHENYL)-N-((6S,9S,11AS,17S,18S)-6,9,10,18-TETRAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)-2-(3-(P-TOLYL)UREIDO)PROPANAMIDE (COMPOUND 25)

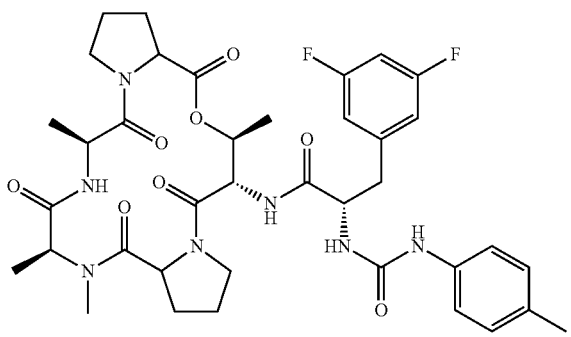 [SMILES: Cc1ccc(NC(=O)N[C@@H](Cc2cc(F)cc(F)c2)C(=O)N[C@@H]2C(=O)N3CCCC3C(=O)N(C)[C@@H](C)C(=O)N[C@@H](C)C(=O)N3CCCC3C(=O)O[C@H]2C)cc1]

Compound 25 was synthesized from macrocycle C (90 mg, 0.134 mmol), p-tolyl isocyanate (21.43 mg, 0.161 mmol) and triethylamine (88 µL, 0.644 mmol) as a white solid (31.6 mg, 30.7%) following the general synthesis pathway described herein above; $^1$H NMR (400 MHz, Chloroform-d) δ 1.20 (d, J=6.6 Hz, 3H), 1.33 (d, J=6.6 Hz, 3H), 1.53 (d, J=6.9 Hz, 3H), 1.83-1.89 (m, 2H), 1.94-2.04 (m, 3H), 2.06-2.20 (m, 2H), 2.29 (s, 3H), 2.31-2.42 (m, 1H), 2.80 (s, 3H), 2.91-3.04 (m, 2H), 3.30-3.39 (m, 1H), 3.49-3.66 (m, 2H), 3.77-3.87 (m, 1H), 4.42 (d, J=8.0 Hz, 1H), 4.47-4.55 (m, 1H), 4.69 (dd, J=9.7, 1.8 Hz, 1H), 4.76 (q, J=6.9 Hz, 1H), 4.89-4.96 (m, 1H), 5.15-5.27 (m, 2H), 5.84 (d, J=7.6 Hz, 1H), 6.62-6.71 (m, 1H), 6.77-6.79 (m, 2H), 6.88 (d, J=9.7 Hz, 1H), 7.08 (d, J=8.2 Hz, 2H), 7.33 (d, J=8.4 Hz, 2H), 7.82 (s, 1H), 8.51 (d, J=9.5 Hz, 1H); ESI-MS: [m/z+H$^+$]=768.60.

l. PREPARATION OF (2S)-3-(3,5-DIFLUORO-PHENYL)-N-((2S,6S,9S,11AS,17S,18S)-2,6,9,10,18-PENTAMETHYL-5,8,11,16,20-PENTAOXO-HEXADECAHYDRO-1H,5H,16H-DIPYRROLO[2,1-C:2',1'-L][1]OXA[4,7,10,13]TETRAAZACYCLOHEXADECIN-17-YL)-2-(3-(P-TOLYL)UREIDO)PROPANAMIDE (COMPOUND 26)

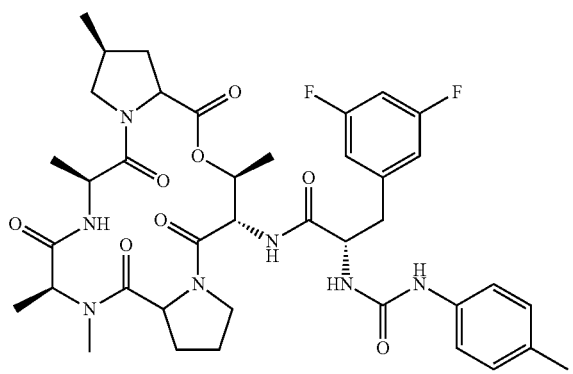 [SMILES: Cc1ccc(NC(=O)N[C@@H](Cc2cc(F)cc(F)c2)C(=O)N[C@@H]2C(=O)N3CCCC3C(=O)N(C)[C@@H](C)C(=O)N[C@@H](C)C(=O)N3C[C@@H](C)CC3C(=O)O[C@H]2C)cc1]

Compound 26 was synthesized from macrocycle C (90 mg, 0.131 mmol), p-tolyl isocyanate (20.99 mg, 0.158 mmol) and triethylamine (86 µL, 0.631 mmol) as a white solid (17.3 mg, 16.9%) following the general synthesis pathway described herein above; $^1$H NMR (400 MHz, Chloroform-d) δ 0.87 (d, J=6.7 Hz, 3H), 1.23 (d, J=6.6 Hz, 3H), 1.33 (d, J=6.5 Hz, 3H), 1.52 (d, J=6.9 Hz, 3H), 1.76-1.84 (m, 1H), 1.93-2.01 (m, 2H), 2.08-2.16 (m, 2H), 2.28 (s, 3H), 2.31-2.41 (m, 1H), 2.58-2.75 (m, 2H), 2.81 (s, 3H), 2.92-3.04 (m, 2H), 3.45-3.56 (m, 1H), 3.76-3.86 (m, 1H), 4.06-4.11 (m, 1H), 4.36-4.51 (m, 2H), 4.66-4.80 (m, 2H), 4.85-4.98 (m, 1H), 5.12-5.21 (m, 1H), 5.25 (dd, J=8.6, 2.7 Hz, 1H), 5.87 (d, J=7.7 Hz, 1H), 6.62-6.72 (m, 1H), 6.78-6.82 (m, 3H), 7.08 (d, J=8.4 Hz, 2H), 7.33 (d, J=8.4 Hz, 2H), 7.56 (s, 1H), 8.54 (d, J=9.5 Hz, 1H); ESI-MS: [m/z+H$^+$]=782.61.

m. PREPARATION OF (2S)-3-(3,5-DIFLUORO-PHENYL)-N-((6S,9S,11AS,17S,18S)-6,9,10,18-TETRAMETHYL-5,8,11,16,20-PENTAOXO-HEXADECAHYDRO-1H,5H,16H-DIPYRROLO[2,1-C:2',1'-L][1]OXA[4,7,10,13]TETRAAZACYCLOHEXADECIN-17-YL)-2-(3-(4-(TRIFLUOROMETHOXY)PHENYL)UREIDO)PROPANAMIDE (COMPOUND 27)

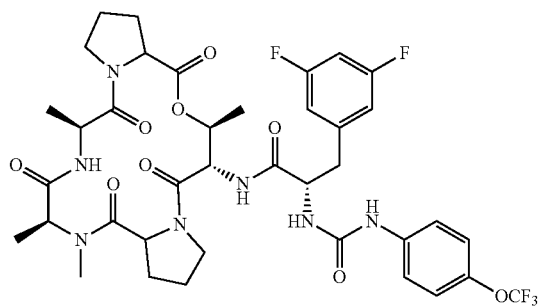 [SMILES: C[C@@H]1NC(=O)[C@H](C)N(C)C(=O)C2CCCN2C(=O)[C@@H](NC(=O)[C@H](Cc2cc(F)cc(F)c2)NC(=O)Nc2ccc(OC(F)(F)F)cc2)[C@H](C)OC(=O)C2CCCN2C1=O]

Compound 27 was synthesized from macrocycle C (90 mg, 0.134 mmol), 1-isocyanato-4-(trifluoromethoxy)benzene (32.7 mg, 0.161 mmol) and triethylamine (88 µL, 0.644 mmol) as a white solid (18 mg, 16%) following the general synthesis pathway described herein above; $^1$H NMR (400 MHz, Chloroform-d) δ 1.19 (d, J=6.6 Hz, 3H), 1.35 (d, J=6.6 Hz, 3H), 1.53 (d, J=6.9 Hz, 3H), 1.83-1.94 (m, 2H), 1.94-2.07 (m, 3H), 2.11-2.16 (m, 2H), 2.30-2.42 (m, 1H), 2.81 (s, 3H), 2.89-3.06 (m, 2H), 3.27-3.36 (m, 1H), 3.45-3.66 (m, 2H), 3.77-3.86 (m, 1H), 4.36-4.46 (m, 2H), 4.68 (dd, J=9.7, 1.9 Hz, 1H), 4.74-4.79 (m, 1H), 4.88-4.98 (m, 1H), 5.18-5.23 (m, 2H), 5.90 (d, J=7.5 Hz, 1H), 6.51 (d, J=9.8 Hz, 1H), 6.63-6.73 (m, 1H), 6.77-6.79 (m, 2H), 7.13 (d, J=8.4 Hz, 2H), 7.47 (d, J=9.0 Hz, 2H), 8.05 (s, 1H), 8.47 (d, J=9.5 Hz, 1H); ESI-MS: [m/z+H$^+$]=838.61.

n. PREPARATION OF (2S)-3-(3,5-DIFLUORO-PHENYL)-N-((2S,6S,9S,11AS,17S,18S)-2,6,9,10,18-PENTAMETHYL-5,8,11,16,20-PENTAOXO-HEXADECAHYDRO-1H,5H,16H-DIPYRROLO[2,1-C:2',1'-L][1]OXA[4,7,10,13]TETRAAZACYCLOHEXADECIN-17-YL)-2-(3-(4-(TRIFLUOROMETHOXY)PHENYL)UREIDO)PROPANAMIDE (COMPOUND 28)

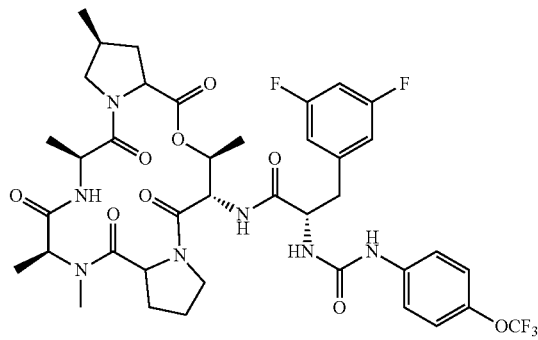 [SMILES: C[C@H]1CC2C(=O)O[C@@H](C)[C@H](NC(=O)[C@H](Cc3cc(F)cc(F)c3)NC(=O)Nc3ccc(OC(F)(F)F)cc3)C(=O)N3CCCC3C(=O)N(C)[C@@H](C)C(=O)N[C@@H](C)C(=O)N2C1]

Compound 28 was synthesized from macrocycle C (90 mg, 0.131 mmol), 1-isocyanato-4-(trifluoromethoxy)benzene (32.0 mg, 0.158 mmol) and triethylamine (86 µL, 0.631 mmol) as a white solid (17.8 mg, 15.9%) following the general synthesis pathway described herein above; $^1$H NMR (400 MHz, Chloroform-d) δ 0.88 (d, J=6.7 Hz, 3H), 1.23 (d, J=6.6 Hz, 3H), 1.34 (d, J=6.5 Hz, 3H), 1.44-1.51 (m, 1H), 1.53 (d, J=6.9 Hz, 3H), 1.91-2.03 (m, 2H), 2.10-2.20 (m, 2H), 2.31-2.41 (m, 1H), 2.58-2.74 (m, 2H), 2.81 (s, 3H), 2.89-3.06 (m, 2H), 3.45-3.56 (m, 1H), 3.76-3.85 (m, 1H), 4.06 (dd, J=11.5, 8.2 Hz, 1H), 4.35-4.45 (m, 2H), 4.66-4.81 (m, 2H), 4.88-4.95 (m, 1H), 5.13-5.28 (m, 2H), 5.93 (d, J=7.6 Hz, 1H), 6.57-6.83 (m, 4H), 7.13 (d, J=8.9 Hz, 2H), 7.48 (d, J=9.0 Hz, 2H), 7.81 (s, 1H), 8.51 (d, J=9.6 Hz, 1H); ESI-MS: [m/z+H$^+$]=838.61.

o. PREPARATION OF (2S)-3-(3,5-DIFLUOROPHENYL)-2-(3-(4-ETHYLPHENYL)UREIDO)-N-((6S,9S,11AS,17S,18S)-6,9,10,18-TETRAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)PROPANAMIDE (COMPOUND 29)

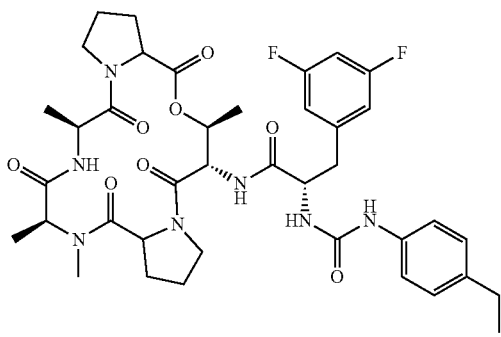 [SMILES: CCc1ccc(NC(=O)N[C@@H](Cc2cc(F)cc(F)c2)C(=O)N[C@@H]2C(=O)N3CCCC3C(=O)N(C)[C@@H](C)C(=O)N[C@@H](C)C(=O)N3CCCC3C(=O)O[C@H]2C)cc1]

Compound 29 was synthesized from macrocycle C (90 mg, 0.134 mmol), 1-ethyl-4-isocyanatobenzene (23.68 mg, 0.161 mmol) and triethylamine (88 µL, 0.644 mmol) as a white solid (37.9 mg, 36.1%) following the general synthesis pathway described herein above; $^1$H NMR (400 MHz, Chloroform-d) δ 1.18-1.22 (m, 6H), 1.34 (d, J=6.6 Hz, 3H), 1.53 (d, J=6.9 Hz, 3H), 1.80-1.91 (m, 2H), 1.93-2.05 (m, 3H), 2.08-2.20 (m, 2H), 2.31-2.41 (m, 1H), 2.56-2.63 (m, 2H), 2.81 (s, 3H), 2.90-3.05 (m, 2H), 3.30-3.39 (m, 1H), 3.47-3.68 (m, 2H), 3.77-3.86 (m, 1H), 4.38-4.53 (m, 2H), 4.69 (dd, J=9.6, 1.7 Hz, 1H), 4.74-4.79 (m, 1H), 4.87-4.98 (m, 1H), 5.17-5.24 (m, 2H), 5.84 (d, J=7.6 Hz, 1H), 6.62-6.83 (m, 4H), 7.10 (d, J=8.4 Hz, 2H), 7.36 (d, J=8.4 Hz, 2H), 7.80 (s, 1H), 8.51 (d, J=9.6 Hz, 1H); ESI-MS: [m/z+H$^+$]=782.61.

p. PREPARATION OF (S)-3-(3,5-DIFLUOROPHENYL)-2-(3-(4-ETHYLPHENYL)UREIDO)-N-((2S,6S,9S,11AS,17S,18S,20AS)-2,6,9,10,18-PENTAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)PROPANAMIDE (COMPOUND 30)

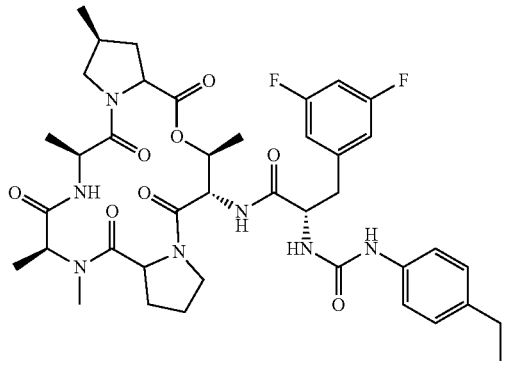 [SMILES: CCc1ccc(NC(=O)N[C@@H](Cc2cc(F)cc(F)c2)C(=O)N[C@@H]2C(=O)N3CCCC3C(=O)N(C)[C@@H](C)C(=O)N[C@@H](C)C(=O)N3C[C@@H](C)CC3C(=O)O[C@H]2C)cc1]

Compound 30 was synthesized from macrocycle C (100 mg, 0.146 mmol), 1-ethyl-4-isocyanatobenzene (25.8 mg, 0.175 mmol) and triethylamine (96 µL, 0.701 mmol) as a white solid (44 mg, 37.9%) following the general synthesis pathway described herein above; $^1$H NMR (400 MHz, Chloroform-d) δ 0.86 (d, J=6.7 Hz, 3H), 1.16-1.28 (m, 6H), 1.33 (d, J=6.5 Hz, 3H), 1.41-1.50 (m, 1H), 1.53 (d, J=6.9 Hz, 3H), 1.91-2.02 (m, 2H), 2.08-2.16 (m, 2H), 2.30-2.41 (m, 1H), 2.56-2.66 (m, 3H), 2.69-2.75 (m, 1H), 2.81 (s, 3H), 2.92-3.04 (m, 2H), 3.44-3.56 (m, 1H), 3.78-3.84 (m, 1H), 4.09 (dd, J=11.6, 8.2 Hz, 1H), 4.36-4.44 (m, 1H), 4.45-4.53 (m, 1H), 4.67-4.82 (m, 2H), 4.86-4.97 (m, 1H), 5.14-5.19 (m, 1H), 5.25 (dd, J=8.6, 2.7 Hz, 1H), 5.88 (d, J=7.7 Hz, 1H), 6.64-6.90 (m, 4H), 7.10 (d, J=8.4 Hz, 2H), 7.35 (d, J=8.5 Hz, 2H), 7.57 (s, 1H), 8.55 (d, J=9.5 Hz, 1H); ESI-MS: [m/z+H$^+$]=796.61.

q. PREPARATION OF (S)-3-(3,5-DIFLUOROPHENYL)-N-((2S,6S,9S,11AS,13R,17S,18S,20AS)-13-HYDROXY-2,6,9,10,18-PENTAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)-2-(3-(P-TOLYL)UREIDO)PROPANAMIDE (COMPOUND 31)

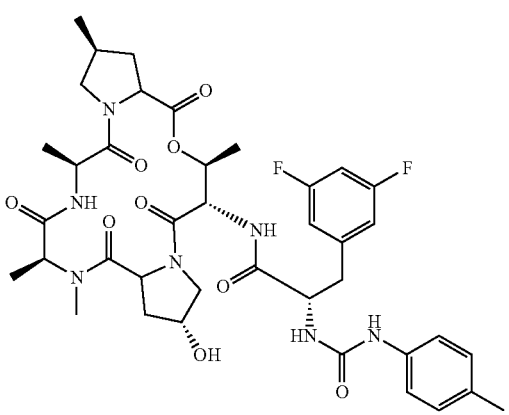 [SMILES: Cc1ccc(NC(=O)N[C@@H](Cc2cc(F)cc(F)c2)C(=O)N[C@@H]2C(=O)N3C[C@H](O)CC3C(=O)N(C)[C@@H](C)C(=O)N[C@@H](C)C(=O)N3C[C@@H](C)CC3C(=O)O[C@H]2C)cc1]

Compound 31 was synthesized from macrocycle C (100 mg, 0.143 mmol), p-tolyl isocyanate (22.79 mg, 0.171 mmol) and triethylamine (94 µL, 0.685 mmol) as a white solid (39.6 mg, 34.8%) following the general synthesis pathway described herein above; $^{1}$H NMR (400 MHz, Chloroform-d) δ 0.88 (d, J=6.7 Hz, 3H), 1.23 (d, J=6.6 Hz, 3H), 1.31 (d, J=6.5 Hz, 3H), 1.42-1.48 (m, 1H), 1.50 (d, J=6.9 Hz, 3H), 2.10-2.17 (m, 2H), 2.29 (s, 3H), 2.36-2.50 (m, 2H), 2.56-2.67 (m, 1H), 2.69-2.77 (m, 1H), 2.80 (s, 3H), 2.98-3.00 (m, 2H), 3.72-3.78 (m, 2H), 4.09 (dd, J=11.6, 8.2 Hz, 1H), 4.38-4.41 (m, 1H), 4.54-4.59 (m, 1H), 4.62 (br.s, 1H), 4.74-4.81 (m, 2H), 4.85-4.92 (m, 1H), 5.18-5.25 (m, 1H), 5.43 (t, J=7.5 Hz, 1H), 5.88 (d, J=7.7 Hz, 1H), 6.62-6.70 (m, 1H), 6.74-6.81 (m, 2H), 7.08 (d, J=8.3 Hz, 2H), 7.13-7.17 (m, 1H), 7.31 (d, J=8.4 Hz, 2H), 7.59 (s, 1H), 8.57 (d, J=9.5 Hz, 1H); ESI-MS: [m/z+H$^{+}$]=798.61.

r. PREPARATION OF (S)-3-(3,5-DIFLUOROPHENYL)-N-((2S,6S,9S,11AS,13R,17S,18S,20AS)-13-HYDROXY-2,6,9,10,18-PENTAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)-2-(3-(4-(TRIFLUOROMETHOXY)PHENYL)UREIDO)PROPANAMIDE (COMPOUND 32)

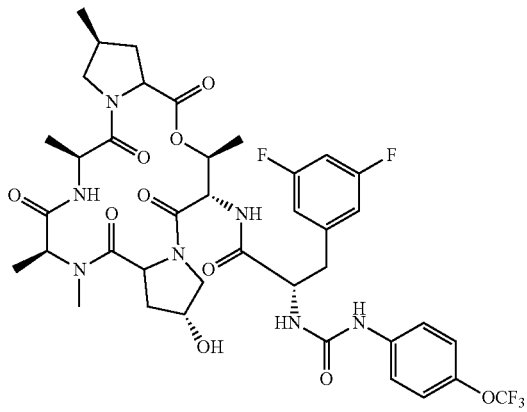 [SMILES: C[C@H]1CC2C(=O)O[C@@H](C)[C@H](NC(=O)[C@H](Cc3cc(F)cc(F)c3)NC(=O)Nc3ccc(OC(F)(F)F)cc3)C(=O)N3C[C@H](O)CC3C(=O)N(C)[C@@H](C)C(=O)N[C@@H](C)C(=O)N2C1]

Compound 32 was synthesized from macrocycle C (100 mg, 0.143 mmol), 1-isocyanato-4-(trifluoromethoxy)benzene (34.8 mg, 0.171 mmol) and triethylamine (94 µL, 0.685 mmol) as a white solid (39.6 mg, 34.8%) following the general synthesis pathway described herein above; $^{1}$H NMR (400 MHz, Chloroform-d) δ 0.88 (d, J=6.7 Hz, 3H), 1.23 (d, J=6.6 Hz, 3H), 1.31 (d, J=6.5 Hz, 3H), 1.43-1.49 (m, 1H), 1.51 (d, J=6.9 Hz, 3H), 2.11-2.21 (m, 2H), 2.33-2.46 (m, 2H), 2.61-2.65 (m, 1H), 2.66-2.75 (m, 1H), 2.80 (s, 3H), 2.98 (d, J=6.6 Hz, 2H), 3.71-3.82 (m, 2H), 4.06 (dd, J=11.5, 8.2 Hz, 1H), 4.38-4.42 (m, 1H), 4.53-4.58 (m, 1H), 4.64 (br.s, 1H), 4.73-4.82 (m, 2H), 4.86-4.94 (m, 1H), 5.18-5.26 (m, 1H), 5.44 (t, J=7.5 Hz, 1H), 5.92 (d, J=7.6 Hz, 1H), 6.62-6.70 (m, 1H), 6.786-6.78 (m, 2H), 7.13-7.20 (m, 3H), 7.46 (d, J=9.0 Hz, 2H), 7.89 (s, 1H), 8.53 (d, J=9.5 Hz, 1H); ESI-MS: [m/z+H$^{+}$]=868.61.

s. PREPARATION OF (S)-3-(3,5-DIFLUOROPHENYL)-2-(3-(P-TOLYL)UREIDO)-N-((6AS,12S,13S,15AS,17S,21S,23AS)-13,17,21-TRIMETHYL-6,11,15,20,23-PENTAOXOOCTADECAHYDRO-6H,11H,15H-[1,4]OXAZINO[3,4-I]DIPYRROLO[2,1-C:2',1'-L][1]OXA[4,7,10,13]TETRAAZACYCLOHEXADECIN-12-YL)PROPANAMIDE (COMPOUND 33)

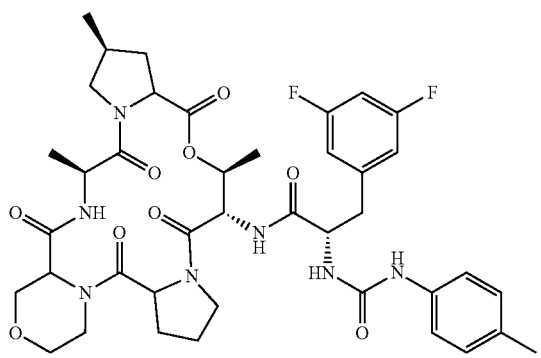 [SMILES: Cc1ccc(NC(=O)N[C@@H](Cc2cc(F)cc(F)c2)C(=O)N[C@@H]2C(=O)N3CCCC3C(=O)N3CCOCC3C(=O)N[C@@H](C)C(=O)N3C[C@@H](C)CC3C(=O)O[C@H]2C)cc1]

Compound 33 was synthesized from macrocycle C (80 mg, 0.112 mmol), p-tolyl isocyanate (17.92 mg, 0.135 mmol) and triethylamine (73.6 µL, 0.538 mmol) as a white solid (43.4 mg, 47.8%) following the general synthesis pathway described herein above; $^{1}$H NMR (400 MHz, Chloroform-d) δ 0.86 (d, J=6.8 Hz, 3H), 1.23 (d, J=6.6 Hz, 3H), 1.38 (d, J=6.6 Hz, 3H), 1.41-1.50 (m, 1H), 1.95-2.04 (m, 2H), 2.08-2.17 (m, 2H), 2.28 (s, 3H), 2.35-2.42 (m, 1H), 2.57-2.68 (m, 1H), 2.69-2.77 (m, 1H), 2.96-3.00 (m, 3H), 3.40-3.47 (m, 2H), 3.48-3.57 (m, 1H), 3.78-3.92 (m, 2H), 4.06 (dd, J=11.5, 8.2 Hz, 1H), 4.47-4.52 (m, 3H), 4.59 (d, J=13.9 Hz, 1H), 4.68 (dd, J=10.0, 1.5 Hz, 1H), 4.84 (d, J=11.3 Hz, 1H), 4.99-5.12 (m, 2H), 5.25 (dd, J=8.6, 2.2 Hz, 1H), 5.86 (d, J=7.9 Hz, 1H), 6.62-6.70 (m, 1H), 6.73-6.78 (m, 2H), 7.064-7.09 (m, 3H), 7.32 (d, J=8.4 Hz, 2H), 7.54 (s, 1H), 8.66 (d, J=9.6 Hz, 1H); ESI-MS: [m/z+H$^{+}$]=810.69.

t. PREPARATION OF (S)-3-(3,5-DIFLUOROPHENYL)-2-(3-(4-(TRIFLUOROMETHOXY)PHENYL)UREIDO)-N-((6AS,12S,13S,15AS,17S,21S,23AS)-13,17,21-TRIMETHYL-6,11,15,20,23-PENTAOXOOCTADECAHYDRO-6H,11H,15H-[1,4]OXAZINO[3,4-I]DIPYRROLO[2,1-C:2',1'-L][1]OXA[4,7,10,13]TETRAAZACYCLOHEXADECIN-12-YL)PROPANAMIDE (COMPOUND 34)

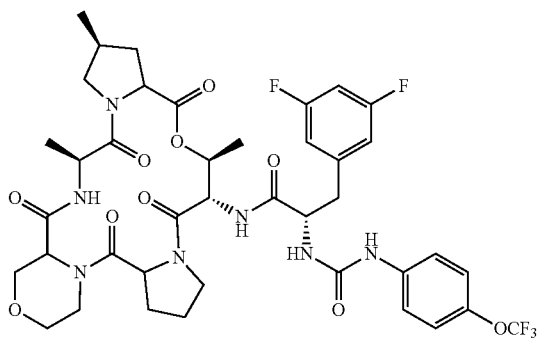 [SMILES: C[C@H]1CC2C(=O)O[C@@H](C)[C@H](NC(=O)[C@H](Cc3cc(F)cc(F)c3)NC(=O)Nc3ccc(OC(F)(F)F)cc3)C(=O)N3CCCC3C(=O)N3CCOCC3C(=O)N[C@@H](C)C(=O)N2C1]

Compound 34 was synthesized from macrocycle C (80 mg, 0.112 mmol), 1-isocyanato-4-(trifluoromethoxy)benzene (27.3 mg, 0.135 mmol) and triethylamine (73.6 μL, 0.538 mmol) as an off-white solid (43 mg, 43.6%) following the general synthesis pathway as described herein above; $^1$H NMR (400 MHz, Chloroform-d) δ 0.87 (d, J=6.7 Hz, 3H), 1.23 (d, J=6.6 Hz, 3H), 1.39 (d, J=6.6 Hz, 3H), 1.43-1.51 (m, 1H), 1.95-2.05 (m, 2H), 2.14-2.21 (m, 1H), 2.34-2.44 (m, 1H), 2.60-2.73 (m, 2H), 2.93-3.05 (m, 3H), 3.37-3.56 (m, 3H), 3.78-3.93 (m, 2H), 4.03 (dd, J=11.5, 8.2 Hz, 1H), 4.40-4.53 (m, 3H), 4.56-4.70 (m, 2H), 4.85 (d, J=11.3 Hz, 1H), 4.99-5.13 (m, 2H), 5.21-5.28 (m, 1H), 5.91 (d, J=7.8 Hz, 1H), 6.685-6.85 (m, 4H), 7.13 (d, J=8.7 Hz, 2H), 7.48 (d, J=9.0 Hz, 2H), 7.79 (s, 1H), 8.61 (d, J=9.6 Hz, 1H); ESI-MS: [m/z+H$^+$]=880.61.

u. PREPARATION OF (S)-3-(3,5-DIFLUOROPHE-NYL)-N-((2S,6S,9S,11AS,17S,18S,20AS)-9-((S)-1-HYDROXYETHYL)-2,6,10,18-TETRAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)-2-(3-(P-TOLYL)UREIDO)PROPANAMIDE (COMPOUND 35)

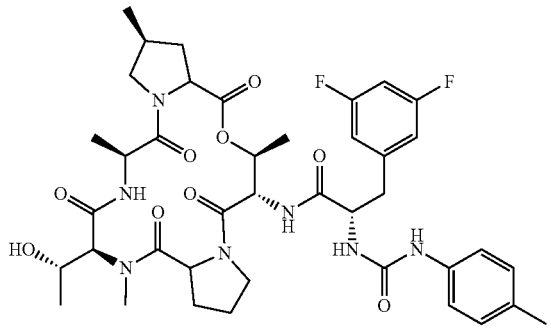 [SMILES: Cc1ccc(NC(=O)N[C@@H](Cc2cc(F)cc(F)c2)C(=O)N[C@@H]2C(=O)N3CCCC3C(=O)N(C)[C@@H]([C@H](C)O)C(=O)N[C@@H](C)C(=O)N3C[C@@H](C)CC3C(=O)O[C@H]2C)cc1]

Compound 35 was synthesized from macrocycle C (100 mg, 0.14 mmol), p-toluene isocyanate (22.3 mg, 0.168 mmol) and triethylamine (92 μL, 0.671 mmol) as an off-white solid (45.6 mg, 40.2%) following the general synthesis pathway described herein above; $^1$H NMR (400 MHz, Chloroform-d) δ 0.86 (d, J=6.7 Hz, 3H), 1.22 (d, J=6.6 Hz, 3H), 1.36 (d, J=6.6 Hz, 3H), 1.41 (d, J=5.9 Hz, 3H), 1.44-1.50 (m, 1H), 1.86-1.96 (m, 1H), 2.08-2.16 (m, 3H), 2.28 (s, 3H), 2.32-2.41 (m, 1H), 2.60-2.80 (m, 3H), 2.92-3.05 (m, 5H), 3.54-3.62 (m, 1H), 3.68-3.82 (m, 1H), 4.05-4.10 (m, 1H), 4.40-4.58 (m, 4H), 4.65 (dd, J=9.9, 1.8 Hz, 1H), 4.92-5.01 (m, 1H), 5.09-5.20 (m, 2H), 5.90 (d, J=7.9 Hz, 1H), 6.62-6.71 (m, 1H), 6.75-6.81 (m, 2H), 6.93 (d, J=9.9 Hz, 1H), 7.07 (d, J=8.2 Hz, 2H), 7.32 (d, J=8.4 Hz, 2H), 7.52 (s, 1H), 8.72 (d, J=9.6 Hz, 1H); ESI-MS: [m/z+H$^+$]=812.69.

v. PREPARATION OF (S)-3-(3,5-DIFLUOROPHE-NYL)-N-((2S,6S,9S,11AS,17S,18S,20AS)-9-((S)-1-HYDROXYETHYL)-2,6,10,18-TETRAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)-2-(3-(4-(TRIFLUOROMETHOXY)PHENYL)UREIDO)PROPANAMIDE (COMPOUND 36)

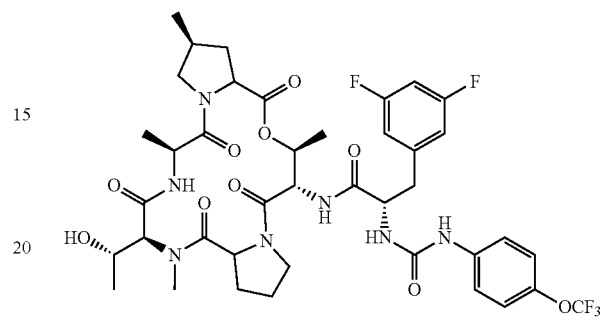

Compound 36 was synthesized from macrocycle C (100 mg, 0.14 mmol), 1-isocyanato-4-(trifluoromethoxy)benzene (34.1 mg, 0.168 mmol) and triethylamine (92 μL, 0.671 mmol) as a light yellow solid (47.8 mg, 38.8%) following the general synthesis pathway described herein above; $^1$H NMR (400 MHz, Chloroform-d) δ 0.87 (d, J=6.7 Hz, 3H), 1.23 (d, J=6.6 Hz, 3H), 1.35 (d, J=6.6 Hz, 3H), 1.41 (d, J=6.0 Hz, 3H), 1.45-1.53 (m, 1H), 1.82 (s, 3H), 1.87-1.95 (m, 1H), 2.09-2.24 (m, 1H), 2.32-2.43 (m, 1H), 2.60-2.73 (m, 2H), 2.78 (d, J=4.5 Hz, 1H), 2.97-3.00 (m, 5H), 3.56-3.65 (m, 1H), 3.70-3.80 (m, 1H), 4.05 (dd, J=11.5, 8.2 Hz, 1H), 4.43-4.55 (m, 4H), 4.66 (dd, J=9.8, 1.7 Hz, 1H), 4.93-5.03 (m, 1H), 5.09-5.21 (m, 2H), 5.94 (d, J=7.8 Hz, 1H), 6.63-6.71 (m, 1H), 6.75-6.80 (m, 2H), 6.97 (d, J=9.8 Hz, 1H), 7.13 (d, J=8.5 Hz, 2H), 7.47 (d, J=9.1 Hz, 2H), 7.82 (s, 1H), 8.69 (d, J=9.6 Hz, 1H); ESI-MS: [m/z+H$^+$]=882.70.

w. PREPARATION OF (S)-3-(3,5-DIFLUORO-PHENYL)-2-(3-(4-ETHYLPHENYL)UREIDO)-N-((2S,6S,9S,11AS,17S,18S,20AS)-9-((S)-1-HY-DROXYETHYL)-2,6,10,18-TETRAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)PROPANAMIDE (COMPOUND 37)

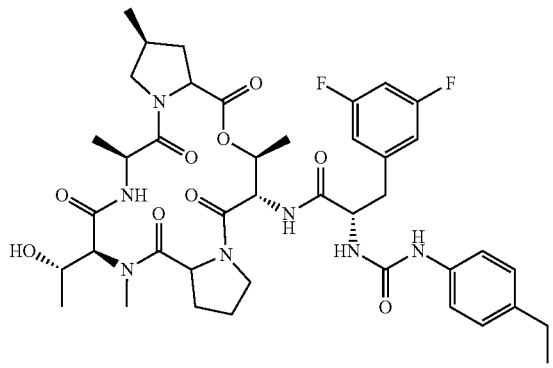 [SMILES: CCc1ccc(NC(=O)N[C@@H](Cc2cc(F)cc(F)c2)C(=O)N[C@@H]2C(=O)N3CCCC3C(=O)N(C)[C@@H]([C@H](C)O)C(=O)N[C@@H](C)C(=O)N3C[C@@H](C)CC3C(=O)O[C@H]2C)cc1]

Compound 37 was synthesized from macrocycle C (100 mg, 0.14 mmol), 1-ethyl-4-isocyanatobenzene (24.7 mg, 0.168 mmol) and triethylamine (92 µL, 0.671 mmol) as a light yellow solid (49.6 mg, 43%) following the general synthesis pathway described herein above; $^1$H NMR (400 MHz, Chloroform-d) δ 0.85 (d, J=6.7 Hz, 3H), 1.17-1.27 (m, 6H), 1.36 (d, J=6.6 Hz, 3H), 1.41 (d, J=5.9 Hz, 3H), 1.43-1.51 (m, 1H), 1.86-1.95 (m, 1H), 2.09-2.25 (m, 3H), 2.31-2.42 (m, 1H), 2.56-2.74 (m, 4H), 2.80 (d, J=4.5 Hz, 1H), 2.94-3.05 (m, 5H), 3.56-3.62 (m, 1H), 3.70-3.79 (m, 1H), 4.07 (dd, J=11.6, 8.1 Hz, 1H), 4.41-4.56 (m, 4H), 4.66 (dd, J=9.9, 1.8 Hz, 1H), 4.94-5.01 (m, 1H), 5.09-5.20 (m, 2H), 5.89 (d, J=7.9 Hz, 1H), 6.63-6.71 (m, 1H), 6.76-6.80 (m, 2H), 6.91 (d, J=9.8 Hz, 1H), 7.10 (d, J=8.5 Hz, 2H), 7.34 (d, J=8.5 Hz, 2H), 7.51 (s, 1H), 8.72 (d, J=9.6 Hz, 1H); ESI-MS: [m/z+H$^+$]=826.69.

x. PREPARATION OF (S)-3-(3,5-DIFLUOROPHENYL)-N-((2R,6S,9S,11AS,17S,18S,20AS)-9-((S)-1-HYDROXYETHYL)-2,6,10,18-TETRAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)-2-(3-(P-TOLYL)UREIDO)PROPANAMIDE (COMPOUND 38)

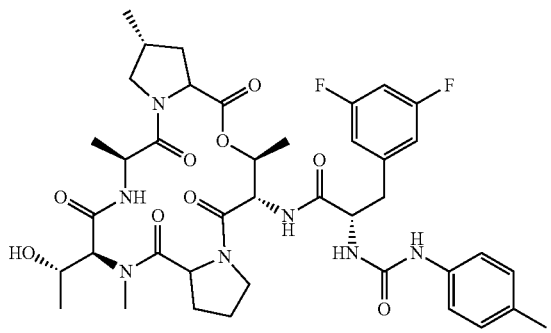 [SMILES: Cc1ccc(NC(=O)N[C@@H](Cc2cc(F)cc(F)c2)C(=O)N[C@@H]2C(=O)N3CCCC3C(=O)N(C)[C@@H]([C@H](C)O)C(=O)N[C@@H](C)C(=O)N3C[C@H](C)CC3C(=O)O[C@H]2C)cc1]

Compound 38 was synthesized from macrocycle C (80 mg, 0.112 mmol), p-tolyl isocyanate (16.89 mg, 0.134 mmol) and triethylamine (73.4 µL, 0.537 mmol) as a white solid (59.3 mg, 65.3%) following the general synthesis pathway described herein above; $^1$H NMR (400 MHz, Chloroform-d) δ 0.94 (d, J=6.5 Hz, 3H), 1.20 (d, J=6.6 Hz, 3H), 1.37 (d, J=6.6 Hz, 3H), 1.42 (d, J=5.7 Hz, 3H), 1.78-1.91 (m, 3H), 2.03-2.15 (m, 2H), 2.19-2.26 (m, 1H), 2.34-2.39 (m, 1H), 2.90-3.05 (m, 5H), 3.05-3.12 (m, 1H), 3.51-3.61 (m, 2H), 3.69-3.78 (m, 1H), 4.44-4.52 (m, 4H), 4.62 (d, J=11.1 Hz, 1H), 4.94-5.01 (m, 1H), 5.06-5.09 (m, 1H), 5.17-5.21 (m, 1H), 5.85 (d, J=7.7 Hz, 1H), 6.60-6.71 (m, 1H), 6.76 (d, J=6.0 Hz, 2H), 6.89 (d, J=9.8 Hz, 1H), 7.07 (d, J=8.3 Hz, 2H), 7.32 (d, J=8.4 Hz, 2H), 7.69 (s, 1H), 8.69 (d, J=9.6 Hz, 1H); ESI-MS: [m/z+H$^+$]=812.69.

y. PREPARATION OF (S)-3-(3,5-DIFLUOROPHENYL)-2-(3-(P-TOLYL)UREIDO)-N-((2R,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 39)

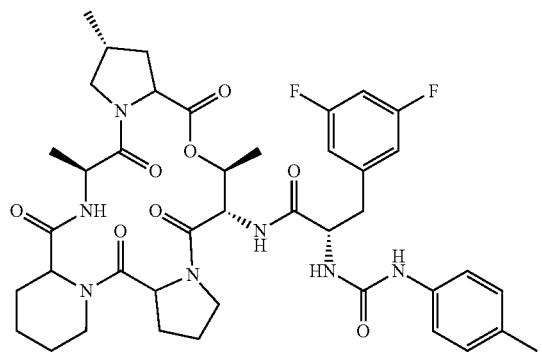 [SMILES: Cc1ccc(NC(=O)N[C@@H](Cc2cc(F)cc(F)c2)C(=O)N[C@@H]2C(=O)N3CCCC3C(=O)N3CCCCC3C(=O)N[C@@H](C)C(=O)N3C[C@H](C)CC3C(=O)O[C@H]2C)cc1]

Compound 39 was synthesized from macrocycle C (60 mg, 0.084 mmol), p-tolyl isocyanate (13.48 mg, 0.101 mmol) and triethylamine (55.4 µL, 0.405 mmol) as a white solid (35.6 mg, 52.2%) following the general synthesis pathway described herein above; $^1$H NMR (400 MHz, Chloroform-d) δ 0.94 (d, J=6.6 Hz, 3H), 1.19 (d, J=6.6 Hz, 3H), 1.36 (d, J=6.6 Hz, 3H), 1.43-1.51 (m, 2H), 1.74-1.86 (m, 2H), 1.93-2.02 (m, 2H), 2.06-2.13 (m, 2H), 2.29 (s, 3H), 2.30-2.42 (m, 2H), 2.54-2.65 (m, 1H), 2.70-2.74 (m, 1H), 2.89-3.03 (m, 2H), 3.07-3.12 (m, 1H), 3.47-3.56 (m, 2H), 3.75-3.86 (m, 1H), 4.38-4.51 (m, 2H), 4.66-4.72 (m, 3H), 4.95-5.05 (m, 1H), 5.12-5.22 (m, 2H), 5.83 (d, J=7.7 Hz, 1H), 6.56-6.80 (m, 4H), 7.08 (d, J=8.2 Hz, 2H), 7.33 (d, J=8.4 Hz, 2H), 7.70 (s, 1H), 8.56 (d, J=9.7 Hz, 1H); ESI-MS: [m/z+H$^+$]=808.69.

z. PREPARATION OF (S)-3-(3,5-DIFLUOROPHENYL)-2-(3-(4-(TRIFLUOROMETHOXY)PHENYL)UREIDO)-N-((2R,6S,8AS,14AS,20S,21S,23AS)-2,6,21-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 40)

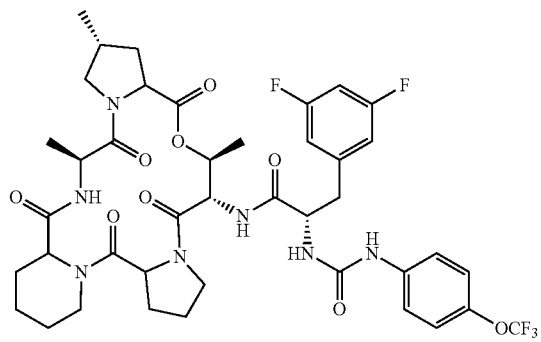 [SMILES: C[C@@H]1CC2C(=O)O[C@@H](C)[C@H](NC(=O)[C@H](Cc3cc(F)cc(F)c3)NC(=O)Nc3ccc(OC(F)(F)F)cc3)C(=O)N3CCCC3C(=O)N3CCCCC3C(=O)N[C@@H](C)C(=O)N2C1]

Compound 40 was synthesized from macrocycle C (70 mg, 0.098 mmol), 1-isocyanato-4-(trifluoromethoxy)benzene (19.99 mg, 0.098 mmol) and triethylamine (64.6 µL, 0.472 mmol) as a white solid (59 mg, 68.3%) following the general synthesis pathway described herein above; $^1$H NMR (400 MHz, Chloroform-d) δ 0.95 (d, J=6.6 Hz, 3H), 1.20 (d, J=6.6 Hz, 3H), 1.34 (d, J=6.6 Hz, 3H), 1.43-1.51 (m, 2H), 1.75-1.87 (m, 2H), 1.93-2.04 (m, 2H), 2.05-2.17 (m, 2H), 2.29-2.42 (m, 2H), 2.53-2.65 (m, 1H), 2.70-2.75 (m, 1H), 2.91-3.02 (m, 2H), 3.04-3.09 (m, 1H), 3.45-3.59 (m, 2H), 3.77-3.87 (m, 1H), 4.47-4.52 (m, 2H), 4.64-4.75 (m, 3H), 4.95-5.07 (m, 1H), 5.13-5.25 (m, 2H), 5.86 (d, J=7.7 Hz, 1H), 6.63-6.77 (m, 3H), 6.84 (d, J=9.7 Hz, 1H), 7.13 (d, J=8.7 Hz, 2H), 7.47 (d, J=9.0 Hz, 2H), 8.01 (s, 1H), 8.53 (d, J=9.7 Hz, 1H); ESI-MS: [m/z+H$^+$]=878.69.

aa. PREPARATION OF (S)-3-(3,5-DIFLUOROPHENYL)-N-((2R,6S,9S,11AS,17S,18S,20AS)-9-((S)-1-HYDROXYETHYL)-2,6,10,18-TETRAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)-2-(3-(4-(TRIFLUOROMETHOXY)PHENYL)UREIDO)PROPANAMIDE (COMPOUND 41)

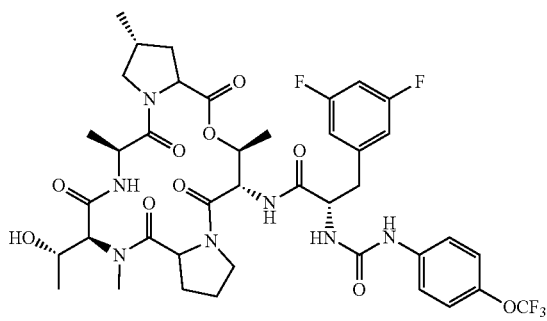 [SMILES: C[C@@H]1CC2C(=O)O[C@@H](C)[C@H](NC(=O)[C@H](Cc3cc(F)cc(F)c3)NC(=O)Nc3ccc(OC(F)(F)F)cc3)C(=O)N3CCCC3C(=O)N(C)[C@@H]([C@H](C)O)C(=O)N[C@@H](C)C(=O)N2C1]

Compound 41 was synthesized from macrocycle C (80 mg, 0.112 mmol), 1-isocyanato-4-(trifluoromethoxy)benzene (22.72 mg, 0.112 mmol) and triethylamine (73.4 µL, 0.537 mmol) as a white solid (67.4 mg, 68.3%) following the general synthesis pathway described herein above; $^1$H NMR (400 MHz, Chloroform-d) δ 0.94 (d, J=6.5 Hz, 3H), 1.20 (d, J=6.6 Hz, 3H), 1.35 (d, J=6.6 Hz, 3H), 1.42 (d, J=5.9 Hz, 3H), 1.79-1.96 (m, 2H), 2.09-2.15 (m, 2H), 2.19-2.44 (m, 3H), 2.74 (d, J=4.5 Hz, 1H), 2.93-3.01 (m, 5H), 3.04-3.09 (m, 1H), 3.47-3.53 (m, 1H), 3.57-3.66 (m, 1H), 3.70-3.79 (m, 1H), 4.43-4.56 (m, 4H), 4.60-4.67 (m, 1H), 4.93-5.04 (m, 1H), 5.097-5.10 (m, 1H), 5.16-5.25 (m, 1H), 5.88 (d, J=7.8 Hz, 1H), 6.63-6.81 (m, 3H), 6.92 (d, J=9.7 Hz, 1H), 7.13 (d, J=8.4 Hz, 2H), 7.47 (d, J=9.1 Hz, 2H), 7.99 (s, 1H), 8.65 (d, J=9.6 Hz, 1H); ESI-MS: [m/z+H$^+$]=882.70.

bb. PREPARATION OF (S)-3-(3,5-DIFLUOROPHENYL)-2-(3-(4-ETHYLPHENYL)UREIDO)-N-((2R,6S,9S,11AS,17S,18S,20AS)-9-((S)-1-HYDROXYETHYL)-2,6,10,18-TETRAMETHYL-5,8,11,16,20-PENTAOXOHEXADECAHYDRO-1H,5H,16H-DIPYRROLO[2,1-C:2',1'-L][1]OXA[4,7,10,13]TETRAAZACYCLOHEXADECIN-17-YL)PROPANAMIDE (COMPOUND 42)

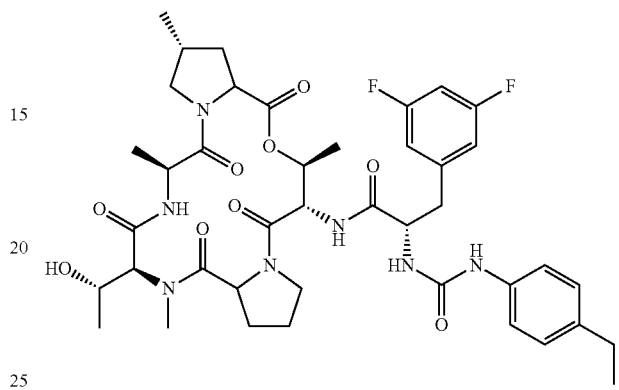

Compound 42 was synthesized from macrocycle C (80 mg, 0.112 mmol), 1-ethyl-4-isocyanatobenzene (16.46 mg, 0.112 mmol) and triethylamine (73.4 µL, 0.537 mmol) as a white solid (60.1 mg, 65.1%) following the general synthesis pathway described herein above; $^1$H NMR (400 MHz, Chloroform-d) δ 0.93 (d, J=6.6 Hz, 3H), 1.18-1.22 (m, 6H), 1.35 (d, J=6.6 Hz, 3H), 1.41 (d, J=5.9 Hz, 3H), 1.77-1.96 (m, 4H), 2.07-2.14 (m, 2H), 2.19-2.43 (m, 3H), 2.58 (q, J=7.6 Hz, 2H), 2.93-3.00 (m, 5H), 3.06-3.11 (m, 1H), 3.49-3.66 (m, 2H), 3.70-3.79 (m, 1H), 4.43-4.58 (m, 4H), 4.64 (d, J=11.5 Hz, 1H), 4.93-5.03 (m, 1H), 5.05-5.13 (m, 1H), 5.17-5.25 (m, 1H), 5.84 (d, J=7.9 Hz, 1H), 6.62-6.82 (m, 3H), 6.95 (d, J=9.7 Hz, 1H), 7.10 (d, J=8.5 Hz, 2H), 7.34 (d, J=8.5 Hz, 2H), 7.70 (s, 1H), 8.69 (d, J=9.6 Hz, 1H); ESI-MS: [m/z+H$^+$]=826.77.

cc. PREPARATION OF (S)—N-((2S,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-3-PHENYL-2-(3-(P-TOLYL)UREIDO)PROPANAMIDE (COMPOUND 43)

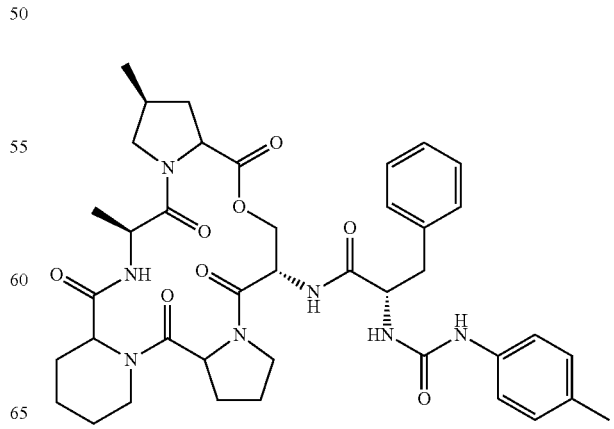

Compound 43 was synthesized from macrocycle C (100 mg, 0.151 mmol), p-tolyl isocyanate (20.14 mg, 0.151 mmol) and triethylamine (83 µL, 0.605 mmol) as a white solid (50 mg, 43.6%) following the general synthesis pathway described herein above; $^1$H NMR (400 MHz, Chloroform-d) δ 0.89 (d, J=6.7 Hz, 3H), 1.38 (d, J=6.5 Hz, 4H), 1.44-1.52 (m, 3H), 1.95-2.02 (m, 2H), 2.07-2.22 (m, 2H), 2.28 (s, 3H), 2.32-2.43 (m, 1H), 2.56-2.68 (m, 2H), 2.71-2.82 (m, 2H), 2.90-3.06 (m, 2H), 3.51-3.62 (m, 2H), 3.69-3.81 (m, 1H), 4.10 (dd, J=11.5, 7.9 Hz, 1H), 4.40-4.51 (m, 2H), 4.58 (t, J=9.2 Hz, 1H), 4.65-4.80 (m, 3H), 4.96-5.07 (m, 1H), 5.12-5.19 (m, 1H), 5.85 (d, J=7.9 Hz, 1H), 6.94 (d, J=9.6 Hz, 1H), 7.07 (d, J=8.4 Hz, 2H), 7.13-7.24 (m, 3H), 7.28-7.35 (m, 4H), 7.63 (s, 1H), 8.72 (d, J=9.5 Hz, 1H); ESI-MS: [m/z+H$^+$]=758.68.

dd. PREPARATION OF (S)—N-((2S,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-3-PHENYL-2-(3-(4-(TRIFLUOROMETHOXY)PHENYL)UREIDO)PROPANAMIDE (COMPOUND 44)

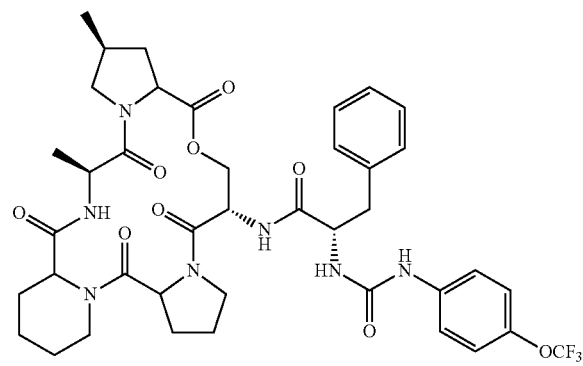 [SMILES: C[C@H]1CC2C(=O)OC[C@H](NC(=O)[C@H](Cc3ccccc3)NC(=O)Nc3ccc(OC(F)(F)F)cc3)C(=O)N3CCCC3C(=O)N3CCCCC3C(=O)N[C@@H](C)C(=O)N2C1]

Compound 44 was synthesized from macrocycle C (100 mg, 0.151 mmol), 1-isocyanato-4-(trifluoromethoxy)benzene (29.2 mg, 0.144 mmol) and triethylamine (83 µL, 0.605 mmol) as a white solid (50 mg, 39.9%) following the general synthesis pathway described herein above; $^1$H NMR (400 MHz, Chloroform-d) δ 0.90 (d, J=6.7 Hz, 3H), 1.38 (d, J=6.5 Hz, 4H), 1.45-1.54 (m, 3H), 1.93-2.04 (m, 2H), 2.09-2.23 (m, 2H), 2.30-2.43 (m, 1H), 2.56-2.68 (m, 2H), 2.71-2.80 (m, 2H), 2.87-3.07 (m, 2H), 3.50-3.62 (m, 2H), 3.73-3.79 (m, 1H), 4.06 (dd, J=11.5, 7.9 Hz, 1H), 4.36-4.45 (m, 1H), 4.49 (dd, J=9.5, 4.8 Hz, 1H), 4.58 (t, J=9.3 Hz, 1H), 4.66-4.82 (m, 3H), 4.97-5.08 (m, 1H), 5.12-5.20 (m, 1H), 5.90 (d, J=7.8 Hz, 1H), 6.81 (d, J=9.6 Hz, 1H), 7.09-7.24 (m, 5H), 7.28-7.32 (m, 2H), 7.49 (d, J=9.0 Hz, 2H), 7.88 (s, 1H), 8.69 (d, J=9.6 Hz, 1H); ESI-MS: [m/z+H$^+$]=828.69.

ee. PREPARATION OF (S)-3-(3,5-DIFLUOROPHENYL)-N-((2S,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-P-TOLYL)UREIDO)PROPANAMIDE (COMPOUND 45)

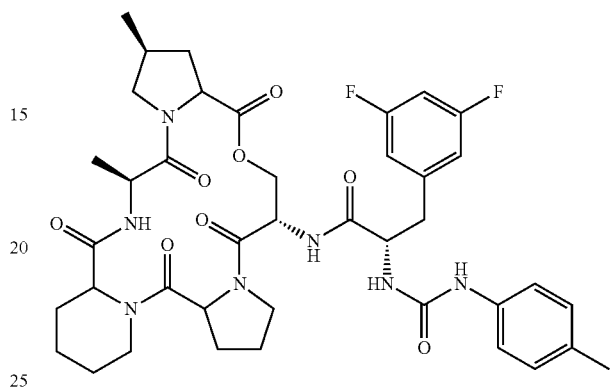

Compound 45 was synthesized from macrocycle C (100 mg, 0.143 mmol), p-tolyl isocyanate (19.1 mg, 0.143 mmol) and triethylamine (78 µL, 0.574 mmol) as a white solid (30 mg, 26.3%) following the general synthesis pathway described herein above; $^1$H NMR (400 MHz, Chloroform-d) δ 0.91 (d, J=6.7 Hz, 3H), 1.34 (d, J=6.6 Hz, 4H), 1.43-1.55 (m, 3H), 1.92-2.03 (m, 2H), 2.08-2.22 (m, 2H), 2.29 (s, 3H), 2.33-2.43 (m, 1H), 2.56-2.85 (m, 4H), 2.87-3.02 (m, 2H), 3.52-3.64 (m, 2H), 3.74-3.85 (m, 1H), 4.10 (dd, J=11.5, 7.9 Hz, 1H), 4.42-4.52 (m, 2H), 4.57 (t, J=9.8 Hz, 1H), 4.66-4.82 (m, 3H), 4.95-5.06 (m, 1H), 5.12-5.19 (m, 1H), 5.84 (d, J=7.7 Hz, 1H), 6.60-6.81 (m, 3H), 7.02-7.09 (m, 3H), 7.33 (d, J=8.4 Hz, 2H), 7.61 (s, 1H), 8.61 (d, J=9.6 Hz, 1H); ESI-MS: [m/z+H$^+$]=794.69.

ff. PREPARATION OF (S)-2-(3-(BENZO[D][1,3]DIOXOL-5-YL)UREIDO)-3-(3,5-DIFLUOROPHENYL)-N-((2S,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 46)

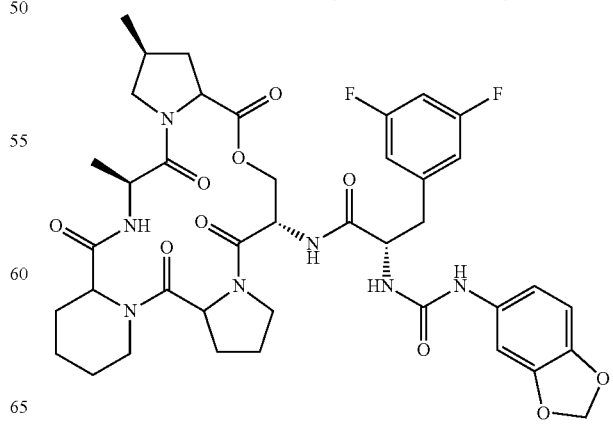

Compound 46 was synthesized from macrocycle C (100 mg, 0.143 mmol), 5-isocyanatobenzo[d][1,3]dioxole (23.4 mg, 0.143 mmol) and triethylamine (78 µL, 0.574 mmol) as a white solid (30 mg, 25.4%) following the general synthesis pathway described herein above; $^1$H NMR (400 MHz, Chloroform-d) δ 0.95 (d, J=6.7 Hz, 3H), 1.34 (d, J=6.5 Hz, 3H), 1.44-1.57 (m, 3H), 1.93-2.04 (m, 2H), 2.11-2.21 (M, 3H), 2.31-2.43 (m, 1H), 2.56-2.66 (m, 2H), 2.71-2.72 (M, 1H), 2.77-2.85 (m, 1H), 2.88-3.03 (m, 2H), 3.51-3.64 (m, 2H), 3.73-3.84 (m, 1H), 4.04-4.15 (m, 1H), 4.42-4.62 (m, 3H), 4.69-4.80 (M, 3H), 4.95-5.05 (m, 1H), 5.11-5.21 (m, 1H), 5.81 (d, J=7.7 Hz, 1H), 5.91 (s, 2H), 6.61-6.80 (m, 6H), 7.12 (d, J=9.6 Hz, 1H), 7.18 (s, 1H), 7.61 (s, 1H), 8.60 (d, J=9.5 Hz, 1H); ESI-MS: [m/z+H$^+$]=824.69.

gg. PREPARATION OF (S)-3-(3,5-DIFLUORO-PHENYL)-2-(3-(P-TOLYL)UREIDO)-N-((6AS,12S, 13S,15AS,17R,21S,23AS)-13,17,21-TRIMETHYL-6,11,15,20,23-PENTAOXOOCTADECAHYDRO-6H,11H,15H-[1,4]OXAZINO[3,4-I]DIPYRROLO[2,1-C:2',1'-L][1]OXA[4,7,10,13]TETRAAZACYCLOHEXADECIN-12-YL)PROPANAMIDE (COMPOUND 47)

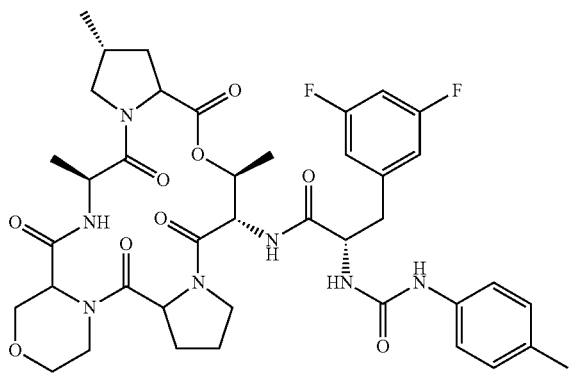 [SMILES: Cc1ccc(NC(=O)N[C@@H](Cc2cc(F)cc(F)c2)C(=O)N[C@@H]2C(=O)N3CCCC3C(=O)N3CCOCC3C(=O)N[C@@H](C)C(=O)N3C[C@H](C)CC3C(=O)O[C@H]2C)cc1]

Compound 47 was synthesized from macrocycle C (60 mg, 0.084 mmol), p-tolyl isocyanate (11.2 mg, 0.084 mmol) and triethylamine (55.2 µL, 0.404 mmol) as a white solid (36 mg, 52.8%) following the general synthesis pathway described herein; $^1$H NMR (400 MHz, Chloroform-d) δ 0.95 (d, J=6.6 Hz, 3H), 1.20 (d, J=6.6 Hz, 3H), 1.40 (d, J=6.5 Hz, 3H), 1.75-1.86 (m, 1H), 1.95-2.05 (m, 2H), 2.29 (s, 3H), 2.31-2.47 (m, 3H), 2.87-3.15 (m, 5H), 3.37-3.59 (m, 4H), 3.78-3.94 (m, 2H), 4.43-4.70 (m, 5H), 4.85 (d, J=11.3 Hz, 1H), 5.00-5.16 (m, 2H), 5.18-5.25 (m, 1H), 5.82 (d, J=7.7 Hz, 1H), 6.64-6.74 (m, 3H), 7.07 (d, J=8.3 Hz, 2H), 7.33 (d, J=8.3 Hz, 2H), 7.71 (d, J=9.9 Hz, 1H), 7.78 (s, 1H), 8.66 (d, J=9.6 Hz, 1H); ESI-MS: [m/z+H$^+$]=810.69.

hh. PREPARATION OF (S)-3-(3,5-DIFLUORO-PHENYL)-N-((2S,6S,8AS,14AS,20S,23AS)-2,6-DIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(3,4-DIMETHYLPHENYL)UREIDO)PROPANAMIDE (COMPOUND 48)

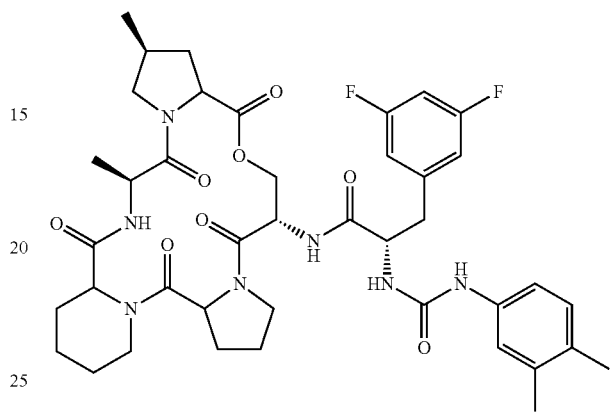

Compound 48 was synthesized from macrocycle C (100 mg, 0.143 mmol), 4-isocyanato-1,2-dimethylbenzene (21.1 mg, 0.143 mmol) and triethylamine (78 µL, 0.574 mmol) as a white solid (47.6 mg, 41.1%) following the general synthesis pathway described herein; $^1$H NMR (400 MHz, Chloroform-d) δ 0.92 (d, J=6.7 Hz, 3H), 1.36 (d, J=6.5 Hz, 3H), 1.44-1.55 (m, 3H), 1.92-2.03 (m, 2H), 2.09-2.19 (m, 2H), 2.20 (s, 4H), 2.23 (s, 3H), 2.32-2.43 (m, 1H), 2.57-2.68 (m, 2H), 2.68-2.85 (m, 2H), 2.87-3.05 (m, 2H), 3.50-3.62 (m, 2H), 3.76-3.82 (m, 1H), 4.11 (dd, J=11.4, 7.9 Hz, 1H), 4.37-4.45 (m, 1H), 4.47-4.61 (m, 2H), 4.67-4.81 (m, 3H), 4.97-5.04 (m, 1H), 5.12-5.19 (m, 1H), 5.86 (d, J=7.5 Hz, 1H), 6.60-6.72 (m, 1H), 6.74-6.82 (m, 3H), 7.01-7.16 (m, 2H), 7.52 (s, 1H), 8.60 (d, J=9.5 Hz, 1H); ESI-MS: [m/z+H$^+$]=808.69.

ii. PREPARATION OF (S)-3-(3,5-DIFLUORO-PHENYL)-2-(3-(P-TOLYL)UREIDO)-N-((6S,8AS, 14AS,20S,23AS)-2,2,6-TRIMETHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)PROPANAMIDE (COMPOUND 49)

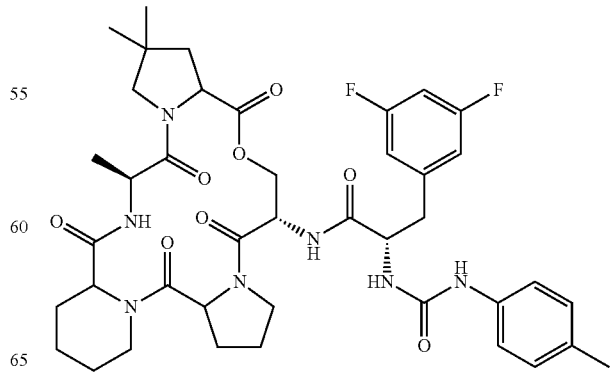

Compound 49 was synthesized from macrocycle C (70 mg, 0.098 mmol), p-tolyl isocyanate (13.11 mg, 0.098 mmol) and triethylamine (64.6 μL, 0.472 mmol) as a white solid (27.6 mg, 34.7%) following the general synthesis pathway described herein above; $^1$H NMR (400 MHz, Chloroform-d) δ 0.93 (s, 3H), 0.96 (s, 3H), 1.36 (d, J=6.5 Hz, 3H), 1.43-1.51 (m, 2H), 1.67-1.75 (m, 2H), 1.92-2.04 (m, 2H), 2.10-2.22 (m, 2H), 2.29 (s, 3H), 2.34-2.39 (m, 1H), 2.58-2.63 (m, 1H), 2.70-2.72 (m, 1H), 2.88-3.02 (m, 3H), 3.52-3.63 (m, 2H), 3.70 (d, J=11.3 Hz, 1H), 3.75-3.81 (m, 1H), 4.43-4.61 (m, 3H), 4.65-4.81 (m, 3H), 5.00-5.07 (m, 1H), 5.13-5.15 (m, 1H), 5.81 (d, J=7.7 Hz, 1H), 6.62-6.80 (m, 3H), 7.08 (d, J=8.2 Hz, 2H), 7.32 (d, J=8.2 Hz, 2H), 7.58 (s, 1H), 8.61 (d, J=9.5 Hz, 1H); ESI-MS: [m/z+H$^+$]=808.69.

jj. PREPARATION OF (S)-3-(3,5-DIFLUORO-PHENYL)-N-((2S,6S,8AS,14AS,20S,23AS)-2-FLUORO-6-METHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(P-TOLYL)UREIDO)PROPANAMIDE (COMPOUND 50)

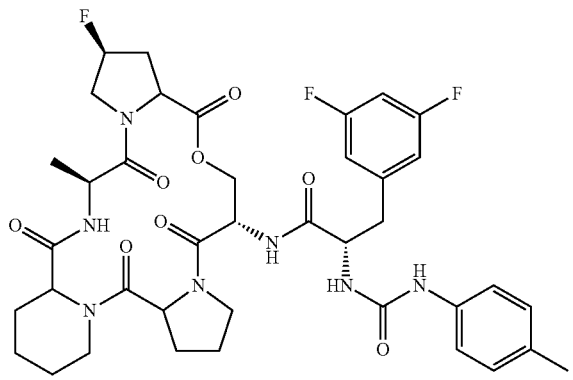 [SMILES: Cc1ccc(NC(=O)N[C@@H](Cc2cc(F)cc(F)c2)C(=O)N[C@H]2COC(=O)C3C[C@H](F)CN3C(=O)[C@H](C)NC(=O)C3CCCCN3C(=O)C3CCCN3C2=O)cc1]

Compound 50 was synthesized from macrocycle C (120 mg, 0.175 mmol), p-tolyl isocyanate (23.26 mg, 0.175 mmol) and triethylamine (96 μL, 0.699 mmol) as a white solid (35.1 mg, 25.2%) following the general synthesis pathway described herein above; $^1$H NMR (400 MHz, Chloroform-d) δ 1.35 (d, J=6.6 Hz, 3H), 1.43-1.51 (m, 3H), 1.60-1.68 (m, 2H), 1.95-2.03 (m, 2H), 2.11-2.23 (m, 2H), 2.29 (s, 3H), 2.34-2.41 (m, 2H), 2.55-2.63 (m, 1H), 2.79-2.71 (m 1H), 2.92-2.99 (m, 2H), 3.51-3.65 (m, 3H), 3.71-3.83 (m, 1H), 3.95-4.11 (m, 1H), 4.50-4.57 (m, 2H), 4.59-4.76 (m, 3H), 4.89 (d, J=11.6 Hz, 1H), 4.97-5.21 (m, 3H), 5.71 (d, J=7.8 Hz, 1H), 6.61-6.79 (m, 3H), 7.09 (d, J=8.2 Hz, 2H), 7.15 (d, J=9.5 Hz, 1H), 7.33 (d, J=8.4 Hz, 2H), 7.65 (s, 1H), 8.65 (d, J=9.7 Hz, 1H); ESI-MS: [m/z+H$^+$]=798.69.

kk. PREPARATION OF (S)-3-(3,5-DIFLUORO-PHENYL)-N-((2R,6S,8AS,14AS,20S,23AS)-2-FLUORO-6-METHYL-5,8,14,19,23-PENTAOXOOCTADECAHYDRO-1H,5H,14H,19H-PYRIDO[2,1-I]DIPYRROLO[2,1-C:2',1'-L][1]OXA[4,7,10,13]TETRAAZACYCLOHEXADECIN-20-YL)-2-(3-(P-TOLYL)UREIDO)PROPANAMIDE (COMPOUND 51)

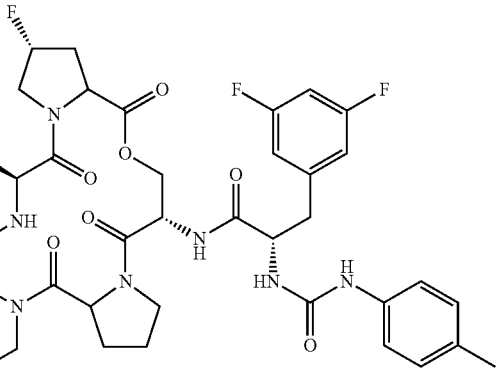

Compound 51 was synthesized from macrocycle C (98 mg, 0.147 mmol), p-tolyl isocyanate (20.61 mg, 0.155 mmol) and triethylamine (81 μL, 0.590 mmol) as a white solid (21 mg, 17.9%) following the general synthesis pathway described herein above; $^1$H NMR (400 MHz, Chloroform-d) δ 1.37 (d, J=6.5 Hz, 3H), 1.46-1.50 (m, 2H), 1.65-1.69 (m, 2H), 1.93-2.04 (m, 2H), 2.10-2.20 (m, 2H), 2.26-2.33 (m, 4H), 2.34-2.43 (m, 1H), 2.55-2.76 (m, 3H), 2.87-3.01 (m, 2H), 3.39-3.61 (m, 3H), 3.74-3.82 (m, 1H), 4.07-4.16 (m, 1H), 4.45-4.60 (m, 2H), 4.66-4.77 (m, 4H), 5.03-5.22 (m, 3H), 5.74 (d, J=7.7 Hz, 1H), 6.64-6.77 (m, 3H), 7.06-7.13 (m, 3H), 7.33 (d, J=8.4 Hz, 2H), 7.59 (s, 1H), 8.55 (d, J=9.5 Hz, 1H); ESI-MS: [m/z+H$^+$]=798.61.

5. ADEP REFERENCE COMPOUNDS

Activity of the disclosed compounds was compared to several reference compounds. These compounds are shown below and are commercially available or prepared per methods described in the literature.

ADEP4

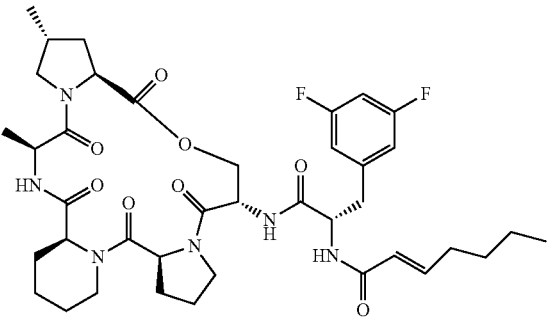

ADEP 2719

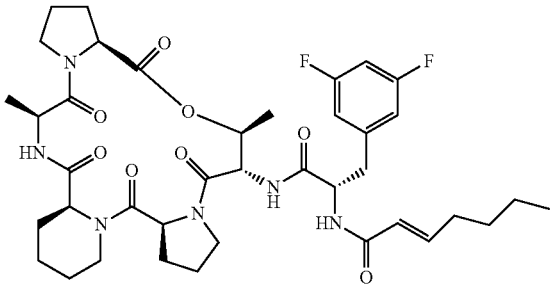

-continued

ADEP 2914

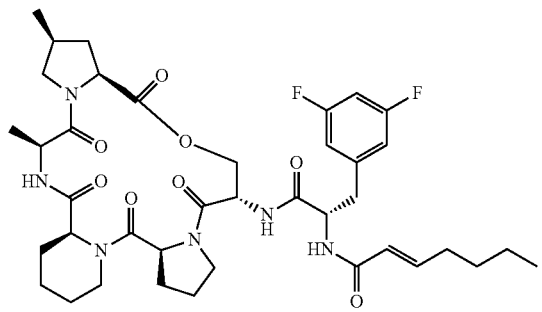

ADEP 2378

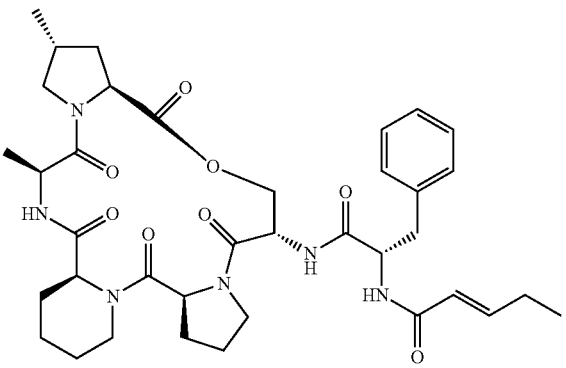

ADEP 2591

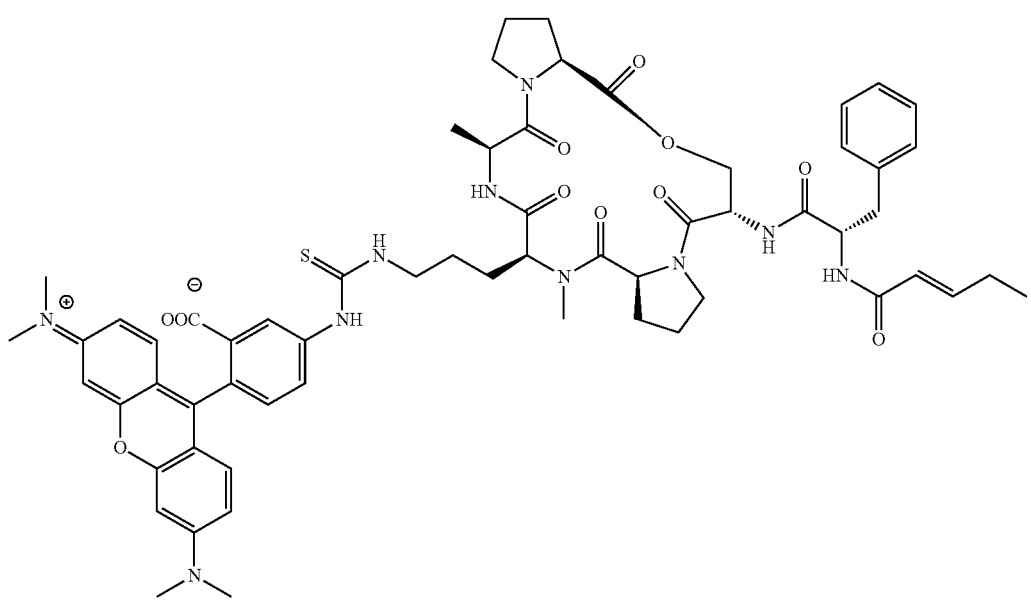

The compounds above (ADEP4, ADEP 2719, ADEP 2914, and ADEP 2378) were prepared as follows: ADEP4, "Synthesis of antibacterial macrocyclic oligopeptides for use in treatment of diseases in humans or animals" Hinzen, Berthold; Brotz, Heike; Endermann, Rainer; Henninger, Kerstin; Paulsen, Holger; Raddatz, Siegfried; Lampe, Thomas; Hellwig, Veronika; Schumacher, Andreas, PCT Int. Appl. (2003), WO 2003024996 A2 20030327; ADEP 2719, "Restriction of the Conformational Dynamics of the Cyclic Acyldepsipeptide Antibiotics Improves Their Antibacterial Activity", Daniel W. Carney, Karl R. Schmitz, Jonathan V. Truong, Robert T. Sauer, and Jason K. Sello, J. Am. Chem. Soc., 2014, 136 (5), 1922-1929; and ADEP 2914 and ADEP 2378, "Synthesis of antibacterial macrocyclic oligopeptides for use in treatment of diseases in humans or animals" Hinzen, Berthold; Brotz, Heike; Endermann, Rainer; Henninger, Kerstin; Paulsen, Holger; Raddatz, Siegfried; Lampe, Thomas; Hellwig, Veronika; Schumacher, Andreas, PCT Int. Appl. (2003), WO 2003024996 A2 20030327.

6. CASEIN-BODIPY ASSAY

The compounds were assayed in a casein digestion assay in order to determine their effect on C1pP activation. Briefly, the assay was carried out using *S. aureus* C1pP ("Sa-C1pP") overexpressed in *E. coli* BL21(DE3) and purified in a two-step process. Purity of the protein was assessed through SDS PAGE analysis. $EC_{50}$ evaluations were conducted in triplicate in a 20 µl assay format using a method adapted from Maurizi et al. (Methods Enzymol. (1994) 244:314-331.). Each well contained 10 µM saC1pP, 25 µg/ml BODIPY FL casein (Invitrogen Corporation, San Diego, Calif.), and test compound in concentrations ranging between 0-1000 µM in assay buffer (50 mM Tris pH 8, 200 mM KCl, and 1 mM TCEP). The reaction took place at 37° C. Fluorescence (excitation 485 nm; emission 528 nm) was measured in five minute intervals over a 45 min period using a BioTek HT fluorescence microplate reader (BioTek Instruments, Inc., Winooski, Vt.). Velocity of each reaction was calculated and data was fit to a dose response curve using GraphPad Prism® software (GraphPad Software, Inc., La Jolla, Calif.). $EC_{50}$ is the effective concentration of compound which causes 50% activation of *S. aureus* C1pP in the foregoing BODIPY FL casein assay.

Alternatively, the assay was carried out using EnzCheck Protease Assay (Molecular Probes, Catalog #E6638). The assay was performed in black 384 well, flat bottom, low volume plates (Greiner Bio-One, Monroe, N.C., catalog #784076). 10 µL of Tris.HCl buffer, pH 8.0 with 0.01% Triton X-100 was pipetted into each well using a Well-Mate (Thermo Scientific, Waltham, Mass.). 0.4 µL test compounds or controls (2% DMSO v/v) were added to each well using a Biomek FX liquid handling robot (Beckman Coulter, Indianapolis Ind.). After addition of test compounds and controls, 10 µL of master mix containing 2 µM Sa-C1pP and 2 µM substrate (Bodipy-FL labeled casein) in Tris.HCl buffer, pH 8.0 with 0.01% (v/v) Triton X-100, was pipetted into each well. All assays were performed in triplicate, under linear velocity conditions. Increase in fluorescent signal following activation of Sa-C1pP by test compounds and controls was measured over time period of 30 mins using filters with excitation at 485±15 nm and emission at 520±25 nm on a PHERAstar FS Multilabel reader (BMG, Cary, N.C.). Instrument gains and enzyme linear velocity conditions were determined and validated using ADEP4, a known Sa-C1pP activator. Data analysis was done by measuring rate of casein degradation over time (slopes). Computed degradation rates (slopes) were normalized to positive (ADEP4) or negative (DMSO) controls. Using nonlinear regression curve fitting $EC_{50}$ values and % activation were determined using the equation "log [agonist] vs. Response-variable slope (four parameters)-symmetrical" in the program Prism 6 (GraphPad Software, La Jolla, Calif. USA, www.graphpad.com).

7. ADEP DISPLACEMENT FLUORESCENCE POLARIZATION ASSAY

A fluorescence polarization (FP) assay was used to determine the activity of the disclosed compounds in displacing an ADEP analogue from C1pP. Briefly, the assay was performed in black 384 well, flat bottom, low volume plates (Greiner Bio-One, Monroe, N.C., catalog #784076). 20 µL of a pre-equilibrated (1 hr, room temperature) master mix (15 µM Sa-C1pP, 2% DMSO (v/v) and 50 nM FP probe in Tris.HCl, pH 8.0)) was pipetted into each well using a Well-Mate (Thermo Scientific, Waltham, Mass.). Sa-C1pP was prepared as described above for the C1pP activation assay. The FP probe was ADEP 2591 (structure shown above). The ADEP 2591 comprises a TAMRA fluorophore linked to a core based on modified ADEP 2378 via a short alkyl linker. Using pin transfer, approximately 0.4 µL (2% v/v DMSO) of each compound or control was added per well. After addition of compounds and controls, plates were allowed to incubate for an additional 120 minutes at room temperature. All assays were performed in triplicate. Polarization was monitored using an EnVision Multilabel reader (Perkin-Elmer, Waltham, Mass.) by exciting the FP probe at 530±25 nm, and monitoring fluorescence intensity of both parallel and perpendicular polarized light at 579±25 nm. Readout was in millipolarization units (mP).

Signal gain and G factors were determined in wells containing 200 µM ADEP 2378, which had been previously verified (data not shown) as containing completely unbound ADEP 2591. Data collected was normalized to values obtained from positive (200 µM ADEP 2378) or negative (DMSO) controls. Curves were fit with non-linear regression using the equation "log [inhibitor] vs. Response-variable slope (four parameters)-symmetrical" in the program Prism 6 (GraphPad Software, La Jolla, Calif. USA, www.graphpad.com). The structures for ADEP 2378 and ADEP 2591 are shown above. ADEP 2378 is (E)-N—((S)-1-(((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-l][1]oxa[4,7,10,13]tetraazacyclohexadecin-20-yl)amino)-1-oxo-3-phenylpropan-2-yl)pent-2-enamide. ADEP 2591 is 5-(3-(3-((6S,9S,11aS,17S,20aS)-6,10-dimethyl-5,8,11,16,20-pentaoxo-17-((S)-2-((E)-pent-2-enamido)-3-phenylpropanamido)hexadecahydro-1H,5H,16H-dipyrrolo[2,1-c:2',1'-l][1]oxa[4,7,10,13]tetraazacyclohexadecin-9-yl)propyl)thioureido)-2-(6-(dimethylamino)-3-(dimethyliminio)-3H-xanthen-9-yl)benzoate.

8. CYTOTOXICITY ASSAY

Cytotoxicity was determined by determining the effect of compounds on cell viability. Vero (kidney epithelial cells; ATCC CCL-81) monolayers were trypsinized and 5000 cells/well were seeded (10-15% confluency) into white-wall, flat bottom 96 well microwell plates (Corning) using enriched Dulbecco's Modified Eagle's Medium (Hyclone: DMEM/High Glucose) containing 10% Fetal Bovine Serum (ATCC-30-2020). Plates were incubated overnight at 37° C. in the presence of 5% CO2. Drug-free media was then replaced with media containing serial dilutions of test compound or DMSO carrier. After an additional 72 hours of incubation, viability was indirectly measured using the CellTiter-Glo® Luminescent Cell Viability (Promega) assay. Assay plates were read at peak emission wavelength of 560 nm using a EnVision® Multilabel Plate Reader (Perkin Elmer) or PHERAstar FS Multilabel reader (BMG, Cary, N.C.). The concentration of test compounds that inhibited growth by 50% ($IC_{50}$ value) was computed using nonlinear regression based fitting of inhibition curves using log [inhibitor] vs. response-variable slope (four parameters)—symmetrical equation, in GraphPad Prism version 6 [GraphPad Software, La Jolla Calif. USA, www.graphpad.com]. For each experiment, compounds were tested in duplicate. $IC_{50}$ values presented are the range of two biologically independent experiments.

9. MICROSOMAL METABOLIC STABILITY DETERMINATION

Compounds were initially prepared by dissolving them into DMSO at a final concentration of 10 mM. NADPH regenerating solutions A and B and mouse liver microsomes (CD-1) were obtained from BD Gentest (Woburn, Mass.). Ninety-six well deep well plates were obtained from Mid-West Scientific Inc (Valley Park, Mo.).

Sample preparation for microsomal stability was modified from methods of Di, L., et al., Int J Pharm. 2005 Jun. 13; 297(1-2):110-9. A set of incubation times of 0, 15, 30, 60, 120, and 240 minutes were used. Mouse liver microsomal solutions were prepared by adding 58 µL of concentrated human or mouse liver microsomes (20 mg/mL protein concentration) to 1.756 mL of 0.1 M potassium phosphate buffer (pH 7.4) and 5 µL of 0.5 M EDTA to make a 0.6381 mg/mL (protein) microsomal solution. NADPH regenerating agent contained 113 µL of NADPH A, 23 µL of NADPH B, and 315 µL of 0.1 M potassium phosphate buffer (pH 7.4). The diluted test compound solutions (2 µL) were each added directly to a 1.79 mL of liver microsomal solution. This solution was mixed and 90 µL was transferred to 6 time points plates (each in triplicate wells). For the time 0 plate, 225 µL of cold acetonitrile with internal standard (4 mg/ml warfarin) was added to each well, followed by addition of NADPH regenerating agent (22.5 µL) and no incubation. For other five time points' plate, NADPH regenerating agent (22.5 µL) was added to each well to initiate the reaction. The plates were incubated at 37° C. for the required time, followed by quenching of the reaction by adding 225 µL of cold acetonitrile with internal standard (4 µg/ml warfarin).

All of the plates were sealed and mixed well at 600 rpm for 10 minutes followed by centrifugation at 4000 rpm for 20 minutes. The supernatants (120 µL) were transferred to analytical plates for analysis by LCMS. LCMS conditions were described in the materials and instrumentation section above. The metabolic stability is evaluated via the half-life from least-squares fit of the multiple time points based on first-order kinetics.

10. MINIMAL INHIBITORY CONCENTRATION ASSAY

Minimal inhibitory concentrations ("MICs") were determined using the microbroth dilution method according to Clinical Laboratory Standards Institute (CLSI; National, C.F. C. L. S., Methods for Dilution Antimicrobial Susceptibility Tests for Bacteria Grow aerobically-Seventh Edition: Approved Standard M7-A7, CLSI, Wayne, Pa., USA, 2008) and were read by visual inspection. Two fold serial dilutions of test compound in 100 µL of the appropriate broth media were first prepared in 96-well round bottom microtiter plates (Nalgene Nunc International, Rochester, N.Y., USA). An equivalent volume (100 µL) of bacterial broth inocula containing approximately $10^5$ bacterial cfu/mL was added to each well to give final concentrations of test compound starting at 200 µM. The plates were then incubated aerobically at 37° C. All strains were incubated overnight. After incubations, in all cases the MIC was recorded as the lowest concentration of drug that prevented bacterial growth. The bacterial strains for which MIC was determined as described in Table 4.

11. ACTIVITY OF SUBSTITUTED UREA DEPSIPEPTIDE ANALOGS IN IN VITRO ASSAYS

Substituted urea depsipeptide analogs were synthesized as described above. Activity was determined using the assays described above, and the data are shown in Table 3. The $EC_{50}$ for C1pP activation was determined in the Sa-C1pP in casein-BODIPY assay as described above. The $IC_{50}$ for ADEP displacement was determined in the ADEP displacement fluorescent polarization assay as described above; and the $IC_{50}$ for growth inhibition was determined in the Vero cell cytotoxicity assay as described above. The compound number corresponds to the compound numbers used in Tables 1 and 2 and the experimental examples described above.

TABLE 3*

| Compound No. | ClpP Activation $EC_{50}$ (µM) | ADEP Displacement $IC_{50}$ (µM) | Cytotoxicity $IC_{50}$ (µM) |
|---|---|---|---|
| 1 | 3.6 ± 0.4** | 6.72 ± 0.4 | >100 |
| 2 | 2.6 ± 0.4**, 0.5 ± 0.05† | 7.66 ± 0.3 | 88.3 ± 15.2 |
| 3 | 3.3 ± 0.2**, 1.5 ± 0.14† | 9.25 ± 0.5 | 63.0 ± 5.8 |
| 4 | 1.4 ± 0.1**, 5.5 ± 0.18† | 28.98 ± 2.1 | 73.7 ± 8.4 |
| 5 | 1.3 ± 0.2**, 1.5 ± 0.12† | 28.04 ± 2.3 | 91.3 ± 12.7 |
| 6 | 2.0 ± 0.1**, 0.8 ± 0.07† | 27.7 ± 1.5 | >100 |
| 7 | 34.6 ± 6.8**, 1.6 ± 0.07† | 129.61 ± 11.3 | >100 |
| 8 | 3.0 ± 0.4**, 1.3 ± 0.07† | 16.3 ± 0.8 | >100 |
| 9 | 1.0 ± 0.1**, 1.1 ± 0.06† | 25.38 ± 2.2 | 89.0 ± 5.0 |
| 10 | 1.5 ± 0.6**, 0.9 ± 0.03† | 13.63 ± 1.7 | 74.8 ± 4.6 |
| 11 | 2.3 ± 0.3**, 1.1 ± 0.04† | 4.45 ± 0.3 | 76.0 ± 10.6 |
| 12 | 3.2 ± 0.5** | 6.81 ± 0.4 | 90.0 ± 7.6 |
| 13 | 3.2 ± 0.6**, | 5.69 ± 0.5 | 70.9 ± 8.9 |
| 14 | 2.5 ± 0.6**, | 61.34 ± 5.0 | 70.5 ± 13.5 |
| 15 | 4.6 ± 0.9**, 0.70 ± 0.03† | 8.4 ± 0.2 | 39.7 ± 6.6 |
| 16 | 4.4 ± 0.7**, 0.55 ± 0.03† | 8.3 ± 0.6 | 74.3 ± 9.0 |
| 17 | 3.6 ± 0.6**, 0.72 ± 0.03† | 7.2 ± 0.4 | 46.5 ± 9.8 |
| 18 | 7.0 ± 0.9**, 0.32 ± 0.02† | 5.6 ± 0.3 | 26.7 ± 3.6 |
| 19 | 3.2 ± 0.1**, 0.33 ± 0.0† | 5.7 ± 0.3 | 36.8 ± 4.1 |
| 20 | 1.6 ± 0.3**, 0.36 ± 0.03† | 6.0 ± 0.3 | 52.8 ± 4.9 |
| 21 | 1.1 ± 0.3**, 0.33 ± 0.01† | 7.3 ± 0.3 | 68.5 ± 6.6 |
| 22 | 3.6 ± 0.4**, 0.32 ± 0.02† | 8.9 ± 0.3 | 52.3 ± 7.7 |
| 23 | 2.6 ± 0.4**, 0.5 ± 0.02† | 7.1 ± 0.3 | 74.0 ± 7.7 |
| 24 | 3.3 ± 0.2**, 0.4 ± 0.02† | 8.6 ± 0.5 | 93.8 ± 4.8 |
| 25 | 0.48 ± 0.03† | 8.9 ± 0.3 | 10.8 ± 1.0 |
| 26 | 0.29 ± 0.0† | 8.2 ± 0.3 | 40.5 ± 3.8 |
| 27 | 0.31 ± 0.0† | 7.7 ± 0.2 | 10.5 ± 1.4 |
| 28 | 0.19 ± 0.0† | 5.6 ± 0.2 | 16.1 ± 2.4 |
| 29 | 0.25 ± 0.02† | 5.9 ± 0.2 | 26.8 ± 1.3 |
| 30 | 0.43 ± 0.02† | 4.0 ± 0.1 | 28.8 ± 3.7 |
| 31 | 0.37 ± 0.03† | 5.8 ± 0.3 | >100 |
| 32 | 0.40 ± 0.0† | 7.0 ± 0.4 | 28.3 ± 0.6 |
| 33 | 0.39 ± 0.02† | 5.6 ± 0.3 | 41.0 ± 4.3 |
| 34 | 0.33 ± 0.0† | 6.1 ± 0.4 | 26.0 ± 2.6 |
| 35 | 0.48 ± 0.03† | 6.6 ± 0.4 | 55.7 ± 3.6 |
| 36 | 0.43 ± 0.0† | 6.4 ± 0.5 | 25.4 ± 1.8 |
| 37 | 0.35 ± 0.0† | 7.0 ± 0.4 | 33.8 ± 1.6 |
| 38 | 0.33 ± 0.0† | 6.52 ± 0.3 | 46.1 ± 5.5 |
| 39 | 0.48 ± 0.03† | 9.00 ± 0.4 | 40.0 ± 4.1 |
| 40 | 0.36 ± 0.03† | 12.69 ± 0.7 | 43.8 ± 5.1 |
| 41 | 0.31 ± 0.0† | 7.53 ± 0.2 | 23.9 ± 2.0 |
| 42 | 0.25 ± 0.03† | 7.12 ± 0.2 | 24.9 ± 2.6 |
| 43 | 0.37 ± 0.03† | 6.57 ± 0.2 | 74.5 ± 8.8 |
| 44 | 0.28 ± 0.0† | 6.76 ± 0.3 | 83.8 ± 6.6 |
| 45 | 0.54 ± 0.03† | 6.62 ± 0.2 | 56.8 ± 6.7 |
| 46 | 0.32 ± 0.02† | 4.61 ± 0.2 | 71.8 ± 5.4 |
| 47 | 0.4 ± 0.0† | 7.01 ± 0.3 | ND |
| 48 | 0.7 ± 0.03† | 8.1 ± 0.3 | ND |
| 49 | 2.3 ± 0.20† | 12.7 ± 0.2 | ND |
| 50 | 0.9 ± 0.07† | 7.66 ± 0.2 | ND |
| 51 | 2.5 ± 0.20† | 9.71 ± 0.3 | ND |
| ADEP4 | 7.5 ± 0.7**, 0.32 ± 0.01† | 5.23 ± 0.2 | 39.7 ± 2.7 |
| ADEP 2719 | 0.38 ± 0.0† | 6.20 ± 0.3 | 37.7 ± 3.4 |
| ADEP 2914 | 0.31 ± 0.02† | 4.86 ± 0.2 | 60.5 ± 6.4 |

*"ND" indicates that the experimental parameter was not determined.

**Assay method and $EC_{50}$ calculation using the first described ClpP activation assay above.

†Assay method and $EC_{50}$ calculation using the second described ClpP activation assay above.

12. ACTIVITY OF SUBSTITUTED UREA DEPSIPEPTIDE ANALOGS IN THE MINIMAL INHIBITORY CONCENTRATION ASSAY

Substituted urea depsipeptide analogs were synthesized as described above. Minimal inhibitory concentrations were determined using microbroth dilution assay as described above, and the data are shown in Table 4. The compound number corresponds to the compound numbers used in Tables 1 and 2 and the experimental examples described above.

TABLE 4

| No. | S. aureus ATCC 29213 | S. aureus NRS70 | S. aureus USA 300 | S. aureus USA 300 ΔClpP | S. pyogenes ATCC 700294 |
|---|---|---|---|---|---|
| | Minimal Inhibitory Concentrations* (μM) | | | | |
| 1 | 6.25 | 6.25 | ND | ND | 1.56 |
| 2 | 0.39 | 0.20 | ND | ND | 0.10 |
| 3 | 1.56 | 0.78 | ND | ND | 0.39 |
| 4 | 0.78 | 0.39 | ND | ND | 0.20 |
| 5 | 6.25 | 1.56 | ND | ND | 0.78 |
| 6 | 3.13 | 3.13 | ND | ND | 0.39 |
| 7 | 12.50 | 12.50 | ND | ND | 3.13 |
| 8 | 3.13 | 3.13 | ND | ND | 0.78 |
| 9 | 3.13 | 1.56 | ND | ND | 1.56 |
| 10 | 0.6 | 0.6 | ND | ND | 0.6 |
| 11 | 2.5 | 1.25 | ND | ND | 0.6 |
| 12 | 2.5 | 2.5 | ND | ND | 0.6 |
| 13 | 0.05 | 0.8 | ND | ND | 0.15 |
| 14 | 0.1 | 0.08 | ND | ND | 0.8 |
| 15 | 0.6 | 0.3 | <0.1 | 100 | 0.6 |
| 16 | 0.4 | 0.8 | 0.8 | 3.1 | 1.5 |
| 17 | 3.1 | 3.1 | 3.1 | 200 | 1.5 |
| 18 | 0.1 | 0.1 | 0.1 | 100 | <0.1 |
| 19 | 0.1 | 0.1 | 0.1 | 6.2 | 0.4 |
| 20 | 0.8 | 0.4 | 0.8 | 200 | 0.4 |
| 23 | 0.4 | 0.4 | 0.1 | ND | <0.2 |
| 24 | 0.5 | 0.5 | ND | ND | 0.5 |
| 25 | 0.78 | 0.78 | 0.78 | 200 | 1.0 |
| 26 | 0.2 | 0.2 | 0.39 | 200 | 0.50 |
| 27 | 0.2 | 0.2 | 0.2 | 100 | 0.23 |
| 28 | 0.05 | 0.05 | 0.1 | 25 | 0.23 |
| 29 | 0.2 | 0.2 | 0.2 | 100 | 0.13 |
| 30 | 0.1 | 0.2 | 0.1 | 50 | 0.03 |
| 31 | 0.39 | 0.39 | 1.56 | >200 | 0.78 |
| 32 | 0.1 | 0.1 | 0.39 | 100 | 0.2 |
| 33 | 0.2 | 0.1 | 0.2 | 200 | 0.39 |
| 34 | 0.05 | 0.02 | 0.05 | 50 | 0.1 |
| 35 | 0.2 | 0.1 | 0.2 | 200 | 0.39 |
| 36 | 0.1 | 0.05 | 0.1 | 50 | 0.2 |
| 37 | 0.1 | 0.1 | 0.1 | 100 | 0.1 |
| 38 | 0.05 | 0.05 | 0.1 | 200 | 0.1 |
| 39 | 0.05 | 0.05 | 0.05 | 100 | 0.2 |
| 40 | 0.05 | 0.02 | 0.05 | 25 | 0.4 |
| 41 | 0.02 | 0.01 | 0.02 | 50 | 0.1 |
| 42 | 0.05 | 0.02 | 0.1 | 100 | 0.05 |
| 43 | 1.6 | 1.6 | 3.1 | >200 | 0.8 |
| 44 | 0.4 | 0.4 | 0.8 | 50 | 0.2 |
| 45 | 0.4 | 0.2-0.4 | 0.4 | 100 | 0.4 |
| 46 | 3.1 | 1.6 | 3.1 | 200 | 0.8 |
| 47 | 0.003 | 0.0002 | 0.01 | >200 | 0.02 |
| 48 | 1.6 | 0.4 | 1.6 | 200 | 3.1 |
| 49 | 12.5 | 12.5 | 25 | 100 | 25 |
| 50 | 3.1 | 1.6 | 3.1 | >200 | 1.6 |
| 51 | 12.5 | 6.3 | 12.5 | >200 | 12.5 |
| Tetracycline | 0.10 | 0.05 | 0.1 | 0.1 | 0.1 |
| Kanamycin | 1.56 | 50 | ND | ND | 12.5 |
| Chloroamphenicol | 3.13 | 3.1 | 3.1 | 6.3 | 1.6 |
| Spectinomycin | 50 | >800 | 50 | 25 | 12.5 |
| ADEP4 | 0.1 | 0.10 | 0.1 | 100 | <0.1 |
| ADEP 2719 | 0.07 | 0.08 | <0.19 | 500 | <0.2 |
| ADEP 2914 | 0.4 | 0.2 | 0.4 | >200 | 0.1 |

| No. | S. pneumoniae R6 | S. pneumoniae DAW27 | B. subtilis ATCC 23857 | E. faecails ATCC 33186 | E. coli K12ΔtolC |
|---|---|---|---|---|---|
| | Minimal Inhibitory Concentrations* (μM) | | | | |
| 1 | ND | 0.78 | 1.56 | 3.13 | 200 |
| 2 | ND | 0.02 | 0.20 | 0.02 | 12.5 |
| 3 | ND | 0.20 | 0.78 | 0.20 | 25 |
| 4 | ND | 0.04 | 0.20 | 0.10 | 25 |
| 5 | ND | 0.39 | 0.78 | 0.78 | 50 |
| 6 | ND | 0.20 | 1.56 | 0.78 | 50 |

TABLE 4-continued

| | | | | | |
|---|---|---|---|---|---|
| 7 | ND | 0.78 | 6.25 | 3.13 | 200 |
| 8 | ND | 0.39 | 3.13 | 1.56 | 200 |
| 9 | ND | 0.78 | 1.56 | 1.56 | 25 |
| 10 | ND | 0.3 | 0.6 | 0.3 | ND* |
| 11 | ND | 0.3 | 1.25 | 0.6 | ND |
| 12 | ND | 0.3 | 2.5 | 1.25 | ND |
| 13 | ND | 0.04 | 0.08 | 0.04 | ND |
| 14 | ND | 0.04 | 0.08 | 0.04 | ND |
| 15 | 0.3 | ND | <0.1 | 0.3 | ND |
| 16 | 0.8 | ND | 0.4 | <0.1 | ND |
| 17 | 0.8 | ND | 0.4 | <0.1 | ND |
| 18 | <0.1 | ND | <0.1 | 0.8 | ND |
| 19 | 0.8 | ND | <0.1 | 0.39 | ND |
| 20 | <0.1 | ND | <0.1 | <0.1 | ND |
| 23 | <0.2 | ND | <0.2 | <0.2 | ND |
| 24 | ND | ND | 2.2 | ND | ND |
| 25 | 0.254 | ND | 0.02 | ND | ND |
| 26 | 0.125 | ND | 0.03 | ND | ND |
| 27 | 0.058 | ND | 0.02 | ND | ND |
| 28 | 0.029 | ND | 0.01 | ND | ND |
| 29 | 0.031 | ND | 0.01 | ND | ND |
| 30 | 0.008 | ND | 0.001 | ND | ND |
| 31 | 0.195 | ND | 0.39 | ND | ND |
| 32 | 0.049 | ND | 0.39 | ND | ND |
| 33 | 0.098 | ND | 0.2 | ND | ND |
| 34 | 0.049 | ND | 0.02 | ND | ND |
| 35 | 0.049 | ND | 0.2 | ND | ND |
| 36 | 0.024 | ND | 0.1 | ND | ND |
| 37 | 0.024 | ND | 0.05 | ND | ND |
| 38 | 0.02 | ND | 0.05 | ND | ND |
| 39 | 0.05 | ND | 0.02 | ND | ND |
| 40 | 0.1 | ND | 0.02 | ND | ND |
| 41 | 0.02 | ND | 0.01 | ND | ND |
| 42 | 0.01 | ND | 0.01 | ND | ND |
| 44 | 0.1 | ND | 0.1 | ND | ND |
| 43 | 0.2 | ND | 0.4 | ND | ND |
| 45 | 0.1 | ND | ND | ND | ND |
| 46 | 0.4 | ND | 0.4 | ND | ND |
| 47 | 0.002 | ND | 0.8 | ND | ND |
| 48 | 0.8 | ND | 0.2 | ND | ND |
| 49 | 6.3 | ND | 0.4 | ND | ND |
| 50 | 0.8 | ND | >200 | ND | ND |
| 51 | 6.3 | ND | >200 | ND | ND |
| Tetracycline | 0.2 | 0.10 | 1.6 | 0.05 | 12.5 |
| Kanamycin | ND | 25 | 0.10 | 25 | 0.4 |
| Chloro-amphenicol | 1.6 | 0.78 | 3.1 | 0.39 | 0.78 |
| Spectinomycin | 6.3 | ND | 6.3 | ND | ND |
| ADEP4 | <0.1 | ND | <0.1 | <0.1 | ND |
| ADEP 2719 | <0.2 | ND | <0.01 | 0.08 | ND |
| ADEP 2914 | 0.1 | ND | 0.2 | ND | ND |

*"ND" indicates that the experimental parameter was not determined.

13. ACTIVITY OF SUBSTITUTED UREA DEPSIPEPTIDE ANALOGS IN THE MICROSOMAL METABOLIC STABILITY DETERMINATION

Substituted urea depsipeptide analogs were synthesized as described above. Activity was determined in the microsomal metabolic stability assay as described above, and the data are shown in Table 5. The compound number corresponds to the compound numbers used in Tables 1 and 2 and the experimental examples described above.

TABLE 5

| No. | $t_{1/2}$ (hr) |
|---|---|
| 15 | 0.3 ± 0.0 |
| 16 | 0.7 ± 0 |
| 17 | 8.1 ± 1.1 |
| 18 | 1.0 ± 0.1 |
| 19 | 0.5 ± 0 |
| 20 | 6.9 ± 1.3 |
| 23 | 2.96 ± 0.3 |
| ADEP4 | 0.13 ± 0.01 |
| ADEP 2719 | 0.1 ± 0.0 |

14. PROPHETIC EXEMPLARY COMPOUNDS

The compounds in Table 8 can be synthesized with methods identical or analogous to those described herein. The requisite starting materials are commercially available, described in the literature, or readily synthesized by one skilled in the art of organic synthesis.

TABLE 8

| No. | Structure | Name |
|---|---|---|
| 52 | 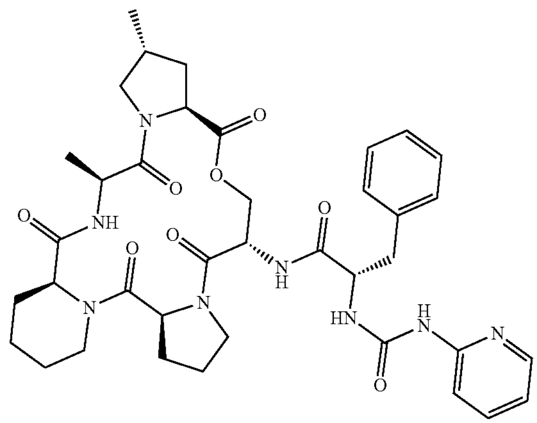 [SMILES: C[C@@H]1C[C@H]2C(=O)OC[C@H](NC(=O)[C@H](Cc3ccccc3)NC(=O)Nc3ccccn3)C(=O)N3CCC[C@H]3C(=O)N3CCCC[C@H]3C(=O)N[C@@H](C)C(=O)N2C1] | (S)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(pyridin-2-yl)ureido)propanamide |
| 53 | 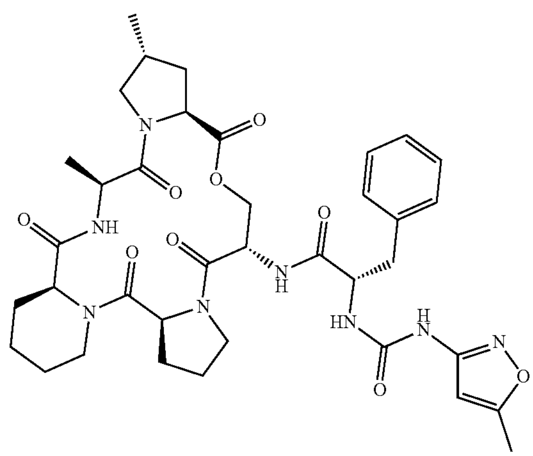 [SMILES: Cc1cc(NC(=O)N[C@@H](Cc2ccccc2)C(=O)N[C@H]2COC(=O)[C@@H]3C[C@@H](C)CN3C(=O)[C@H](C)NC(=O)[C@@H]3CCCCN3C(=O)[C@@H]3CCCN3C2=O)no1] | (S)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(5-methylisoxazol-3-yl)ureido)-3-phenylpropanamide |
| 54 | 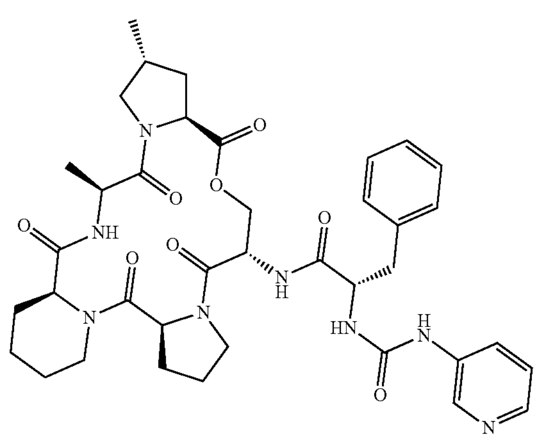 [SMILES: C[C@@H]1C[C@H]2C(=O)OC[C@H](NC(=O)[C@H](Cc3ccccc3)NC(=O)Nc3cccnc3)C(=O)N3CCC[C@H]3C(=O)N3CCCC[C@H]3C(=O)N[C@@H](C)C(=O)N2C1] | (S)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(pyridin-3-yl)ureido)propanamide |

TABLE 8-continued

| No. | Structure | Name |
|---|---|---|
| 55 | 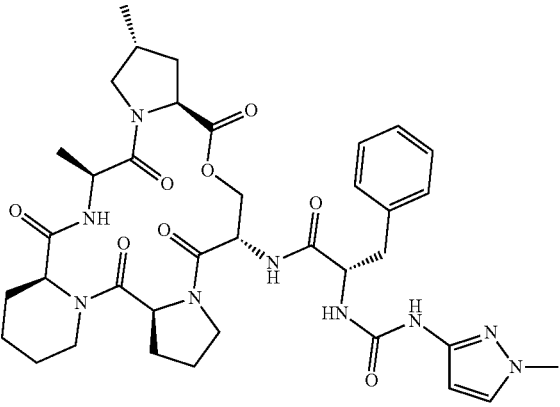 [SMILES: C[C@@H]1C[C@H]2C(=O)OC[C@H](NC(=O)[C@H](Cc3ccccc3)NC(=O)Nc3ccn(C)n3)C(=O)N3CCC[C@H]3C(=O)N3CCCC[C@H]3C(=O)N[C@@H](C)C(=O)N2C1] | (S)-N((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(1-methyl-1H-pyrazol-3-yl)ureido)-3-phenylpropanamide |
| 56 | 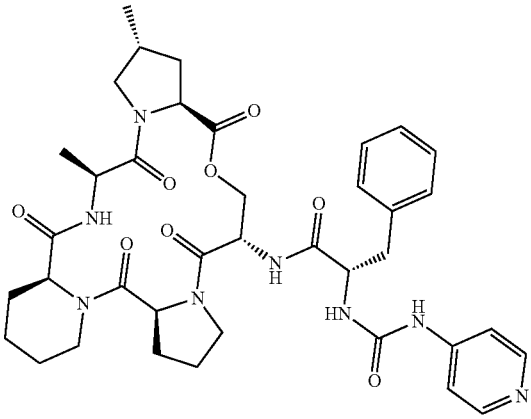 [SMILES: C[C@@H]1C[C@H]2C(=O)OC[C@H](NC(=O)[C@H](Cc3ccccc3)NC(=O)Nc3ccncc3)C(=O)N3CCC[C@H]3C(=O)N3CCCC[C@H]3C(=O)N[C@@H](C)C(=O)N2C1] | (S)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(pyridin-4-yl)ureido)propanamide |
| 57 | 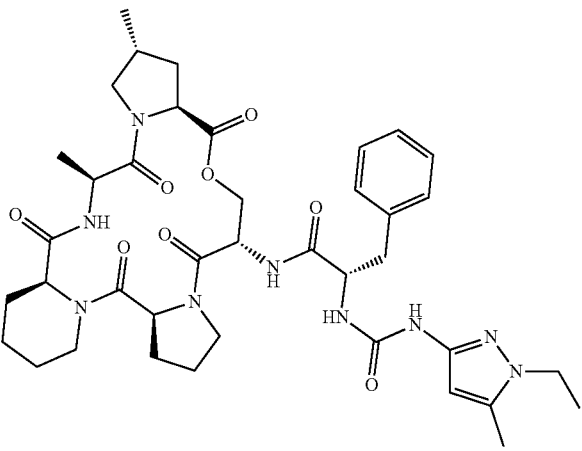 [SMILES: CCn1nc(NC(=O)N[C@@H](Cc2ccccc2)C(=O)N[C@H]2COC(=O)[C@@H]3C[C@@H](C)CN3C(=O)[C@H](C)NC(=O)[C@@H]3CCCCN3C(=O)[C@@H]3CCCN3C2=O)cc1C] | (S)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(1-ethyl-5-methyl-1H-pyrazol-3-yl)ureido)-3-phenylpropanamide |

| No. | Structure | Name |
|---|---|---|
| 58 | 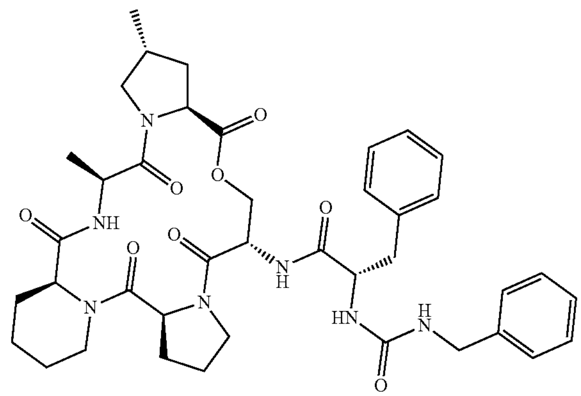 [SMILES: C[C@@H]1C[C@H]2C(=O)OC[C@H](NC(=O)[C@H](Cc3ccccc3)NC(=O)NCc3ccccc3)C(=O)N3CCC[C@H]3C(=O)N3CCCC[C@H]3C(=O)N[C@@H](C)C(=O)N2C1] | (S)-2-(3-benzylureido)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenylpropanamide |
| 59 | 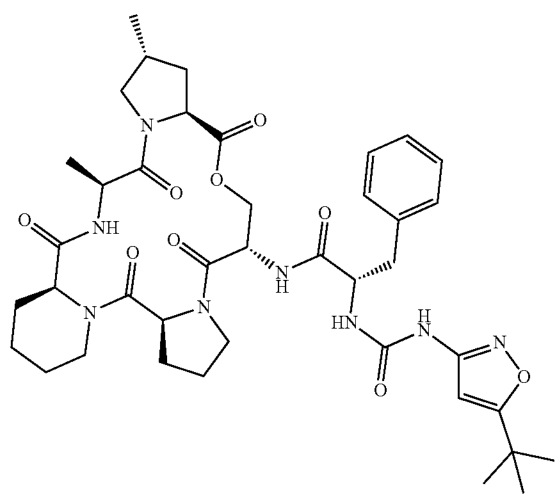 [SMILES: C[C@@H]1C[C@H]2C(=O)OC[C@H](NC(=O)[C@H](Cc3ccccc3)NC(=O)Nc3cc(C(C)(C)C)on3)C(=O)N3CCC[C@H]3C(=O)N3CCCC[C@H]3C(=O)N[C@@H](C)C(=O)N2C1] | (S)-2-(3-(5-(tert-butyl)isoxazol-3-yl)ureido)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenylpropanamide |
| 60 | 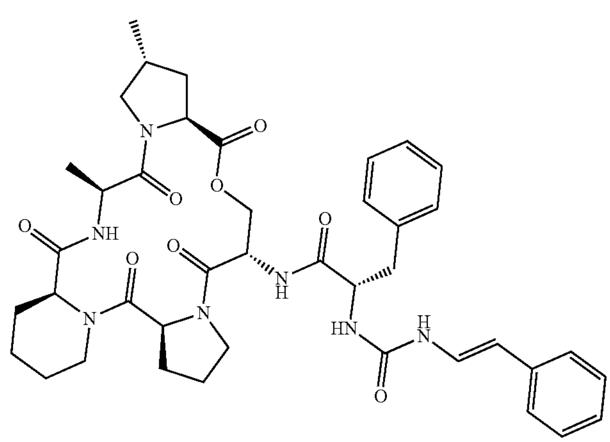 [SMILES: C[C@@H]1C[C@H]2C(=O)OC[C@H](NC(=O)[C@H](Cc3ccccc3)NC(=O)N/C=C/c3ccccc3)C(=O)N3CCC[C@H]3C(=O)N3CCCC[C@H]3C(=O)N[C@@H](C)C(=O)N2C1] | (S)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-((E)-styryl)ureido)propanamide |

TABLE 8-continued

| No. | Structure | Name |
| --- | --- | --- |
| 61 | 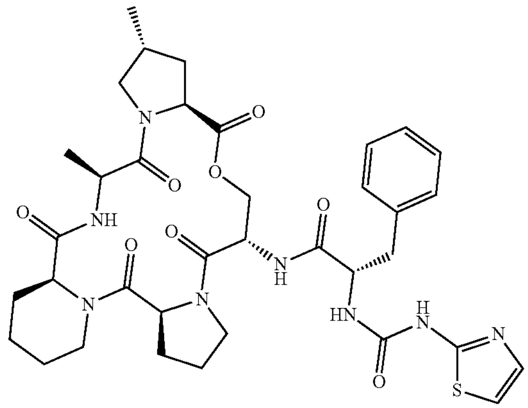 [SMILES: C[C@@H]1C[C@H]2C(=O)OC[C@H](NC(=O)[C@H](Cc3ccccc3)NC(=O)Nc3nccs3)C(=O)N3CCC[C@H]3C(=O)N3CCCC[C@H]3C(=O)N[C@@H](C)C(=O)N2C1] | (S)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(thiazol-2-yl)ureido)propanamide |
| 62 | 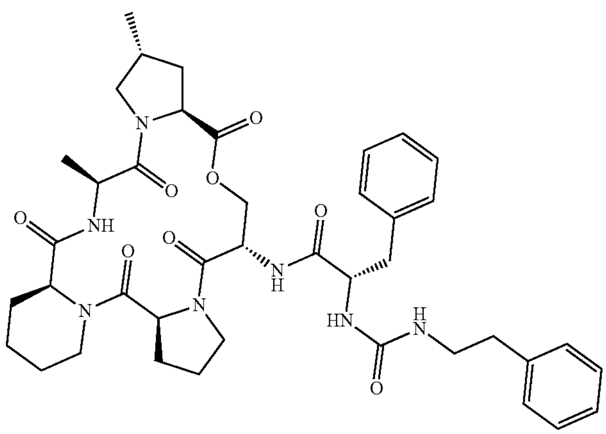 [SMILES: C[C@@H]1C[C@H]2C(=O)OC[C@H](NC(=O)[C@H](Cc3ccccc3)NC(=O)NCCc3ccccc3)C(=O)N3CCC[C@H]3C(=O)N3CCCC[C@H]3C(=O)N[C@@H](C)C(=O)N2C1] | (S)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-phenethylureido)-3-phenylpropanamide |
| 63 | 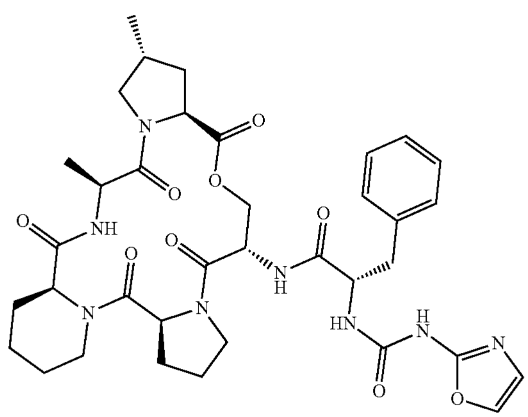 [SMILES: C[C@@H]1C[C@H]2C(=O)OC[C@H](NC(=O)[C@H](Cc3ccccc3)NC(=O)Nc3ncco3)C(=O)N3CCC[C@H]3C(=O)N3CCCC[C@H]3C(=O)N[C@@H](C)C(=O)N2C1] | (S)-N-((2R,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(oxazol-2-yl)ureido)-3-phenylpropanamide |

TABLE 8-continued

| No. | Structure | Name |
|---|---|---|
| 64 | 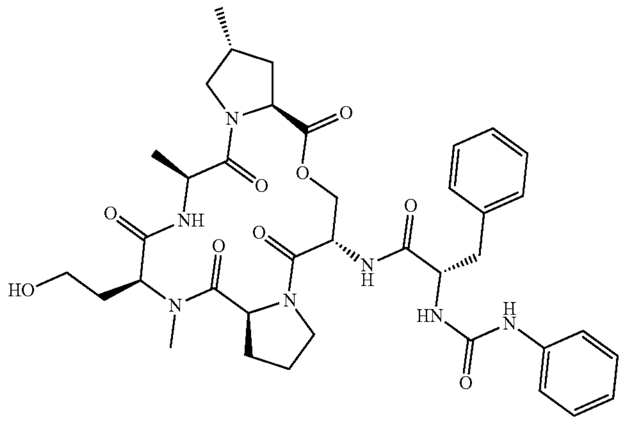 [SMILES: C[C@@H]1C[C@H]2C(=O)OC[C@H](NC(=O)[C@H](Cc3ccccc3)NC(=O)Nc3ccccc3)C(=O)N3CCC[C@H]3C(=O)N(C)[C@@H](CCO)C(=O)N[C@@H](C)C(=O)N2C1] | (S)-N-((2R,6S,9S,11aS,17S,20aS)-9-(2-hydroxyethyl)-2,6,10-trimethyl-5,8,11,16,20-pentaoxohexadecahydro-1H,5H,16H-dipyrrolo[2,1-c:2',1'-l][1]oxa[4,7,10,13]tetraazacyclohexadecin-17-yl)-3-phenyl-2-(3-phenylureido)propanamide |
| 65 | 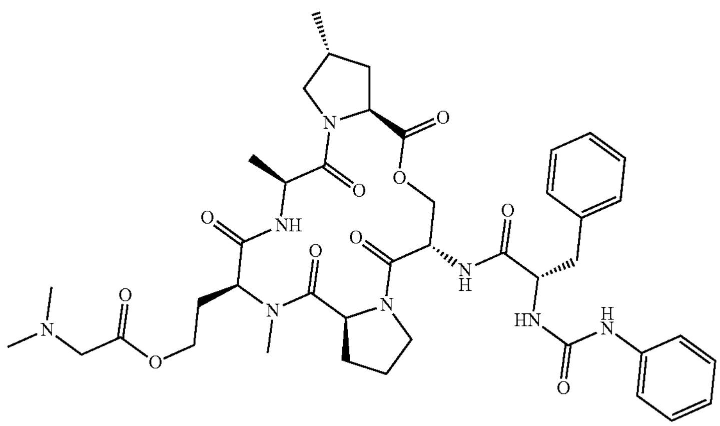 [SMILES: C[C@@H]1C[C@H]2C(=O)OC[C@H](NC(=O)[C@H](Cc3ccccc3)NC(=O)Nc3ccccc3)C(=O)N3CCC[C@H]3C(=O)N(C)[C@@H](CCOC(=O)CN(C)C)C(=O)N[C@@H](C)C(=O)N2C1] | 2-((2R,6S,9S,11aS,17S,20aS)-2,6,10-trimethyl-5,8,11,16,20-pentaoxo-17-((S)-3-phenyl-2-(3-phenylureido)propanamido)hexadecahydro-1H,5H,16H-dipyrrolo[2,1-c:2',1'-l][1]oxa[4,7,10,13]tetraazacyclohexadecin-9-yl)ethyl dimethylglycinate |
| 66 | 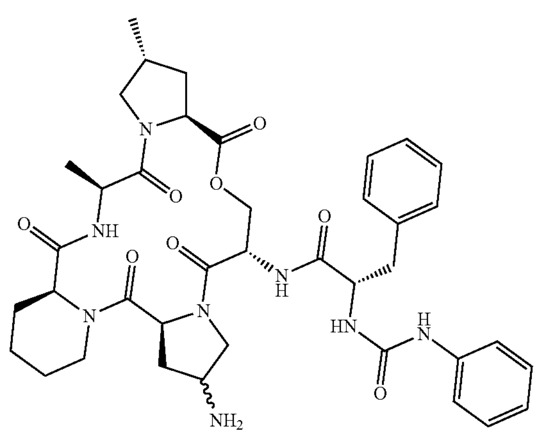 | (2S)-N-((2R,6S,8aS,14aS,20S,23aS)-16-amino-2,6-dimethyl-5,8,14,19,23-pentaoxooctadecahydro-1H,5H,14H,19H-pyrido[2,1-i]dipyrrolo[2,1-c:2',1'-l][1]oxa[4,7,10,13]tetraazacyclohexadecin-20-yl)-3-phenyl-2-(3-phenylureido)propanamide |

TABLE 8-continued

| No. | Structure | Name |
|---|---|---|
| 67 | 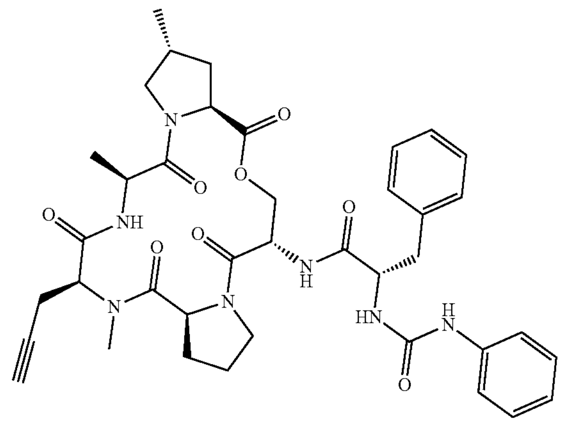 [SMILES: C#CC[C@H]1C(=O)N[C@@H](C)C(=O)N2C[C@H](C)C[C@H]2C(=O)OC[C@H](NC(=O)[C@H](Cc2ccccc2)NC(=O)Nc2ccccc2)C(=O)N2CCC[C@H]2C(=O)N1C] | (S)-3-phenyl-2-(3-phenylureido)-N-((2R,6S,9S,11aS,17S,20aS)-2,6,10-trimethyl-5,8,11,16,20-pentaoxo-9-(prop-2-yn-1-yl)hexadecahydro-1H,5H,16H-dipyrrolo[2,1-c:2',1'-1][1]oxa[4,7,10,13]tetraaza-cyclohexadecin-17-yl)propanamide |
| 68 | 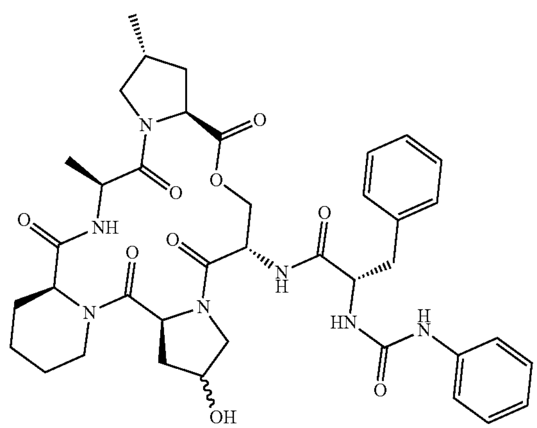 | (2S)-N-((2R,6S,8aS,14aS,20S,23aS)-16-hydroxy-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-phenylureido)propanamide |
| 69 | 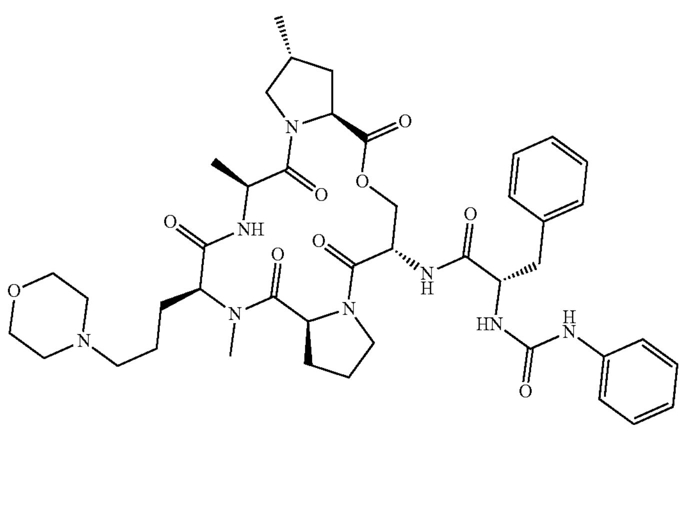 [SMILES: C[C@@H]1C[C@H]2C(=O)OC[C@H](NC(=O)[C@H](Cc3ccccc3)NC(=O)Nc3ccccc3)C(=O)N3CCC[C@H]3C(=O)N(C)[C@@H](CCCN3CCOCC3)C(=O)N[C@@H](C)C(=O)N2C1] | (S)-3-phenyl-2-(3-phenylureido)-N-((2R,6S,9S,11aS,17S,20aS)-2,6,10-trimethyl-9-(3-morpholinopropyl)-5,8,11,16,20-pentaoxohexadecahydro-1H,5H,16H-dipyrrolo[2,1-c:2',1'-1][1]oxa[4,7,10,13]tetraazacyclohexadecin-17-yl)propanamide |

TABLE 8-continued

| No. | Structure | Name |
| --- | --- | --- |
| 70 | 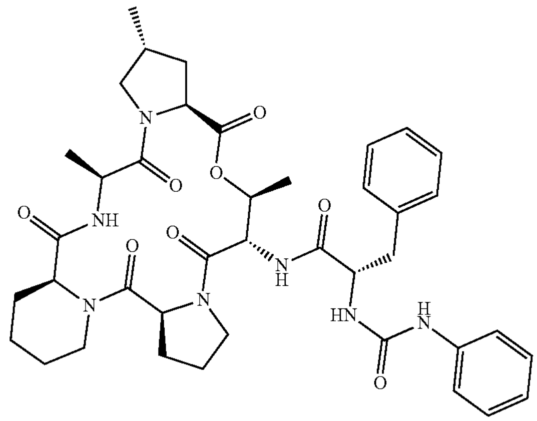 [SMILES: C[C@@H]1C[C@H]2C(=O)O[C@@H](C)[C@H](NC(=O)[C@H](Cc3ccccc3)NC(=O)Nc3ccccc3)C(=O)N3CCC[C@H]3C(=O)N3CCCC[C@H]3C(=O)N[C@@H](C)C(=O)N2C1] | (S)-3-phenyl-2-(3-phenylureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-l][1]oxa[4,7,10,13]tetraazacyclohexadecin-20-yl)propanamide |
| 71 | 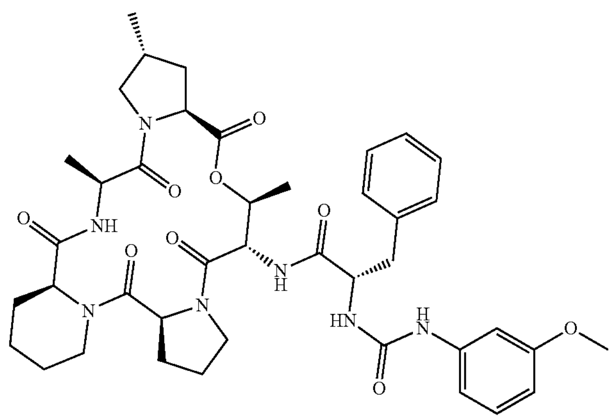 [SMILES: COc1cccc(NC(=O)N[C@@H](Cc2ccccc2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)c1] | (S)-2-(3-(3-methoxyphenyl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-l][1]oxa[4,7,10,13]tetraazacyclohexadecin-20-yl)propanamide |
| 72 | 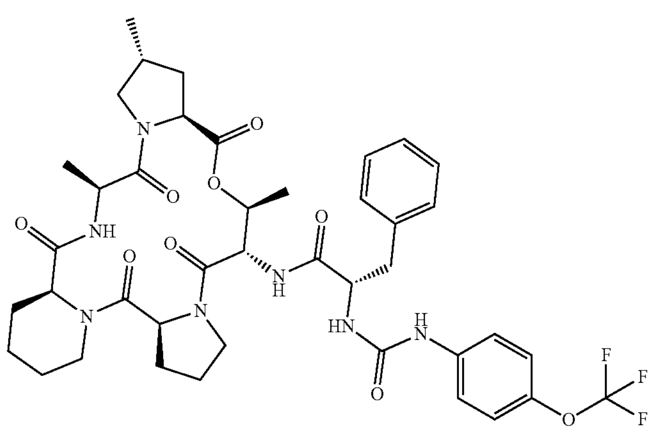 [SMILES: C[C@@H]1C[C@H]2C(=O)O[C@@H](C)[C@H](NC(=O)[C@H](Cc3ccccc3)NC(=O)Nc3ccc(OC(F)(F)F)cc3)C(=O)N3CCC[C@H]3C(=O)N3CCCC[C@H]3C(=O)N[C@@H](C)C(=O)N2C1] | (S)-3-phenyl-2-(3-(4-(trifluoromethoxy)phenyl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-l][1]oxa[4,7,10,13]tetraazacyclohexadecin-20-yl)propanamide |

TABLE 8-continued

| No. | Structure | Name |
|---|---|---|
| 73 | 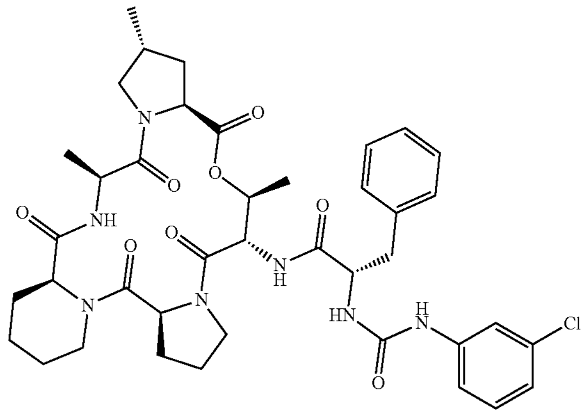 [SMILES: C[C@@H]1C[C@H]2C(=O)O[C@@H](C)[C@H](NC(=O)[C@H](Cc3ccccc3)NC(=O)Nc3cccc(Cl)c3)C(=O)N3CCC[C@H]3C(=O)N3CCCC[C@H]3C(=O)N[C@@H](C)C(=O)N2C1] | (S)-2-(3-(3-chlorophenyl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 74 | 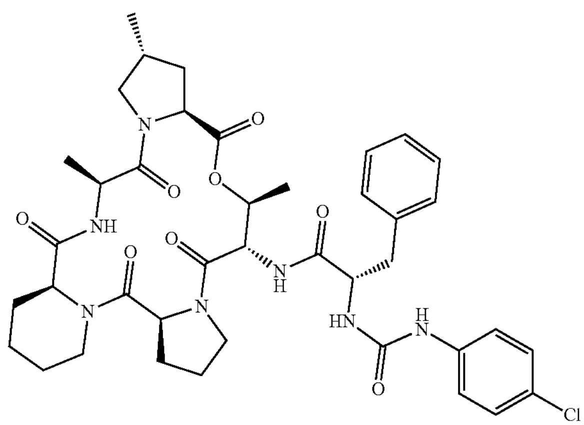 [SMILES: C[C@@H]1C[C@H]2C(=O)O[C@@H](C)[C@H](NC(=O)[C@H](Cc3ccccc3)NC(=O)Nc3ccc(Cl)cc3)C(=O)N3CCC[C@H]3C(=O)N3CCCC[C@H]3C(=O)N[C@@H](C)C(=O)N2C1] | (S)-2-(3-(4-chlorophenyl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 75 | 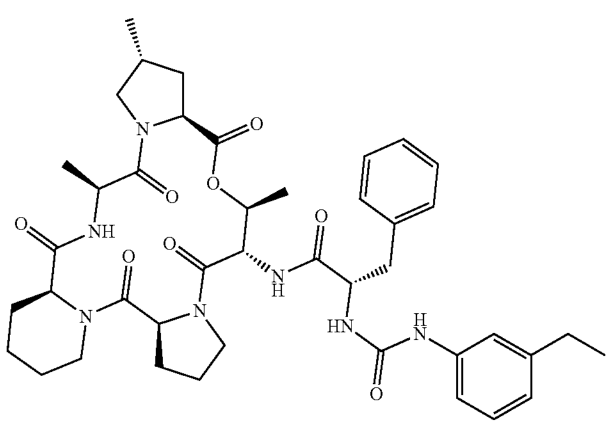 [SMILES: CCc1cccc(NC(=O)N[C@@H](Cc2ccccc2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)c1] | (S)-2-(3-(3-ethylphenyl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
| --- | --- | --- |
| 76 | 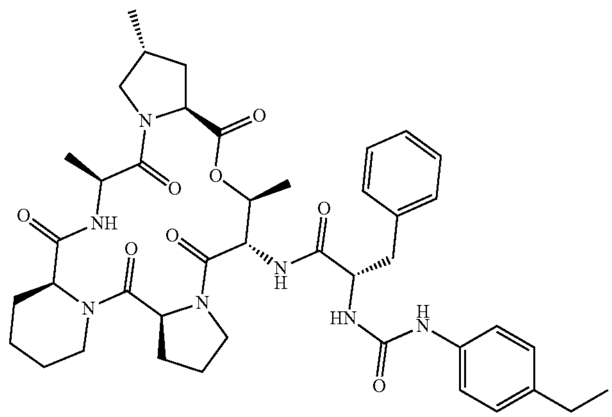 [SMILES: CCc1ccc(NC(=O)N[C@@H](Cc2ccccc2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)cc1] | (S)-2-(3-(4-ethylphenyl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 77 | 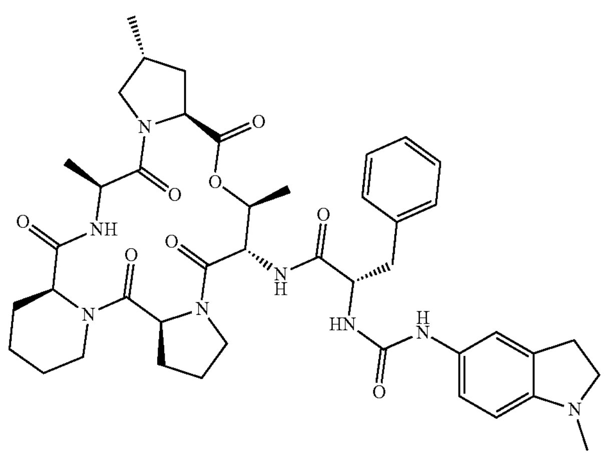 [SMILES: C[C@@H]1C[C@H]2C(=O)O[C@@H](C)[C@H](NC(=O)[C@H](Cc3ccccc3)NC(=O)Nc3ccc4c(c3)CCN4C)C(=O)N3CCC[C@H]3C(=O)N3CCCC[C@H]3C(=O)N[C@@H](C)C(=O)N2C1] | (S)-2-(3-(1-methylindolin-5-yl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 78 | 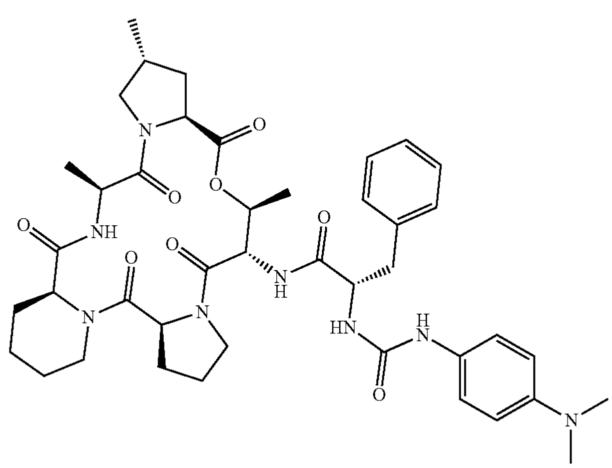 [SMILES: C[C@@H]1C[C@H]2C(=O)O[C@@H](C)[C@H](NC(=O)[C@H](Cc3ccccc3)NC(=O)Nc3ccc(N(C)C)cc3)C(=O)N3CCC[C@H]3C(=O)N3CCCC[C@H]3C(=O)N[C@@H](C)C(=O)N2C1] | (S)-2-(3-(4-(dimethylamino)phenyl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|---|---|---|
| 79 | 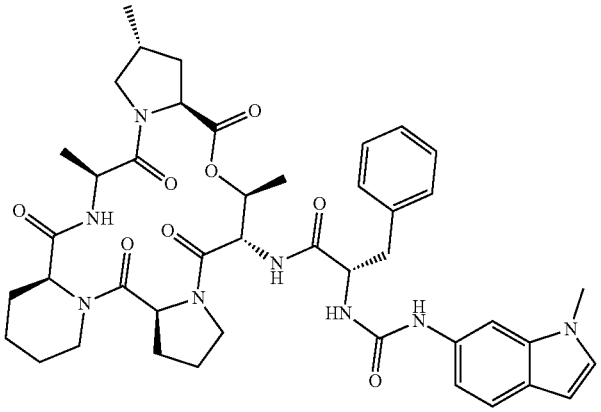 [SMILES: C[C@@H]1C[C@H]2C(=O)O[C@@H](C)[C@H](NC(=O)[C@H](Cc3ccccc3)NC(=O)Nc3ccc4ccn(C)c4c3)C(=O)N3CCC[C@H]3C(=O)N3CCCC[C@H]3C(=O)N[C@@H](C)C(=O)N2C1] | (S)-2-(3-(1-methyl-1H-indol-6-yl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 80 | 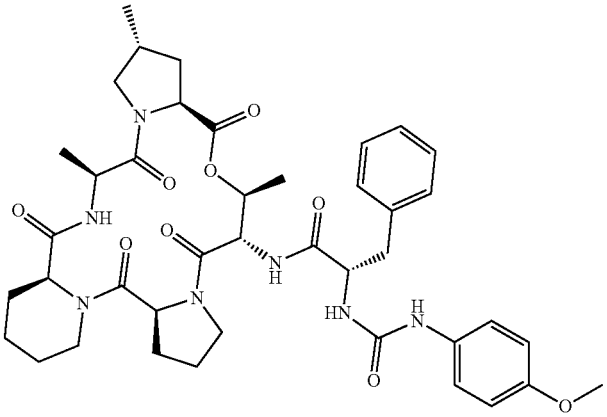 [SMILES: COc1ccc(NC(=O)N[C@@H](Cc2ccccc2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)cc1] | (S)-2-(3-(4-methoxyphenyl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 81 | 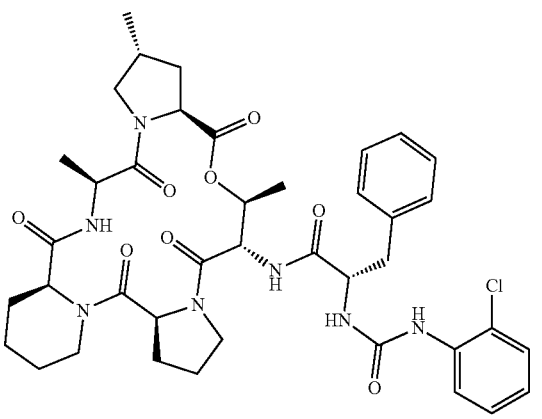 [SMILES: C[C@@H]1C[C@H]2C(=O)O[C@@H](C)[C@H](NC(=O)[C@H](Cc3ccccc3)NC(=O)Nc3ccccc3Cl)C(=O)N3CCC[C@H]3C(=O)N3CCCC[C@H]3C(=O)N[C@@H](C)C(=O)N2C1] | (S)-2-(3-(2-chlorophenyl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|---|---|---|
| 82 | 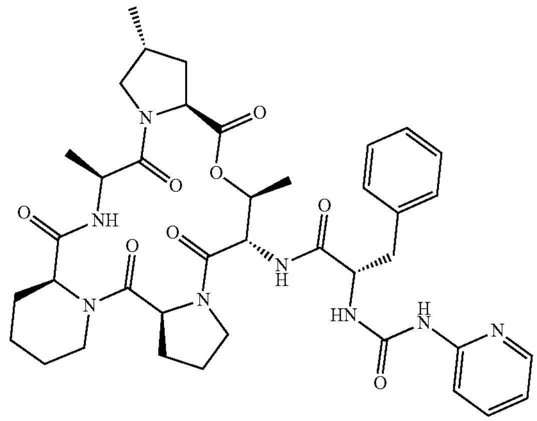 [SMILES: C[C@@H]1C[C@H]2C(=O)O[C@@H](C)[C@H](NC(=O)[C@H](Cc3ccccc3)NC(=O)Nc3ccccn3)C(=O)N3CCC[C@H]3C(=O)N3CCCC[C@H]3C(=O)N[C@@H](C)C(=O)N2C1] | (S)-3-phenyl-2-(3-(pyridin-2-yl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 83 | 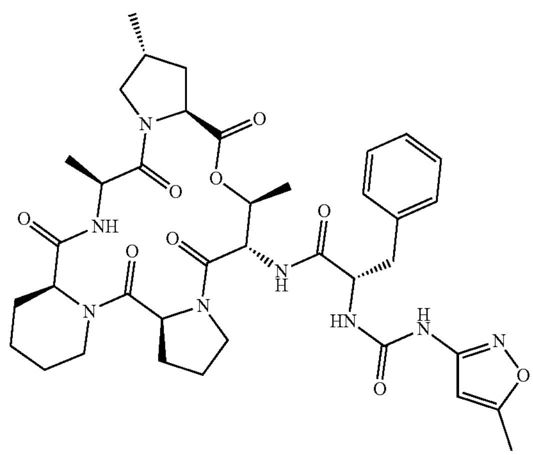 [SMILES: Cc1cc(NC(=O)N[C@@H](Cc2ccccc2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)no1] | (S)-2-(3-(5-methylisoxazol-3-yl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 84 | 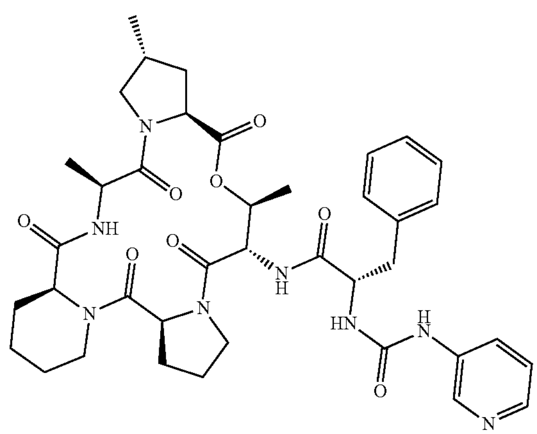 [SMILES: C[C@@H]1C[C@H]2C(=O)O[C@@H](C)[C@H](NC(=O)[C@H](Cc3ccccc3)NC(=O)Nc3cccnc3)C(=O)N3CCC[C@H]3C(=O)N3CCCC[C@H]3C(=O)N[C@@H](C)C(=O)N2C1] | (S)-3-phenyl-2-(3-(pyridin-3-yl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|---|---|---|
| 85 | 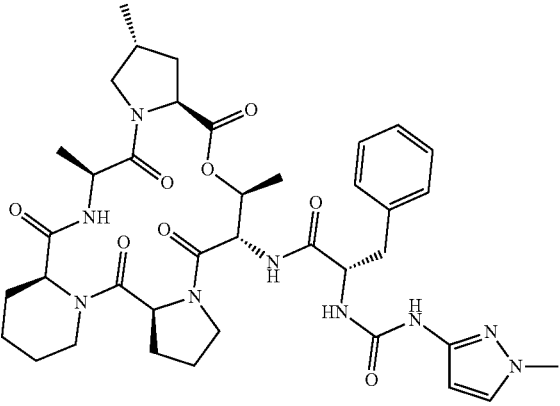 [SMILES: C[C@@H]1C[C@H]2C(=O)O[C@@H](C)[C@H](NC(=O)[C@H](Cc3ccccc3)NC(=O)Nc3ccn(C)n3)C(=O)N3CCC[C@H]3C(=O)N3CCCC[C@H]3C(=O)N[C@@H](C)C(=O)N2C1] | (S)-2-(3-(1-methyl-1H-pyrazol-3-yl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 86 | 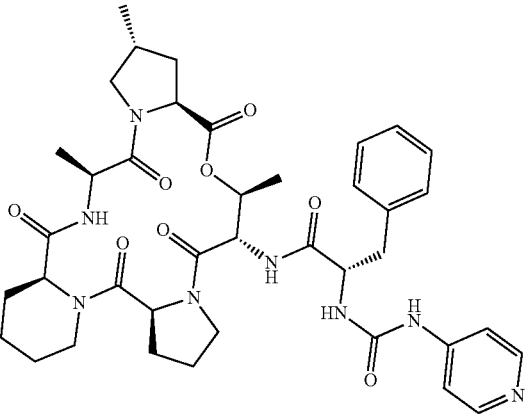 [SMILES: C[C@@H]1C[C@H]2C(=O)O[C@@H](C)[C@H](NC(=O)[C@H](Cc3ccccc3)NC(=O)Nc3ccncc3)C(=O)N3CCC[C@H]3C(=O)N3CCCC[C@H]3C(=O)N[C@@H](C)C(=O)N2C1] | (S)-3-phenyl-2-(3-(pyridin-4-yl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 87 | 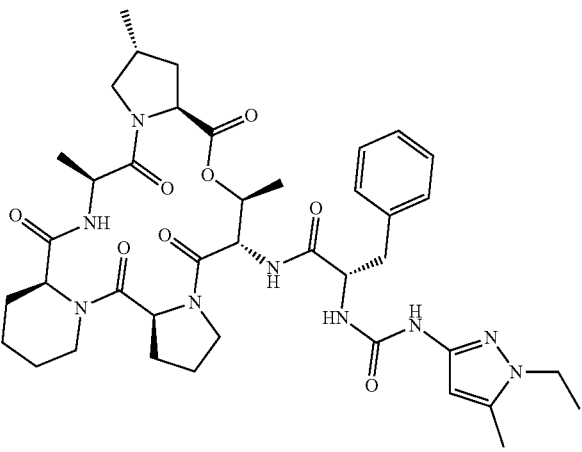 [SMILES: CCn1nc(NC(=O)N[C@@H](Cc2ccccc2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)cc1C] | (S)-2-(3-(1-ethyl-5-methyl-1H-pyrazol-3-yl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|---|---|---|
| 88 | 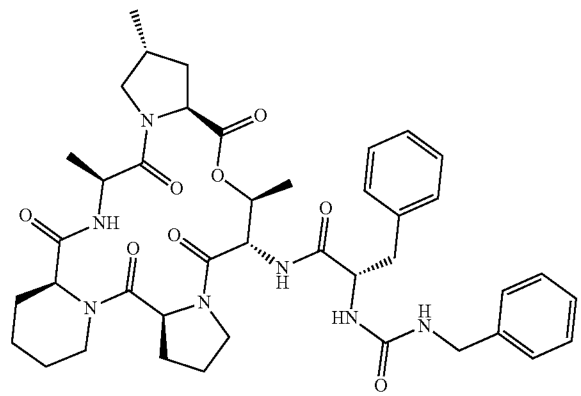 [SMILES: C[C@@H]1C[C@H]2C(=O)O[C@@H](C)[C@H](NC(=O)[C@H](Cc3ccccc3)NC(=O)NCc3ccccc3)C(=O)N3CCC[C@H]3C(=O)N3CCCC[C@H]3C(=O)N[C@@H](C)C(=O)N2C1] | (S)-2-(3-benzylureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 89 | 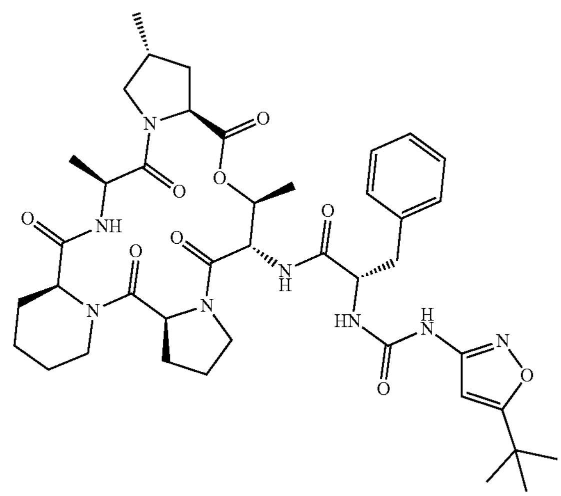 [SMILES: C[C@@H]1C[C@H]2C(=O)O[C@@H](C)[C@H](NC(=O)[C@H](Cc3ccccc3)NC(=O)Nc3cc(C(C)(C)C)on3)C(=O)N3CCC[C@H]3C(=O)N3CCCC[C@H]3C(=O)N[C@@H](C)C(=O)N2C1] | (S)-2-(3-(5-(tert-butyl)isoxazol-3-yl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 90 | 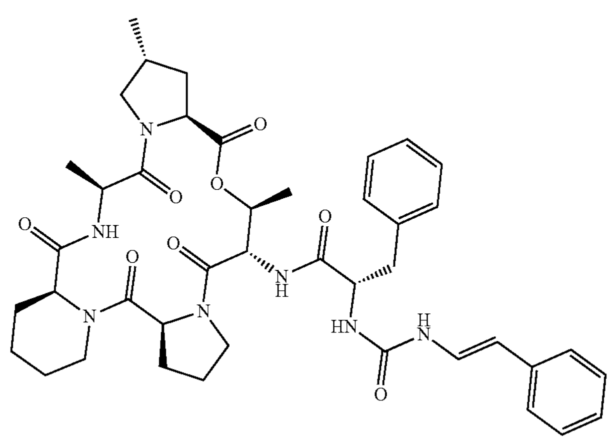 [SMILES: C[C@@H]1C[C@H]2C(=O)O[C@@H](C)[C@H](NC(=O)[C@H](Cc3ccccc3)NC(=O)N/C=C/c3ccccc3)C(=O)N3CCC[C@H]3C(=O)N3CCCC[C@H]3C(=O)N[C@@H](C)C(=O)N2C1] | (S)-3-phenyl-2-(3-((E)-styryl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|---|---|---|
| 91 | 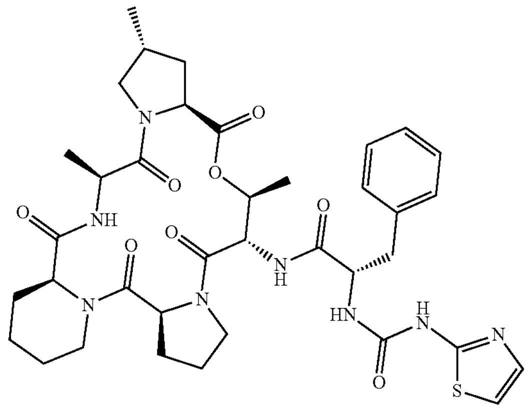 [SMILES: C[C@@H]1C[C@H]2C(=O)O[C@@H](C)[C@H](NC(=O)[C@H](Cc3ccccc3)NC(=O)Nc3nccs3)C(=O)N3CCC[C@H]3C(=O)N3CCCC[C@H]3C(=O)N[C@@H](C)C(=O)N2C1] | (S)-3-phenyl-2-(3-(thiazol-2-yl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 92 | 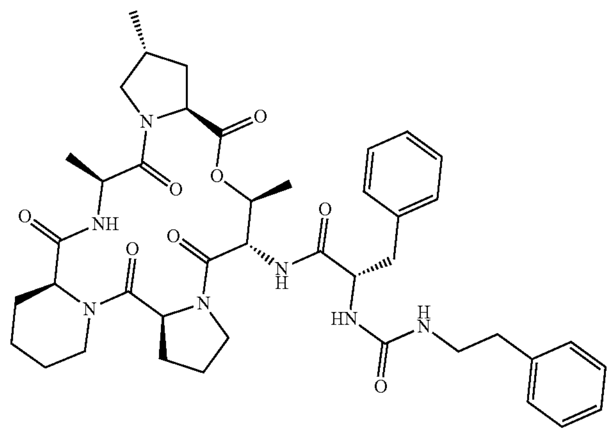 [SMILES: C[C@@H]1C[C@H]2C(=O)O[C@@H](C)[C@H](NC(=O)[C@H](Cc3ccccc3)NC(=O)NCCc3ccccc3)C(=O)N3CCC[C@H]3C(=O)N3CCCC[C@H]3C(=O)N[C@@H](C)C(=O)N2C1] | (S)-2-(3-phenethylureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 93 | 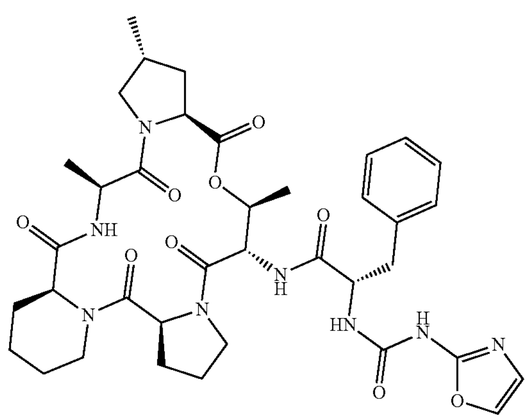 [SMILES: C[C@@H]1C[C@H]2C(=O)O[C@@H](C)[C@H](NC(=O)[C@H](Cc3ccccc3)NC(=O)Nc3ncco3)C(=O)N3CCC[C@H]3C(=O)N3CCCC[C@H]3C(=O)N[C@@H](C)C(=O)N2C1] | (S)-2-(3-(oxazol-2-yl)ureido)-3-phenyl-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
| --- | --- | --- |
| 94 | 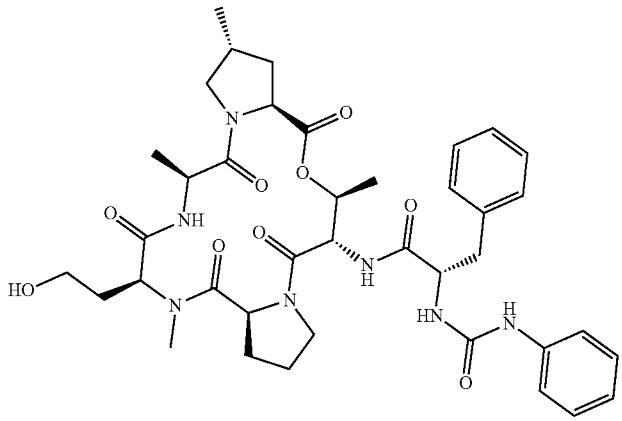 [SMILES: C[C@@H]1C[C@H]2C(=O)O[C@@H](C)[C@H](NC(=O)[C@H](Cc3ccccc3)NC(=O)Nc3ccccc3)C(=O)N3CCC[C@H]3C(=O)N(C)[C@@H](CCO)C(=O)N[C@@H](C)C(=O)N2C1] | (S)-N-((2R,6S,9S,11aS,17S,18S,20aS)-9-(2-hydroxyethyl)-2,6,10,18-tetramethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-3-phenyl-2-(3-phenylureido)propanamide |
| 95 | 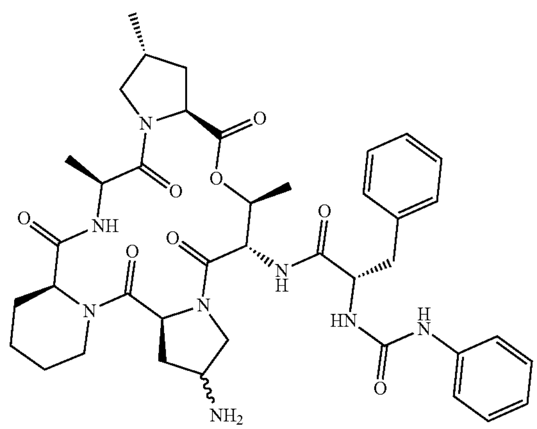 | (2S)-N-((2R,6S,8aS,14aS,20S,21S,23aS)-16-amino-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-phenylureido)propanamide |
| 96 | 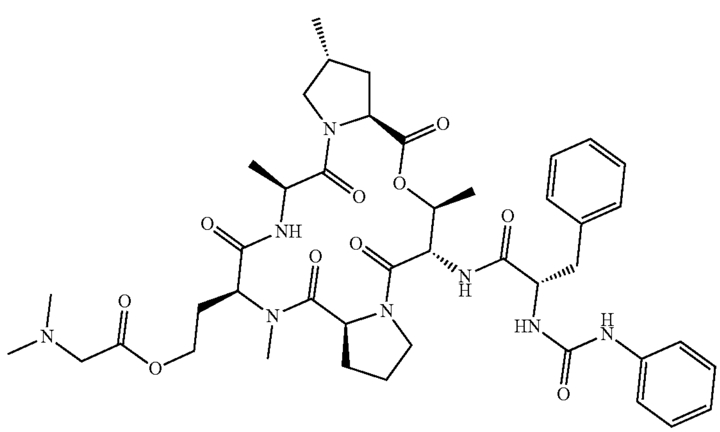 [SMILES: C[C@@H]1C[C@H]2C(=O)O[C@@H](C)[C@H](NC(=O)[C@H](Cc3ccccc3)NC(=O)Nc3ccccc3)C(=O)N3CCC[C@H]3C(=O)N(C)[C@@H](CCOC(=O)CN(C)C)C(=O)N[C@@H](C)C(=O)N2C1] | 2-((2R,6S,9S,11aS,17S,18S,20aS)-2,6,10,18-tetramethyl-5,8,11,16,20-pentaoxo-17-((S)-3-phenyl-2-(3-phenylureido)propanamido)hexadecahydro-1H,5H,16H-dipyrrolo[2,1-c:2'1'-1][1]oxa[4,7,10,13]tetraazacyclohexadecin-9-yl)ethyldimethylglycinate |

TABLE 8-continued

| No. | Structure | Name |
| --- | --- | --- |
| 97 | 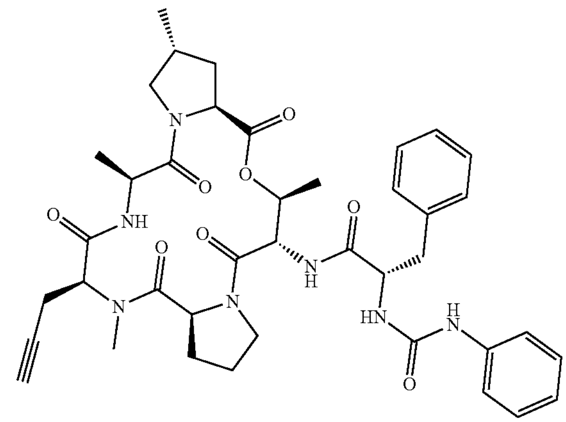 [SMILES: C#CC[C@H]1C(=O)N[C@@H](C)C(=O)N2C[C@H](C)C[C@H]2C(=O)O[C@@H](C)[C@H](NC(=O)[C@H](Cc2ccccc2)NC(=O)Nc2ccccc2)C(=O)N2CCC[C@H]2C(=O)N1C] | (S)-3-phenyl-2-(3-phenylureido)-N-((2R,6S,9S,11aS,17S,18S,20aS)-2,6,10,18-tetramethyl-5,8,11,16,20-pentaoxo-9-(prop-2-yn-1-yl)hexadecahydro-1H,5H,16H-dipyrrolo[2,1-c:2',1'-1][1]oxa[4,7,10,13]tetraazacyclohexadecin-17-yl)propanamide |
| 98 | 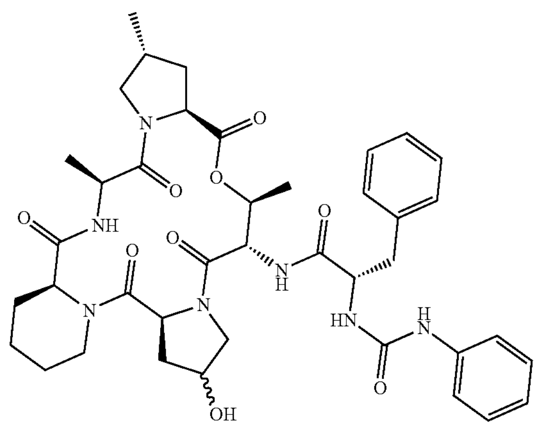 | (2S)-N-((2R,6S,8aS,14aS,20S,21S,23aS)-16-hydroxy-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-phenylureido)propanamide |
| 99 | 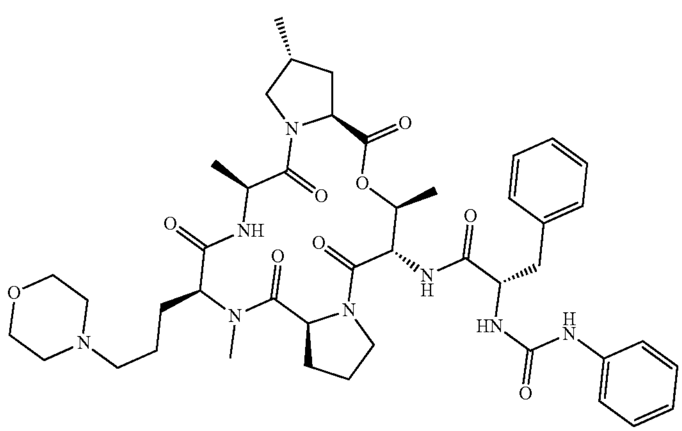 [SMILES: C[C@@H]1C[C@H]2C(=O)O[C@@H](C)[C@H](NC(=O)[C@H](Cc3ccccc3)NC(=O)Nc3ccccc3)C(=O)N3CCC[C@H]3C(=O)N(C)[C@@H](CCCN3CCOCC3)C(=O)N[C@@H](C)C(=O)N2C1] | (S)-3-phenyl-2-(3-phenylureido)-N-((2R,6S,9S,11aS,17S,18S,20aS)-2,6,10,18-tetramethyl-9-(3-morpholinopropyl)-5,8,11,16,20-pentaoxohexadecahydro-1H,5H,16H-dipyrrolo[2,1-c:2',1'-1][1]oxa[4,7,10,13]tetraazacyclohexadecin-17-yl)propanamide |

TABLE 8-continued

| No. | Structure | Name |
| --- | --- | --- |
| 100 | 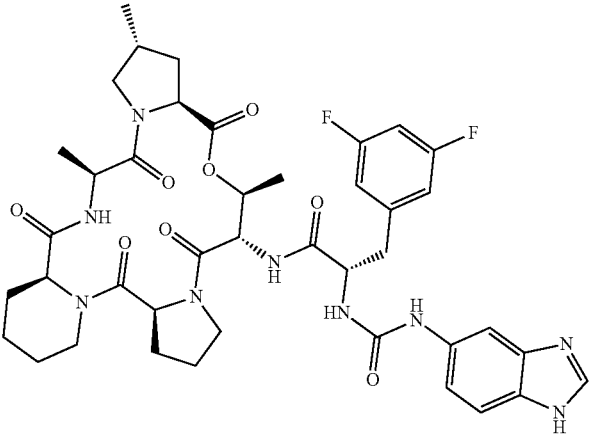 [SMILES: C[C@@H]1C[C@H]2C(=O)O[C@@H](C)[C@H](NC(=O)[C@H](Cc3cc(F)cc(F)c3)NC(=O)Nc3ccc4[nH]cnc4c3)C(=O)N3CCC[C@H]3C(=O)N3CCCC[C@H]3C(=O)N[C@@H](C)C(=O)N2C1] | (S)-2-(3-(1H-benzo[d]imidazol-5-yl)ureido)-3-(3,5-difluorophenyl)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 101 | 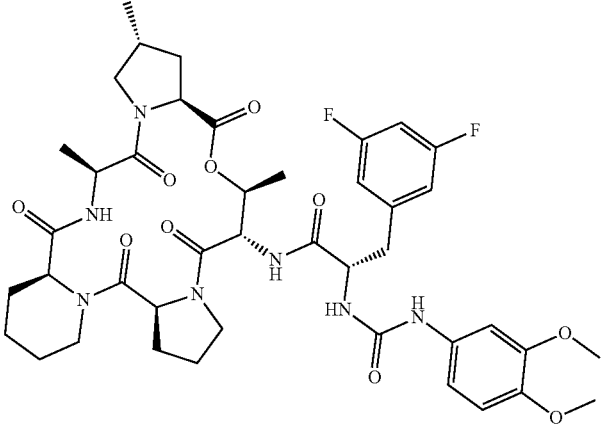 [SMILES: COc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)cc1OC] | (S)-3-(3,5-difluorophenyl)-2-(3-(3,4-dimethoxyphenyl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 102 | 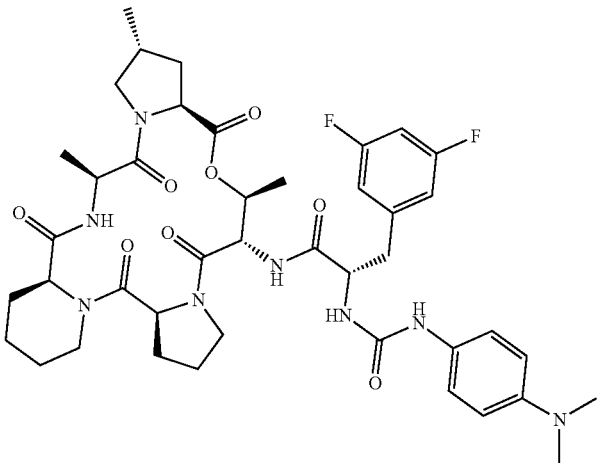 [SMILES: C[C@@H]1C[C@H]2C(=O)O[C@@H](C)[C@H](NC(=O)[C@H](Cc3cc(F)cc(F)c3)NC(=O)Nc3ccc(N(C)C)cc3)C(=O)N3CCC[C@H]3C(=O)N3CCCC[C@H]3C(=O)N[C@@H](C)C(=O)N2C1] | (S)-3-(3,5-difluorophenyl)-2-(3-(4-(dimethylamino)phenyl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|---|---|---|
| 103 | 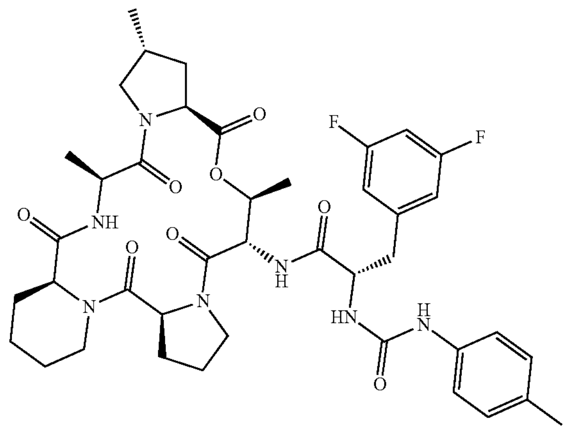 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)cc1] | (S)-3-(3,5-difluorophenyl)-2-(3-(p-tolyl)ureido)-N-((2R,6S,8aS,14aS,20S,21R,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 104 | 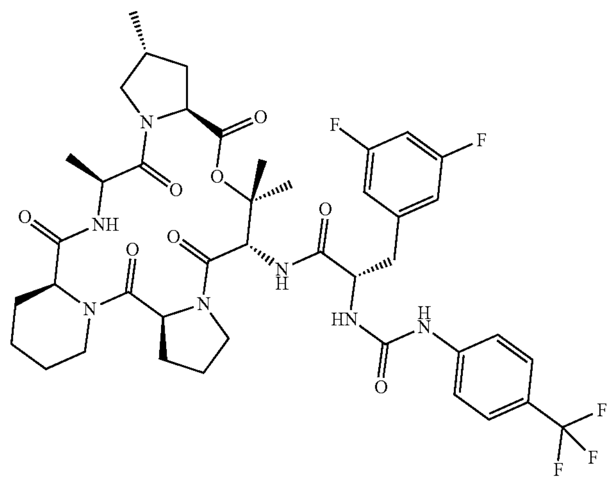 | (S)-3-(3,5-difluorophenyl)-N-((2R,6S,8aS,14aS,20S,23aS)-2,6,21,21-tetramethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(4-(trifluoromethyl)phenyl)ureido)propanamide |
| 105 | 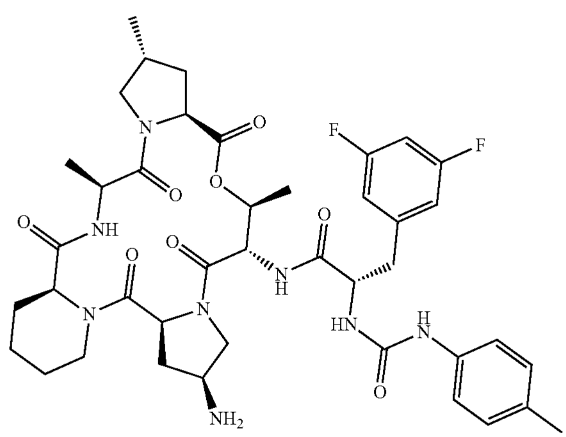 [SMILES: Cc1ccc(NC(=O)N[C@@H](Cc2cc(F)cc(F)c2)C(=O)N[C@@H]2C(=O)N3C[C@@H](N)C[C@H]3C(=O)N3CCCC[C@H]3C(=O)N[C@@H](C)C(=O)N3C[C@H](C)C[C@H]3C(=O)O[C@H]2C)cc1] | (S)-N-((2R,6S,8aS,14aS,16S,20S,21S,23aS)-16-amino-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-(3,5-difluorophenyl)-2-(3-(p-tolyl)ureido)propanamide |

TABLE 8-continued

| No. | Structure | Name |
|---|---|---|
| 106 | | (S)-3-(3,5-difluorophenyl)-N-((2R,6S,9S,11aS,17S,18S,20aS)-2,6,9,10,18-pentamethyl-5,8,11,16,20-pentaoxohexadecahydro-1H,5H,16H-dipyrrolo[2,1-c:2',1'-1][1]oxa|4,7,10,13]tetraazacyclohexadecin-17-yl)-2-(3-(p-tolyl)ureido)propanamide |
| 107 | 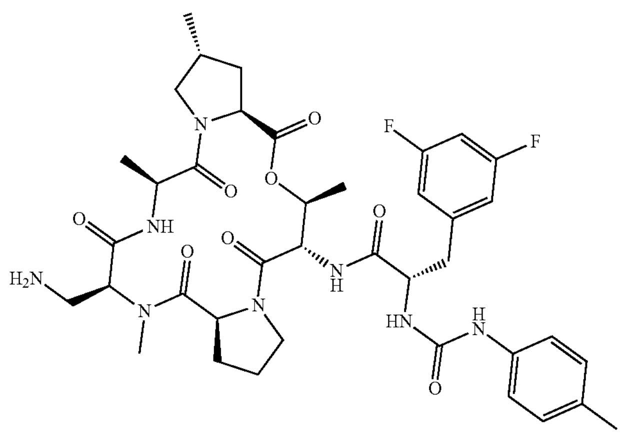 [SMILES: Cc1ccc(NC(=O)N[C@@H](Cc2cc(F)cc(F)c2)C(=O)N[C@@H]2C(=O)N3CCC[C@H]3C(=O)N(C)[C@@H](CN)C(=O)N[C@@H](C)C(=O)N3C[C@H](C)C[C@H]3C(=O)O[C@H]2C)cc1] | (S)-N-((2R,6S,9S,11aS,17S,18S,20aS)-9-(aminomethyl)-2,6,10,18-tetramethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-3-(3,5-difluorophenyl)-2-(3-(p-tolyl)ureido)propanamide |
| 108 | 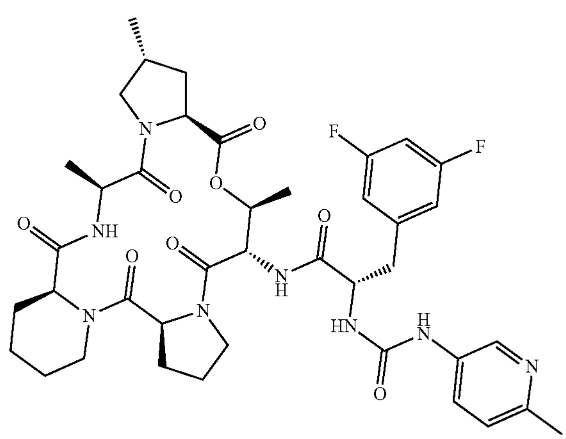 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)cn1] | (S)-3-(3,5-difluorophenyl)-2-(3-(6-methylpyridin-3-yl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|-----|-----------|------|
| 109 | 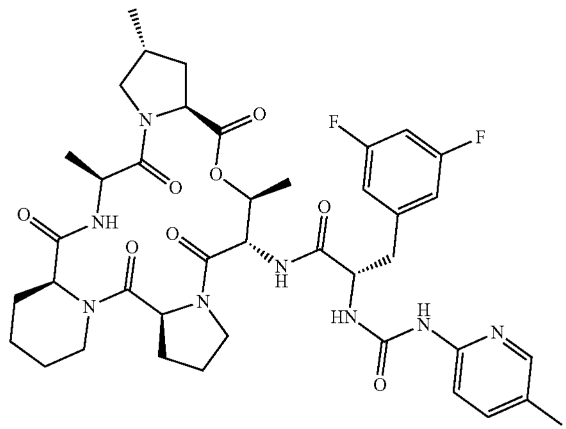 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)nc1] | (S)-3-(3,5-difluorophenyl)-2-(3-(5-methylpyridin-2-yl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 110 | 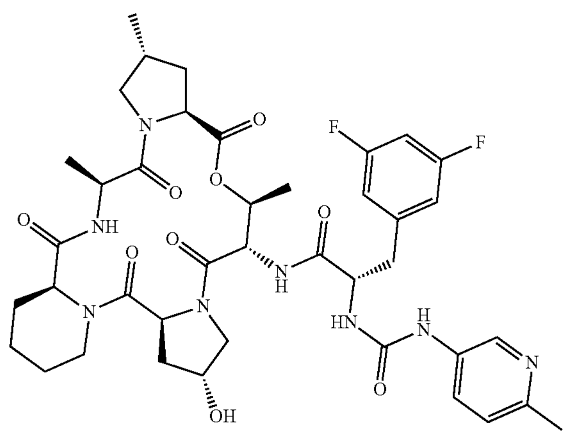 [SMILES: Cc1ccc(NC(=O)N[C@@H](Cc2cc(F)cc(F)c2)C(=O)N[C@@H]2C(=O)N3C[C@H](O)C[C@H]3C(=O)N3CCCC[C@H]3C(=O)N[C@@H](C)C(=O)N3C[C@H](C)C[C@H]3C(=O)O[C@H]2C)cn1] | (S)-3-(3,5-difluorophenyl)-N-((2R,6S,8aS,14aS,16R,20S,21S,23aS)-16-hydroxy-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(6-methylpyridin-3-yl)ureido)propanamide |
| 111 | 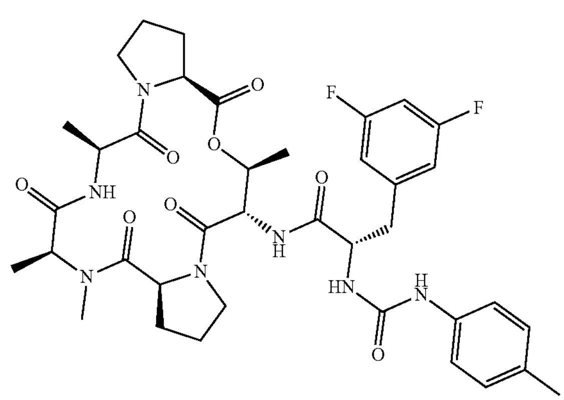 | (S)-3-(3,5-difluorophenyl)-N-((6S,9S,11aS,17S,18S,20aS)-6,9,10,18-tetramethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-2-(3-(p-tolyl)ureido)propanamide |

TABLE 8-continued

| No. | Structure | Name |
|---|---|---|
| 112 | 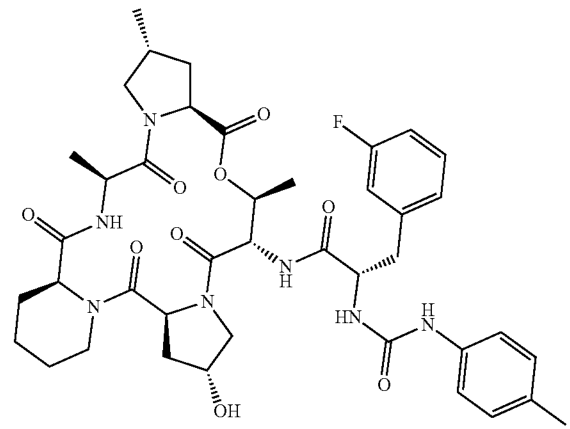 [SMILES: Cc1ccc(NC(=O)N[C@@H](Cc2cccc(F)c2)C(=O)N[C@@H]2C(=O)N3C[C@H](O)C[C@H]3C(=O)N3CCCC[C@H]3C(=O)N[C@@H](C)C(=O)N3C[C@H](C)C[C@H]3C(=O)O[C@H]2C)cc1] | (S)-3-(3-fluorophenyl)-N-((2R,6S,8aS,14aS,16R,20S,21S,23aS)-16-hydroxy-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(p-tolyl)ureido)propanamide |
| 113 | 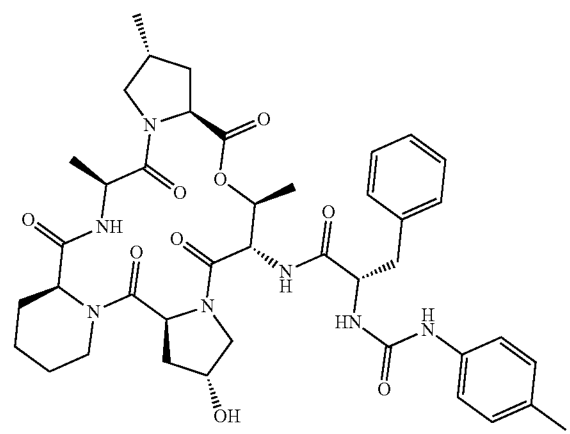 [SMILES: Cc1ccc(NC(=O)N[C@@H](Cc2ccccc2)C(=O)N[C@@H]2C(=O)N3C[C@H](O)C[C@H]3C(=O)N3CCCC[C@H]3C(=O)N[C@@H](C)C(=O)N3C[C@H](C)C[C@H]3C(=O)O[C@H]2C)cc1] | (S)-N-((2R,6S,8aS,14aS,16R,20S,21S,23aS)-16-hydroxy-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(p-tolyl)ureido)propanamide |
| 114 | 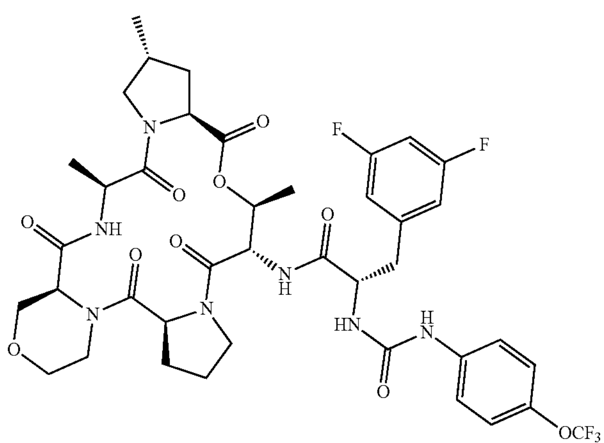 [SMILES: C[C@@H]1C[C@H]2C(=O)O[C@@H](C)[C@H](NC(=O)[C@H](Cc3cc(F)cc(F)c3)NC(=O)Nc3ccc(OC(F)(F)F)cc3)C(=O)N3CCC[C@H]3C(=O)N3CCOC[C@H]3C(=O)N[C@@H](C)C(=O)N2C1] | (S)-3-(3,5-difluorophenyl)-2-(3-(4-(trifluoromethoxy)phenyl)ureido)-N-((6aS,12S,13S,15aS,17R,21S,23aS)-13,17,21-trimethy-6,11,15,20,23-pentaoxooctadecahydro-6H,11H,15H-[1,4]oxazino[3,4-i]dipyrrolo[2,1-c:2',1'-1][1]oxa[4,7,10,13]tetraazacyclohexadecin-12-yl)propanamide |

TABLE 8-continued

| No. | Structure | Name |
| --- | --- | --- |
| 115 | 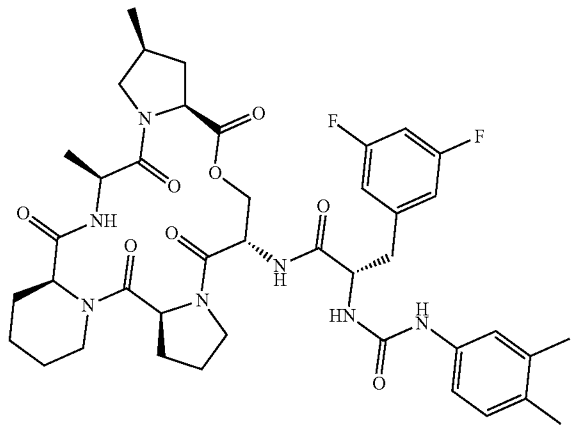 [SMILES: Cc1ccc(NC(=O)N[C@@H](Cc2cc(F)cc(F)c2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)cc1C] | (S)-3-(3,5-difluorophenyl)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-l][1]oxa[4,7,10,13]tetraazacyclohexadecin-20-yl)-2-(3-(3,4-dimethylphenyl)ureido)propanamide |
| 119 | 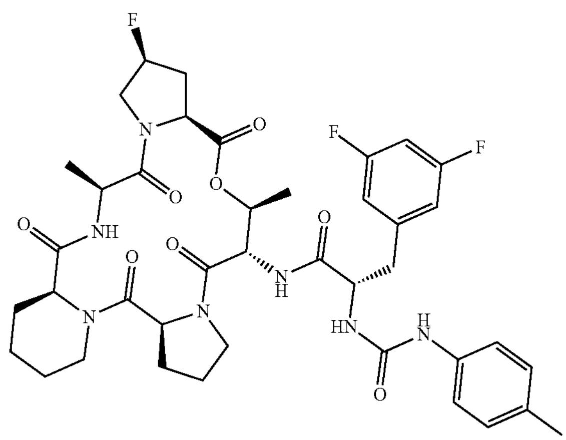 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@@H](F)C[C@H]3C(=O)O[C@H]2C)cc1] | (S)-3-(3,5-difluorophenyl)-N-((2S,6S,8aS,14aS,20S,21S,23aS)-2-fluoro-6,21-dimethyl-5,8,14,19,23-pentaoxooctadecahydro-1H,5H,14H,19H-pyrido[2,1-i]dipyrrolo[2,1-c:2',1'-l][1]oxa[4,7,10,13]tetraazacyclohexadecin-20-yl)-2-(3-(p-tolyl)ureido)propanamide |
| 120 | 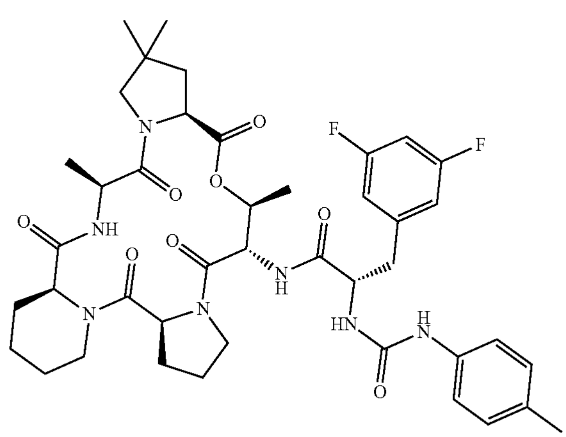 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3CC(C)(C)C[C@H]3C(=O)O[C@H]2C)cc1] | (S)-3-(3,5-difluorophenyl)-N-((6S,8aS,14aS,20S,21S,23aS)-2,2,6,21-tetramethyl-5,8,14,19,23-pentaoxooctadecahydro-1H,5H,14H,19H-pyrido[2,1-i]dipyrrolo[2,1-c:2',1'-l][1]oxa[4,7,10,13]tetraazacyclohexadecin-20-yl)-2-(3-(p-tolyl)ureido)propanamide |

TABLE 8-continued

| No. | Structure | Name |
|---|---|---|
| 121 | 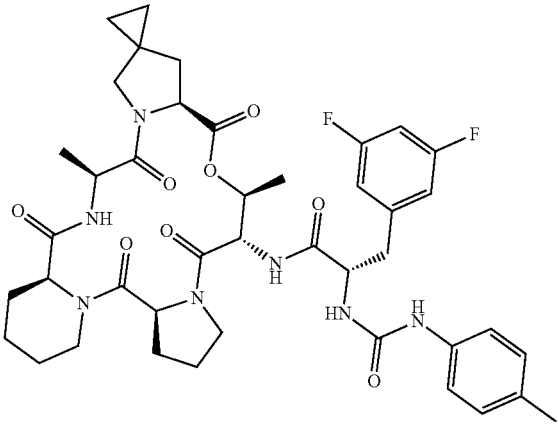 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3CC4(CC4)C[C@H]3C(=O)O[C@H]2C)cc1] | (S)-3-(3,5-difluorophenyl)-N-((6'S,8a'S,14a'S,20'S,21'S,23a'S)-6',21'-dimethyl-5',8',14',19',23'-pentaoxohexadecahydro-1'H,3'H,5'H,14'H,19'H-spiro[cyclopropane-1,2'-pyrido[2,1-i]dipyrrolo[2,1-c:2',1'-1][1]oxa[4,7,10,13]tetraazacyclohexadecin]-20'-yl)-2-(3-(p-tolyl)ureido)propanamide |
| 122 | 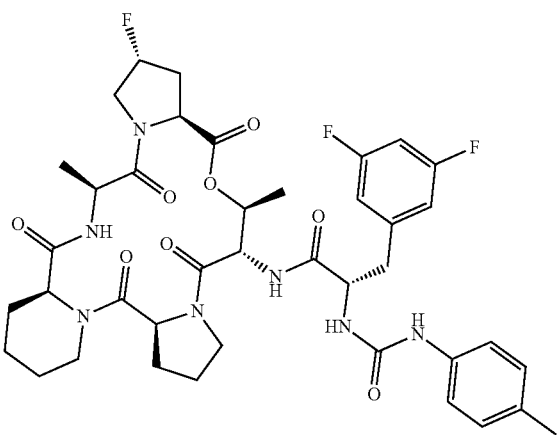 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@H](F)C[C@H]3C(=O)O[C@H]2C)cc1] | (S)-3-(3,5-dinuorophenyl)-N-((2R,6S,8aS,14aS,20S,21S,23aS)-2-fluoro-6,21-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(p-tolyl)ureido)propanamide |
| 123 | 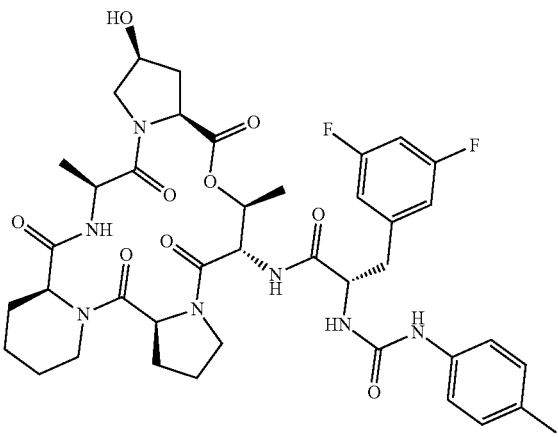 | (S)-3-(3,5-difluorophenyl)-N-((2S,6S,8aS,14aS,20S,21S,23aS)-2-hydroxy-6,21-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(p-tolyl)ureido)propanamide |

TABLE 8-continued

| No. | Structure | Name |
|---|---|---|
| 124 | 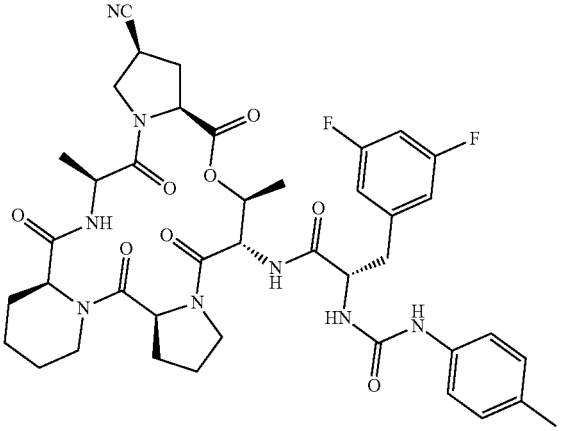 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@@H](C#N)C[C@H]3C(=O)O[C@H]2C)cc1] | (S)-N-((2S,6S,8aS,14aS,20S,21S,23aS)-2-cyano-6,21-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-(3,5-difluorophenyl)-2-(3-(p-tolyl)ureido)propanamide |
| 125 | 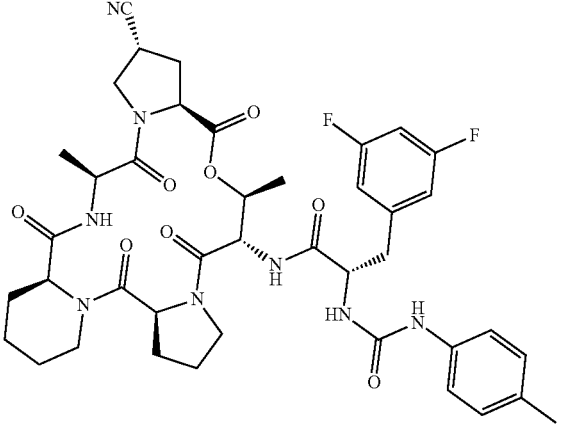 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@H](C#N)C[C@H]3C(=O)O[C@H]2C)cc1] | (S)-N-((2R,6S,8aS,14aS,20S,21S,23aS)-2-cyano-6,21-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-(3,5-difluorophenyl)-2-(3-(p-tolyl)ureido)propanamide |
| 126 | 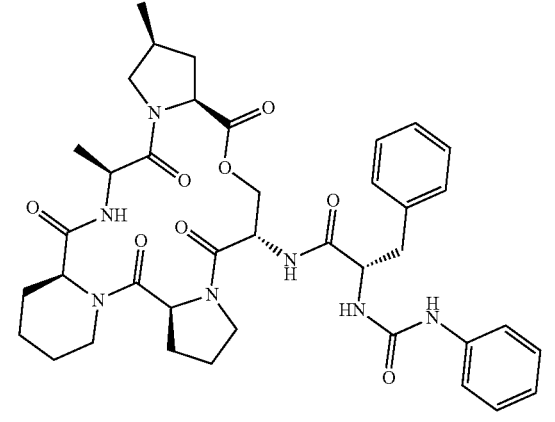 [SMILES: C[C@H]1C[C@H]2C(=O)OC[C@H](NC(=O)[C@H](Cc3ccccc3)NC(=O)Nc3ccccc3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-phenylureido)propanamide |

TABLE 8-continued

| No. | Structure | Name |
|---|---|---|
| 127 | 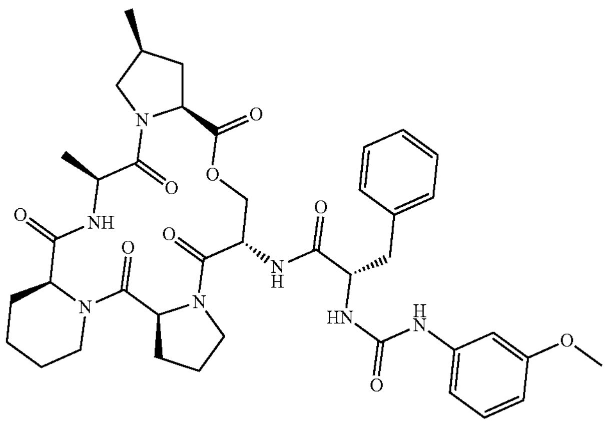 [SMILES: COc1cccc(NC(=O)N[C@@H](Cc2ccccc2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)c1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2'1'-1][1]oxa[4,7,10,13]tetraazacyclohexadecin-20-yl)-2-(3-(3-methoxyphenyl)ureido)-3-phenylpropanamide |
| 128 | 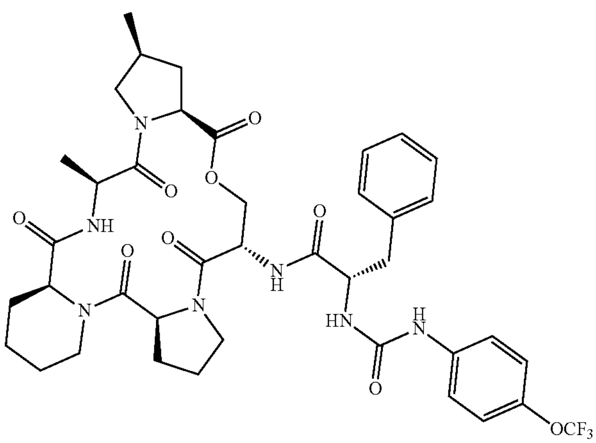 [SMILES: C[C@H]1C[C@H]2C(=O)OC[C@H](NC(=O)[C@H](Cc3ccccc3)NC(=O)Nc3ccc(OC(F)(F)F)cc3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2;1-c:2',1'-1][1]oxa[4,7,10,13]tetraazacyclohexadecin-20-yl)-3-phenyl-2-(3-(4-(trifluoromethoxy)phenyl)ureido)propanamide |
| 129 | 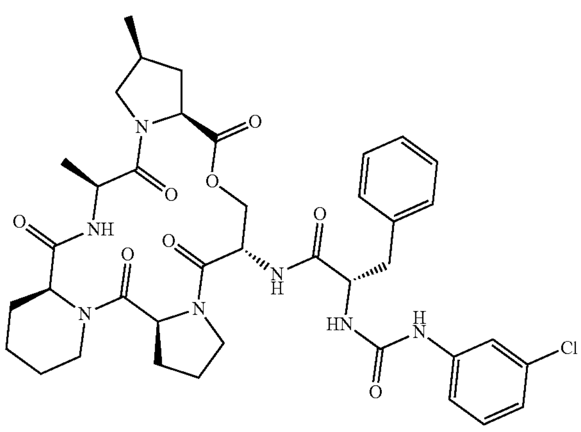 [SMILES: C[C@H]1C[C@H]2C(=O)OC[C@H](NC(=O)[C@H](Cc3ccccc3)NC(=O)Nc3cccc(Cl)c3)C(=O)N3CCC[C@H]3C(=O)N3CCCC[C@H]3C(=O)N[C@@H](C)C(=O)N2C1] | (S)-2-(3-(3-chlorophenyl)ureido)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenylpropanamide |

TABLE 8-continued

| No. | Structure | Name |
| --- | --- | --- |
| 130 | 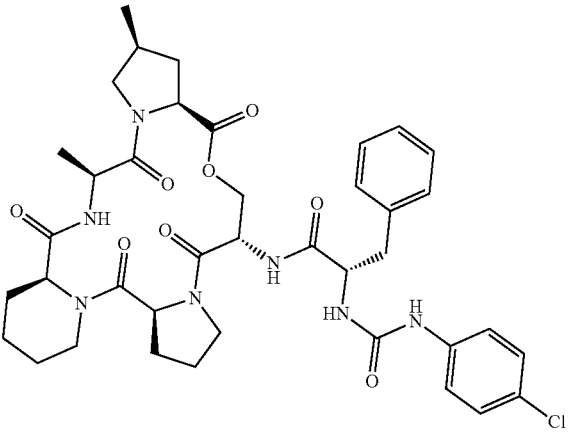 [SMILES: C[C@H]1C[C@H]2C(=O)OC[C@H](NC(=O)[C@H](Cc3ccccc3)NC(=O)Nc3ccc(Cl)cc3)C(=O)N3CCC[C@H]3C(=O)N3CCCC[C@H]3C(=O)N[C@@H](C)C(=O)N2C1] | (S)-2-(3-(4-chlorophenyl)ureido)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenylpropanamide |
| 131 | 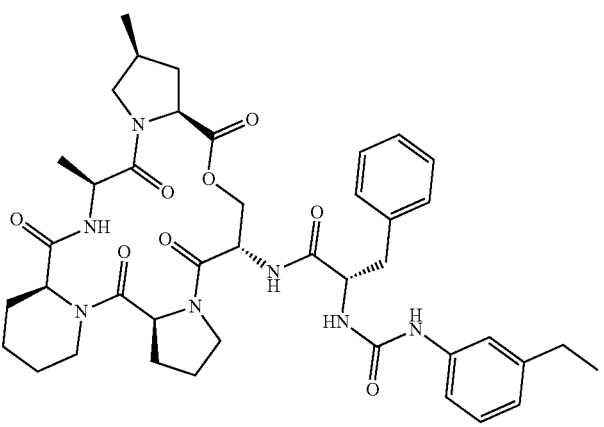 [SMILES: CCc1cccc(NC(=O)N[C@@H](Cc2ccccc2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)c1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(3-ethylphenyl)ureido)-3-phenylpropanamide |
| 132 | 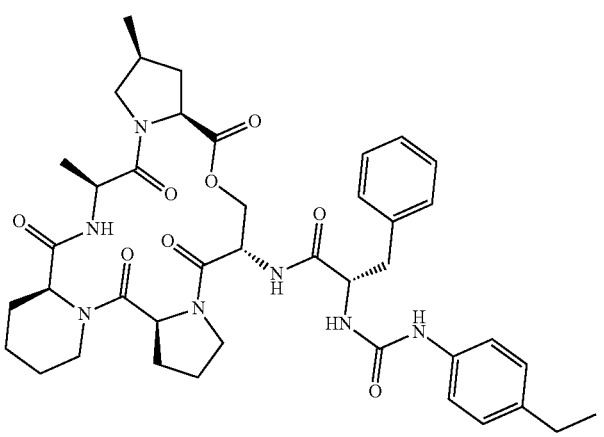 [SMILES: CCc1ccc(NC(=O)N[C@@H](Cc2ccccc2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)cc1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]-oxa[4,7,10,13]tetraazacyclohexadecin-20-yl)-2-(3-(4-ethylphenyl)ureido)-3-phenylpropanamide |

TABLE 8-continued

| No. | Structure | Name |
|---|---|---|
| 133 | 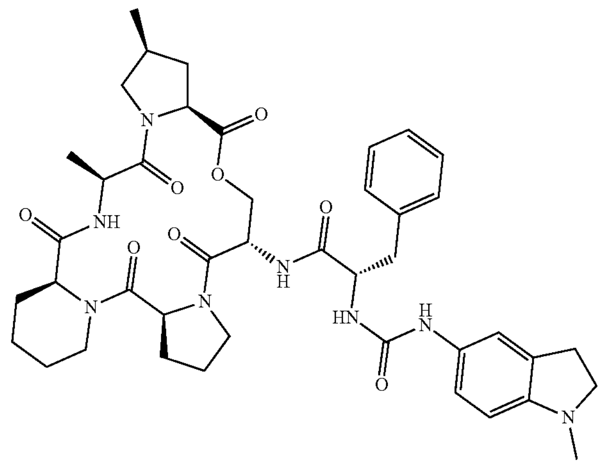 [SMILES: C[C@H]1C[C@H]2C(=O)OC[C@H](NC(=O)[C@H](Cc3ccccc3)NC(=O)Nc3ccc4c(c3)CCN4C)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(1-methylindolin-5-yl)ureido)-3-phenylpropanamide |
| 134 | 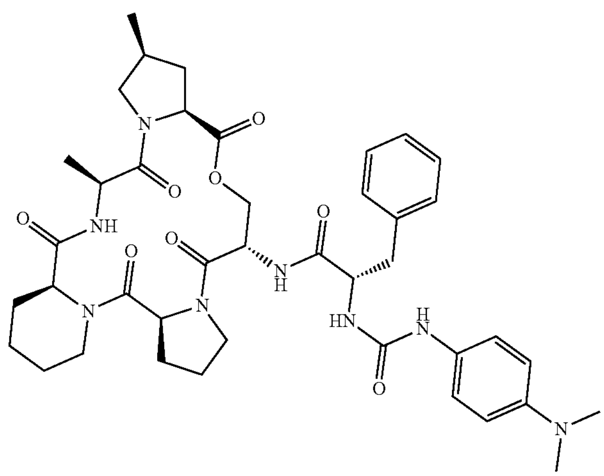 [SMILES: C[C@H]1C[C@H]2C(=O)OC[C@H](NC(=O)[C@H](Cc3ccccc3)NC(=O)Nc3ccc(N(C)C)cc3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(4-(dimethylamino)phenyl)ureido)-3-phenylpropanamide |
| 135 | 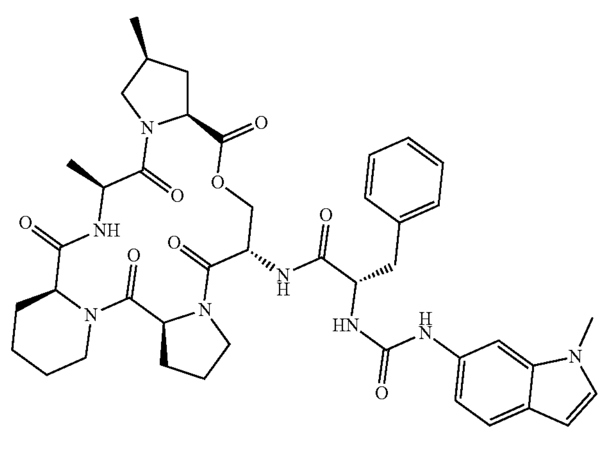 [SMILES: C[C@H]1C[C@H]2C(=O)OC[C@H](NC(=O)[C@H](Cc3ccccc3)NC(=O)Nc3ccc4ccn(C)c4c3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(1-methyl-1H-indol-6-yl)ureido)-3-phenylpropanamide |

TABLE 8-continued

| No. | Structure | Name |
|---|---|---|
| 136 | 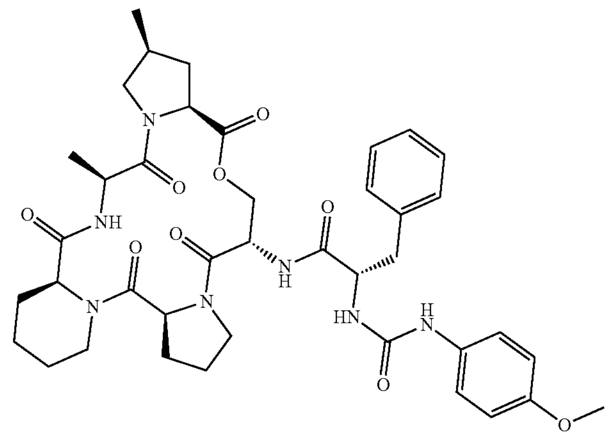 [SMILES: COc1ccc(NC(=O)N[C@@H](Cc2ccccc2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)cc1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(4-methoxyphenyl)ureido)-3-phenylpropanamide |
| 137 | | (S)-2-(3-(2-chlorophenyl)ureido)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenylpropanamide |
| 138 | 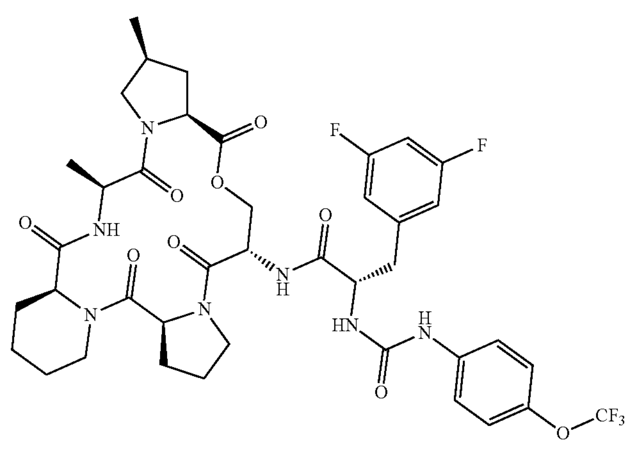 [SMILES: C[C@H]1C[C@H]2C(=O)OC[C@H](NC(=O)[C@H](Cc3cc(F)cc(F)c3)NC(=O)Nc3ccc(OC(F)(F)F)cc3)C(=O)N3CCC[C@H]3C(=O)N3CCCC[C@H]3C(=O)N[C@@H](C)C(=O)N2C1] | (S)-3-(3,5-difluorophenyl)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(4-(trifluoromethoxy)phenyl)ureido)propanamide |

TABLE 8-continued

| No. | Structure | Name |
|---|---|---|
| 139 | 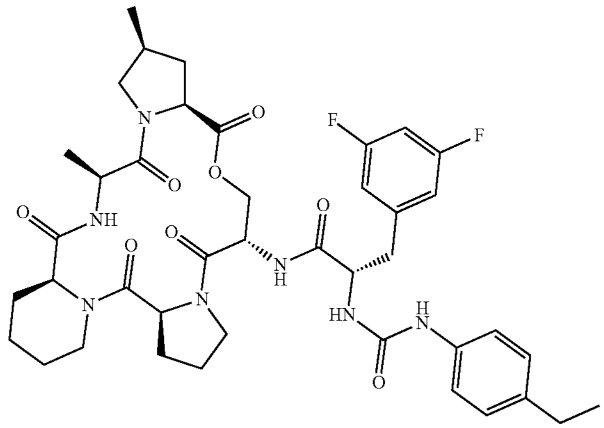 [SMILES: CCc1ccc(NC(=O)N[C@@H](Cc2cc(F)cc(F)c2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)cc1] | (S)-3-(3,5-difluorophenyl)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(4-ethylphenyl)ureido)propanamide |
| 140 | 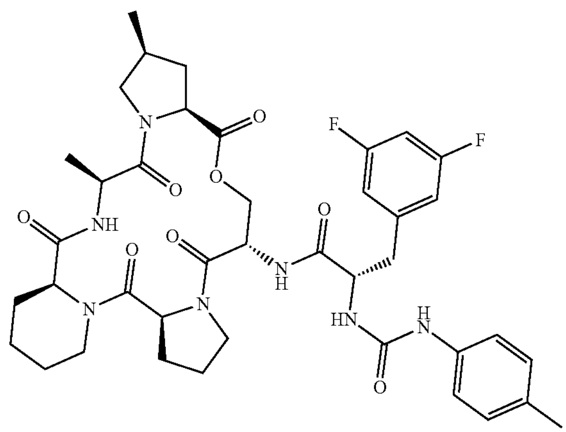 [SMILES: Cc1ccc(NC(=O)N[C@@H](Cc2cc(F)cc(F)c2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)cc1] | (S)-3-(3,5-dinuorophenyl)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(p-tolyl)ureido)propanamide |
| 141 | 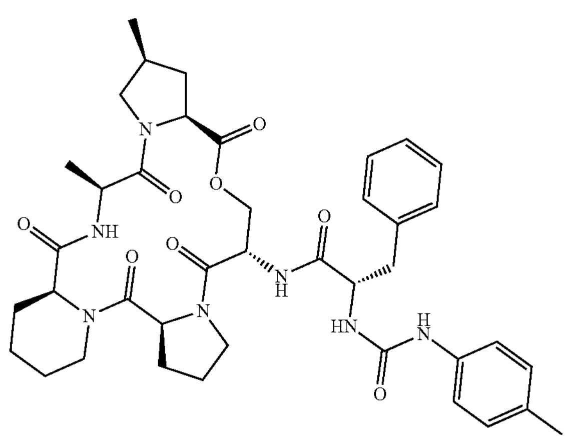 [SMILES: Cc1ccc(NC(=O)N[C@@H](Cc2ccccc2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)cc1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(p-tolyl)ureido)propanamide |

TABLE 8-continued

| No. | Structure | Name |
|---|---|---|
| 142 | 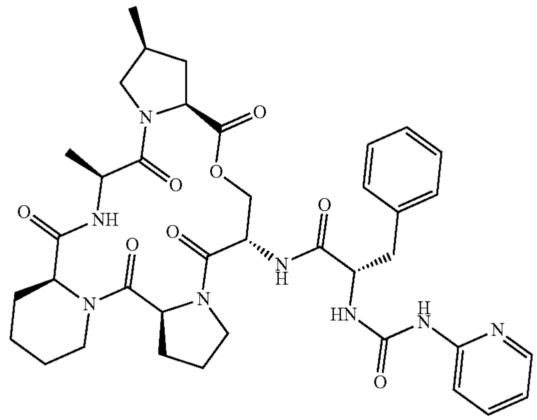 [SMILES: C[C@H]1C[C@H]2C(=O)OC[C@H](NC(=O)[C@H](Cc3ccccc3)NC(=O)Nc3ccccn3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(pyridin-2-yl)ureido)propanamide |
| 143 | 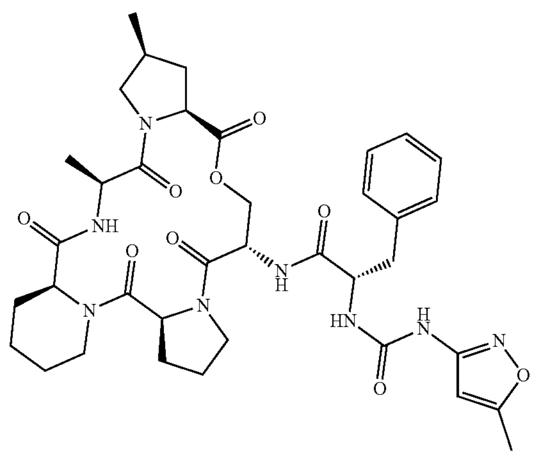 [SMILES: Cc1cc(NC(=O)N[C@@H](Cc2ccccc2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)no1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(5-methylisoxazol-3-yl)ureido)-3-phenylpropanamide |
| 144 | 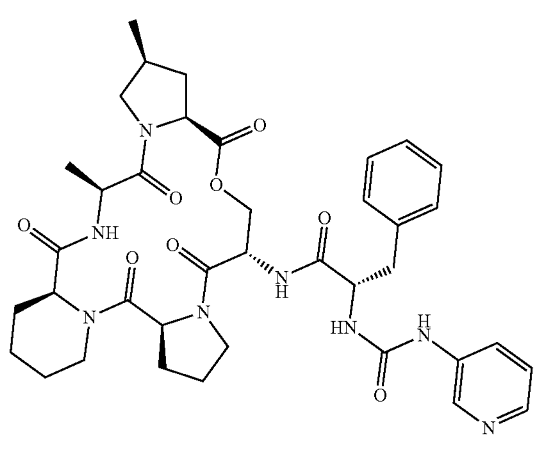 [SMILES: C[C@H]1C[C@H]2C(=O)OC[C@H](NC(=O)[C@H](Cc3ccccc3)NC(=O)Nc3cccnc3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(pyridin-3-yl)ureido)propanamide |

TABLE 8-continued

| No. | Structure | Name |
|---|---|---|
| 145 | 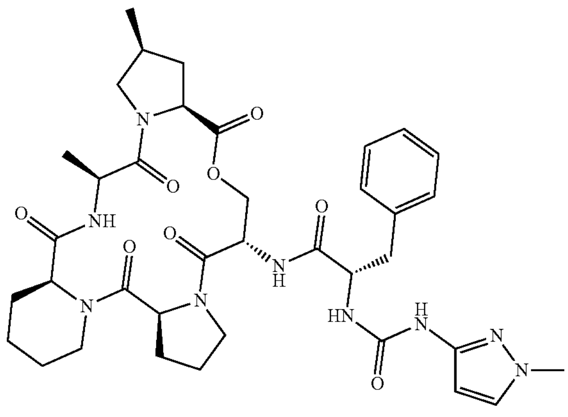 [SMILES: C[C@H]1C[C@H]2C(=O)OC[C@H](NC(=O)[C@H](Cc3ccccc3)NC(=O)Nc3ccn(C)n3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(pyridin-4-yl)ureido)propanamide |
| 146 | 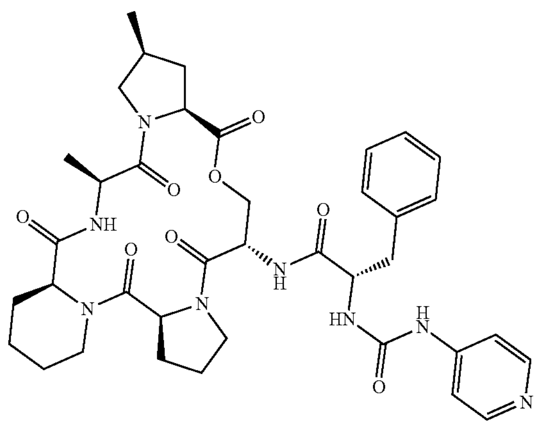 [SMILES: C[C@H]1C[C@H]2C(=O)OC[C@H](NC(=O)[C@H](Cc3ccccc3)NC(=O)Nc3ccncc3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(pyridin-4-yl)ureido)propanamide |
| 147 | 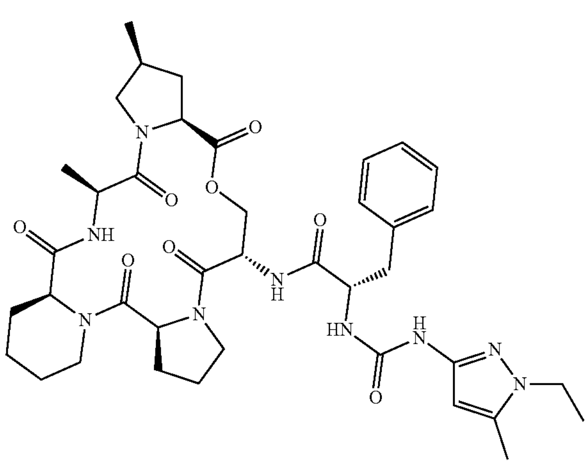 [SMILES: CCn1nc(NC(=O)N[C@@H](Cc2ccccc2)C(=O)N[C@H]2COC(=O)[C@@H]3C[C@H](C)CN3C(=O)[C@H](C)NC(=O)[C@@H]3CCCCN3C(=O)[C@@H]3CCCN3C2=O)cc1C] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(1-ethyl-5-methyl-1H-pyrazol-3-yl)ureido)-3-phenylpropanamide |

TABLE 8-continued

| No. | Structure | Name |
|---|---|---|
| 148 | 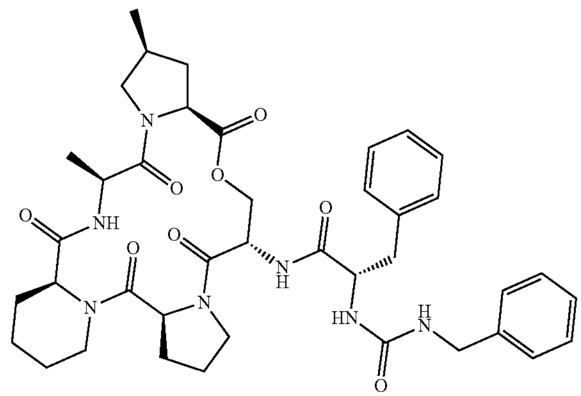 [SMILES: C[C@H]1C[C@H]2C(=O)OC[C@H](NC(=O)[C@H](Cc3ccccc3)NC(=O)NCc3ccccc3)C(=O)N3CCC[C@H]3C(=O)N3CCCC[C@H]3C(=O)N[C@@H](C)C(=O)N2C1] | (S)-2-(3-benzylureido)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenylpropanamide |
| 149 | 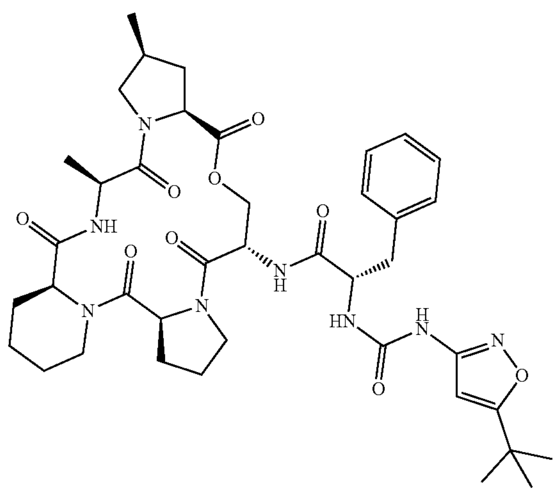 [SMILES: C[C@H]1C[C@H]2C(=O)OC[C@H](NC(=O)[C@H](Cc3ccccc3)NC(=O)Nc3cc(C(C)(C)C)on3)C(=O)N3CCC[C@H]3C(=O)N3CCCC[C@H]3C(=O)N[C@@H](C)C(=O)N2C1] | (S)-2-(3-(5-(tert-butyl)isoxazol-3-yl)ureido)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-2-yl)-3-phenylpropanamide |
| 150 | 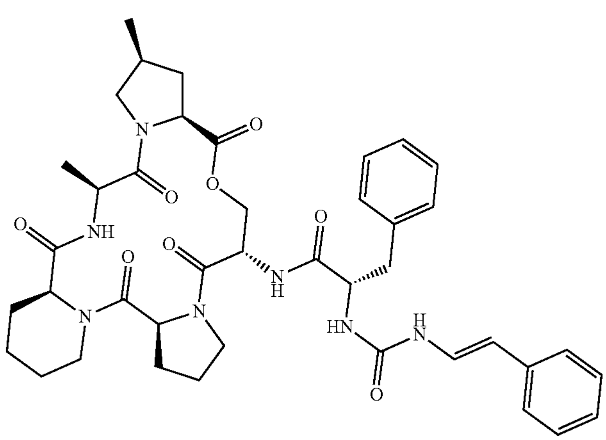 [SMILES: C[C@H]1C[C@H]2C(=O)OC[C@H](NC(=O)[C@H](Cc3ccccc3)NC(=O)N/C=C/c3ccccc3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-((E)-styryl)ureido)propanamide |

TABLE 8-continued

| No. | Structure | Name |
|---|---|---|
| 151 | 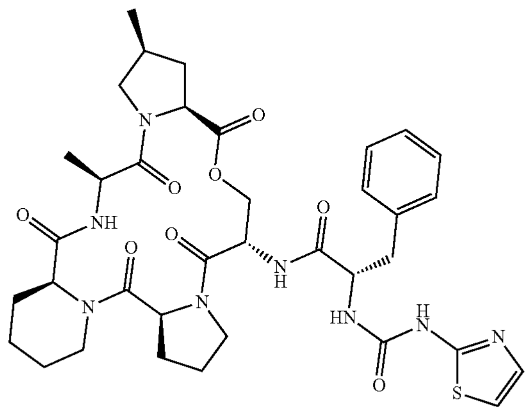 [SMILES: C[C@H]1C[C@H]2C(=O)OC[C@H](NC(=O)[C@H](Cc3ccccc3)NC(=O)Nc3nccs3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-(thiazol-2-yl)ureido)propanamide |
| 152 | 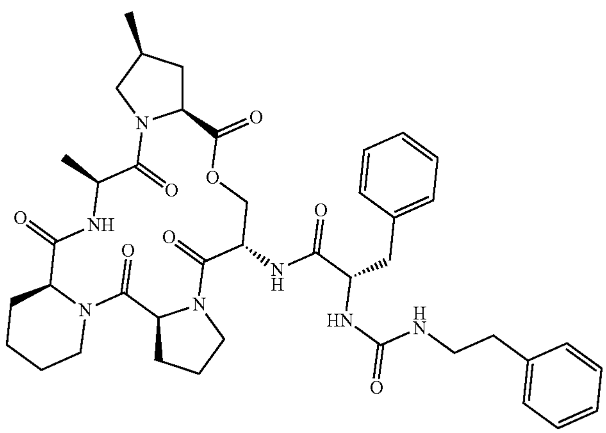 [SMILES: C[C@H]1C[C@H]2C(=O)OC[C@H](NC(=O)[C@H](Cc3ccccc3)NC(=O)NCCc3ccccc3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-phenethylureido)-3-phenylpropanamide |
| 153 | 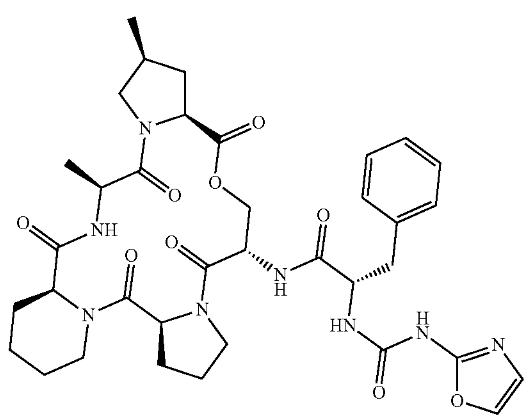 [SMILES: C[C@H]1C[C@H]2C(=O)OC[C@H](NC(=O)[C@H](Cc3ccccc3)NC(=O)Nc3ncco3)C(=O)N3CCC[C@H]3C(=O)N3CCCC[C@H]3C(=O)N[C@@H](C)C(=O)N2C1] | (S)-N-((2S,6S,8aS,14aS,20S,23aS)-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(oxazol-2-yl)ureido)-3-phenylpropanamide |

TABLE 8-continued

| No. | Structure | Name |
| --- | --- | --- |
| 154 | 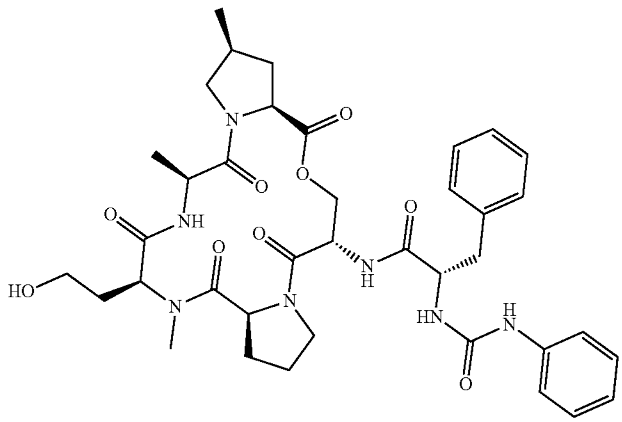 [SMILES: C[C@H]1C[C@H]2C(=O)OC[C@H](NC(=O)[C@H](Cc3ccccc3)NC(=O)Nc3ccccc3)C(=O)N3CCC[C@H]3C(=O)N(C)[C@@H](CCO)C(=O)N[C@@H](C)C(=O)N2C1] | (S)-N-((2S,6S,9S,11aS,17S,20aS)-9-(2-hydroxyethyl)-2,6,10-trimethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-3-phenyl-2-(3-phenylureido)propanamide |
| 155 | 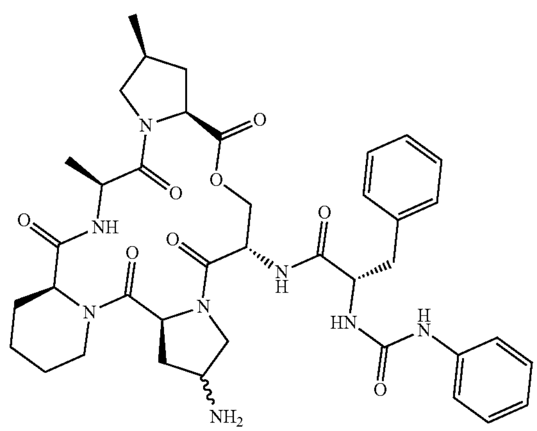 | (2S)-N-((2S,6S,8aS,14aS,20S,23aS)-16-amino-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-phenylureido)propanamide |
| 156 | 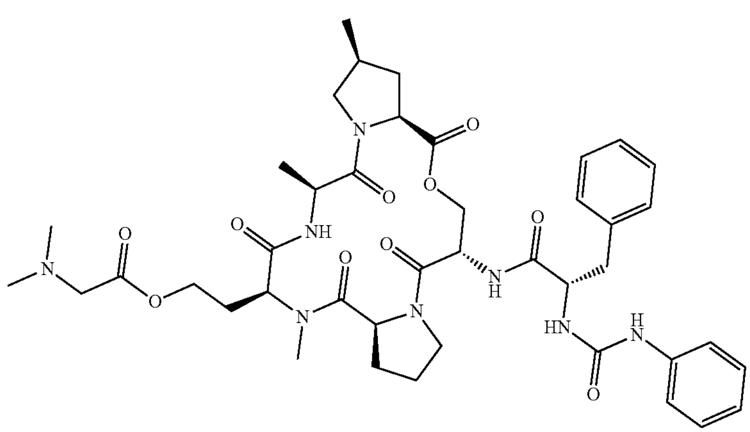 [SMILES: C[C@H]1C[C@H]2C(=O)OC[C@H](NC(=O)[C@H](Cc3ccccc3)NC(=O)Nc3ccccc3)C(=O)N3CCC[C@H]3C(=O)N(C)[C@@H](CCOC(=O)CN(C)C)C(=O)N[C@@H](C)C(=O)N2C1] | 2-((2S,6S,9S,11aS,17S,20aS)-2,6,10-trimethyl-5,8,11,16,20-pentaoxo-17-((S)-3-phenyl-2-(3-phenylureido)propanamido)hexadecahydro-1H,5H,16H-dipyrrolo[2,1-c:2',1'-1][1]oxa[4,7,10,13]tetraazacyclohexadecin-9-yl)ethyl dimethylglycinate |

TABLE 8-continued

| No. | Structure | Name |
|---|---|---|
| 157 | 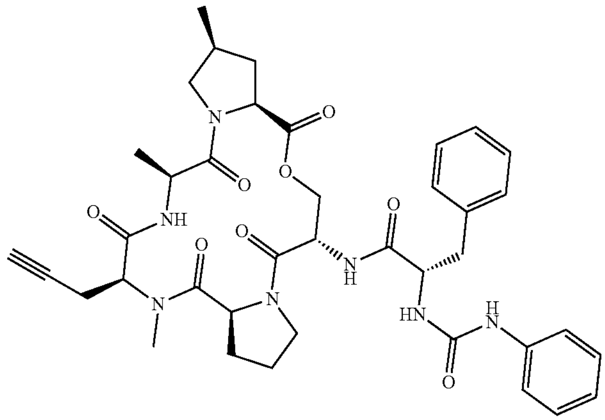 [SMILES: C#CC[C@H]1C(=O)N[C@@H](C)C(=O)N2C[C@@H](C)C[C@H]2C(=O)OC[C@H](NC(=O)[C@H](Cc2ccccc2)NC(=O)Nc2ccccc2)C(=O)N2CCC[C@H]2C(=O)N1C] | (S)-3-phenyl-2-(3-phenylureido)-N-((2S,6S,9S,11aS,17S,20aS)-2,6,10-trimethyl-5,8,11,16,20-pentaoxo-9-(prop-2-yn-1-yl)hexadecahydro-1H,5H,16H-dipyrrolo[2,1-c:2',1'-1][1]oxa[4,7,10,13]tetraazacyclohexadecin-17-yl)propanamide |
| 158 | 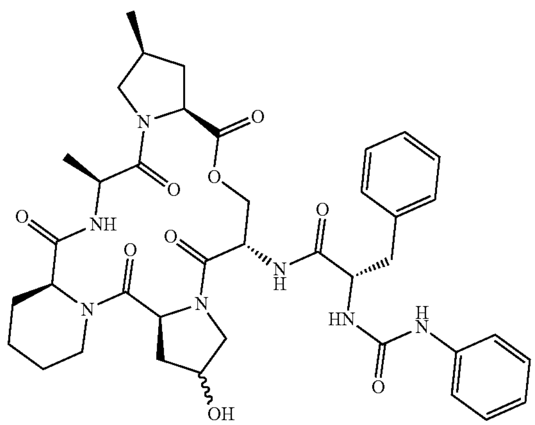 | (2S)-N-((2S,6S,8aS,14aS,20S,23aS)-16-hydroxy-2,6-dimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-phenyl-2-(3-phenylureido)propanamide |
| 159 | 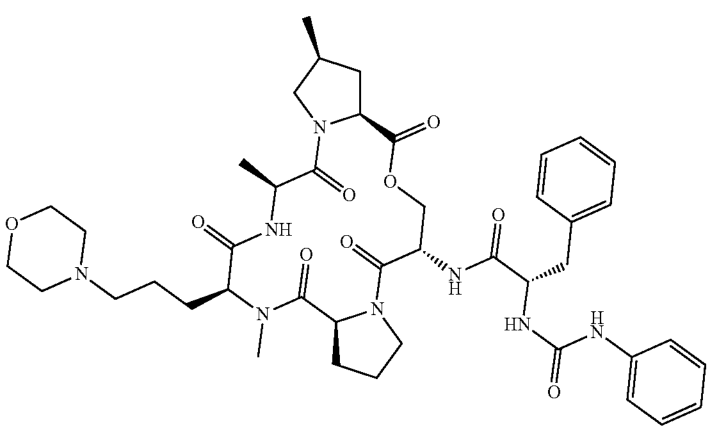 [SMILES: C[C@H]1C[C@H]2C(=O)OC[C@H](NC(=O)[C@H](Cc3ccccc3)NC(=O)Nc3ccccc3)C(=O)N3CCC[C@H]3C(=O)N(C)[C@@H](CCCN3CCOCC3)C(=O)N[C@@H](C)C(=O)N2C1] | (S)-3-phenyl-2-(3-phenylureido)-N-((2S,6S,9S,11aS,17S,20aS)-2,6,10-trimethyl-9-(3-morpholinopropyl)-5,8,11,16,20-pentaoxohexadecahydro-1H,5H,16H-dipyrrolo[2,1-c:2',1'-1][1]oxa[4,7,10,13]tetraazacyclohexadecin-17-yl)propanamide |

TABLE 8-continued

| No. | Structure | Name |
|---|---|---|
| 160 | 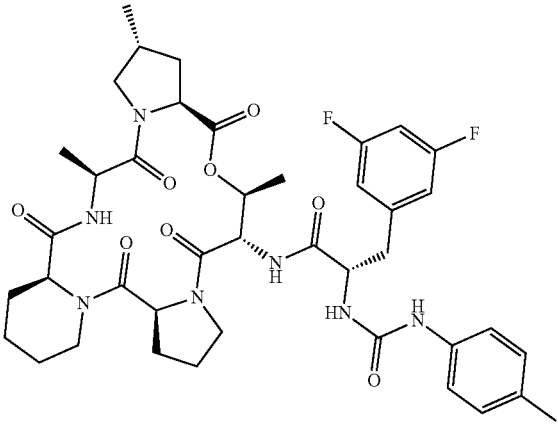 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)cc1] | (S)-3-(3,5-difluorophenyl)-2-(3-(p-tolyl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 161 | 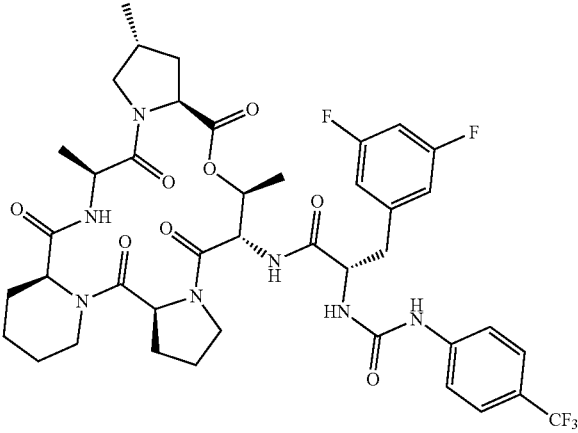 [SMILES: C[C@@H]1C[C@H]2C(=O)O[C@@H](C)[C@H](NC(=O)[C@H](Cc3cc(F)cc(F)c3)NC(=O)Nc3ccc(C(F)(F)F)cc3)C(=O)N3CCC[C@H]3C(=O)N3CCCC[C@H]3C(=O)N[C@@H](C)C(=O)N2C1] | (S)-3-(3,5-difluorophenyl)-2-(3-(4-(trifluoromethyl)phenyl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 162 | 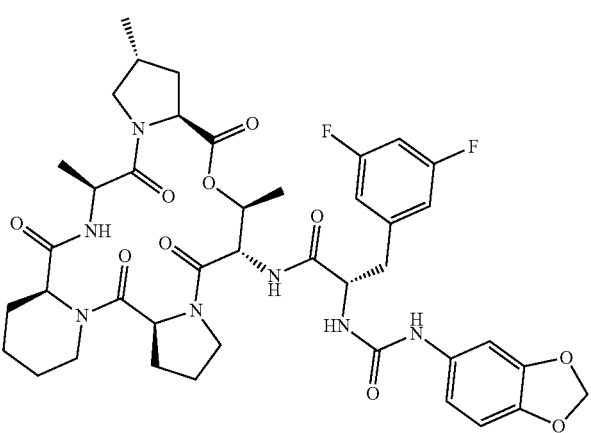 [SMILES: C[C@@H]1C[C@H]2C(=O)O[C@@H](C)[C@H](NC(=O)[C@H](Cc3cc(F)cc(F)c3)NC(=O)Nc3ccc4c(c3)OCO4)C(=O)N3CCC[C@H]3C(=O)N3CCCC[C@H]3C(=O)N[C@@H](C)C(=O)N2C1] | (S)-2-(3-(benzo[d][1,3]dioxol-5-yl)ureido)-3-(3,5-difluorophenyl)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
| --- | --- | --- |
| 163 | 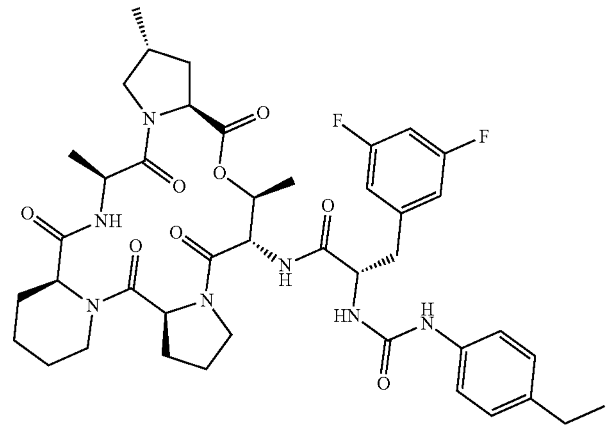 [SMILES: CCc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@H](C)C[C@H]3C(=O)O[C@H]2C)cc1] | (S)-3-(3,5-difluorophenyl)-2-(3-(4-ethylphenyl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 164 | 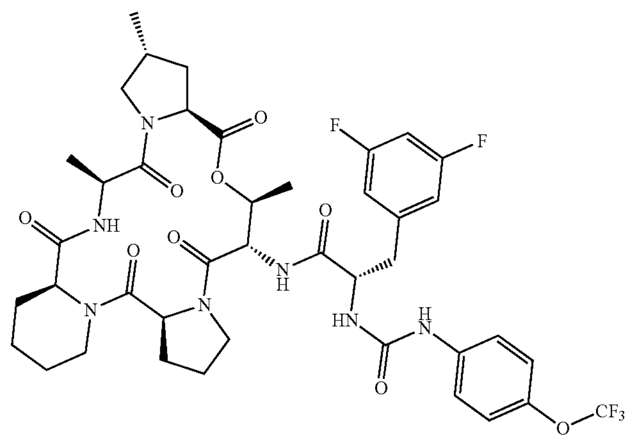 [SMILES: C[C@@H]1C[C@H]2C(=O)O[C@@H](C)[C@H](NC(=O)[C@H](Cc3cc(F)cc(F)c3)NC(=O)Nc3ccc(OC(F)(F)F)cc3)C(=O)N3CCC[C@H]3C(=O)N3CCCC[C@H]3C(=O)N[C@@H](C)C(=O)N2C1] | (S)-3-(3,5-difluorophenyl)-2-(3-(4-(trifluoromethoxy)phenyl)ureido)-N-((2R,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 165 | 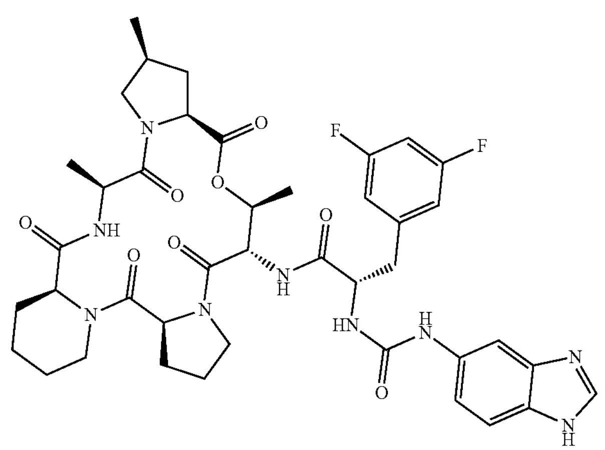 [SMILES: C[C@H]1C[C@H]2C(=O)O[C@@H](C)[C@H](NC(=O)[C@H](Cc3cc(F)cc(F)c3)NC(=O)Nc3ccc4[nH]cnc4c3)C(=O)N3CCC[C@H]3C(=O)N3CCCC[C@H]3C(=O)N[C@@H](C)C(=O)N2C1] | (S)-2-(3-(1H-benzo[d]imidazol-5-yl)ureido)-3-(3,5-difluorophenyl)-N-((2S,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|---|---|---|
| 166 | 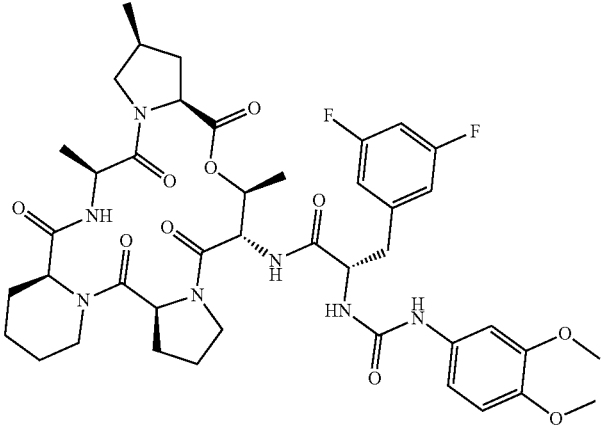 [SMILES: COc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@@H](C)C[C@H]3C(=O)O[C@H]2C)cc1OC] | (S)-3-(3,5-difluorophenyl)-2-(3-(3,4-dimethoxyphenyl)ureido)-N-((2S,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 167 | 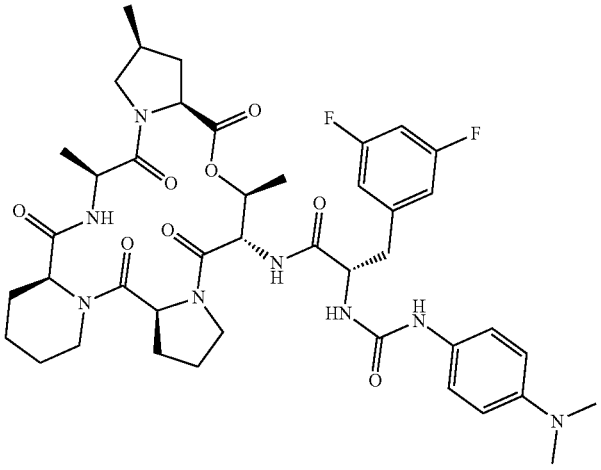 [SMILES: C[C@H]1C[C@H]2C(=O)O[C@@H](C)[C@H](NC(=O)[C@H](Cc3cc(F)cc(F)c3)NC(=O)Nc3ccc(N(C)C)cc3)C(=O)N3CCC[C@H]3C(=O)N3CCCC[C@H]3C(=O)N[C@@H](C)C(=O)N2C1] | (S)-3-(3,5-difluorophenyl)-2-(3-(4-(dimethylamino)phenyl)ureido)-N-((2S,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 168 | 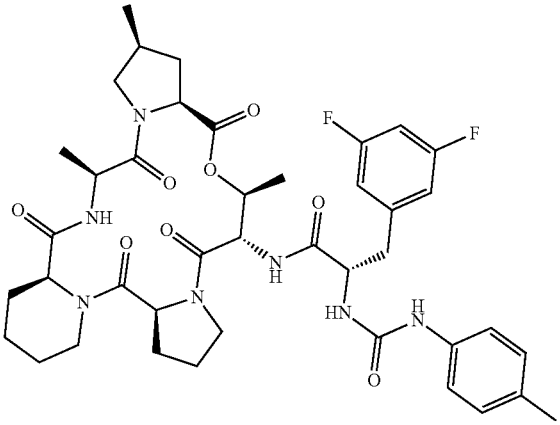 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@@H](C)C[C@H]3C(=O)O[C@H]2C)cc1] | (S)-3-(3,5-difluorophenyl)-2-(3-(p-tolyl)ureido)-N-((2S,6S,8aS,14aS,20S,21R,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|---|---|---|
| 169 | 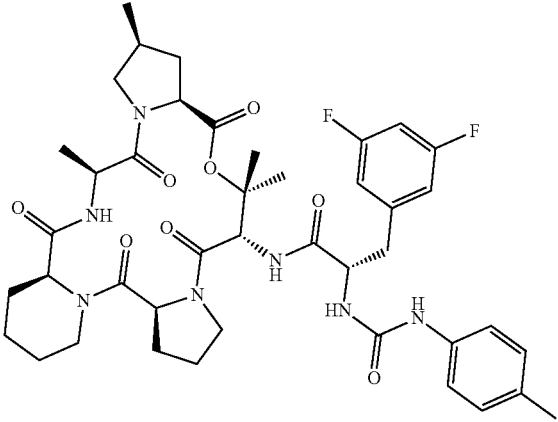 | (S)-3-(3,5-difluorophenyl)-N-((2S,6S,8aS,14aS,20S,23aS)-2,6,21,21-tetramethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(p-tolyl)ureido)propanamide |
| 170 | 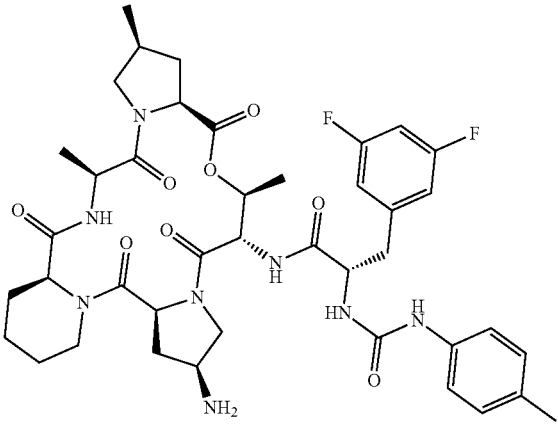 [SMILES: Cc1ccc(NC(=O)N[C@@H](Cc2cc(F)cc(F)c2)C(=O)N[C@@H]2C(=O)N3C[C@@H](N)C[C@H]3C(=O)N3CCCC[C@H]3C(=O)N[C@@H](C)C(=O)N3C[C@@H](C)C[C@H]3C(=O)O[C@H]2C)cc1] | (S)-N-((2S,6S,8aS,14aS,16S,20S,21S,23aS)-16-amino-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-3-(3,5-difluorophenyl)-2-(3-(p-tolyl)ureido)propanamide |
| 171 | 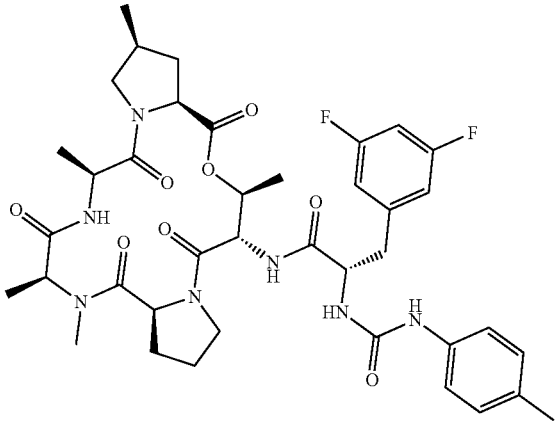 | (S)-3-(3,5-difluorophenyl)-N-((2S,6S,9S,11aS,17S,18S,20aS)-2,6,9,10,18-pentamethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-2-(3-(p-tolyl)ureido)propanamide |

TABLE 8-continued

| No. | Structure | Name |
|---|---|---|
| 172 | 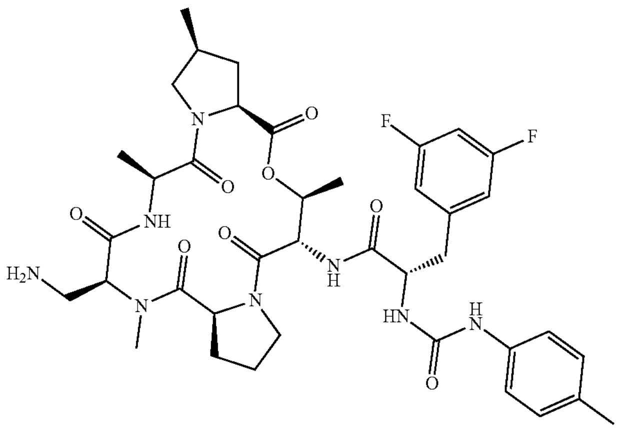 [SMILES: Cc1ccc(NC(=O)N[C@@H](Cc2cc(F)cc(F)c2)C(=O)N[C@@H]2C(=O)N3CCC[C@H]3C(=O)N(C)[C@@H](CN)C(=O)N[C@@H](C)C(=O)N3C[C@@H](C)C[C@H]3C(=O)O[C@H]2C)cc1] | (S)-N-((2S,6S,9S,11aS,17S,18S,20aS)-9-(aminomethyl)-2,6,10,18-tetramethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-3-(3,5-difluorophenyl)-2-(3-(p-tolyl)ureido)propanamide |
| 173 | 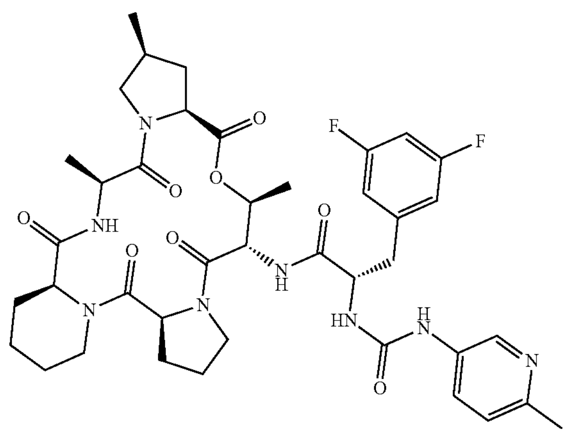 | (S)-3-(3,5-difluorophenyl)-2-(3-(6-methylpyridin-3-yl)ureido)-N-((2S,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 174 | 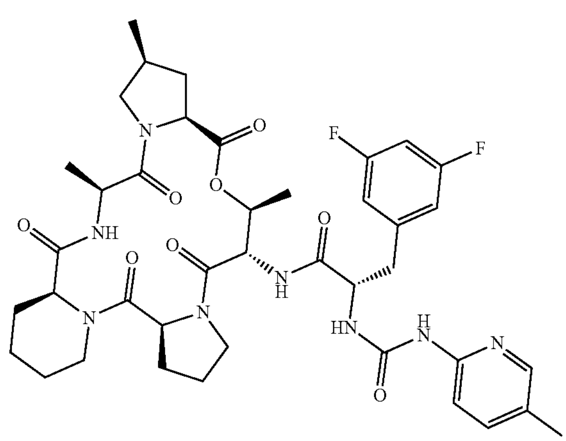 [SMILES: Cc1ccc(NC(=O)N[C@@H](Cc2cc(F)cc(F)c2)C(=O)N[C@@H]2C(=O)N3CCC[C@H]3C(=O)N3CCCC[C@H]3C(=O)N[C@@H](C)C(=O)N3C[C@@H](C)C[C@H]3C(=O)O[C@H]2C)nc1] | (S)-3-(3,5-difluorophenyl)-2-(3-(5-methylpyridin-2-yl)ureido)-N-((2S,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |

TABLE 8-continued

| No. | Structure | Name |
|---|---|---|
| 175 | 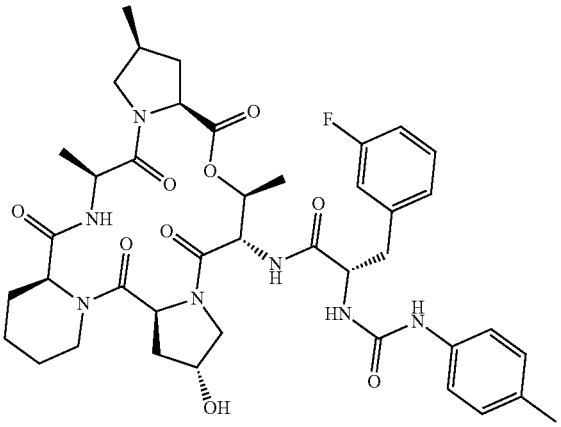 [SMILES: Cc1ccc(NC(=O)N[C@@H](Cc2cccc(F)c2)C(=O)N[C@@H]2C(=O)N3C[C@H](O)C[C@H]3C(=O)N3CCCC[C@H]3C(=O)N[C@@H](C)C(=O)N3C[C@@H](C)C[C@H]3C(=O)O[C@H]2C)cc1] | (S)-3-(3-fluorophenyl)-N-((2S,6S,8aS,14aS,16R,20S,21S,23aS)-16-hydroxy-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)-2-(3-(p-tolyl)ureido)propanamide |
| 176 | 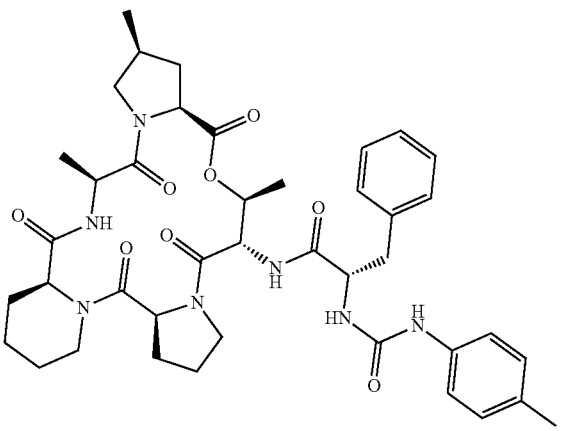 [SMILES: Cc1ccc(NC(=O)N[C@@H](Cc2ccccc2)C(=O)N[C@@H]2C(=O)N3CCC[C@H]3C(=O)N3CCCC[C@H]3C(=O)N[C@@H](C)C(=O)N3C[C@@H](C)C[C@H]3C(=O)O[C@H]2C)cc1] | (S)-3-phenyl-2-(3-(p-tolyl)ureido)-N-((2S,6S,8aS,14aS,20S,21S,23aS)-2,6,21-trimethyl-5,8,14,19,23-pentaoxooctadecahydro-1H,5H,14H,19H-pyrido[2,1-i]dipyrrolo[2,1-c:2',1'-1][1]oxa[4,7,10,13]tetraazacyclohexadecin-20-yl)propanamide |
| 177 | 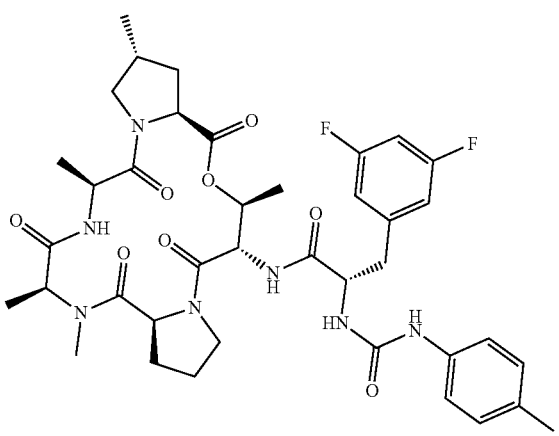 | (S)-3-(3,5-difluorophenyl)-N-((2R,6S,9S,11aS,17S,18S,20aS)-2,6,9,10,18-pentamethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-2-(3-(p-tolyl)ureido)propanamide |

TABLE 8-continued

| No. | Structure | Name |
|---|---|---|
| 178 | 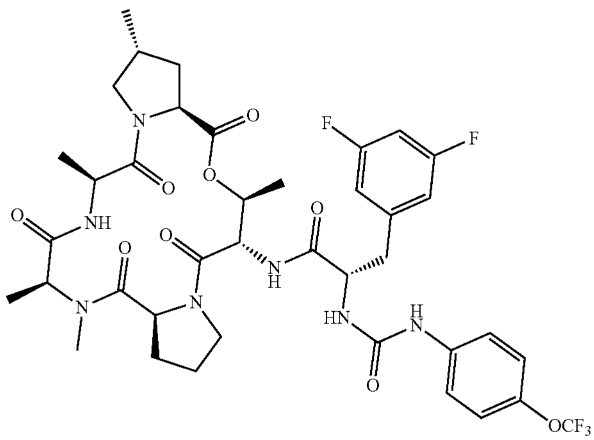 [SMILES: C[C@@H]1C[C@H]2C(=O)O[C@@H](C)[C@H](NC(=O)[C@H](Cc3cc(F)cc(F)c3)NC(=O)Nc3ccc(OC(F)(F)F)cc3)C(=O)N3CCC[C@H]3C(=O)N(C)[C@@H](C)C(=O)N[C@@H](C)C(=O)N2C1] | (S)-3-(3,5-difluorophenyl)-N-((2R,6S,9S,11aS,17S,18S,20aS)-2,6,9,10,18-pentamethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-2-(3-(4-(trifluoromethoxy)phenyl)ureido)propanamide |
| 179 | | (S)-3-(3,5-difluorophenyl)-2-(3-(4-ethylphenyl)ureido)-N-((2R,6S,9S,11aS,17S,18S,20aS)-2,6,9,10,18-pentamethyl-5,8,11,16,20-pentaoxohexadecahydro-1H,5H,16H-dipyrrolo[2,1-c:2',1'-1][1]oxa|4,7,10,13]tetraazacyclohexadecin-17-yl)propanamide |
| 180 | 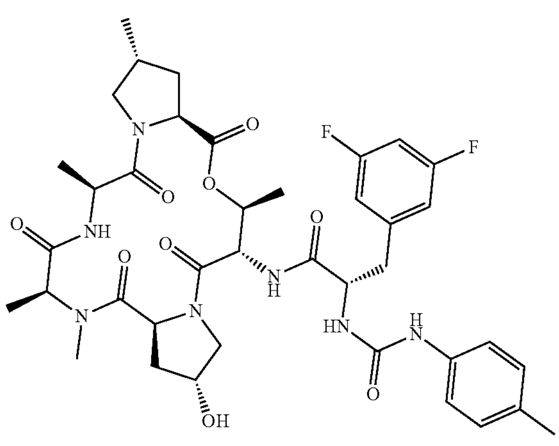 | (S)-3-(3,5-difluorophenyl)-N-((2R,6S,9S,11aS,13R,17S,18S,20aS)-13-hydroxy-2,6,9,10,18-pentamethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-2-(3-(p-tolyl)ureido)propanamide |

TABLE 8-continued

| No. | Structure | Name |
|---|---|---|
| 181 | 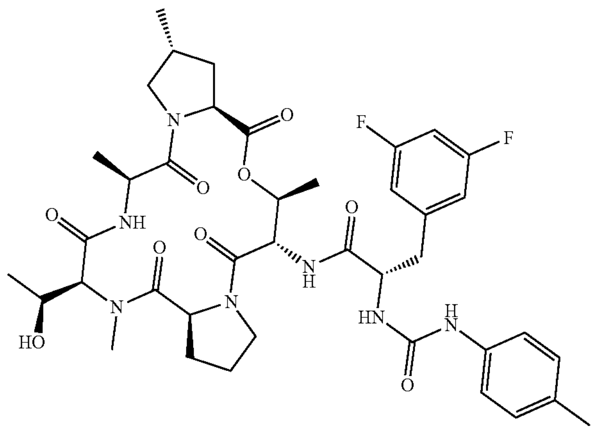 [SMILES: Cc1ccc(NC(=O)N[C@@H](Cc2cc(F)cc(F)c2)C(=O)N[C@@H]2C(=O)N3CCC[C@H]3C(=O)N(C)[C@@H]([C@H](C)O)C(=O)N[C@@H](C)C(=O)N3C[C@H](C)C[C@H]3C(=O)O[C@H]2C)cc1] | (S)-3-(3,5-difluorophenyl)-N-((2R,6S,9S,11aS,17S,18S,20aS)-9-((S)-1-hydroxyethyl)-2,6,10,18-tetramethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-2-(3-(p-tolyl)ureido)propanamide |
| 182 | 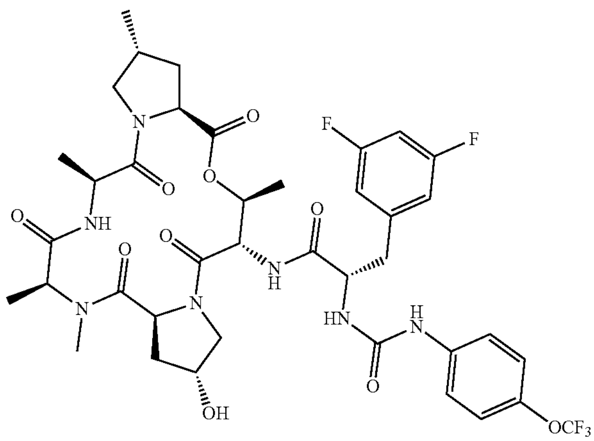 [SMILES: C[C@@H]1C[C@H]2C(=O)O[C@@H](C)[C@H](NC(=O)[C@H](Cc3cc(F)cc(F)c3)NC(=O)Nc3ccc(OC(F)(F)F)cc3)C(=O)N3C[C@H](O)C[C@H]3C(=O)N(C)[C@@H](C)C(=O)N[C@@H](C)C(=O)N2C1] | (S)-3-(3,5-difluorophenyl)-N-((2R,6S,9S,11aS,13R,17S,18S,20aS)-13-hydroxy-2,6,9,10,18-pentamethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-2-(3-(4-(trifluoromethoxy)phenyl)ureido)propanamide |
| 183 | 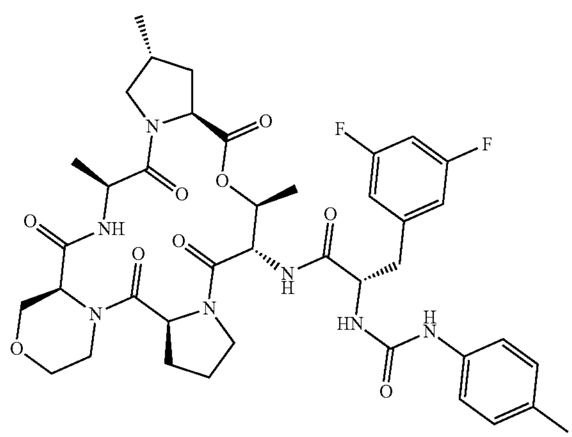 [SMILES: Cc1ccc(NC(=O)N[C@@H](Cc2cc(F)cc(F)c2)C(=O)N[C@@H]2C(=O)N3CCC[C@H]3C(=O)N3CCOC[C@H]3C(=O)N[C@@H](C)C(=O)N3C[C@H](C)C[C@H]3C(=O)O[C@H]2C)cc1] | (S)-3-(3,5-difluorophenyl)-2-(3-(p-tolyl)ureido)-N-((6aS,12S,13S,15aS,17R,21S,23aS)-13,17,21-trimethyl-6,11,15,20,23-pentaoxooctadecahydro-6H,11H,15H-[1,4]oxazino[3,4-i]dipyrrolo[2,1-c:2',1'-1][1]oxa[4,7,10,13]tetraazacyclohexadecin-12-yl)propanamide |

TABLE 8-continued

| No. | Structure | Name |
|---|---|---|
| 184 | 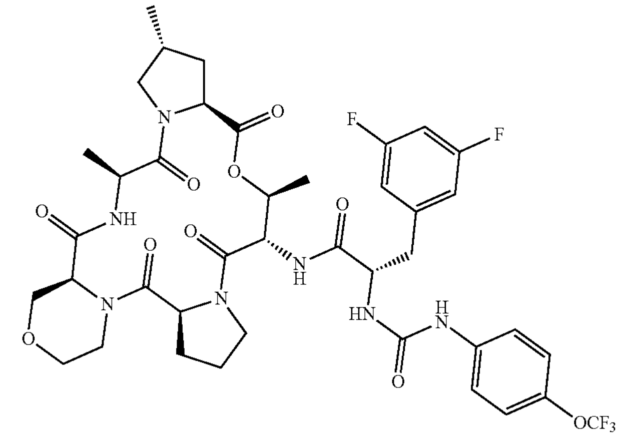 [SMILES: C[C@@H]1C[C@H]2C(=O)O[C@@H](C)[C@H](NC(=O)[C@H](Cc3cc(F)cc(F)c3)NC(=O)Nc3ccc(OC(F)(F)F)cc3)C(=O)N3CCC[C@H]3C(=O)N3CCOC[C@H]3C(=O)N[C@@H](C)C(=O)N2C1] | (S)-3-(3,5-difluorophenyl)-2-(3-(4-(trifluoromethoxy)phenyl)ureido)-N-((6aS,12S,13S,15aS,17R,21S,23aS)-13,17,21-trimethyl-6,11,15,20,23-pentaoxooctadecahydro-6H,11H,15H-[1,4]oxazino[3,4-i]dipyrrolo[2,1-c:2',1'-1][1]oxa[4,7,10,13]tetraazacyclohexadecin-12-yl)propanamide |
| 185 | 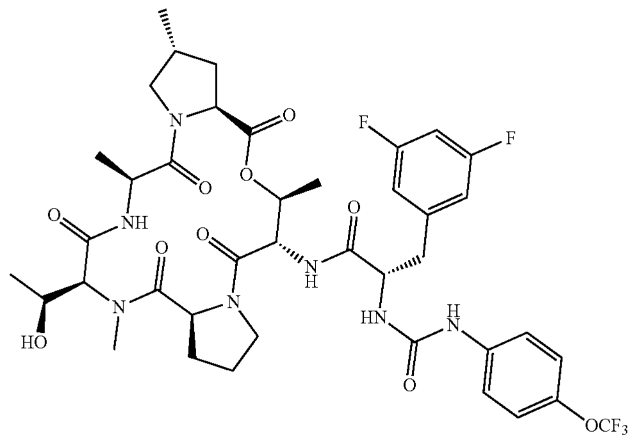 [SMILES: C[C@@H]1C[C@H]2C(=O)O[C@@H](C)[C@H](NC(=O)[C@H](Cc3cc(F)cc(F)c3)NC(=O)Nc3ccc(OC(F)(F)F)cc3)C(=O)N3CCC[C@H]3C(=O)N(C)[C@@H]([C@H](C)O)C(=O)N[C@@H](C)C(=O)N2C1] | (S)-3-(3,5-difluorophenyl)-N-((2R,6S,9S,11aS,17S,18S,20aS)-9-((S)-1-hydroxyethyl)-2,6,10,18-tetramethyl-5,8,11,16,20-pentaoxohexadecahydro-1H,5H,16H-dipyrrolo[2,1-c:2',1'-1][1]oxa[4,7,10,13]tetraazacyclohexadecin-17-yl)-2-(3-(4-(trifluoromethoxy)phenyl)ureido)propanamide |
| 186 | 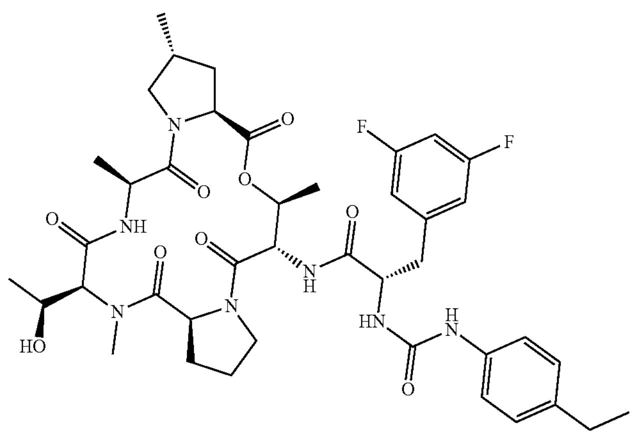 [SMILES: CCc1ccc(NC(=O)N[C@@H](Cc2cc(F)cc(F)c2)C(=O)N[C@@H]2C(=O)N3CCC[C@H]3C(=O)N(C)[C@@H]([C@H](C)O)C(=O)N[C@@H](C)C(=O)N3C[C@H](C)C[C@H]3C(=O)O[C@H]2C)cc1] | (S)-3-(3,5-difluorophenyl)-2-(3-(4-ethylphenyl)ureido)-N-((2R,6S,9S,11aS,17S,18S,20aS)-9-((S)-1-hydroxyethyl)-2,6,10,18-tetramethyl-5,8,11,16,20-pentaoxohexadecahydro-1H,5H,16H-dipyrrolo[2,1-c: 2',1'-1][1]oxa[4,7,10,13]tetraazacyclohexadecin-17-yl)propanamide |

15. PROPHETIC PHARMACEUTICAL COMPOSITION EXAMPLES

"Active ingredient" as used throughout these examples relates to one or more disclosed compounds or products of disclosed methods of making as described hereinbefore, or a pharmaceutically acceptable salt, solvate, or polymorph thereof. The following examples of the formulation of the compounds of the present invention in tablets, suspension, injectables and ointments are prophetic. Typical examples of recipes for the formulation of the invention are as given below.

Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press).

The disclosure of this reference is hereby incorporated herein by reference.

a. Pharmaceutical Composition for Oral Administration

A tablet can be prepared as follows:

| Component | Amount |
| --- | --- |
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is molded using a customary tablet press (e.g. tablet format: diameter 8 mm, curvature radius 12 mm). The molding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
| --- | --- |
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 µm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 µm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for the treatment of a bacterial infection in a mammal, the method comprising the step of administering to the mammal a therapeutically effective amount of a compound having a structure represented by a formula:

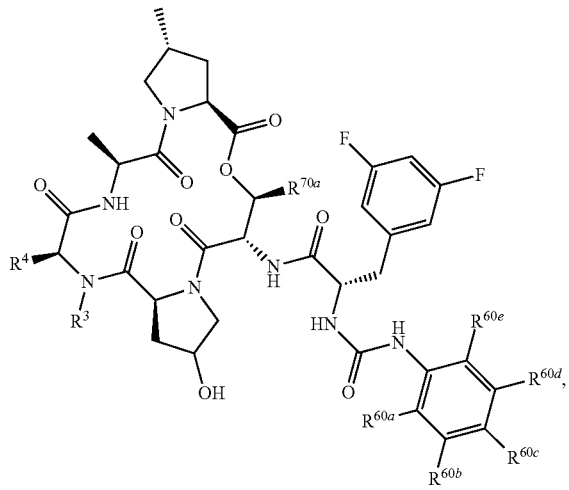

wherein $R^3$ and $R^4$ are covalently bonded, together with the intermediate atoms, comprise a piperazinyl ring substituted with methyl group;

wherein each of $R^{60a}$, $R^{60b}$, $R^{60c}$, $R^{60d}$, and $R^{60e}$ is independently selected from hydrogen, —F, —Cl, and methyl, provided that no more than three of $R^{60a}$, $R^{60b}$, $R^{60c}$, $R^{60d}$, and $R^{60e}$ are not hydrogen; and wherein $R^{70a}$ is methyl, or a pharmaceutically acceptable salt thereof, thereby treating the bacterial infection in the mammal.

2. The method of claim 1, wherein the mammal is a human.

3. The method of claim 2, wherein the human has been diagnosed with a bacterial infection.

4. The method of claim 2, wherein the human has been diagnosed with a biofilm mediated disease.

5. The method of claim 4, wherein the biofilm mediated disease is bacterial endocarditis and osteomyelitis.

6. The method of claim 4, further comprising the step of identifying a mammal in need of treatment of the biofilm mediated disease.

7. The method of claim 1, wherein the mammal has been diagnosed with a need for treatment of the bacterial infection prior to the administering step.

8. The method of claim 1, further comprising the step of identifying a mammal in need of treatment of the bacterial infection.

9. The method of claim 1, further comprising administering to the mammal a therapeutically effective amount of at least one antibacterial agent.

* * * * *